US008530646B2

(12) United States Patent
Suzuki et al.

(10) Patent No.: US 8,530,646 B2
(45) Date of Patent: *Sep. 10, 2013

(54) OXAZOLIDINONE DERIVATIVE HAVING 7-MEMBERED HETERO RING

(75) Inventors: Hideyuki Suzuki, Tokyo-to (JP); Iwao Utsunomiya, Yokohama (JP); Koichi Shudo, Tokyo-to (JP); Tsutomu Iwaki, Osaka (JP); Tatsuro Yasukata, Osaka (JP)

(73) Assignees: Research Foundation Itsuu Laboratory, Tokyo (JP); Shionogi & Co., Ltd., Osaka (JP)

( * ) Notice: Subject to any disclaimer, the term of this patent is extended or adjusted under 35 U.S.C. 154(b) by 371 days.

This patent is subject to a terminal disclaimer.

(21) Appl. No.: 12/733,954

(22) PCT Filed: Oct. 1, 2008

(86) PCT No.: PCT/JP2008/067843
§ 371 (c)(1),
(2), (4) Date: Mar. 31, 2010

(87) PCT Pub. No.: WO2009/044777
PCT Pub. Date: Apr. 9, 2009

(65) Prior Publication Data
US 2010/0256355 A1 Oct. 7, 2010

(30) Foreign Application Priority Data
Oct. 2, 2007 (JP) ................................ 2007-258898

(51) Int. Cl.
C07D 273/06 (2006.01)
C07D 255/00 (2006.01)
C07D 255/02 (2006.01)

(52) U.S. Cl.
USPC .......................................... 540/545; 540/554

(58) Field of Classification Search
None
See application file for complete search history.

(56) References Cited

U.S. PATENT DOCUMENTS

| | | | |
|---|---|---|---|
| 1,543,081 A | 6/1925 | Hansen | |
| 4,801,706 A * | 1/1989 | Winkley et al. | 540/554 |
| 4,882,323 A | 11/1989 | Winkley et al. | |
| 4,935,515 A | 6/1990 | Winkley et al. | |
| 5,523,403 A | 6/1996 | Barbachyn | |
| 5,529,998 A | 6/1996 | Häbich et al. | |
| 5,574,055 A | 11/1996 | Borgulya et al. | |
| 6,218,413 B1 | 4/2001 | Hester, Jr. et al. | |
| 6,239,152 B1 | 5/2001 | Gordeev et al. | |
| 6,255,304 B1 | 7/2001 | Hester, Jr. et al. | |
| 6,342,513 B1 | 1/2002 | Hester, Jr. et al. | |
| 6,362,189 B1 | 3/2002 | Hester, Jr. et al. | |
| 6,537,986 B2 | 3/2003 | Hester, Jr. et al. | |
| 6,734,307 B2 | 5/2004 | Mehta et al. | |
| 6,956,040 B2 | 10/2005 | Mehta et al. | |
| 2003/0153610 A1 | 8/2003 | Straub et al. | |
| 2005/0004174 A1 | 1/2005 | Gordeev et al. | |
| 2005/0234076 A1 | 10/2005 | Gebauer et al. | |
| 2006/0258724 A1 | 11/2006 | Straub et al. | |
| 2007/0167421 A1 | 7/2007 | Ito et al. | |
| 2008/0090815 A1 | 4/2008 | Straub et al. | |

FOREIGN PATENT DOCUMENTS

| | | |
|---|---|---|
| EP | 1 130 016 | 9/2001 |
| EP | 2 009 012 | 12/2008 |
| GB | 1 543 081 | 3/1979 |
| JP | 63-256951 | 10/1988 |
| JP | 09-221476 | 8/1997 |
| JP | 11-228576 | 8/1999 |
| JP | 11-322729 | 11/1999 |
| KR | 2008007764 | * 1/2008 |
| PL | 97 062 | 5/1978 |
| WO | 89/08111 | 9/1989 |
| WO | 95/07271 | 3/1995 |
| WO | 95/34540 | 12/1995 |
| WO | 97/09328 | 3/1997 |
| WO | 97/10223 | 3/1997 |
| WO | 99/12914 | 3/1999 |
| WO | 99/24428 | 5/1999 |

(Continued)

OTHER PUBLICATIONS

U.S. Appl. No. 13/372,848, filed Feb. 2012, Suzuki.*

(Continued)

Primary Examiner — Noble Jarrell
(74) Attorney, Agent, or Firm — Wenderoth, Lind & Ponack, L.L.P.

(57) ABSTRACT

The present invention provides a novel oxazolidinone derivative of the formula (I):

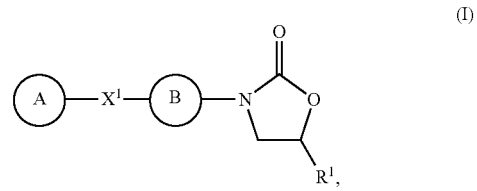

wherein Rings A and B are defined as in the specification; $X^1$ is a single bond, or a heteroatom-containing group selected from the group consisting of —O—, —S—, —NR$^2$—, —CO—, —CS—, —CONR$^3$—, —NR$^4$CO—, —SONR$^5$—, and NR$^6$SO$_2$—, wherein R$^2$, R$^3$, R$^4$, R$^5$, and R$^6$ are independently hydrogen or lower alkyl, or lower alkylene or lower alkenylene each optionally interrupted by said heteroatom containing group; and R$^1$ is hydrogen, or an organic residue which is able to bind to the 5-position of the oxazolidinone ring in oxazolidinone antimicrobial agents, pharmaceutically acceptable salts and solvates thereof which are useful as an antibacterial agent.

8 Claims, No Drawings

(56) References Cited

FOREIGN PATENT DOCUMENTS

| | | |
|---|---|---|
| WO | 99/37630 | 7/1999 |
| WO | 99/47525 | 9/1999 |
| WO | 99/64417 | 12/1999 |
| WO | 00/29396 | 5/2000 |
| WO | 00/32599 | 6/2000 |
| WO | 01/09107 | 2/2001 |
| WO | 01/30782 | 5/2001 |
| WO | 02/06278 | 1/2002 |
| WO | 02/24704 | 3/2002 |
| WO | 02/24709 | 3/2002 |
| WO | 03/002560 | 1/2003 |
| WO | 03/007870 | 1/2003 |
| WO | 03/008389 | 1/2003 |
| WO | 03/011859 | 2/2003 |
| WO | 03/072553 | 9/2003 |
| WO | 03/072575 | 9/2003 |
| WO | 03/091254 | 11/2003 |
| WO | 2004/002967 | 1/2004 |
| WO | 2004/014392 | 2/2004 |
| WO | 2004/026848 | 4/2004 |
| WO | 2004/096221 | 11/2004 |
| WO | 2004/101552 | 11/2004 |
| WO | 2005/019213 | 3/2005 |
| WO | 2005/058888 | 6/2005 |
| WO | 2005/079798 | 9/2005 |
| WO | 2006/056877 | 6/2006 |
| WO | 2006/109156 | 10/2006 |
| WO | 2007/000644 | 1/2007 |
| WO | 2007/114326 | 10/2007 |

OTHER PUBLICATIONS

Rodriguez-Spong. Advanced Drug Delivery Reviews, 2004, 56, 241-74.*
Szotor. Dissertationes Pharmaceuticae et Pharmacologicae, 1972, 24(4), 385-90.*
Supplementary European Search Report dated Mar. 29, 2011, issued in corresponding European Application No. 08 83 6063, in the English language.
International Preliminary Report on Patentability with Written Opinion mailed Apr. 15, 2010 in International (PCT) Application No. PCT/JP2008/067843.
International Preliminary Report on Patentability with Written Opinion mailed May 14, 2010 in International (PCT) Application No. PCT/JP2008/067843.
Jerzy Szotor et al., "Synthesis of Hexahydrotriazepine-1,2,5 Derivatives", Dissertationes Pharmaceuticae et Pharmacologicae, 24(4), 1972, pp. 385-390.
Stan D'Andrea et al., "Synthesis and antibacterial activity of dihydro-1,2-oxazine and 2-pyrazoline oxazolidinones: novel analogs of linezolid", Bioorganic & Medicinal Chemistry Letters, 15, 2005, pp. 2834-2839.
Biswajit Das et al., "Synthesis and SAR of novel oxazolidinones: Discovery of ranbezolid", Bioorganic & Medicinal Chemistry Letters, 15, 2005, pp. 4261-4267.
28-Heterocycles, Chemical Abstract, vol. 90, 1979, p. 623.
28-Heterocycles, Chemical Abstract, vol. 99, 1983, pp. 621 and 622.
Partial European Search Report issued Aug. 18, 2010 in corresponding European Application No. 10 00 5451, in the English language.

* cited by examiner

OXAZOLIDINONE DERIVATIVE HAVING 7-MEMBERED HETERO RING

FIELD OF INVENTION

The invention relates to oxazolidinone derivatives having a 7-membered hetero ring, a pharmaceutical (e.g., antimicrobial) composition comprising the same and synthetic intermediates thereof.

BACKGROUND ART

Various oxazolidinone derivatives having antimicrobial activity were known in the art, as disclosed, for example, in U.S. Pat. No. 6,255,304 (Patent Document 1), U.S. Pat No. 6,218,413 (Patent Document 2), U.S. Pat. No. 6,362,189 (Patent Document 3), U.S. Pat. No. 6,342,513 (Patent Document 4), U.S. Pat. No. 6,537,986 (Patent Document 5), WO2000/032599 (Patent Document 6), WO99/24428 (Patent Document 7), WO97/10223 (Patent Document 8), WO97/09328 (Patent Document 9), U.S. Pat. No. 5,523,403 (Patent Document 10), WO95/07271 (Patent Document 11), WO2004/014392 (Patent Document 12), U.S. Pat. No. 6,956,040 (Patent Document 13), U.S. Pat. No. 6,734,307 (Patent Document 14), WO2002/006278 (Patent Document 15), WO2003/008389 (Patent Document 16), WO2003/007870 (Patent Document 17), WO2005/058888 (Patent Document 18), WO2004/096221 (Patent Document 19), EP697412A (Patent Document 20), WO2000/027830 (Patent Document 21), Japanese Patent Application Publication 11-322729 (Patent Document 22), Japanese Patent Application Publication 9-221476 (Patent Document 23), WO95/34540 (Patent Document 24), WO2003/002560 (Patent Document 25), WO99/64417 (Patent Document 26), EP657440B (Patent Document 27), WO2005/019213 (Patent Document 28), Japanese Patent Application Publication 2005-524660 (Patent Document 29), U.S. Pat. No. 6,239,152 (Patent Document 30), U.S. Patent Application Publication No. 2005/4174A1 (Patent Document 31), Japanese Patent Application Publication 2003-513885 (Patent Document 32), WO99/37630 (Patent Document 33), Japanese Patent Application Publication 2003-519141 (Patent Document 34), Japanese Patent Application Publication2000-204084 (Patent Document 35), Japanese Patent Application Publication 11-322729 (Patent Document 36), Japanese Patent Application Publication 11-158164 (Patent Document 37), WO2004/101552 (Patent Document 38), WO2004/026848 (Patent Document 39), WO2003/11859 (Patent Document 40), WO2004/002967 (Patent Document 41).

Particularly, (S)-N-[[3-[3-fluoro-4-(4-morpholinyl)phenyl]-2-oxo-5-oxazolidinyl]methyl]acetamide ("linezolid"), as disclosed in WO95/07271 (Patent Document 11), has a potent antimicrobial activity against methicillin-resistant *Staphylococcus aureus* (MRSA) and vancomycin-resistant *Enterococci* (VRE) and it has been approved and marketed as a VRE anti-infectious drug.

Triazacycloheptane derivative was also known but its antimicrobial activity and use as an intermediate were not disclosed (Patent Document 42, Patent Document 43, Patent Document 44, Patent Document 46, Non-patent Document 1).

Also, the applicant has filed a patent application for oxazolidinone derivatives having 7-membered hetero ring as an antimicrobial agent (Patent Document 45).

[Patent Document 1] U.S. Pat. No. 6,255,304
[Patent Document 2] U.S. Pat. No. 6,218,413
[Patent Document 3] U.S. Pat. No. 6,362,189
[Patent Document 4] U.S. Pat. No. 6,342,513
[Patent Document 5] U.S. Pat. No. 6,537,986
[Patent Document 6] WO2000/032599
[Patent Document 7] WO99/24428
[Patent Document 8] WO97/10223
[Patent Document 9] WO97/09328
[Patent Document 10] U.S. Pat. No. 5,523,403
[Patent Document 11] WO95/07271
[Patent Document 12] WO2004/014392
[Patent Document 13] U.S. Pat. No. 6,956,040
[Patent Document 14] U.S. Pat. No. 6,734,307
[Patent Document 15] WO2002/006278
[Patent Document 16] WO2003/008389
[Patent Document 17] WO2003/007870
[Patent Document 18] WO2005/058888
[Patent Document 19] WO2004/096221
[Patent Document 20] EP Patent No. Publication EP697412A
[Patent Document 21] WO2000/027830
[Patent Document 22] Japanese Patent Publication 11-322729
[Patent Document 23] Japanese Patent Publication 9-221476
[Patent Document 24] WO95/34540
[Patent Document 25] WO2003/002560
[Patent Document 26] WO99/64417
[Patent Document 27] EP Patent No. 657440B
[Patent Document 28] WO2005/019213
[Patent Document 29] Japanese Patent Publication 2005-524660
[Patent Document 30] U.S. Pat. No. 6,239,152
[Patent Document 31] US Application Publication 2005/4174A1
[Patent Document 32] Japanese Patent Publication 2003-513885
[Patent Document 33] WO99/37630
[Patent Document 34] Japanese Patent Publication 2003-519141
[Patent Document 35] Japanese Patent Publication 2000-204084
[Patent Document 36] Japanese Patent Publication 11-322729
[Patent Document 37] Japanese Patent Publication 11-158164
[Patent Document 38] WO2004/101552
[Patent Document 39] WO2004/026848
[Patent Document 40] WO2003/11859
[Patent Document 41] WO2004/002967
[Patent Document 42] UK Patent No. 1543081
[Patent Document 43] EP Patent No. 358749
[Patent Document 44] U.S. Pat. No. 4,801,706
[Patent Document 45] International Application PCT/JP2007/057060 (WO2007/114326)
[Patent Document 46] Japanese Patent Publication 2-503321
[Non-patent Document 1] Dissertationes Pharmaceuticae et Pharmacologicae (1972), 24 (4), 385-390

DISCLOSURE OF THE INVENTION

Problems to be Resolved by the Invention

There is still need for developments in antimicrobial agent that has strong antimicrobial activity against wide range of microorganisms. Additionally, there is need for a novel antimicrobial agent which is effective against resistant strains to currently used antimicrobials. The invention provides a novel oxazolidinone derivative and pharmaceutically acceptable salts thereof useful as an timicrobial agent, and an timicrobial drug comprising the same as an active ingredient. More preferably, the invention provides a compound having good solubility and pharmacokinetics, etc. Still more preferably, the invention provides a compound with reduced side effect, compared with conventional antimicrobial agents.

Also, the invention provides synthetic intermediates of such compound.

Means of Solving the Problems

The invention has been accomplished on the basis of the inventors' discovery of novel oxazolidinone derivatives that have an timicrobial activity.

(1) A compound of the formula:

[Chemical Formula 1]

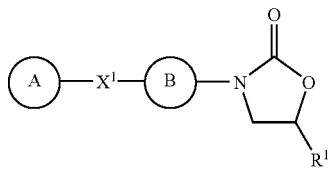

(I)

or a pharmaceutically acceptable salt or solvate thereof wherein

Ring A is (A-1) a 7-membered monocyclic heterocycle containing three N atoms;

(A-2) a 7-membered monocyclic heterocycle containing two N atoms and one O atom; or (A-3) a 7-membered monocyclic heterocycle containing two N atoms and one S atom, SO or $SO_2$, wherein said monocyclic heterocycle is optionally substituted, optionally unsaturated and optionally fused with another ring;

$X^1$ is a single bond, or a heteroatom-containing group selected from the group consisting of —O—, —S—, —CO—, —CS—, —CONR$^3$—, —NR$^4$CO—, —SO$_2$NR$^5$—, and —NR$^6$SO$_2$—, wherein $R^2$, $R^3$, $R^4$, $R^5$ and $R^6$ are independently hydrogen or lower alkyl, or lower alkylene or lower alkenylene each optionally interrupted by said heteroatom-containing group;

Ring B is optionally substituted carbocycle or optionally substituted heterocycle; and $R^1$ is hydrogen, or an organic residue which is able to bind to the 5-position of the oxazolidinone ring in oxazolidinone antimicrobial agents, with the proviso that the compound is not the compound as specifically described in the Examples of the specification as originally filed in the International Patent Application PCT/JP2007/057060.

(2) The compound according to (1) represented by the formula:

[Chemical Formula 2]

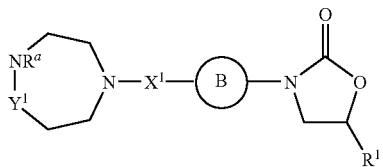

(I-1)

or a pharmaceutically acceptable salt or solvate thereof wherein $Y^1$ is $NR^b$, O, S, SO or $SO_2$;

$R^a$ and $R^b$ are independently hydrogen, a substituent selected from Substituent Group Si, or $R^a$ and $R^b$ may be taken together with N atom to which they are attached to form optionally substituted heterocycle;

Substituent Group S1 consists of optionally substituted lower alkyl, optionally substituted lower alkenyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted (lower alkyl)oxythiocarbonyl, optionally substituted arylcarbonyl, optionally substituted aryloxycarbonyl, optionally substituted heterocyclecarbonyl, optionally substituted heterocycleoxycarbonyl, optionally substituted carbamoyl, optionally substituted carbamoylcarbonyl, optionally substituted thiocarbamoyl, optionally substituted (lower alkyl)thiocarbonyl, optionally substituted cycloalkylthiocarbonyl, optionally substituted arylthiocarbonyl, optionally substituted heterocyclethiocarbonyl, optionally substituted (lower alkyl)sulfonyl, optionally substituted phenylsulfonyl, optionally substituted aromatic heterocyclesulfonyl, optionally substituted aminosulfonyl, optionally substituted aryl, optionally substituted heterocyclic group, cyano, optionally substituted thioformyl, optionally substituted (lower alkenyl)carbonyl, and optionally substituted heterocycleoxycarbonyl;

$X^1$ is a single bond, or a heteroatom-containing group selected from the group consisting of —O—, —S—, —NR$^2$—, —CO—, —CS—, —CONR$^3$—, —NR$^4$CO—, —SO$_2$NR$^5$—, and —NR$^6$SO$_2$—, wherein $R^2$, $R^3$, $R^4$, $R^5$ and $R^6$ are independently hydrogen or lower alkyl, or lower alkylene or lower alkenylene each optionally interrupted by said heteroatom-containing group;

Ring B is optionally substituted carbocycle or optionally substituted heterocycle; and $R^1$ is hydrogen, or an organic residue which is able to bind to the 5-position of the oxazolidinone ring in oxazolidinone antimicrobial agents, with the proviso that the compound is not the compound as specifically described in the Examples of the specification as originally filed in the International Patent Application PCT/JP2007/057060.

In one embodiment, Substituent Group S1 in the above (2) is Substituent Group S1-1, which consists of optionally substituted lower alkyl, optionally substituted cycloalkyl, optionally substituted formyl, optionally substituted (lower alkyl) carbonyl, optionally substituted cycloalkylcarbonyl, optionally substituted (lower alkyl)oxycarbonyl, optionally substituted arylcarbonyl, optionally substituted heterocyclecarbonyl, optionally substituted carbamoyl, optionally substituted (lower alkyl)thiocarbonyl, optionally substituted cycloalkylthiocarbonyl, optionally substituted arylthiocarbonyl, optionally substituted (lower alkyl) sulfonyl, optionally substituted phenylsulfonyl, optionally substituted aromatic heterocyclesulfonyl, optionally substituted aminosulfonyl, optionally substituted aryl, optionally substituted heterocyclic group, cyano, optionally substituted thioformyl, optionally substituted (lower alkenyl)carbonyl, and optionally substituted heterocycleoxycarbonyl.

In one embodiment, Substituent Group S1 in the above (2) is Substituent Group S1-2, which consists of optionally substituted lower alkenyl, optionally substituted (lower alkyl)

oxythiocarbonyl, optionally substituted aryloxycarbonyl, optionally substituted heterocycleoxycarbonyl, optionally substituted carbamoylcarbonyl, optionally substituted thiocarbamoyl, and optionally substituted heterocyclethiocarbonyl.

(3) A compound according to (2) represented by the formula:

[Chemical Formula 3]

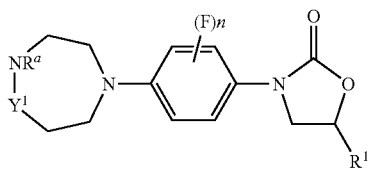

(I-2)

or a pharmaceutically acceptable salt or solvate thereof wherein
$Y^1$ is $NR^b$ or O; n is an integer from 1 to 4; $R^a$, $R^b$ and $R^1$ are as defined above in (2),
with the proviso that the compound is not the compound as specifically described in the Examples of the specification as originally filed in the International Patent Application PCT/JP2007/057060.

In one preferred embodiment of the compounds in (1) to (3), $R^1$ is —CH$_2$NHCSOCH$_3$.

In another preferred embodiment of the compound in (1) to (3), $R^1$ is —CH$_2$NHCSCH$_3$, —CH$_2$NHCSCH$_2$CH$_3$, —CH$_2$NHCSCHF$_2$, —CH$_2$NHCSNHCH$_3$, —CH$_2$NHCSNHCH$_2$CH$_3$, or —CH$_2$NHCSSCH$_3$.

In further preferred embodiment of the compound in (1) to (3), $R^1$ is —CH$_2$-heterocycle or —CH$_2$NH-heterocycle wherein said heterocycle is preferably 5- to 7-membered and optionally substituted with lower alkyl.

(4) The compound according to any one of (1) to (3) or a pharmaceutically acceptable salt or solvate thereof wherein $R^1$ is optionally substituted aminomethylene, optionally substituted hydroxymethylene, optionally substituted thiolmethylene, or optionally substituted heterocyclemethylene.

(5) The compound according to any one of (1) to (3) or a pharmaceutically acceptable salt or solvate thereof wherein $R^1$ is —CH$_2$NHCOR$^7$ wherein $R^7$ is hydrogen, optionally substituted lower alkyl, optionally substituted (lower alkyl)oxy, cycloalkyl, optionally substituted heterocyclic group, amino, (lower alkyl)amino or optionally substituted phenyl; —CH$_2$NHCSR$^8$ wherein $R^8$ is hydrogen, optionally substituted lower alkyl, optionally substituted (lower alkyl)oxy, optionally substituted (lower alkyl)thio, cycloalkyl, optionally substituted heterocyclic group, amino, (lower alkyl)amino or optionally substituted phenyl; —CH$_2$NHR$^9$ wherein $R^9$ is hydrogen or heterocyclic group; —CH$_2$R$^{10}$ wherein $R^{10}$ is heterocyclic group; —CH$_2$OR$^{11}$ wherein $R^{11}$ is hydrogen, (lower alkyl)carbonyl or heterocyclic group; —CH$_2$SR$^{12}$ wherein $R^{12}$ is hydrogen or heterocyclic group or —CH$_2$SCN.

(6) The compound according to (1) which is an oxazolidinone derivative described in any one of Examples A1 to A97, or a pharmaceutically acceptable salt or solvate thereof.

(7) The compound according to (1) which is an oxazolidinone derivative described in any one of Examples B1 to B53, or a pharmaceutically acceptable salt or solvate thereof.

(8) The compound according to (1) represented by the formula:

[Chemical Formula 4]

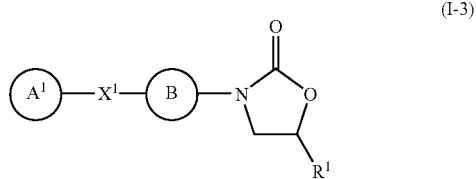

(I-3)

or a pharmaceutically acceptable salt or solvate thereof wherein
Ring $A^1$ is
(A-1) a 7-membered monocyclic heterocycle containing three N atoms and one double bond;
(A-2) a 7-membered monocyclic heterocycle containing two N atoms, one O atom and one double bond; or
(A-3) a 7-membered monocyclic heterocycle containing two N atoms, one S atom, SO or SO$_2$ and one double bond, wherein said monocyclic heterocycle is optionally substituted and optionally fused with another ring;
$X^1$ is a single bond, or a heteroatom-containing group selected from the group consisting of —O—, —S—, —NR$^2$—, —CO—, —CS—, —CONR$^3$—, —NR$^4$CO—, —SO$_2$NR$^5$—, and —NR$^6$SO$_2$—, wherein $R^2$, $R^3$, $R^4$, $R^5$ and $R^6$ are independently hydrogen or lower alkyl, or lower alkylene or lower alkenylene each optionally interrupted by said heteroatom-containing group;
Ring B is optionally substituted carbocycle or optionally substituted heterocycle; and
$R^1$ is hydrogen, or an organic residue which is able to bind to the 5-position of the oxazolidinone ring in oxazolidinone antimicrobial agents.

(9) The compound according to (8) or a pharmaceutically acceptable salt or solvate thereof wherein ring $A^1$ is (A-1) a 7-membered monocyclic heterocycle containing three N atoms and one double bond.

(10) The compound according to (8) or a pharmaceutically acceptable salt or solvate thereof wherein ring $A^1$ is a 7-membered monocyclic heterocycle containing two N atoms, one group of the formula —NR$^a$— wherein $R^a$ is as defined above in (2), and one double bond.

(11) The compound according to (8) or a pharmaceutically acceptable salt or solvate thereof wherein ring $A^1$ is (A-2) a 7-membered monocyclic heterocycle containing two N atoms, one O atom and one double bond.

(12) The compound according to (8) or a pharmaceutically acceptable salt or solvate thereof wherein ring $A^1$ is (A-3) a 7-membered monocyclic heterocycle containing two N atoms, one S atom, SO or SO$_2$ and one double bond.

(13) The compound according to (8) represented by the formula:

[Chemical Formula 5]

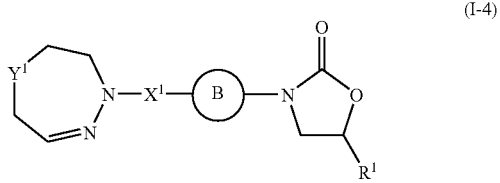

(I-4)

or a pharmaceutically acceptable salt or solvate thereof wherein

Y$^1$ is NR$^a$, O, S, SO or SO$_2$;

R$^a$ is hydrogen, or a substituent selected from Substituent Group S1 as defined above in (2), which preferably consists of optionally substituted lower alkyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted arylcarbonyl, optionally substituted heterocyclecarbonyl, optionally substituted carbamoyl, optionally substituted (lower alkyl)thiocarbonyl, optionally substituted cycloalkylthiocarbonyl, optionally substituted arylthiocarbonyl, optionally substituted (lower alkyl)sulfonyl, optionally substituted phenylsulfonyl, optionally substituted aromatic heterocyclesulfonyl, optionally substituted aminosulfonyl, optionally substituted aryl, optionally substituted heterocyclic group, cyano, optionally substituted thioformyl, optionally substituted (lower alkenyl)carbonyl, and optionally substituted heterocycleoxycarbonyl;

X$^1$ is a single bond, or a heteroatom-containing group selected from the group consisting of —O—, —S—, —NR$^2$—, —CO—, —CS—, —CONR$^3$—, —NR$^4$CO—, —SO$_2$NR$^5$—, and —NR$^6$SO$_2$—, wherein R$^2$, R$^3$, R$^4$, R$^5$ and R$^6$ are independently hydrogen or lower alkyl, or lower alkylene or lower alkenylene each optionally interrupted by said heteroatom-containing group;

Ring B is optionally substituted carbocycle or optionally substituted heterocycle; and R$^1$ is hydrogen, or an organic residue which is able to bind to the 5-position of the oxazolidinone ring in oxazolidinone antimicrobial agents.

(14) The compound according to (13) or a pharmaceutically acceptable salt or solvate thereof wherein Y$^1$ is NR$^a$ and R$^a$ is as defined in (13).

(15) The compound according to (13) or a pharmaceutically acceptable salt or solvate thereof wherein Y$^1$ is NR$^a$ and R$^a$ is optionally substituted lower alkyl, optionally substituted formyl, optionally substituted (lower alkyl) carbonyl, optionally substituted heterocyclecarbonyl, optionally substituted carbamoyl, optionally substituted (lower alkyl) thiocarbonyl, optionally substituted aryl, optionally substituted heterocyclic group, cyano, thioformyl, optionally substituted (lower alkenyl)carbonyl or optionally substituted heterocycleoxycarbonyl.

(16) The compound according to (13) or a pharmaceutically acceptable salt or solvate thereof wherein Y$^1$ is NR$^a$; and R$^a$ is any one of the following groups:

[Chemical Formula 6]

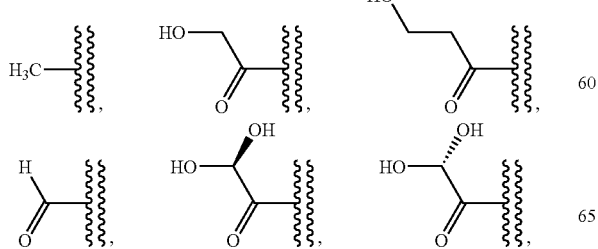

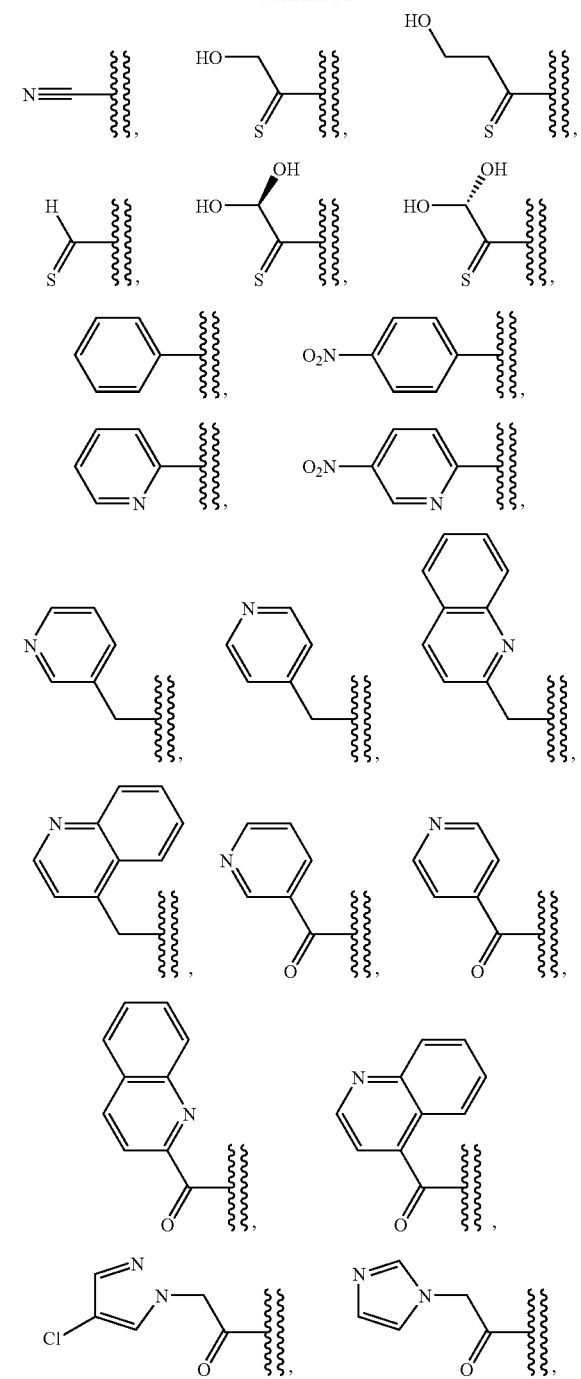

-continued

-continued

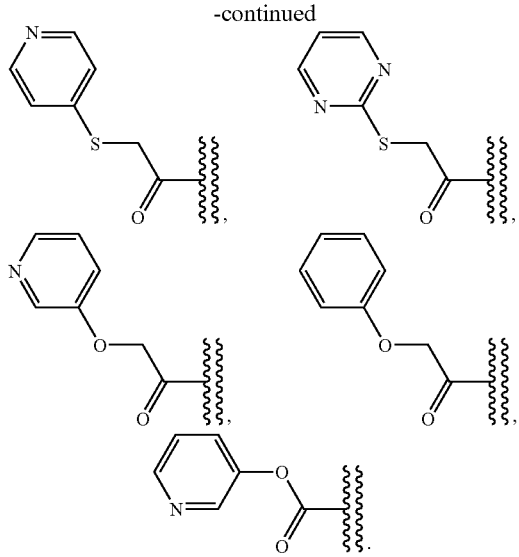

(17) The compound according to (13) or a pharmaceutically acceptable salt or solvate thereof wherein $X^1$ is a single bond.
(18) The compound according to (13) or a pharmaceutically acceptable salt or solvate thereof wherein ring B is optionally substituted benzene ring or optionally substituted 5- to 7-membered aromatic heterocycle.
(19) The compound according to (13) or a pharmaceutically acceptable salt or solvate thereof wherein ring B is optionally substituted benzene ring.
(20) The compound according to (13) or a pharmaceutically acceptable salt or solvate thereof wherein ring B is benzene ring optionally substituted with one or two halogen atom(s).
(21) The compound according to (13) or a pharmaceutically acceptable salt or solvate thereof wherein ring B is any one of the following groups:

[Chemical Formula 7]

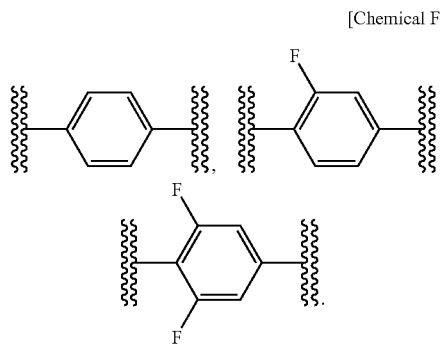

(22) The compound according to (13) or a pharmaceutically acceptable salt or solvate thereof wherein $R^1$ is optionally substituted aminomethylene, optionally substituted hydroxymethylene, optionally substituted thiolmethylene, or optionally substituted heterocyclemethylene.
(23) The compound according to (13) or a pharmaceutically acceptable salt or solvate thereof wherein $R^1$ is optionally substituted aminomethylene or optionally substituted heterocyclemethylene.
(24) The compound according to (13) or a pharmaceutically acceptable salt or solvate thereof wherein $R^1$ is a substituted aminomethylene or a non-substituted heterocyclemethylene.
(25) The compound according to (13) or a pharmaceutically acceptable salt or solvate thereof wherein $R^1$ is —$CH_2NHCOR^7$ wherein $R^7$ is optionally substituted lower alkyl, optionally substituted (lower alkyl)oxy, cycloalkyl, optionally substituted heterocyclic group, (lower alkyl)amino or optionally substituted phenyl; —$CH_2NHCSR^8$ wherein $R^8$ is optionally substituted lower alkyl, optionally substituted (lower alkyl)oxy, optionally substituted (lower alkyl)thio, cycloalkyl, optionally substituted heterocyclic group, (lower alkyl)amino or optionally substituted phenyl; —$CH_2NHR^9$ wherein $R^9$ is heterocyclic group or —$CH_2R^{10}$ wherein $R^{10}$ is heterocyclic group.
(26) The compound according to (13) or a pharmaceutically acceptable salt or solvate thereof wherein $R^1$ is —$CH_2NHCOR^7$ wherein $R^7$ is methyl; —$CH_2NHCSR^8$ wherein $R^8$ is methyl, ethyl, difluoromethyl, methoxy or methylthio; —$CH_2NHR^9$ wherein $R^9$ is isoxazolyl or —$CH_2R^{10}$ wherein $R^{10}$ is 1,2,3-triazolyl.
(27) The compound according to (13) or a pharmaceutically acceptable salt or solvate thereof wherein $Y^1$ is $NR^a$ and $R^a$ is any one of the following groups:

[Chemical Formula 8]

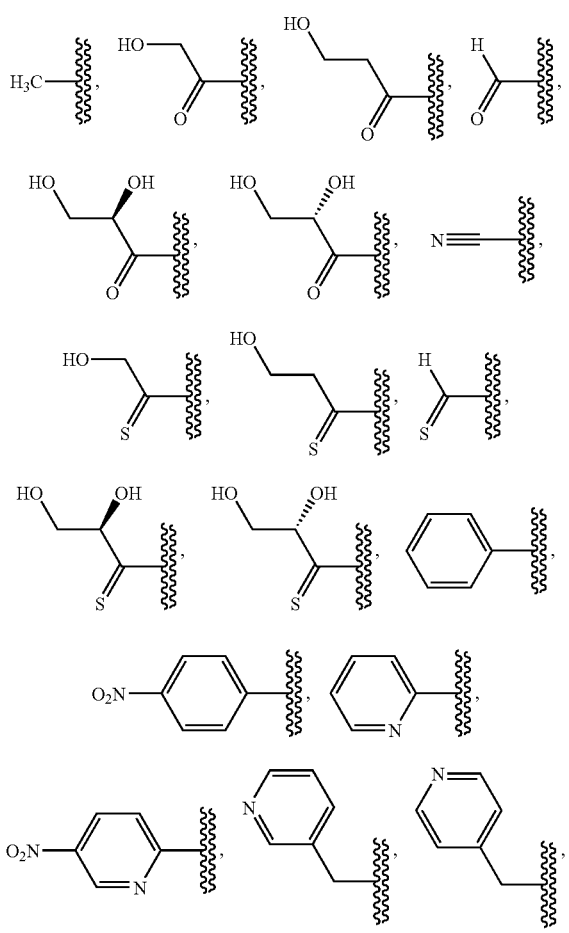

-continued
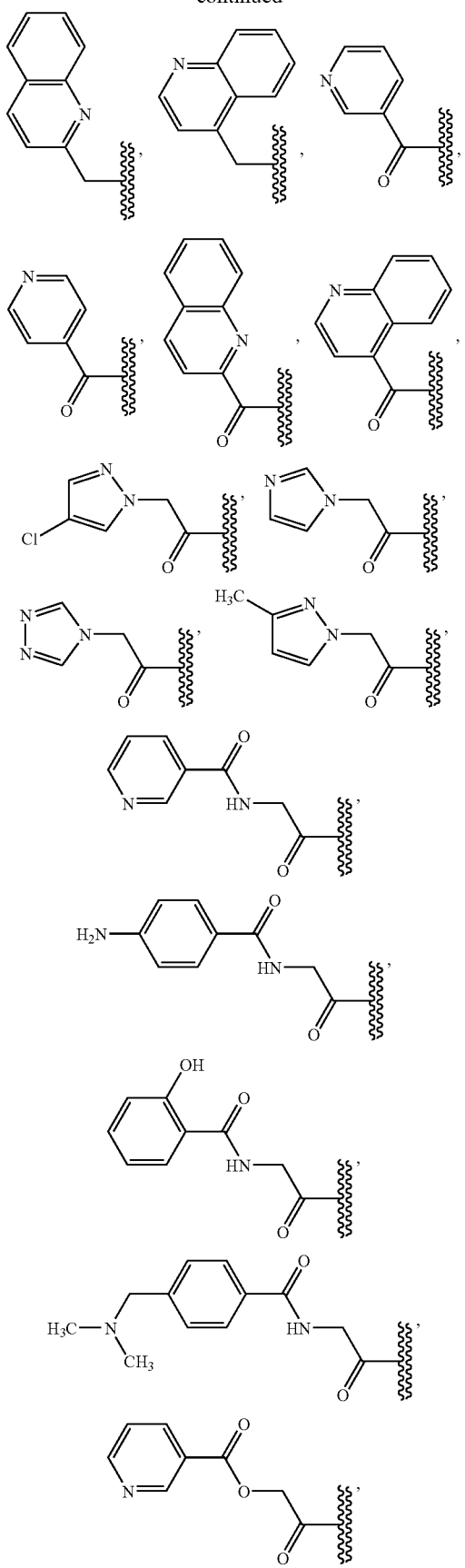
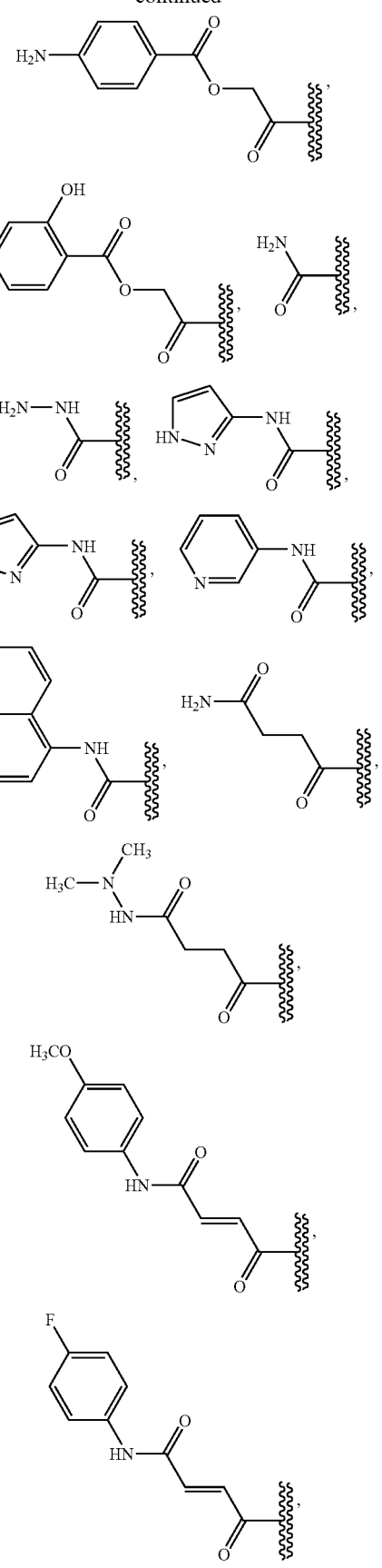

-continued

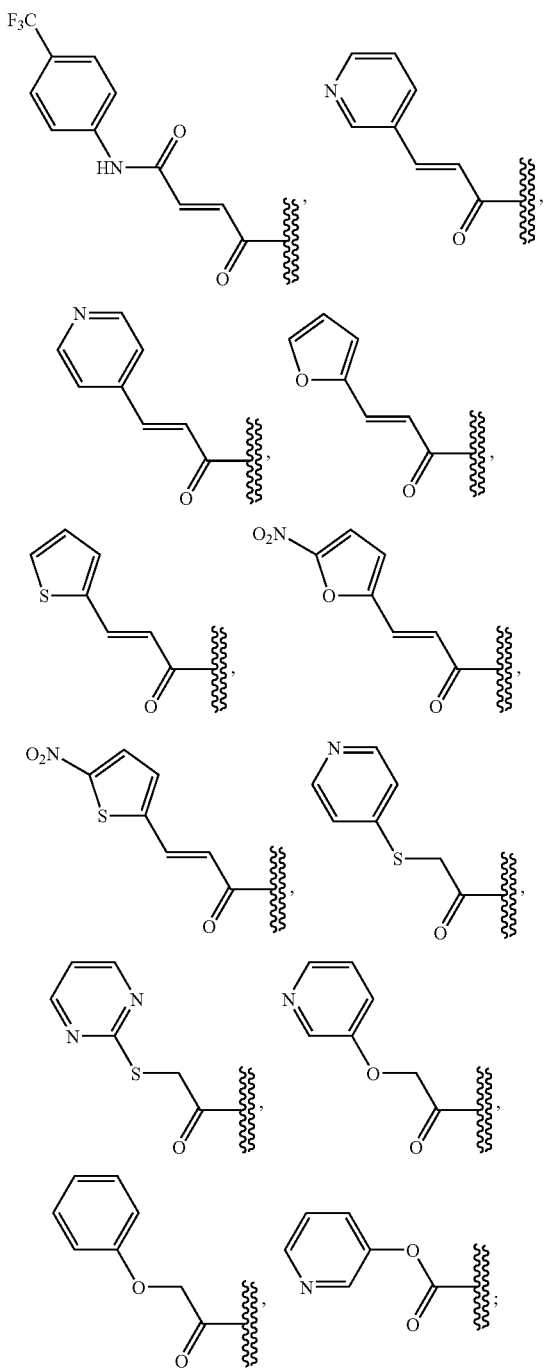

$X^1$ is a single bond;
Ring B is any one of the following groups:

[Chemical Formula 9]

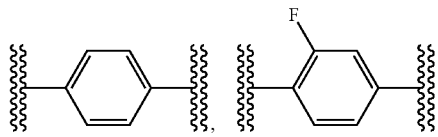

-continued and
R$^1$ is —CH$_2$NHCOR$^7$ wherein R$^7$ is methyl; —CH$_2$NHCSR$^8$ wherein R$^8$ is methyl, ethyl, difluoromethyl, methoxy or methylthio; —CH$_2$NHR$^9$ wherein R$^9$ is isoxazolyl or —CH$_2$R$^{10}$ wherein R$^{10}$ is 1,2,3-triazolyl.

(28) A compound of the formula:

[Chemical Formula 10]

(I-5)

$$Y^1 \overset{\displaystyle \diagup\!\!\!\diagdown}{\underset{\displaystyle \diagdown\!\!\!\!=\!\!\!\!\diagup}{N}}\!\!-\!X^1\!-\!B$$

or a pharmaceutically acceptable salt or solvate thereof wherein
Y$^1$ is NR$^a$, O, S, SO or SO$_2$;
R$^a$ is hydrogen, or a substituent selected from Substituent Group S1 or an amino protecting group;
Substituent Group S1 is as defined above in (2), which preferably consists of optionally substituted lower alkyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted arylcarbonyl, optionally substituted heterocyclecarbonyl, optionally substituted carbamoyl, optionally substituted (lower alkyl)thiocarbonyl, optionally substituted cycloalkylthiocarbonyl, optionally substituted arylthiocarbonyl, optionally substituted (lower alkyl)sulfonyl, optionally substituted phenylsulfonyl, optionally substituted aromatic heterocyclesulfonyl, optionally substituted aminosulfonyl, optionally substituted aryl, optionally substituted heterocyclic group, cyano, optionally substituted thioformyl, optionally substituted (lower alkenyl)carbonyl, and optionally substituted heterocycleoxycarbonyl;
X$^1$ is a single bond, or a heteroatom-containing group selected from the group consisting of —O—, —S—, —NR$^2$—, —CO—, —CS—, —CONR$^3$—, —NR$^4$CO—, —SO$_2$NR$^5$—, and —NR$^6$SO$_2$—, wherein R$^2$, R$^3$, R$^4$, R$^5$ and R$^6$ are independently hydrogen or lower alkyl, or lower alkylene or lower alkenylene each optionally interrupted by said heteroatom-containing group;
Ring B is optionally substituted carbocycle or optionally substituted heterocycle.
(29) The compound according to (28) or a pharmaceutically acceptable salt or solvate thereof wherein X$^1$ is a single bond and ring B is optionally substituted carbocycle.
(30) The compound according to (28) or a pharmaceutically acceptable salt or solvate thereof wherein X$^1$ is a single bond and ring B is optionally substituted heterocycle.
(31) The compound according to (28) or a pharmaceutically acceptable salt or solvate thereof wherein X$^1$ is a single bond and ring B is benzene ring substituted with nitro or optionally with another substituent.

(32) The compound according to (28) or a pharmaceutically acceptable salt or solvate thereof wherein $Y^1$ is $NR^a$.

(33) The compound according to (28) or a pharmaceutically acceptable salt or solvate thereof wherein $Y^1$ is $NR^a$ and $R^a$ is hydrogen.

(34) The compound according to (28) or a pharmaceutically acceptable salt or solvate thereof wherein $Y^1$ is $NR^a$ and $R^a$ is an amino protecting group.

(35) The compound according to (28) or a pharmaceutically acceptable salt or solvate thereof wherein $Y^1$ is $NR^a$ and $R^a$ is optionally substituted lower alkyl.

(36) A compound of the formula:

[Chemical Formula 11]

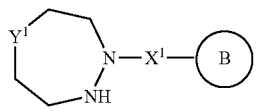

(I-6)

or a pharmaceutically acceptable salt or solvate thereof wherein $Y^1$ is $NR^a$, O, S, SO or $SO_2$;

$R^a$ is hydrogen, a substituent selected from Substituent Group S1 or an amino protecting group;

$X^1$ is a single bond, or a heteroatom-containing group selected from the group consisting of —O—, —S—, —$NR^2$—, —CO—, —CS—, —$CONR^3$—, —$NR^4CO$—, —$SO_2NR^5$—, and —$NR^6SO_2$—, wherein $R^2$, $R^3$, $R^4$, $R^5$ and $R^6$ are independently hydrogen or lower alkyl, or lower alkylene or lower alkenylene each optionally interrupted by said heteroatom-containing group;

Ring B is optionally substituted carbocycle or optionally substituted heterocycle.

(37) The compound according to (36) or a pharmaceutically acceptable salt or solvate thereof wherein $X^1$ is a single bond and ring B is optionally substituted carbocycle.

(38) The compound according to (36) or a pharmaceutically acceptable salt or solvate thereof wherein $X^1$ is a single bond and ring B is optionally substituted heterocycle.

(39) The compound according to (36) or a pharmaceutically acceptable salt or solvate thereof wherein $X^1$ is a single bond and ring B is benzene ring substituted with nitro or optionally with another substituent.

(40) The compound according to (36) or a pharmaceutically acceptable salt or solvate thereof wherein $Y^1$ is $NR^a$.

(41) The compound according to (36) or a pharmaceutically acceptable salt or solvate thereof wherein $Y^1$ is $NR^a$ and $R^a$ is hydrogen.

(42) The compound according to (36) or a pharmaceutically acceptable salt or solvate thereof wherein $Y^1$ is $NR^a$ and $R^a$ is an amino protecting group.

(43) The compound according to (36) or a pharmaceutically acceptable salt or solvate thereof wherein $Y^1$ is $NR^a$ and $R^a$ is optionally substituted lower alkyl.

(44) A compound of the formula:

[Chemical Formula 12]

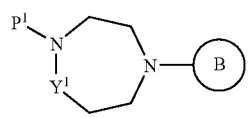

(I-7)

or a pharmaceutically acceptable salt or solvate thereof wherein $Y^1$ is $NP^2$ or O;

$P^1$ and $P^2$ are independently hydrogen, a substituent selected from Substituent Group S1 or an amino protecting group;

Substituent Group S1 is as defined above in (2), which preferably consists of optionally substituted lower alkyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted arylcarbonyl, optionally substituted heterocyclecarbonyl, optionally substituted carbamoyl, (lower alkyl)thio, cycloalkylthio, arylthio, optionally substituted (lower alkyl)sulfonyl, optionally substituted phenylsulfonyl, optionally substituted aromatic heterocycle (lower)alkyl, optionally substituted aryl, optionally substituted heterocyclic group;

Ring B is optionally substituted and optionally fused benzene ring or optionally substituted heterocycle;

with the proviso that the compound is not the following compounds:

[Chemical Formula 13]

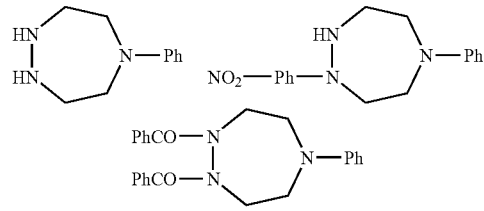

wherein Ph is phenyl.

(45) The compound according to (44) or a pharmaceutically acceptable salt or solvate thereof wherein ring B is substituted with one or more substituent selected from the group consisting of halogen, nitro, amino, amino protected with an amino protecting group, optionally substituted amide, formyl, carboxyl. carboxamide, optionally substituted alkyl, lower alkoxy, and hydroxyimino.

(46) The compound according to (44) of the formula:

[Chemical Formula 14]

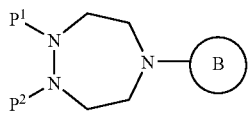

(I-8)

or a pharmaceutically acceptable salt or solvate thereof wherein $P^1$ and $P^2$ are independently hydrogen, a substituent selected from Substituent Group S1 or an amino protecting group;

Substituent Group S1 is as defined above in (2), which preferably consists of optionally substituted lower alkyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted arylcarbonyl, optionally substituted heterocyclecarbonyl, optionally substituted carbamoyl, (lower alkyl)thio, cycloalkylthio, arylthio, optionally substituted (lower alkyl)sulfonyl, optionally substituted phenylsulfonyl, optionally substituted aromatic heterocycle (lower)alkyl, optionally substituted aryl, optionally substituted heterocyclic group;

Ring B is optionally substituted benzene ring or optionally substituted 5- to 7-membered heterocycle.

(47) The compound according to (46) or a pharmaceutically acceptable salt or solvate thereof wherein ring B is benzene ring, pyridine ring, or thiophene ring, each optionally substituted with halogen, nitro, formyl or carboxyl.

(48) The compound according to (46) or a pharmaceutically acceptable salt or solvate thereof wherein $P^1$ and $P^2$ are independently an amino protecting group.

(49) The compound according to (46) or a pharmaceutically acceptable salt or solvate thereof wherein $P^1$ and $P^2$ are independently tert-butoxycarbonyl or benzyloxycarbonyl.

(50) The compound according to (46) or a pharmaceutically acceptable salt or solvate thereof wherein the compound is selected from the following compounds:

[Chemical Formula 15]

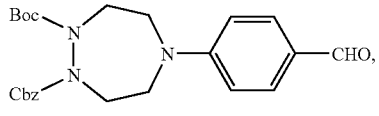
T-14

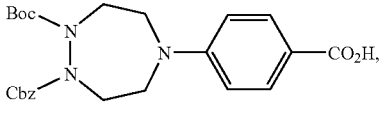
T-15

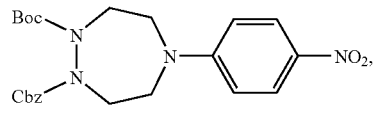
T-16

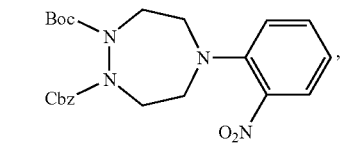
T-17

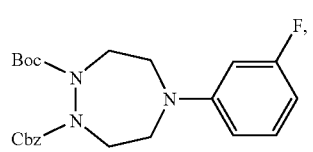
T-18

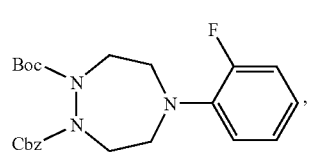
T-19

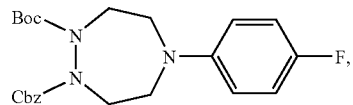
T-20

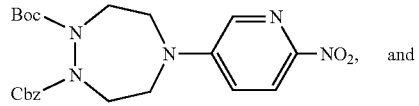
T-21
and

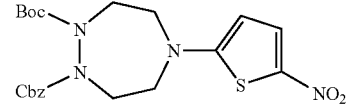
T-22 wherein Boc is tert-butoxycarbonyl and Cbz is benzyloxycarbonyl.

(51) The compound according to (44) of the formula:

[Chemical Formula 16]

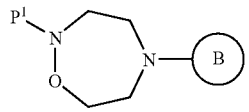
(I-9)

or a pharmaceutically acceptable salt or solvate thereof wherein $P^1$ is hydrogen, a substituent selected from Substituent Group S1 or an amino protecting group;

Substituent Group S1 is as defined above in (2), which preferably consists of optionally substituted lower alkyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted arylcarbonyl, optionally substituted heterocyclecarbonyl, optionally substituted carbamoyl, (lower alkyl)thio, cycloalkylthio, arylthio, optionally substituted (lower alkyl)sulfonyl, optionally substituted phenylsulfonyl, optionally substituted aromatic heterocycle (lower)alkyl, optionally substituted aryl, optionally substituted heterocyclic group;

Ring B is optionally substituted and optionally fused benzene ring or optionally substituted heterocycle.

(52) The compound according to (51) or a pharmaceutically acceptable salt or solvate thereof wherein ring B is benzene ring, pyridine ring, or thiophene ring, each optionally substituted with halogen, nitro, formyl or carboxyl.

(53) The compound according to (51) or a pharmaceutically acceptable salt or solvate thereof wherein $P^1$ is an amino protecting group.

(54) The compound according to (51) or a pharmaceutically acceptable salt or solvate thereof wherein $P^1$ is tert-butoxycarbonyl or benzyloxycarbonyl.

(55) The compound according to (51) or a pharmaceutically acceptable salt or solvate thereof wherein the compound is selected from the following compounds:

[Chemical Formula 17]

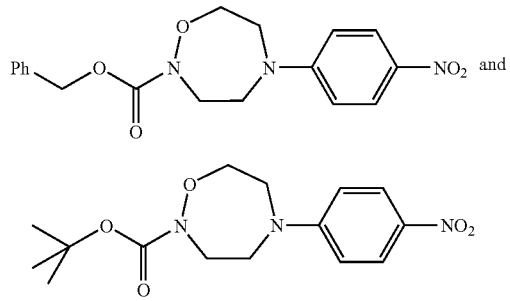

wherein Ph is phenyl.

(56) A compound of the formula:

[Chemical Formula 18]

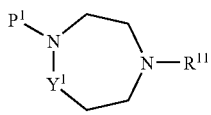

or a pharmaceutically acceptable salt or solvate thereof wherein $Y^1$ is $NP^2$ or O;

$P^1$ and $P^2$ are independently hydrogen, a substituent selected from Substituent Group S1 or an amino protecting group;

$R^{11}$ is hydrogen, a substituent selected from Substituent Group S1 or an amino protecting group, with the proviso that $R^{11}$ is not —CO(CH$_2$)$_3$—CO$_2$H, -Ph, —CH$_2$Ph, and —(CH$_2$)$_3$CH(4—F-Ph)$_2$ wherein Ph is phenyl;

Substituent Group S1 is as defined above in (2), which preferably consists of optionally substituted lower alkyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted arylcarbonyl, optionally substituted heterocyclecarbonyl, optionally substituted carbamoyl, (lower alkyl)thio, cycloalkylthio, arylthio, optionally substituted (lower alkyl)sulfonyl, optionally substituted phenylsulfonyl, optionally substituted aromatic heterocycle (lower)alkyl, optionally substituted aryl, optionally substituted heterocyclic group;

with the proviso that the compound is not the following compound:

[Chemical Formula 19]

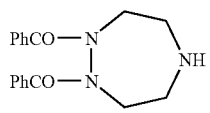

wherein Ph is phenyl.

(57) The compound according to (56) of the formula:

[Chemical Formula 20]

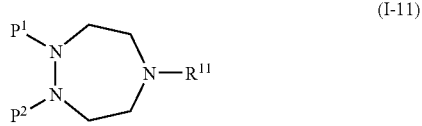

or a pharmaceutically acceptable salt or solvate thereof wherein $P^1$ and $P^2$ are independently hydrogen, a substituent selected from Substituent Group S1 or an amino protecting group;

$R^{11}$ is hydrogen, a substituent selected from Substituent Group S1 or an amino protecting group, with the proviso that $R^{11}$ is not —CO(CH$_2$)$_3$—CO$_2$H, -Ph, —CH$_2$Ph, and —(CH$_2$)$_3$CH(4—F-Ph)$_2$ wherein Ph is phenyl;

Substituent Group S1 is as defined above in (2), which preferably consists of optionally substituted lower alkyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted arylcarbonyl, optionally substituted heterocyclecarbonyl, optionally substituted carbamoyl, (lower alkyl)thio, cycloalkylthio, arylthio, optionally substituted (lower alkyl)sulfonyl, optionally substituted phenylsulfonyl, optionally substituted aromatic heterocycle (lower)alkyl, optionally substituted aryl, optionally substituted heterocyclic group;

with the proviso that the compound is not the following compound:

[Chemical Formula 21]

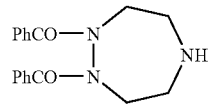

wherein Ph is phenyl.

(58) The compound according to (57) or a pharmaceutically acceptable salt or solvate thereof wherein only one of $P^1$, $P^2$ and $R^{11}$ is hydrogen.

(59) The compound according to (57) or a pharmaceutically acceptable salt or solvate thereof wherein only one of $P^1$ and $P^2$ is hydrogen and $R^{11}$ is not hydrogen.

(60) The compound according to (57) or a pharmaceutically acceptable salt or solvate thereof wherein $R^{11}$ is hydrogen and $P^1$ and $P^2$ are not hydrogen.

(61) The compound according to (57) or a pharmaceutically acceptable salt or solvate thereof wherein $P^1$, $P^2$ and $R^{11}$ are independently hydrogen, lower alkyl, (lower alkyl)carbonyl optionally substituted with halogen, lower alkyl substituted with hydroxy, an amino protecting group, optionally substituted phenyl, or optionally substituted heterocyclic group.

(62) The compound according to (57) or a pharmaceutically acceptable salt or solvate thereof wherein $P^1$, $P^2$ and $R^{11}$ are independently hydrogen, lower alkyl, (lower alkyl)carbonyl optionally substituted with halogen, lower alkyl substituted with hydroxy, tert-butoxycarbonyl, benzyloxycarbonyl, optionally substituted phenyl (substituent: nitro, carboxy, halogen, formyl or hydroxy) or optionally substituted heterocyclic group (substituent: nitro, carboxy, halogen, formyl or hydroxy).

(63) The compound according to (57) or a pharmaceutically acceptable salt or solvate thereof wherein P¹ is hydrogen; P² is an amino protecting group, R¹¹ is lower alkyl, (lower alkyl)carbonyl optionally substituted with halogen, lower alkyl substituted with hydroxy, an amino protecting group, optionally substituted phenyl or optionally substituted heterocyclic group.

(64) The compound according to (57) or a pharmaceutically acceptable salt or solvate thereof wherein P¹ is hydrogen; P² is an amino protecting group, and R¹¹ is an amino protecting group.

(65) The compound according to (57) or a pharmaceutically acceptable salt or solvate thereof wherein R¹¹ is hydrogen; P¹ and P² are independently lower alkyl, (lower alkyl)carbonyl optionally substituted with halogen, lower alkyl substituted with hydroxy, an amino protecting group, optionally substituted phenyl or optionally substituted heterocyclic group.

(66) The compound according to (57) or a pharmaceutically acceptable salt or solvate thereof wherein R¹¹ is hydrogen; P¹ and P² are independently an amino protecting group.

(67) The compound according to any one of (63) to (66) or a pharmaceutically acceptable salt or solvate thereof wherein the an amino protecting group is independently tert-butoxycarbonyl or benzyloxycarbonyl.

(68) The compound according to (57) or a pharmaceutically acceptable salt or solvate thereof wherein the compound is selected from the following compounds:

[Chemical Formula 22]

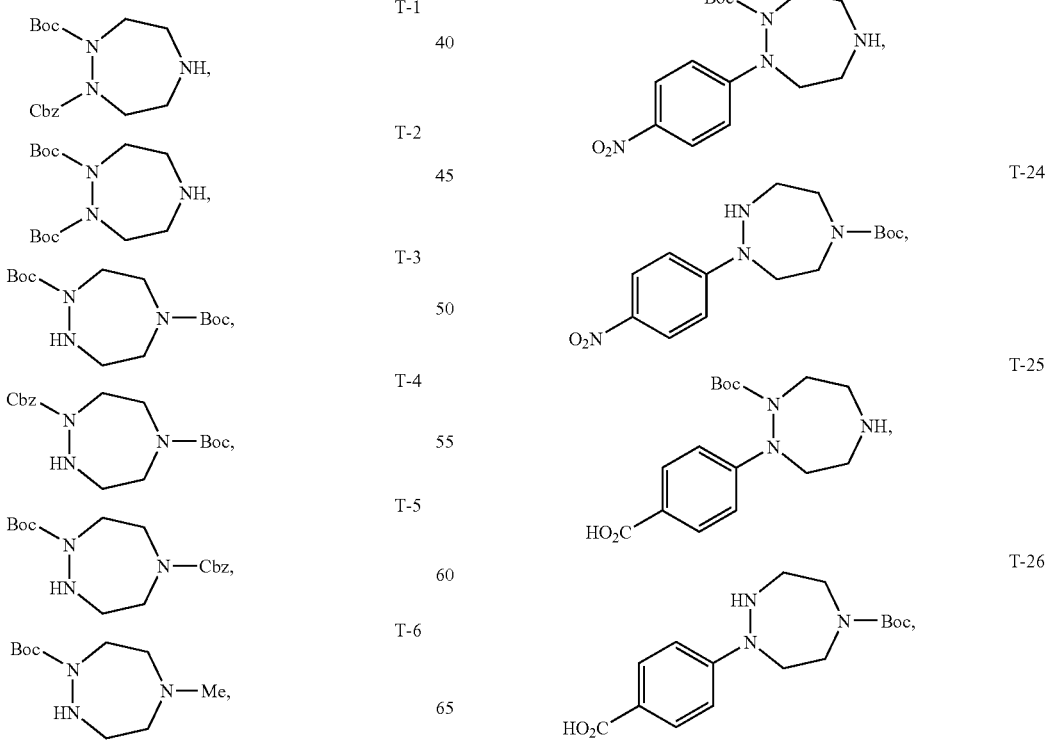

-continued

T-27 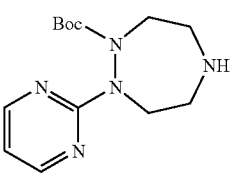

T-28 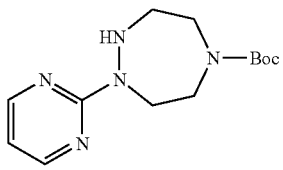

[Chemical Formula 23]

T-29 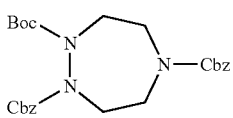

T-30 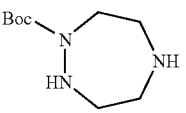

T-31 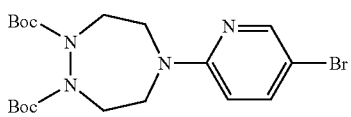

T-32 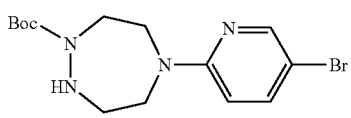

T-33 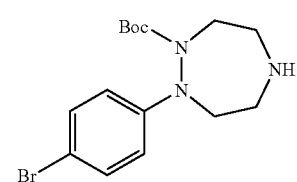

T-34 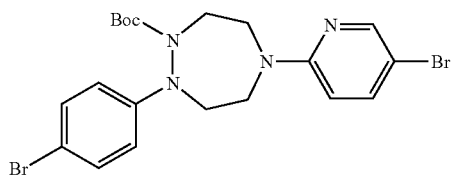

T-35 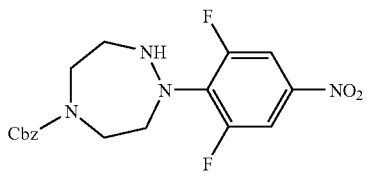

T-36 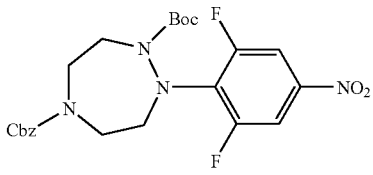

T-37 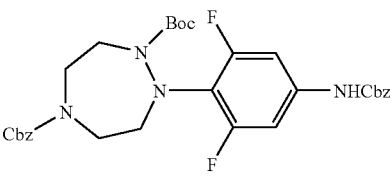

wherein Boc is tert-butoxycarbonyl and Cbz is benzyloxycarbonyl.

(69) The compound according to (56) of the formula:

[Chemical Formula 24]

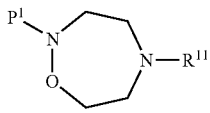

(I-12)

or a pharmaceutically acceptable salt or solvate thereof wherein
  $P^1$ is hydrogen, a substituent selected from Substituent Group S1 or an amino protecting group;
  $R^{11}$ is hydrogen, a substituent selected from Substituent Group S1 or an amino protecting group, with the proviso that $R^{11}$ is not —CO(CH$_2$)$_3$—CO$_2$H, -Ph and —CH$_2$Ph wherein Ph is phenyl;
  Substituent Group S1 is as defined above in (2), which preferably consists of optionally substituted lower alkyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted arylcarbonyl, optionally substituted heterocyclecarbonyl, optionally substituted carbamoyl, (lower alkyl)thio, cycloalkylthio, arylthio, optionally substituted (lower alkyl)sulfonyl, optionally substituted phenylsulfonyl, optionally substituted aromatic heterocycle (lower)alkyl, optionally substituted aryl, optionally substituted heterocyclic group.

(70) The compound according to (69) or a pharmaceutically acceptable salt or solvate thereof wherein $P^1$ and $R^{11}$ are independently hydrogen, an amino protecting group, or lower alkyl optionally substituted with hydroxy.

(71) The compound according to (69) or a pharmaceutically acceptable salt or solvate thereof wherein $P^1$ is hydrogen; and $R^{11}$ is an amino protecting group or lower alkyl optionally substituted with hydroxy.

(72) The compound according to (69) or a pharmaceutically acceptable salt or solvate thereof wherein $P^1$ is hydrogen; and $R^{11}$ is tert-butoxycarbonyl, benzyloxycarbonyl or lower alkyl optionally substituted with hydroxy.

(73) The compound according to (69) or a pharmaceutically acceptable salt or solvate thereof wherein $R^{11}$ is hydrogen; and $P^1$ is an amino protecting group or lower alkyl optionally substituted with hydroxy.

(74) The compound according to (69) or a pharmaceutically acceptable salt or solvate thereof wherein $R^{11}$ is hydrogen; and $P^1$ is lower alkyl optionally substituted with hydroxy, or tert-butoxycarbonyl or benzyloxycarbonyl.

(75) The compound according to (69) or a pharmaceutically acceptable salt or solvate thereof wherein the compound is selected from the following compounds:

[Chemical Formula 25]

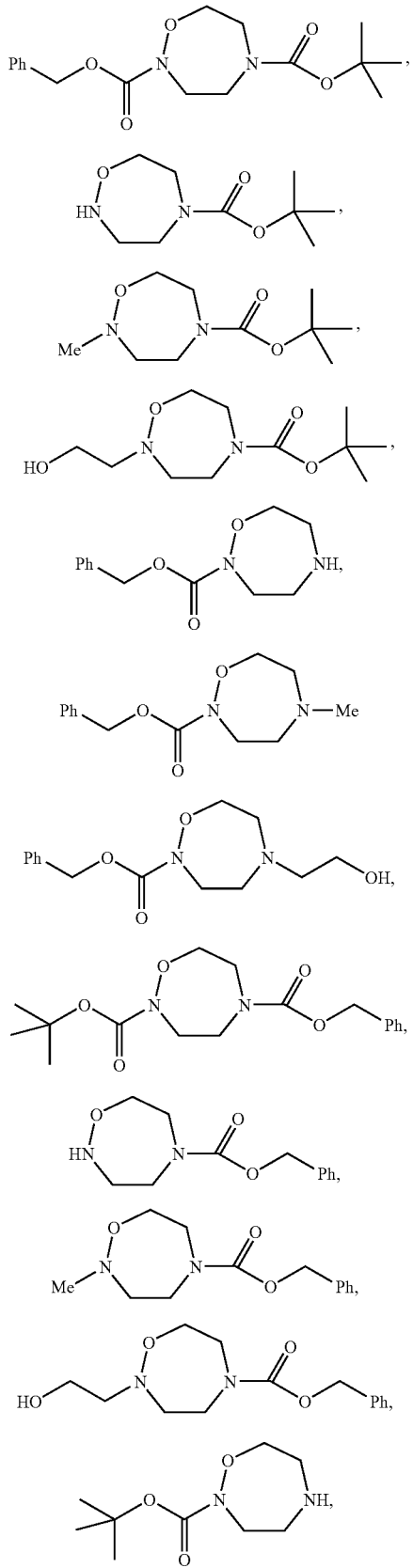

O-1
O-2
O-3
O-4
O-5
O-6
O-8
O-9
O-10
O-11
O-12
O-13

-continued

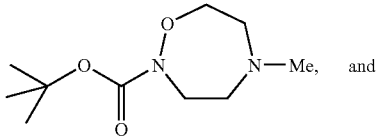

O-14

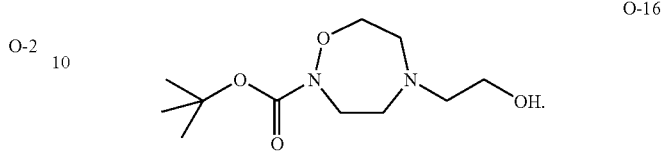

O-16

(76) The compound according to (8) of the formula:

[Chemical Formula 26]

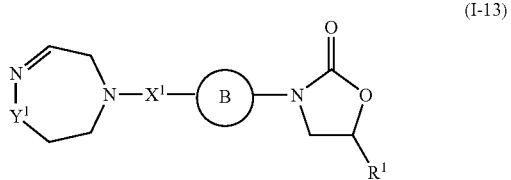

(I-13)

or a pharmaceutically acceptable salt or solvate thereof wherein
$Y^1$ is $NR^a$, O, S, SO or $SO_2$;
$R^a$ is hydrogen or a substituent selected from Substituent Group S1 as defined above in (2);
$X^1$ is a single bond, or a heteroatom-containing group selected from the group consisting of —O—, —S—, —$NR^2$—, —CO—, —CS—, —$CONR^3$—, —$NR^4CO$—, —$SO_2NR^5$—, and —$NR^6SO_2$—, wherein $R^2$, $R^3$, $R^4$, $R^5$ and $R^6$ are independently hydrogen or lower alkyl, or lower alkylene or lower alkenylene each optionally interrupted by said heteroatom-containing group;
Ring B is optionally substituted carbocycle or optionally substituted heterocycle; and
$R^1$ is hydrogen, or an organic residue which is able to bind to the 5-position of the oxazolidinone ring in oxazolidinone antimicrobial agents.

(77) The compound according to (1) of the formula:

[Chemical Formula 27]

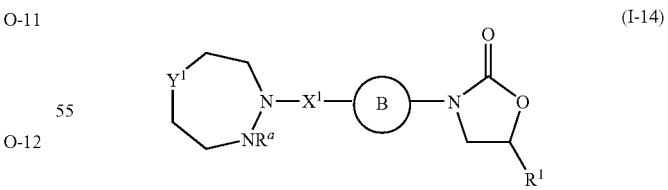

(I-14)

or a pharmaceutically acceptable salt or solvate thereof wherein
$Y^1$ is $NR^b$, O, S, SO or $SO_2$;
$R^a$ and $R^b$ are independently hydrogen, or a substituent selected from Substituent Group S1 as defined above in (2); or $R^a$ and $R^b$ may be taken together with N atom to which they are attached to form optionally substituted heterocycle;

$X^1$ is a single bond, or a heteroatom-containing group selected from the group consisting of —O—, —S—, —NR²—, —CO—, —CS—, —CONR³—, —NR⁴CO—, —SO₂NR⁵—, and —NR⁶SO₂—, wherein $R^2$, $R^3$, $R^4$, $R^5$ and $R^6$ are independently hydrogen or lower alkyl, or lower alkylene or lower alkenylene each optionally interrupted by said heteroatom-containing group;

Ring B is optionally substituted carbocycle or optionally substituted heterocycle; and $R^1$ is hydrogen, or an organic residue which is able to bind to the 5-position of the oxazolidinone ring in oxazolidinone antimicrobial agents.

As presented by the formula (I), the oxazolidinone derivative of the invention is characterized in its structure that Ring A, which is a 7-membered heterocycle optionally substituted, optionally unsaturated and optionally fused with another ring, binds to the N atom at position 3 of oxazolidinone ring via one carbocycle or heterocycle and an optional spacer.

Effect of the Invention

The oxazolidinone derivative of the invention is useful as a pharmaceutical active ingredient (e.g., antimicrobial) or a synthetic intermediate thereof. Also, the oxazolidinone derivative of the invention has a potent antimicrobial activity against gram-positive bacteria and gram-negative bacteria. Especially, the compound exhibits antimicrobial activity with wide spectrum against drug-resistant gram-positive bacteria, including methicillin-resistant *Staphylococcus aureus* (MRSA), vancomycin resistant enterococcus (VRE), penicillin resistant *pneumococcus* (PRSP). More preferably, the compound of the invention is effective against linezolid resistant (LZD-R) organisms. The compound of the invention more preferably shows good solubility or oral absorbability, which allows for administration by injection. Still more preferably, the compound of the invention reduces the side-effects concerned in conventional antimicrobial agents (e.g., linezolid), such as bone marrow suppression, monoamine oxidase (MAO) inhibiting activity, neurotoxicity. Decreased MAO inhibition is preferred because side-effects such as metabolism suppression of dopamine, serotonin, etc., blood pressure elevation, agitation, etc. are concerned by such-inhibition. Additionally, a preferred compound of the invention also shows good profiles in pharmacokinetics such as CYP inhibition, PK profile, plasma stability. Further, a preferred compound of the invention shows potent bacteriostatic or bactericidal effect by a low amount of dose or exposure.

Additionally, the synthetic intermediate of the invention is useful as an intermediate for vairouns pharmaceutical compounds and agricultural chemicals having a 7-membered heterocycle. Particularly, such intermediate as a partial structure in oxazolidinone derivatives would lead to development of desired pharmacological effect, decreased side-effect or improveent of in vivo kinetics.

BEST MODE FOR CARRYING OUT THE INVENTION

The terms as used herein are described bellow. Each term, alone or in combination with another term, has the following meaning unless otherwise specifically indicated.

The term "lower alkyl" refers to C1-C6 straight or branched monovalent hydrocarbon radical. For example, methyl, ethyl, n-propyl, isopropyl, n-butyl, isobutyl, sec-butyl, tert-butyl, n-pentyl, isopentyl, neo-pentyl, n-hexyl, isohexyl and the like.

The term "lower alkylene" refers to straight or branched C1-C6 alkylene and includes methylene, ethylene, trimethylene, propylene, tetramethylene, ethylethylene, pentamethylene, hexamethylene and the like.

The term "lower alkenylene" refers to straight or branched chain group of 2 to 6 carbon atoms having one or more double bond in the "lower alkylene" as defined above and includes, for example, vinylene, propenylene, butenylene and the like.

The term "carbocycle" refers to aryl, cycloalkyl or cycloalkenyl and includes cyclobutane, cyclopentane, cyclohexane, cycloheptane, benzene, naphthalene and the like. 5- to 7-membered ring is preferable, and 6-membered ring is especially preferable.

The term "heterocycle" and "heterocyclic group", as used herein, refers to a ring wherein a carbon atom in the above "carbocycle" is replaced with at least one hetero atom independently selected from nitrogen atom, oxygen atom or sulphur atom. For example, heteroaryl, non-aromatic heterocycle, etc. are exemplified.

The term "monocyclic heterocycle" refers to aromatic cyclic group or non-aromatic cyclic group containing at least one hetero atom selected from nitrogen atom, oxygen atom or sulphur atom in its ring.

The term "heteroaryl" refers to monocyclic aromatic heterocyclic group or condensed aromatic heterocyclic group. The monocyclic aromatic heterocyclic group refers to a group derived from a 5- to 8-membered aromatic ring that has a point of attachement at any substitutable position and contains one to four O, S, P and/or N atom in the ring. The condensed aromatic heterocyclic group refers to a group that has a point of attachement at any substitutable position and wherein a 5- to 8-membered aromatic ring containing one to four O, S, P and/or N is fused with one to four 5- to 8-membered aromatic carbocycle(s) or other 5- to 8-membered aromatic heteroring(s). Examples include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazolyl-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazole-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), dibenzofuryl, benzoxazolyl (e.g., 2-benzoxazolyl, 4-benzoxazolyl, 5-benzoxazolyl, 6-benzoxazolyl, 7-benzoxazolyl, 8-benzoxazolyl), quinoxalyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazynyl (e.g., 1-phenazinyl, 2-phenazinyl) or phenothiazinyl (e.g., 1-phenothiazinyl, 2-phenothiazinyl, 3-phenothiazinyl, 4-phenothiazinyl), etc.

The term "non-aromatic heterocycle" refers to a non-aromatic heterocyclic group having a point of attachement at any substitutable position and at least one N, O and/or S atom in the ring. The term "non-aromatic heterocyclic group" refers to a group that contains one or more O, S or N atom and is derived from a 5- to 7-membered non-aromatic ring or a condensed ring wherein two or more of such rings are fused together. Examples include 1-pyrrolinyl, 2-pyrrolinyl, 3-pyrrolinyl, pyrrolidino, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, piperazino, 2-piperazinyl, 2-morpholinyl, 3-morpholinyl, morpholino, tetrahydropyranyl, etc. The term "non-aromatic heterocyclic group" may be saturated or unsaturated as far as it is non-aromatic.

The term "cycloalkyl" includes cycloalkyl of three to eight carbon atoms. Examples include cyclopropyl, cyclobutyl, cyclopentyl, cyclohexyl, cycloheptyl and cyclooctyl.

The term "aryl" refers to monocyclic or condensed aromatic hydrocarbon. Examples include phenyl, 1-naphthyl, 2-naphthyl, anthryl and the like.

Examples of "(lower alkyl)carbonyl" include acetyl, propionyl, butyryl, isobutyryl, valeryl, isovaleryl, pivaloyl, hexanoyl, octanoyl, methoxyethylcarbonyl, 2,2,2-trifluoroethylcarbonyl, ethoxycarbonylmethylcarbonyl, and the like.

Examples of "cycloalkylcarbonyl" include cyclopropylcarbonyl, cyclohexylcarbonyl and the like.

Examples of "(lower alkyl)oxycarbonyl" include methyloxycarbonyl, ethyloxycarbonyl, n-propyloxycarbonyl, isopropyloxycarbonyl, n-butyloxycarbonyl, t-butyloxycarbonyl, n-pentyloxycarbonyl and the like.

Examples of "arylcarbonyl" include benzoyl, naphthylcarbonyl and the like.

Unless specifically indicated, substituent(s) for "optionally substituted" may be one or more same or different group(s) selected from Substituent Group B. Substituent Group B includes, for example, hydroxy; carboxy; halogen such as F, Cl, Br, I; haloalkyl such as $CF_3$, $CH_2CF_3$, $CH_2CCl_3$, etc.; haloalkoxy such as $COF_3$; alkyl such as methyl, ethyl, isopropyl, tert-butyl, etc.; alkenyl such as vinyl; alkynyl such as ethynyl; cycloalkyl such as cyclopropyl; cycloalkenyl such as cyclopropenyl; alkoxy such as methoxy, ethoxy, propoxy, butoxy, etc.; alkenyloxy such as vinyloxy, allyloxy, etc.; alkoxycarbonyl such as methoxycarbonyl, ethoxycarbonyl, tert-butoxycarbonyl, etc.; carboxy; carboxamide; nitro; nitroso; optionally substituted amino such as alkylamino (e.g., methylamino, ethylamino, dimethylamino, amino protected with an amino protecting group, etc.), acylamino (e.g., acetylamino, benzoylamino, etc.); optionally substituted amide; aralkylamino such as benzylamino, tritylamino, hydroxyamino, etc.; azide; aryl such as phenyl, etc.; aralkyl such as benzyl, etc.; cyano; isocyano; isocyanato; thiocyanato; isothiocyanato; mercapto; alkylthio such as methylthio, etc.; alkylsulfonyl such as methanesulfonyl, ethanesulfonyl; optionally substituted carbamoyl such as alkylcarbamoyl (e.g., methylcarbamoyl, ethylcarbamoyl, dimethylcarbamoyl, etc.); sulfamoyl; acyl such as formyl, acetyl, etc.; formyl; formyloxy; haloformyl; oxalo; thioformyl; thiocarboxy; dithiocarboxy; thiocarbamoyl; sulfino; sulfo; sulfoamino; hydrazino; azide; ureido; amidino; guanidino; phthalimido; oxo; optionally substituted alkyl; lower alkoxy; optionally substituted oxazolidinone; optionally substituted isoxazole; and substituents as disclosed in the following Examples.

For "an amino protecting group", any an amino protecting group well known in the art can be used, and preferably, it can be (lower alkoxy)carbonyl such as t-butoxycarbonyl; optionally substituted aralkyloxycarbonyl such as benzyloxycarbonyl, p-nitrobenzyloxycarbonyl; or lower alkyl.

The present invention provides an oxazolidinone derivative of the formula:

[Chemical Formula 28]

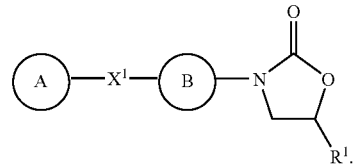

(I)

Ring A is
(A-1) a 7-membered monocyclic heterocycle containing three N atoms;
(A-2) a 7-membered monocyclic heterocycle containing two N atoms and one O atom; or
(A-3) a 7-membered monocyclic heterocycle containing two N atoms and one S atom, and
said monocyclic heterocycle is optionally substituted, optionally unsaturated and optionally fused with another ring.

In one preferable embodiment of ring A, one N atom binds via a single bond to the adjacent N or O atom in the ring.

In another preferable embodiment, ring A includes one to three, preferably one, unsaturated bond(s). Such unsaturated bond is preferably represented by "—N=CH—". The N atom, preferably, binds to the adjacent N or O atom via a single bond.

More preferably, ring A binds to $X^1$ at any one of N atoms in the ring. In ring A, at least one of the two atoms adjacent to the N atom is preferably carbon atom, and more preferably, both are carbon atoms.

More preferably, ring A is a monocyclic heterocycle as defined above in (A-1) or (A-2).

Ring A preferably contains a heteroatom-containing groups shown by —$NR^a$— and —$Y^1$—, which are preferably adjacent to each other in the ring.

Ring A is preferably a 7-membered monocyclic heterocycle of the formula:

[Chemical Formula 29]

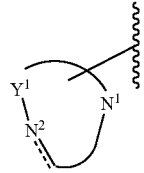

wherein the arc represents a part of the ring; $Y^1$ is $NR^a$, O, S, SO or $SO_2$, preferably $NR^a$ ($R^a$ is as defined bellow); $N^1$ and $N^2$ are independently N, NH or substituted imino (example of substituent: $R^a$); and the broken line represents presence of absence of a bond. Said 7-membered monocyclic heterocycle is optionally substituted and may be fused with a ring, which is preferably 5- to 7-membered and optionally fused with a ring.

More preferably, ring A is a 7-membered monocyclic heterocycle of the formula:

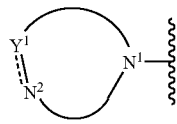

[Chemical Formula 30]

wherein $N^1$ is N; and the other variables are as defined above.

In another embodiment, ring A is a 7-membered monocyclic heterocycle of the formula:

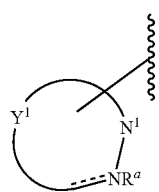

[Chemical Formula 31]

wherein the arc represents a part of the ring; $Y^1$ is $NR^a$, O, S, SO or $SO_2$, preferably $NR^a$, O or S, and more preferably $NR^a$ ($R^a$ is as defined bellow); $N^1$ is N, NH or substituted imino (example of substituent: $R^a$); and the broken line represents presence of absence of a bond; with the proviso that $R^a$ is absent when the broken line represent presence of a bond.

More preferably, ring A is a 7-membered monocyclic heterocycle of the formula:

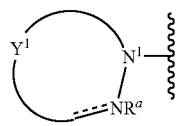

[Chemical Formula 32]

wherein $N^1$ is N; and the other variables are as defined above.

The compound of the formula (I) is preferably the compound (I-1), more preferably the compound (I-2), of the formulae:

[Chemical Formula 33]

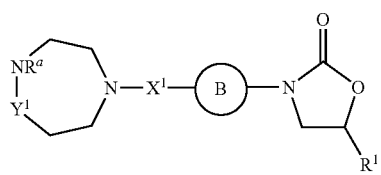

(I-1)

wherein $Y^1$ is $NR^b$, O, S, SO or $SO_2$, preferably $NR^b$ or O;

[Chemical Formula 34]

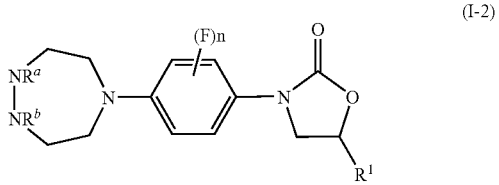

(I-2)

wherein $R^b$ and $R^a$ are independently hydrogen or a substituent selected from Substituent Group S1. Preferably, one of which is hydrogen and the other is a substituent selected from Substituent Group S1, or both of which are substituent selected from Substituent Group S1.

The compound of the formula (I) includes the compound (I-14) of the formula:

[Chemical Formula 35]

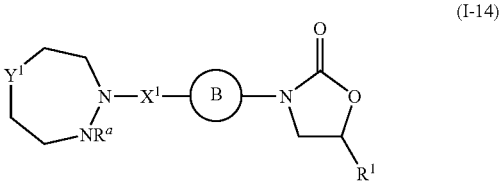

(I-14)

wherein the variables are as defined above.

$X^1$ is preferably a single bond.

$Y^1$ is preferably O or $NR^b$, $R^b$ is preferably optionally substituted lower alkyl, optionally substituted formyl, optionally substituted (lower alkyl)carbonyl (example of substituent: halogen, lower alkoxy), optionally substituted carbamoyl (example of substituent: lower alkyl, optionally substituted aryl(lower)alkyl, optionally substituted heterocycle(lower)alkyl).

Substituent Group S1 consists of Substituent Group S1-1 (optionally substituted lower alkyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted arylcarbonyl, optionally substituted heterocyclecarbonyl, optionally substituted carbamoyl, optionally substituted (lower alkyl)thiocarbonyl, cycloalkylthiocarbonyl, optionally substituted arylthiocarbonyl, optionally substituted (lower alkyl)sulfonyl, optionally substituted phenylsulfonyl, optionally substituted aromatic heterocycle(lower)sulfonyl, optionally substituted aminosulfonyl, optionally substituted aryl, optionally substituted heterocyclic group, cyano, optionally substituted thioformyl, optionally substituted (lower alkenyl)carbonyl and optionally substituted heterocycleoxycarbonyl).

Also, Substituent Group S1 includes Substituent Group S1-2, which consists of optionally substituted lower alkenyl, optionally substituted (lower alkyl)oxythiocarbonyl, optionally substituted aryloxycarbonyl, optionally substituted heterocycleoxycarbonyl, optionally substituted carbamoylcarbonyl, optionally substituted thiocarbamoyl, optionally substituted cycloalkylthiocarbonyl and optionally substituted heterocyclethiocarbonyl.

Substituents for "optionally substituted" in Substituent Group S1 is preferably selected from the group consisting of amino, optionally substituted (lower alkyl)amino, optionally substituted (lower alkyl)carbonylamino, halogen, halogenated lower alkyl, lower alkyl, optionally substituted lower alkoxy (e.g., halogenated lower alkoxy), optionally substituted (lower alkyl)thio (e.g., halogenated (lower alkyl)thio), carboxy, oxo, hydroxy, (lower alkoxy)carbonyl, (lower alkyl)carbonyloxy, optionally substituted phenylcarbonylamino, optionally substituted aryl, optionally substituted aryloxy, optionally substituted arylthio, optionally substituted arylcarbonyl, optionally substituted arylcarbonyloxy, optionally substituted aralkyl, optionally substituted aralkyloxy, optionally substituted aralkylthio, optionally substituted heterocyclic group, preferably 5- to 7-membered heterocyclic ring or a fused ring thereof with benzene, optionally substituted heterocycle-lower alkyl, optionally substituted heterocycleoxy, optionally substituted heterocyclethio, optionally substituted heterocyclecarbonyl, optionally substituted heterocyclecarbonylamino, optionally substituted heterocyclecarbonyloxy, carbamoyl, (lower alkyl)carbamoyl, nitro, cycloalkyl, oxo, etc.

For the above described optionally substituted aryl, optionally substituted phenyl, optionally substituted aryloxy, optionally substituted arylthio, optionally substituted arylcarbonyl, optionally substituted aralkyl, optionally substituted aralkyloxy, optionally substituted aralkylthio, optionally substituted heterocyclic group, optionally substituted heterocycle-lower alkyl, optionally substituted heterocyclecarbonyl, optionally substituted cycloalkyl, substituents include preferably amino, nitro, (lower alkyl)amino, halogen, halogenated lower alkyl, halogenated lower alkoxy, lower alkyl, lower alkoxy, carboxy, oxo, hydroxy, (lower alkyl)carbonyl, (lower alkoxy)carbonyl, morpholino, cyano, amino lower alkyl optionally substituted with lower alkyl, etc.

For the above described optionally substituted lower alkyl or optionally substituted lower alkenyl, substituents include preferably hydroxy, lower alkoxy, carboxy, (lower alkoxy)carbonyl, (lower alkyl)carbonyloxy, amino, optionally substituted (lower alkyl)amino, (lower alkyl)carbonylamino, cycloalkylcarbonylamino, hydroxyamino, (lower alkoxy)amino, halogen, carbamoyl, (lower alkyl)carbamoyl, nitro, cycloalkyl, optionally substituted phenyl, optionally substituted phenyloxy, optionally substituted phenylcarbonyl, optionally substituted heterocyclic group (preferably 5- or 6-membered aromatic heterocyclic group), optionally substituted heterocycleoxy, optionally substituted heterocyclethio, optionally substituted heterocyclecarbonyl, oxo, cyanoimino. For optionally substituted (lower alkyl)amino, substituents include halogen, hydroxy, lower alkoxy, amino, carboxy, optionally substituted heterocyclic group (preferably 5- or 6-membered aromatic heterocyclic group), and phenyl. For optionally substituted phenyl or optionally substituted heterocyclic group, substituents include amino, halogen, hydroxy, lower alkyl, lower alkoxy, carboxy, (lower alkoxy)carbonyl, (lower alkyl)carbonyloxy, nitro, morpholino.

For optionally substituted formyl, optionally substituted thioformyl, substituents include optionally substituted amino, optionally substituted (lower alkyl)oxy, optionally substituted (lower alkyl)thio, optionally substituted (lower alkyl)oxycarbonyl, carboxy, optionally substituted phenyl, optionally substituted phenylcarbonyl, optionally substituted phenyloxy, optionally substituted phenyloxycarbonyl, optionally substituted heterocyclic group (preferably 5- or 6-membered), optionally substituted heterocyclecarbonyl, optionally substituted heterocycleoxy preferably (preferably 5- or 6-membered), optionally substituted heterocycleoxycarbonyl, optionally substituted heterocyclethio (preferably 5- or 6-membered), optionally substituted cycloalkyl, optionally substituted carbamoyl. For said optionally substituted amino, substituents include hydroxy, lower alkoxy, (lower alkoxy)carbonyl, lower alkyl, optionally substituted heterocyclic group (substituent: lower alkyl, lower alkoxy, hydroxy, carboxy, amino, nitro, (lower alkyl)amino, hydroxy lower alkyl; said hetercyclic group is preferably 5- or 6-membered, more preferably aromatic heterocyclic group such as triazole, tetrazole, pyridyl), optionally substituted heterocycle lower alkyl, mono- or di-(lower alkyl)amino, —C(=NH)N(CH$_3$)$_2$. Substituents for optionally substituted (lower alkyl)oxy include optionally substituted aryl (e.g., phenyl). Substituents for optionally substituted phenyl or optionally substituted heterocyclic group include amino, halogen, hydroxy, lower alkyl, lower alkoxy, carboxy, (lower alkoxy)carbonyl, (lower alkyl)carbonyloxy, nitro, morpholino. Substituents for optionally substituted cycloalkyl include (lower alkyl)carbonyl, (lower alkoxy)carbonyl.

Substituents for optionally substituted (lower alkyl)carbonyl or optionally substituted (lower alkenyl)carbonyl include preferably hydroxy, optionally substituted lower alkoxy (substituent: halogen, carboxy, hydroxy, optionally substituted phenyl or optionally substituted heterocyclic group, preferably 5- or 6-membered aromatic heterocyclic group), cyano, amino, hydroxyamino, (lower alkoxy)amino, optionally substituted (lower alkyl)amino (substituent: halogen, carboxy, hydroxy, optionally substituted phenyl or optionally substituted heterocyclic group, preferably 5- or 6-membered aromatic heterocycic group), cycloalkylamino, (lower alkyl)carbonyloxy, (lower alkoxy)carbonyl, optionally substituted (lower alkyl)carbonylamino, optionally substituted (lower alkenyl)carbonylamino, optionally substituted phenylcarbonylamino, carboxy, halogen, optionally substituted phenyloxy, optionally substituted phenylthio, optionally substituted heterocyclic group (preferably 5- or 6-membered heterocyclic group), optionally substituted heterocycleoxy, optionally substituted heterocyclethio, optionally substituted heterocyclecarbonylamino, carbamoyl, (lower alkyl)carbamoyl, (lower alkyl)sulfonylamino, oxo, and preferably hydroxy, amino, (lower alkyl)carbonylamino, optionally substituted arylcarbonylamino, optionally substituted phenylcarbonylamino. More preferably, optionally substituted (lower alkyl)carbonyl includes —COCH$_3$, —COCH$_2$CH$_3$, —COCH$_2$OH, —COCH$_2$NH$_2$, in particular preferably —COCH$_2$OH. Substituents for optionally substituted phenyl, optionally substituted heterocyclic group include amino, halogen, hydroxy, lower alkyl, lower alkoxy, carboxy, (lower alkoxy)carbonyl, (lower alkyl)carbonyloxy, nitro, morpholino.

For the above "optionally substituted isoxazol", "optionally substituted heterocyclic group (preferably, 5- or 6-membered)", substituents include, for example, groups as defined for R$^1$ in the compound of the formula (I).

For optionally substituted carbamoyl, optionally substituted thiocarbamoyl, substituents include preferably optionally substituted lower alkyl (substituent: e.g., hydroxy, carboxy, lower alkoxy, (lower alkoxy)carbonyl, carbamoyl, amino, (lower alkyl)amino), optionally substituted aryl, optionally substituted heterocyclic group (preferably 5- to 7-membered), optionally substituted aryl lower alkyl, optionally substituted heterocycle lower alkyl, amino, (lower alkyl)amino, (lower alkyl)carbonylamino, optionally substituted arylcarbonylamino, optionally substituted heterocyclecarbonylamino, (lower alkyl)sulfonyl, optionally substituted arylsulfonyl, (lower alkyl)sulfonylamino, optionally substituted arylsulfonylamino, carbamoylamino, (lower alkyl)carbamoylamino. For optionally substituted aryl and optionally substituted heterocyclic group, substituents include lower alkyl, lower alkoxy, amino, nitro, halogen, hydroxy, carboxy, optionally substituted aryl and optionally substituted heterocyclic group.

In the compound (I-2), in particular preferably, $R^b$ is hydrogen;

$R^a$ is optionally substituted formyl, optionally substituted (lower alkyl)carbonyl, optionally substituted (lower alkenyl)carbonyl, optionally substituted heterocyclic group (preferably 5- to 7-membered) (lower alkyl)oxycarbonyl, carbamoyl, (lower alkyl)carbamoyl, aminocarbamoyl, optionally substituted heterocyclic group (preferably 5- to 7-membered) carbonyl, optionally substituted heterocyclic group (preferably 5- to 7-membered) carbamoyl, optionally substituted heterocyclic group (preferably 5- to 7-membered) (lower alkyl)carbamoyl, hydroxycarbamoyl, hydroxy (lower alkyl)carbamoyl, (lower alkyl)oxycarbonyl, (lower alkoxy)carbonylamino, hydroxy (lower alkyl)carbonyl, (halogenated) (lower alkyl)carbonyl, (halogenated) (lower alkoxy)carbonyl, optionally substituted heterocyclic group (preferably 5- to 7-membered) oxycarbonyl, optionally substituted heterocyclic group (preferably 5- to 7-membered) carbonylamino lower alkyl, optionally substituted heterocyclic group (preferably 5- to 7-membered) oxy (lower alkyl)carbonyl, optionally substituted heterocyclic group (preferably 5- to 7-membered) oxy (lower alkenyl)carbonyl, optionally substituted heterocyclic group (preferably 5- to 7-membered) (lower alkyl)carbonyl, optionally substituted heterocyclic group (preferably 5- to 7-membered) (lower alkenyl)carbonyl, optionally substituted heterocyclic group (preferably 5- to 7-membered) thio (lower alkyl)carbonyl, optionally substituted heterocyclic group (preferably 5- to 7-membered) oxy (lower alkyl)carbonyl, or phenyloxycarbonyl optionally substituted and optionally fused with heterocycle, optionally substituted (lower alkyl)carbonylamino (lower alkyl)carbonyl, optionally substituted heterocyclic group (preferably 5- to 7-membered) carbonylcarbonyl, optionally substituted heterocyclic group (preferably 5- to 7-membered) (lower alkyl)carbonylamino (lower alkyl)carbonyl, optionally substituted heterocyclic group (preferably 5- to 7-membered) aminocarbonylcarbonyl, optionally substituted heterocyclecarbonylamino (lower alkyl) carbonyl.

Substituents for "optionally substituted" preferably include halogen, optionally substituted amino, optionally substituted carbamoyl, optionally substituted aminocarbonyl, optionally substituted aryl, optionally substituted heterocyclic group, lower alkoxy, (lower alkenyl)oxy, optionally substituted aryloxy, optionally substituted heterocycleoxy, hydroxy, lower alkyl, halogenated lower alkyl, halogenated lower alkoxy, nitro.

More preferably, $R^a$ is onr of the following groups:

[Chemical Formula 36]

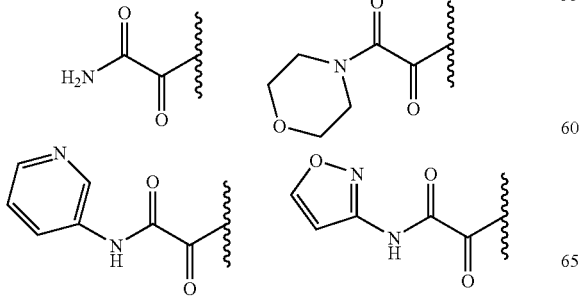

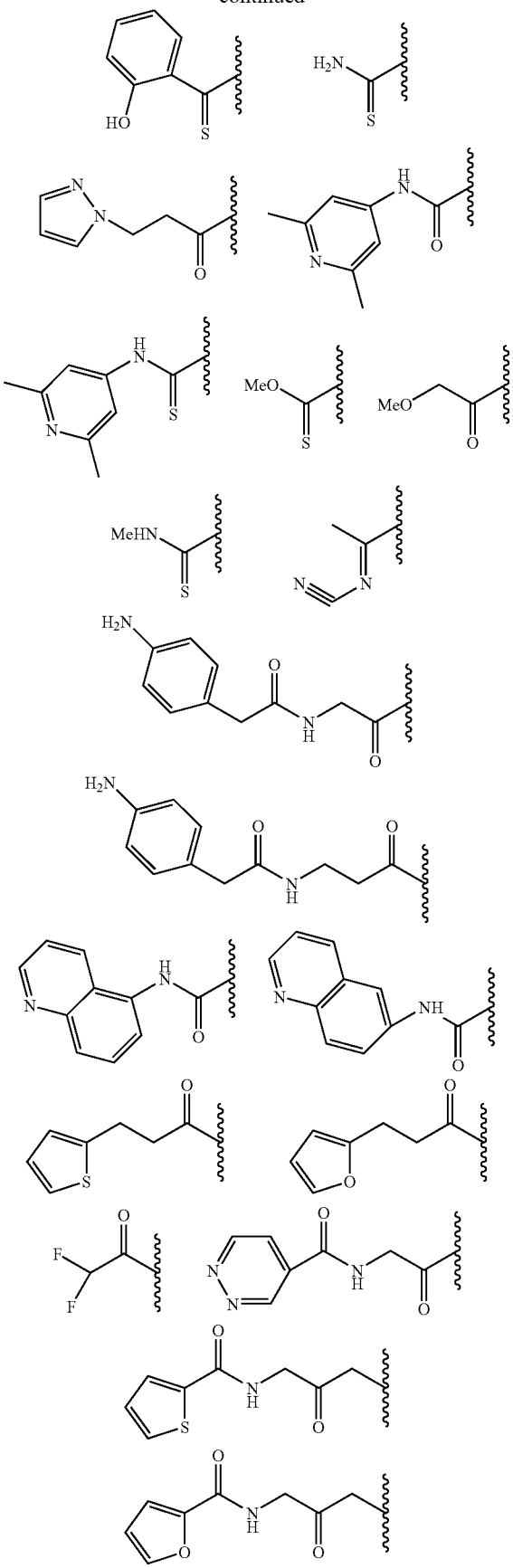

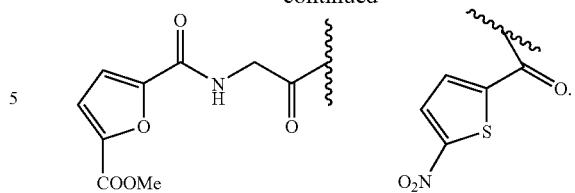

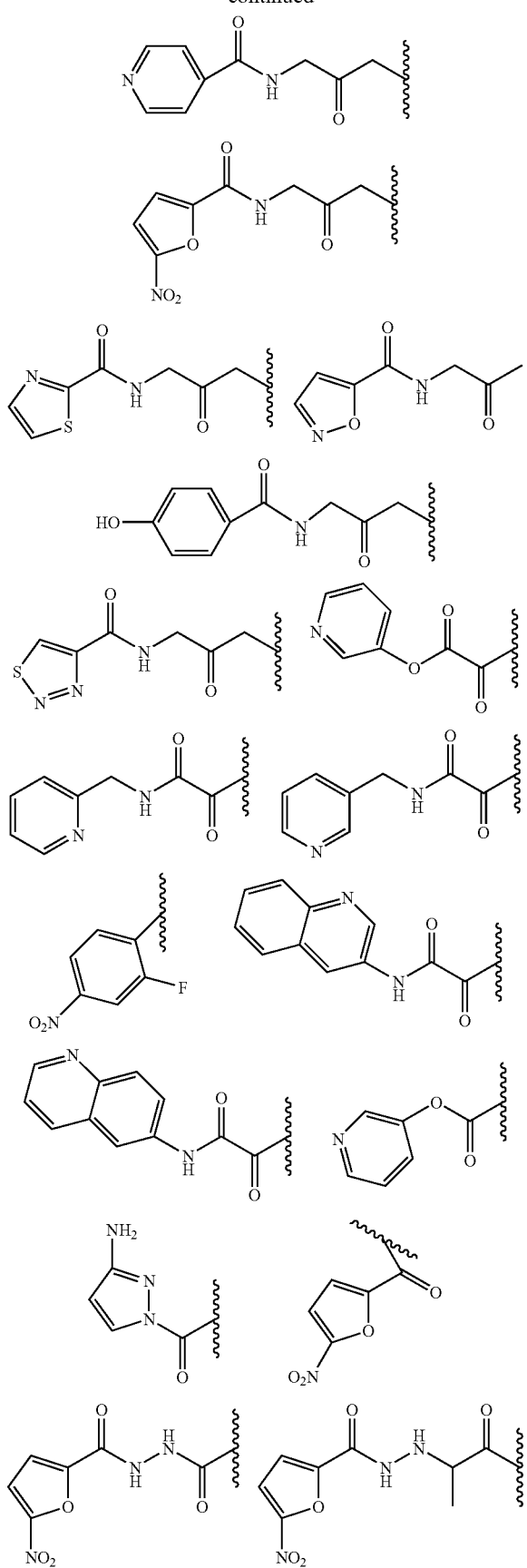

In the compound (I-1) wherein $Y^1$ is O, in particular preferably, $R^a$ is, for example, hydrogen, optionally substituted phenylsulfonyl (substituent: e.g., halogen, lower alkyl, lower alkoxy, amino, (lower alkyl)amino, hydroxy, (lower alkyl) carbonylamino, nitro), optionally substituted phenylcarbonyl (substituent: e.g., halogen, lower alkyl, lower alkoxy, amino, (lower alkyl)amino, hydroxy, (lower alkyl)carbonylamino, nitro), optionally substituted heterocyclic group (preferably 5- to 7-membered), optionally substituted heterocyclic group (preferably 5- to 7-membered) (lower alkyl)oxycarbonyl, carbamoyl, (lower alkyl)carbamoyl, optionally substituted heterocyclic group (preferably 5- to 7-membered) carbamoyl, optionally substituted heterocyclic group (preferably 5- to 7-membered) (lower alkyl) carbamoyl, hydroxycarbamoyl, hydroxy (lower alkyl)carbamoyl, (lower alkoxy)carbonylamino, hydroxy (lower alkyl)carbonyl, (halogenated) (lower alkyl)carbonyl, (halogenated) (lower alkoxy)carbonyl, optionally substituted heterocyclic group (preferably 5- to 7-membered) oxycarbonyl, or phenyloxycarbonyl optionally substituted and optionally fused with a heterocycle, (lower alkyl)thiocarbonyl.

$R^a$ and $R^b$ may be taken together with N atom to which they are attached to form optionally substituted, preferably 4- to 7-membered, more preferably 5- or 6-membered, heterocycle. Such heterocicle may be further fused with another ring.

The substituent on the heterocycle is, for example, optionally substituted amino (e.g., (lower alkyl)amino, acetylamino), halogen, halogenated lower alkyl, halogenated lower alkoxy, lower alkyl, lower alkoxy, carboxy, oxo, hydroxy, optionally substituted phenyl or heterocyclic group.

$R^a$ and $R^b$, preferably, may be taken together with N atom to which they are attached to form a 5- or 6-membered heterocycle D, which is optionally substituted with one or two oxo, and said heterocicle D is optionally substituted with the substituent R at another position. The substituent R is selected from lower alkyl, lower alkenyl, lower alkynyl, lower alkoxy, cycloalkyl, optionally substituted phenyl or optionally substituted heterocyclic group (preferably, 5- or 6-membered aromatic heterocyclic group) (substituent: e.g., carboxy, amino, halogen, lower alkoxy, halogenated lower alkyl) or a fused ring thereof with another ring, optionally substituted phenyl lower alkyl, optionally substituted heterocycle lower alkyl, acyl, carboxy, (lower alkoxy)carbonyl, (lower alkoxy) carbonylamino, (lower alkyl)sulfonyl, hydroxy, halogen, amino, (lower alkyl)amino, carbamoyl, (lower alkyl)carbamoyl, nitro, etc.

The heterocicle D may be fused with an optionally substituted 5- or 6-membered carbocycle or heterocycle, such as ring H described bellow. The substituent on such carbocycle or heterocycle is preferably, for example, carboxy, amino, optionally substituted acetylamino (substituent: carboxy, hydroxy, amino, morpholino), halogen, optionally substituted heterocyclecarbonylamino (substituent: e.g., lower alkyl, amino, nitro, halogens), nitro, lower alkyl, halogen, hydroxy, (lower alkoxy)carbonyl. In this embodiment, ring $A^1$ is preferably a condensed cyclic group as follows:

[Chemical Formula 37]

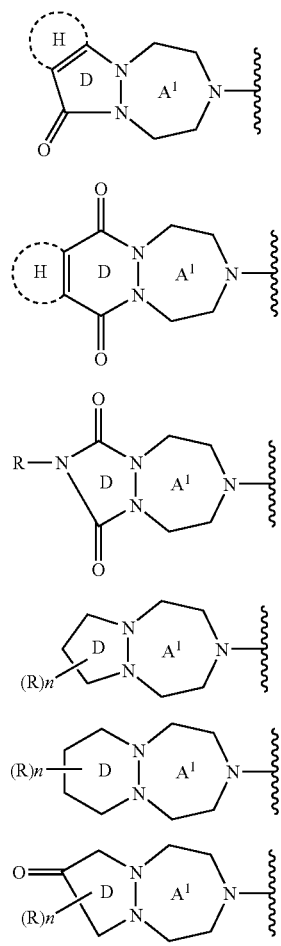

[Chemical Formula 38]

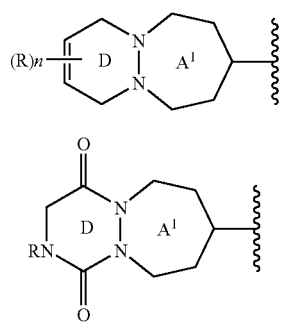

wherein ring D is as defined above; ring H is optionally substituted monocyclic heterocycle; R is as defined above, n is 1 or 2.

Ring H is preferably a 5- or 6-membered cycle, more preferably an aromatic heterocycle, further more preferably an nitrogen-containing aromatic heterocycle, such as pyridine ring, pyrimidine ring, pyrazine ring, etc. The substituent on the ring H is, for example, lower alkyl, hydroxy, carboxy, lower alkoxy, amino, nitro, halogen, (lower alkyl)amino, optionally substituted acetylamino (substituent: hydroxy, carboxy, amino, lower alkoxy), heterocycleamino or heterocyclecarbonylamino wherein the heterocycle is preferably 5- or 6-membered aliphatic ring.

Any one of the ring A may further be fused with another ring. When the ring A is a condensed ring, it may be fused with one to four 5- to 8-membered carbocycles (5- to 8-membered aromatic carbocycle) and/or other 5- to 8-membered heterocycles which optionally contain one to four oxygen atom, sulphur atom, and/or nitrogen atom in the ring. Preferably, a 5- or 6-membered ring is fused in the condensed ring.

The substituent on such condensed ring is, for example, amino, (lower alkyl)amino, halogen, halogenated lower alkyl, halogenated lower alkoxy, lower alkyl, lower alkoxy, carboxy, oxo, hydroxyetc.

$X^1$ is a single bond or an optional spacer moiety. Such spacer includes a heteroatom-containing group selected from the group consisting of —O—, —S—, —NR$^2$—, —CO—, —CS—, —CONR$^3$—, —NR$^4$CO—, —SO$_2$NR$^5$—, and —NR$^6$SO$_2$—, wherein $R^2$, $R^3$, $R^4$, $R^5$ and $R^6$ are independently hydrogen or lower alkyl, or lower alkylene or a lower alkenylene each optionally interrupted by said heteroatom-containing group. The position of the heteroatom-containing group is not limited, and it may be present at any position within the lower alkylene or the lower alkenylene. Also, it may be present between the carbon atom of the lower alkylene or the lower alkenylene and the ring $A^1$ or B. The number of such a heteroatom-containing group is not limited but preferably one to three atom length. $X^1$ is more preferably a single bond. The lower alkylene is preferably C1-C3 alkylene, and the lower alkenylene is preferably C2-C3 alkenylene.

Ring B is benzene ring optionally substituted and optionally fused to another ring or a heterocycle optionally substituted. Such heterocycle is the heterocycle as defined above and may be monocyclic ring or condensed ring. It is more preferably 5- to 7-membered, in particular preferably 5- or 6-membered, and still more preferably benzene ring optionally substituted. When the ring B is benzene ring, it is preferably represented by the formula:

[Chemical Formula 39]

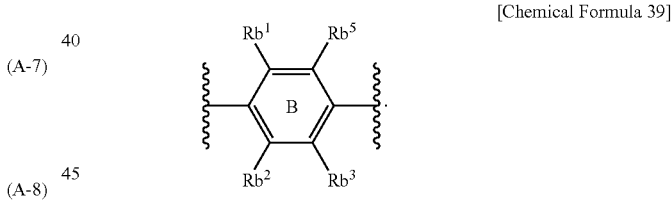

Preferably, the substituents $Rb^1$, $Rb^2$, $Rb^3$ and $Rb^5$ may be amino, (lower alkyl)amino, halogen, halogenated lower alkyl, halogenated lower alkoxy, lower alkyl, lower alkoxy, carboxy, oxo, hydroxy, etc., and halogen is preferable. Preferably, one to four, preferably one or two of these substituents is present.

In one preferable embodiment, any one or two of $Rb^1$, $Rb^2$, $Rb^3$ and $Rb^5$ is halo, particularly F, and the others are hydrogen.

More preferably, the ring B is any one of the following rings:

[Chemical Formula 40]

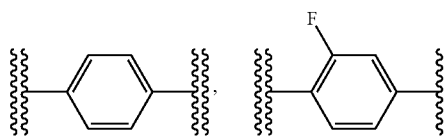

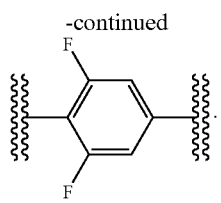

When the ring B is a heterocycle, it is preferably 5- to 7-membered ring, more preferably an aromatic heterocycle such as pyridine.

The term "an organic residue which is able to bind to the 5-position of oxazolidinone ring in oxazolidinone antimicrobial agents" for $R^1$ refers to any organic residue that can bind to the 5-position of the oxazolidinone ring of an oxazolidinone antimicrobial compound, which is known as disclosed in the patents listed above in the section "Background Art", capable of synthesis by a person skilled in the art, or may be disclosed in the future. Examples of such organic residue include optionally substituted alkyl, optionally substituted cycloalkyl, optionally substituted alkenyl, optionally substituted cycloalkenyl, optionally substituted aryl, optionally substituted heteroaryl, —CN, optionally substituted carbamoyl, optionally substituted (lower alkoxy)carbonyl, optionally substituted amino and the like. Examples of the substituent for "optionally substituted" include optionally substituted amino, optionally substituted hydroxy, optionally substituted thiol, lower alkyl, lower alkenyl, lower alkynyl, lower alkoxy, (lower alkyl)carbonyl, (lower alkyl)sulfonyloxy, halo, carboxy, halogenated lower alkyl, halogenated lower alkoxy, (lower alkyl)carbonyl, (lower alkoxy)carbonyl, carbamoyl, (lower alkyl)carbamoyl and heterocyclic group, which is preferably 5- to 7-membered and/or an aromatic ring, etc. Examples of the substituent for optionally substituted amino include —$COR^7$, —$CSR^8$ or $R^9$ as described bellow, (lower alkyl)sulfonyl, (lower alkyl)aminosulfonyl, lower alkyl, (lower alkyl)carbonylamino, aminosulfonyl. Preferable examples of the substituent for optionally substituted hydroxy and optionally substituted thiol include lower alkyl, heterocyclic group which is preferably 5- to 7-membered ring and/or an aromatic ring, (lower alkyl)carbonyl, cyano.

Preferably, $R^1$ is optionally substituted alkyl (substituent: optionally substituted amino, optionally substituted hydroxy, azide, halo, —NCS, etc.), more preferably, optionally substituted aminomethylene, optionally substituted hydroxymethylene, or optionally substituted heterocyclemethylene (it is preferably 5- to 7-membered and more preferably an aromatic ring and still more preferably contains a nitrogen atom), still more preferably, substituted aminomethylene, even more preferably —$CH_2NHCOR^7$ or —$CH_2NHCSR^8$. $R^7$ may be hydrogen, optionally substituted lower alkyl, optionally substituted lower alkoxy, optionally substituted (lower alkyl) thio, cycloalkyl, optionally substituted heterocyclic group which is preferably nitrogen-containing 5- to 7-membered ring, amino, (lower alkyl)amino, (lower alkyl)sulfonyl or optionally substituted phenyl, and optionally substituted lower alkyl is preferable. Preferable substituents for said amino, lower alkyl, heterocycle or phenyl include halo, hydroxy, lower alkoxy, optionally substituted phenyl, optionally substituted phenyloxy, lower alkyl, carboxy, (lower alkoxy)carbonyl, (lower alkyl)sulfonyl, amino, (lower alkyl) amino, and preferably halo, hydroxy, lower alkoxy, more preferably halogen (e.g., F). Particular preferably, $R^7$ is lower alkyl optionally substituted with halogen (e.g., —$CH_3$, —$CHF_2$). $R^8$ is hydrogen, optionally substituted lower alkyl, optionally substituted (lower alkyl)oxy, optionally substituted (lower alkyl)thio, cycloalkyl, optionally substituted heterocyclic group which is preferably nitrogen-containing 5- to 7-membered ring, amino, (lower alkyl)amino or optionally substituted phenyl, and optionally substituted (lower alkyl) oxy is preferable. Preferable substituents for said (lower alkyl)oxy are halo, hydroxy, lower alkoxy, optionally substituted phenyl, optionally substituted phenyloxy, and halo (e.g., F) is preferable. More preferably, $R^8$ is (lower alkyl)oxy (e.g., —$OCH_3$).

Preferably, $R^1$ is —$CH_2NHR^9$ wherein $R^9$ is hydrogen, heterocyclic group (preferably, nitrogen-containing 5- to 7-membered ring, —$SO_2NH_2$), or —$CH_2R^{10}$ wherein $R^{10}$ is heterocyclic group (preferably, nitrogen-containing 5- to 7-membered ring), —$CH_2OR^{11}$ wherein $R^{11}$ is hydrogen, (lower alkyl)carbonyl, heterocyclic group (preferably, nitrogen-containing 5- to 7-membered ring), —$CH_2SR^{12}$ wherein $R^{12}$ is hydrogen, heterocyclic group (preferably, nitrogen-containing 5- to 7-membered ring), —$CH_2SCN$.

For optionally substituted hydroxymethylene, examples of the substituent are as described in $R^7$. In one preferable embodiment, $R^1$ is —$CH_2NHCOR^7$ wherein $R^7$ is hydrogen or methyl; —$CH_2NHCSR^8$ wherein $R^8$ is hydrogen, methyl, ethyl, difluoromethyl, methoxy, or methylthio, amino, methylamino; —$CH_2NHR^9$ wherein $R^9$ is isoxazolyl, pyridyl; or —$CH_2R^{10}$ wherein $R^{10}$ is thiazole, 1,2,3-triazolyl, tetrazole optionally substituted with lower alkyl, pyridyl; —$CH_2OR^{11}$ wherein $R^{11}$ is hydrogen, thiazole, 1,2,3-triazolyl, tetrazole optionally substituted with lower alkyl, pyridyl; —$CH_2SR^{12}$ wherein $R^{12}$ is hydrogen, thiazole, 1,2,3-triazolyl, tetrazole optionally substituted with lower alkyl, pyridyl.

Particularly preferably, $R^1$ is any one of the following groups:

[Chemical Formula 41]

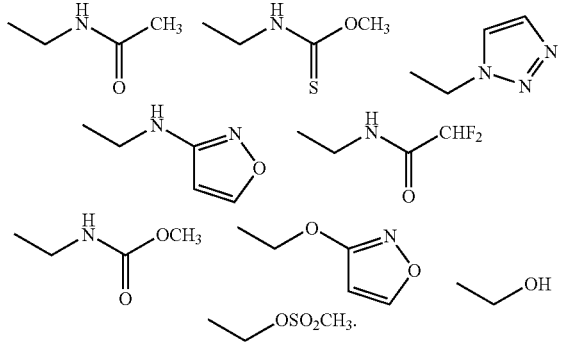

The present invention also provides a compound of the formula:

[Chemical Formula 42]

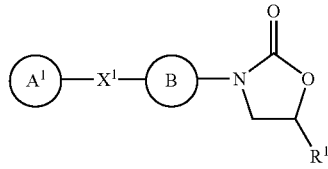

(I-3)

wherein

Ring $A^1$ is
(A-1) a 7-membered monocyclic heterocycle containing three N atoms and one double bond,
(A-2) a 7-membered monocyclic heterocycle containing two N atoms and one O atom and one double bond, or
(A-3) a 7-membered monocyclic heterocycle containing two N atoms and one S atom and one double bond, and
said monocyclic heterocycle is optionally substituted and optionally fused with another ring; and
the other variables are as defined above.

In any one of ring $A^1$ as defined above, one N atom (hereinafter "$N^1$") preferably binds to $X^1$. More preferably, $N^1$ is neighbored with another N atom (herein after "$N^2$").

The position of the double bond in ring $A^1$ is not limited but preferably on $N^2$.

Ring $A^1$ is preferably a 7-membered monocyclic heterocyclic ring of the formula:

[Chemical Formula 43]

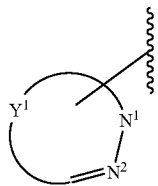

wherein $N^1$ is, N, NH, or substituted imino (substituent: e.g., $R^a$), and said monocyclic heterocyclic ring is optionally substituted and optionally fused with a ring (e.g., 5- to 7-membered carbocycle or heterocyclic ring).

More preferably, ring $A^1$ is a 7-membered monocyclic heterocyclic ring of the formula:

[Chemical Formula 44]

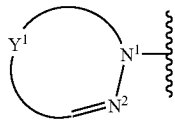

wherein the arc represents a part of the ring; $Y^1$ is $NR^a$, O, S, SO or $SO_2$, preferably $NR^a$ ($R^a$ is as defined bellow), O or S, and more preferably $NR^a$ or O.

Ring $A^1$ is more preferably a heterocycle as defined in (A-1).

The compound (I-3) is preferably (I-4) of the formula:

[Chemical Formula 45]

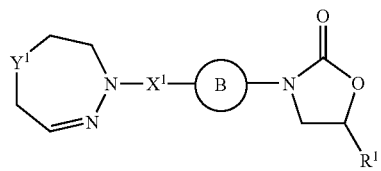

(I-4)

wherein
$Y^1$ is $NR^a$, O, S, SO or $SO_2$;
$R^a$ is hydrogen, or a substituent selected from Substituent Group S1;

Substituent Group S1 includes Substituent Group S1-1, which consists of optionally substituted lower alkyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted arylcarbonyl, optionally substituted heterocyclecarbonyl, optionally substituted carbamoyl, optionally substituted (lower alkyl)thiocarbonyl, cycloalkylthiocarbonyl, arylthiocarbonyl, optionally substituted (lower alkyl)sulfonyl, optionally substituted phenylsulfonyl, optionally substituted aromatic heterocyclesulfonyl, optionally substituted aminosulfonyl, optionally substituted aryl, optionally substituted heterocyclic group, cyano, optionally substituted thioformyl, optionally substituted (lower alkenyl)carbonyl, and optionally substituted heterocycleoxycarbonyl. Also, Substituent Group S1 includes Substituent Group S1-2, which consists of optionally substituted lower alkenyl, optionally substituted (lower alkyl)oxythiocarbonyl, optionally substituted aryloxycarbonyl, optionally substituted heterocycleoxycarbonyl, optionally substituted carbamoylcarbonyl, optionally substituted thiocarbamoyl, optionally substituted cycloalkylthiocarbonyl, and optionally substituted heterocyclethiocarbonyl.

$X^1$ is a single bond, or a heteroatom-containing group selected from the group consisting of —O—, —S—, —$NR^2$—, —CO—, —CS—, —$CONR^3$—, —$NR^4CO$—, —$SO_2NR^5$—, and —$NR^6SO_2$—, wherein $R^2$, $R^3$, $R^4$, $R^5$ and $R^6$ are independently hydrogen or lower alkyl, or lower alkylene or lower alkenylene each optionally interrupted by said heteroatom-containing group;

Ring B is optionally substituted carbocycle or optionally substituted heterocycle; and $R^1$ is hydrogen, or an organic residue which is able to bind to the 5-position of the oxazolidinone ring in oxazolidinone antimicrobial agents.

In the compound (I-4), $Y^1$ is preferably $NR^a$ or O.

$R^a$ is preferably as defined for the compound (I-2), or optionally substituted lower alkyl, optionally substituted formyl, optionally substituted (lower alkyl)carbonyl, optionally substituted heterocyclecarbonyl, optionally substituted carbamoyl, optionally substituted (lower alkyl)thiocarbonyl, optionally substituted aryl, optionally substituted heterocyclic group, cyano, optionally substituted thioformyl, optionally substituted (lower alkenyl)carbonyl, or optionally substituted heterocycleoxycarbonyl.

Substituents for each "optionally substituted" are the same as those defined for $R^a$ in the compound (I-2) but preferably are as follows.

More preferably, for optionally substituted lower alkyl, optionally substituted (lower alkyl)carbonyl, optionally substituted (lower alkenyl)carbonyl, substituents include hydroxy, optionally substituted phenyl (substituent: e.g., OH, halo, optionally substituted lower alkyl (substituent: e.g., amino, (lower alkyl)amino), lower alkoxy, amino, (lower alkyl)amino, nitro, halogenated lower alkyl), optionally substituted heterocyclic group (preferably 5- to 10-membered, more preferably 5- to 7-membered; substituent: e.g., OH, halo, lower alkyl, lower alkoxy, amino, nitro, halogenated lower alkyl), optionally substituted amino (substituent: e.g., lower alkyl, (lower alkyl)carbonyl, optionally substituted phenyl, optionally substituted heterocyclic group), optionally substituted phenylcarbonyloxy, optionally substituted heterocyclecarbonyloxy, carbamoyl, (lower alkyl)carbamoyl, optionally substituted phenyloxy, optionally substituted phenylthio, optionally substituted heterocycleoxy, optionally substituted heterocyclethio.

More preferably, for optionally substituted formyl or optionally substituted thioformyl, substituents include optionally substituted heterocyclic group (preferably 5- to 10-membered, more preferably 5- to 7-membered; substituent: e.g., OH, halo, lower alkyl, lower alkoxy, amino, nitro).

More preferably, for optionally substituted heterocyclecarbonyl or optionally substituted heterocycleoxycarbonyl, substituents include OH, halo, lower alkyl, lower alkoxy, amino, nitro.

More preferably, for optionally substituted carbamoyl or optionally substituted (lower alkyl)thiocarbonyl, substituents include lower alkyl, optionally substituted phenyl (substituent: e.g., OH, halo, optionally substituted lower alkyl (substituent: e.g., amino, (lower alkyl)amino), lower alkoxy, amino, (lower alkyl)amino, nitro, halogenated lower alkyl), optionally substituted heterocyclic group (preferably 5- to 10-membered, more preferably 5- to 7-membered; substituent: e.g., OH, halo, lower alkyl, lower alkoxy, amino, nitro, halogenated lower alkyl).

Preferably, $R^a$ is any one of the following groups:

[Chemical Formula 46]

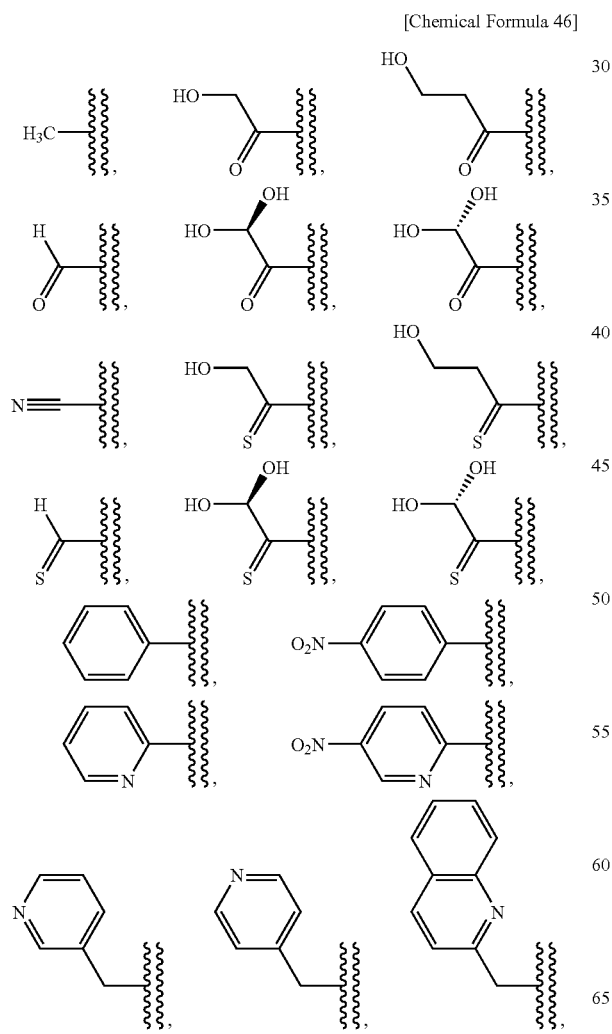
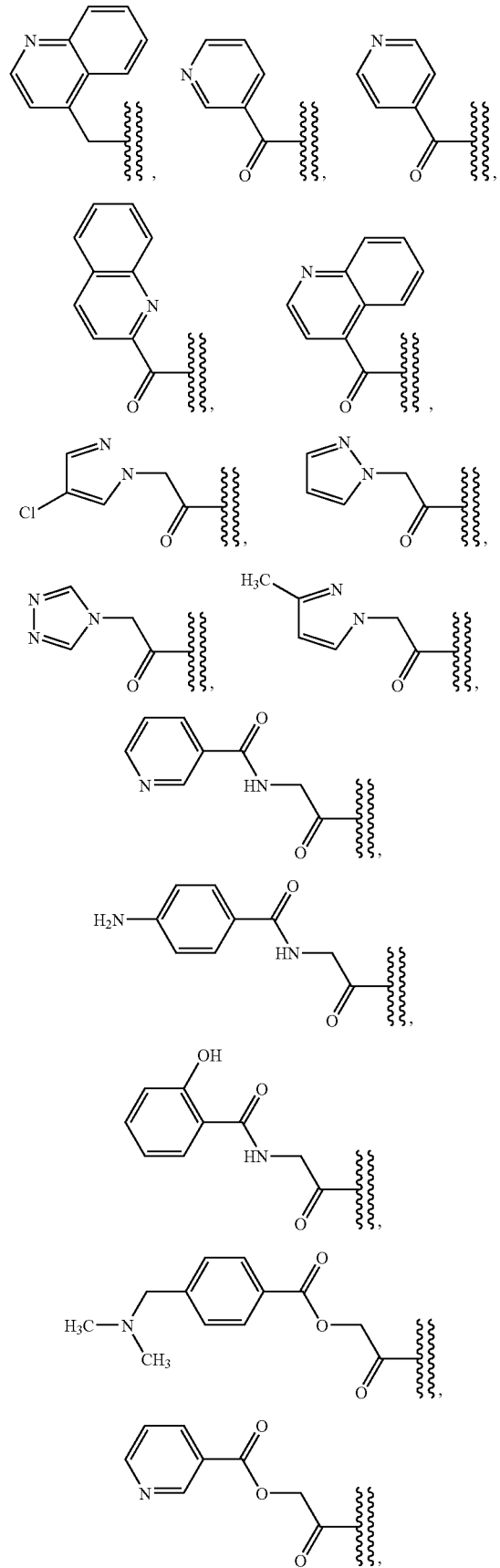

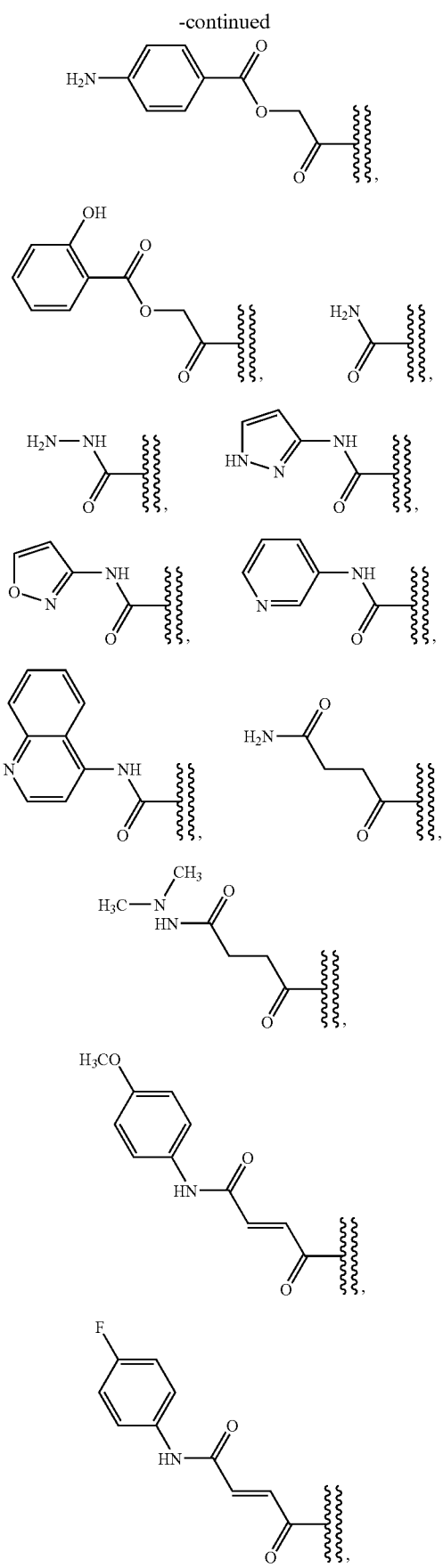
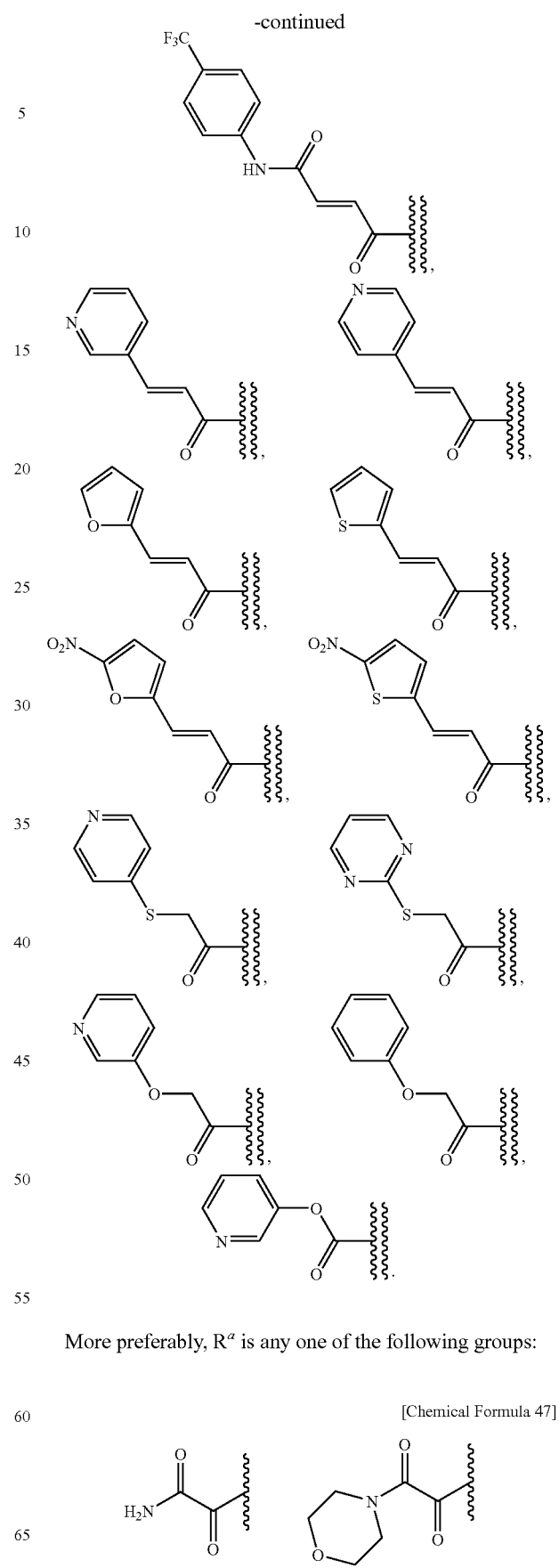
More preferably, $R^a$ is any one of the following groups:
[Chemical Formula 47]

51
-continued
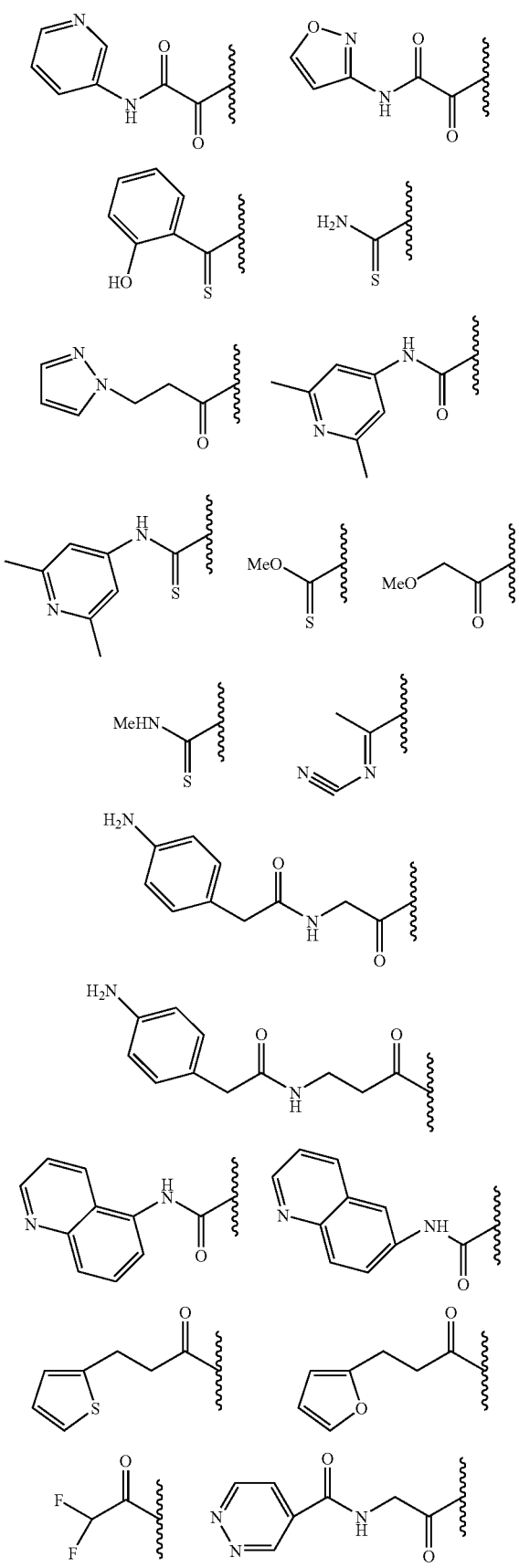
52
-continued
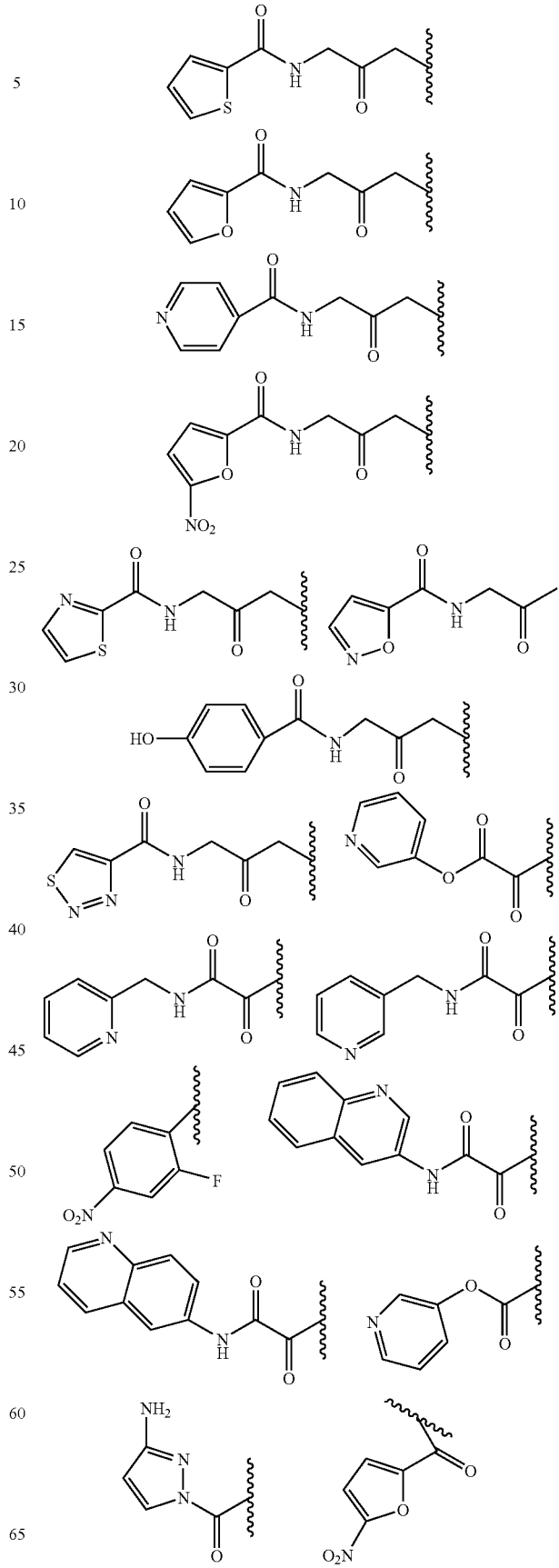

-continued

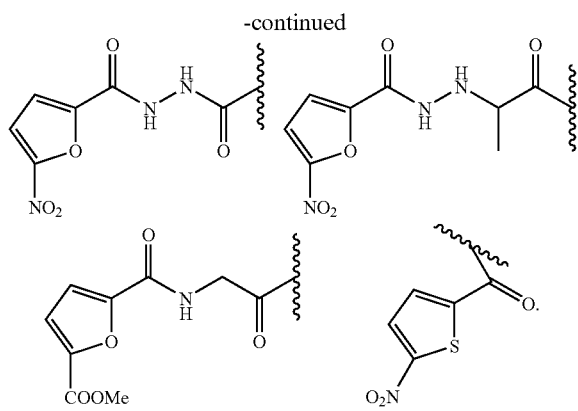

Another preferable embodiment of the compound (I-3) is the compound (I-13) of the formula:

[Chemical Formula 48]

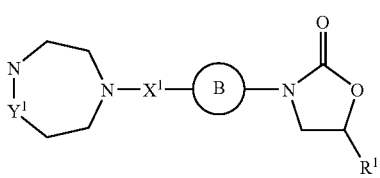

(I-13)

wherein $Y^1$ is $NR^a$, O, S, SO or $SO_2$;

$R^a$ is hydrogen, or a substituent selected from Substituent Group S1, which consists of optionally substituted lower alkyl, optionally substituted lower alkenyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted (lower alkyl)oxythiocarbonyl, optionally substituted arylcarbonyl, optionally substituted aryloxycarbonyl, optionally substituted heterocyclecarbonyl, optionally substituted heterocycleoxycarbonyl, optionally substituted carbamoyl, optionally substituted carbamoylcarbonyl, optionally substituted thiocarbamoyl, optionally substituted (lower alkyl)thiocarbonyl, optionally substituted cycloalkylthiocarbonyl, optionally substituted arylthiocarbonyl, optionally substituted heterocyclethiocarbonyl, optionally substituted (lower alkyl)sulfonyl, optionally substituted phenylsulfonyl, optionally substituted aromatic heterocyclesulfonyl, optionally substituted aminosulfonyl, optionally substituted aryl, optionally substituted heterocyclic group, cyano, optionally substituted thioformyl, optionally substituted (lower alkenyl)carbonyl, and optionally substituted heterocycleoxycarbonyl;

$X^1$ is a single bond, or a heteroatom-containing group selected from the group consisting of —O—, —S—, —$NR^2$—, —CO—, —CS—, —$CONR^3$—, —$NR^4CO$—, —$SO_2NR^5$—, and —$NR^6SO_2$—, wherein $R^2$, $R^3$, $R^4$, $R^5$ and $R^6$ are independently hydrogen or lower alkyl, or lower alkylene or lower alkenylene each optionally interrupted by said heteroatom-containing group;

Ring B is optionally substituted carbocycle or optionally substituted heterocycle; and $R^1$ is hydrogen, or an organic residue which is able to bind to the 5-position of the oxazolidinone ring in oxazolidinone antimicrobial agents.

In the compound (I-13), $Y^1$ is more preferably O or $NR^a$, and $R^a$ is preferably hydrogen, optionally substituted lower alkyl, or optionally substituted aryl (substituent: e.g., halo, nitro, lower alkyl).

The compound of the invention can be prepared according to the procedure as shown in Scheme I and II. Reagents and conditions used in the reaction can be selected appropriately by a skilled person in the art, for example, according to the description in Japanese Patent Publication NO. 7-508665.

Scheme I

[Chemical Formula 49]

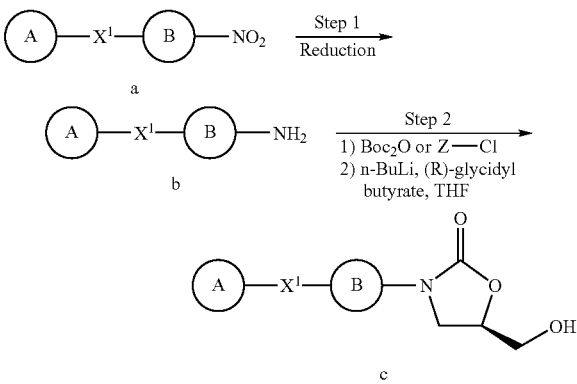

wherein Ring A, $X^1$ and Ring B are as defined above; Ph is phenyl, Ms is methanesulfonyl; and Z is benzyloxycarbonyl.

In Step 1, the nitro group of Compound a is reduced to obtain Compound b according to a reduction process, e.g., hydrogenation with a catalyst such as platinum oxide, Raney nickel, palladium carbon or the like, or a reaction using iron powder with hydrochloric acid, acetic acid or the like. Compound a is commercially available or can be prepared easily from a reagent commercially available by a skilled person in the art.

In Step 2, Compound b is urethanated in an appropriate organic solvent such as methanol, THF using di-tert-butyl dicarbonate or urethanated using benzyloxycarbonyl chloride in the presence of a base such as triethylamine, potassium carbonate, sodium carbonate, sodium bicarbonate, etc., in water or an organic solvent such as acetone, methanol, THF or a combined solvent thereof. The obtained compound is then treated with a base such as n-butyllithium in an appropriate aprotic organic solvent, such as THF, N,N-dimethylformamide, at a temperature in a range from −78° C. to the reflux temperature of the solvent, and followed by reaction with glycidyl butyrate to obtain Compound c.

Additionally, Compound c obtained in Scheme I may be further converted to Compound g, according to the following Scheme II.

Scheme II

[Chemical Formula 50]

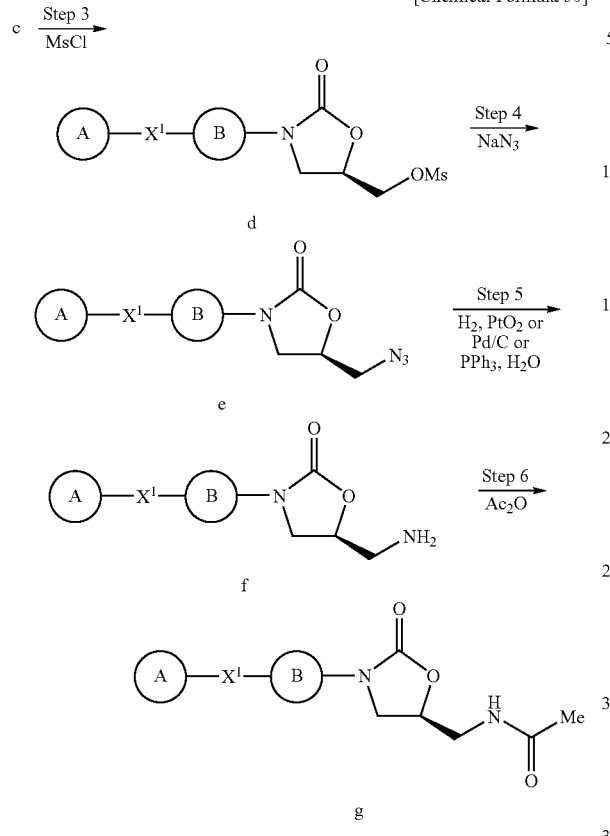

In Step 3, Compound c is reacted with methanesulfonyl chloride in the presence of a base such as triethylamine in an organic solvent, such as dichloromethane, THF, etc., at a temperature in a range of under ice cooling to the reflux temperature of the solvent to obtain Compound d.

In Step 4, Compound d is reacted with sodium azide in an organic solvent, such as THF, N,N-dimethylformamide, etc., at a temperature in a range of under ice cooling to the reflux temperature of the solvent to obtain Compound e.

In Step 5, the azide group of Compound e is reduced according to an appropriate reduction method, e.g., hydrogenation reduction using a catalyst such as platinum oxide, palladium carbon or the like, or treatment with triphenylphosphine and water, to obtain Compound f.

In Step 6, Compound f is acylated with an appropriate anhydrous acid such as acetic anhydride in a basic solvent such as pyridine to obtain Compound g.

Optionally, the compound obtained above may further be modified with any substituent at 5-position of the oxazolidinone ring to obtain various oxazolidinone derivatives. Also, Ring A, Ring B, and $X^1$ moiety may further be modified. Such modification is within a level of a person skilled in the art and is readily practiced by a person skilled in the art.

According to the same method above, various derivatives of the oxazolidinone having a heterocycle at 5-position of the ring can be synthesized from Compound c.

During the synthesis of the invention, in case where a functional group is located in an intermediate (e.g., —OH, —NH$_2$, —COOH), it may be protected appropriately before the reaction. For example, it may be protected with an appropriate protecting group, such as t-butoxycarbonyl group, ben-zyloxycarbonyl group, and readily removed thereafter at an appropriate time, as described in Greene, T. W., Wuts, P. G. M., "Protective Groups in Organic Synthesis", 2nd ed,; John Wiley & Sons: New York (1991).

The compound (I-3) of the invention, particularly the compound (I-4), can be prepared according to the following procedure:

Scheme III

[Chemical Formula 51]

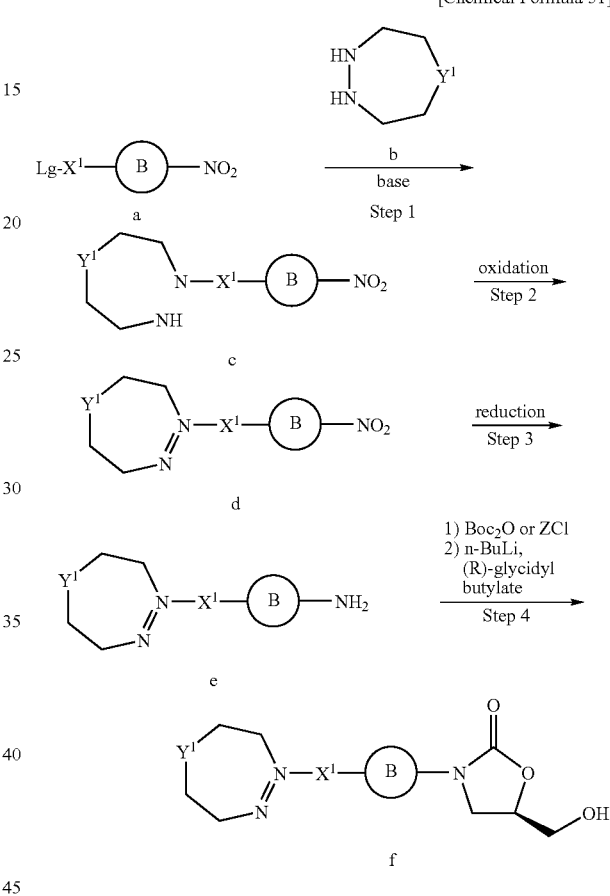

wherein Ring B and $X^1$ are as defined above and $Y^1$ is $NR^a$, O, S, SO or SO$_2$, and $R^a$ is hydrogen, a substituent selected from Substituent Group S1 or an amino protecting group such as tert-butoxycarbonyl or benzyloxycarbonyl, Lg is a group to be removed by nucleophilic substitution reaction (e.g., halo, sulfonate ester, etc.).

(Step 1)

Compound a is reacted with Compound b or a salt thereof in the presence of an appropriate base such as triethylamine, in an alcoholic solvent (e.g., methanol, ethanol, 1-propanol, 2-propanol) to afford Compound c. Compound a is commercially available or prepared readily by a skilled person in the art. Compound b is prepared readily by a skilled person in the art according to the procedure as described in WO99/47525.

(Step 2)

Compound c is oxidized with an oxidizing agent, such as those appropriate for DNSO oxidation (e.g., dimethylsulphoxide, oxalyl chloride), in an appropriate solvent (e.g., dichloromethane, THF) and followed by treatment with an appropriate base such as triethylamine to afford Compound d. The reaction temperature is generally about −78° C. to about 25° C., preferably about −78° C. to about −50° C. The reaction time is several minutes to tens of hours, preferably several minutes to one hour. Other oxidation methods can be available. In an oxidation with a halogen (e.g., $Br_2$), examples of the solvent include carbon tetrachloride, chloroform, acetic acid, and the reaction temperature is generally about 0° C. to about 100° C., preferably about 25° C. to about 80° C. The reaction time is generally several minutes to tens of hours, preferably several minutes to three hours. For oxygen oxidation (e.g., $O_2$), examples of the solvent include KOH-ethanol, and the reaction temperature is generally about 25° C. to about 100° C., preferably about 25° C. to about 80° C. The reaction time is generally several minutes to tens of hours, preferably several minutes to three hours.

(Step 3)

The nitro group of Compound d is reduced by an appropriate reduction method, e.g., hydrogenation using an catalyst such as platinum oxide, Raney nickel, palladium carbon, other oxidation methods using iron powder and hydrochloric acid, acetic acid, etc., to afford Compound e.

(Step 4)

Compound e is urethanated with di-tert-butyl dicarbonate in an appropriate organic solvent, such as methanol, THF, or with benzyloxycarbonyl chloride in water or an organic solvent such as acetone, methanol, THF, or a mixed solvent thereof, in the presence of a base such as triethylamine, potassium carbonate, sodium carbonate, sodium bicarbonate. It is then treated with a base such as n-butyllithium in an appropriate aprotic solvent such as THF, N,N-dimethylformamide, at a temperature from −78° C. to the reflux temperature of the solvent, followed by reaction with glycidyl butyrate to afford Compound f.

Step 3 and Step 4 can be conducted according to the method as described in Bioorganic & Medicinal Chemistry Letters 15 (2005) 2834-2839.

(Step 5)

Another compound of the invention may be derived from Compound f by the modification of the 5-position of the oxazolidinone ring according to the procedure as shown in Scheme II.

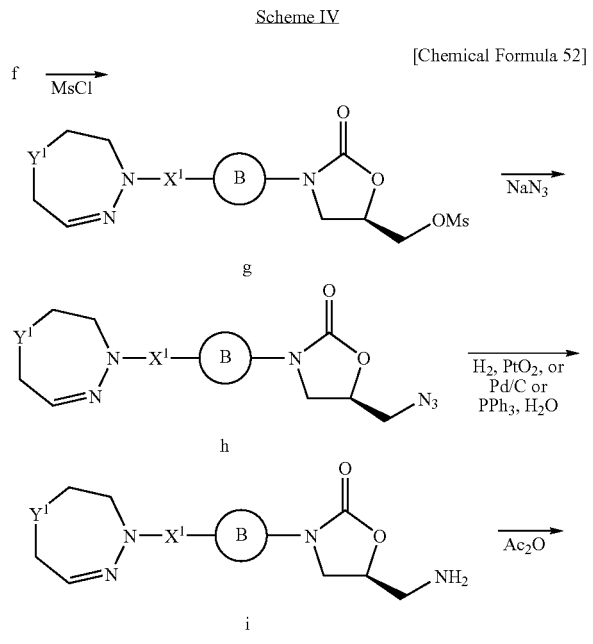

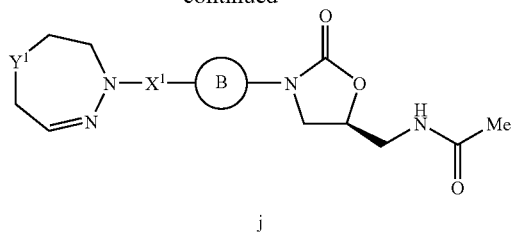

Also, the compound of the invention having an unsaturated 7-membered ring, such as Compounds (I-3), (I-5) and (I-13), can be synthesized by oxidation of a compound having the corresponding saturated 7-membered ring. Preferable oxidizing agents include manganese dioxide, $(COCl)_2$/dimethylsulfoxide (DMSO).

The present invention further provides a compound useful as a synthetic intermediate in the preparation of pharmaceuticals or agricultural chemicals, and various heterocyclic compounds.

[Chemical Formula 53]

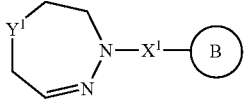

(I-5)

[Chemical Formula 54]

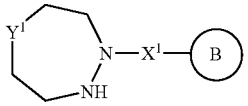

(I-6)

wherein $Y^1$ is $NR^a$, O, S, SO or $SO_2$;

$R^a$ is hydrogen, a substituent selected from Substituent Group S1 or an amino protecting group;

$X^1$ is a single bond, or a heteroatom-containing group selected from the group consisting of —O—, —S—, —$NR^2$—, —CO—, —CS—, —$CONR^3$—, —$NR^4CO$—, —$SO_2NR^5$—, and —$NR^6SO_2$—, wherein $R^2$, $R^3$, $R^4$, $R^5$ and $R^6$ are independently hydrogen or lower alkyl, or lower alkylene or lower alkenylene each optionally interrupted by said heteroatom-containing group; and Ring B is optionally substituted carbocycle or optionally substituted heterocycle.

Compound (I-6) can be converted to Compound (I-5) by an oxidation according to the procedure as shown in Scheme III. As described, Compounds (I-5) and (I-6) are useful, for example, as an intermediate of the antibacterial agent of the invention. Preferable embodiment of each substituent in Compounds (I-5) and (I-6) is as defined for Compound (I-4), but more preferably is as follows.

(1) $X^1$ is a single bond; Ring B is optionally substituted carbocycle. The substituent on ring B is preferably a functional group such as halo, nitro, OH, COOH, amino. The group such as OH, COOH and amino may be protected with a protecting group.

(2) $X^1$ is a single bond; Ring B is optionally substituted heterocycle preferably 5- to 7-membered.

(3) $X^1$ is a single bond; Ring B is benzene ring substituted with nitro and optionally with another substituent (e.g., halo).

(4) $Y^1$ is $NR^a$. $R^a$ is preferably hydrogen, an amino protecting group, optionally substituted lower alkyl, optionally substituted formyl, optionally substituted (lower alkyl)carbonyl, optionally substituted heterocyclecarbonyl, optionally substituted carbamoyl, optionally substituted (lower alkyl) thiocarbonyl, optionally substituted aryl, optionally substituted heterocyclic group, cyano, optionally substituted thioformyl, optionally substituted (lower alkenyl)carbonyl, and optionally substituted heterocycleoxycarbonyl.

The present invention further provides compounds (I-7) to (I-12), which are a synthetic intermediate useful in the preparation of pharmaceuticals or agricultural chemicals, and various heterocyclic compounds.

[Chemical Formula 55]

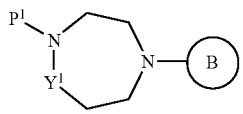

(I-7)

wherein
each variable and its preferable embodiment is as defined above.
$Y^1$ is $NP^2$ or O;
$P^1$ and $P^2$ are independently hydrogen, a substituent selected from Substituent Group S1 or an amino protecting group;
Ring B is optionally substituted and optionally fused benzene ring or optionally substituted heterocycle which is preferably 5- to 7-membered, and more preferably aromatic ring.
More preferably, Ring B is substituted with one or more substituent selected from the group consisting of halo, nitro, amino, amino protected with an amino protecting group, optionally substituted amide, formyl, carboxyl, carboxamide, optionally substituted alkyl group, lower alkoxy, and hydroxyimino, still more preferably, substituted with one or more substituent selected from the group consisting of halo, nitro, amino, formyl and carboxyl.
Preferably, the Compound (I-7) is a compound of the formula (I-8):

[Chemical Formula 56]

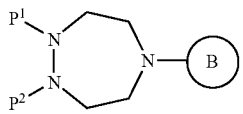

(I-8)

wherein
each variable and its preferable embodiment is as defined above.
More preferably, Ring B is benzene ring, pyridine ring or thiophene ring, each optionally substituted with halo, nitro, formyl or carboxyl.
More preferably, $P^1$ and $P^2$ are independently an amino protecting group such as (lower alkoxy)carbonyl (e.g., tert-butoxycarbonyl), optionally substituted aralkyloxycarbonyl (e.g., benzyloxycarbonyl, p-nitrobenzyloxycarbonyl).
More preferably, Compound (I-8) is the compound as follows. The an amino protecting group (Boc: tert-butoxycarbonyl, Cbz: benzyloxycarbonyl) may be another an amino protecting group.

[Chemical Formula 57]

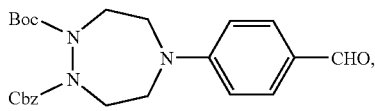
T-14

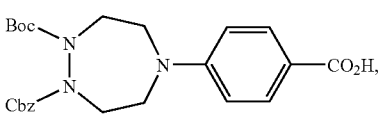
T-15

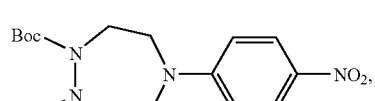
T-16

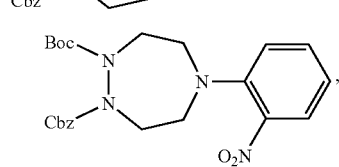
T-17

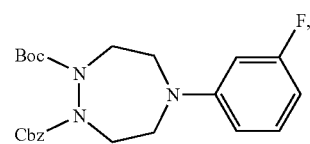
T-18

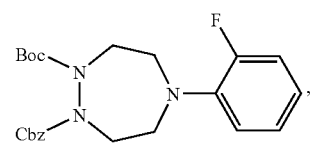
T-19

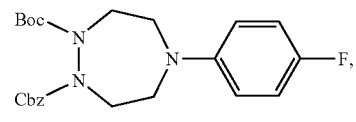
T-20

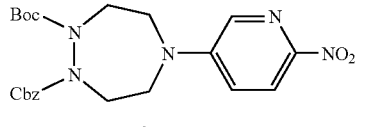
T-21 and

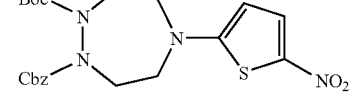
T-22

Preferably, Compound (I-7) is a compound of the formula (I-9):

[Chemical Formula 58]

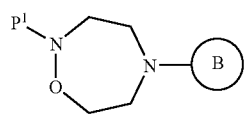

(I-9)

wherein each variable and its preferable embodiment is as defined above.

More preferably, Ring B is benzene ring, pyrydine ring or thiophene ring, each optionally substituted with halo, nitro, formyl or carboxyl.

More preferably, $P^1$ is an amino protecting group such as (lower alkoxy)carbonyl (e.g., tert-butoxycarbonyl), optionally substituted aralkyloxycarbonyl (e.g., benzyloxycarbonyl, p-nitrobenzyloxycarbonyl).

Preferably, Compound (I-9) is the compound as follows. The an amino protecting group (Boc: tert-butoxycarbonyl, Cbz: benzyloxycarbonyl) may be another an amino protecting group.

[Chemical Formula 59]

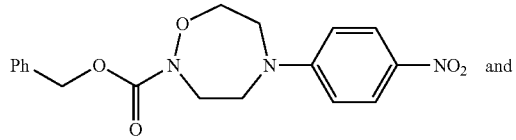

O-7 and

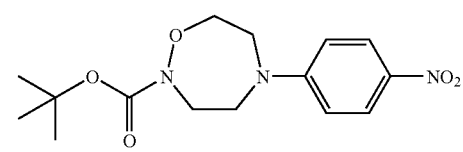

O-15 wherein Ph is phenyl.

Compounds (I-5), (I-6), (I-7) to (I-9), as described above, can be prepared using the following Compounds (I-10) to (I-12) as a starting material.

[Chemical Formula 60]

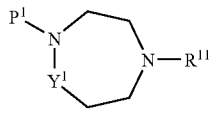

(I-10)

wherein each variable and its preferable embodiment is as defined above.

Preferably, Compound (I-10) is a compound of the formula (I-11).

[Chemical Formula 61]

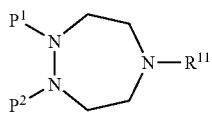

(I-11)

wherein each variable and its preferable embodiment is as defined above.

More preferably, only one of $P^1$, $P^2$ and $P^{11}$ is hydrogen. Still more preferably, either of $P^1$ or $P^2$ is hydrogen, and $P^{11}$ is not hydrogen.

In another preferable embodiment, $P^{11}$ is hydrogen and $P^1$ and $P^2$ are not hydrogen.

In another preferable embodiment, $P^1$ and $P^2$ and $P^{11}$ are independently hydrogen, lower alkyl, (lower alkyl)carbonyl optionally substituted with halo, lower alkyl substituted with hydroxy, an amino protecting group such as (lower alkoxy)carbonyl (e.g., tert-butoxycarbonyl), optionally substituted aralkyloxycarbonyl (e.g., benzyloxycarbonyl, p-nitrobenzyloxycarbonyl), optionally substituted phenyl, or optionally substituted heterocyclic group which is preferably 5- to 7-membered ring, more preferably aromatic ring.

More preferably, $P^1$ and $P^2$ and $P^{11}$ are independently hydrogen, lower alkyl, (lower alkyl)carbonyl optionally substituted with halo, lower alkyl substituted with hydroxy, tert-butoxycarbonyl, benzyloxycarbonyl, optionally substituted phenyl (substituent: nitro, carboxy, halogen, formyl, or hydroxy), or optionally substituted heterocyclic group which is preferably 5- to 7-membered ring, more preferably aromatic ring; substituent: nitro, carboxy, halo, formyl, or hydroxy.

More preferably, $P^1$ is hydrogen; $P^2$ is an amino protecting group; and $P^{11}$ is lower alkyl, (lower alkyl)carbonyl optionally substituted with halo, lower alkyl substituted with hydroxy, an amino protecting group, optionally substituted phenyl or optionally substituted heterocyclic group. More preferably, $P^1$ is hydrogen; $P^2$ is an amino protecting group; and $P^{11}$ is an amino protecting group.

In another preferable embodiment, $P^{11}$ is hydrogen; $P^1$ and $P^2$ are independently lower alkyl, (lower alkyl)carbonyl optionally substituted with halo, lower alkyl substituted with hydroxy, an amino protecting group, optionally substituted phenyl, or optionally substituted heterocyclic group. More preferably, $P^{11}$ is hydrogen; $P^1$ and $P^2$ are independently an amino protecting group.

Particularly preferably, Compound (I-11) is the compound as follows.

[Chemical Formula 62]

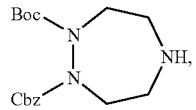

T-1

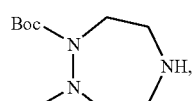

T-2

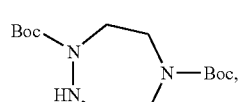

T-3

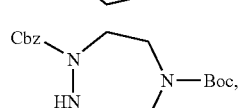

T-4

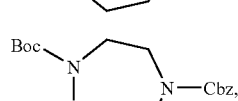

T-5

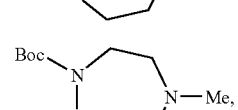

T-6

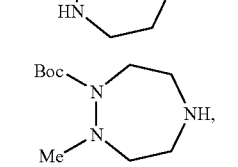

T-7

-continued

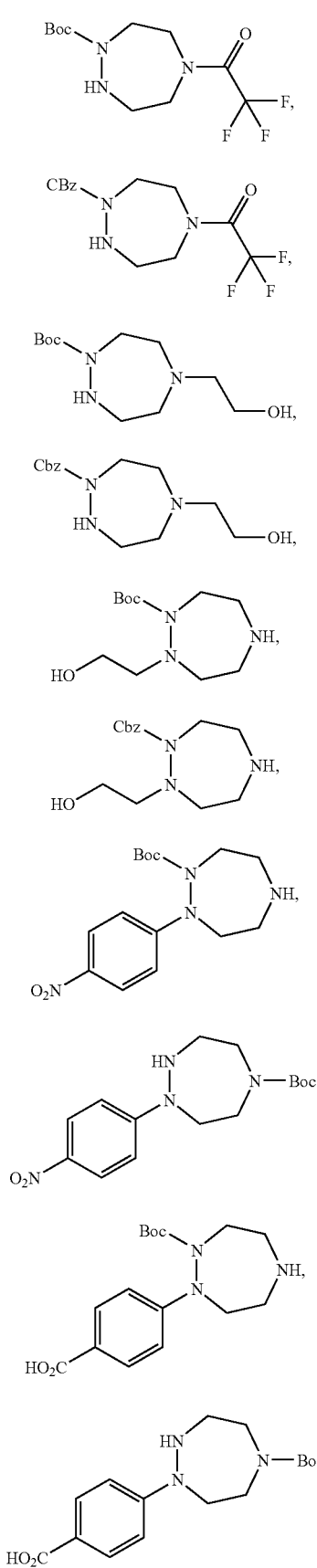

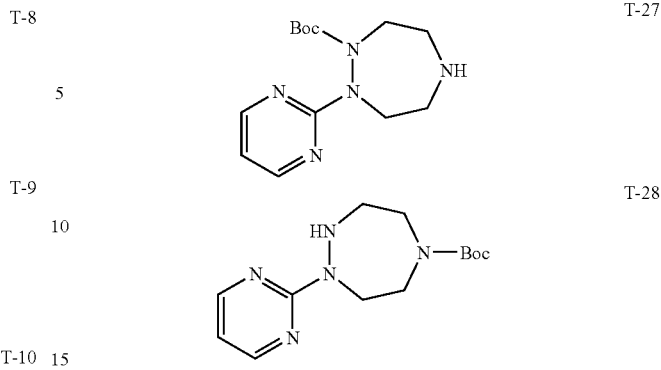

T-29 to T-36 described bellow in Examples E-2 are also preferable.

Compound (I-10) is preferably Compound (I-12).

[Chemical Formula 63]

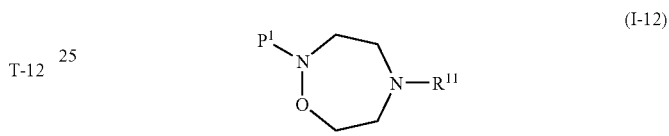

(I-12)

wherein each variable and its preferable embodiment is as defined above.

More preferably, $P^1$ and $P^{11}$ are independently hydrogen, an amino protecting group such as (lower alkoxy)carbonyl (e.g., tert-butoxycarbonyl), optionally substituted aralkyloxycarbonyl (e.g., benzyloxycarbonyl, p-nitrobenzyloxycarbonyl) or lower alkyl optionally substituted with hydroxy.

More preferably, $P^1$ is hydrogen; $P^{11}$ is an amino protecting group or lower alkyl optionally substituted with hydroxy.

In another preferable embodiment, $P^{11}$ is hydrogen; $P^1$ is an amino protecting group or lower alkyl optionally substituted with hydroxy. More preferably, $P^{11}$ is hydrogen; $P^1$ is lower alkyl optionally substituted with hydroxy, or tert-butoxycarbonyl or benzyloxycarbonyl.

More preferably, Compound (I-12) is the compound as follows.

[Chemical Formula 64]

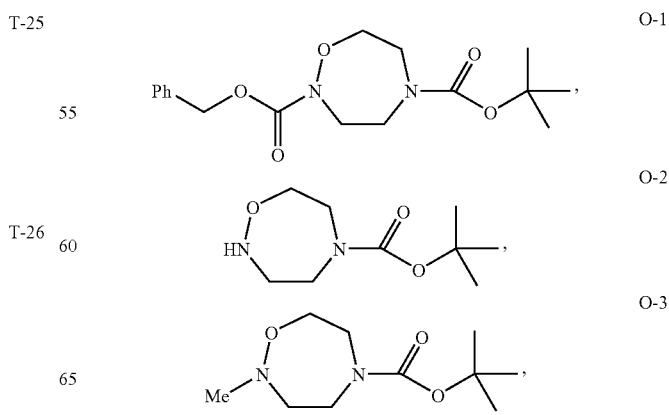

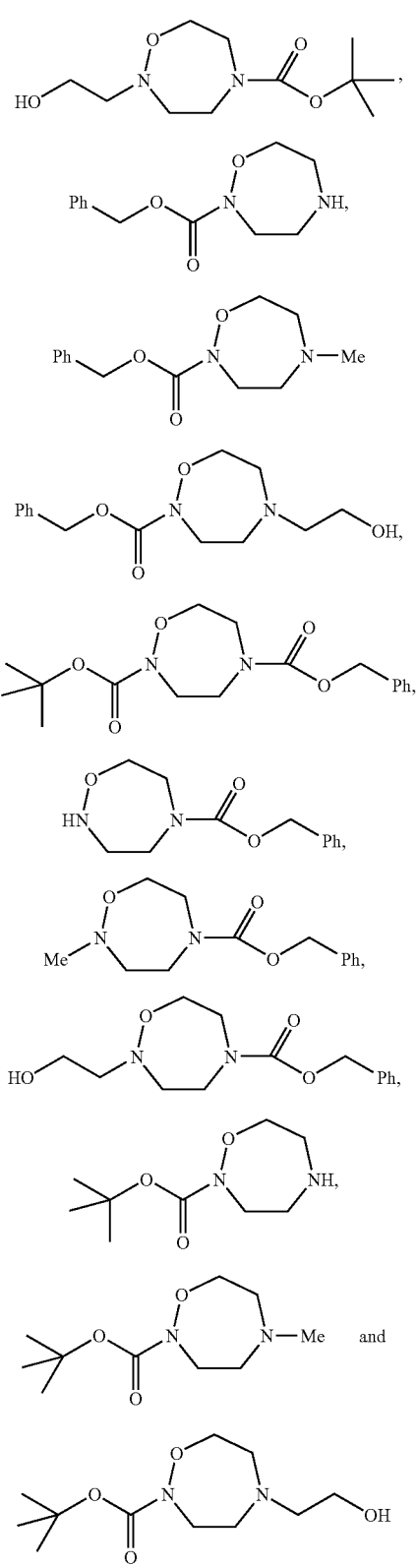

The present invention also provides a pharmaceutical composition comprising a compound of the invention or a pharmaceutically acceptable salt thereof or a hydrate thereof as an active ingredient. Based on the antimicrobial activity of the compound, one example of such pharmaceutical composition is an timicrobial drug. When the compound of the invention is used in a treatment, the compound, a salt thereof or solvate thereof is administered to an imal, including human, which is affected with infection in a therapeutically effective amount. Route for administration may be oral or parenteral. For this purpose, the compound of the invention or a salt thereof is combined with a pharmaceutically acceptable carrier, diluent or excipient and incorporated into a capsule or compressed into a tablet. Alternatively, the composition may be in a dosage form such as powder or granule. For parenteral administration, it is formulated into an aqueous solution or suspension suitable for subcutaneous injection, intravenous injection, intraperitoneal injection, intramuscular injection, etc. Also, the composition can be provided as suppositories, topical formulations, eye-drops and the like.

Pharmaceutically acceptable salts of the compound of the invention include salts with an inorganic base, ammonia, organic base, inorganic acid, organic acid, basic amino acid, halogen ion, etc., or intramolecular salts. Examples of the inorganic base include alkali metals (Na, K, etc.), alkaline earth metals (Ca, Mg, etc.). Examples of the organic base include trimethylamine, triethylamine, choline, procaine, ethanolamine, etc. Examples of the inorganic acid include hydrochloric acid, hydrobromic acid, sulphuric acid, nitric acid, phosphoric acid and the like. Examples of organic acid include p-toluenesulphonic acid, methanesulphonic acid, formic acid, trifluoro acetate, maleic acid and the like. Examples of basic amino acid include lysine, arginine, ornithine, histidine and the like. The above salts may be a solvate.

Oral administration can be practiced in a solid or liquid dosage form prepared according to a conventional method, such as tablet, powder, capsule, granule, suspension, liquid, syrup, lozenge, sublingual tablet and other dosage forms. If necessary, unit dosage form for oral administration can be microcapsulated. Also, such formulation may be coated or embedded into polymer or wax, in order to prolong the duration of activity or provide sustained release.

Parenteral administration can be practiced in a liquid dosage form prepared according to a conventional method, such as an injectable solution and suspension. Among others, oral administration and intravenous administration by injection are preferred. Of course, administration should be practiced in a dosage form suitable for each fashion of the administration.

For oral administration, daily dose is generally about 10 mg to 4000 mg, preferably 100 mg to 2000 mg per day. For parenteral administration, the daily dose is about 10 mg to 4000 mg, preferably 50 mg to 2000 mg per day.

The Examples are described bellow.
(Abbreviations)
Ac=acetyl group, Et=ethyl group, Me=methyl group, Ph=phenyl group, Boc=t-butoxycarbonyl group, Cbz=benzyloxycarbonyl group, Bn=benzyl group.

REFERENCE EXAMPLE 1

[Chemical Formula 65]

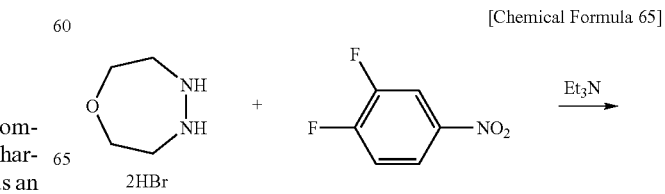

-continued

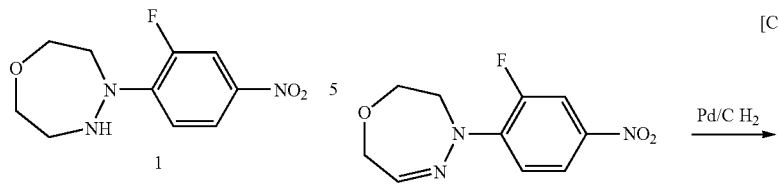

(1) Hydrobromide (1 g, 3.79 mmol) was suspended in 2-propanol (10 mL) and added with triethylamine (0.63 ml, 4.55 mmol) and 3,4-difluoronitrobenzene, and heated under reflux for four hours. Purified water and EtOAc were added, and 2-propanol was removed. The aqueous layer was extracted with EtOAc, and the organic layer was washed with purified water and brine, and dried over magnesium sulphate. The drying reagent was removed, and the solvent was evaporated. The residue was subjected to silica gel chromatography to afford Compound 1 as a yellow solid (222 mg).

$^1$ H-NMR (CDCl$_3$) δ: 3.14 (2H, q, J=5.8 Hz), 3.64 (1H, t, J=6.6 Hz), 3.7 6-3.80 (2H, m), 3.8 5-3.88 (2H, m), 3.94 (2H, t, J=4.4 Hz), 7.55 (1H, t, J=9.1 Hz), 7.88 (1H, dd, J=13.6, 2.5 Hz), 7.95 (1H, dd, J=9.1, 2.5 Hz).

[Chemical Formula 66]

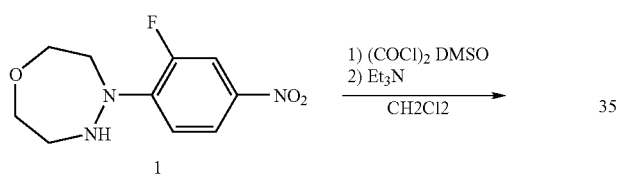

(2) Dimethylsulphoxide (0.889 mL, 12.51 mmol) was dissolved in dichloromethane (5 mL) and added dropwise with oxalyl chloride (0.548 mL, 0.626 mmol) at −78° C. Compound 1 (150 mg) in dichloromethane (1.5 mL) was added dropwise and stirred for 30 minutes. Triethylamine (2.6 mL, 18.77 mmol) was added and stirred for additional 30 minutes. Water was added and the aqueous layer was extracted with EtOAc. The organic layer was washed with purified water and brine, dried over magnesium sulphate. The drying reagent was removed, and the solvent was evaporated. The residue was subjected to silica gel chromatography to afford compound 2 as a yellow solid (158 mg).

$^1$H-NMR (CDCl$_3$) δ: 3.74 (2H, dq, J=5.6, 1.8 Hz), 3.97-4.00 (2H, m), 4.36 (2H, d, J=3.7 Hz), 7.05 (1H, t, J=3.7 Hz), 7.86-8.03 (3H, m).

[Chemical Formula 67]

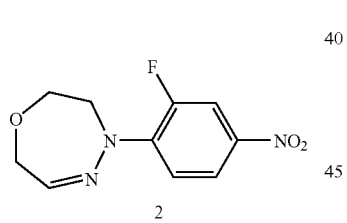

(3) Compound 2 (155 mg) was dissolved in methanol (1.5 mL) and tetrahydrofuran (1.5 mL), and 10% palladium on carbon (31 mg) was added and stirred for 4 hours under hydrogen atmosphere. The reaction was filtered and concentrated, and the residue was subjected to silica gel chromatography to afford Compound 3 as a yellow oil (77 mg).

$^1$ H-NMR (CDCl$_3$) δ: 3.40-3.46 (2H, m), 3.63 (2H, br s), 3.81-3.86 (2H, m), 4.26 (2H, d, J=3.9 Hz), 6.39-6.44 (2H, m), 6.90 (1H, t, J=3.9 Hz), 7.40-7.32 (1H, m).

[Chemical Formula 68]

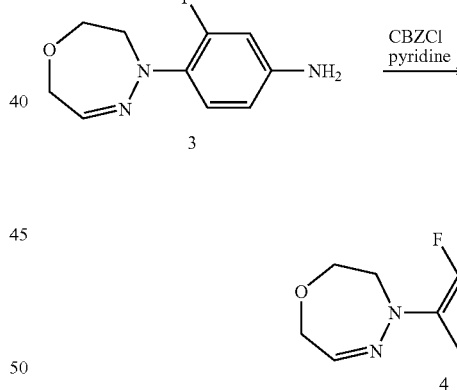

(4) Compound 3 was dissolved in tetrahydrofuran (0.75 mL), and pyridine (0.034 mL), and benzyl chloroformate (0.055 mL) were added and stirred at 0° C. for 4 hours. Purified water was added, and the aqueous layer was extracted with EtOAc. The organic layer was washed with purified water and brine, dried over magnesium sulphate. The drying reagent was removed, and the solvent was evaporated. The residue was subjected to silica gel chromatography to afford Compound 4 as a yellow oil (95 mg).

$^1$ H-NMR (CDCl$_3$) δ: 3.45-3.50 (2H, m), 3.85-3.91 (2H, m), 4.28 (2H, d, J=3.9 Hz), 5.20 (2H, s), 6.63 (1H, br s), 6.90-6.97 (2H, m), 7.29-7.41 (6H, m), 7.59 (1H, t, J=9.1 Hz).

(5) Compound 4 was dissolved in tetrahydrofuran (1 mL) and cooled to -78° C. N-butyllithium (0.38 mL, 1.61M in n-hexane) was added dropwise. (R)-glycidylbutyrate (88 mg) was added and warmed to room temperature and stirred for 3 hours. Purified water was added, and the aqueous layer was extracted with EtOAc. The organic layer was washed with purified water and brine, and dried over magnesium sulphate. The drying reagent was removed, and the solvent was evaporated. The residue was subjected to silica gel chromatography to afford Compound 5 as white amorphous powders (36 mg).

$^{1}$H-NMR (CD$_{3}$OD) δ: 3.51 (2H, td, J=4.4, 1.2 Hz), 3.68 (1H, dd, J=12.2, 4.4 Hz), 3.80-3.94 (4H, m), 4.11 (1H, t, J=8.2 Hz), 4.29 (2H, d, J=3.7 Hz), 4.68-4.78 (1H, m), 6.92 (1H, t, J=3.7 Hz), 7.17-7.24 (1H, m), 7.51-7.67 (2H, m).

The compounds in Reference Examples 2 to 7 were prepared as described in PCT/JP2007/057060. As described, these synthetic intermediates of the invention are useful as a starting material for antimacrobial agents.

REFERENCE EXAMPLE 2

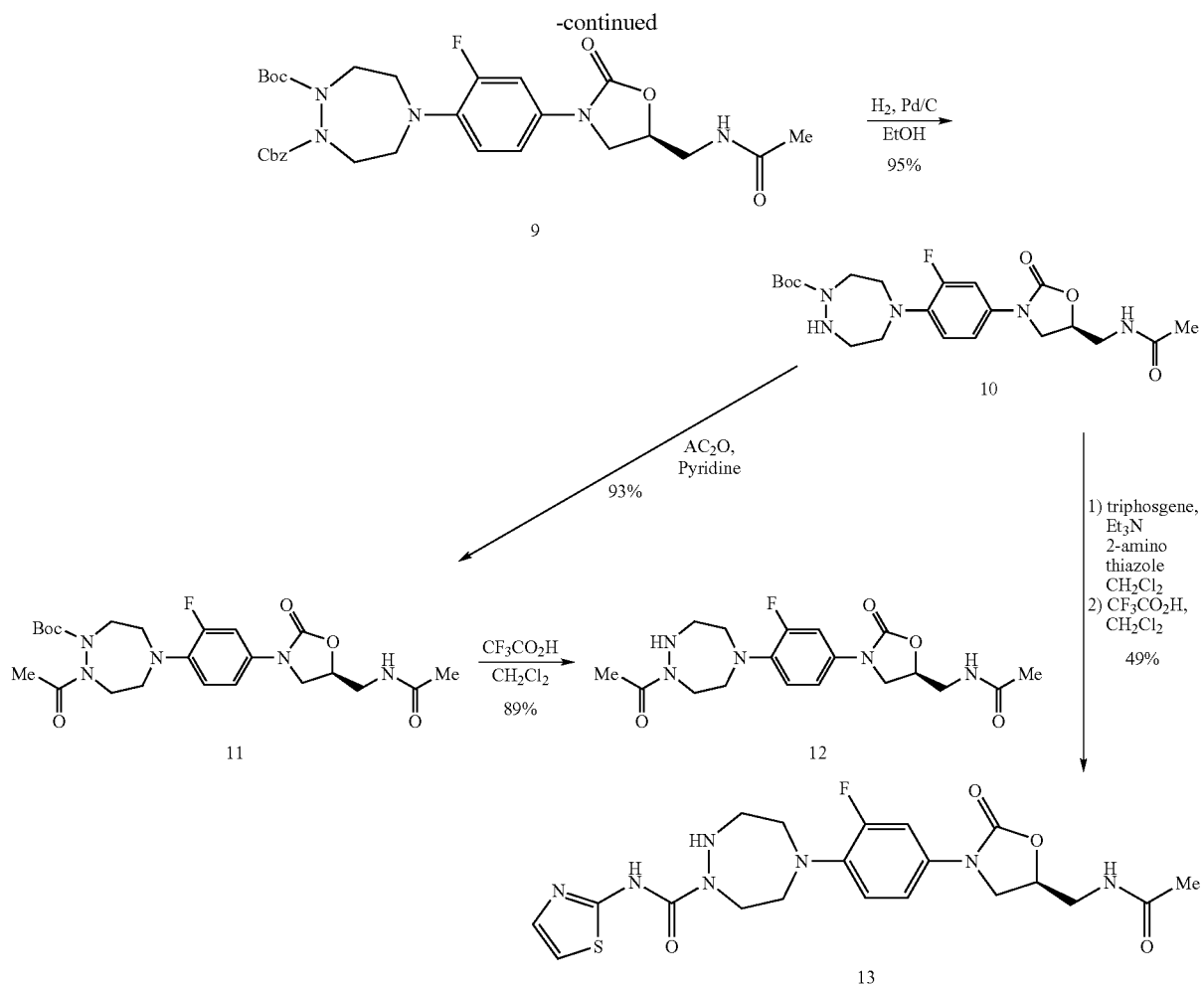

a. Compound 3

An eggplant-shape flask was charged with NaH (60% in mineral oil; 1.2714 g, 31.79 mmol) and washed three times with n-hexane (5 cm³×3). After residual n-hexane was removed under reduced pressure, dimethylformamide (50 cm³) was added. Compound 1 (3.6313 g, 13.64 mmol) was added at room temperature and stirred for 30 minutes at this temperature. Then, Compound 2 (5.6310 g, 15.22 mmol) was added dropwise at room temperature and stirred for 20 minutes at this temperature. The mixture was poured into water (200 cm³), followed by addition of EtOAc (100 cm³) for separation, extraction twice with EtOAc, washing once with water and once with brine, and dryness over anhydrous sodium sulfate. The drying reagent was filtered out, and the solvent was concentrated in vacuo. The residue was purified by silica gel column chromatography (BW-200, 120 g, eluant: 20%→40% EtOAc/n-hexane) to afford Compound 3 (4.9678 g, 10.47 mmol). Yield: 77%.

$^1$H NMR (CDCl$_3$) δ=1.32-1.48 (9H, t-Bu), 3.21-4.32 (8H), 5.03-5.25 (2H, m, CH$_2$Ph), 6.74-6.85 (1H, m), 7.22-7.42 (5H, m), and 7.84-7.95 (2H, m).

b. Compound 4

Compound 3 (4.9678 g, 10.47 mmol) was dissolved in ethanol (200 cm³), and SnCl$_2$.2H$_2$O (13.0278 g, 57.73 mmol) was added and heated to 80-90° C. and stirred for two hours. At the same temperature, NaBH$_4$ (0.2778 g, 7.34 mmol) in ethanol (10 cm³) was added slowly dropwise and stirred for additional one hour. About two-thirds of ethanol was removed, and saturated aqueous sodium bicarbonate was added carefully until any effervescent does not occurred. The mixture was extracted four times with EtOAc, washed with brine, and dried over anhydrous sodium sulfate. The drying reagent was filtered out, the solvent was concentrated in vacuo. The residue was purified by silica gel column chromatography (BW-200, 80 g, eluant: 10%→20%→50%→100% EtOAc/n-hexane) to afford Compound 4 (1.6021 g, 3.60 mol). Also, the compound wherein the Boc-group has been removed was obtained (M=344.38, 1.6304 g, 4.73 mmol, 45%). Yield: 34%.

$^1$H NMR (CDCl$_3$) δ=1.32-1.50 (9H, Boc), 3.00-3.58 (8H, m), 3.90-4.24 (2H, m), 5.05-5.30 (2H, m, CH$_2$Ph), 6.30-6.45 (2H, m), 6.72-6.82 (1H, m), and 7.28-7.37 (5H, m, CH$_2$Ph).

c. Compound 5

Compound 4 (1.6021 g, 3.60 mmol) was dissolved in methanol (20 cm³), and sodium carbonate (0.5856 g, 5.53 mmol) and Boc$_2$O (1.1708 g, 5.36 mmol) was added. The mixture was stirred for 17 hours at room temperature and separated by addition of water (30 cm³) and EtOAc (50 cm³), followed by washing twice with EtOAc, and dryness over anhydrous sodium sulfate. The drying reagent was filtered out, the solvent was concentrated in vacuo. The residue was purified by silica gel column chromatography (BW-200, 50 g, eluant: 10%→20%→30% EtOAc/n-hexane) to afford Compound 5 (1.8683 g, 3.43 mmol). Yield: 95%.

¹H NMR (CDCl₃) δ=1.34-1.52 (18H, Boc), 3.10-3.52 (6H, m), 3.95-4.28 (2H, m), 5.05-5.29 (2H, m, CH₂Ph), 6.38 (1H, brs, NHBoc), 6.77-6.89 (2H, m), and 7.21-7.36 (6H, m).

d. Compound 6

Compound 5 (1.8683 g, 3.43 mmol) in dried THF (20 cm³) was subjected to aryl substitution and cooled to −78° C. To this solution, n-BuLi (1.54 M in n-hexane; 2.5 cm³, 3.85 mmol) was added slowly dropwise, and stirred at this temperature for 10 min. (R)-glycidylbutyrate (0.6084 g, 4.22 mmol) in dried THF (3 cm³) was added slowly dropwise, and the mixture was cooled to room temperature and stirred for 20 minutes. Water (30 cm³) was added, and the mixture was extracted five times with EtOAc and dried over anhydrous sodium sulfate. After filtration, the solvent was removed to obtain the residue (2.2370 g). The residue was dissolved in methanol (20 cm³), added with potassium carbonate (5.0776 g, 36.74 mmol) and stirred for 6 hours at room temperature. Water (30 cm³) was added, and the mixture was extracted five times with EtOAc and dried over anhydrous sodium sulfate. The drying reagent was filtered out, and the solvent was concentrated in vacuo. The residue was purified by silica gel column chromatography (BW-200, 30 g, eluant: 50%→100% EtOAc/n-hexane→2% methanol/dichloromethane) to afford Compound 6 (1.5838 g, 3.01 mmol). Yield: 88%.

¹H NMR (CDCl₃) δ=1.34-1.47 (9H, Boc), 2.59 (1H, br, OH), 3.16-3.40 (6H, m), 3.70-3.82 (1H, m), 3.89-4.27 (5H, m), 4.68-4.78 (1H, m, CH₂CHCH₂OH), 5.06-5.30 (2H, m, CH₂Ph), 6.83-6.93 (1H, m), 7.02-7.13 (1H, m), and 7.27-7.46 (6H, m).

e. Compound 7

A solution of Compound 6 (1.5834 g, 3.01 mmol), triethylamine (0.65 cm³, 4.62 mmol) and dried dichloromethane (30 cm³), which has been cooled to 0° C. and diluted with dried dichloromethane (3 cm³), was added dropwise with methanesulfonyl chloride (0.3 cm³, 3.88 mmol) and stirred for 20 minutes at 0° C. Saturated aqueous NaHCO₃ (50 cm³) was added, and the mixture was extracted three times with trichloromethane and dried over anhydrous sodium sulfate. After filtration, the solvent was removed to obtain the residue (1.9525 g). The residue was dissolved in dimethylformamide (15 cm³), which was added with sodium azide (0.5870 g, 9.03 mmol) and stirred for two hours at 80 to 90° C. Water (50 cm³) was added, the mixture was extracted three times with EtOAc. The organic layer was washed sequentially with water and brine, and dried over anhydrous sodium sulfate. After filtration, the solvent was removed to obtain the residue. Purification by silica gel column chromatography (BW-200, 40 g, eluant: 25%→30%→50% EtOAc/n-hexane) afforded Compound 7 (1.5894 g, 2.79 mmol). Yield: 93%.

¹H NMR (CDCl₃) δ=1.34-1.47 (9H, Boc), 3.18-4.28 (12H, m), 4.73-4.83 (1H, m, CH₂CHCH₂N₃), 5.06-5.28 (2H, m, CH₂Ph), 6.85-6.93 (1H, m), 7.02-7.13 (1H, m), and 7.28-7.45 (6H, m).

f. Compound 8

Compound 7 (1.5894 g, 2.79 mmol) was dissolved in THF (20 cm³), followed by added with triphenylphosphine (1.1128 g, 4.240 mmol) and water (1 cm³) at room temperature. The mixture was stirred for 16 hours at room temperature, warmed to about 60° C. and stirred for two hours. After confirming the consumption of the starting material, the solvent was removed, and the residue was purified by silica gel column chromatography (BW-200, 30 g, eluant: EtOAc →5%→15% methanol/trichloromethane) to afford Compound 8 (1.4394 g, 2.65 mmol). Yield: 95%.

¹H NMR (CDCl₃) δ=1.34-1.48 (9H, Boc), 2.95 (1H, dd, J=5.8, 13.7 Hz), 3.11 (1H, dd, J=4.0, 13.7 Hz), 3.16-3.59 (6H, m), 3.76-3.84 (1H, m), 3.94-4.27 (3H, m), 4.62-4.72 (1H, m, CH₂CHCH₂N₃), 5.06-5.29 (2H, m, CH₂Ph), 6.84-6.92 (1H, m), 7.03-7.14 (1H, m), and 7.25-7.48 (6H, m).

g. Compound 9

Compound 8 (1.4394 g, 2.65 mmol) was dissolved in pyridine (20 cm³). Acetic anhydride (2.0 cm³) was added and stirred for 1 hour at room temperature. The solvent was removed, and the residue was purified by silica gel column chromatography (BW-200, 30 g, eluant: 0%→3%→5% methanol/trichloromethane) to afford Compound 9 (1.4769 g, 2.52 mmol). Yield: 95%.

h. Compound 10

Compound 9 (1.1139 g, 1.902 mmol) was dissolved in 95% ethanol (50 cm³). 10% Pd/C (0.2073 g) was added for H₂ Substitution carefully, and the mixture was stirred at room temperature for 90 hours. After filtration through celite, the solvent was removed, and the residue was purified by silica gel column chromatography (BW-200, 30 g, eluant: 0%→2%→4% methanol/trichloromethane) to afford Compound 10 (0.8159 g, 1.807 mmol). Yield: 95%

¹H NMR (CDCl₃) δ=1.38 (9H, brs, Boc), 2.03 (3H, s, ac), 3.08-3.16 (2H, m), 3.40-3.48 (2H, m), 3.53-3.77 (8H, m), 4.00 (1H, t, J=9.0 Hz), 4.72-4.81 (1H, m), 6.45 (1H, brs, NHAc), 6.87 (1H, t, J=9.0 Hz), 6.99 (1H, dd, J=2.4, 9.0 Hz), and 7.36 (1H, dd, J=2.4, 15.1 Hz).

i. Compound 11

Compound 10 (0.2016 g, 0.477 mmol) was dissolved in pyridine (5 cm³). Acetic anhydride (3 cm³) was added and stirred for 18 hours at room temperature. The solvent was removed, and the residue was purified by silica gel column chromatography (BW-200, 15 g, eluant: 50%→100% EtOAc/n-hexane→4% methanol/trichloromethane) to afford Compound 11 (0.2055 g, 0.416 mmol). Yield: 93%.

¹H NMR (CDCl₃) δ=1.48 (9H, s, Boc), 2.03 (3H, s, NHAc), 2.05 (3H, s, NNAc), 3.08-3.78 (10H, m), 4.01 (1H, dt, J=3.0, 9.1 Hz), 4.25-4.40 (1H, m), 4.72-4.82 (1H, m), 6.08 (1H, t, J=6.0 Hz, NHAc), 6.89 (1H, t, J=9.1 Hz), 7.05 (1H, br d, J=9 Hz), and 7.40 (1H, dd, J=2.5, 14.6 Hz).

j. Compound 12

Compound 11 (0.1462 g, 0.296 mmol) was dissolved in dichloromethane (5 cm³). Trifluoroacetic acid (1 cm³) was added and stirred at room temperature for two hours. Saturated aqueous potassium carbonate was added to adjust to neutral pH, and followed by extraction five times with trichloromethane. After dryness over anhydrous sodium sulfate, the drying reagent was filtered out, and the solvent was removed. The residue was purified by silica gel column chromatography (BW-200, 15 g, eluant: 0%→5%→10% methanol/trichloromethane) to afford Compound 12 (0.1034 g, 0.263 mmol). Yield: 89%.

¹H NMR (CDCl₃) δ=1.97 (3H, s, NNAc), 2.03 (3H, s, NHAc), 3.06-3.14 (1H, m), 3.16-3.23 (1H, m), 3.34-3.44 (3H, m), 3.54-3.80 (6H, m), 3.88-3.94 (1H, m), 4.01 (1H, t, J=8.8 Hz), 4.72-4.81 (1H, m), 6.08-6.16 (1H, br), 6.84-6.93 (1H, m), 6.96-6.75 (1H, m), and 7.37-7.48 (1H, m).

k. Compound 13

2-aminothiazole (135.6 mg, 1.354 mmol) was dissolved in dichloromethane (10 cm³). Triphosgene (138.1 mg, 0.465 mmol) was added at 0° C. Triethylamine (0.4 cm³, 2.846 mmol) was added dropwise, and Compound 10 (154.4 mg, 0.342 mmol) was added. The mixture was left to cool at room temperature and stirred for 75 hours. 10% aqueous citric acid (20 cm$^3$) was added and extracted twice with trichloromethane. After dryness over anhydrous sodium sulfate, the drying reagent was filtered out. The solvent was removed, and the residue was dissolved in dichloromethane (10 cm$^3$), followed by addition with trifluoroacetic acid (1.0 cm$^3$) and stirred at room temperature for 24 hours. The mixture was neutralized with saturated aqueous sodium carbonate and extracted five times with 10% methanol/trichloromethane. After dryness over anhydrous sodium sulfate, the drying reagent was filtered out. The solvent was removed, and the residue was purified by silica gel column chromatography (BW-200, 10 g, eluant: 1%→3%→5% methanol/trichloromethane) to afford Compound 13 (80.0 mg, 0.168 mmol). Yield: 49%.

$^1$H NMR (CDCl$_3$) δ=2.02 (3H, s, Ac), 3.22-4.25 (12H, m), 4.70-4.81 (1H, m), 6.73 (1H, t, J=6.1 Hz, NHAc), 6.84-7.03 (3H, m), 7.33-7.43 (2H, m), and 9.84 (1H, s, N=C—NHC=O).

REFERENCE EXAMPLE 3

[Chemical Formula 71]

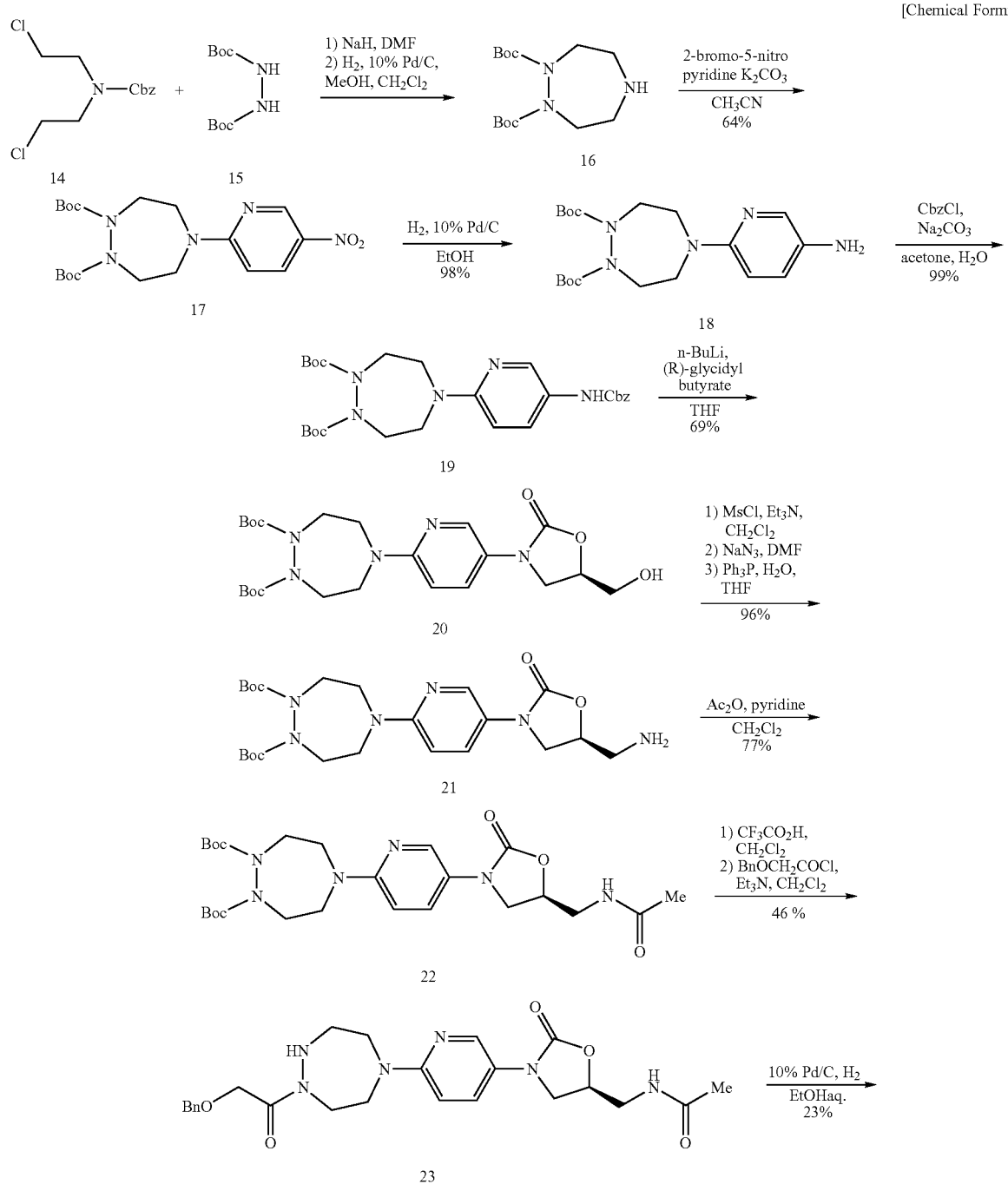

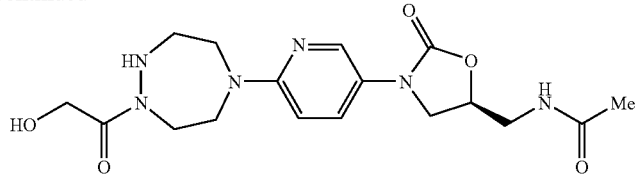

24 a. Compound 16

To a suspension of commercially available bis(chloroethyl)amine monohydrate (5.7974 g, 32.48 mmol) and sodium carbonate (3.6300 g, 34.25 mmol) in methanol (80 cm$^3$) and water (40 cm$^3$), benzyl chloroformate (6.0 cm$^3$, 33.77 mmol) was added slowly dropwise at 0° C., and the mixture was stirred for 3 hours at this temperature. Methanol was removed by half, water (50 cm$^3$) was added, followed by extraction four times with dichloromethane, and washing with brine. After dryness over sodium sulfate, filtration and concentration to obtain the residue containing Compound 14 as a main product (10.674 g).

Another eggplant-shape flask was charged with NaH (60% in mineral oil; 2.0544 g, 51.36 mmol) and washed with n-hexane (5 cm$^3$×3). Residual n-hexane was removed under reduced pressure, dimethylformamide (80 cm$^3$) was added for aryl substitution. After cooling to 0° C., Compound 15 (4.1983 g, 18.07 mmol) was added and stirred for 10 min. at this temperature. The above residue containing Compound 14 (10.674 g) was dissolved in dimethylformamide (20 cm$^3$) and added dropwise to the mixture, which is stirred gently for 41 hours with cooling to room temperature. The mixture was poured into water (400 cm$^3$), extracted three times with EtOAc and once with water, and washed with brine.

Purification by silica gel column chromatography (BW-200, 150 g, eluant: 15%→20%→30% EtOAc/n-hexane) afforded 7.1642 g of residue containing desired 7-membered ring compound (5-Cbz derivative) as a main product. The residue was dissolved in methanol (120 cm$^3$) and dichloromethane (40 cm$^3$), and 10% Pd/C (0.7241 g) added for H$_2$ substitution and stirred at room temperature for 23 hours. After celite filtration, the filtrate was concentrated, and the residue was purified by silica gel column chromatography (BW-200, 100 g, eluant: EtOAc→methanol:triethylamine:dichloromethane=10:2:88) to afford Compound 16 (3.4838 g, 11.56 mmol). Yield: 64%.

$^1$H NMR (CDCl$_3$) δ=1.43-1.51 (18H, Boc×2), 2.96-3.54 (6H, m), and 3.98-4.26 (2H, m), and 6.62 (1H, brs, NH).

b. Compound 17

Compound 16 (5.6532 g, 18.76 mmol) was dissolved in CH$_3$CN (40 cm$^3$), followed by added with potassium carbonate (2.8864 g, 20.88 mmol) and 2-chloro-5-nitro pyridine (3.5675 g, 22.50 mmol). The mixture was heated under reflux for 19 hours. Water (50 cm$^3$) was added to the mixture, which was then extracted four times with EtOAc. After dryness over anhydrous sodium sulfate, the drying reagent was filtered out. The solvent was removed, and the residue was purified by silica gel column chromatography (BW-200, 120 g, eluant: 10%→20%→30% EtOAc/n-hexane) to afford solid Compound 17 (5.0881 g, 12.02 mmol). Yield: 64%

$^1$H NMR (CDCl$_3$) δ=1.43 (18H, s, Boc×2), 3.12-3.45 (2H, m), 3.66-4.31 (6H, m), 6.53 (1H, d, J=9.6 Hz), 8.23 (1H, dd, J=2.8, 9.6 Hz), and 9.04 (1H, m).

c. Compound 18

Compound 17 (5.2346 g, 12.36 mmol) was dissolved in ethanol (100 cm$^3$), followed by added with 10% Pd/C (1.4253 g) to obtain a suspension. The suspension was subjected to hydrogen substitution and stirred at room temperature for 3.5 hours. After filtration through celite, the solvent was removed. The residue (0.8354 g) was purified by silica gel column chromatography (BW-200, 80 g, eluant: 30%→50%→100% EtOAc/n-hexane) to afford Compound 18 (4.7463 g, 12.06 mmol). Yield: 98%.

d. Compound 19

Compound 18 (4.7463 g, 12.06 mmol) was dissolved in acetone (40 cm$^3$) and water (20 cm$^3$), followed by added with sodium carbonate (1.7605 g, 16.61 mmol) and benzyl chloroformate (2.60 cm$^3$, 14.63 mmol), and stirred at room temperature for 1 hour. Acetone was removed, and EtOAc (100 cm$^3$) was added to separate the phase. After dryness over anhydrous sodium sulfate, the drying reagent was filtered out. The solvent was removed, and the residue was purified by silica gel column chromatography (BW-200, 90 g, eluant: 10%→35% EtOAc/n-hexane) to afford Compound 19 (6.2841 g, 11.91 mmol).

e. Compound 20

Compound 19 (6.2841 g, 11.91 mmol) was dissolved in dried THF (50 cm$^3$) and subjected to aryl substitution and cooled to −78° C. To this solution, n-BuLi (1.58 M in n-hexane; 8.0 cm$^3$, 12.64 mmol) was added slowly dropwise, followed by stirring at this temperature for 5 min. (R)-glycidyl butyrate (1.9001 g, 13.18 mmol) in dried THF (2 cm$^3$) was added dropwise slowly, and left to cool at room temperature and stirred for 21 hour. Water (50 cm$^3$) was added, and the mixture was extracted four times with EtOAc, and washed once with brine. After dryness over anhydrous sodium sulfate, the drying reagent was filtered out. The solvent was removed, and the residue was purified by silica gel column chromatography (BW-200, 80 g, eluant: 50%→100% EtOAc/n-hexane) to afford Compound 20 (4.0759 g, 8.258 mmol). Yield: 69%.

$^1$H NMR (CDCl$_3$) δ=1.43 (18H, s, Boc×2), 2.75 (1H, brs, OH), 3.10-4.26 (12H, m), 4.69-4.79 (1H, m), 6.53 (1H, d, J=9.3 Hz), 7.82-7.92 (1H, m), and 8.07-8.12 (1H, m).

f. Compound 21

Compound 20 (4.0759 g, 8.26 mmol), triethylamine (1.8 cm$^3$, 12.81 mmol) and dried dichloromethane (80 cm$^3$) were charged and cooled to 0° C., and methanesulfonyl chloride (0.8 cm$^3$, 10.34 mmol) was added dropwise, and the mixture was stirred at 0° C. for 20 min. Saturated aqueous sodium bicarbonate (50 cm$^3$) was added to separate the phase, and the aqueous layer was extracted twice with trichloromethane. The organic layer was combined and dried over anhydrous sodium sulfate, filtered, and removed the solvent. The residue (4.8528 g) was dissolved in dimethylformamide (40 cm$^3$), followed by added with sodium azide (1.0125 g, 15.57 mmol) and stirred at 40 to 50° C. for 15 hours. Water (150 cm$^3$) was added, extracted three times with EtOAc and washed once with brine. After dryness over anhydrous sodium sulfate, the drying reagent was filtered out, and the solvent was removed. The residue (4.4467 g) was dissolved in THF (40 cm$^3$), followed by added with triphenylphosphine (3.2983 g, 12.58 mmol) and water (2.0 cm$^3$) at room temperature. The mixture was stirred for two hours at 50° C. The solvent was removed, and the residue was purified by silica gel column chromatography (BW-200, 100 g, eluant: EtOAc→15% methanol/ trichloromethane) to afford Compound 21 (3.8884 g, 7.89 mmol). Yield: 96%.

$^1$H NMR (CDCl$_3$) δ=1.43 (18H, s, Boc×2), 2.88-4.26 (12H, m), 4.63-4.75 (1H, m), 6.55 (1H, d, J=9.3 Hz), 7.86-7.96 (1H, m), and 8.06-8.12 (1H, m).

g. Compound 22

Compound 21 (1.0932 g, 2.219 mmol) in dichloromethane (10 cm$^3$) was added with pyridine (1.0 cm$^3$) and acetic anhydride (1.0 cm$^3$), and the mixture was stirred at room temperature for 25 hours. The solvent was removed, and the residue was purified by silica gel column chromatography (BW-200, 40 g, eluant: 50% EtOAc/n-hexane→3% methanol/ EtOAc→3% methanol/trichloromethane) to afford Compound 22 (0.9087 g, 1.700 mmol). Yield: 77%.

$^1$H NMR (CDCl$_3$) δ=1.43 (18H, s, Boc×2), 2.03 (3H, s, ac), 3.10-4.26 (12H, m), 4.73-4.82 (1H, m), 6.02 (1H, t, J=6.2 Hz, NHAc), 6.55 (1H, d, J=9.3 Hz), 7.76-7.83 (1H, m), and 8.07-8.11 (1H, m).

h. Compound 23

Compound 22 (0.2444 g, 0.457 mmol) in dichloromethane (10 cm$^3$) was added with trifluoroacetic acid (1.0 cm$^3$) and stirred at room temperature for 3 hours. The solvent was removed, and the residue was dissolved in dichloromethane (10 cm$^3$), followed by added with BnOCH$_2$COCl (0.1293 g, 0.700 mmol) in triethylamine (0.5 cm$^3$) and dichloromethane (2 cm$^3$) and stirred at room temperature for 21 hours. Water (20 cm$^3$) was added and extracted five times with 10% methanol/trichloromethane. After dryness over anhydrous sodium sulfate, the drying reagent was filtered out. The solvent was removed, and the residue was purified by silica gel column chromatography (BW-200, 10 g, eluant: 3% methanol/ trichloromethane) to afford Compound 23 (0.1010 g, 0.209 mmol). Yield: 46%.

i. Compound 24

Compound 23 (0.1010 g, 0.209 mmol) in ethanol (5 cm$^3$) was added with 10% Pd/C (0.0981 g) to obtain a suspension. The suspension was subjected to hydrogen substitution, and stirred at room temperature for 64 hours. After filtration through celite, the solvent was removed. The residue (0.8354 g) was purified by silica gel column chromatography (BW-200, 80 g, eluant: 3%→10% methanol/trichloromethane) to afford Compound 24 (0.0190 g, 0.0484 mmol). Yield: 23%.

$^1$H NMR (CDCl$_3$) δ=2.03 (3H, s, ac), 3.00-4.04 (12H, m), 4.33 (2H, s, CH$_2$OH), 4.73-4.83 (1H, m), 6.37 (1H, t, J=6.0 Hz, NHAc), 6.51-6.57 (1H, m), 7.75-7.82 (1H, m), and 8.09-8.12 (1H, m).

REFERENCE EXAMPLE 4

[Chemical Formula 72]

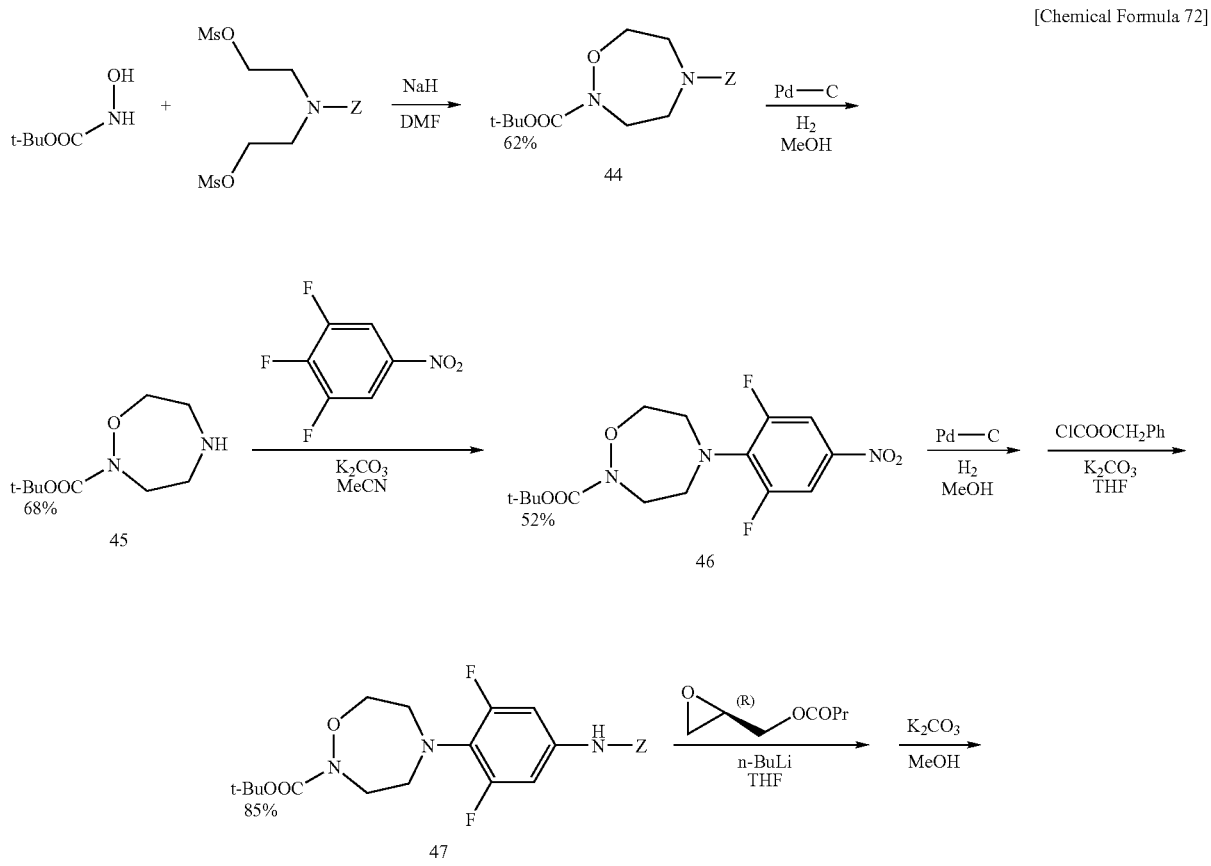

-continued
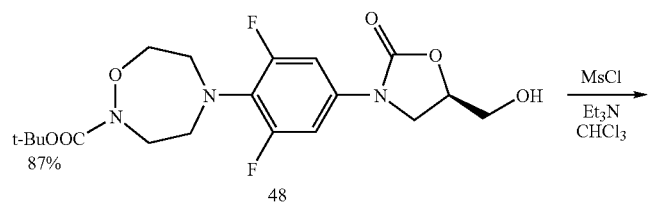
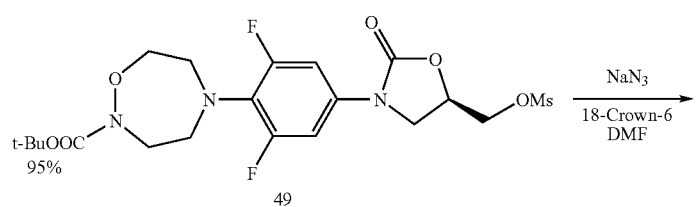
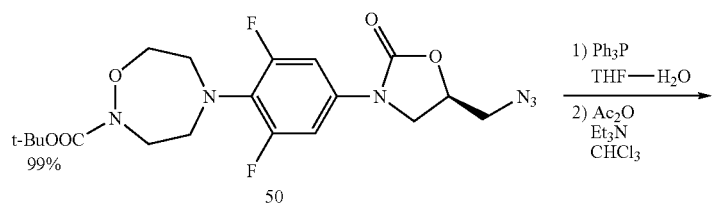
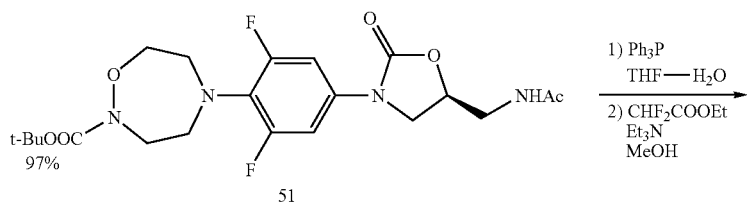
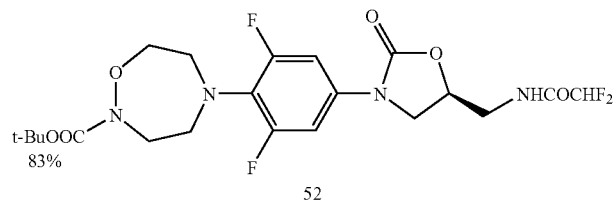
(Z = —COO—CH₂Ph; Ph = phenyl)

Synthesis of Compound (44)

To a solution of tert-Butyl N-hydroxycarbamate (4.01 g) in DMF (40 ml), 60% NaH (2.61 g) is added portionwise at room temperature, at which effervescence occurs. After 15 minutes, mesyl compound (11.59 g) in DMF (40 ml) is dropped slowly, and stirred at room temperature for 15 minutes. The temperature is raised to 100-110° C. and continued stirring carefully for additional 15 minutes. After the reaction, under reduced pressure, the solvent is removed and aqueous $NH_4Cl$ solution is added and extracted with ethyl acetate. After dryness ($Na_2SO_4$), the solvent is removed, and the residue is purified by silica gel chromatography (hexane-ethyl acetate (2:1)) to afford Compound (44) (6.11 g, 62%) as a colorless oil.

44: colorless oil; 1 H-NMR (300MHz, $CDCl_3$) δ 1.48 (s, 9H), 3.56-3.75 (m, 6H), 3.94-4.05 (m, 2H), 5.14 (s, 2H), 7.32 (s, 5H); IR ($CHCl_3$) $v_{max}$ 1693 $cm^{-1}$; MS e/m 277 (3), 206 (3), 115 (10), 101 (29), 91 (99), 57 (100).

Synthesis of Compound (45)

To a solution of oxadiazepane compound (44, 6.84 g) in methanol (70 ml), 10% Pd—C (1.01 g) is added for hydrogenation for 6 hours. After the reaction, the mixture is filtered, and the solvent is removed from the filtrate. The residue is purified by silica gel chromatography (chloroform-methanol (9:1)). Recrystallization from ethanol affords a colorless amorphous Compound (45) (2.80 g, 68%).

45: colorless amorphous, mp 156.5-157.5° C. (EtOH) (decomp.); 1 H-NMR (300MHz, $CDCl_3$) δ 1.51 (s, 9H), 3.41-3.53 (m, 4H), 3.99 (t, 6, 2H), 4.32 (t, 5, 2H)); IR (KBr) $v_{max}$ 1705, 1667 $cm^{-1}$; MS e/m 202 ($M^+$, 1), 129 (9), 99 (12), 72 (17), 57 (100), 43 (86).

Synthesis of Compound (46)

To a solution of amine compound (45, 6.84 g) and 3,4,5-trifluoronitrobenzene (3.11 g) in acetonitrile (60 ml), potassium carbonate (3.19 g) is added, and the mixture is heated at reflux for 15 hours. After the reaction, aqueous $NH_4Cl$ solution is added mad extracted with chloroform-methanol (9:1). After dryness ($Na_2SO_4$), the solvent is removed, and the residue is purified by silica gel chromatography (hexane-ethyl acetate (2:1)).

Recrystallization from hexane affords 3.31 g (52%) of Compound (46) as yellow needle-like crystal.

46: yellow needle-like crystal mp: 87-88° C. (Hexane); 1 H-NMR (300 MHz, $CDCl_3$) δ 1.51 (s, 9H), 3.63-3.71 (m, 4H), 3.84 (t, 6, 2H), 4.13 (t, 5, 2H), 7.72-7.84 (m, 2H); IR (KBr) $v_{max}$ 1678 $cm^{-1}$; MS e/m 359 ($M^+$, 0.3), 303 (1), 286 (1), 256 (4), 201 (7), 172 (7), 57 (100).

Synthesis of Compound (47)

To a solution of the nitro compound (46, 2.90 g) in methanol (40 ml), 10% Pd—C (646 mg) is added, and the mixture is subjected to hydrogenation for 2 hours. After the reaction, the mixture is filtered, and the solvent is removed. After dryness, potassium carbonate (4.6 g) is added to a solution of the residue and carbobenzoxy chloride (3.0 ml) in THF (50 ml), and the solution is stirred for 15 hours. After the reaction, ice-cold water is added and extracted with chloroform. After dryness ($Na_2SO_4$), the solvent is removed. The residue is purified by silica gel chromatography (hexane-ethyl acetate (2:1)). Recrystallization from chloroform-hexane affords 3.19 g (85%) of Compound (47) as colorless prismatic crystal.

47: colorless prismatic, mp 100-101° C. ($CHCl_3$-Hexane); 1 H-NMR (300 MHz, $CDCl_3$) δ 1.51 (s, 9H), 3.63-3.71 (m, 4H), 3.84 (t, 6, 2H), 4.13 (t, 5, 2H), 7.72-7.84 (m, 2H); IR (KBr) $v_{max}$ 1731, 1687 $cm^{-1}$; MS e/m 463 ($M^+$, 4), 334 (4), 305 (4), 225 (6), 197 (6), 165 (14), 108 (10), 91 (91), 79 (12), 57 (100).

Synthesis of Compound (48)

To a solution of carbobenzoxy compound (47, 363 mg) in THF (10 ml), 1.54M BuLi hexane solution (0.60 ml) is added and stirred under argon atmosphere at −78° C. After 10 minutes, (R)-glycidyl butyrate (241 mg) in THF (2 ml) is added and stirred at the temperature for 10 min. and additional 19 hours at room temperature. After the reaction, aqueous $NH_4Cl$ solution is added and extracted with chloroform-methanol (9:1). After dryness ($Na_2SO_4$), the solvent is removed. The residue in methanol (10 ml) is added with potassium carbonate (173 mg) and stirred for 15 minutes. Aqueous $NH_4Cl$ solution is added and extracted with chloroform-methanol (9:1). After dryness ($Na_2SO_4$), the solvent is removed. The residue is purified by silica gel chromatography (chloroform-methanol (9:1)) to afford 291 mg (87%) of Compound (48) as colorless syrup.

48: colorless syrup; 1 H-NMR (300 MHz, $CDCl_3$) δ 1.51 (s, 9H), 3.33-3.43 (m, 4H), 3.71-3.82 (m, 3H), 3.90-4.02 (m, 3H), 4.07 (t, 5, 2H), 4.70-4.79 (m, 1H), 7.06-7.17 (m, 2H); IR ($CHCl_3$) $v_{max}$ 1752, 1705, 1690 $cm^{-1}$; MS e/m 429 ($M^+$, 6), 326 (5), 299 (9), 271 (17), 242 (11), 168 (10), 154 (8), 57 (100).

Synthesis of Compound (49)

To a solution of the hydroxy compound (48, 364 mg) and triethylamine (0.5 ml) in chloroform (10 ml), methanesulfonyl chloride (0.2 ml) is added and stirred under ice-cooling for 15 minutes. After the reaction, aqueous $NaHCO_3$ solution is added and extracted with chloroform-methanol (9:1). After dryness ($Na_2SO_4$), the solvent is removed. The residue is purified by silica gel chromatography (chloroform-methanol (19:1)) to afford 409 mg (95%) of Compound (49) as colorless syrup.

49: colorless syrup; 1 H-NMR (300 MHz, $CDCl_3$) δ 1.51 (s, 9H), 3.11 (s, 3H), 3.33-3.45 (m, 4H), 3.77 (t, 6, 2H), 3.89 (dd, 9, 6, 1H), 4.07 (t, 5, 2H), 4.13 (dd, 9, 9, 1H), 4.43 (dd, 12, 3.5, 1H), 4.53 (dd, 12, 3, 1H), 4.96 (dddd, 9, 6, 3.5, 3, 1H), 7.07-7.18 (m, 2H); IR ($CHCl_3$) $v_{max}$ 1760, 1702, 1688 $cm^{-1}$; MS e/m 507 ($M^+$, 6), 404 (4), 378 (10), 349 (10), 335 (16), 320 (10), 180 (12), 79 (9), 57 (100).

Synthesis of Compound (50)

To a solution of the mesyl compound (49, 406 mg) and 18-Crown-6 (77 mg) in DMF (3 ml), $NaN_3$ (213 mg) is added and heated to 100-110° C. After 1 hour, the solvent is removed. Water is added, and the mixture is extracted with chloroform. After dryness ($Na_2SO_4$), the solvent is removed. The residue is purified by column chromatography (chloroform-methanol (19:1)) to afford 360 mg (99%) of colorless gummy Compound (50).

50: colorless gum; 1 H-NMR (300 MHz, $CDCl_3$) δ 1.51 (s, 9H), 3.34-3.44 (m, 4H), 3.60 (dd, 13.5, 4, 1H), 3.71-3.85 (m, 4H), 4.01-4.13 (m, 3H), 4.78-4.88 (m, 1H), 7.08-7.19 (m, 2H); IR ($CHCl_3$) $v_{max}$ 2105, 1757, 1690 $cm^{-1}$; MS e/m 454 ($M^+$, 5), 404 (4), 325 (4), 267 (5), 154 (11), 57 (100).

Synthesis of Compound (51)

A combined solution of the azide compound (50, 101 mg) and triphenylphosphine (123 mg) in THF (5 ml) and water (0.5 ml) is heated under reflux. After 1 hour, the solvent is removed and dried. The residue and triethylamine (1 ml) in chloroform (10 ml) is added with acetic anhydride (0.25 ml) dropwise and stirred for 1 hour. After the reaction, aqueous NaHCO$_3$ solution is added, and the mixture is extracted with chloroform-methanol (9:1). After dryness (Na$_2$SO$_4$), the solvent is removed. The residue is purified by preparative thin-layer chromatography (chloroform-methanol (19:1)) to afford 101 mg (97%) of colorless gummy compound (51).

51: colorless gum; 1 H-NMR (300 MHz, CDCl$_3$) δ 1.51 (s, 9H), 2.03 (s, 3H), 3.34-3.43 (m, 4H), 3.60-3.71 (m, 2H), 3.72-3.81 (m, 3H), 4.01 (dd, 9, 9, 1H), 4.07 (t, 5, 2H), 4.76-4.85 (m, 1H), 6.99 (br t, 6, NH), 7.04-7.15 (m, 2H)); IR (CHCl$_3$) ν$_{max}$ 1750, 1673 cm$^{-1}$; MS e/m 470 (M$^+$, 14), 367 (6), 341 (9), 312 (10), 298 (10), 239 (14), 183 (9), 180 (13), 154 (9), 57 (100).

Synthesis of Compound (52)

A combined solution of the azide compound (50, 633 mg) and triphenylphosphine (579 mg) in THF (10 ml) and water (1 ml) is heated at reflux. After 30 minutes, the solvent is removed. The dried residue and triethylamine (2 ml) in methanol (10 ml) is added dropwise with CHF$_2$COOEt (1 ml) and stirred for 3 hours. After the reaction, the solvent is removed. The residue is purified by column chromatography (chloroform-methanol (19:1)) to afford 587 mg (83%) of colorless gummy compound (52).

52: colorless gum; 1 H-NMR (300 MHz, CDCl$_3$) δ 1.51 (s, 9H), 3.33-3.43 (m, 4H), 3.63-3.82 (m, 5H), 4.02-4.11 (m, 3H), 4.80-4.90 (m, 1H), 5.96 (t, 54, 1H), 7.02-7.14 (m, 2H), 7.65-7.84 (br, NH); IR (CHCl$_3$) ν$_{max}$ 1758, 1706 cm$^{-1}$; MS e/m 506 (M$^+$, 5), 403 (4), 377 (9), 348 (9), 334 (12), 319 (7), 180 (11), 57 (100).

REFERENCE EXAMPLE 5

[Chemical Formula 73]

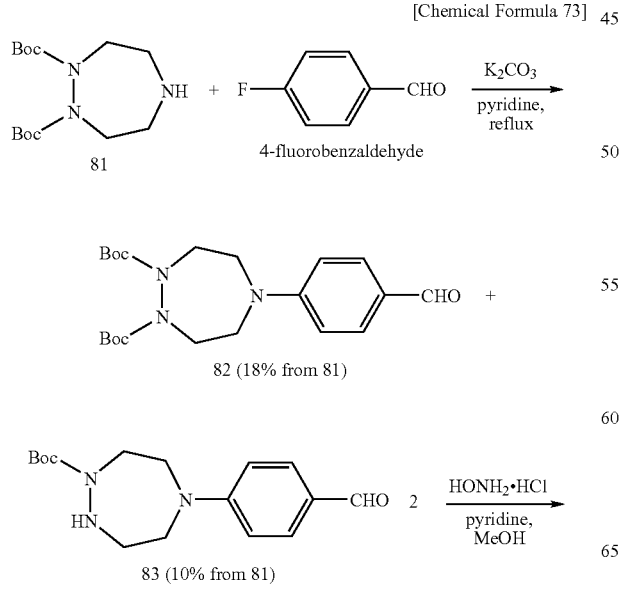

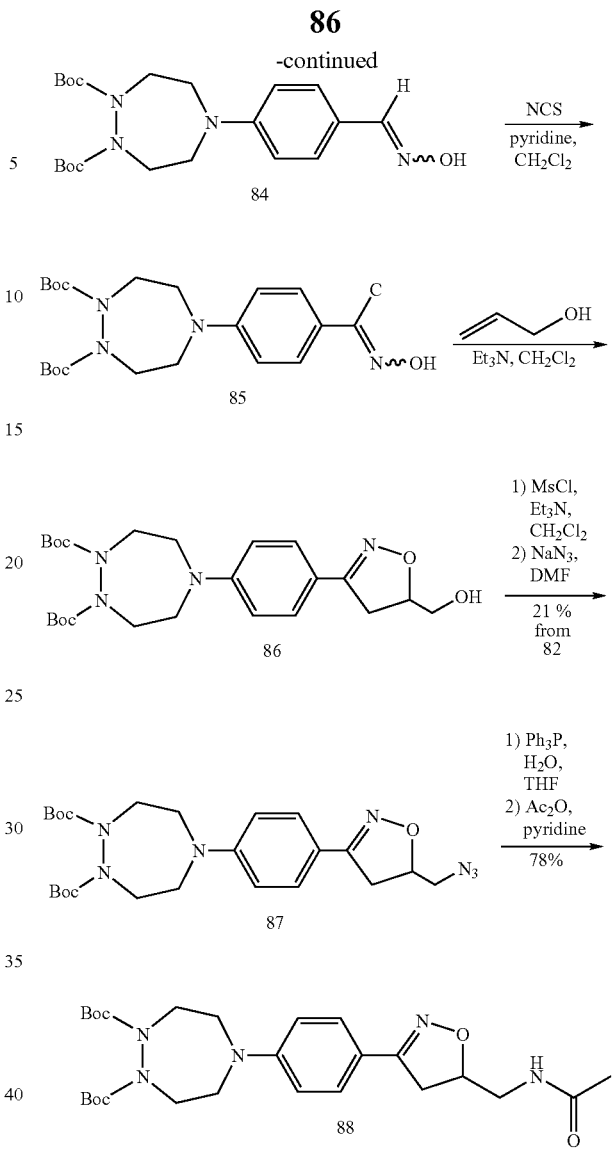

Compounds 82 and 83

To 50 cm$^3$ egg-plant flask, charged with Compound 81 (3.1291 g, 10.38 mmol), 4-fluorobenzaldehyde (1.9321 g, 15.57 mmol) and K$_2$CO$_3$ (2.9080 g, 21.04 mmol), pyridine (10 cm$^3$) was added to obtain a suspension. The suspension was heated under reflux for 88 hours. Pyridine was removed to obtain the residue, which was then added with H$_2$O (100 cm$^3$), extracted three times with AcOEt, washed with brine, dried over Na$_2$SO$_4$, filtrated and concentrated. The resultant residue was purified by silica gel column chromatography (BW-200, 30 g, eluent; 5%→10%→50% AcOEt/n-hexane→10% MeOH/CH$_2$Cl$_2$) to afford Compound 82 (0.7581 g, 1.87 mmol) and compound 83 (0.3143 g, 1.03 mmol). The respective carboxyl compounds of Compounds 82 and 83, wherein the formyl group is oxidized, were also obtained.

Yield: 18% (Compound 82), 10% (Compound 83), Compound 81 unreacted (65%) was recovered.

Compound 82: $^1$H NMR (CDCl$_3$) δ=1.33 & 1.36 & 1.41 (18H, three singlet peaks of the conformers, t-Bu×2), 3.14-3.91 (6H, m), 4.10-4.32 (2H, m), 6.77 (2H, d, J=9.1 Hz), 7.74 (2H, d, J=9.1 Hz), and 9.75 (1H, s, CHO)

Compound 83: $^1$H NMR (CDCl$_3$) δ=1.20 (9H, s, t-Bu), 3.09 (2H, t, J=5.2 Hz), 3.70 (2H, t, J=5.2 Hz), 3.70-3.86 (4H, m), 4.82 (1H, br s, NH), 6.76 (2H, d, J=8.5 Hz), 7.73 (2H, d, J=8.5 Hz), and 9.73 (1H, s, CHO).

Compound 84

To 100 cm$^3$ egg-plant flask, charged with Compound 82 (1.2082 g, 2.98 mmol), pyridine (1 cm$^3$) and MeOH (10 cm$^3$) were added to prepare a solution. To this solution, hydroxylamine hydrochloride (0.3584 g, 5.16 mmol) was added, and the mixture was stirred at room temperature for 21 hours. After removing pyridine and MeOH, H$_2$O (50 cm$^3$) and AcOEt (100 cm$^3$) were added to separate the phase, and the aqueous layer was extracted once with AcOEt. The combined organic layer was washed once with H$_2$O and once with brine, dried over Na$_2$SO$_4$, filtrated, and concentrated to afford the residue (1.1838 g) containing Compound 84 as main product.

Compound 85

A 100 cm$^3$ egg-plant flask was charged with the residue containing Compound 84 (1.1838 g), and pyridine (3 cm$^3$) and CH$_2$Cl$_2$ (15 cm$^3$) were added to dissolve. To this solution, NCS (0.5020 g, 3.76 mmol) was added at 0° C., and the mixture was stirred at this temperature for 3 hours and for additional 15 hours at room temperature. The residue was added with H$_2$O (50 cm$^3$) and AcOEt (100 cm$^3$) to separate the phase, and the aqueous layer was extracted once with AcOEt. The combined organic layer was washed once with H$_2$O and once with brine, dried over Na$_2$SO$_4$, filtrated, and concentrated to afford the residue containing Compound 85 as main product.

Compound 86

A 100 cm$^3$ egg-plant flask was charged with the residue containing Compound 85 (1.1838 g), and Et$_3$N (0.80 cm$^3$, 5.69 mmol) and CH$_2$Cl$_2$ (20 cm$^3$) were added to dissolve. To this solution, allyl alcohol (0.40 cm$^3$, 5.85 mmol) was added at room temperature and stirred for 24 hours at this temperature. The solvent was removed to obtain the residue, which was then subjected to purification by silica gel column chromatography (BW-200, 30 g, eluent; AcOEt→5% MeOH/CH$_2$Cl$_2$) for purification, but there were fractions containing substantial residual by-product, and therefore, the fraction containing Compound 86 was only collected.

$^1$H NMR (CDCl$_3$) δ=1.34-1.42 (18H, t-Bu), 2.19 (1H, br s, OH), 3.13-3.86 (10H), 4.09-4.28 (2H), 4.74-4.86 (1H, m), 6.71 (2H, d, J=8.8 Hz), and 7.53 (2H, d, J=8.8 Hz).

Compound 87

The residue (1.0953 g), which was obtained from concentration of the above fraction containing Compound 86, was dissolved in CH$_2$Cl$_2$ (20 cm$^3$) and Et$_3$N (0.80 cm$^3$, 5.69 mmol) was added. MsCl (0.40 cm$^3$, 5.17 mmol) in CH$_2$Cl$_2$ (5 cm$^3$) was added dropwise at 0° C., and warmed to room temperature and stirred for 2.5 hours. The reaction was quenched with saturated aqueous NaHCO$_3$ (30 cm$^3$), extracted four times with CH$_2$Cl$_2$, washed once with brine, dried over Na$_2$SO$_4$, filtered, and concentrated to obtain the residue (1.2848 g). The residue was dissolved in DMF (20 cm$^3$), added with NaN$_3$ (0.6000 g, 9.23 mmol) and stirred at 60° C. for 3 hours and at room temperature for additional 40 hours. The solution was added with H$_2$O (50 cm$^3$) and AcOEt (40 cm$^3$) to separate the phase, the aqueous layer was extracted once with AcOEt. The combined organic layer was washed once with H$_2$O and once with brine, dried over Na$_2$SO$_4$, filtrated, and concentrated. The residue was purified by silica gel column chromatography (BW-200, 30 g, eluent; 50%→80% AcOEt/n-hexane) to afford 0.3171 g (0.632 mmol) of Compound 87.

Yield from 82: 21%

$^1$H NMR (CDCl$_3$) δ=1.34-1.48 (18H, t-Bu), 3.06-3.86 (10H), 4.07-4.28 (2H), 4.78-4.91 (1H, m), 6.65-6.73 (2H, m), and 7.44-7.56 (2H, m).

Synthesis of Compound 88

A 50 cm$^3$ egg-plant flask was charged with Compound 87 (0.3171 g, 0.632 mmol), and added with THF (3 cm$^3$) to dissolve. To this solution, Ph$_3$P (0.2525 g, 0.963 mmol) and H$_2$O (0.20 cm$^3$, 11.1 mmol) were added at room temperature, and stirred at room temperature for 52 hours. The solvent was removed to obtain the residue, which was then purified by silica gel column chromatography (BW-200, 30 g, eluent; 50%→100% AcOEt/n-hexane 10% MeOH/CHCl$_3$) to afford 0.2413 g (0.507 mmol, 80%) of amine.

The amine (0.2413 g, 0.507 mmol) was charged in a 50 cm$^3$ egg-plant flask, and added with pyridine (5 cm$^3$) to dissolve. Ac$_2$O (2.0 cm$^3$) was added at room temperature and stirred at this temperature for 15 hours. The solvent was removed to obtain the residue (0.2556 g) as Compound 88.

Yield: 78%

$^1$H NMR (CDCl$_3$) δ=1.27-1.41 (18H, t-Bu), 1.90 (3H, s, Ac), 2.80-3.68 (10H), 4.02-4.20 (2H), 4.66-4.78 (1H, m), 6.10 (1H, t, J=6.0 Hz), 6.63 (2H, d, J=8.8 Hz), and 7.42 (2H, d, J=8.8 Hz).

REFERENCE EXAMPLE 6

Synthesis of Compound 94

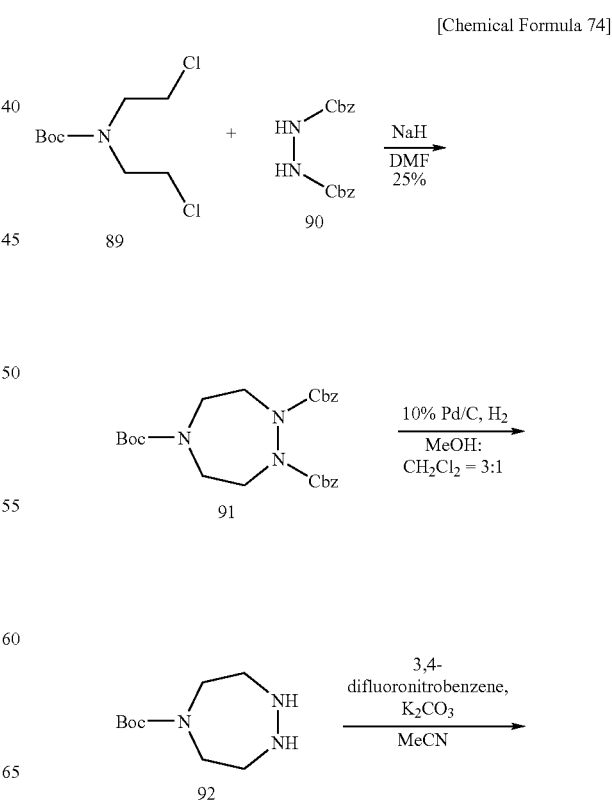

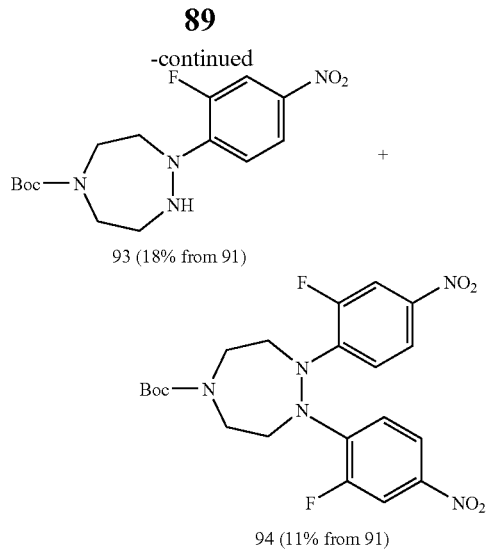

93 (18% from 91)

94 (11% from 91)

Compound 91

NaH (60% in mineral oil; 3.4311 g, 85.8 mmol), charged in a 200 cm³ egg-plant flask, was washed three times with n-hexane. Residual n-hexane was removed under reduced pressure, and DMF (150 cm³) was added. Compound 90 (10.26 g, 34.2 mmol) was added at room temperature, and the mixture was stirred at this temperature for 10 min. Compound 89 (9.8497 g, 40.7 mmol) in DMF (50 cm³) was then added dropwise to this mixture, and the mixture was stirred at this temperature for 18 hours. The mixture was poured into H₂O (500 cm³), extracted three times with AcOEt, washed once with water and with brine, dried over anhydrous Na₂SO₄, filtered, and concentrated. The resultant residue was purified by silica gel column chromatography (BW-200, 150 g, eluent; 10%→20%→30%→50% AcOEt/n-hexane) to afford Compound 91 (3.9235 g, 8.36 mmol).

Yield: 25%

¹H NMR (CDCl₃) δ=1.31-1.43 (9H, t-Bu), 3.08-3.74 (6H), 4.00-4.28 (2H), 4.98-5.24 (4H, m, CH₂Ph), and 7.20-7.38 (10H, m).

Compounds 93 and 94

A 500 cm³ egg-plant flask was charged with Compound 91 (3.9235 g, 8.36 mmol), and 10% Pd/C (0.7777 g), MeOH (60 cm³) and CH₂Cl₂ (20 cm³) were added to obtain a suspension. The suspension was subjected to H₂ substitution and stirred for 7 days. The reaction was filtered through celite Pad, and the filtrate was concentrated to obtain the crude product (92). The crude product (2.2861 g) was dissolved in MeCN (50 cm³), and K₂CO₃ (3.3520 g, 24.25 mmol) and 3,4-difluoro nitro benzene (3.6271 g, 22.80 mmol) were added, and the mixture was heated with stirring for 14 hours. H₂O (50 cm³) was added, and the mixture was extracted five times with AcOEt, washed with brine, dried over anhydrous Na₂SO₄, filtrated and concentrated. The resultant residue was purified by silica gel column chromatography (BW-200, 60 g, eluent; 10%→20%→30%→40% AcOEt/n-hexane) to afford Compound 93 (0.5019 g, 1.47 mmol) and Compound 94 (0.4347 g, 0.91 mmol).

Yield: 18% (Compound 93), 11% (Compound 94).

Compound 93: ¹H NMR (CDCl₃) δ=1.45 (9H, s, t-Bu), 3.00-3.14 (2H), 3.36-3.74 (7H), 7.48 (1H, t=9.1 Hz), and 7.84-8.01 (2H, m).

Compound 94: ¹H NMR (CDCl₃) δ=1.53-1.57 (9H, t-Bu), 3.38-5.76 (8H), 6.61 (2H, t, J=8.6 Hz), and 7.84-8.01 (4H, m).

REFERENCE EXAMPLE 7

[Chemical Formula 75]

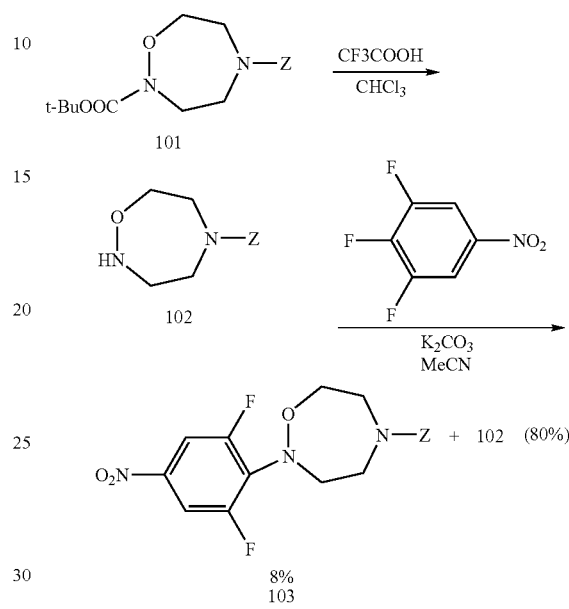

Z = Cbz (benzyloxycarbonyl)

Compound 102

To a solution of BOC compound (101, 1.01 g) in chloroform (25 ml), trifluoroacetic acid (2 ml) was added and stirred at room temperature for 19 hours. After the reaction, saturated aqueous NaHCO₃ was added, and the mixture was extracted with chloroform-methanol (9:1). After dryness (Na₂SO₄), the solvent was removed. The residue was purified by silica gel chromatography (hexane-ethyl acetate (1:1)) to afford 526 mg (74%) of Compound (102) as colorless syrup.

102: colorless syrup; 1H-NMR (300 MHz, CDCl₃) δ 3.09 (t, 5.5, 1H), 3.14 (t, 5.5, 1H), 3.54-3.70 (m, 4H), 3.82 (t, 5.5, 1H), 3.91 (t, 5.5, 1H), 5.16 (s, 2H), 5.84 (br, NH), 7.29-7.40 (m, 5H)

Compound 103

To a solution of the amino compound (102, 321 mg) and 3,4,5-trifluoro nitrobenzene (487 mg) in acetonitrile (12 ml), K₂CO₃ (561 mg) was added, and the mixture was heated under reflux with stirring for 21 hours. After the reaction, aqueous NH₄Cl was added, and the mixture was extracted with chloroform-methanol (9:1). After dryness (Na₂SO₄), the solvent was removed. The residue was purified by silica gel chromatography (hexane-ethyl acetate (2:1)) to obtain 45 mg (8%) of pale-yellow candy-like compound (103) in the first fraction, and 258 mg (80%) of the starting material was recovered in the fraction eluted with hexane-ethyl acetate (1:1).

103: pale-yellow candy-like material; ¹H-NMR (300 MHz, CDCl₃) δ 3.55 (br t, 5.5, 1H), 3.62 (br t, 5.5, 1H), 3.70-3.81 (m, 4H), 4.01 (t, 5.5, 1H), 4.09 (t, 5.5, 1H), 5.19 (s, 2H), 7.31-7.39 (m, 5H), 7.75-7.84 (m, 2H).

The following compounds were prepared as previously described.

EXAMPLE A1

[Chemical Formula 76]

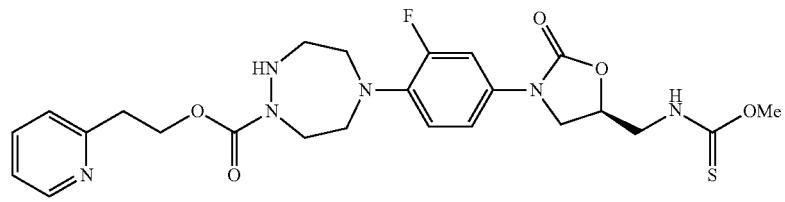

$^1$H NMR (CDCl$_3$) δ 2.95-3.20 (4H, br), 3.34-3.43 (2H, m), 3.48-3.70 (4H, m), 3.81 (1H, dd, J=6.9, 9.1 Hz), 3.90-4.10 (3H, m), 4.00 (3H, s, CH$_3$OC=S), 4.35-4.50 (2H, br), 4.84-4.94 (1H, m), 6.83 (1H, t, J=9.1 Hz), 6.99 (1H, dd, J=2.5, 9.1 Hz), 6.99-7.17 (3H, m), 7.36 (1H, dd, J=2.5, 14.6 Hz), 7.58 (1H, br t, J=6 Hz), 8.53 (1H, d, J=4.4 Hz).

EXAMPLE A2

[Chemical Formula 77]

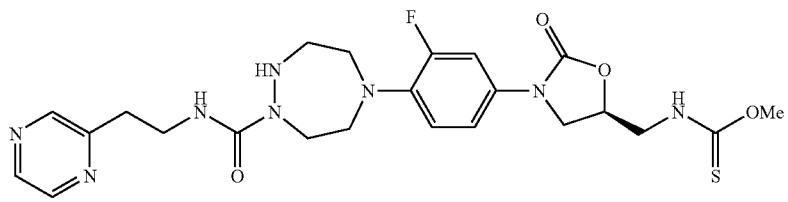

$^1$H NMR (CDCl$_3$) δ 3.04 (2H, t, J=6.6 Hz), 3.04-3.12 (2H, m), 3.31-3.40.(4H, m), 3.64 (2H, q, J=6.6 Hz), 3.78-4.12 (6H, m), 4.00 (3H, s, CH$_3$OC=S), 4.86-4.96 (1H, m), 6.69 (1H, t, J=6.2 Hz), 6.88 (1H, t, J=9.1 Hz), 7.01 (1H, dd, J=2.5, 9.1 Hz), 7.11 (1H, t, J=6.0 Hz), 7.39 (1H, dd, J=2.5, 14.6 Hz), 8.41-8.52 (2H, m).

EXAMPLE A3

[Chemical Formula 78]

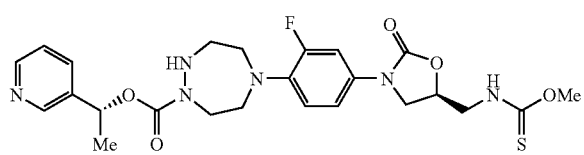

$^1$H NMR (CDCl$_3$) δ 1.52 (3H, br, CH$_3$), 3.05-4.12 (12H, m), 4.00 (3H, s, CH$_3$OC=S), 4.85-4.95 (1H, m), 5.81 (1H, br), 6.87 (1H, br t, J=9 Hz), 6.94-7.04 (2H, m), 7.10-7.22 (2H, m), 7.37 (1H, br d, J=15 Hz), 7.61 (1H, br), 8.54 (1H, br s).

EXAMPLE A4

[Chemical Formula 79]

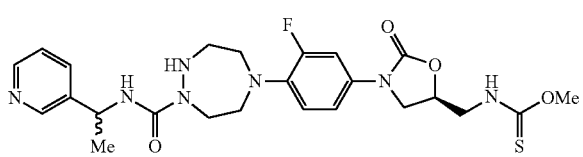

$^1$H NMR (CDCl$_3$) δ 1.50 (3H, d, J=7.0 Hz, CH$_3$), 3.14-3.22 (2H, m), 3.33-3.41 (4H, m), 3.58-4.09 (6H, m), 3.99 (3H, s, CH$_3$OC=S), 4.85-4.95 (1H, m), 4.97 (1H, quint, J=7.0 Hz), 6.76 (1H, d, J=8.2 Hz), 6.88 (1H, t, J=9.1 Hz), 7.00 (1H, dd, J=2.5, 9.1 Hz), 7.21-7.27 (1H, m), 7.36-7.46 (2H, m), 7.63 (1H, br d, J=8 Hz), 8.47 (1H, dd, J=1.7, 4.9 Hz), 8.60 (1H, d, J=1.7 Hz).

EXAMPLE A5

[Chemical Formula 80]

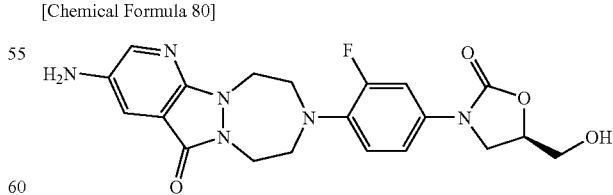

$^1$H NMR (CD$_3$OD+CDCl$_3$) δ 3.38-3.54 (4H, m), 3.71 (1H, dd, J=3.9, 12.6 Hz), 3.86-4.06 (4H, m), 4.23-4.38 (4H, m), 4.68-4.78 (1H, m), 7.02 (1H, t, J=9.1 Hz), 7.12 (1H, dd, J=2.5, 8.8 Hz), 7.46 (1H, d, J=2.8 Hz), 7.47 (1H, dd, J=2.5, 14.5 Hz), 8.15 (1H, d, J=2.8 Hz).

EXAMPLE A6

[Chemical Formula 81]

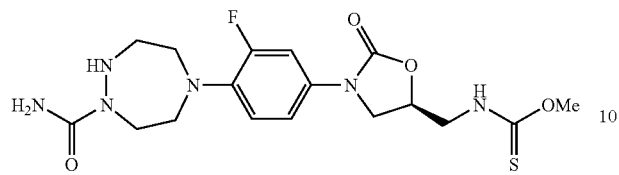

$^1$H NMR (CD$_3$OD) δ 3.10-3.15 (2H, m), 3.34-3.45 (4H, m), 3.77-3.91 (5H, m), 3.95 (3H, s, CH$_3$OC=S), 4.12 (1H, t, J=9.1 Hz), 4.88-4.98 (1H, m), 7.01 (1H, t, J=9.1 Hz), 7.09 (1H, dd, J=2.8, 9.1 Hz), 7.43 (1H, dd, J=2.8, 15.1 Hz).

EXAMPLE A7

[Chemical Formula 82]

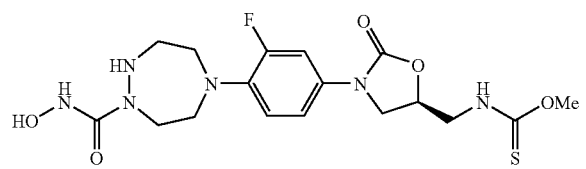

$^1$H NMR (CD$_3$OD) δ 3.06-3.13 (2H, m), 3.28-3.46 (4H, m), 3.75-4.14 (6H, m), 3.95 (3H, s, CH$_3$OC=S), 4.88-4.98 (1H, m), 6.95-7.15 (2H, m), 7.36-7.51 (1H, m).

EXAMPLE A8

[Chemical Formula 83]

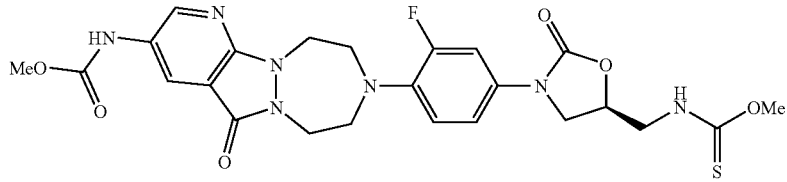

$^1$H NMR (CD$_3$OD+CDCl$_3$) δ 3.39-3.53 (4H, m), 3.62-4.11 (4H, m), 3.80 (3H, s, CH$_3$OC=O), 4.00 (3H, s, CH$_3$OC=S), 4.38-4.44 (4H, m), 4.90-5.00 (1H, m), 7.03 (1H, t, J=9.1 Hz), 7.14 (1H, dd, J=2.5, 9.1 Hz), 7.47 (1H, dd, J=2.5, 14.0 Hz), 8.15 (1H, d, J=2.2 Hz), 8.78 (1H, br s, NHC=O).

EXAMPLE A9

[Chemical Formula 84]

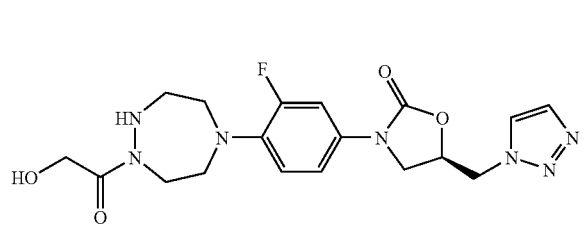

$^1$H NMR (CDCl$_3$) δ 3.15-3.23 (2H, m), 3.30-3.45 (4H, m), 3.87-3.99 (3H, m), 4.12 (1H, t, J=9.1 Hz), 4.63 (2H, s, CH$_2$O), 4.78 (2H, AB), 5.00-5.10 (1H, m), 6.85 (1H, t, J=9.1 Hz), 6.92 (1H, dd, J=2.5, 9.1 Hz), 7.27 (1H, dd, J=2.5, 14.8 Hz), 7.75 (1H, br s), 7.79 (1H, br s).

EXAMPLE A10

[Chemical Formula 85]

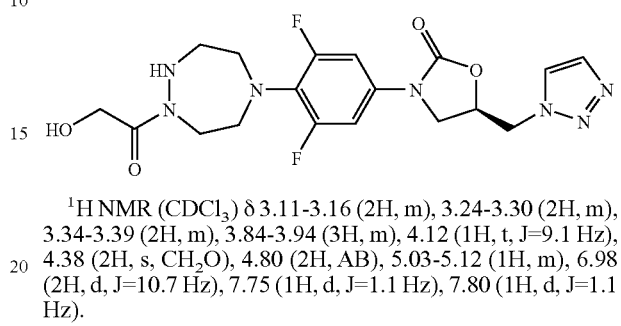

$^1$H NMR (CDCl$_3$) δ 3.11-3.16 (2H, m), 3.24-3.30 (2H, m), 3.34-3.39 (2H, m), 3.84-3.94 (3H, m), 4.12 (1H, t, J=9.1 Hz), 4.38 (2H, s, CH$_2$O), 4.80 (2H, AB), 5.03-5.12 (1H, m), 6.98 (2H, d, J=10.7 Hz), 7.75 (1H, d, J=1.1 Hz), 7.80 (1H, d, J=1.1 Hz).

EXAMPLE A11

[Chemical Formula 86]

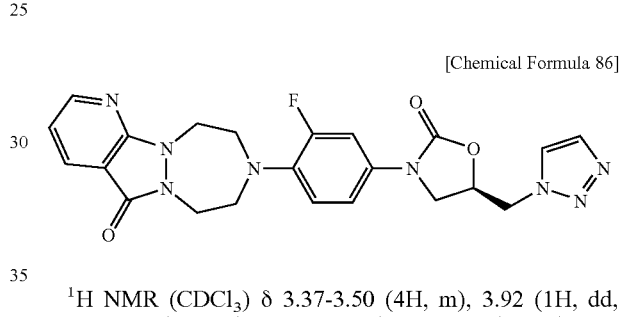

$^1$H NMR (CDCl$_3$) δ 3.37-3.50 (4H, m), 3.92 (1H, dd, J=6.1, 9.1 Hz), 4.15 (1H, t, J=9.1 Hz), 4.37-4.47 (4H, m), 4.80 (2H, AB), 5.02-5.12 (1H, m), 6.92-7.00 (2H, m), 7.08 (1H, dd, J=4.7, 7.7 Hz), 7.32 (1H, br d, J=15 Hz), 7.75 (1H, br s), 7.79 (1H, br s), 8.17 (1H, d, J=7.7 Hz), 8.53 (1H, d, J=4.7 Hz).

EXAMPLE A12

[Chemical Formula 87]

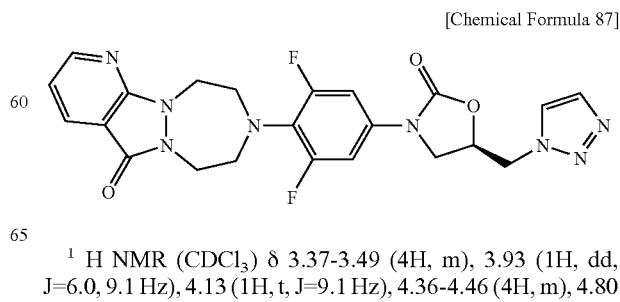

$^1$H NMR (CDCl$_3$) δ 3.37-3.49 (4H, m), 3.93 (1H, dd, J=6.0, 9.1 Hz), 4.13 (1H, t, J=9.1 Hz), 4.36-4.46 (4H, m), 4.80

(2H, AB), 5.04-5.13 (1H, m), 7.02 (2H, d, J=10.7 Hz), 7.07 (1H, dd, J=4.8, 7.7 Hz), 7.32 (1H, br d, J=15 Hz), 7.76 (1H, d, J=1.1 Hz), 7.78 (1H, d, J=1.1 Hz), 8.18 (1H, dd, J=1.7, 7.7 Hz), 8.53 (1H, dd, J=1.7, 4.7 Hz).

EXAMPLE A13

[Chemical Formula 88]

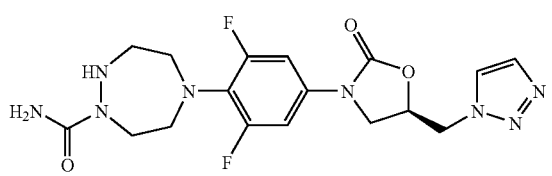

$^1$H NMR (CD$_3$OD+CDCl$_3$) δ 3.10-3.16 (2H, m), 3.27-3.36 (4H, m), 3.74-3.79 (2H, m), 3.90 (1H, dd, J=6.1, 9.1 Hz), 4.14 (1H, t, J=9.1 Hz), 4.81 (2H, AB), 5.05-5.14 (1H, m), 7.01 (2H, d, J=10.7 Hz), 7.75 (1H, d, J=1.1 Hz), 7.80 (1H, d, J=1.1 Hz).

EXAMPLE A14

[Chemical Formula 89]

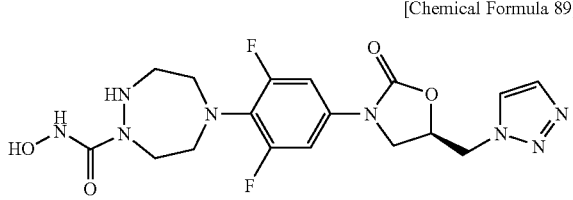 [SMILES: O=C(NO)N1CCN(c2c(F)cc(N3C[C@H](Cn4ccnn4)OC3=O)cc2F)CCN1]

$^1$H NMR (CD$_3$OD+CDCl$_3$) δ 3.07-3.13 (2H, m), 3.24-3.37 (4H, m), 3.74-3.79 (2H, m), 3.90 (1H, br dd, J=6, 9 Hz), 4.15 (1H, t, J=9.1 Hz), 4.82 (2H, AB), 5.05-5.14 (1H, m), 7.02 (2H, d, J=10.7 Hz), 7.75 (1H, br s), 7.88 (1H, br s).

EXAMPLE A15

[Chemical Formula 90]

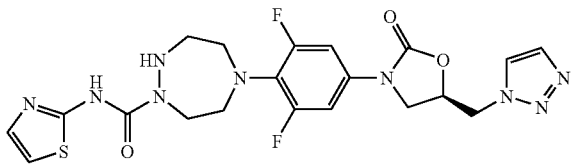

$^1$H NMR (CDCl$_3$) δ 3.18-3.24 (2H, m), 3.26-3.35 (2H, m), 3.36-3.45 (2H, m), 3.66-3.74 (2H, m), 3.90 (1H, dd, J=6.0, 9.1 Hz), 4.12 (1H, t, J=9.1 Hz), 4.80 (2H, AB), 5.03-5.12 (1H, m), 6.87 (1H, d, J=3.6 Hz), 6.99 (2H, d, J=10.7 Hz), 7.37 (1H, d, J=3.6 Hz), 7.74 (1H, s), 7.79 (1H, s), 9.86 (1H, br s, heterocycle-NHC=O).

EXAMPLE A16

[Chemical Formula 91]

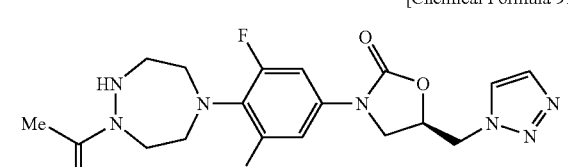

$^1$H NMR (CDCl$_3$) δ 2.11 & 2.21 (3H, s, CH$_3$C=O), 2.96-3.01 & 3.10-3.16 & 3.24-3.35 & 3.46-3.52 & 3.63-3.68 & 3.80-3.85 (8H, m), 3.90 (1H, dd, J=6.1, 9.1 Hz), 4.13 (1H, t, J=9.1 Hz), 4.80 (2H, AB), 5.04-5.13 (1H, m), 6.98 (2H, d, J=10.7 Hz), 7.74 (1H, d, J=1.1 Hz), 7.80 (1H, d, J=1.1 Hz).

EXAMPLE A17

[Chemical Formula 92]

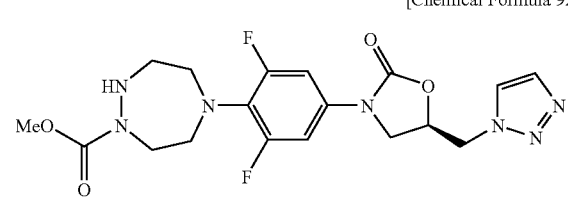

$^1$H NMR (CDCl$_3$) δ 3.03-3.08 (2H, m), 3.23-3.29 (2H, m), 3.37-3.43 (2H, m), 3.59-3.67 (2H, m), 3.76 (3H, s, CH$_3$OC=O), 3.89 (1H, dd, J=6.1, 9.1 Hz), 4.12 (1H, t, J=9.1 Hz), 4.79 (2H, AB), 5.02-5.12 (1H, m), 6.96 (2H, d, J=10.7 Hz), 7.75 (1H, d, J=1.1 Hz), 7.79 (1H, d, J=1.1 Hz).

EXAMPLE A18

[Chemical Formula 93]

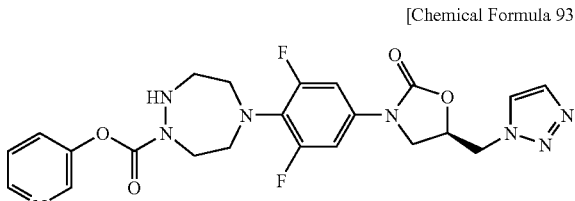

$^1$H NMR (CDCl$_3$) δ 3.08-3.26 (2H, m), 3.30-3.36 (2H, m), 3.46-3.54 (2H, m), 3.71-3.91 (2H, m), 3.88 (1H, dd, J=6.1, 9.1 Hz), 4.11 (1H, t, J=9.1 Hz), 4.79 (2H, AB), 5.02-5.12 (1H, m), 6.99 (2H, d, J=10.7 Hz), 7.34 (1H, dd, J=4.8, 8.2 Hz), 7.55 (1H, ddd, J=1.4, 2.5, 8.2 Hz), 7.73 (1H, d, J=1.1 Hz), 7.79 (1H, d, J=1.1 Hz), 8.44-8.48 (2H, m).

EXAMPLE A19

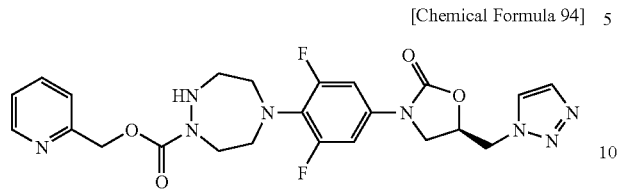

[Chemical Formula 94]

¹H NMR (CDCl₃) δ 3.05-3.11 (2H, m), 3.24-3.30 (2H, m), 3.41-3.47 (2H, m), 3.68-3.75 (2H, m), 3.89 (1H, dd, J=6.1, 9.1 Hz), 4.12 (1H, t, J=9.1 Hz), 4.79 (2H, AB), 5.02-5.12 (1H, m), 5.32 (2H, s, CH₂OC=O), 6.97 (2H, d, J=10.7 Hz), 7.23 (1H, br dd, J=4, 8 Hz), 7.36 (1H, br d, J=8 Hz), 7.70 (1H, dt, J=1.7, 7.7 Hz), 7.73 (1H, d, J=1.1 Hz), 7.79 (1H, d, J=1.1 Hz), 8.57 (1H, br d, J=4 Hz).

EXAMPLE A20

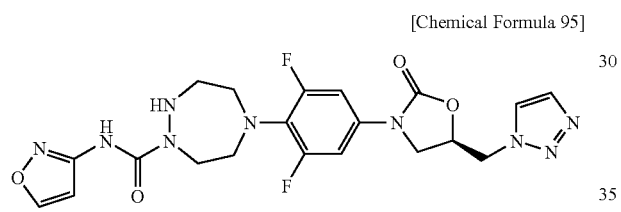

[Chemical Formula 95]

¹H NMR (CDCl₃) δ 3.17-3.24 (2H, m), 3.28-3.41 (4H, m), 3.87-3.95 (3H, m), 4.11 (1H, t, J=9.1 Hz), 4.79 (2H, AB), 5.02-5.11 (1H, m), 6.99 (2H, d, J=10.7 Hz), 7.03 (1H, d, J=1.7 Hz), 7.75 (1H, d, J=1.0 Hz), 7.78 (1H, d, J=1.0 Hz), 8.23 (1H, d, J=1.7 Hz), 9.24 (1H, br s, NHC=O).

EXAMPLE A21

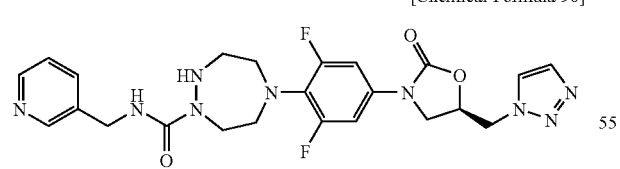

[Chemical Formula 96]

¹H NMR (CDCl₃) δ 3.06-3.14 (2H, m), 3.26-3.36 (4H, m), 3.73-3.85 (2H, m), 3.89 (1H, dd, J=6.1, 9.1 Hz), 4.12 (1H, t, J=9.1 Hz), 4.44 (2H, AB), 4.79 (2H, AB), 5.02-5.11 (1H, m), 6.89 (1H, t, J=6.2 Hz, NHC=O), 6.98 (2H, d, J=10.7 Hz), 7.25 (1H, dd, J=4.7, 7.7 Hz), 7.67 (1H, dt, J=7.7, 1.9 Hz), 7.73 (1H, d, J=1.1 Hz), 7.79 (1H, d, J=1.1 Hz), 8.49 (1H, dd, J=1.9, 4.7 Hz), 8.56 (1H, d, J=1.9 Hz).

EXAMPLE A22

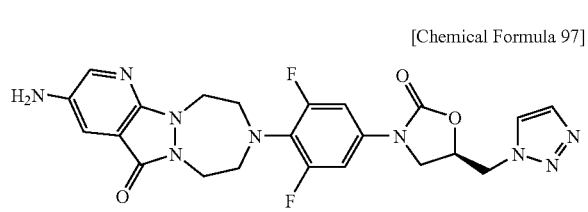 [SMILES: Nc1cnc2c(c1)c(=O)n1n2CCN(c2c(F)cc(N3C[C@H](Cn4ccnn4)OC3=O)cc2F)CC1]

[Chemical Formula 97]

¹H NMR (CDCl₃+CD₃OD) δ 3.36-3.52 (4H, m), 3.91 (1H, dd, J=6.1, 9.1 Hz), 4.16 (1H, t, J=9.1 Hz), 4.24-4.36 (4H, m), 4.82 (2H, AB), 5.06-5.15 (1H, m), 7.06 (2H, d, J=10.7 Hz), 7.47 (1H, d, J=2.8 Hz), 7.75 (1H, d, J=1.1 Hz), 7.79 (1H, d, J=1.1 Hz), 8.15 (1H, d, J=2.8 Hz).

EXAMPLE A23

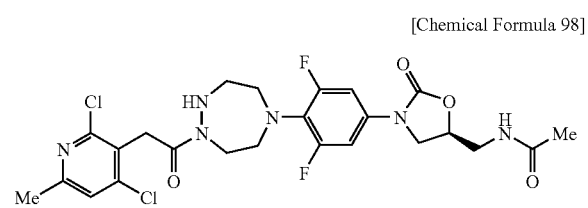 [SMILES: CC(=O)NC[C@H]1CN(c2cc(F)c(N3CCNN(C(=O)Cc4c(Cl)cc(C)nc4Cl)CC3)c(F)c2)C(=O)O1]

[Chemical Formula 98]

¹H NMR (CDCl₃) δ 2.01 (3H, CH₃C=O), 2.50 (3H, s, CH₃), 3.21-3.39 (6H, m), 3.56-4.03 (6H, m), 4.26 (2H, s, CH₂C=O), 4.72-4.82 (1H, m), 6.27 (1H, t, J=6.0 Hz, NHC=O), 7.10 (2H, d, J=10.7 Hz), 7.16 (1H, s).

EXAMPLE A24

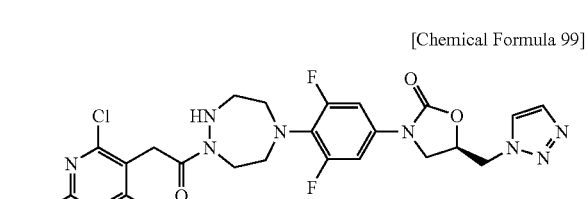

[Chemical Formula 99]

¹H NMR (CDCl₃) δ 2.49 (3H, s, CH₃), 3.20-3.38 (6H, m), 3.82-3.97 (3H, m), 4.11 (1H, t, J=9.1 Hz), 4.26 (2H, s, CH₂C=O), 4.78 (2H, AB), 5.02-5.12 (1H, m), 6.99 (2H, d, J=10.7 Hz), 7.16 (1H, s), 7.74 (1H, d, J=1.1 Hz), 7.78 (1H, d, J=1.1 Hz).

EXAMPLE A25

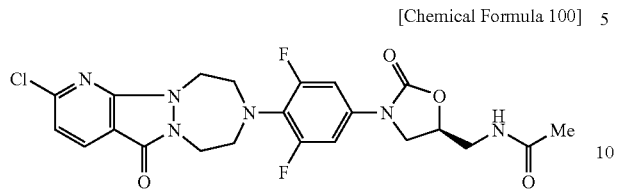

[Chemical Formula 100]

$^1$H NMR (CDCl$_3$) δ 2.03 (3H, CH$_3$C=O), 3.37-3.47 (4H, m), 3.62-3.78 (3H, m), 4.00 (1H, t, J=9.1 Hz), 4.36-4.48 (4H, m), 4.74-4.84 (1H, m), 6.06 (1H, t, J=6.0 Hz, NHC=O), 7.04 (1H, d, J=8.2 Hz), 7.15 (2H, d, J=10.7 Hz), 8.09 (1H, d, J=8.2 Hz).

EXAMPLE A26

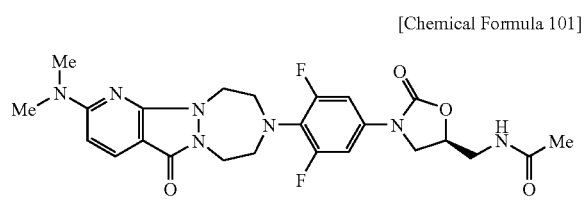 [SMILES: CC(=O)NC[C@H]1CN(c2cc(F)c(N3CCn4c(=O)c5ccc(N(C)C)nc5n4CC3)c(F)c2)C(=O)O1]

[Chemical Formula 101]

$^1$H NMR (CDCl$_3$) δ 2.03 (3H, CH$_3$C=O), 3.16 (6H, s, CH$_3$NCH$_3$), 3.35-3.45 (4H, m), 3.57-3.77 (3H, m), 4.00 (1H, t, J=9.1 Hz), 4.23-4.31 (4H, m), 4.74-4.84 (1H, m), 6.04 (1H, br t, J=6 Hz, NHC=O), 6.30 (1H, d, J=8.8 Hz), 7.13 (2H, d, J=10.7 Hz), 7.83 (1H, d, J=8.8 Hz).

EXAMPLE A27

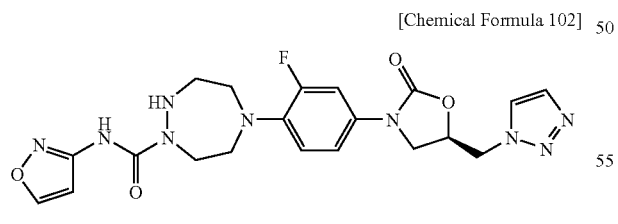

[Chemical Formula 102]

$^1$H NMR (CDCl$_3$) δ 3.22-3.29 (2H, m), 3.36-3.45 (4H, m), 3.82-3.93 (3H, m), 4.12 (1H, t, J=9.1 Hz), 4.78 (2H, AB), 5.00-5.09 (1H, m), 6.87 (1H, t, J=8.8 Hz), 6.92 (1H, dd, J=2.5, 8.8 Hz), 7.00 (1H, d, J=1.7 Hz), 7.26 (1H, dd, J=2.5, 14.6 Hz), 7.75 (1H, d, J=1.1 Hz), 7.79 (1H, d, J=1.1 Hz), 8.23 (1H, d, J=1.7 Hz), 9.20 (1H, br s, NHC=O).

EXAMPLE A28

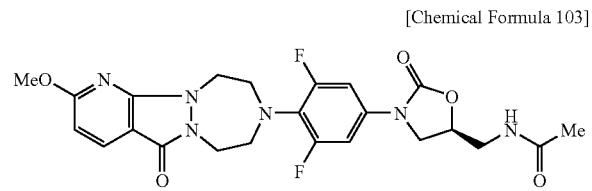 [SMILES: COc1ccc2c(=O)n3n(c2n1)CCN(c1c(F)cc(N2C[C@H](CNC(C)=O)OC2=O)cc1F)CC3]

[Chemical Formula 103]

$^1$H NMR (CDCl$_3$) δ 2.03 (3H, CH$_3$C=O), 3.37-3.47 (4H, m), 3.56-3.78 (3H, m), 3.98 (3H, s, CH$_3$O), 4.00 (1H, t, J=9.1 Hz), 4.30-4.40 (4H, m), 4.74-4.84 (1H, m), 6.23 (1H, br t, J=6 Hz, NHC=O), 6.46 (1H, d, J=8.5 Hz), 7.14 (2H, d, J=10.7 Hz), 7.97 (1H, d, J=8.5 Hz).

EXAMPLE A29

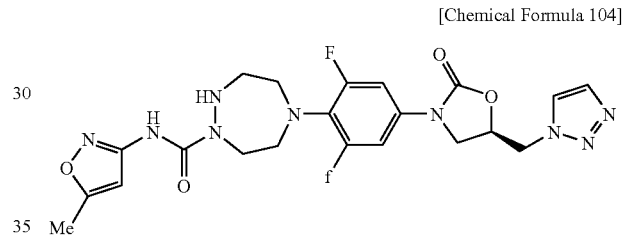

[Chemical Formula 104]

$^1$H NMR (CDCl$_3$) δ 2.38 (3H, s, CH$_3$), 3.15-3.23 (2H, m), 3.28-3.40 (4H, m), 3.83-3.93 (3H, m), 4.11 (1H, t, J=9.1 Hz), 4.79 (2H, AB), 5.02-5.11 (1H, m), 6.65 (1H, s), 6.99 (2H, d, J=10.7 Hz), 7.75 (1H, d, J=1.1 Hz), 7.78 (1H, d, J=1.1 Hz), 9.12 (1H, br s, NHC=O).

EXAMPLE A30

[Chemical Formula 105]

$^1$H NMR (CDCl$_3$) δ 3.20-3.27 (2H, m), 3.30-3.36 (2H, m), 3.37-3.45 (2H, m), 3.87-3.95 (3H, m), 4.11 (1H, t, J=9.1 Hz,), 4.79 (2H, AB), 5.03-5.12 (1H, m), 6.99 (2H, d, J=10.7 Hz), 7.75 (1H, d, J=1.1 Hz), 7.78 (1H, d, J=1.1 Hz), 8.74 (1H, s), 10.07 (1H, br s, NHC=O).

EXAMPLE A31

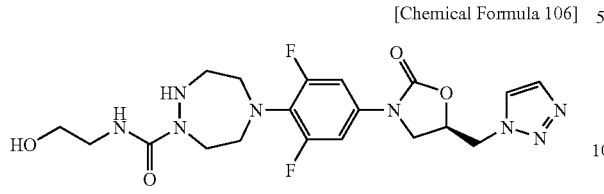

[Chemical Formula 106]

$^1$H NMR (CDCl$_3$) δ 3.07-3.15 (2H, m), 3.26-3.35 (4H, m), 3.35-3.42 (2H, m), 3.68-3.83 (5H, m), 3.89 (1H, dd, J=6.1, 9.1 Hz), 4.12 (1H, t, J=9.1 Hz), 4.80 (2H, AB), 5.03-5.13 (1H, m), 6.82 (1H, br t, J=6 Hz, NHC=O), 6.98 (2H, d, J=10.7 Hz), 7.74 (1H, d, J=1.1 Hz), 7.79 (1H, d, J=1.1 Hz).

EXAMPLE A32

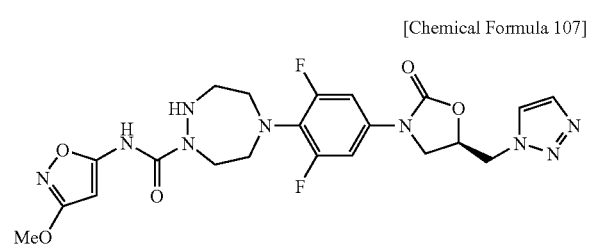 [SMILES: COc1cc(NC(=O)N2CCN(c3c(F)cc(N4C[C@H](Cn5ccnn5)OC4=O)cc3F)CCN2)on1]

[Chemical Formula 107]

$^1$H NMR (CDCl$_3$) δ 2.45 (3H, s, CH$_3$), 3.18-3.27 (2H, m), 3.34-3.45 (4H, m), 3.85-3.98 (3H, m), 4.12 (1H, t, J=9.1 Hz), 4.80 (2H, AB), 5.04-5.13 (1H, m), 6.15 (1H, s), 6.99 (2H, d, J=10.7 Hz), 7.74 (1H, br s), 7.79 (1H, br s).

EXAMPLE A33

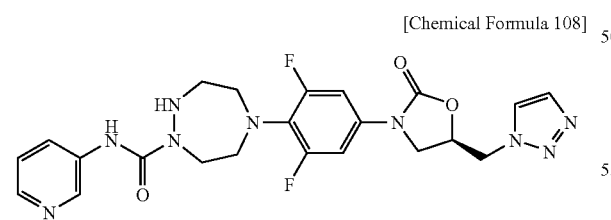

[Chemical Formula 108]

$^1$H NMR (CDCl$_3$) δ 3.19-3.26 (2H, m), 3.32-3.42 (4H, m), 3.86-3.95 (3H, m), 4.11 (1H, t, J=9.1 Hz), 4.79 (2H, AB), 5.03-5.12 (1H, m), 6.99 (2H, d, J=10.7 Hz), 7.21-7.27 (1H, m), 7.75 (1H, d, J=1.1 Hz), 7.78 (1H, d, J=1.1 Hz), 8.15 (1H, ddd, J=1.4, 2.8, 8.2 Hz), 8.26 (1H, dd, J=1.4, 4.7 Hz), 8.50 (1H, d, J=2.8 Hz), 8.72 (1H, br s, NHC=O).

EXAMPLE A34

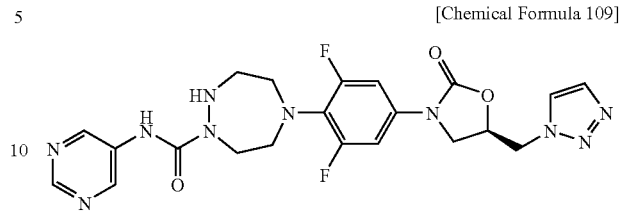

[Chemical Formula 109]

$^1$H NMR (CDCl$_3$) δ 3.18-3.43 (6H, m), 3.84-3.95 (3H, m), 4.11 (1H, t, J=9.1 Hz), 4.79 (2H, AB), 5.01-5.11 (1H, m), 6.99 (2H, d, J=10.7 Hz), 7.75 (1H, br s), 7.78 (1H, br s), 8.71 (1H, s), 8.88 (1H, s), 8.95 (2H, s).

EXAMPLE A35

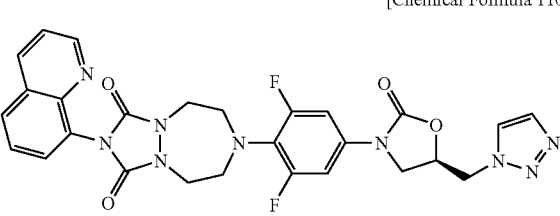

[Chemical Formula 110]

$^1$H NMR (CDCl$_3$) δ 3.47-3.54 (4H, m), 3.92 (1H, dd, J=6.1, 9.1 Hz), 4.12 (1H, t, J=9.1 Hz), 4.14-4.22 (4H, m), 4.79 (2H, AB), 5.01-5.12 (1H, m), 7.03 (2H, d, J=10.7 Hz), 7.47 (1H, dd, J=4.4, 8.2 Hz), 7.65 (1H, t, J=7.7 Hz), 7.75 (1H, br s), 7.78 (1H, br s), 7.79 (1H, br d, J=7 Hz), 7.95 (1H, br d, J=8 Hz), 8.21 (1H, br d, J=8 Hz), 8.95 (1H, br d, J=4 Hz).

EXAMPLE A36

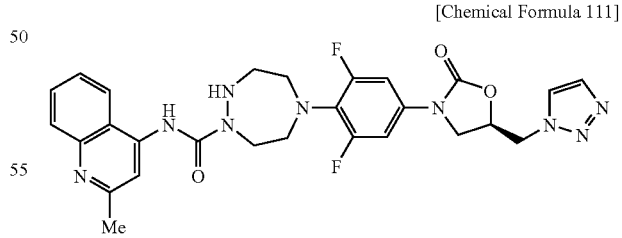

[Chemical Formula 111]

$^1$H NMR (CDCl$_3$) δ 2.71 (3H, s, CH$_3$), 3.30-3.47 (6H, m), 3.91 (1H, dd, J=6.1, 9.1 Hz), 4.11 (1H, t, J=9.1 Hz), 4.79 (2H, AB), 5.02-5.11 (1H, m), 6.99 (2H, d, J=10.7 Hz), 7.48 (1H, br t, J=7 Hz), 7.63-7.76 (2H, m), 7.75 (1H, br s), 7.78 (1H, br s), 8.02 (1H, d, J=8.3 Hz), 8.22 (1H, s), 9.80 (1H, br s, NHC=O).

EXAMPLE A37

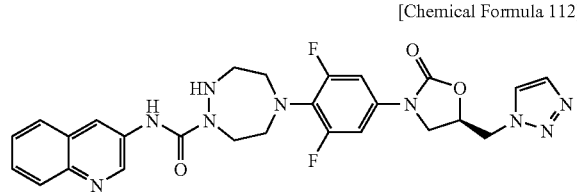

[Chemical Formula 112]

$^1$H NMR (CDCl$_3$) δ 3.24-3.32 (2H, m), 3.34-3.45 (4H, m), 3.85-4.01 (3H, m), 4.11 (1H, t, J=9.1 Hz), 4.79 (2H, AB), 5.01-5.12 (1H, m), 6.99 (2H, d, J=10.7 Hz), 7.47-7.61 (2H, m), 7.75 (1H, br s), 7.76-7.81 (1H, m), 7.78 (1H, br s), 8.01 (1H, d, J=8.5 Hz), 8.67 (1H, d, J=2.2 Hz), 8.73 (1H, d, J=2.8 Hz), 8.94 (1H, br s, NHC=O).

EXAMPLE A38

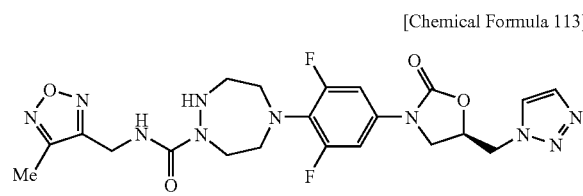 [SMILES: Cc1nonc1CNC(=O)N1CCN(c2c(F)cc(N3C[C@H](Cn4ccnn4)OC3=O)cc2F)CCN1]

[Chemical Formula 113]

$^1$H NMR (CDCl$_3$) δ 2.42 (3H, s, CH$_3$), 3.08-3.15 (2H, m), 3.25-3.36 (4H, m), 3.70-3.84 (2H, m), 3.90 (1H, dd, J=6.1, 9.1 Hz), 4.12 (1H, t, J=9.1 Hz), 4.58 (2H, d, J=6.0 Hz), 4.79 (2H, AB), 5.02-5.12 (1H, m), 6.94 (1H, br t, J=6 Hz, NHC=O), 6.99 (2H, d, J=10.7 Hz), 7.74 (1H, br s), 7.78 (1H, br s).

EXAMPLE A39

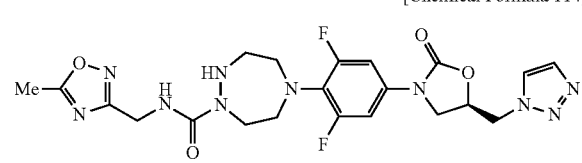

[Chemical Formula 114]

$^1$H NMR (CDCl$_3$) δ 2.58 (3H, s, CH$_3$), 3.11-3.18 (2H, m), 3.27-3.35 (4H, m), 3.70-3.84 (2H, m), 3.89 (1H, dd, J=6.1, 9.1 Hz), 4.12 (1H, t, J=9.1 Hz), 4.54 (2H, d, J=5.8 Hz), 4.79 (2H, AB), 5.02-5.12 (1H, m), 6.97 (1H, br t, J=6 Hz, NHC=O), 6.97 (2H, d, J=10.7 Hz), 7.74 (1H, br s), 7.78 (1H, br s).

EXAMPLE A40

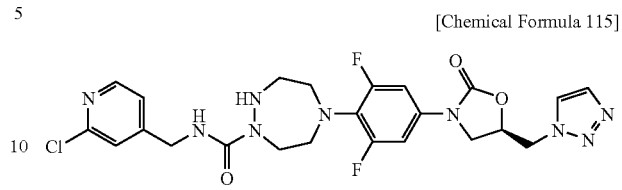

[Chemical Formula 115]

$^1$H NMR (CDCl$_3$) δ 3.05-3.14 (2H, m), 3.23-3.39 (4H, m), 3.75-3.85 (2H, m), 3.90 (1H, dd, J=6.1, 9.1 Hz), 4.12 (1H, t, J=9.1 Hz), 4.40 (2H, d, J=5.8 Hz), 4.79 (2H, AB), 5.02-5.12 (1H, m), 6.88 (1H, br t, J=6 Hz, NHC=O), 6.98 (2H, d, J=10.7 Hz), 7.27 (1H, s), 7.60-7.68 (1H, m), 7.74 (1H, br s), 7.78 (1H, br s), 8.27-8.33 (1H, m).

EXAMPLE A41

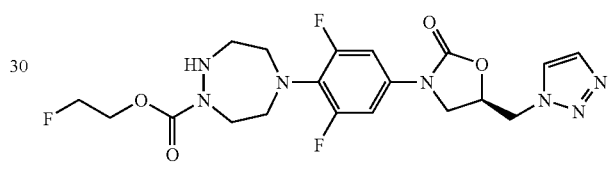

$^1$H NMR (CDCl$_3$) δ 3.04-3.09 (2H, m), 3.23-3.29 (2H, m), 3.39-3.46 (2H, m), 3.63-3.69 (2H, m), 3.88 (1H, dd, J=6.1, 9.1 Hz), 4.12 (1H, t, J=9.1 Hz), 4.32-4.36 (1H, m), 4.42-4.46 (1H, m), 4.52-4.57 (1H, m), 4.68-4.72 (1H, m), 4.79 (2H, AB), 5.02-5.12 (1H, m), 6.97 (2H, d, J=10.7 Hz), 7.73 (1H, d, J=1.1 Hz), 7.79 (1H, d, J=1.1 Hz).

EXAMPLE A42

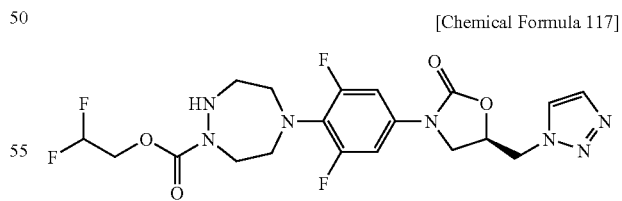

[Chemical Formula 117]

$^1$H NMR (CDCl$_3$) δ 3.03-3.10 (2H, m), 3.23-3.29 (2H, m), 3.38-3.45 (2H, m), 3.62-3.69 (2H, m), 3.89 (1H, dd, J=6.1, 9.1 Hz), 4.12 (1H, t, J=9.1 Hz), 4.34 (2H, dt, J=3.9, 13.5 Hz, CH$_2$O), 4.79 (2H, AB), 5.02-5.12 (1H, m), 5.98 (1H, tt, J=3.9, 55.2 Hz, CHF$_2$), 6.97 (2H, d, J=10.7 Hz), 7.74 (1H, d, J=1.1 Hz), 7.79 (1H, d, J=1.1 Hz).

EXAMPLE A43

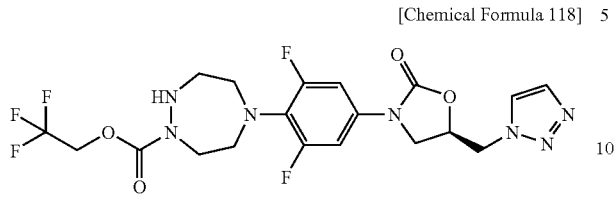

$^1$H NMR (CDCl$_3$) δ 3.04-3.10 (2H, m), 3.24-3.30 (2H, m), 3.39-3.46 (2H, m), 3.64-3.71 (2H, m), 3.89 (1H, dd, J=6.1, 9.1 Hz), 4.11 (1H, t, J=9.1 Hz), 4.55 (2H, AB, CF$_3$CH$_2$O), 4.79 (2H, AB), 5.02-5.12 (1H, m), 6.97 (2H, d, J=10.7 Hz), 7.75 (1H, d, J=1.1 Hz), 7.78 (1H, d, J=1.1 Hz).

EXAMPLE A44

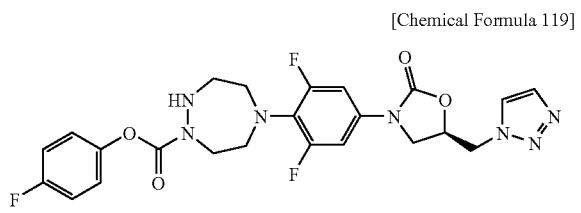 [SMILES: O=C(Oc1ccc(F)cc1)N1CCN(c2c(F)cc(N3C[C@H](Cn4ccnn4)OC3=O)cc2F)CCN1]

$^1$H NMR (CDCl$_3$) δ 3.07-3.20 (2H, m), 3.29-3.36 (2H, m), 3.45-3.53 (2H, m), 3.70-3.86 (2H, m), 3.89 (1H, dd, J=6.1, 9.1 Hz), 4.10 (1H, t, J=9.1 Hz), 4.79 (2H, AB), 5.02-5.12 (1H, m), 6.99 (2H, d, J=10.7 Hz), 7.00-7.15 (4H, m), 7.74 (1H, br s), 7.78 (1H, br s).

EXAMPLE A45

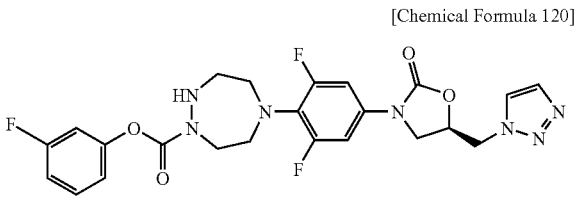 [SMILES: O=C(Oc1cccc(F)c1)N1CCN(c2c(F)cc(N3C[C@H](Cn4ccnn4)OC3=O)cc2F)CCN1]

$^1$H NMR (CDCl$_3$) δ 3.08-3.20 (2H, m), 3.29-3.36 (2H, m), 3.45-3.53 (2H, m), 3.70-3.86 (2H, m), 3.89 (1H, dd, J=6.1, 9.1 Hz), 4.10 (1H, t, J=9.1 Hz), 4.79 (2H, AB), 5.02-5.12 (1H, m), 6.89-6.98 (3H, m), 6.99 (2H, d, J=10.7 Hz), 7.28-7.38 (1H, m), 7.74 (1H, br s), 7.78 (1H, br s).

EXAMPLE A46

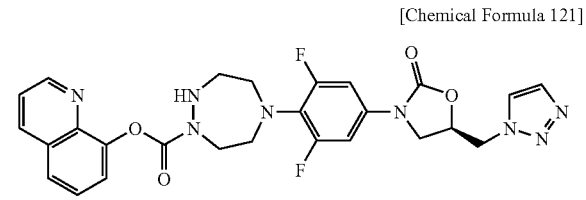 [SMILES: O=C(Oc1cccc2cccnc12)N1CCN(c2c(F)cc(N3C[C@H](Cn4ccnn4)OC3=O)cc2F)CCN1]

$^1$H NMR (CDCl$_3$) δ 3.16-3.24 (2H, br), 3.38-3.48 (2H, br), 3.50-3.64 (2H, br), 3.76-3.88 (2H, m), 3.84 (1H, dd, J=6.1, 9.1 Hz), 4.06 (1H, t, J=9.1 Hz), 4.73 (2H, AB), 4.96-5.06 (1H, m), 6.99 (2H, d, J=10.7 Hz), 7.43 (1H, dd, J=4.1, 8.3 Hz), 7.49-7.58 (2H, m), 7.68-7.74 (1H, m), 7.73 (1H, br s), 7.76 (1H, br s), 8.17 (1H, br d, J=8 Hz), 8.90 (1H, br d, J=4 Hz).

EXAMPLE A47

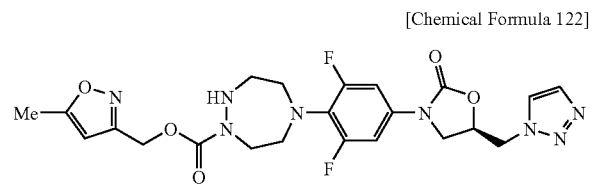 [SMILES: Cc1cc(COC(=O)N2CCN(c3c(F)cc(N4C[C@H](Cn5ccnn5)OC4=O)cc3F)CCN2)no1]

$^1$H NMR (CDCl$_3$) δ 2.41 (3H, s, CH$_3$), 3.02-3.10 (2H, m), 3.22-3.29 (2H, m), 3.36-3.45 (2H, m), 3.61-3.69 (2H, m), 3.89 (1H, dd, J=6.1, 9.1 Hz), 4.13 (1H, t, J=9.1 Hz), 4.80 (2H, AB), 5.04-5.13 (1H, m), 5.20 (2H, s, CH$_2$O), 6.05 (1H, s), 6.97 (2H, d, J=10.7 Hz), 7.73 (1H, br s), 7.80 (1H, br s).

EXAMPLE A48

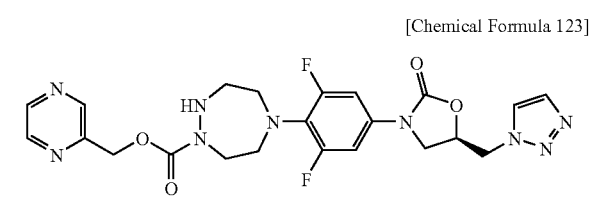 [SMILES: O=C(OCc1cnccn1)N1CCN(c2c(F)cc(N3C[C@H](Cn4ccnn4)OC3=O)cc2F)CCN1]

$^1$H NMR (CDCl$_3$) δ 3.05-3.12 (2H, m), 3.24-3.31 (2H, m), 3.41-3.47 (2H, m), 3.68-3.73 (2H, m), 3.89 (1H, dd, J=6.1, 9.1 Hz), 4.13 (1H, t, J=9.1 Hz), 4.80 (2H, AB), 5.03-5.12 (1H, m), 5.36 (2H, s, CH$_2$O), 6.97 (2H, d, J=10.7 Hz), 7.74 (1H, br s), 7.80 (1H, br s), 8.50-8.58 (2H, m), 8.67 (1H, br s).

EXAMPLE A49

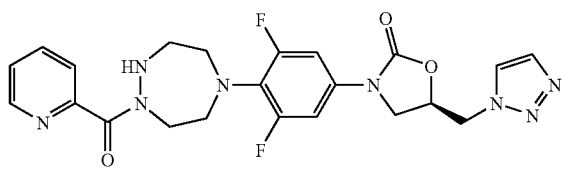

[Chemical Formula 124]

$^1$H NMR (CDCl$_3$) δ 2.80-2.86 & 3.18-3.56 & 3.80-3.92 & 3.95-4.01 & 4.05-4.15 (10H, m), 4.79 (2H, AB), 5.01-5.11 (1H, m), 6.91-7.00 (2H, m), 7.31-7.41 & 7.67-7.90 & 8.50-8.62 (4H, m), 7.74 (1H, br s), 7.78 (1H, br s).

EXAMPLE A50

[Chemical Formula 125]

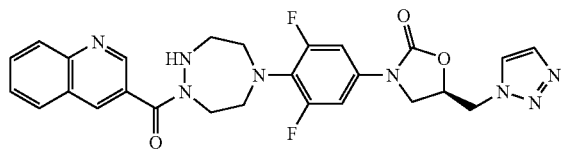

$^1$H NMR (CDCl$_3$) δ 3.00-3.12 & 3.16-3.56 & 3.28-3.38 & 3.44-3.52 & 3.62-3.72 (8H, br), 3.90 (1H, dd, J=6.1, 9.1 Hz), 4.11 (1H, t, J=9.1 Hz), 4.79 (2H, AB), 5.02-5.12 (1H, m), 6.99 (2H, d, J=10.7 Hz), 7.53-7.90 & 8.09-8.16 & 8.25-8.35 & 8.45-8.53 & 8.95-9.05 & 9.15-9.24 (6H, br), 7.74 (1H, br s), 7.78 (1H, br s).

EXAMPLE A51

[Chemical Formula 126]

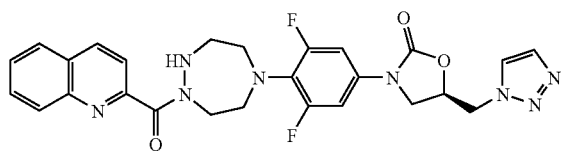

$^1$H NMR (CDCl$_3$) δ 2.83-2.89 & 3.23-3.32 & 3.36-3.42 & 3.47-3.60 & 3.83-3.97 & 4.01-4.14 (10H, m), 4.76-4.80 (2H, m), 5.00-5.11 (1H, m), 6.91-7.01 (2H, m), 7.57-7.65 & 7.72-7.81 & 7.84-7.94 & 8.04-8.12 & 8.25-8.32 (8H, m).

EXAMPLE A52

[Chemical Formula 127]

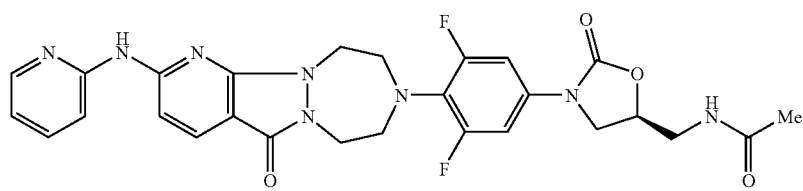

$^1$H NMR (CDCl$_3$) δ 2.03 (3H, CH$_3$C=O), 3.35-3.45 (4H, m), 3.58-3.70 (2H, m), 3.75 (1H, dd, J=6.9, 9.1 Hz), 4.00 (1H, t, J=9.1 Hz), 4.28-4.38 (4H, m), 4.74-4.84 (1H, m), 6.23 (1H, br t, J=6 Hz, NHC=O), 6.45 (1H, d, J=8.5 Hz), 7.13 (2H, d, J=10.7 Hz), 7.26-7.32 (1H, m), 7.90 (1H, d, J=8.5 Hz), 8.05 (1H, ddd, J=1.4, 2.8, 8.2 Hz), 8.32 (1H, dd, J=1.4, 4.7 Hz), 8.90 (1H, d, J=2.8 Hz).

EXAMPLE A53

[Chemical Formula 128]

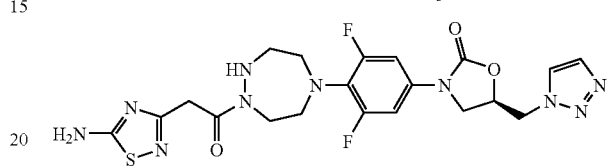

$^1$H NMR (CDCl$_3$+DMSO-d$_6$) δ 3.01-4.16 (10H, m), 3.78 & 4.01 (2H, s, CH$_2$C=O), 4.81 (2H, AB), 5.04-5.14 (1H, m), 6.56 & 6.73 (2H, br s, NH$_2$), and 6.94 & 7.00 (2H, d, J=10.7 Hz), 7.74 & 7.75 (1H, br s), 7.82 & 7.83 (1H, br s).

EXAMPLE A54

[Chemical Formula 129]

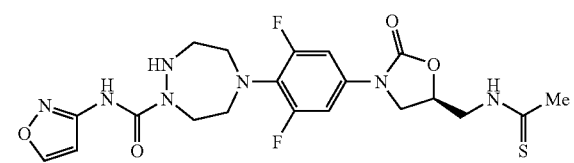

$^1$H NMR (CDCl$_3$) δ 2.60 (3H, CH$_3$C=S), 3.18-3.26 (2H, m), 3.30-3.36 (2H, m), 3.36-3.42 (2H, m), 3.81 (1H, dd, J=6.9, 9.1 Hz), 3.82-3.92 (2H, m), 3.98-4.27 (3H, m), 4.95-5.06 (1H, m), 7.01 (1H, d, J=1.9 Hz), 7.08 (2H, d, J=10.7 Hz), 8.24 (1H, d, J=1.9 Hz), 8.39 (1H, br t, J=6 Hz, NHC=S), 9.27 (1H, s, NHC=O).

EXAMPLE A55

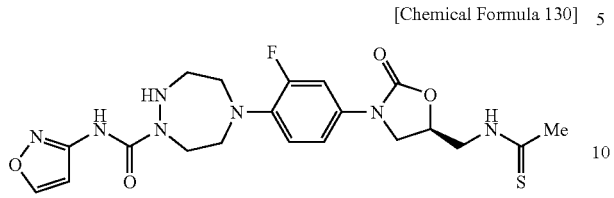

¹H NMR (CDCl₃) δ 2.60 (3H, CH₃C=S), 3.24-3.31 (2H, m), 3.37-3.47 (4H, m), 3.80 (1H, dd, J=6.9, 9.1 Hz), 3.85-4.30 (5H, m), 4.92-5.03 (1H, m), 6.90 (1H, t, J=9.1 Hz), 7.00 (1H, d, J=1.9 Hz), 7.02 (1H, d, br dd, J=2, 9 Hz), 7.38 (1H, dd, J=2.5, 14.6 Hz), 8.15 (1H, br t, J=6 Hz, NHC=S), 8.23 (1H, d, J=1.9 Hz), 9.21 (1H, s, NHC=O).

EXAMPLE A56

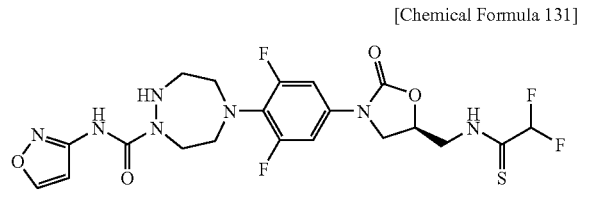 [SMILES: O=C(Nc1ccon1)N1CCN(c2c(F)cc(N3C[C@H](CNC(=S)C(F)F)OC3=O)cc2F)CCN1]

¹H NMR (CDCl₃) δ 3.18-3.25 (2H, m), 3.30-3.36 (2H, m), 3.36-3.43 (2H, m), 3.78 (1H, dd, J=6.6, 9.1 Hz), 3.82-3.92 (2H, m), 4.02-4.32 (3H, m), 4.98-5.08 (1H, m), 6.21 (1H, t, J=55.8 Hz, CHF₂C=S), 7.00 (1H, d, J=1.8 Hz), 7.08 (2H, d, J=10.7 Hz), 8.23 (1H, d, J=1.8 Hz), 9.05 (1H, br, NHC=S), 9.29 (1H, s, NHC=O).

EXAMPLE A57

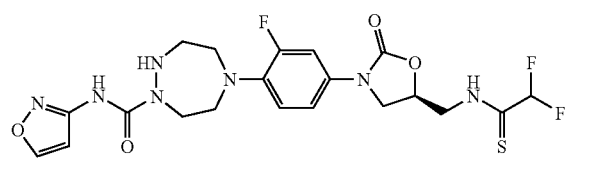

¹H NMR (CDCl₃) δ 3.23-3.31 (2H, m), 3.38-3.47 (4H, m), 3.77 (1H, dd, J=6.6, 9.1 Hz), 3.86-3.98 (2H, m), 3.98-4.35 (3H, m), 4.94-5.04 (1H, m), 6.21 (1H, t, J=55.8 Hz, CHF₂C=S), 6.91 (1H, t, J=9.1 Hz), 7.00 (1H, d, J=1.7 Hz), 7.03 (1H, br dd, J=2, 9 Hz), 7.37 (1H, dd, J=2.5, 14.6 Hz), 8.23 (1H, d, J=1.7 Hz), 8.81 (1H, br, NHC=S), 9.22 (1H, s, NHC=O).

EXAMPLE A58

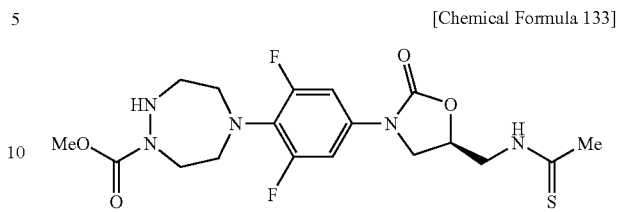

¹H NMR (CDCl₃) δ 2.60 (3H, CH₃C=S), 3.03-3.09 (2H, m), 3.24-3.32 (2H, m), 3.38-3.45 (2H, m), 3.61-3.68 (2H, m), 3.77 (3H, s, CH₃OC=O), 3.79 (1H, dd, J=6.9, 9.1 Hz), 4.00-4.15 (2H, m), 4.18-4.28 (1H, m), 4.94-5.04 (1H, m), 7.05 (2H, d, J=1.9 Hz), 8.30 (1H, br t, J=6 Hz, NHC=S).

EXAMPLE A59

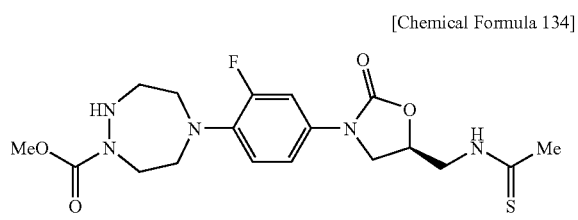 [SMILES: COC(=O)N1CCN(c2ccc(N3C[C@H](CNC(C)=S)OC3=O)cc2F)CCN1]

¹H NMR (CDCl₃) δ 2.60 (3H, CH₃C=S), 3.08-3.16 (2H, m), 3.39-3.46 (2H, m), 3.54-3.60 (2H, m), 3.64-3.74 (2H, br), 3.69 (3H, s, CH₃OC=O), 3.80 (1H, dd, J=6.9, 9.1 Hz), 4.01-4.11 (2H, m), 4.18-4.28 (1H, m), 4.92-5.02 (1H, m), 6.87 (1H, t, J=9.1 Hz), 6.99 (1H, br dd, J=3, 9 Hz), 7.32 (1H, dd, J=2.5, 15.1 Hz) 8.43 (1H, br t, J=6 Hz, NHC=S).

EXAMPLE A60

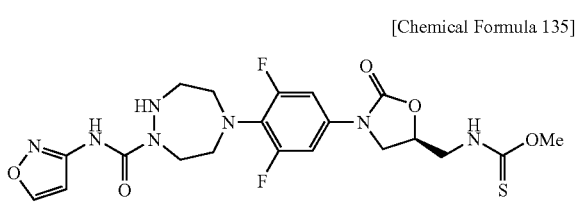 [SMILES: COC(=S)NC[C@H]1CN(c2cc(F)c(N3CCNN(C(=O)Nc4ccon4)CC3)c(F)c2)C(=O)O1]

¹H NMR (CDCl₃) δ 3.18-3.25 (2H, m), 3.31-3.42 (4H, m), 3.80-4.14 (6H, m), 4.01 (3H, s, CH₃OC=S), 4.87-4.97 (1H, m), 6.66 (1H, br t, J=6 Hz, NHC=S), 7.03 (1H, d, J=1.6 Hz), 7.12 (2H, d, J=10.6 Hz), 8.23 (1H, d, J=1.6 Hz), 9.24 (1H, s, NHC=O).

EXAMPLE A61

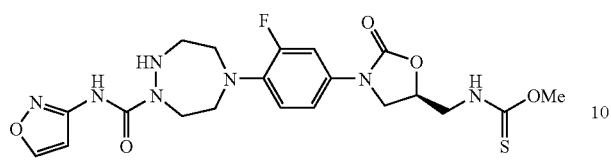

[Chemical Formula 136]

$^1$H NMR (CDCl$_3$+DMSO-d$_6$) δ 3.20-3.28 (2H, m), 3.37-3.50 (4H, m), 3.83-4.07 (6H, m), 3.99 (3H, s, CH$_3$OC=S), 4.89-4.99 (1H, m), 6.92 (1H, t, J=9.1 Hz), 6.99 (1H, br s), 7.05 (1H, br d, J=9 Hz), 7.43 (1H, br d, J=15 Hz), 8.26 (1H, br s), 8.69 (1H, br t, J=6 Hz, NHC=S), 9.27 (1H, s, NHC=O).

EXAMPLE A62

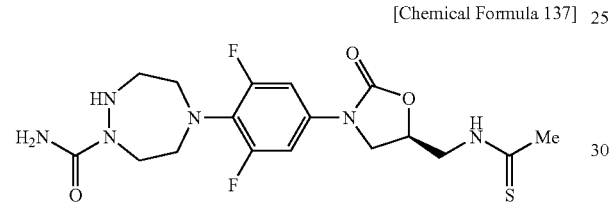

[Chemical Formula 137]

$^1$H NMR (CDCl$_3$) δ 2.60 (3H, s, CH$_3$C=S), 3.12-3.20 (2H, m), 3.29-3.37 (4H, m), 3.75-3.85 (4H, m), 4.05 (1H, t, J=9.1 Hz), 4.26 (1H, ddd, J=2.8, 6.0, 14.6 Hz), 4.93-5.03 (1H, m), 5.37 (2H, br s, H$_2$NC=O), 7.08 (2H, d, J=10.7 Hz), 8.10 (1H, br t, J=6 Hz, NHC=S).

EXAMPLE A63

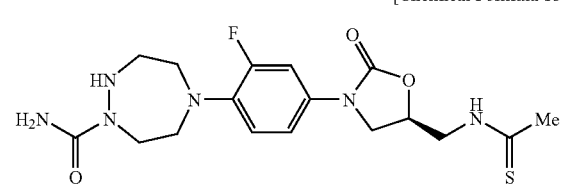

[Chemical Formula 138]

$^1$H NMR (CDCl$_3$+DMSO-d$_6$) δ 2.58 (3H, s, CH$_3$C=S), 3.17-3.25 (2H, m), 3.36-3.44 (4H, m), 3.79-3.90 (4H, m), 4.04 (1H, t, J=9.1 Hz), 4.16 (1H, ddd, J=2.7, 5.8, 14.3 Hz), 4.93-5.02 (1H, m), 5.43 (2H, br s, H$_2$NC=O), 6.90 (1H, t, J=9.1 Hz), 7.02 (1H, dd, J=2.6, 8.8 Hz), 7.41 (1H, dd, J=2.6, 14.7 Hz), 9.45 (1H, br t, J=6 Hz, NHC=S).

EXAMPLE A64

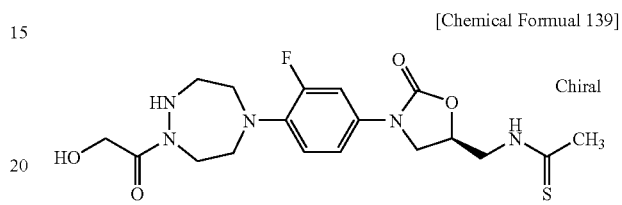

[Chemical Formual 139]

$^1$H-NMR (DMSO-d$_6$) δ: 2.43 (3H, s), 2.95-3.04 (1H, m), 3.26-3.35 (5H, m), 3.42 (2H, t, J=5.19 Hz), 3.71-3.82 (2H, m), 3.83-3.97 (2H, m), 4.10 (1H, t, J=9.00 Hz), 4.17 (2H, s), 4.85-4.99 (1H, m), 5.22 (1H, t, J=6.25 Hz), 7.01 (1H, t, J=9.53 Hz), 7.11 (1H, dd, J=8.85, 2.44 Hz), 7.43 (1H, dd, J=15.56, 2.44 Hz), 10.35 (1H, t, J=4.88 Hz)

EXAMPLE A65

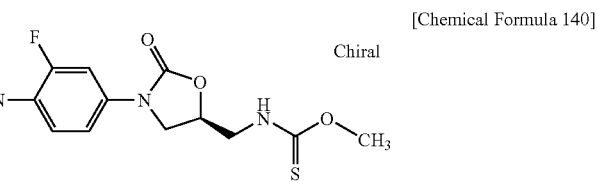

[Chemical Formula 140]

$^1$H-NMR (CDCl$_3$) δ: 3.22-3.09 (2H, m), 3.51-3.56 (2H, m), 3.59-3.75 (9H, m), 3.79-4.10 (10H, m), 4.45 (2H, s), 4.99-4.69 (1H, m), 6.88 (1H, t, J=9.15 Hz), 7.02 (1H, t, J=7.72 Hz), 7.20 (1H, t, J=6.04 Hz), 7.36-7.50 (1H, m).

EXAMPLE A66

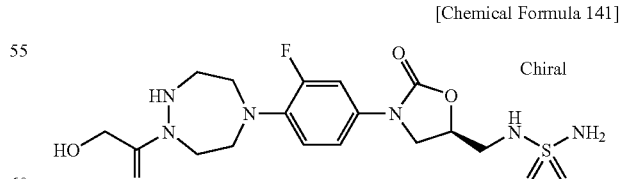

[Chemical Formula 141]

$^1$H-NMR (DMSO-d$_6$) δ: 2.97-3.02 (2H, m), 3.19 (2H, t, J=5.79 Hz), 3.42 (2H, t, J=5.20 Hz), 3.73 (2H, t, J=5.37 Hz), 3.82 (1H, dd, J=9.06, 6.21 Hz), 4.06 (1H, t, J=8.98 Hz), 4.18 (2H, s), 4.75 (1H, dt, J=14.21, 5.71 Hz), 5.22 (1H, t, J=6.21 Hz), 6.97-7.05 (2H, m), 7.13 (1H, dd, J=8.90, 2.35 Hz), 7.44 (1H, dd, J=15.44, 2.52 Hz).

EXAMPLE A67
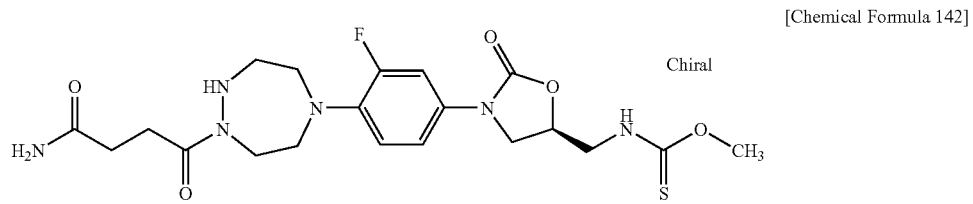 [SMILES: COC(=S)NC[C@H]1CN(c2ccc(N3CCNN(C(=O)CCC(N)=O)CC3)c(F)c2)C(=O)O1]
[Chemical Formula 142]
¹H-NMR (DMSO-d₆) δ: 2.24 (2H, t, J=7.30 Hz), 2.66 (2H, t, J=7.30 Hz), 3.07-2.90 (2H, m), 3.38 (2H, t, J=5.12 Hz), 3.63-3.80 (5H, m), 3.94-3.86 (4H, m), 4.05-4.13 (1H, m), 4.70-4.90 (1H, m), 5.25 (1H, t, J=6.13 Hz), 6.66 (1H, s), 7.07-6.97 (1H, m), 7.11 (1H, dd, J=8.90, 2.35 Hz), 7.23 (1H, s), 7.42 (1H, dd, J=15.44, 2.35 Hz), 9.55-9.40 (1H, m).
EXAMPLE A68
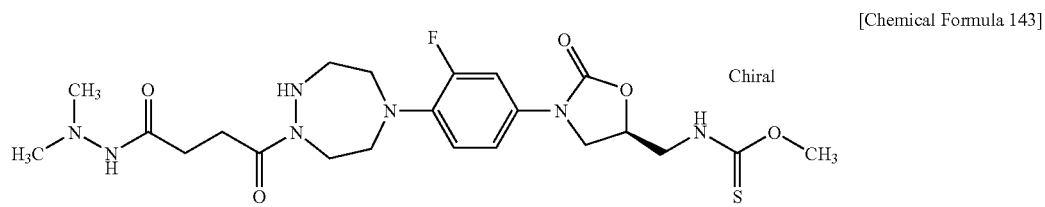
[Chemical Formula 143]
¹H-NMR (DMSO-d₆) δ: 2.13 (2H, t, J=7.39 Hz), 2.66 (2H, t, J=7.47 Hz), 3.07-2.91 (2H, m), 3.68-3.80 (5H, m), 3.88-3.93 (3H, m), 4.03-4.15 (1H, m), 4.68-4.95 (1H, m), 5.25 (1H, t, J=6.13 Hz), 6.96-7.17 (2H, m), 7.42 (1H, dd, J=15.53, 2.43 Hz), 8.12-8.21 (0H, m), 8.67 (1H, s), 9.39-9.62 (1H, m).
EXAMPLE A69
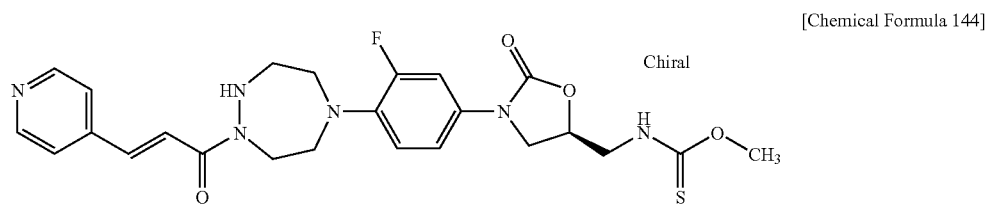 [SMILES: COC(=S)NC[C@H]1CN(c2ccc(N3CCNN(C(=O)/C=C/c4ccncc4)CC3)c(F)c2)C(=O)O1]
[Chemical Formula 144]
¹H-NMR (DMSO-d₆) δ: 2.13 (2H, t, J=7.39 Hz), 2.66 (2H, t, J=7.47 Hz), 3.02 (2H, s), 3.68-3.80 (5H, m), 3.88-3.93 (3H, m), 4.03-4.15 (1H, m), 4.68-4.95 (1H, m), 5.25 (1H, t, J=6.13 Hz), 6.96-7.17 (2H, m), 7.42 (1H, dd, J=15.53, 2.43 Hz), 8.12-8.21 (0H, m), 8.67 (1H, s), 9.39-9.62 (1H, m).
EXAMPLE A70
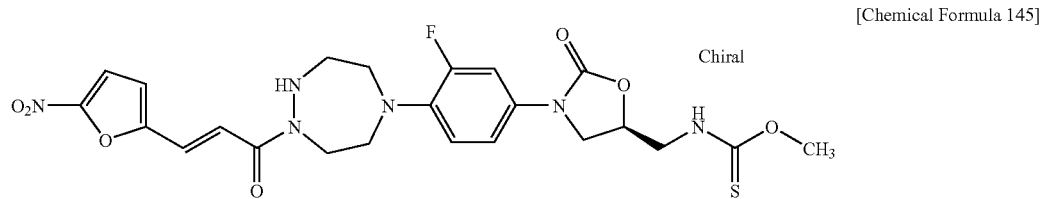 [SMILES: COC(=S)NC[C@H]1CN(c2ccc(N3CCNN(C(=O)/C=C/c4ccc([N+](=O)[O-])o4)CC3)c(F)c2)C(=O)O1]
[Chemical Formula 145]

The compound was prepared according to the following procedure.

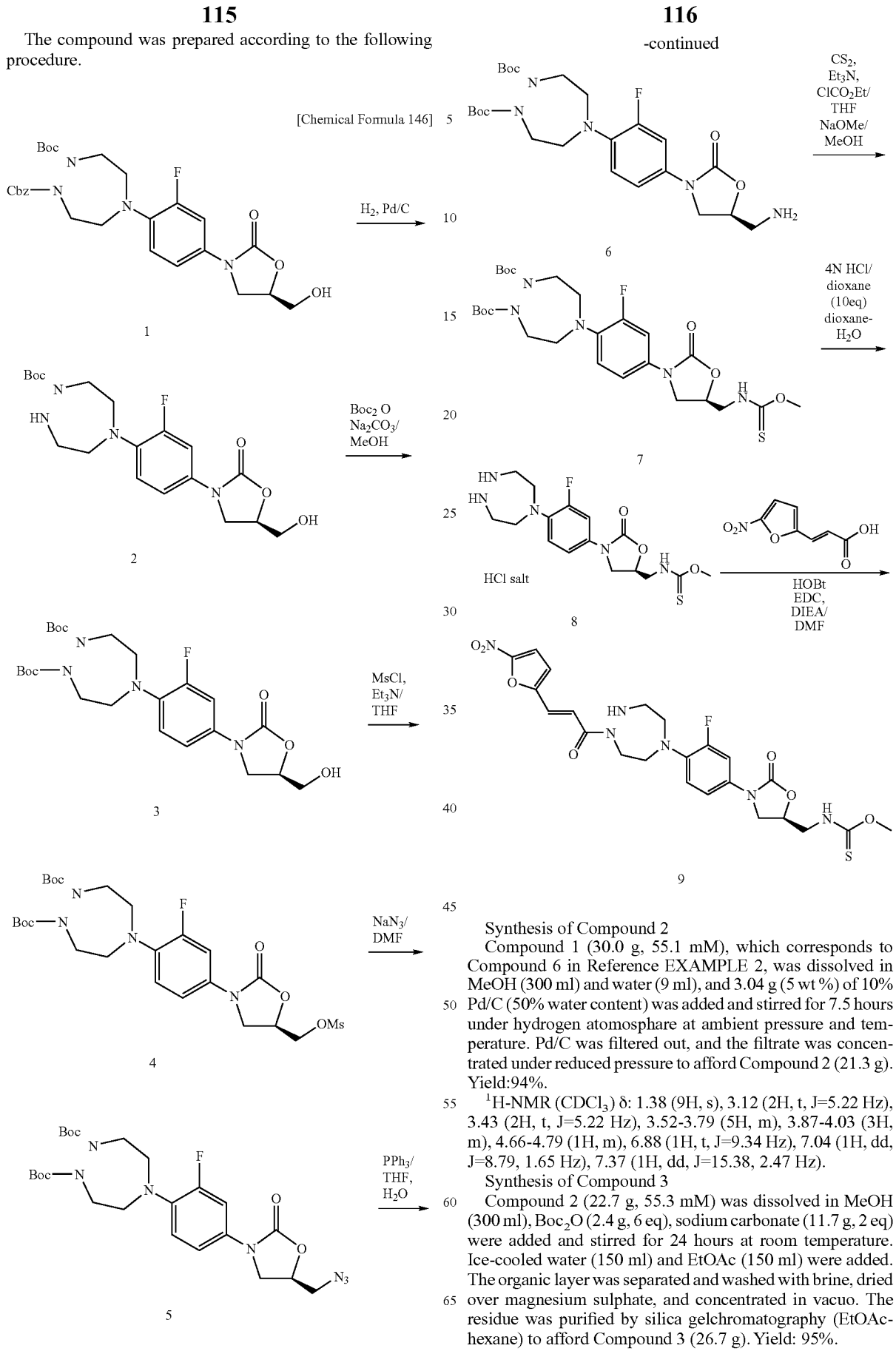

Synthesis of Compound 2

Compound 1 (30.0 g, 55.1 mM), which corresponds to Compound 6 in Reference EXAMPLE 2, was dissolved in MeOH (300 ml) and water (9 ml), and 3.04 g (5 wt %) of 10% Pd/C (50% water content) was added and stirred for 7.5 hours under hydrogen atomosphare at ambient pressure and temperature. Pd/C was filtered out, and the filtrate was concentrated under reduced pressure to afford Compound 2 (21.3 g). Yield:94%.

$^1$H-NMR (CDCl$_3$) δ: 1.38 (9H, s), 3.12 (2H, t, J=5.22 Hz), 3.43 (2H, t, J=5.22 Hz), 3.52-3.79 (5H, m), 3.87-4.03 (3H, m), 4.66-4.79 (1H, m), 6.88 (1H, t, J=9.34 Hz), 7.04 (1H, dd, J=8.79, 1.65 Hz), 7.37 (1H, dd, J=15.38, 2.47 Hz).

Synthesis of Compound 3

Compound 2 (22.7 g, 55.3 mM) was dissolved in MeOH (300 ml), Boc$_2$O (2.4 g, 6 eq), sodium carbonate (11.7 g, 2 eq) were added and stirred for 24 hours at room temperature. Ice-cooled water (150 ml) and EtOAc (150 ml) were added. The organic layer was separated and washed with brine, dried over magnesium sulphate, and concentrated in vacuo. The residue was purified by silica gelchromatography (EtOAc-hexane) to afford Compound 3 (26.7 g). Yield: 95%.

¹H-NMR (CDCl₃) δ: 1.48 (18H, s), 3.18-3.59 (5H, m), 3.78 (1H, dd, J=12.64, 3.85 Hz), 3.90-4.07 (4H, m), 4.10-4.26 (2H, m), 4.70-4.82 (1H, m), 6.92 (1H, t, J=9.34 Hz), 7.11 (1H, t, J=9.75 Hz), 7.35-7.50 (1H, m).

Synthesis of Compound 4

Compound 3 (19.5 g, 38 mM) was disslved in THF (150 ml). Under ice-cooling, triethylamine (6.9 ml, 1.3 eq) and methanesulfonyl chloride (3.5 ml, 1.2 eq) were added and stirred for 20 minutes. After concentration to reduce the volume to about ½, ice-cold water (100 ml) and EtOAc (200 ml) were added. The organic layer was separated, washed sequentially with water and brine. Drying over magnesium sulphate and concentration in vacuo afforded Compound 4 (23.3 g). Yield: 104%.

¹H-NMR (CDCl₃) δ: 1.48 (18H, s), 3.13 (3H, s), 3.23-3.40 (4H, m), 3.47-3.56 (3H, m), 3.87-4.23 (3H, m), 4.40-4.56 (2H, m), 4.87-4.99 (1H, m), 6.93 (1H, t, J=9.20 Hz), 7.02-7.15 (1H, m), 7.33-7.50 (1H, m).

Synthesis of Compound 5

Compound 4 (23.27 g, 38 mM) was dissolved in DMF (100 ml). Sodium azide (3.72 g, 1.5 eq) was added and stirred at 60° C. for 10 hours. After cooling to room temperature, water (200 ml) and EtOAc (400 ml) were added. The organic layer was separated and washed sequentially with water (×3) and brine. After drying over magnesium sulphate and concentrated in vacuo, the residue was purified by silica gelchromatography (EtOAc-hexane) to afford Compound 5 (16.95 g). Yield: 83%.

¹H-NMR (CDCl₃) δ: 1.48 (18H, s), 3.20-3.41 (4H, m), 3.42-3.89 (4H, m), 3.94-4.26 (4H, m), 4.73-4.87 (1H, m), 6.93 (1H, t, J=9.06 Hz), 7.04-7.19 (1H, m), 7.33-7.50 (1H, m).

Synthesis of Compound 6

Compound 5 (16.94 g, 31.6 mM) was dissolved in THF (180 ml). Water (5 ml) and triphenylphosphine (9.95 g, 1.2 eq) were added and stirred at 50° C. for 1.5 hours. The reaction was concentrated in vacuo, the residue was pulified by silica gel chromatography (chloroform-methanol) to afford Compound 6 (15.46 g). Yield: 96%.

¹H-NMR (CDCl₃) δ: 1.50 (18H, s), 2.97-3.60 (8H, m), 3.79-3.90 (1H, m), 3.98-4.25 (3H, m), 4.67-4.78 (1H, m), 6.93 (1H, t, J=9.40 Hz), 7.06-7.19 (1H, m), 7.35-7.45 (1H, m).

Synthesis of Compound 7

Compound 6 (13.46 g, 26 mM) was dissolved in THF (150 ml). Triethylamine (7.2 ml, 2.0 eq) and carbon disulfide (3.9 ml, 2.5 eq) were added and stirred at room temperature for 1 hour. Then, ethyl chloroformate (2.7 ml, 1.1 eq) was added, stirred at room temperature for 15 minutes, and concentrated to reduce the volume to about ½. Ice-cooled water (200 ml) and EtOAc (200 ml) were added. The organic layer was separated, and washed sequentially with water and brine, dried over magnesium sulphate, and concentrated in vacuo to obtain 14.36 g of the residue.

The residue (12.0 g, 21.5 mM) was dissloved in MeOH (100 ml). Under ice-cooling, 1N NaOMe/MeOH (21.5 ml, 1 eq) was added and stirred at 0° C. for 1 hour. Saturated aqueous ammonium chloride (40 ml) was added, and concentrated to reduce the volume to about ½ under reduced pressure. Ice-cooled water (200 ml) and EtOAc (200 ml) were added. The organic layer was separated, washed with brine, dried over magnesium sulphate, and concentrated in vacuo. The redidue was purified by silica gel chromatography (EtOAc-hexane) to afford compound 7 (9.50 g). Yield: 76%.

¹H-NMR (CDCl₃) δ: 1.50 (18H, s), 3.19-3.78 (6H, m), 3.81-3.91 (1H, m), 3.95-4.29 (5H, m), 4.74-5.01 (1H, m), 6.79 (1H, t, J=6.04 Hz), 6.94 (1H, t, J=9.06 Hz), 7.13-7.03 (1H, m), 7.50-7.35 (1H, m).

Synthesis of Compound 8

Compound 7 (9.32 g, 16 mM) was dissolved in 1,4-dioxane (51 ml) and H₂O (10 ml). Under ice-cooling, 4N HCl/1,4-dioxanesolutions (44 ml) was added and stirred at room temperature for 3 hours. Toluene (120 ml) was added and concentrated in vacuo to afford Compound 8 (8.51 g). Yield: 104% (1.5HCl)

¹H-NMR (D₂O) δ: 3.50-3.53 (8H, m), 3.75-3.75 (3H, m), 3.91-4.04 (4H, m), 4.16-4.28 (1H, m), 7.21-7.12 (2H, m), 7.36 (1H, d, J=14.4 Hz).

Synthesis of Compound 9

Compound 8 (200 mg, 0.4 mM) was dissolved in dimethylformamide (2 ml). Under ice-cooling, 1-ethyl-3-(3'-dimethylaminopropyl)carbodiimide hydrochloric salt (119 mg, 1.3 eq), N-hydroxybenztriazole (84 mg, 1.3 eq), 3-(5-nitro-2-furyl)acrylic acid (113 mg, 1.3 eq), diisopropylethylamine (0.17 ml, 2 eq) were added and stirred at room temperature for 1.5 hours. Saturated aqueous sodium bicarbonate (20 ml) and EtOAc (20 ml) were added. The organic layer was separated, and washed sequentially with water (×3) and brine, dried over magnesium sulphate, and concentrated under reduced pressure. The residue was purified by silica gel chromatography (chloroform-methanol) to afford desired Compound 9 (205 mg). Yield: 93%.

¹H-NMR (DMSO-d₆) δ: 3.12 (2H, s), 3.50 (2H, s), 3.73-3.85 (3H, m), 3.86-3.97 (3H, m), 4.06-4.18 (1H, m), 4.70-4.96 (1H, m), 5.62 (1H, t, J=5.77 Hz), 6.99-7.25 (3H, m), 7.32-7.51 (2H, m), 7.61 (1H, d, J=15.93 Hz), 7.75-7.80 (1H, m), 9.60-9.41 (1H, m).

EXAMPLE A71

[Chemical Formula 147]

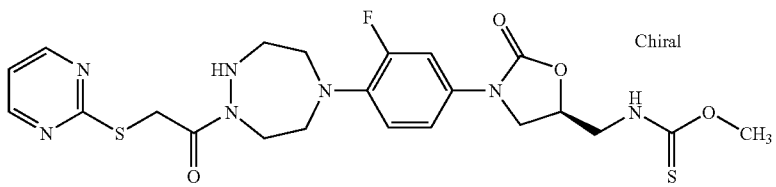

¹H-NMR (DMSO-d₆) δ: 3.13 (2H, s), 3.42 (2H, s), 3.70-3.82 (3H, m), 3.86-3.95 (2H, m), 4.02-4.17 (1H, m), 4.29 (1H, s), 4.67-4.93 (1H, m), 5.49 (1H, t, J=6.18 Hz), 6.99-7.22 (3H, m), 7.43 (1H, dd, J=15.52, 2.33 Hz), 8.53-8.62 (2H, m), 9.57-9.39 (1H, m).

EXAMPLE A72

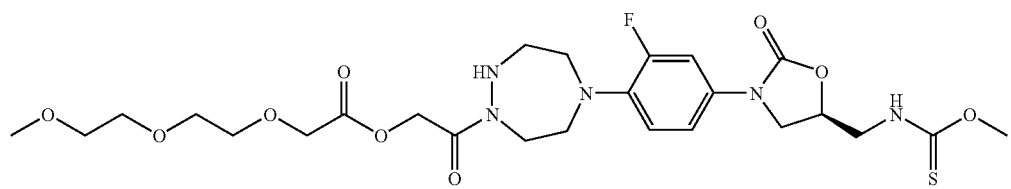

[Chemical Formula 148]

¹H NMR (CDCl₃) δ 3.21-3.28 (2H, m), 3.34-3.42 (2H, m), 3.38 (3H, s), 3.54-3.58 (2H, m), 3.64-4.10 (14H, m), 4.00 (3H, s), 4.30 (2H, s), 4.86-4.96 (2H, m), 5.04 (2H, s), 6.78 (1H, t, J=6.3 Hz), 6.89 (1H, t, J=9.3 Hz), 7.04 (1H, dd, J=2.4, 8.7 Hz), and 7.41 (1H, dd, J=2.4, 14.4 Hz).

EXAMPLE A73

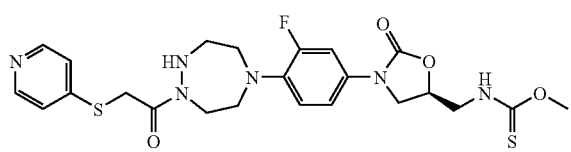

[Chemical Formula 149]

¹H NMR (DMSO-d₆) δ 3.08-3.16 (2H, m), 3.38-3.45 (2H, m), 3.70-4.14 (8H, m), 3.88 (3H, s), 4.16 (2H, s), 4.82-4.90 (1H, m), 5.52 (1H, t, J=6.6 Hz), 7.03 (1H, t, J=9.9 Hz), 7.12 (1H, dd, J=2.1, 8.7 Hz), 7.27 (2H, d, J=6.0 Hz), 7.44 (1H, dd, J=2.1, 15.6 Hz), 8.33 (2H, d, J=6.3 Hz), and 9.52 (1H, t, J=5.7 Hz).

EXAMPLE A74

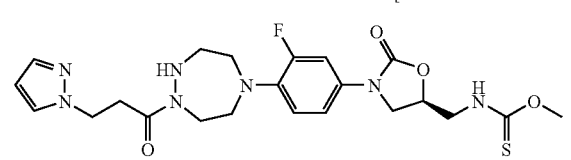

[Chemical Formula 150]

¹H NMR (DMSO-d₆) δ 2.93-3.04 (4H, m), 3.23-3.81 (10H, m), 3.88 (3H, s), 4.05-4.15 (1H, m), 4.29 (2H, t, J=7.2 Hz), 4.82-4.92 (1H, m), 5.29 (1H, t, J=6.0 Hz), 6.16 (1H, t, J=2.1 Hz), 7.00 (1H, t, J=9.6 Hz), 7.12 (1H, dd, J=1.5, 9.0 Hz), 7.39 (1H, d, J=0.9 Hz), 7.64 (1H, d, J=2.4 Hz), and 9.52 (1H, t, J=5.4 Hz).

EXAMPLE A75

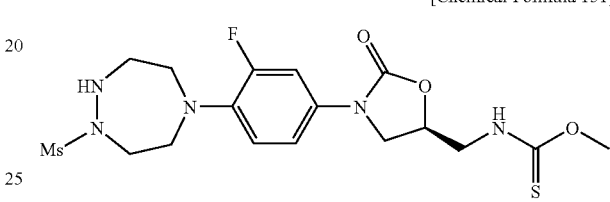

[Chemical Formula 151]

¹H-NMR (DMSO-d₆) δ: 2.88 (3H, s), 2.93-3.03 (2H, m), 3.36-3.45 (5H, m), 3.49-3.52 (4H, m), 3.70-3.81 (3H, m), 3.90 (3H, s), 4.04-4.15 (1H, m), 4.72-4.92 (2H, m), 7.04 (1H, t, J=9.2 Hz), 7.12 (1H, dd, J=9.2, 2.4 Hz), 7.42 (1H, dd, J=15.8, 2.4 Hz), 9.56-9.40 (1H, m).

EXAMPLE A76

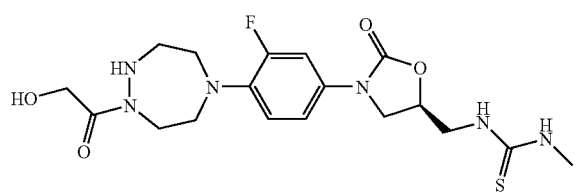

[Chemical Formula 152]

¹H-NMR (DMSO-d₆) δ: 2.81-2.84 (2H, m), 2.94-3.03 (2H, m), 3.25-3.36 (5H, m), 3.25-3.32 (2H, m), 3.68-3.83 (4H, m), 4.07 (1H, t, J=8.9 Hz), 4.18 (3H, br s), 4.77-4.89 (1H, br m), 5.22 (1H, t, J=6.3 Hz), 7.01 (1H, t, J=9.1 Hz), 7.11 (1H, dd, J=9.1, 2.5 Hz), 7.43 (1H, dd, J=15.6, 2.5 Hz), 7.71-7.78 (1H, m).

EXAMPLE A77

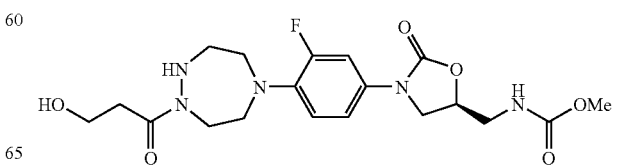

[Chemical Formula 153]

$^1$H-NMR (DMSO-$d_6$) δ: 2.63 (2H, t, J=6.9 Hz), 2.96-3.06 (2H, m), 3.26-3.31 (2H, m), 3.35-3.41 (2H, m), 3.65-3.54 (2H, m), 3.65-3.80 (5H, m), 3.86-3.94 (3H, m), 4.10 (1H, t, J=8.8 Hz), 4.44 (1H, t, J=5.5 Hz), 4.69-4.92 (1H, m), 5.27 (1H, t, J=5.9 Hz), 7.01 (1H, t, J=9.3 Hz), 7.11 (1H, d, J=9.3 Hz), 7.42 (1H, d, J=15.7 Hz), 9.44-9.52 (1H, m).

EXAMPLE A78

[Chemical Formula 154]

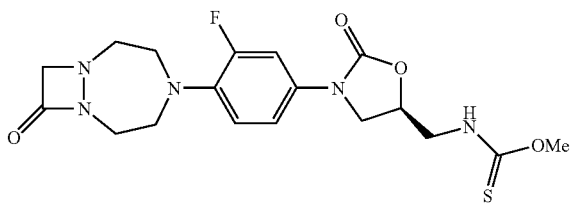

$^1$H-NMR (DMSO-$d_6$) δ: 2.81 (1H, m), 3.19 (1H, m), 3.27 (1H, m), 3.41 (1H, m), 3.48 (1H, m), 3.65 (1H, m), 3.69 (1H, m), 3.75 (2H, m), 3.80 (1H, m), 3.81 (1H, m), 3.86 (1H, d, J=13.5 Hz), 3.88 (3H, s), 4.11 (1H, m), 4.35 (1H, d, J=13.5 Hz), 4.87 (1H, m), 7.07 (1H, brd, J=9.6 Hz), 7.13 (1H, brd, J=9.6 Hz), 7.42 (1H, brd, J=16.3 Hz), 9.51 (1H, t, J=7.6 Hz).

EXAMPLE A79

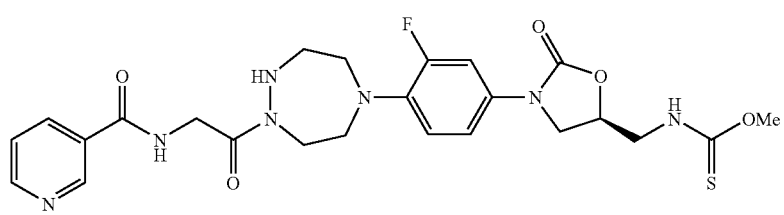

$^1$H-NMR (DMSO-$d_6$) δ: 3.08-3.11 (2H, m), 3.45-3.49 (3H, m), 3.63-3.81 (5H, m), 3.88-3.93 (3H, m), 4.10 (1H, t, J=8.9 Hz), 4.28 (2H, d, J=5.9 Hz), 4.70-4.93 (1H, m), 5.35-5.45 (1H, m), 7.04 (1H, t, J=9.2 Hz), 7.13 (1H, dd, J=9.2, 1.9 Hz), 7.43 (1H, dd, J=15.4, 1.9 Hz), 7.51 (1H, dd, J=7.9, 4.8 Hz), 8.19 (1H, d, J=7.9 Hz), 8.68-8.71 (2H, m), 8.98-9.04 (1H, m), 9.38-9.56 (1H, m).

EXAMPLE A80

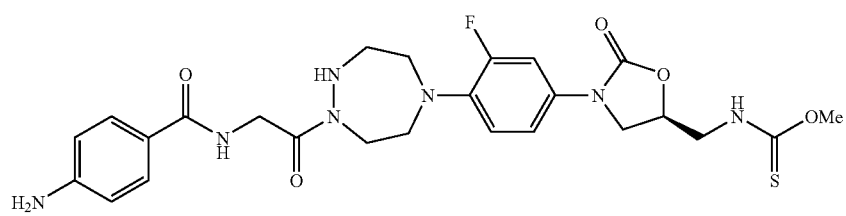

$^1$H-NMR (DMSO-$d_6$) δ: 3.07-3.10 (2H, m), 3.32-3.36 (2H, m), 3.67-3.82 (6H, m), 3.87-3.93 (3H, m), 4.10 (1H, t, J=8.2 Hz), 4.17-4.24 (2H, m), 4.69-4.92 (1H, m), 6.76 (2H, d, J=8.1 Hz), 7.03 (1H, t, J=9.1 Hz), 7.12 (1H, dd, J=9.1, 2.2 Hz), 7.43 (1H, dd, J=15.4, 2.2 Hz), 7.65 (2H, d, J=8.1 Hz), 8.01-8.11 (1H, m), 9.56-9.39 (1H, m).

EXAMPLE A81

[Chemical Formula 157]

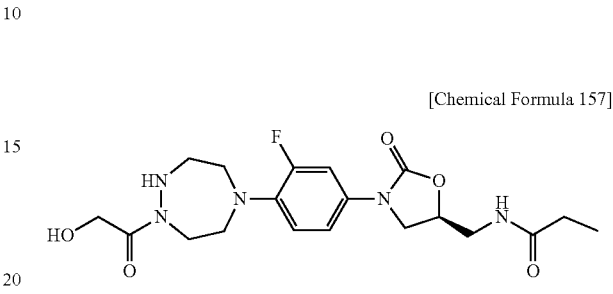

$^1$H-NMR (DMSO-$d_6$) δ: 0.95 (3H, t, J=7.6 Hz), 2.09 (2H, q, J=7.6 Hz), 2.94-3.03 (2H, m), 3.35-3.46 (4H, m), 3.64-3.76 (4H, m), 4.05 (1H, t, J=8.9 Hz), 4.17 (3H, s), 4.74-4.63 (1H, m), 5.21 (1H, t, J=6.3 Hz), 7.00 (1H, t, J=9.2 Hz), 7.10 (1H, dd, J=9.2, 2.5 Hz), 7.41 (1H, dd, J=15.6, 2.5 Hz), 8.14 (1H, t, J=5.4 Hz).

[Chemical Formula 155]

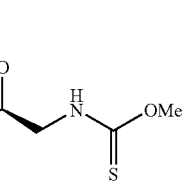

EXAMPLE A82

[Chemical Formula 158]

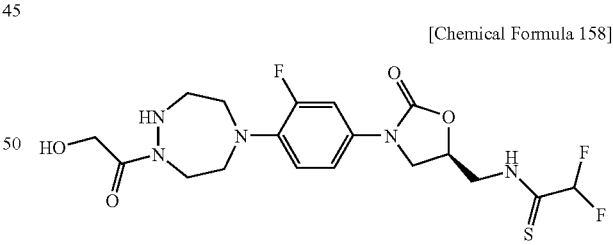

[Chemical Formula 156]

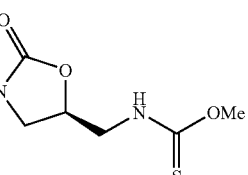

¹H-NMR (DMSO-d₆) δ 2.95-3.03 (2H, m), 3.38-3.47 (2H, m), 3.67-3.85 (4H, m), 3.92-3.99 (2H, m), 4.09-4.20 (4H, m), 4.90-5.04 (1H, m), 5.22 (1H, t, J=6.2 Hz), 6.48 (1H, t, J=55.1 Hz), 7.01 (1H, t, J=9.1 Hz), 7.11 (1H, dd, J=9.1, 2.5 Hz), 7.42 (1H, dd, J=15.5, 2.5 Hz), 11.10 (1H, s).

EXAMPLE A83

[Chemical Formula 159]

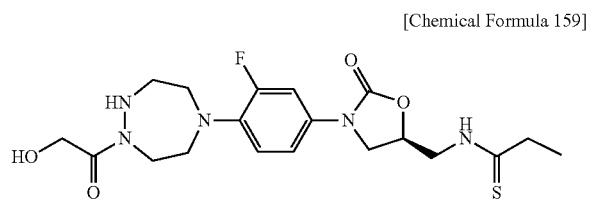 [SMILES: CCC(=S)NC[C@H]1CN(c2ccc(N3CCNN(C(=O)CO)CC3)c(F)c2)C(=O)O1]

¹H-NMR (DMSO-d₆) δ: 1.14 (3H, t, J=7.3 Hz), 2.58 (2H, q, J=7.3 Hz), 2.95-3.03 (2H, m), 3.25-3.32 (2H, m), 3.38-3.45 (2H, m), 3.67-3.85 (2H, m), 3.90 (2H, t, J=5.4 Hz), 4.10 (1H, t, J=8.7 Hz), 4.16 (3H, s), 4.86-4.98 (1H, m), 5.18-5.25 (1H, m), 7.01 (1H, t, J=9.2 Hz), 7.11 (1H, dd, J=9.2, 2.4 Hz), 7.42 (1H, dd, J=15.6, 2.4 Hz), 10.28 (1H, t, J=4.9 Hz).

EXAMPLE A84

[Chemical Formula 160]

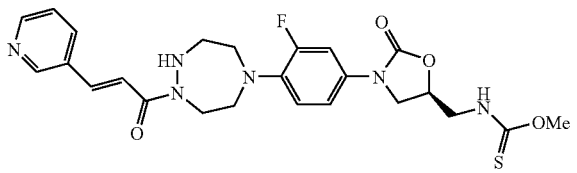

¹H-NMR (DMSO-d₆) δ 3.04-3.13 (2H, m), 3.44-3.51 (3H, m), 3.71-3.79 (3H, m), 3.83-3.94 (5H, m), 4.10 (1H, t, J=8.8 Hz), 4.66-4.93 (1H, m), 5.52 (1H, t, J=5.9 Hz), 7.03 (1H, t, J=9.1 Hz), 7.12 (1H, d, J=9.1 Hz), 7.37-7.53 (3H, m), 7.62 (1H, d, J=16.2 Hz), 8.08 (1H, d, J=8.2 Hz), 8.55 (1H, d, J=3.8 Hz), 8.78-8.82 (1H, m), 9.47 (1H, d, J=24.4 Hz).

EXAMPLE A85

[Chemical Formula 161]

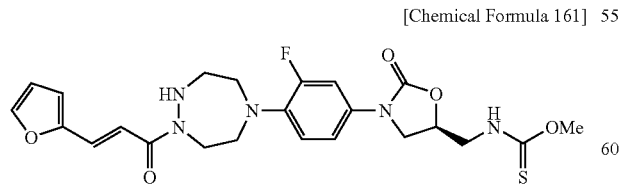

¹H-NMR (DMSO-d₆) δ: 3.01-3.11 (2H, m), 3.42-3.51 (3H, m), 3.71-3.94 (8H, m), 4.10 (1H, t, J=8.5 Hz), 4.66-4.93 (1H, m), 5.46 (1H, t, J=5.9 Hz), 6.59 (1H, dd, J=3.3, 1.6 Hz), 6.79 (1H, d, J=3.3 Hz), 7.03 (1H, t, J=9.2 Hz), 7.12 (1H, dd, J=9.2, 2.2 Hz), 7.24 (1H, d, J=15.7 Hz), 7.31 (1H, d, J=15.7 Hz), 7.43 (1H, dd, J=15.7, 2.2 Hz), 7.75-7.79 (1H, m), 9.39-9.56 (1H, m).

EXAMPLE A86

[Chemical Formula 162]

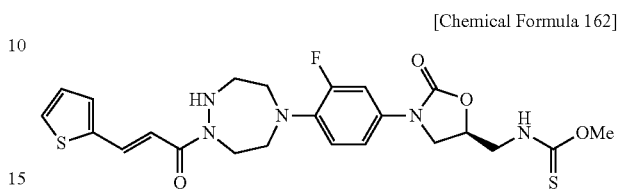

¹H-NMR (DMSO-d₆) δ: 3.00-3.11 (2H, m), 3.41-3.52 (2H, m), 3.71-3.95 (9H, m), 4.10 (1H, t, J=8.7 Hz), 4.67-4.94 (1H, m), 5.46 (1H, t, J=5.9 Hz), 6.97-7.15 (3H, m), 7.24 (1H, d, J=15.7 Hz), 7.37-7.48 (2H, m), 7.57-7.66 (2H, m), 9.39-9.55 (1H, m).

EXAMPLE A87

[Chemical Formula 163]

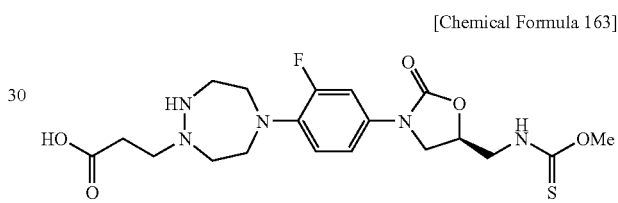

¹H-NMR (DMSO-d₆) δ: 2.42 (2H, t, J=6.7 Hz), 2.71 (2H, t, J=6.7 Hz), 2.82-2.93 (4H, m), 3.35-3.36 (3H, m), 3.75 (3H, t, J=5.9 Hz), 3.87-3.94 (3H, m), 4.10 (1H, t, J=8.8 Hz), 4.68-4.92 (1H, m), 7.02 (1H, t, J=9.2 Hz), 7.11 (1H, d, J=9.2 Hz), 7.40 (1H, d, J=15.7 Hz), 9.56-9.39 (1H, m).

EXAMPLE A88

[Chemical Formula 164]

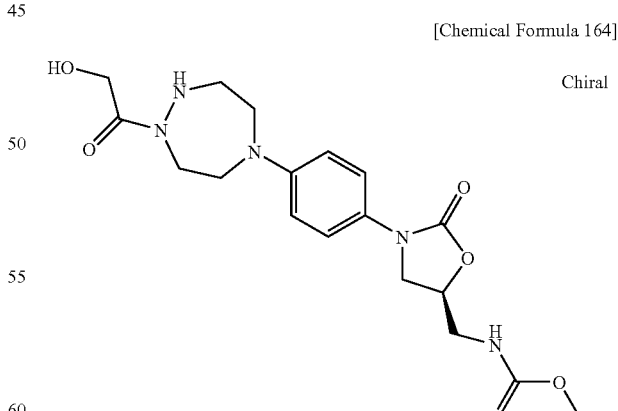

¹H-NMR (DMSO-d₆) δ: 2.90-3.15 (2.0H, m), 3.55-3.70 (2.0H, m), 3.70-3.79 (2.0H, m), 3.79-3.92 (4.0H, m), 3.96-4.02 (3.0H, m), 4.02-4.06 (2.0H, m), 4.08-4.30 (3.0H, m), 4.73-5.03 (1.0H, m), 5.16-5.33 (1.0H, m), 6.81-7.03 (2.0H, m), 7.31-7.53 (2.0H, m), 9.50-9.73 (1.0H, m).

EXAMPLE A89
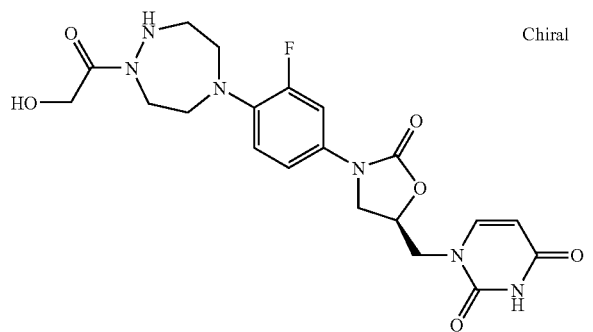
$^1$H-NMR (DMSO-$d_6$) δ: 2.94-3.07 (2.0H, m), 3.39-3.47 (2.0H, m), 3.62-3.84 (4.0H, m), 4.01-4.09 (2.0H, m), 4.10-4.15 (1.0H, m), 4.16-4.24 (4.0H, m), 4.80-4.98 (1.0H, m), 5.19-5.44 (1.0H, m), 5.59-5.67 (1.0H, m), 7.02 (1.0H, t, J=19.83 Hz), 7.13 (1.0H, d, J=9.76 Hz), 7.42 (1.0H, d, J=16.78 Hz), 7.64 (1.0H, d, J=8.39 Hz), 11.38 (1.0H, s).
EXAMPLE A90
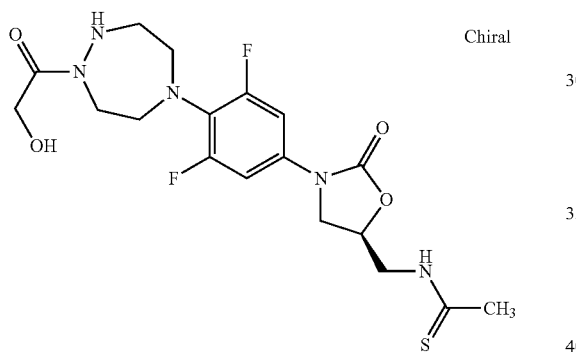
$^1$H-NMR (DMSO-$d_6$) δ: 2.44 (3.0H, s), 2.89-3.01 (2.0H, m), 3.14-3.21 (2.0H, m), 3.32-3.40 (3.0H, m), 3.64-3.73 (2.0H, m), 3.73-3.83 (1.0H, m), 3.84-3.97 (2.0H, m), 4.08-4.18 (1.0H, m), 4.21 (2.0H, s), 4.82-5.04 (1.0H, m), 5.19-5.28 (1.0H, m), 7.26 (1.0H, s), 7.29 (1.0H, s), 10.41 (1.0H, s).
EXAMPLE A91
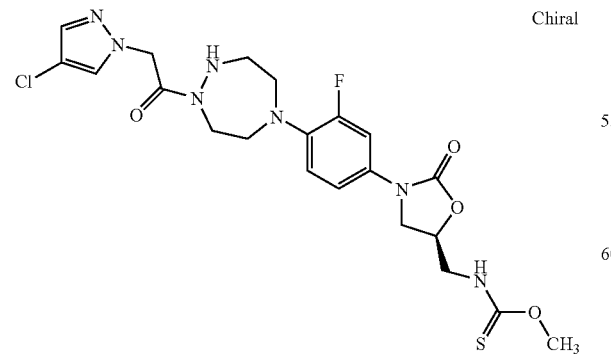
$^1$H-NMR (DMSO-$d_6$) δ: 3.04-3.15 (2.0H, m), 3.15-3.26 (2.0H, m), 3.24-3.30 (2.0H, m), 3.65-3.82 (6.0H, m), 3.87 (2.0H, s), 3.91-3.94 (1.0H, m), 4.02-4.16 (1.0H, m), 4.81-4.91 (1.0H, m), 5.07 (1.0H, s), 5.40-5.45 (1.0H, m), 6.99-7.08 (1.0H, m), 7.09-7.17 (1.0H, m), 7.32 (1.0H, s), 7.38-7.47 (1.0H, m), 7.49 (1.0H, s), 9.51 (1.0H, s).
EXAMPLE A92
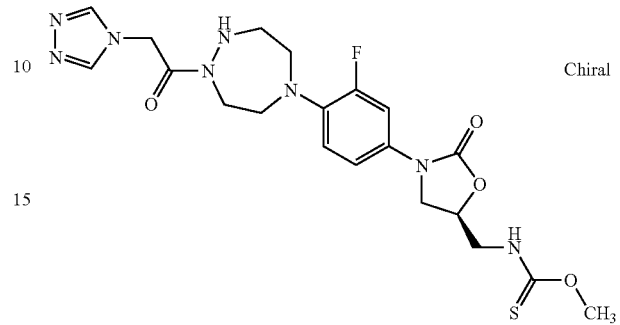
$^1$H-NMR (DMSO-$d_6$) δ: 3.05-3.12 (2.0H, m), 3.15-3.26 (2.0H, m), 3.24-3.30 (2.0H, m), 3.65-3.82 (6.0H, m), 3.87 (2.0H, s), 3.91-3.94 (1.0H, m), 4.02-4.16 (1.0H, m), 4.81-4.91 (1.0H, m), 5.07 (1.0H, s), 5.40-5.45 (1.0H, m), 6.99-7.08 (1.0H, m), 7.09-7.17 (1.0H, m), 7.32 (1.0H, s), 7.38-7.47 (1.0H, m), 7.49 (1.0H, s), 9.51 (1.0H, s).
EXAMPLE A93
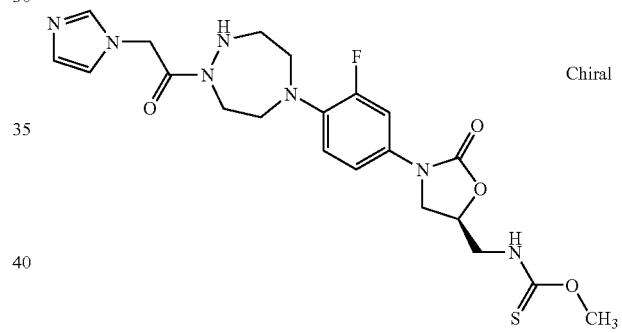
$^1$H-NMR (DMSO-$d_6$) δ: 3.07-3.17 (2.0H, m), 3.68-3.84 (8.0H, m), 3.86-3.91 (3.0H, m), 3.91-3.97 (2.0H, m), 4.05-4.17 (2.0H, m), 4.71-4.94 (1.0H, m), 5.06 (1.0H, s), 5.40-5.47 (1.0H, m), 6.84 (1.0H, s), 7.00-7.18 (2.0H, m), 7.38-7.49 (1.0H, m), 7.55 (1.0H, s), 9.42-9.58 (1.0H, m).
EXAMPLE A94
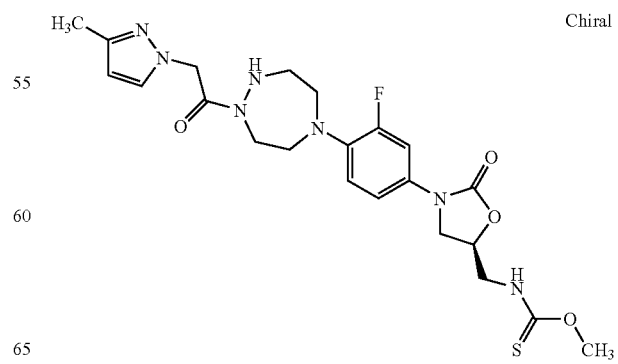

¹H-NMR (DMSO-d₆) δ: 2.10 (3.0H, s), 3.01-3.15 (2.0H, m), 3.15-3.26 (2.0H, m), 3.24-3.30 (2.0H, m), 3.65-3.82 (6.0H, m), 3.87 (2.0H, s), 3.91-3.94 (1.0H, m), 4.02-4.16 (1.0H, m), 4.81-4.91 (1.0H, m), 5.07 (1.0H, s), 5.40-5.45 (1.0H, m), 5.95-6.00 (1.0H, m), 6.99-7.08 (1.0H, m), 7.09-7.17 (1.0H, m), 7.38-7.47 (1.0H, m), 7.49 (1.0H, d, J=9.76 Hz), 9.51 (1.0H, s).

EXAMPLE A95

[Chemical Formula 171]

Chiral

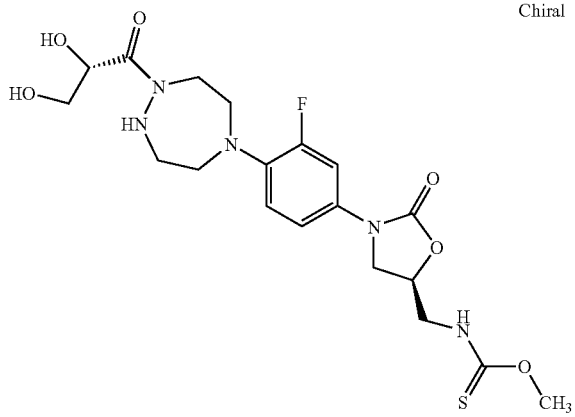

¹H-NMR (DMSO-d₆) δ: 2.98-3.09 (2.0H, m), 3.16-3.25 (2.0H, m), 3.37-3.41 (1.0H, m), 3.43-3.51 (2.0H, m), 3.55-3.68 (2.0H, m), 3.70-3.83 (4.0H, m), 3.87 (2.0H, s), 3.92 (1.0H, s), 4.05-4.15 (1.0H, m), 4.41 (1.0H, d, J=7.63 Hz), 4.54-4.65 (2.0H, m), 4.82-4.90 (1.0H, m), 5.34 (1.0H, t, J=5.49 Hz), 7.02 (1.0H, t, J=9.91 Hz), 7.10-7.13 (1.0H, m), 7.40-7.45 (1.0H, m), 9.42-9.55 (1.0H, m).

EXAMPLE A96

[Chemical Formula 172]

Chiral

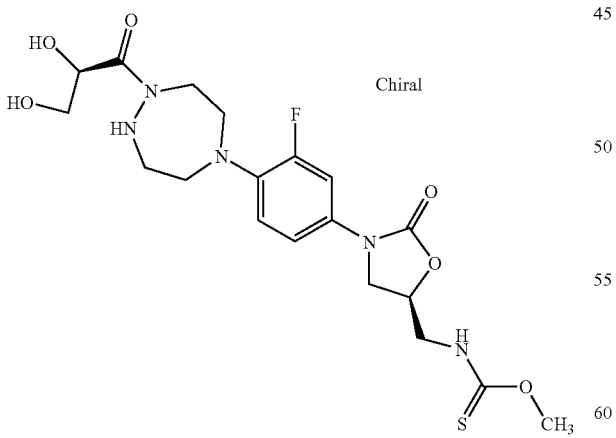

¹H-NMR (CDCl₃) δ: 3.21-3.29 (2.0H, m), 3.31-3.43 (2.0H, m), 3.60-3.98 (11.0H, m), 4.00 (2.0H, s), 4.03-4.16 (3.0H, m), 4.67-4.74 (1.0H, m), 4.84-4.96 (1.0H, m), 6.76-6.84 (1.0H, m), 6.89 (1.0H, t, J=10.37 Hz), 7.04 (1.0H, d, J=8.39 Hz), 7.40 (1.0H, d, J=12.20 Hz).

EXAMPLE A97

[Chemical Formula 173]

Chiral

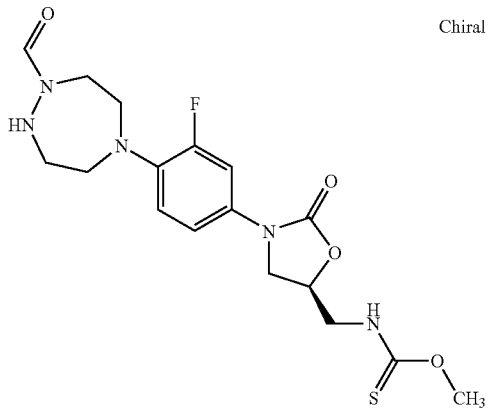

¹H-NMR (DMSO-d₆) δ: 3.08-3.19 (2.0H, m), 3.24-3.37 (3.0H, m), 3.49-3.60 (4.0H, m), 3.64-3.77 (2.0H, m), 3.79-3.90 (2.0H, m), 3.97 (2.0H, s), 4.12-4.24 (1.0H, m), 4.89-5.00 (1.0H, m), 5.65 (1.0H, t, J=5.77 Hz), 7.11 (1.0H, t, J=7.42 Hz), 7.16-7.24 (1.0H, m), 7.44-7.57 (1.0H, m), 8.38 (1.0H, s), 9.50-9.64 (1.0H, m).

EXAMPLE A98

[Chemical Formula 174]

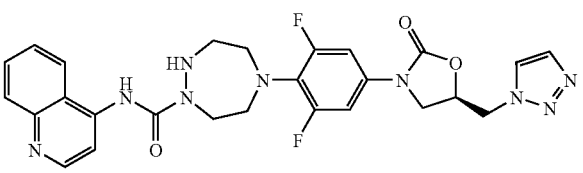

¹H NMR (CDCl₃) δ 3.30-3.47 (7H, m), 3.90 (1H, dd, J=6.0, 9.1 Hz), 4.11 (1H, t, J=9.1 Hz), 4.18 (1H, t, J=6.1 Hz), 4.78 (2H, d, J=4.1 Hz), 5.02-5.11 (1H, m), 7.00 (2H, d, J=10.5 Hz), 7.55 (1H, J=8 Hz), 7.71 (1H, br t, J=8 Hz), 7.74 (1H, br s), 7.77 (1H, br s), 7.79 (1H, br d, J=8 Hz), 8.10 (1H, br d, J=8 Hz), 8.30 (1H, d, J=5.2 Hz), 8.80 (1H, d, J=5.2 Hz), and 9.88 (1H, s).

EXAMPLE A99

[Chemical Formula 175]

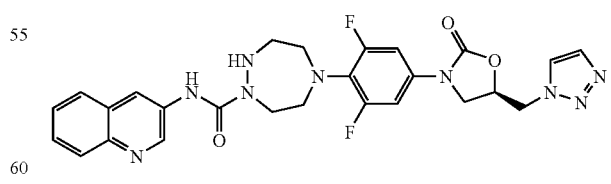

¹H NMR (CDCl₃) δ 3.24-3.32 (2H, m), 3.34-3.45 (4H, m), 3.85-4.01 (3H, m), 4.11 (1H, t, J=9.1 Hz), 4.79 (2H, AB), 5.01-5.12 (1H, m), 6.99 (2H, d, J=10.7 Hz), 7.47-7.61 (2H, m), 7.75 (1H, br s), 7.76-7.81 (1H, m), 7.78 (1H, br s), 8.01 (1H, d, J=8.5 Hz), 8.67 (1H, d, J=2.2 Hz), 8.73 (1H, d, J=2.8 Hz), and 8.94 (1H, br s).

EXAMPLE A100

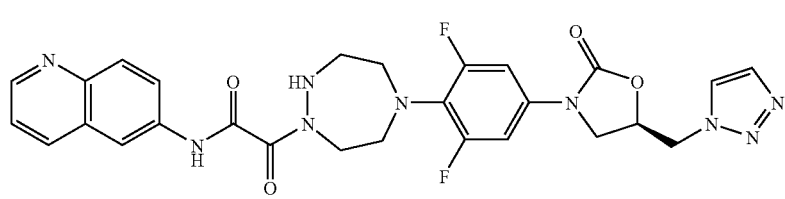

[Chemical Formula 176]

$^1$H NMR (CDCl$_3$+CD$_3$OD) δ 3.14-4.30 (10H, m), 4.79-4.86 (2H, m), 5.05-5.16 (1H, m), 7.02 & 7.05 (2H, d, J=10.5 Hz), 7.45-7.51 (1H, m), 7.72-8.10 (4H, m), 8.25 (1H, br d, J=8 Hz), 8.46 (1H, br s), and 8.75-8.81 (1H, m).

EXAMPLE A101

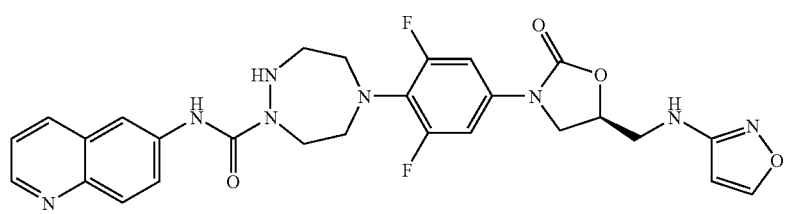

[Chemical Formula 177]

$^1$H NMR (CDCl$_3$) δ 3.21-3.30 (2H, m), 3.33-3.45 (4H, m), 3.56-3.98 (5H, m), 4.02 (1H, t, J=9.1 Hz), 4.55 (1H, t, J=6.6 Hz), 4.89-4.99 (1H, m), 5.86 (1H, d, J=1.7 Hz), 7.10 (2H, d, J=10.7 Hz), 7.34 (1H, dd, J=4.1, 8.2 Hz), 7.57 (1H, dd, J=2.5, 9.2 Hz), 8.00 (1H, d, J=9.2 Hz), 8.05 (1H, d, J=1.7 Hz), 8.08 (1H, d, J=8.2 Hz), 8.26 (1H, br s), 8.76 (1H, br d, J=4.1 Hz), and 8.92 (1H, s).

EXAMPLE A102

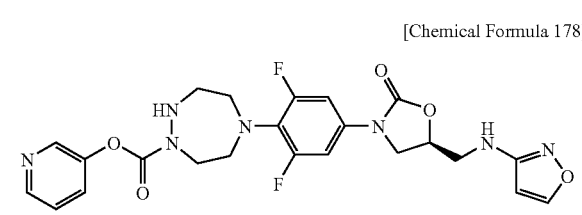

[Chemical Formula 178]

$^1$H NMR (CDCl$_3$) δ 3.10-3.25 (2H, m), 3.31-3.37 (2H, m), 3.48-3.55 (2H, m), 3.55-3.88 (5H, m), 4.03 (1H, t, J=9.1 Hz), 4.63 (1H, t, J=6.6 Hz, NH), 4.89-4.99 (1H, m), 5.86 (1H, d, J=1.9 Hz), 7.11 (2H, d, J=10.7 Hz), 7.33 (1H, dd, J=4.9, 8.2 Hz), 7.55 (1H, br d, J=8 Hz), 8.06 (1H, d, J=1.9 Hz), and 8.47 (2H, br d, J=5 Hz).

EXAMPLE A103

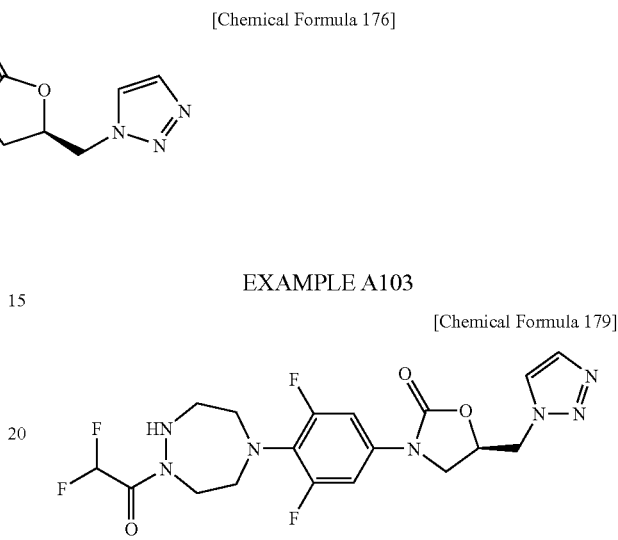

[Chemical Formula 179]

$^1$H-NMR (DMSO-d$_6$) δ: 2.93-3.13 (2H, m), 3.13-3.33 (2H, m), 3.71 (2H, d, J=5.37 Hz), 3.88 (1H, dd, J=9.40, 5.71 Hz), 4.22 (1H, t, J=9.23 Hz), 4.85 (2H, d, J=5.04 Hz), 5.07-5.27 (1H, m), 5.64 (1H, t, J=5.88 Hz), 6.79 (1H, t, J=51 Hz), 7.20 (2H, d, J=15.0 Hz), 7.78 (1H, s), 8.26 (1H, s).

EXAMPLE A104

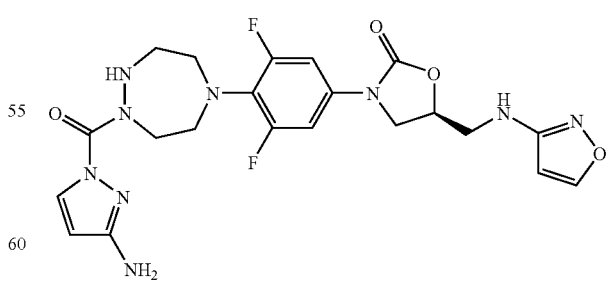

[Chemical Formula 180]

$^1$H-NMR (DMSO-d$_6$) δ: 2.92-2.96 (2H, m), 3.47 (4H, t, J=5.29 Hz), 3.80-3.91 (3H, m), 4.70-4.95 (1H, m), 5.77 (1H, s), 6.02 (1H, s), 7.25 (2H, d, J=11.58 Hz), 7.97 (1H, s), 8.35 (1H, s).

EXAMPLE A105

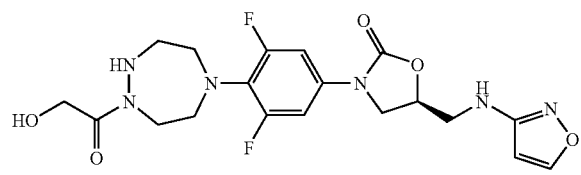

$^1$H-NMR (DMSO-d$_6$) δ: 2.88-3.08 (2H, m), 3.08-3.28 (2H, m), 3.21-3.41 (2H, m), 4.77-4.97 (1H, m), 5.95 (1H, s), 7.27 (2H, d, J=11.29 Hz), 8.39 (1H, s).

EXAMPLE A106

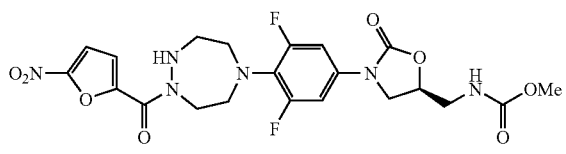

$^1$H NMR (CDCl$_3$+DMSO-d$_6$) δ 3.18-4.08 (12H, m), 3.67 (3H, s), 4.72-4.82 (1H, m), 6.78 (1H, br t, J=6 Hz), 7.15 (2H, d, J=11.0 Hz), 7.38 (1H, d, J=3.6 Hz), and 7.48 (1H, d, J=3.6 Hz).

EXAMPLE A107

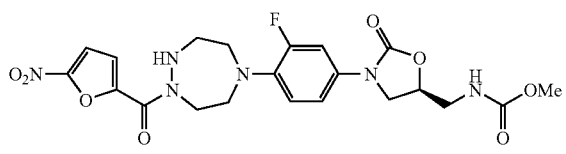

$^1$H NMR (CDCl$_3$+DMSO-d$_6$) δ 3.22-4.10 (12H, m), 3.67 (3H, s), 4.71-4.82 (1H, m), 6.68 (1H, br t, J=6 Hz), 6.92 (1H, t, J=9.1 Hz), 7.05 (1H, br dd, J=2, 9 Hz), 7.37 (1H, d, J=3.6 Hz), 7.44 (1H, br dd, J=2, 15 Hz), and 7.48 (1H, d, J=3.6 Hz).

EXAMPLE A108

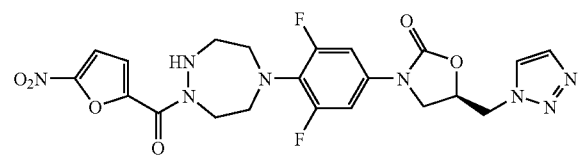

$^1$H NMR (CDCl$_3$+DMSO-d$_6$) δ 3.12-4.21 (10H, m), 4.84 (2H, AB), 5.08-5.18 (1H, m), 7.05 (2H, d, J=10.7 Hz), 7.38 (1H, d, J=3.8 Hz), 7.48 (1H, d, J=3.8 Hz), 7.72 (1H, br s), and 7.89 (1H, br s).

EXAMPLE A109

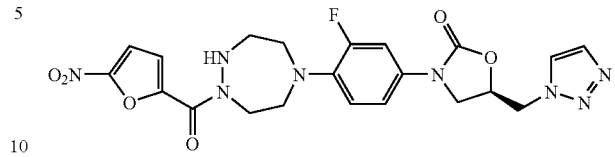

$^1$H NMR (CDCl$_3$+DMSO-d$_6$) δ 3.12-4.20 (10H, m), 4.83 (2H, AB), 5.05-5.15 (1H, m), 6.88 (1H, t, J=8.8 Hz), 6.94 (1H, dd, J=2.5, 8.8 Hz), 7.30 (1H, dd, J=2.5, 14.5 Hz), 7.37 (1H, d, J=3.8 Hz), 7.47 (1H, d, J=3.8 Hz), 7.72 (1H, br s), and 7.88 (1H, br s).

EXAMPLE A110

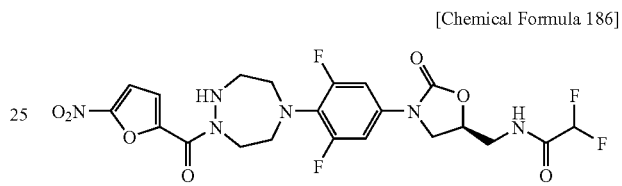

$^1$H NMR (CDCl$_3$+DMSO-d$_6$) δ 3.19-4.11 (12H, m), 4.79-4.88 (1H, m), 5.96 (1H, t, J=54.0 Hz), 7.13 (2H, d, J=10.7 Hz), 7.36 (1H, d, J=3.8 Hz), 7.46 (1H, d, J=3.8 Hz), and 8.80 (1H, br t, J=6 Hz).

EXAMPLE A111

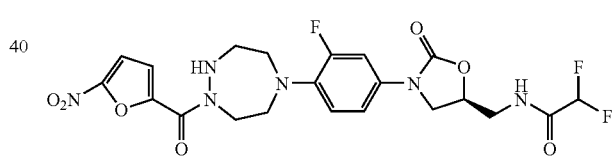

$^1$H NMR (CDCl$_3$+DMSO-d$_6$) δ 3.22-4.14 (12H, m), 4.77-4.87 (1H, m), 5.97 (1H, t, J=54.0 Hz), 6.92 (1H, t, J=8.8 Hz), 7.03 (1H, br dd, J=2, 9 Hz), 7.36 (1H, d, J=3.8 Hz), 7.42 (1H, br dd, J=2, 15 Hz), 7.46 (1H, d, J=3.8 Hz), and 8.81 (1H, br t, J=6 Hz).

EXAMPLE A112

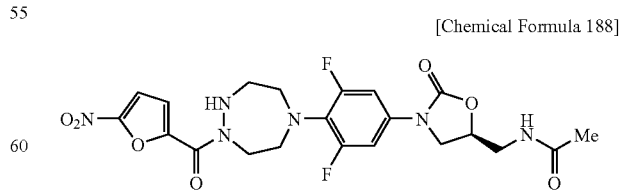

$^1$H NMR (CDCl$_3$+DMSO-d$_6$) δ 1.99 (3H, s), 3.18-4.10 (12H, m), 4.74-4.84 (1H, m), 7.14 (2H, d, J=10.7 Hz), 7.37 (1H, d, J=3.6 Hz), 7.48 (1H, d, J=3.6 Hz), and 7.87 (1H, br t, J=6 Hz).

EXAMPLE A113

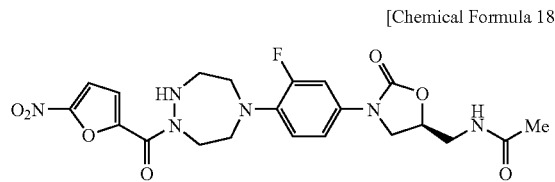

[Chemical Formula 189]

$^1$H NMR (CDCl$_3$+DMSO-d$_6$) δ 2.00 (3H, s), 3.23-4.15 (12H, m), 4.71-4.81 (1H, m), 6.92 (1H, t, J=9.3 Hz), 7.03 (1H, br dd, J=3, 9 Hz), 7.35 (1H, d, J=3.6 Hz), 7.44 (1H, br dd, J=3, 15 Hz), 7.46 (1H, d, J=3.6 Hz), and 7.57 (1H, br t, J=6 Hz).

EXAMPLE A114

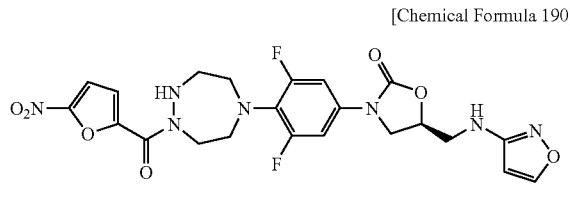

[Chemical Formula 190]

$^1$H NMR (CDCl$_3$+DMSO-d$_6$) δ 3.18-4.10 (12H, m), 4.90-5.00 (1H, m), 5.83 (1H, br t, J=6 Hz), 5.93 (1H, d, J=1.7 Hz), 7.14 (2H, d, J=10.7 Hz), 7.38 (1H, d, J=3.6 Hz), 7.48 (1H, d, J=3.6 Hz), and 8.05 (1H, d, J=1.7 Hz).

EXAMPLE A115

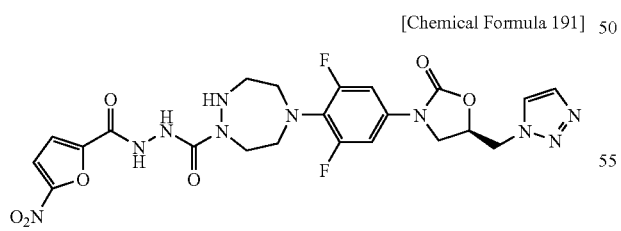

[Chemical Formula 191]

$^1$H NMR (CDCl$_3$+CD$_3$OD) δ 3.19-3.45 (6H, m), 3.77-3.84 (2H, m), 3.90 (1H, t, J=6.0, 9.1 Hz), 4.15 (1H, t, J=9.1 Hz), 4.82 (2H, AB), 5.05-5.14 (1H, m), 7.01 (2H, d, J=10.4 Hz), 7.34 (1H, d, J=3.7 Hz), 7.40 (1H, d, J=3.7 Hz), 7.75 (1H, br s), and 7.86 (1H, br s).

EXAMPLE A116

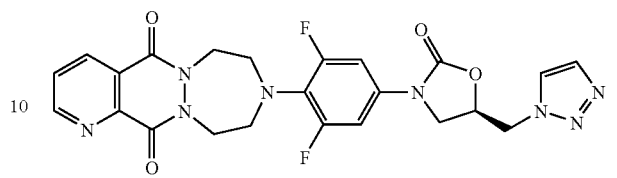

[Chemical Formula 192]

$^1$H NMR (CDCl$_3$+CD$_3$OD) δ 3.45-3.56 (4H, m), 3.94 (1H, dd, J=6.0, 9.1 Hz), 4.20 (1H, t, J=9.1 Hz), 4.66-4.77 (4H, m), 4.85 (2H, AB), 5.09-5.19 (1H, m), 7.10 (2H, d, J=10.4 Hz), 7.75 (1H, br s), 7.87 (1H, dd, J=4.7, 8.2 Hz), 7.94 (1H, br s), 8.70 (1H, br d, J=8 Hz), and 9.12 (1H, br d, J=5 Hz).

EXAMPLE A117

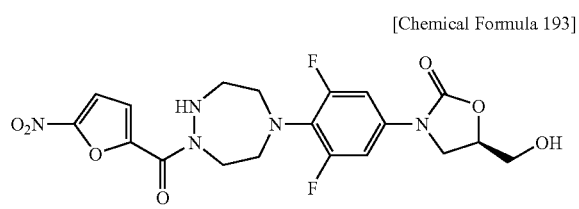 [SMILES: O=C(c1ccc([N+](=O)[O-])o1)N1CCN(c2c(F)cc(N3C[C@H](CO)OC3=O)cc2F)CCN1]

[Chemical Formula 193]

$^1$H NMR (CD$_3$OD+CDCl$_3$) δ 3.20-3.50 (6H, m), 3.68 (1H, dd, J=3.3, 12.6 Hz), 3.89-4.02 (4H, m), 3.91 (1H, dd, J=3.3, 12.6 Hz), 4.68-4.77 (1H, m), 7.15 (2H, d, J=11.0 Hz), 7.36 (1H, d, J=3.8 Hz), and 7.47 (1H, d, J=3.8 Hz).

EXAMPLE A118

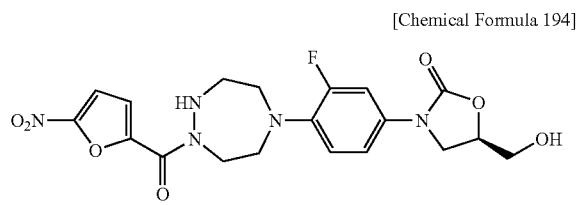 [SMILES: O=C(c1ccc([N+](=O)[O-])o1)N1CCN(c2ccc(N3C[C@H](CO)OC3=O)cc2F)CCN1]

[Chemical Formula 194]

$^1$H NMR (CD$_3$OD+CDCl$_3$) δ 3.22-3.56 (6H, m), 3.70 (1H, dd, J=3.7, 12.6 Hz), 3.89-4.03 (4H, m), 3.90 (1H, dd, J=3.7, 12.6 Hz), 4.67-4.77 (1H, m), 6.94 (1H, t, J=9.1 Hz), 7.08 (1H, br dd, J=2, 9 Hz), 7.35 (1H, d, J=3.8 Hz), 7.43 (1H, br dd, J=2, 15 Hz), and 7.47 (1H, d, J=3.8 Hz).

EXAMPLE A119

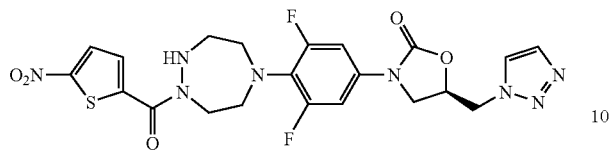
[Chemical Formula 195]

¹H NMR (CD₃OD+CDCl₃) δ 3.27-3.48 (6H, m), 3.91 (1H, dd, J=6.1, 9.3 Hz), 3.95-4.04 (2H, br), 4.14 (1H, t, J=9.1 Hz), 4.81 (2H, AB), 5.05-5.15 (1H, m), 7.02 (2H, d, J=10.4 Hz), 7.75 (1H, s), 7.84 (1H, s), 7.89 (1H, d, J=4.8 Hz), and 7.92 (1H, d, J=4.8 Hz).

EXAMPLE A120

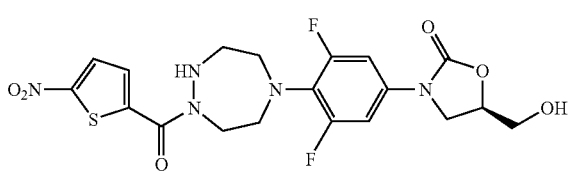
[Chemical Formula 196]

¹H NMR (CD₃OD+CDCl₃) δ 3.24-3.51 (6H, m), 3.70 (1H, dd, J=3.6, 12.6 Hz), 3.89-4.06 (4H, m), 3.90 (1H, dd, J=3.6, 12.6 Hz), 4.69-4.78 (1H, m), 7.17 (2H, d, J=10.7 Hz), 7.90 (1H, d, J=4.7 Hz), and 7.92 (1H, d, J=4.7 Hz).

EXAMPLE A121

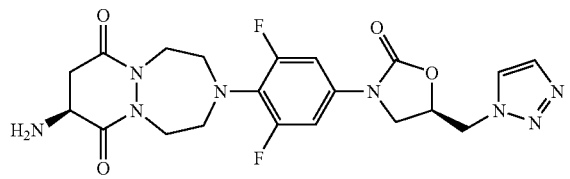
[Chemical Formula 197]

¹H NMR (CDCl₃) δ 2.61 (1H, dd, J=13.5, 15.7 Hz), 2.82 (1H, dd, J=4.7, 15.7 Hz), 3.21-3.41 (4H, m), 3.76 (1H, dd, J=4.7, 13.5 Hz), 3.89-4.22 (6H, m), 4.79 (2H, AB), 5.03-5.12 (1H, m), 7.00 (2H, d, J=10.7 Hz), 7.75 (1H, d, J=1.1 Hz), and 7.77 (1H, d, J=1.1 Hz).

EXAMPLE A122

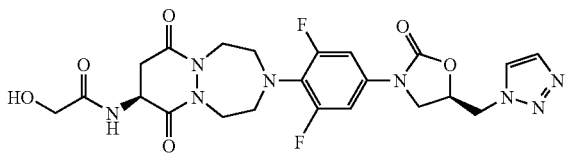
[Chemical Formula 198]

¹H NMR (CD₃OD+CDCl₃) δ 2.73 (1H, dd, J=14.0, 15.4 Hz), 3.00 (1H, dd, J=4.7, 15.7 Hz), 3.20-3.45 (4H, m), 3.91 (1H, dd, J=6.1, 9.3 Hz), 3.94-4.21 (7H, m), 4.82 (2H, AB), 4.86 (1H, dd, =4.9, 14.0 Hz), 5.04-5.14 (1H, m), 7.03 (2H, d, J=10.4 Hz), 7.75 (1H, br s), and 7.85 (1H, br s).

EXAMPLE A123

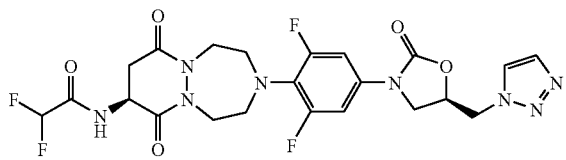
[Chemical Formula 199]

¹H NMR (CDCl₃) δ 2.65 (1H, ddd, J=2.2, 11.7, 15.7 Hz), 3.20 (1H, dd, J=4.7, 15.7 Hz), 3.22-3.43 (4H, m), 3.88-3.98 (2H, m), 4.03-4.22 (4H, m), 4.71-4.82 (1H, m), 4.81 (2H, AB), 5.05-5.14 (1H, m), 5.97 (1H, t, J=54.0 Hz), 7.01 (2H, d, J=10.4 Hz), 7.39 (1H, br t, J=6 Hz), 7.74 (1H, br s), and 7.80 (1H, br s).

EXAMPLE A124

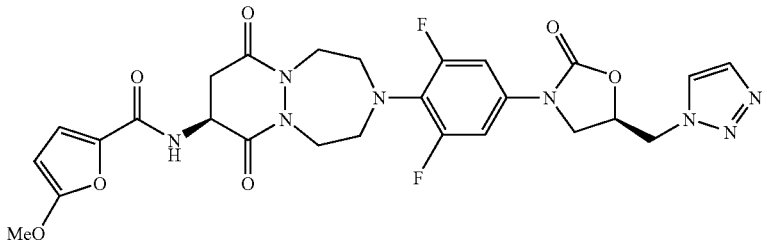
[Chemical Formula 200]

¹H NMR (CD₃OD+CDCl₃) δ 2.71 (1H, dd, J=14.3, 15.7 Hz), 3.12 (1H, dd, J=4.7, 15.7 Hz), 3.24-3.53 (4H, m), 3.87-4.24 (6H, m), 3.94 (3H, s), 4.82 (2H, AB), 4.86-4.96 (1H, m), 5.05-5.15 (1H, m), 5.36 (1H, d, J=3.6 Hz), 7.04 (2H, d, J=10.7 Hz), 7.13 (1H, d, J=3.6 Hz), 7.17 (1H, d, J=6.3 Hz, O=C—NH), 7.75 (1H, br s), and 7.86 (1H, br s).

EXAMPLE A125

[Chemical Formula 201]

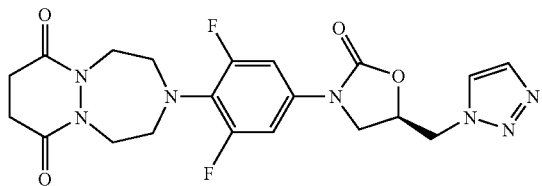

¹H NMR (CDCl₃) δ 2.60 (4H, s), 3.21-3.27 (4H, m), 3.84 (1H, dd, J=6.1, 9.3 Hz), 3.97-4.02 (4H, m), 4.04 (1H, t, J=9.1 Hz), 4.72 (2H, AB), 4.96-5.04 (1H, m), 6.97 (2H, d, J=10.5 Hz), 7.68 (1H, br s), and 7.71 (1H, br s).

EXAMPLE A126

[Chemical Formula 202]

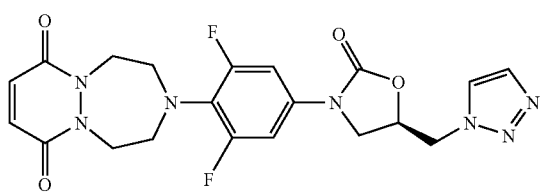

¹H NMR (CDCl₃) δ 3.35-3.41 (4H, m), 3.90 (1H, dd, J=6.0, 9.3 Hz), 4.11 (1H, t, J=9.1 Hz), 4.49-4.45 (4H, m), 4.79 (2H, AB), 5.02-5.12 (1H, m), 6.92 (2H, s), 7.00 (2H, d, J=10.7 Hz), 7.73 (1H, br s), and 7.77 (1H, br s).

EXAMPLE A127

[Chemical Formula 203]

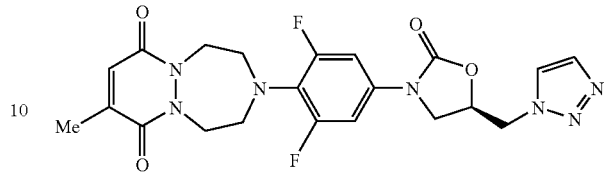

¹H NMR (CDCl₃) δ 2.16 (3H, d, J=1.4 Hz), 3.33-3.40 (4H, m), 3.90 (1H, dd, J=6.0, 9.3 Hz), 4.11 (1H, t, J=9.1 Hz), 4.47-4.56 (4H, m), 4.78 (2H, AB), 5.02-5.11 (1H, m), 6.77 (1H, q, J=1.4 Hz), 6.99 (1H, d, J=10.7 Hz), 7.73 (1H, br s), and 7.76 (1H, br s).

EXAMPLE A128

[Chemical Formula 204]

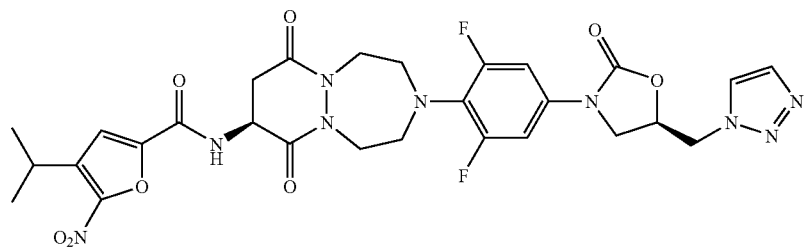

¹H NMR (CDCl₃) δ 1.26 (3H, d, J=7.0 Hz), 1.27 (3H, d, J=7.0 Hz), 2.76 (1H, dd, J=14.0, 15.4 Hz), 3.14 (1H, dd, J=4.7, 15.4 Hz), 3.21-3.43 (4H, m), 3.65 (1H, sept, J=7.0 Hz), 3.88-3.98 (2H, m), 4.08-4.24 (4H, m), 4.81 (2H, AB), 4.95 (1H, ddd, J=4.7, 6.3, 14.0 Hz), 5.04-5.13 (1H, m), 7.00 (2H, d, J=10.4 Hz), 7.25 (1H, s), 7.61 (1H, d, J=6.3 Hz), 7.73 (1H, br s), and 7.78 (1H, br s).

EXAMPLE A129

[Chemical Formula 205]

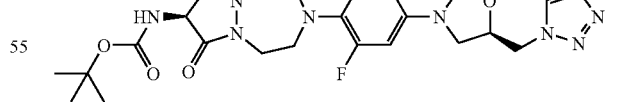

¹H NMR (CDCl₃) δ 1.45 (9H, s), 3.00-3.52 (8H, m), 3.73-3.82 (1H, m), 3.89 (1H, dd, J=6.0, 9.3 Hz), 3.91-4.02 (1H, m), 4.11 (1H, t, J=9.1 Hz), 4.58-4.69 (1H, m), 4.79 (2H, AB), 5.02-5.12 (1H, m), 5.10-5.18 (1H, br d, J=7 Hz), 6.98 (2H, d, J=10.4 Hz), 7.75 (1H, br s), and 7.79 (1H, br s).

EXAMPLE A130

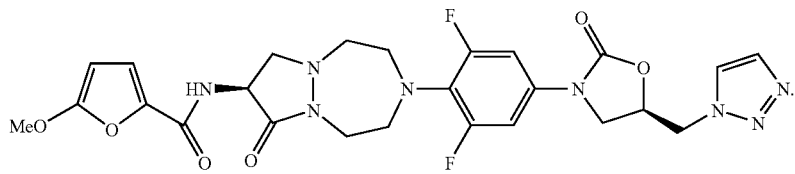

¹H NMR (CDCl₃) δ 3.06-3.53 (8H, m), 3.85-4.06 (2H, m), 3.91 (3H, s), 3.91-4.02 (1H, m), 4.12 (1H, t, J=9.1 Hz), 4.80 (2H, AB), 4.92-5.02 (1H, m, J=7 Hz), 5.03-5.12 (1H, m), 5.31 (1H, d, J=3.6 Hz), 6.71 (1H, d, J=5.0 Hz), 6.98 (2H, d, J=10.7 Hz), 7.07 (1H, d, J=3.6 Hz), 7.75 (1H, br s), and 7.79 (1H, br s).

EXAMPLE B1

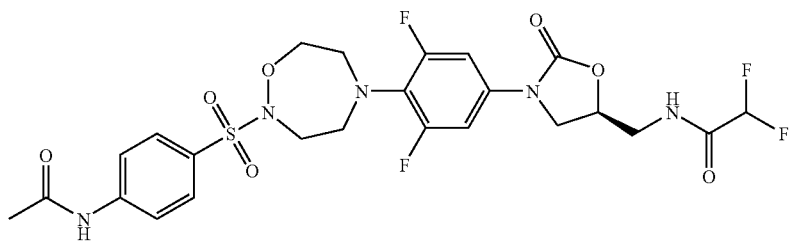

¹H NMR (CDCl₃) δ 2.24 (3H, s), 3.30 (2H, br t, J=5.5 Hz), 3.43 (2H, br t, J=5.5 Hz), 3.52 (2H, br t, J=5.5 Hz), 3.60-3.73 (2H, m), 3.83 (1H, ddd, J=14.5, 6, 3 Hz), 4.00 (2H, t, J=5.5 Hz), 4.03 (1H, dd, J=9, 9 Hz), 4.76-4.86 (1H, m), 5.93 (1H, t, J=54 Hz), 6.91 (NH, br t, J=6 Hz), 6.95-7.08 (2H, m), 7.72 (1H, br d, J=9 Hz), 7.86 (1H, br d, J=9 Hz).

EXAMPLE B2

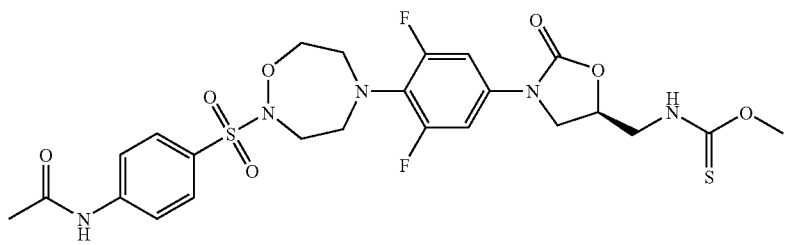

¹H NMR (CDCl₃) δ 2.23 (3H, s), 3.28 (2H, br t, J=5 Hz), 3.40 (2H, br t, J=5 Hz), 3.49 (2H, br t, J=5.5 Hz), 3.78 (1H, dd, J=9, 7 Hz), 3.93-4.09 (5H, m), 3.99 (3H, s), 4.87-4.97 (1H, m), 6.95-7.08 (2H, m), 7.75 (1H, br d, J=9 Hz), 7.83 (1H, br d, J=9 Hz), 8.00 (NH, br s).

¹H NMR (CDCl₃—CD₃OD(9:1)) δ 3.21 (2H, br t, J=5.5 Hz), 3.38 (2H, br t, J=5 Hz), 3.47 (2H, br t, J=5.5 Hz), 3.84-3.93 (3H, m), 4.13 (1H, dd, J=9, 9 Hz), 4.77 (1H, dd, J=15, 4 Hz), 4.82 (1H, dd, J=15, 4 Hz), 5.03-5.12 (1H, m), 6.91-7.03 (2H, m), 7.74 (1H, br s), 7.80 (1H, br s).

EXAMPLE B3

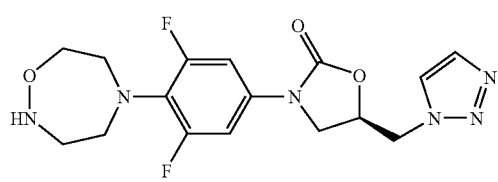

EXAMPLE B4

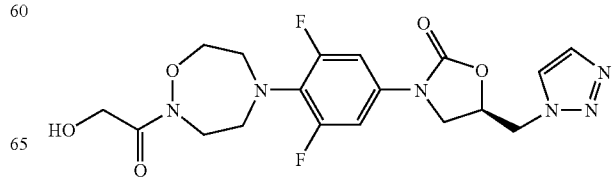

¹H NMR (CDCl₃) δ 3.39 (2H, br t, J=5 Hz), 3.45 (2H, br t, J=5.5 Hz), 3.88-3.97 (3H, m), 4.11 (2H, t, J=5 Hz), 4.14 (1H, dd, J=9, 9 Hz), 4.36 (2H, s), 4.81 (2H, d, J=4.5 Hz), 5.05-5.14 (1H, m), 6.95-7.06 (2H, m), 7.74 (1H, br s), 7.81 (1H, br s).

EXAMPLE B5

[Chemical Formula 211]

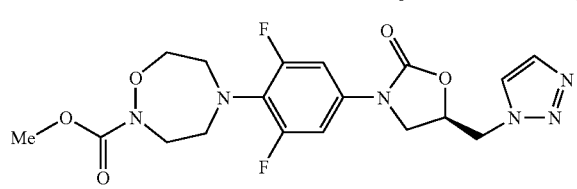

¹H NMR (CDCl₃) δ 3.36-3.44 (4H, m), 3.80 (3H, s), 3.82 (2H, br t, J=5, 5 Hz), 3.90 (1H, dd, J=9, 6 Hz), 4.09 (2H, t, J=5 Hz), 4.14 (1H, dd, J=9, 9 Hz), 4.78 (1H, dd, J=15, 4 Hz), 4.81 (1H, dd, J=15, 4 Hz), 5.09 (1H, dddd, J=9, 6, 4, 4 Hz), 6.94-7.05 (2H, m), 7.74 (1H, br s), 7.80 (1H, br s).

EXAMPLE B6

[Chemical Formula 212]

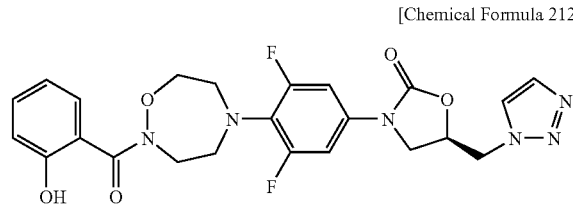

¹H NMR (CDCl₃) δ 3.39 (2H, br t, J=5 Hz), 3.37 (2H, br t, J=5 Hz), 3.50 (2H, br t, J=5.5 Hz), 3.89 (1H, dd, J=9, 6 Hz), 4.02 (2H, t, J=5 Hz), 4.08-4.16 (3H, m), 4.76 (1H, dd, J=15, 4 Hz), 4.81 (1H, dd, J=15, 4 Hz), 5.03-5.12 (1H, m), 6.85 (1H, dd, J=8, 8 Hz), 6.94-7.05 (2H, m), 6.99 (1H, br d, J=8 Hz), 7.37 (1H, ddd, J=8, 8, 1.5 Hz), 7.73 (1H, br s), 7.78 (1H, br s), 8.03 (1H, dd, J=8, 1.5 Hz), 11.25 (OH, br s).

EXAMPLE B7

[Chemical Formula 213]

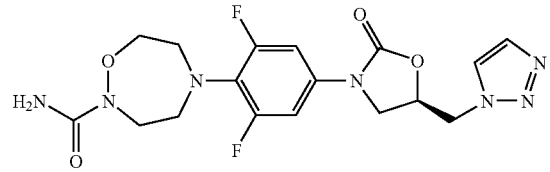

¹H NMR (CDCl₃—CD₃OD (5:1)) δ 3.38-3.48 (4H, m), 3.80 (2H, br t, J=5.5 Hz), 3.90 (1H, dd, J=9, 6 Hz), 4.09 (2H, t, J=5 Hz), 4.15 (1H, dd, J=9, 9 Hz), 4.79 (1H, dd, J=15, 4 Hz), 4.85 (1H, dd, J=15, 4 Hz), 5.10 (1H, dddd, J=9, 6, 5, 4 Hz), 5.68 (NH, br s), 6.96-7.07 (2H, m), 7.75 (1H, d, J=1 Hz), 7.87 (1H, d, J=1 Hz).

EXAMPLE B8

[Chemical Formula 214]

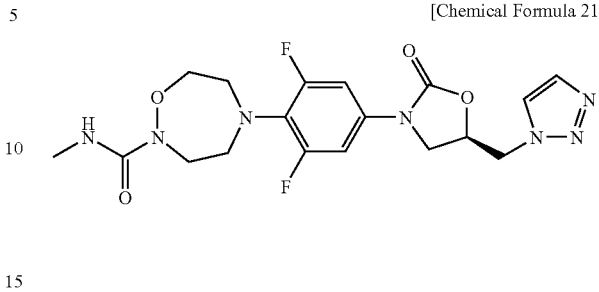

¹H NMR (CDCl₃) δ 2.85 (3H, d, J=5 Hz), 3.39 (2H, br t, J=5.5 Hz), 3.45 (2H, br t, J=5.5 Hz), 3.78 (2H, br t, J=5.5 HZ), 3.89 (1H, dd, J=9, 6 Hz), 4.02 (2H, t, J=5.5 Hz), 4.13 (1H, dd, J=9, 9 Hz), 4.78 (1H, dd, J=15, 4.5 Hz), 4.83 (1H, dd, J=15, 4 Hz), 5.09 (1H, dddd, J=9, 6, 4.5, 4 Hz), 5.88 (NH, br q, J=5 Hz), 6.93-7.04 (2H, m), 7.74 (1H, d, J=1 Hz), 7.80 (1H, d, J=1 Hz).

EXAMPLE B9

[Chemical Formula 215]

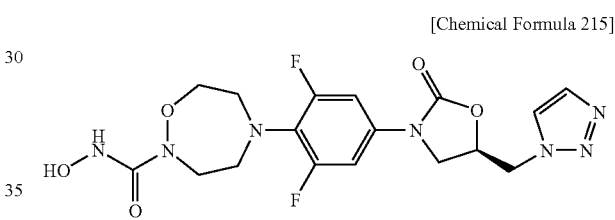

¹H NMR (CDCl₃—CD₃OD (9:1)) δ 3.38-3.46 (4H, m), 3.78 (2H, br t, J=5.5 Hz), 3.90 (1H, dd, J=9, 6 Hz), 4.05 (2H, t, J=5 Hz), 4.16 (1H, dd, J=9, 9 Hz), 4.79 (1H, dd, J=15, 5 Hz), 4.85 (1H, dd, J=15, 4 Hz), 5.10 (1H, dddd, J=9, 6, 5, 4 Hz), 5.68 (NH, br s), 6.96-7.07 (2H, m), 7.75 (1H, d, J=1 Hz), 7.87 (1H, d, J=1 Hz).

EXAMPLE B10

[Chemical Formula 216]

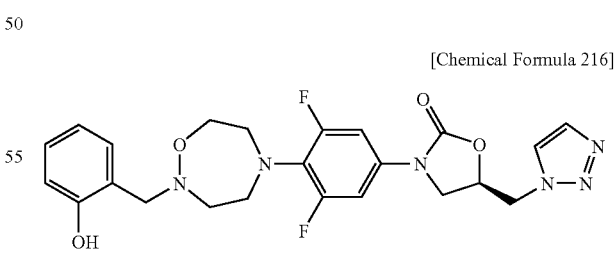

¹H NMR (CDCl₃) δ 3.10 (2H, br t, J=5.5 Hz), 3.39-3.51 (4H, m), 3.84-3.93 (3H, m), 4.06-4.15 (3H, m), 4.78 (2H, d, J=4 Hz), 5.01-5.11 (1H, m), 6.79-7.07 (5H, m), 7.21 (1H, ddd, J=8, 8, 1 Hz), 7.75 (1H, br s), 7.78 (1H, br s), 9.27 (OH, br s).

EXAMPLE B11

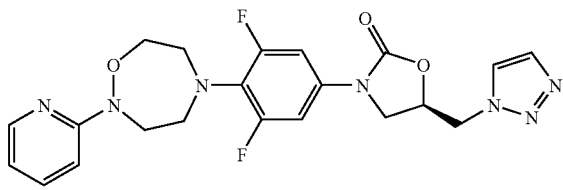

$^1$H NMR (CDCl$_3$) δ 3.49-3.58 (4H, m), 3.97 (2H, t, J=5.5 Hz), 3.87 (1H, dd, J=9, 6 Hz), 4.10 (1H, dd, J=9, 9 Hz), 4.12 (2H, t, J=5.5 Hz), 4.75 (1H, dd, J=15.5, 4.5 Hz), 4.80 (1H, dd, J=15.5, 4), 5.02-5.11 (1H, m), 6.77 (1H, ddd, J=7, 5, 1 Hz), 6.92-7.04 (2H, m), 7.14 (1H, d, J=8.5, Hz), 7.58 (1H, ddd, J=8.5, 7, 1 Hz), 7.73 (1H, d, J=1 Hz), 7.79 (1H, d, J=1 Hz), 8.21 (1H, dd, J=5, 1 Hz).

EXAMPLE B12

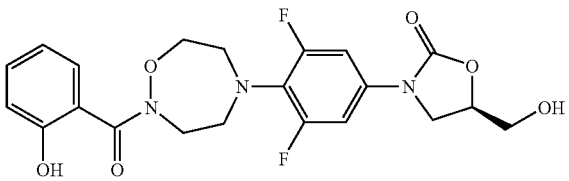

$^1$H NMR (CDCl$_3$) δ 3.25 (OH, br s), 3.37 (2H, br t, J=5 Hz), 3.50 (2H, br t, J=5 Hz), 3.73 (1H, dd, J=13, 3.5 Hz), 3.88-4.06 (5H, m), 4.67-4.78 (1H, m), 6.85 (1H, ddd, J=8, 98, 1 Hz), 6.98 (1H, dd, J=8, 1 Hz), 7.06-7.17 (2H, m), 7.37 (1H, ddd, J=8, 8, 1.5 Hz), 8.03 (1H, dd, J=8, 1.5 Hz), 11.20 (OH, s).

EXAMPLE B13

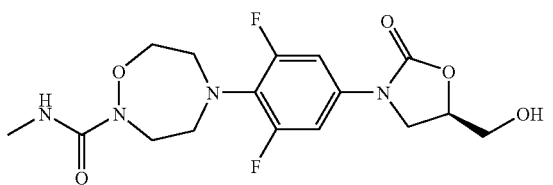

$^1$H NMR (CDCl$_3$) δ 2.84 (3H, d, J=5 Hz), 3.38 (2H, br t, J=5.5 Hz), 3.44 (2H, br t, J=5 Hz), 3.71-3.81 (3H, m), 3.91-4.06 (5H, m), 4.69-4.78 (1H, m), 5.89 (NH, br q, J=5 Hz), 7.06-7.17 (2H, m).

EXAMPLE B14

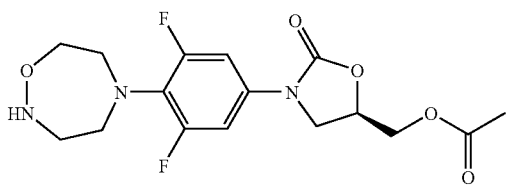

$^1$H NMR (CDCl$_3$) δ 2.10 (3H, s), 3.23 (2H, br t, J=5.5 Hz), 3.40 (2H, br t, J=5.5 Hz), 3.49 (2H, t, J=5.5 Hz), 3.79 (1H, dd, J=9, 6 Hz), 3.90 (2H, t, J=5.5 Hz), 4.07 (1H, dd, J=9, 9 Hz), 4.29 (1H, dd, J=12, 5 Hz), 4.37 (1H, dd, J=12, 4 Hz), 4.87 (1H, dddd, J=9, 6, 5, 4 Hz), 5.78 (NH, br), 7.04-7.16 (2H, m).

EXAMPLE B15

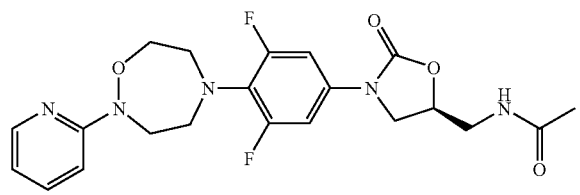

$^1$H NMR (CDCl$_3$) δ 2.02 (3H, s), 3.51-3.59 (4H, m), 3.62-3.68 (2H, m), 3.73 (1H, dd, J=9, 7 Hz), 3.97 (2H, t, J=5.5 Hz), 3.99 (1H, dd, J=9, 9 Hz), 4.13 (2H, br t, J=5.5 Hz), 4.74-4.83 (1H, m), 6.58 (NH, br t, J=6 Hz), 6.77 (1H, ddd, J=7, 5, 1 Hz), 6.95-7.06 (2H, m), 7.13 (1H, ddd, J=8.5, 1, 1 Hz), 7.58 (1H, ddd, J=8.5, 7, 2 Hz), 8.21 (1H, ddd, J=5, 2, 1 Hz).

EXAMPLE B16

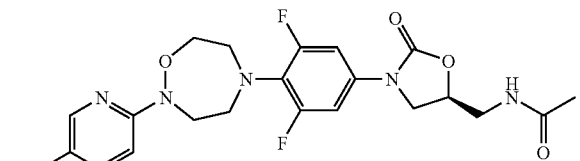

$^1$H NMR (CDCl$_3$) δ 2.03 (3H, s), 3.49 (2H, br t, J=5 Hz), 3.57 (2H, br t, J=5.5 Hz), 3.62-3.70 (2H, m), 3.74 (1H, dd, J=9, 7 Hz), 3.99 (1H, dd, J=9, 9 Hz), 4.12-4.22 (4H, m), 4.74-4.84 (1H, m), 6.25 (NH, br t, J=6 Hz), 6.98 (1H, d, J=9 Hz), 7.06-7.17 (2H, m), 8.30 (1H, dd, J=9, 2.5 Hz), 9.06 (1H, d, J=2.5 Hz).

EXAMPLE B17

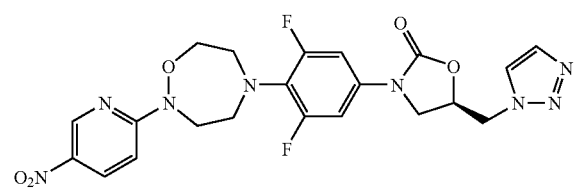

$^1$H NMR (CDCl$_3$) δ 3.48 (2H, br t, J=5 Hz), 3.56 (2H, br t, J=5.5 Hz), 3.90 (1H, dd, J=9, 6 Hz), 4.13 (1H, dd, J=9, 9 Hz), 4.14-4.22 (4H, m), 4.78 (1H, dd, J=14.5, 5 Hz), 4.83 (1H, dd, J=14.5, 3.5 Hz), 5.04-5.13 (1H, m), 6.93-7.06 (2H, m), 6.98 (1H, d, J=9 Hz), 7.75 (1H, br s), 7.82 (1H, br s), 8.30 (1H, dd, J=9, 2.5 Hz), 9.05 (1H, d, J=2.5 Hz).

EXAMPLE B18

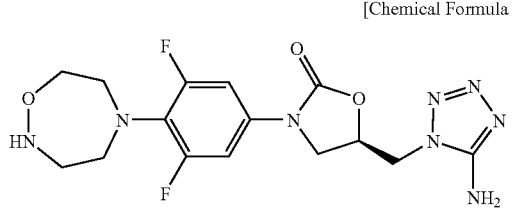

[Chemical Formula 224]

¹H NMR (CDCl₃) δ 3.22 (2H, br t, J=5.5 Hz), 3.39 (2H, br t, J=5 Hz), 3.48 (2H, br t, J=5.5 Hz), 3.89 (2H, t, J=5 Hz), 3.93 (1H, dd, J=9. 6, Hz), 4.12 (1H, dd, J=9, 9 Hz), 4.64 (NH, br s), 4.74 (1H, dd, J=14, 6 Hz), 4.84 (1H, dd, J=14, 5 Hz), 5.12 (1H, dddd, J=9, 6, 6, 5 Hz), 5.81 (NH, br s), 6.98-7.10 (2H, m).

EXAMPLE B19

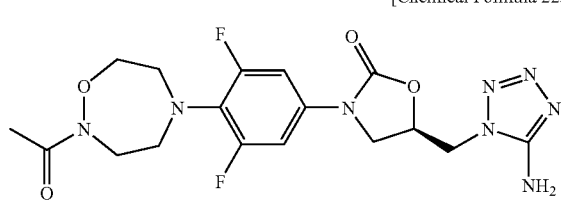

[Chemical Formula 225]

¹H NMR (CDCl₃—CD₃OD (9:1)) δ 2.19 (3H, s), 3.38-3.47 (4H, m), 3.90 (2H, br t, J=5.5 Hz), 3.93 (1H, dd, J=9. 6, Hz), 4.13 (2H, t, J=5 Hz), 4.15 (1H, dd, J=9, 9 Hz), 4.76 (1H, dd, J=14, 5.5 Hz), 4.84 (1H, dd, J=14, 5 Hz), 5.16 (1H, dddd, J=9, 6, 5.5, 5 Hz), 7.03-7.14 (2H, m).

EXAMPLE B20

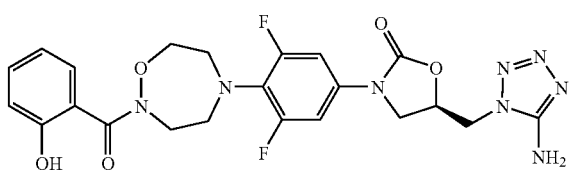

[Chemical Formula 226]

¹H NMR (CDCl₃) δ 3.38 (2H, br t, J=4.5 Hz), 3.51 (2H, br d, J=5.5 Hz), 3.92 (1H, dd, J=9, 6 Hz), 4.02 (2H, br t, J=4.5 Hz), 4.07-4.16 (3H, m), 4.73 (1H, dd, J=14, 6 Hz), 4.83 (1H, dd, J=14, 5 Hz), 5.07-5.17 (1H, m), 6.85 (1H, ddd, J=8, 8, 1 Hz), 6.99 (1H, dd, J=8.5, 1 Hz), 7.02-7.12 (2H, m), 7.37 (1H, ddd, J=8.5, 8, 1.5 Hz), 8.03 (1H, dd, 8, 1.5 Hz), 11.23 (OH, br s).

EXAMPLE B21

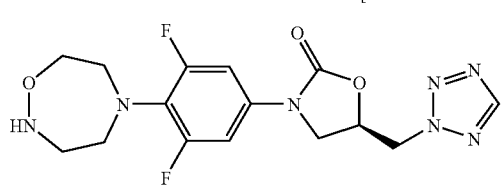

[Chemical Formula 227]

¹H NMR (CDCl₃) δ 3.21 (2H, br t, J=5 Hz), 3.39 (2H, br d, J=5 Hz), 3.49 (2H, br t, J=5.5 Hz), 3.89 (2H, br t, J=5 Hz), 3.96 (1H, dd, J=9, 5.5 Hz), 4.17 (1H,dd, J=9, 9 Hz), 5.01 (1H, dd, J=14, 5.5 Hz), 5.10 (1H, dd, J=14, 5 Hz), 5.23 (1H, dddd, J=9, 5.5, 5.5, 5 Hz), 6.96-7.08 (2H, m), 8.57 (1H, s).

EXAMPLE B22

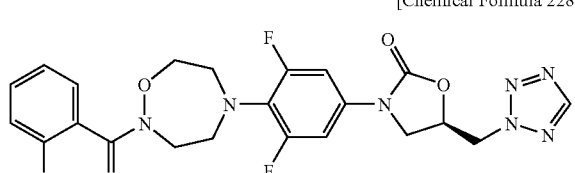

[Chemical Formula 228]

¹H NMR (CDCl₃) δ 3.39 (2H, br t, J=5 Hz), 3.52 (2H, br t, J=5.5 Hz), 3.96 (1H, dd, J=9, 5.5 Hz), 4.03 (2H, br t, J=5 Hz), 4.14 (2H, br t, J=5.5 Hz), 4.15 (1H,dd, J=9, 9 Hz), 4.99 (1H, dd, J=14, 6 Hz), 5.09 (1H, dd, J=14, 5 Hz), 5.21 (1H, dddd, J=9, 6, 5.5, 5 Hz), 6.85 (1H, ddd, J=8, 8, 1 Hz), 6.99 (1H, dd, J=8, 1 Hz), 7.01-7.12 (2H, m), 7.38 (1H, ddd, J=8, 8, 2 Hz), 8.05 (1H, dd, 8, 2 Hz), 8.57 (1H, s), 11.26 (OH, br s).

EXAMPLE B23

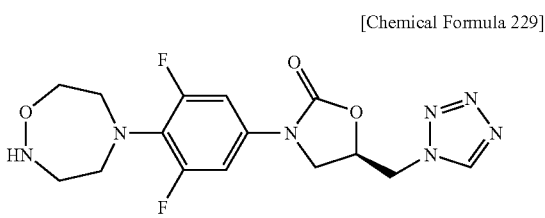 [SMILES: O=C1O[C@@H](Cn2cnnn2)CN1c1cc(F)c(N2CCNOCC2)c(F)c1]

[Chemical Formula 229]

¹H NMR (CDCl₃) δ 3.20 (2H, br t, J=5 Hz), 3.38 (2H, br t, J=5.5 Hz), 3.48 (2H, br t, J=5.5 Hz), 3.84-3.94 (3H, m), 4.21 (1H,dd, J=9, 9 Hz), 4.86 (1H, dd, J=15, 6 Hz), 4.93 (1H, dd, J=15, 4 Hz), 5.07-5.17 (1H, m), 6.93-7.05 (2H, m), 8.95 (1H, s).

EXAMPLE B24

[Chemical Formula 230]

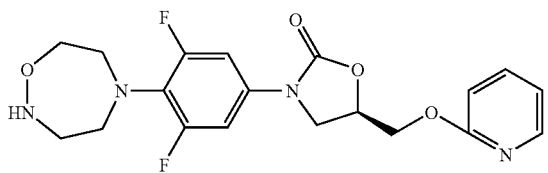

$^1$H NMR (CDCl$_3$) δ 3.22 (2H, br t, J=5.5 Hz), 3.40 (2H, br t, J=5.5 Hz), 3.49 (2H, br t, J=5.5 Hz), 3.87-3.96 (3H, m), 4.01 (1H, dd, J=9, 9 Hz), 4.59 (2H, d, J=4.5 Hz), 4.97-5.07 (1H, m), 6.77 (1H, br d, J=9 Hz), 6.92 (1H, ddd, J=7.5, 5, 1 Hz), 7.07-7.18 (2H, m), 7.60 (1H, ddd, J=9, 7.5, 2 Hz), 8.13 (1H, dd, J=5, 2 Hz).

EXAMPLE B25

[Chemical Formula 231]

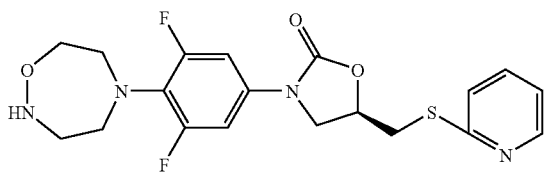

$^1$H NMR (CDCl$_3$) δ 3.21 (2H, br t, J=5.5 Hz), 3.38 (2H, br t, J=5.5 Hz), 3.42-3.52 (3H, m), 3.76-3.92 (4H, m), 4.03 (1H, dd, J=9, 9 Hz), 4.92-5.02 (1H, m), 7.02-7.13 (2H, m), 7.04 (1H, ddd, J=8, 5, 1 Hz), 7.21 (1H, br d, J=8 Hz), 7.51 (1H, ddd, J=8, 8, 2 Hz), 8.41 (1H, ddd, J=5, 2, 1 Hz).

EXAMPLE B26

[Chemical Formula 232]

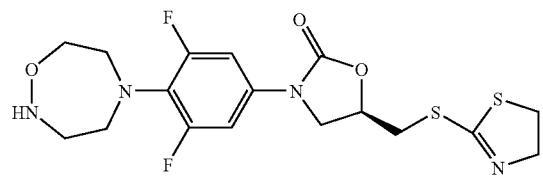

$^1$H NMR (CDCl$_3$) δ 3.22 (2H, br t, J=5.5 Hz), 3.36-3.52 (7H, m), 3.62 (1H, dd, J=14.5, 5 Hz), 3.81 (1H, dd, J=9, 6 Hz), 3.89 (2H, t, J=5.5 Hz), 4.06 (1H, dd, J=9, 9 Hz), 4.20 (2H, t, J=8 Hz), 4.91-5.01 (2H, m), 7.03-7.14 (2H, m).

EXAMPLE B27

[Chemical Formula 233]

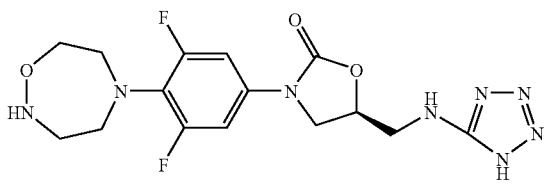

$^1$H NMR (CDCl$_3$—CD$_3$OD (1:1)) δ 3.22 (2H, br t, J=5.5 Hz), 3.41 (2H, br t, J=5.5 Hz), 3.49 (2H, br t, J=5.5 Hz), 3.92 (2H, t, J=5.5 Hz), 3.98 (1H, dd, J=9, 6.5 Hz), 4.19 (1H, dd, J=9, 9 Hz), 4.55 (2H, d, J=5 Hz), 5.10 (1H, ddt, J=9, 6, 5 Hz), 7.03-7.15 (2H, m).

EXAMPLE B28

[Chemical Formula 234]

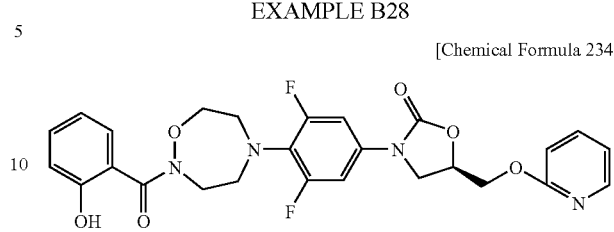

$^1$H NMR (CDCl$_3$) δ 3.39 (2H, br t, J=5 Hz), 3.52 (2H, br d, J=5.5 Hz), 3.92 (1H, dd, J=9, 6 Hz), 4.08 (1H, dd, J=9, 9 Hz), 4.13 (2H, br t, J=5.5 Hz), 4.59 (2H, d, J=4.5 Hz), 5.02 (1H, ddt, J=9, 6, 4.5 Hz), 6.76 (1H, br dd, J=8, 1 Hz), 6.84 (1H, ddd, J=8, 8, 1 Hz), 6.92 (1H, ddd, J=8, 5, 0.5), 7.00 (1H, dd, J=8, 1 Hz), 7.11-7.22 (2H, m), 7.38 (1H, ddd, J=8, 8, 1.5 Hz), 7.60 (1H, ddd, J=8, 8, 2 Hz), 8.05 (1H, dd, 8, 1.5 Hz), 8.13 (1H, br dd, J=5, 2 Hz), 11.29 (OH, br s).

EXAMPLE B29

[Chemical Formula 235]

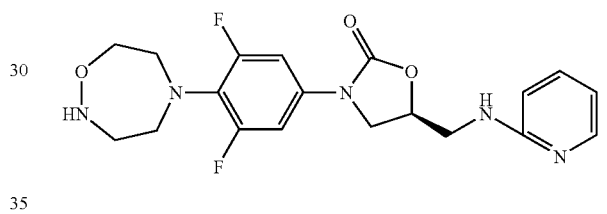

$^1$H NMR (CDCl$_3$) δ 3.21 (2H, br t, J=5.5 Hz), 3.38 (2H, br t, J=5.5 Hz), 3.47 (2H, t, J=5.5 Hz), 3.78-3.86 (2H, m), 3.81 (1H, dd, J=9, 7), 3.89 (2H, t, J=5.5 Hz), 3.99 (1H, dd, J=9, 9 Hz), 4.85-4.95 (1H, m), 5.03 (NH, br t, J=6 Hz), 6.46 (1H, br d, J=8.5 Hz), 6.60 (1H, ddd, J=7, 5.5, 1 Hz), 7.00-7.12 (2H, m), 7.38 (1H, ddd, J=8.5, 7, 1.5 Hz), 8.06 (1H, dd, J=5.5, 1.5 Hz).

EXAMPLE B30

[Chemical Formula 236]

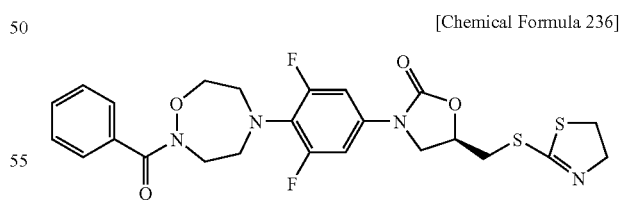

$^1$H NMR (CDCl$_3$) δ 3.35-3.45 (3H, m), 3.44 (2H, t, J=8 Hz), 3.51 (2H, br t, J=5.5 Hz), 3.62 (1H, dd, J=14, 5 Hz), 4.00-4.08 (3H, m), 3.81 (1H, dd, J=9, 6 Hz), 4.11-4.18 (2H, m), 4.19 (2H, t, J=8 Hz), 5.09 (1H, dd, J=14, 5 Hz), 4.91-5.01 (1H, m), 6.85 (1H, ddd, J=8, 8, 1 Hz), 6.99 (1H, dd, J=8, 1 Hz), 7.06-7.18 (2H, m), 7.37 (1H, ddd, J=8, 8, 1.5 Hz), 8.05 (1H, dd, 8, 1.5 Hz).

EXAMPLE B31

[Chemical Formula 237]

¹H NMR (CDCl₃) δ 2.60 (3H, s), 3.22 (2H, t, J=5.5 Hz), 3.40 (2H, br t, J=5.5 Hz), 3.49 (2H, t, J=5.5 Hz), 3.80 (1H, dd, J=9, 7 Hz), 3.90 (2H, br t, J=5.5 Hz), 4.05 (1H, dd, J=9, 9 Hz), 4.13 (1H, ddd, J=14.5, 6, 3 Hz), 4.22 (1H, 1H, ddd, J=14.5, 6, 3 Hz), 5.00 (1H, dddd, J=9, 7, 6, 3 Hz), 6.98-7.09 (2H, m), 8.50 (NH, br s).

EXAMPLE B32

[Chemical Formula 238]

¹H NMR (CDCl₃) δ 3.22 (2H, br t, J=5.5 Hz), 3.36 (2H, d, J=6 Hz), 3.40 (2H, br t, J=5.5 Hz), 3.49 (2H, br t, J=5.5 Hz), 3.84 (1H, dd, J=9, 6 Hz), 3.89 (2H, t, J=5.5 Hz), 4.21 (1H, dd, J=9, 9 Hz), 5.00 (1H, ddt, J=9, 6, 6 Hz), 7.03-7.14 (2H, m).

EXAMPLE B33

[Chemical Formula 239]

¹H NMR (CDCl₃) δ 2.03 (3H, s), 2.19 (3H, s), 3.37-3.45 (4H, m), 3.58-3.74 (2H, m), 3.73 (1H, dd, J=9, 6.5 Hz), 3.90 (2H, br t, 5.5 Hz), 3.99 (1H, dd, J=9, 9 Hz), 4.12 (2H, t, J=5 Hz), 4.73-4.83 (1H, m), 6.27 (NH, br t, J=6 Hz), 7.05-7.16 (2H, m).

EXAMPLE B34

[Chemical Formula 240]

¹H NMR (CDCl₃) δ 2.03 (3H, s), 2.67 (3H, s), 3.40 (2H, br t, J=5 Hz), 3.52 (2H, br t, J=5.5 Hz), 3.66 (1H, dd, J=6, 4.5 Hz), 3.75 (1H, dd, J=9, 7 Hz), 4.00 (1H, dd, J=9, 9 Hz), 4.24 (2H, t, J=5 Hz), 4.40 (2H, t, J=5.5 Hz), 4.75-4.84 (1H, m), 6.45 (NH, br t, J=6 Hz), 7.06-7.17 (2H, m).

EXAMPLE B35

[Chemical Formula 241]

¹H NMR (CDCl₃) δ 2.19 (3H, s), 2.60 (3H, s), 3.38-3.46 (4H, m), 3.80 (1H, dd, J=9, 7 Hz), 3.90 (2H, br t, J=5.5 Hz), 4.05 (1H, dd, J=9, 9 Hz), 4.06-4.15 (3H, m), 4.24 (1H, ddd, J=14.5, 6, 3 Hz), 4.94-5.04 (1H, m), 7.03-7.14 (2H, m), 8.28 (NH, br t, J=5.5 Hz).

EXAMPLE B36

[Chemical Formula 242]

¹H NMR (CDCl₃) δ 2.60 (3H, s), 2.67 (3H, s), 3.41 (2H, br t, J=5 Hz), 3.52 (2H, br t, J=5.5 Hz), 3.84 (1H, dd, J=9, 7 Hz), 4.08 (1H, dd, J=9, 9 Hz), 4.12-4.21 (2H, m), 4.25 (2H, br t, J=5.5 Hz), 4.39 (2H, br t, J=5 Hz), 4.99-5.09 (1H, m), 7.03-7.14 (2H, m), 8.74 (NH, br t, J=6 Hz).

EXAMPLE B37

[Chemical Formula 243]

¹H NMR (CDCl₃) δ 2.60 (3H, s), 3.41 (2H, br t, J=5 Hz), 3.47 (2H, br t, J=5.5 Hz), 3.81 (1H, dd, J=9, 7 Hz), 3.95 (2H, br t, J=5.5 Hz), 4.05 (1H, dd, J=9, 9 Hz), 4.06-4.16 (3H, m), 4.24 (1H, ddd, J=14.5, 6, 3 Hz), 4.36 (2H, s), 4.95-5.05 (1H, m), 7.04-7.15 (2H, m), 8.22 (NH, br t, J=6 Hz).

EXAMPLE B38

[Chemical Formula 244]

¹H NMR (CDCl₃) δ 2.60 (3H, s), 3.39 (2H, br t, J=5 Hz), 3.52 (2H, br t, J=5.5 Hz), 3.81 (1H, dd, J=9, 7 Hz), 4.03 (2H, br t, J=5 Hz), 4.05 (1H, dd, J=9, 9 Hz), 4.05-4.17 (3H, m), 4.22 (1H, ddd, J=14.5, 6, 3 Hz), 4.95-5.05 (1H, m), 6.85 (1H, br dd, J=8, 8 Hz), 7.00 (1H, br d, J=8 Hz), 7.03-7.14 (2H, m), 7.38 (1H, ddd, J=8, 8, 1.5 Hz), 8.04 (1H, dd, 8, 1.5 Hz), 8.29 (NH, br s), 11.22 (OH, br s).

EXAMPLE B39

[Chemical Formula 245]

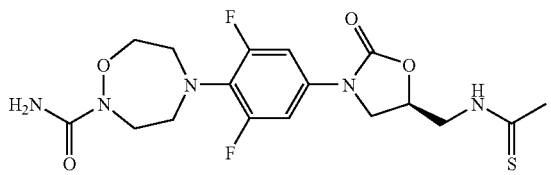

$^1$H NMR (CDCl$_3$) δ 2.59 (3H, s), 3.38-3.49 (4H, m), 3.78-3.87 (3H, m), 4.05 (1H, dd, J=9, 9 Hz), 4.06-4.24 (4H, m), 4.96-5.06 (1H, m), 5.45 (NH, br s), 7.01-7.12 (2H, m), 8.91 (NH, br s).

EXAMPLE B40

[Chemical Formula 246]

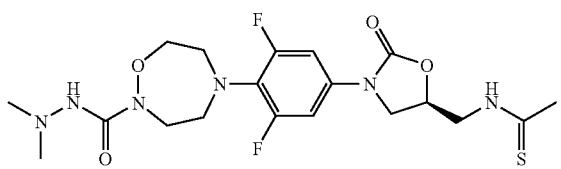

$^1$H NMR (CDCl$_3$) δ 2.61 (3H, s), 2.63 (6H, s), 3.39 (2H, br t, J=5.5 Hz), 3.46 (2H, br t, J=5 Hz), 3.78 (2H, br t, J=5.5 Hz), 3.81 (1H, dd, J=9, 6.5 Hz), 4.00-4.16 (4H, m), 4.21 (1H, ddd, J=14.5, 6, 3 Hz), 4.96-5.06 (1H, m), 6.61 (NH, br s), 7.02-7.13 (2H, m), 8.55 (NH, br s).

EXAMPLE B41

[Chemical Formula 247]

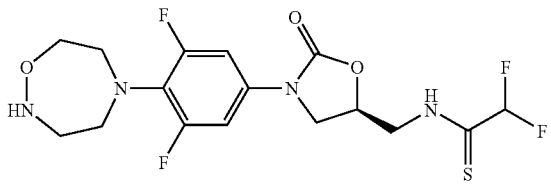

$^1$H NMR (CDCl$_3$) δ 3.23 (2H, br t, J=5.5 Hz), 3.41 (2H, br t, J=5.5 Hz), 3.50 (2H, br t, J=5.5 Hz), 3.73 (1H, dd, J=9, 6.5 Hz), 3.90 (2H, t, J=5.5 Hz), 4.02 (1H, dd, J=14.5, 8 Hz), 4.09 (1H, dd, J=9, 9 Hz), 4.31 (1H, dd, J=14.5, 2.5 Hz), 5.01 (1H, dddd, J=9, 8, 6.5, 2.5 Hz), 5.78 (NH, br s), 6.22 (1H, t, J=54 Hz), 7.00-7.11 (2H, m),

EXAMPLE B42

[Chemical Formula 248]

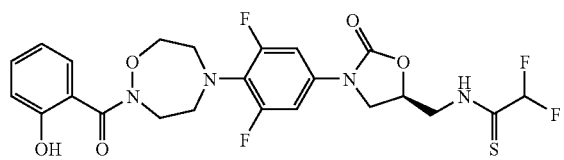

$^1$H NMR (CDCl$_3$) δ 3.39 (2H, br t, J=5 Hz), 3.52 (2H, br t, J=5 Hz), 3.75 (1H, dd, J=9, 6.5 Hz), 3.99-4.16 (6H, m), 4.29 (1H, dd, J=14.5, 3 Hz), 4.96-5.06 (1H, m), 6.21 (1H, t, J=54 Hz), 6.86 (1H, ddd, J=8.5, 8, 1.5 Hz), 7.00 (1H, dd, J=8.5, 1 Hz), 7.03-7.14 (2H, m), 7.38 (1H, ddd, J=8.5, 8, 1.5 Hz), 8.04 (1H, dd, J=8, 1.5 Hz).

EXAMPLE B43

[Chemical Formula 249]

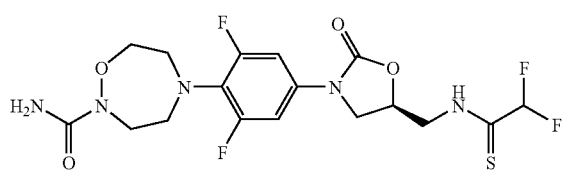

$^1$H NMR (CDCl$_3$) δ 3.41 (2H, br t, J=5.5 Hz), 3.46 (2H, br t, J=5.5 Hz), 3.77 (1H, dd, J=9, 6.5 Hz), 3.81 (2H, br t, J=5.5 Hz), 4.02-4.14 (4H, m), 4.24 (1H, dd, J=14.5, 3.5 Hz), 4.98-5.08 (1H, m), 5.36 (NH, br s), 6.21 (1H, t, J=54 Hz), 7.01-7.12 (2H, m).

EXAMPLE B44

[Chemical Formula 250]

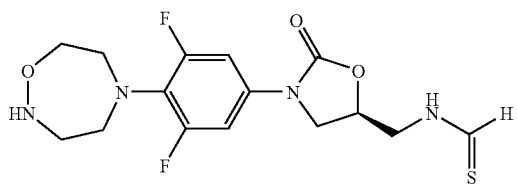

$^1$H NMR (CDCl$_3$) δ 3.22 (2H, br t, J=5.5 Hz), 3.39 (2H, br t, J=5.5 Hz), 3.48 (2H, t, J=5.5 Hz), 3.83 (1H, dd, J=9, 7), 3.89 (2H, t, J=5.5 Hz), 4.06 (1H, dd, J=9, 9 Hz), 4.07-4.32 (2H, m), 4.97-5.06 (1H, m), 6.97-7.10 (2H, m), 9.54 (1H, d, J=6 Hz), 9.21 (NH, br d, J=6 Hz).

EXAMPLE B45

[Chemical Formula 251]

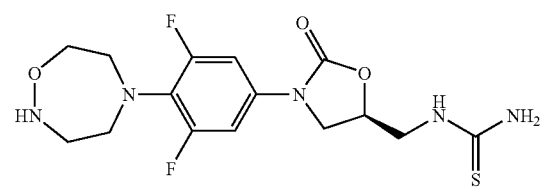

$^1$H NMR (CDCl$_3$—CD$_3$OD (7:1)) δ 3.22 (2H, br t, J=5.5 Hz), 3.41 (2H, br t, J=5.5 Hz), 3.49 (2H, t, J=5.5 Hz), 3.89-3.98 (3H, m), 3.98-4.07 (3H, m), 4.85-4.94 (1H, m), 7.05-7.16 (2H, m).

EXAMPLE B46

[Chemical Formula 252]

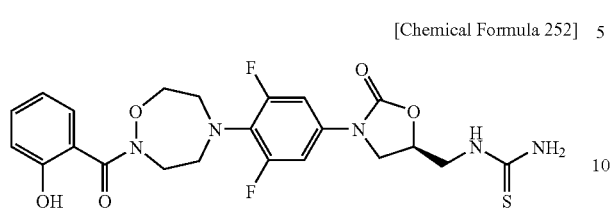

¹H NMR (CDCl₃) δ 3.38 (2H, br t, J=5 Hz), 3.50 (2H, br t, J=5.5 Hz), 3.85-3.96 (1H, m), 3.96-4.07 (4H, m), 4.11 (2H, t, J=5.5 Hz), 4.20-4.34 (1H, m), 4.88-4.97 (1H, m), 6.36 (NH, br s), 6.86 (1H, ddd, J=8, 8, 1 Hz), 6.98 (1H, dd, J=8, 1 Hz), 7.01-7.11 (2H, m), 7.37 (1H, ddd, J=8, 8, 1.5 Hz), 8.00 (1H, dd, J=8, 1.5 Hz).

EXAMPLE B47

[Chemical Formula 253]

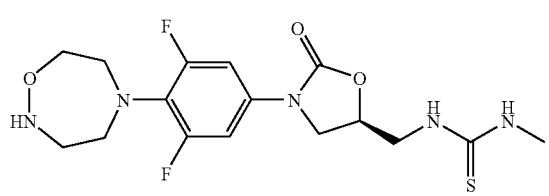

¹H NMR (CDCl₃) δ 3.02 (3H, br d, J=4 Hz), 3.22 (2H, br t, J=5.5 Hz), 3.40 (2H, br t, J=5.5 Hz), 3.44-3.53 (2H, m), 3.90 (2H, t, J=5.5 Hz), 3.94-4.07 (3H, m), 4.21-4.38 (1H, m), 4.88-4.98 (1H, m), 6.66 (NH, br s), 6.97-7.09 (2H, m).

EXAMPLE B48

[Chemical Formula 254]

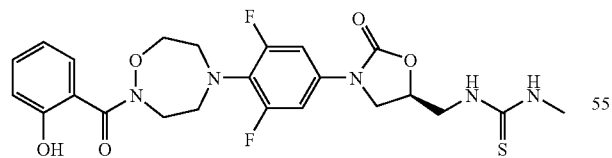

¹H NMR (CDCl₃) δ 3.01 (3H, br d, J=3.5 Hz), 3.39 (2H, br t, J=5 Hz), 3.51 (2H, br t, J=5.5 Hz), 3.92-4.07 (5H, m), 4.12 (2H, br t, J=5.5 Hz), 4.20-4.33 (1H, m), 4.88-4.98 (1H, m), 6.65 (NH, br s), 6.86 (1H, ddd, J=8, 8, 1 Hz), 6.99 (1H, dd, J=8, 1 Hz), 7.02-7.13 (2H, m), 7.37 (1H, ddd, J=8, 8, 1.5 Hz), 8.00 (1H, dd, J=8, 1.5 Hz).

EXAMPLE B49

[Chemical Formula 255]

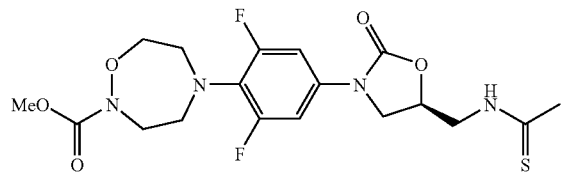

¹H NMR (CDCl₃) δ 2.61 (3H, s), 3.36-3.46 (4H, m), 3.77-3.87 (3H, m), 3.80 (3H, s), 4.05 (1H, dd, J=9, 9 Hz), 4.04-4.17 (3H, m), 4.22 (1H, ddd, J=14.5, 6, 3 Hz), 4.96-5.06 (1H, m), 7.01-7.12 (2H, m), 8.47 (NH, br t, J=6 Hz).

EXAMPLE B50

[Chemical Formula 256]

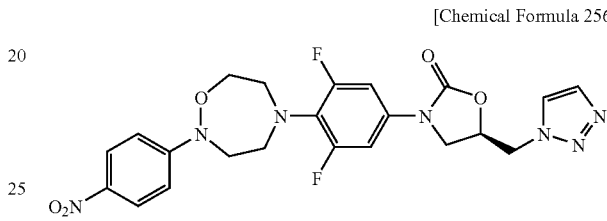

¹H NMR (CDCl₃) δ 3.45 (2H, br t, J=5 Hz), 3.60 (2H, br t, J=5.5 Hz), 3.74 (2H, t, J=5.5 Hz), 3.91 (1H, dd, J=9, 6 Hz), 4.12 (1H, dd, J=9, 9 Hz), 4.17 (2H, t, J=5 Hz), 4.79 (2H, d, J=4 Hz), 5.03-5.12 (1H, m), 6.90 (2H, br d, J=9 Hz), 6.94-7.05 (2H, m), 7.73 (1H, br s), 7.79 (1H, br s), 8.15 (2H, br d, J=9 Hz).

EXAMPLE B51

[Chemical Formula 257]

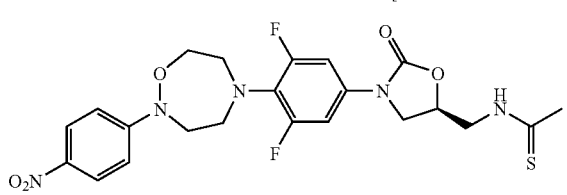

¹H NMR (CDCl₃—CD₃OD (9:1)) δ 2.57 (3H, s), 3.46-3.55 (2H, m), 3.63 (2H, br t, J=5.5 Hz), 3.78 (2H, br t, J=5.5 Hz), 3.83 (1H, dd, 9, 7 Hz), 4.01 (1H, dd, J=14.5, 6.5 Hz), 4.07 (1H, dd, J=9, 9 Hz), 4.14-4.23 (3H, m), 4.94-5.04 (1H, m), 6.93 (2H, br d, J=9 Hz), 7.07-7.18 (2H, m), 8.17 (2H, br d, J=9 Hz).

EXAMPLE B52

[Chemical Formula 258]

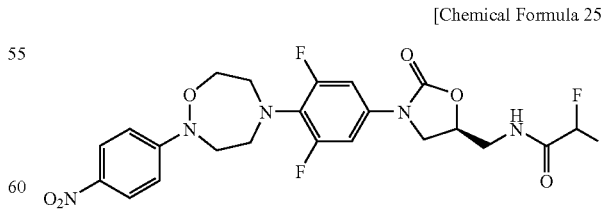

¹H NMR (CDCl₃—CD₃OD (9:1)) δ 3.48 (2H, br t, J=5 Hz), 3.59-3.68 (3H, m), 3.70-3.79 (4H, m), 4.06 (1H, dd, J=9, 9 Hz), 4.19 (2H, t, J=5 Hz), 4.77-4.87 (1H, m), 5.93 (1H, t, J=54 Hz), 6.92 (2H, br d, J=9 Hz), 7.06-7.17 (2H, m), 8.16 (2H, br d, J=9 Hz).

EXAMPLE B53

[Chemical Formula 259]

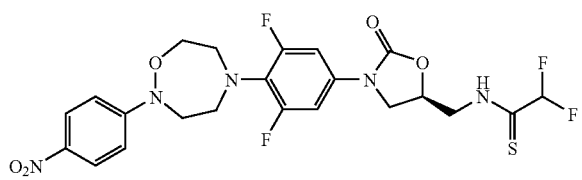

$^1$H NMR (CDCl$_3$—CD$_3$OD (9:1)) δ 3.41-3.72 (2H, m), 3.63 (2H, br t, J=5.5 Hz), 3.78 (2H, br t, J=5.5 Hz), 3.81 (1H, dd, 9, 6.5 Hz), 4.03 (1H, J=14, 7 Hz), 4.09 (1H, dd, J=9, 9 Hz), 4.16-4.24 (3H, m), 4.98-5.08 (1H, m), 6.22 (1H, t, J=54 Hz), 6.93 (2H, br d, J=9 Hz), 7.06-7.18 (2H, m), 8.17 (2H, br d, J=9 Hz).

EXAMPLE B55

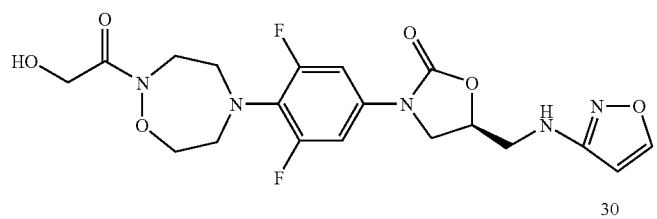

$^1$H NMR (CDCl$_3$) δ 3.40 (2H, br t, J=5 Hz), 3.46 (2H, br t, J=5.5 Hz), 3.62 (1H, ddd, J=6, 6, 15 Hz), 3.74 (1H, ddd, J=3, 6.5, 15 Hz), 3.82 (1H, dd, J=6.5, 9 Hz), 3.95 (2H, br t, J=5.5), 4.04 (1H, dd, J=9, 9 Hz), 4.12 (2H, br t, J=5 Hz), 4.36 (2H, s), 4.95 (1H, dddd, J=3, 6, 6.5, 9 Hz), 5.88 (1H, d, J=1.5 Hz), 7.09-7.19 (2H, m), and 8.06 (1H, d, J=1.5 Hz).

EXAMPLE B56

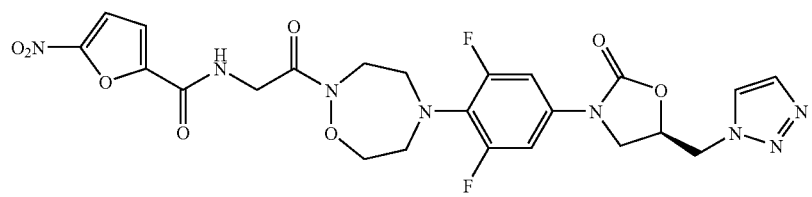

$^1$H NMR (CDCl$_3$) δ 3.39-3.49 (4H, m), 3.88-3.98 (3H, m), 4.14 (1H, dd, J=9, 9 Hz), 4.20 (2H, br t, J=4.5 Hz), 4.44 (2H, br d, J=5 Hz), 4.82 (2H, d, J=4 Hz), 5.06-5.15 (1H, m), 6.95-7.06 (2H, m), 7.27 (1H, d, J=3.5 Hz), 7.36 (1H, d, J=3.5 Hz), 7.56 (1H, br s), 7.74 (1H, br s), and 7.81 (1H, br s).

EXAMPLE B57

[Chemical Formula 262]

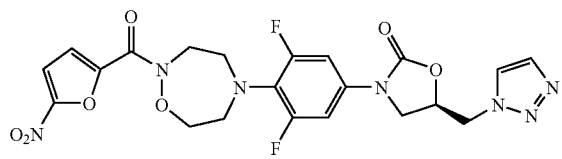

$^1$H NMR (CDCl$_3$—CD$_3$OD (9:1)) δ 3.42-3.57 (4H, m), 3.91 (1H, dd, J=6.5, 9), 4.07 (2H, br t, J=5 Hz), 4.15 (1H, dd, J=9, 9 Hz), 4.32 (2H, br t, J=4.5 Hz), 4.75-4.88 (2H, m), 5.05-5.15 (1H, m), 6.98-7.09 (2H, m), 7.32 (1H, d, J=4 Hz), 7.40 (1H, d, J=4 Hz), 7.75 (1H, d, J=1 Hz), and 7.86 (1H, d, J=1 Hz).

EXAMPLE B58

[Chemical Formula 263]

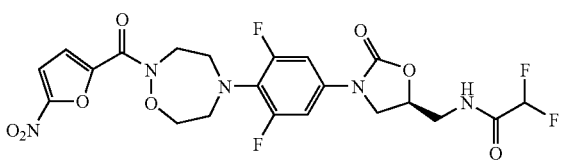

$^1$H NMR (CDCl$_3$—CD$_3$OD (5:1)) δ 3.48 (2H, br t, J=4.5 Hz), 3.56 (2H, br t, J=5.5 Hz), 3.69-3.84 (2H, m), 3.64 (1H, dd, J=6, 15 Hz), 4.03-4.13 (3H, m), 4.33 (2H, t, 4.5 Hz), 4.79-4.89 (1H, m), 5.95 (1H, t, J=54 Hz), 7.09-7.20 (2H, m), 7.33 (1H, d, J=4 Hz), and 7.42 (1H, d, J=4 Hz).

[Chemical Formula 260]

EXAMPLE B59

[Chemical Formula 264]

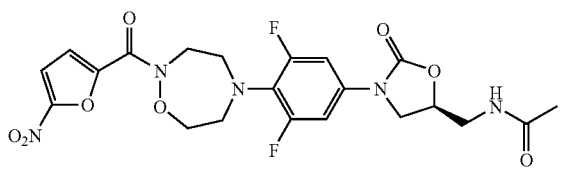

[Chemical Formula 261]

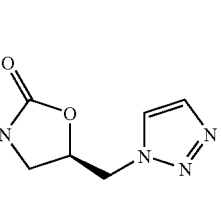

$^1$H NMR (CDCl$_3$—CD$_3$OD (9:1)) δ 2.01 (3H, s), 3.47 (2H, br t, J=4.5 Hz), 3.51-3.67 (4H, m), 3.74 (1H, dd, J=6.5, 9 Hz), 4.02 (1H, dd, J=9, 9 Hz), 4.07 (2H, br t, J=5.5 Hz), 4.33 (2H, t, J=4.5 Hz), 4.73-4.83 (1H, m), 7.08-7.19 (2H, m), 7.32 (1H, d, J=4 Hz), and 7.39 (1H, d, J=4 Hz).

EXAMPLE B60

[Chemical Formula 265]

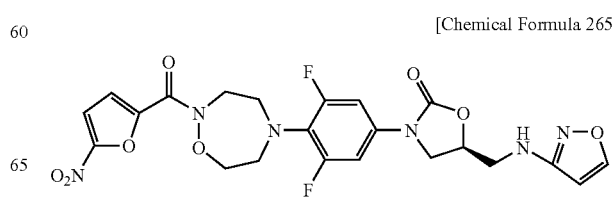

¹H NMR (CDCl₃—CD₃OD (6:1)) δ 3.48 (2H, br t, J=4.5 Hz), 3.55 (2H, br t, J=5.5 Hz), 3.58 (1H, dd, J=6, 15 Hz), 3.66 (1H, dd, J=4, 15 Hz), 3.84 (1H, dd, J=7, 9 Hz), 4.04-4.13 (3H, m), 4.32 (2H, t, J=4.5 Hz), 4.90-5.00 (1H, m), 5.94 (1H, d, J=1.5 Hz), 7.10-7.21 (2H, m), 7.34 (1H, d, J=4 Hz), 7.43 (1H, d, J=4 Hz), and 8.07 (1H, d, J=1.5 Hz).

Hz), 4.08 (2H, br t, J=5.5 Hz), 4.14 (1H, dd, J=9, 9 Hz), 4.33 (2H, br t, J=4.5 Hz), 4.44 (1H, dd, J=4, 12 Hz), 4.53 (1H, dd, J=3.5, 12 Hz), 4.97 (1H, dddd, J=3.5, 4, 6, 9 Hz), 7.12-7.23 (2H, m), 7.33 (1H, d, J=4 Hz), and 7.41 (1H, d, J=4 Hz).

EXAMPLE B63

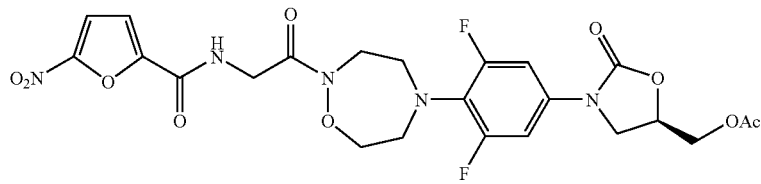

[Chemical Formula 268]

EXAMPLE B61

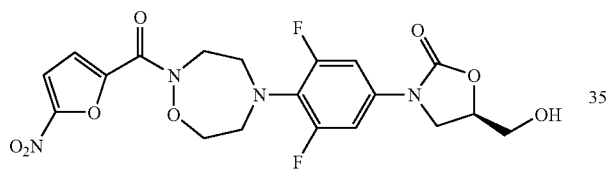

[Chemical Formula 266]

¹H NMR (CDCl₃—CD₃OD (7:1)) δ 2.12 (3H, s), 3.43-3.53 (4H, m), 3.81 (1H, dd, J=6, 9 Hz), 3.96 (2H, br t, J=5.5 Hz), 4.12 (1H, dd, J=9, 9 Hz), 4.25 (2H, br t, J=4.5 Hz), 4.30 (1H, dd, J=5, 12.5 Hz), 4.40 (1H, dd, J=3.5, 12.5 Hz), 4.44 (2H, s), 4.92 (1H, dddd, 3.5, 5, 6, 9 Hz), 7.02-7.13 (2H, m), 7.32 (1H, d, J=4 Hz), and 7.42 (1H, d, J=4 Hz).

EXAMPLE B64

¹H NMR (CDCl₃—CD₃OD (9:1)) δ 3.48 (2H, br t, J=4.5 Hz), 3.56 (2H, br t, J=5.5 Hz), 3.69 (1H, dd, J=3.5, 12.5 Hz), 3.91 (1H, dd, J=3.5, 12.5 Hz), 3.94 (1H, dd, J=6.5, 9 Hz), 4.00 (1H, dd, J=9, 9 Hz), 4.08 (2H, br t, J=5.5 Hz), 4.33 (2H, t, J=4.5 Hz), 4.73 (1H, dddd, J=3.5, 3.5, 6.5, 9 Hz), 7.13-7.23 (2H, m), 7.33 (1H, d, J=3.5 Hz), and 7.41 (1H, d, J=3.5 Hz).

EXAMPLE B62

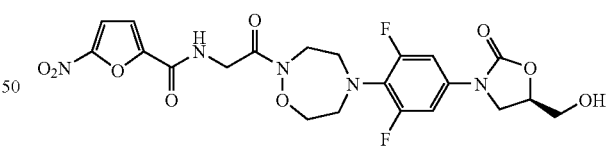

[Chemical Formula 269]

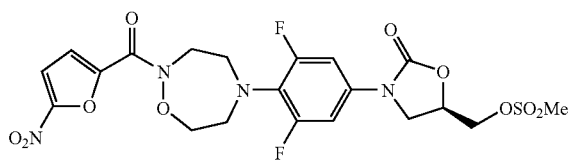

[Chemical Formula 267]

¹H NMR (CDCl₃—CD₃OD (6:1)) δ 3.13 (3H, s), 3.49 (2H, br t, J=4.5 Hz), 3.57 (2H, br t, J=5.5 Hz), 3.92 (1H, dd, J=6, 9

¹H NMR (CDCl₃—CD₃OD (7:1)) δ 3.48 (2H, br t, J=4.5 Hz), 3.56 (2H, br t, J=5.5 Hz), 3.70 (1H, dd, J=4, 12.5 Hz), 3.79 (2H, s), 3.87-3.98 (2H, m), 4.01 (1H, dd, J=9, 9 Hz), 4.08 (2H, br t, J=5.5 Hz), 4.33 (2H, br t, J=4.5 Hz), 4.70-4.79 (1H, m), 7.13-7.23 (2H, m), 7.33 (1H, d, J=4 Hz), and 7.42 (1H, d, J=4 Hz).

EXAMPLE B65

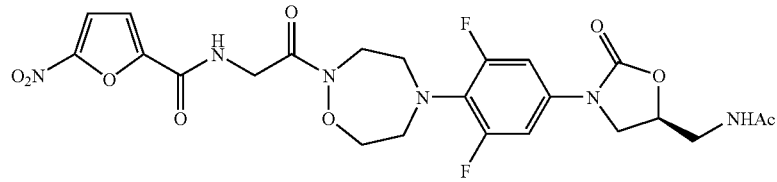

[Chemical Formula 270]

$^1$H NMR (CDCl$_3$) δ 2.03 (3H, s), 3.40-3.50 (4H, m), 3.68 (2H, br t, J=5.5 Hz), 3.76 (1H, dd, J=7, 9 Hz), 3.95 (2H, br t, J=5.5 Hz), 4.01 (1H, dd, J=9, 9 Hz), 4.22 (2H, br t, J=4.5 Hz), 4.45 (2H, d, J=4.5 Hz), 4.77-4.86 (1H, m), 6.73 (1H, br t, J=6 Hz), 7.05-7.16 (2H, m), 7.29 (1H, d, J=1 Hz), 7.37 (1H, d, J=1 Hz), and 7.64 (1H, br t, J=4.5 Hz).

EXAMPLE B66

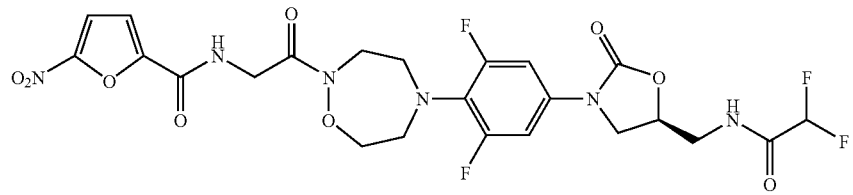

[Chemical Formula 271]

$^1$H NMR (CDCl$_3$—CD$_3$OD (9:1)) δ 3.41-3.51 (4H, m), 3.70-3.79 (2H, m), 3.65 (iH, dd, J=6, 14 Hz), 3.95 (2H, br t, J=5.5 Hz), 4.08 (1H, dd, J=9, 9 Hz), 4.23 (2H, br t, J=4.5 Hz), 4.44 (2H, s), 4.80-4.90 (1H, m), 5.95 (1H, t, J=54 Hz), 7.06-7.17 (2H, m), 7.30 (1H, d, J=4 Hz), and 7.40 (1H d, J=4 Hz).

EXAMPLE B67

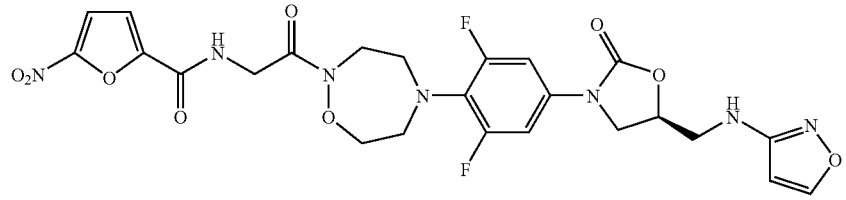

[Chemical Formula 272]

$^1$H NMR (CDCl$_3$—CD$_3$OD (9:1)) δ 3.39-3.51 (4H, m), 3.51-3.74 (2H, m), 3.82 (1H, dd, J=6.5, 9 Hz), 3.95 (2H, br t, J=5 Hz), 4.06 (1H, dd, J=9, 9 Hz), 4.22 (2H, br t, J=4.5 Hz), 4.44 (2H, s), 4.89-4.99 (1H, m), 5.90 (1H, d, J=1.5 Hz), 7.08-7.19 (2H, m), 7.30 (1H, d, J=4 Hz), 7.39 (1H, d, J=4 Hz), and 8.06 (1H, d, J=1.5 Hz).

EXAMPLE B68

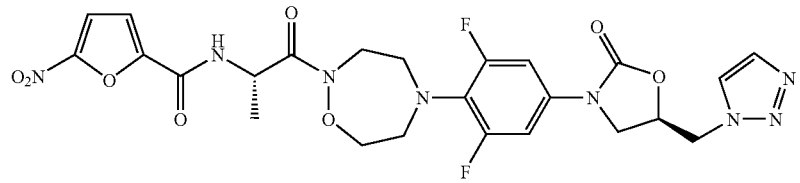

[Chemical Formula 273]

$^1$H NMR (CDCl$_3$) δ 1.52 (3H, d, J=7 Hz), 3.32-3.55 (4H, m), 3.64-3.74 (1H, m), 3.91 (1H, dd, J=6, 9 Hz), 4.14 (1H, dd, J=9, 9 Hz), 4.16-4.33 (3H, m), 4.81 (2H, d, J=4 Hz), 5.09 (1H, ddt, J=6, 9, 4 Hz), 5.17 (1H, dq, J=8, 7 Hz), 6.94-7.05 (2H, m), 7.24 (1H, d, J=3.5 Hz), 7.35 (1H, d, J=3.5 Hz), 7.56 (1H, br d, J=8 Hz), 7.74 (1H, br s), and 7.80 (1H, br s).

EXAMPLE B69

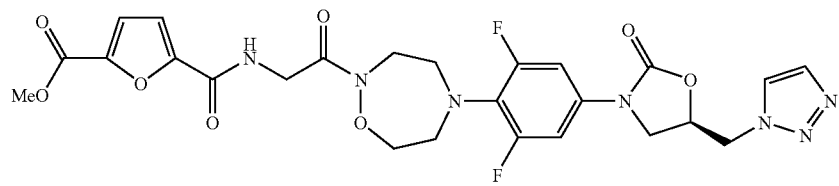

[Chemical Formula 274]

¹H NMR (CDCl₃) δ 3.38-3.49 (4H, m), 3.88-3.98 (3H, m), 3.92 (3H, s), 4.14 (1H, dd, J=9, 9 Hz), 4.20 (2H, br t, J=4.5 Hz), 4.44 (2H, d, J=4.5 Hz), 4.82 (2H, d, J=4 Hz), 5.05-5.15 (1H, m), 6.95-7.06 (2H, m), 7.18 (1H, d, J=4 Hz), 7.21 (1H, d, J=4Hz), 7.43 (1H, br t, J=4.5 Hz), 7.74 (1H, d, J=1 Hz), and 7.80 (1H, d, J=1 Hz).

EXAMPLE B70

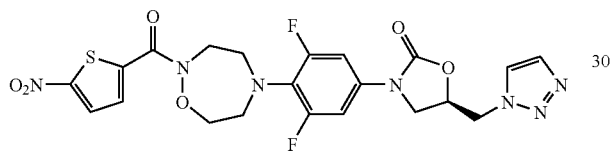

[Chemical Formula 275]

¹H NMR (DMSO-d₆) δ 3.85 (1H, dd, J=6, 9 Hz), 4.00 (2H, br t, J=5.5 Hz), 4.19 (1H, dd, J=9, 9 Hz), 4.26 (2H, br t, J=4.5 Hz), 4.81 (2H, d, J=5 Hz), 5.14 (1H, ddt, J=6, 9, 5 Hz), 7.18-7.29 (2H, m), 7.76 (1H, d, J=1 Hz), 7.86 (1H, d, J=4.5 Hz), 8.14 (1H, d, J=4.5 Hz), and 8.15 (1H, d, J=1 Hz).

EXAMPLE B71

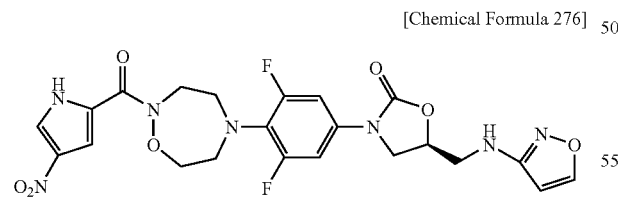

[Chemical Formula 276]

¹H NMR (CDCl₃—CD₃OD (5:1)) δ 3.46 (2H, br t, J=4.5 Hz), 3.51-3.60 (3H, m), 3.66 (1H, dd, J=4, 14.5 Hz), 3.83 (1H, dd, J=7, 9 Hz), 4.06 (2H, br t, J=5.5 Hz), 4.07 (1H, dd, J=9, 9 Hz), 4.27 (2H, br t, J=4.5 Hz), 4.89-4.99 (1H, m), 5.92 (1H, d, J=2 Hz), 7.09-7.20 (2H, m), 7.43 (1H, d, J=1.5 Hz), 7.80 (1H, d, J=1.5 Hz), and 8.07 (1H, d, J=2 Hz).

EXAMPLE C

The present invention provides a compound of the formula (I'):

[Chemical Formula 277]

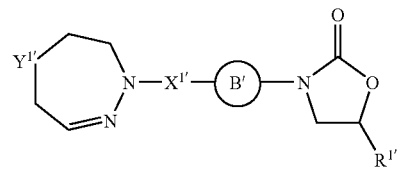

(I')

wherein
X¹' is a single bond;
Y¹' is as defined in Tables 1 to 4;
B' is as defined in Table 5; and
R¹' is as defined in Table 6.

EXAMPLE C1

[Chemical Formula 278]

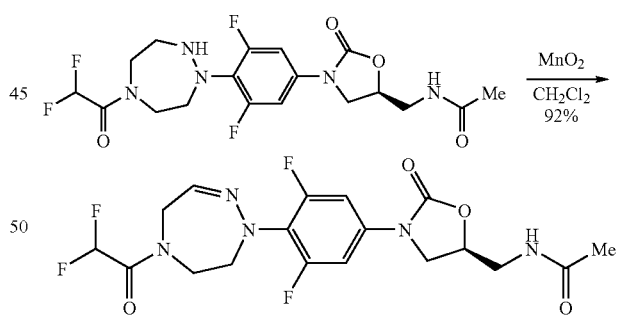

A 50 cm³ eggplant-shape flask was charged with the starting compound (64.8 mg, 0.145 mmol) to dissolve in CH₂Cl₂ (5 cm³). Active MnO₂ (328.6 mg) was added and stirred for 1 hour. After filtration through celite pad, the solvent was concentrated to obtain a residue, which was then purified by silica gel column chromatography (BW-200, 6 g, eluent; 3%→5% MeOH/CHCl₃) to afford C1 (59.6 mg, 0.134 mmol, 92%).

¹H NMR (CDCl₃) δ 2.02 (3H, s), 3.63-3.79 (5H, m), 3.86-3.92 (2H, m), 4.01 (1H, t, J=9.1 Hz), 4.35-4.41 (2H, m), 4.74-4.84 (1H, m), 6.16 (0.5H, t, J=53.6 Hz), 6.18 (0.5H, t, J=53.6 Hz), 6.33 (1H, br t, J=6 Hz), 6.93 (0.5H, t, J=4.1 Hz), 6.94 (0.5H, t, J=4.1 Hz), and 7.17 (2H, d, J=10.2 Hz).

EXAMPLE C2

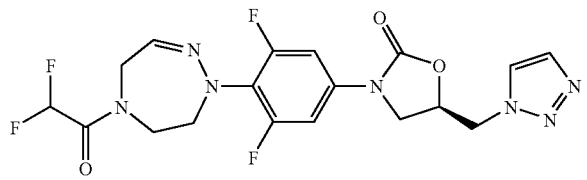

[Chemical Formula 279]

$^1$H NMR (CDCl$_3$) δ 3.63-3.73 (2H, m), 3.85-3.95 (3H, m), 4.13 (1H, t, J=9.1 Hz), 4.34-4.41 (2H, m), 4.79 (2H, AB), 5.04-5.13 (1H, m), 6.15 (0.5H, t, J=53.8 Hz), 6.18 (0.5H, t, J=53.8 Hz), 6.93 (1H, t, J=4.0 Hz), 7.07 (2H, d, J=10.1 Hz), 7.74 (1H, br s), and 7.78 (1H, br s).

EXAMPLE C3

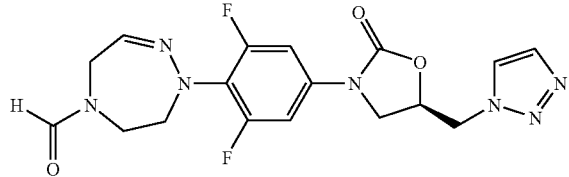

[Chemical Formula 280]

$^1$H NMR (CDCl$_3$) δ 3.62-3.71 (4H, m), 3.77-3.82 (1H, m), 3.89-3.96 (1H, m), 4.13 (1H, t, J=9.1 Hz), 4.17 (1H, d, J=4.1 Hz), 4.31 (1H, d, J=4.1 Hz), 4.79 (2H, AB), 5.04-5.14 (1H, m), 6.83 (0.5H, t, J=4.1 Hz), 6.87 (0.5H, t, J=4.1 Hz), 7.07 (1H, d, J=10.4 Hz), 7.08 (1H, d, J=10.4 Hz), 7.75 (1H, br s), 7.77 (1H, br s), 8.12 (0.5H, s), and 8.13 (0.5H, s).

EXAMPLE C4

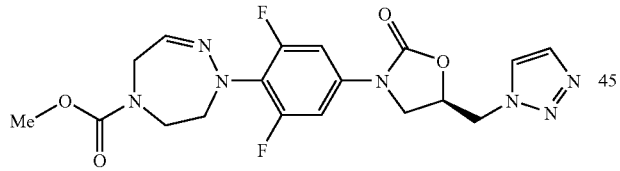

[Chemical Formula 281]

$^1$H NMR (CDCl$_3$) δ 3.57-3.64 (2H, m), 3.68-3.78 (2H, m), 3.74 (3H, s), 3.88 (1H, dd, J=6.3, 9.3 Hz), 4.13 (1H, t, J=9.3 Hz), 4.20 (1H, br s), 4.27 (1H, br s), 4.79 (2H, AB), 5.03-5.13 (1H, m), 6.89 (1H, t, J=4.0 Hz), 7.06 (2H, d, J=10.0 Hz), 7.74 (1H, br s), and 7.77 (1H, br s).

EXAMPLE C5

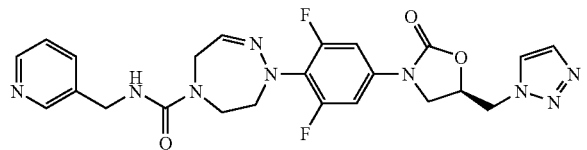

[Chemical Formula 282]

$^1$H NMR (CDCl$_3$) δ 3.63-3.75 (4H, m), 3.92 (1H, dd, J=6.0, 9.3 Hz), 4.12 (1H, t, J=9.3 Hz), 4.30 (2H, d, J=4.1 Hz), 4.47 (2H, d, J=5.5 Hz), 4.79 (2H, AB), 5.02 (1H, br t, J=6 Hz), 5.03-5.13 (1H, m), 6.83 (1H, t, J=4.1 Hz), 7.06 (2H, d, J=10.2 Hz), 7.24-7.30 (1H, m), 7.66-7.78 (3H, m), and 8.50-8.56 (2H, m).

EXAMPLE C6

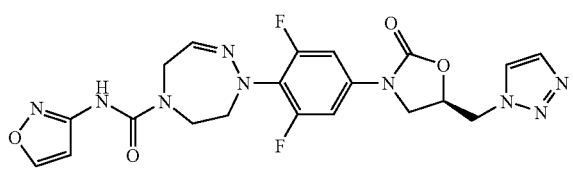

[Chemical Formula 283]

$^1$H NMR (CDCl$_3$) δ 3.73-3.79 (2H, m), 3.82-3.89 (2H, m), 3.90 (1H, dd, J=6.0, 9.1 Hz), 4.12 (1H, t, J=9.1 Hz), 4.39 (2H, d, J=3.9 Hz), 4.79 (2H, AB), 5.01-5.11 (1H, m), 6.90 (1H, t, J=3.9 Hz), 7.00 (1H, d, J=1.9 Hz), 7.06 (2H, d, J=10.5 Hz), 7.74 (1H, br s), 7.77 (1H, br s), 8.22 (1H, d, J=1.9 Hz), and 8.50 (1H, s).

Examples of the compounds of the above formula (I') are listed in Tables 7 to 27, in which "No." means the EXAMPLE No.

TABLE 1

| No. | Y$^{1'}$ | R$^{a'}$— |
|---|---|---|
| a-1 | NR$^{a'}$ | H$_3$C— |
| a-2 | NR$^{a'}$ | HO-CH$_2$-C(=O)— |
| a-3 | NR$^{a'}$ | HO-CH$_2$-CH$_2$-C(=O)— |
| a-4 | NR$^{a'}$ | H-C(=O)— |
| a-5 | NR$^{a'}$ | HO-CH$_2$-CH(OH)-C(=O)— |
| a-6 | NR$^{a'}$ | HO-CH$_2$-CH(OH)-CH(OH)-C(=O)— |

TABLE 1-continued

| No. | Y¹' | Rᵃ'— |
|---|---|---|
| a-7 | NRᵃ' | N≡C— |
| a-8 | NRᵃ' | HOCH₂-C(=S)— |
| a-9 | NRᵃ' | HOCH₂CH₂-C(=S)— |
| a-10 | NRᵃ' | H-C(=S)— |
| a-11 | NRᵃ' | HOCH₂-CH(OH)-C(=S)— |
| a-12 | NRᵃ' | HOCH₂-CH(OH)-C(=S)— |
| a-13 | NRᵃ' | phenyl— |
| a-14 | NRᵃ' | 4-O₂N-C₆H₄— |
| a-15 | NRᵃ' | pyridin-2-yl— |
| a-16 | NRᵃ' | 5-O₂N-pyridin-2-yl— |
| a-17 | NRᵃ' | pyridin-3-yl-CH₂— |

TABLE 1-continued

| No. | Y¹' | Rᵃ'— |
|---|---|---|
| a-18 | NRᵃ' | pyridin-4-yl-CH₂— |
| a-19 | NRᵃ' | quinolin-2-yl-CH₂— |
| a-20 | NRᵃ' | quinolin-4-yl-CH₂— |

TABLE 2

| No. | Y¹' | Rᵃ'— |
|---|---|---|
| a-21 | NRᵃ' | pyridin-3-yl-C(=O)— |
| a-22 | NRᵃ' | pyridin-4-yl-C(=O)— |
| a-23 | NRᵃ' | quinolin-2-yl-C(=O)— |
| a-24 | NRᵃ' | quinolin-4-yl-C(=O)— |

TABLE 2-continued
| No. | Y¹' | Rᵃ'— |
|---|---|---|
| a-25 | NRᵃ' | 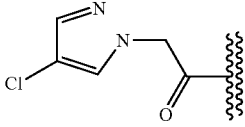 [SMILES: *C(=O)CN/C=C(/Cl)C=N] |
| a-26 | NRᵃ' | 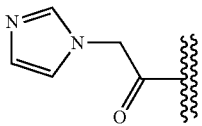 |
| a-27 | NRᵃ' | 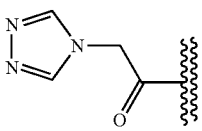 |
| a-28 | NRᵃ' | 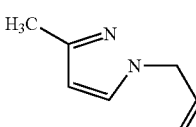 |
| a-29 | NRᵃ' | 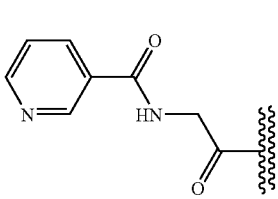 [SMILES: *C(=O)CNC(=O)c1cccnc1] |
| a-30 | NRᵃ' | 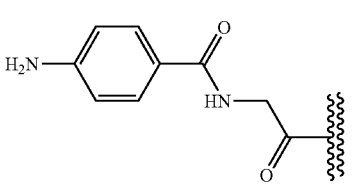 [SMILES: *C(=O)CNC(=O)c1ccc(N)cc1] |
| a-31 | NRᵃ' | 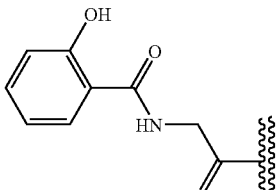 |
| a-32 | NRᵃ' | 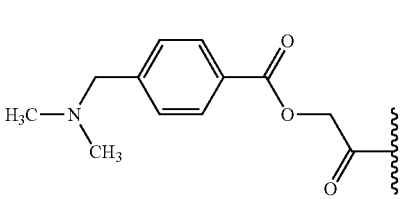 [SMILES: *C(=O)COC(=O)c1ccc(CN(C)C)cc1] |
| a-33 | NRᵃ' | 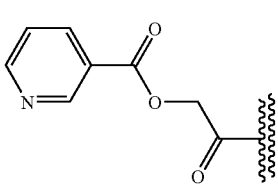 [SMILES: *C(=O)COC(=O)c1cccnc1] |
| a-34 | NRᵃ' | 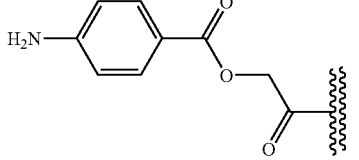 |
| a-35 | NRᵃ' | 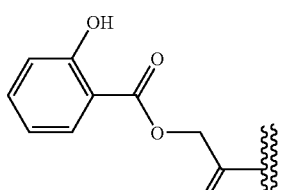 |
| a-36 | NRᵃ' | 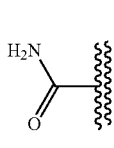 |
| a-37 | NRᵃ' | 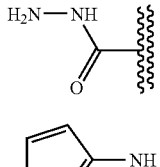 |
| a-38 | NRᵃ' | 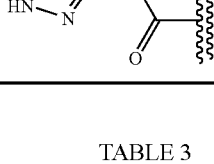 |
TABLE 3
| No. | Y¹' | Rᵃ'— |
|---|---|---|
| a-39 | NRᵃ' | 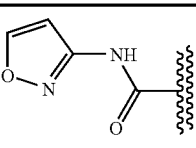 |
| a-40 | NRᵃ' | 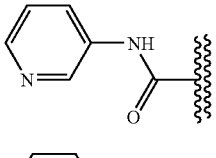 |
| a-41 | NRᵃ' | 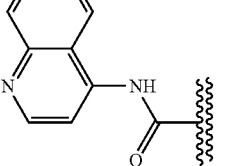 |
| a-42 | NRᵃ' | 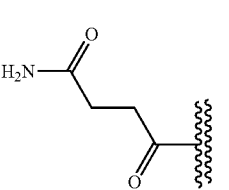 |

TABLE 3-continued
| No. | Y¹' | Rᵃ'— |
|---|---|---|
| a-43 | NRᵃ' | 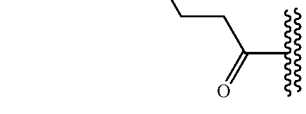 |
| a-44 | NRᵃ' | 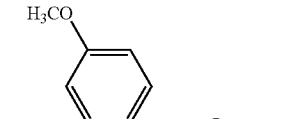 |
| a-45 | NRᵃ' | 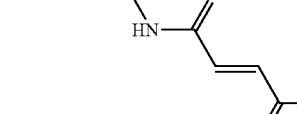 |
| a-46 | NRᵃ' | 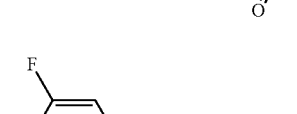 |
| a-47 | NRᵃ' | 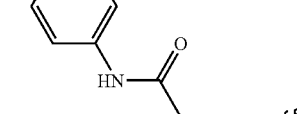 |
| a-48 | NRᵃ' |  |
| a-49 | NRᵃ' | 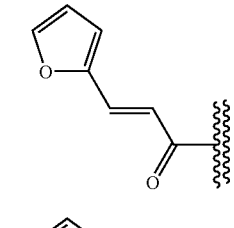 |
| a-50 | NRᵃ' | 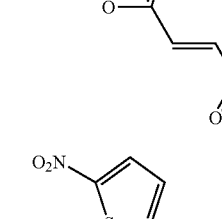 |
| a-51 | NRᵃ' | (structure with O₂N-furan) |
| a-52 | NRᵃ' | (structure with O₂N-thiophene) |
TABLE 4
| No. | Y¹' | Rᵃ'— |
|---|---|---|
| a-53 | NRᵃ' | 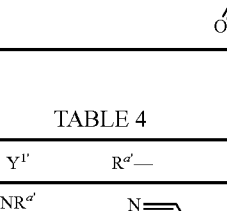 |
| a-54 | NRᵃ' | 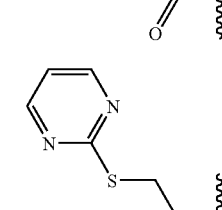 |
| a-55 | NRᵃ' |  |

TABLE 4-continued
| No. | Y¹' | Rᵃ'— |
|---|---|---|
| a-56 | NRᵃ' | 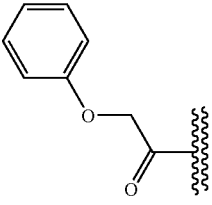 [SMILES: *C(=O)COc1ccccc1] |
| a-57 | NRᵃ' | 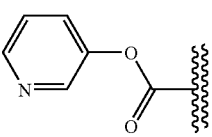 [SMILES: *C(=O)Oc1cccnc1] |
| a-58 | O | — |
| a-59 | S | — |
| a-60 | SO | — |
| a-61 | SO$_2$ | — |
TABLE 5
| No. | Ring B' |
|---|---|
| b-1 |  |
| b-2 | 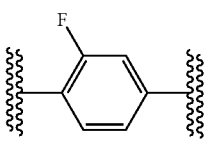 [SMILES: *c1ccc(*)c(F)c1] |
| b-3 | 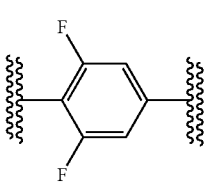 [SMILES: *c1cc(F)c(*)c(F)c1] |
TABLE 6
| No. | R¹' |
|---|---|
| c-1 | 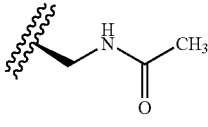 |
| c-2 | 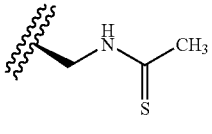 |
| c-3 | 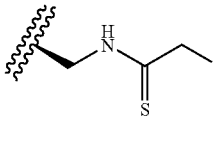 |
TABLE 6-continued
| No. | R¹' |
|---|---|
| c-4 | 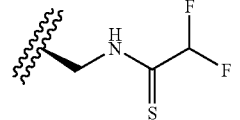 |
| c-5 | 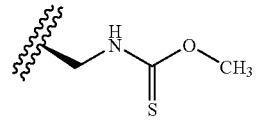 |
| c-6 | 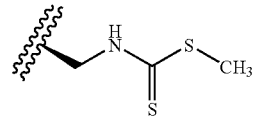 |
| c-7 | 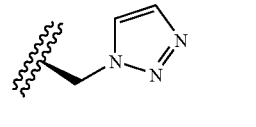 |
| c-8 | 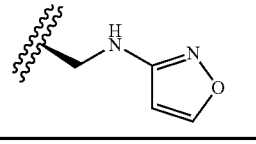 |
TABLE 7
| No. | A' | B' | R¹' |
|---|---|---|---|
| 1-1 | a-1 | b-1 | c-1 |
| 1-2 | a-1 | b-1 | c-2 |
| 1-3 | a-1 | b-1 | c-3 |
| 1-4 | a-1 | b-1 | c-4 |
| 1-5 | a-1 | b-1 | c-5 |
| 1-6 | a-1 | b-1 | c-6 |
| 1-7 | a-1 | b-1 | c-7 |
| 1-8 | a-1 | b-1 | c-8 |
| 1-9 | a-1 | b-2 | c-1 |
| 1-10 | a-1 | b-2 | c-2 |
| 1-11 | a-1 | b-2 | c-3 |
| 1-12 | a-1 | b-2 | c-4 |
| 1-13 | a-1 | b-2 | c-5 |
| 1-14 | a-1 | b-2 | c-6 |
| 1-15 | a-1 | b-2 | c-7 |
| 1-16 | a-1 | b-2 | c-8 |
| 1-17 | a-1 | b-3 | c-1 |
| 1-18 | a-1 | b-3 | c-2 |
| 1-19 | a-1 | b-3 | c-3 |
| 1-20 | a-1 | b-3 | c-4 |
| 1-21 | a-1 | b-3 | c-5 |
| 1-22 | a-1 | b-3 | c-6 |
| 1-23 | a-1 | b-3 | c-7 |
| 1-24 | a-1 | b-3 | c-8 |
| 2-1 | a-2 | b-1 | c-1 |
| 2-2 | a-2 | b-1 | c-2 |
| 2-3 | a-2 | b-1 | c-3 |
| 2-4 | a-2 | b-1 | c-4 |
| 2-5 | a-2 | b-1 | c-5 |
| 2-6 | a-2 | b-1 | c-6 |
| 2-7 | a-2 | b-1 | c-7 |
| 2-8 | a-2 | b-1 | c-8 |
| 2-9 | a-2 | b-2 | c-1 |
| 2-10 | a-2 | b-2 | c-2 |
| 2-11 | a-2 | b-2 | c-3 |
| 2-12 | a-2 | b-2 | c-4 |
| 2-13 | a-2 | b-2 | c-5 |

TABLE 7-continued

| No. | A' | B' | R¹' |
|---|---|---|---|
| 2-14 | a-2 | b-2 | c-6 |
| 2-15 | a-2 | b-2 | c-7 |
| 2-16 | a-2 | b-2 | c-8 |
| 2-17 | a-2 | b-3 | c-1 |
| 2-18 | a-2 | b-3 | c-2 |
| 2-19 | a-2 | b-3 | c-3 |
| 2-20 | a-2 | b-3 | c-4 |
| 2-21 | a-2 | b-3 | c-5 |
| 2-22 | a-2 | b-3 | c-6 |
| 2-23 | a-2 | b-3 | c-7 |
| 2-24 | a-2 | b-3 | c-8 |
| 3-1 | a-3 | b-1 | c-1 |
| 3-2 | a-3 | b-1 | c-2 |
| 3-3 | a-3 | b-1 | c-3 |
| 3-4 | a-3 | b-1 | c-4 |
| 3-5 | a-3 | b-1 | c-5 |
| 3-6 | a-3 | b-1 | c-6 |
| 3-7 | a-3 | b-1 | c-7 |
| 3-8 | a-3 | b-1 | c-8 |
| 3-9 | a-3 | b-2 | c-1 |
| 3-10 | a-3 | b-2 | c-2 |
| 3-11 | a-3 | b-2 | c-3 |
| 3-12 | a-3 | b-2 | c-4 |
| 3-13 | a-3 | b-2 | c-5 |
| 3-14 | a-3 | b-2 | c-6 |
| 3-15 | a-3 | b-2 | c-7 |
| 3-16 | a-3 | b-2 | c-8 |
| 3-17 | a-3 | b-3 | c-1 |
| 3-18 | a-3 | b-3 | c-2 |
| 3-19 | a-3 | b-3 | c-3 |
| 3-20 | a-3 | b-3 | c-4 |
| 3-21 | a-3 | b-3 | c-5 |
| 3-22 | a-3 | b-3 | c-6 |
| 3-23 | a-3 | b-3 | c-7 |
| 3-24 | a-3 | b-3 | c-8 |

TABLE 8

| No. | A' | B' | R¹' |
|---|---|---|---|
| 4-1 | a-4 | b-1 | c-1 |
| 4-2 | a-4 | b-1 | c-2 |
| 4-3 | a-4 | b-1 | c-3 |
| 4-4 | a-4 | b-1 | c-4 |
| 4-5 | a-4 | b-1 | c-5 |
| 4-6 | a-4 | b-1 | c-6 |
| 4-7 | a-4 | b-1 | c-7 |
| 4-8 | a-4 | b-1 | c-8 |
| 4-9 | a-4 | b-2 | c-1 |
| 4-10 | a-4 | b-2 | c-2 |
| 4-11 | a-4 | b-2 | c-3 |
| 4-12 | a-4 | b-2 | c-4 |
| 4-13 | a-4 | b-2 | c-5 |
| 4-14 | a-4 | b-2 | c-6 |
| 4-15 | a-4 | b-2 | c-7 |
| 4-16 | a-4 | b-2 | c-8 |
| 4-17 | a-4 | b-3 | c-1 |
| 4-18 | a-4 | b-3 | c-2 |
| 4-19 | a-4 | b-3 | c-3 |
| 4-20 | a-4 | b-3 | c-4 |
| 4-21 | a-4 | b-3 | c-5 |
| 4-22 | a-4 | b-3 | c-6 |
| 4-23 | a-4 | b-3 | c-7 |
| 4-24 | a-4 | b-3 | c-8 |
| 5-1 | a-5 | b-1 | c-1 |
| 5-2 | a-5 | b-1 | c-2 |
| 5-3 | a-5 | b-1 | c-3 |
| 5-4 | a-5 | b-1 | c-4 |
| 5-5 | a-5 | b-1 | c-5 |
| 5-6 | a-5 | b-1 | c-6 |
| 5-7 | a-5 | b-1 | c-7 |
| 5-8 | a-5 | b-1 | c-8 |
| 5-9 | a-5 | b-2 | c-1 |
| 5-10 | a-5 | b-2 | c-2 |
| 5-11 | a-5 | b-2 | c-3 |

TABLE 8-continued

| No. | A' | B' | R¹' |
|---|---|---|---|
| 5-12 | a-5 | b-2 | c-4 |
| 5-13 | a-5 | b-2 | c-5 |
| 5-14 | a-5 | b-2 | c-6 |
| 5-15 | a-5 | b-2 | c-7 |
| 5-16 | a-5 | b-2 | c-8 |
| 5-17 | a-5 | b-3 | c-1 |
| 5-18 | a-5 | b-3 | c-2 |
| 5-19 | a-5 | b-3 | c-3 |
| 5-20 | a-5 | b-3 | c-4 |
| 5-21 | a-5 | b-3 | c-5 |
| 5-22 | a-5 | b-3 | c-6 |
| 5-23 | a-5 | b-3 | c-7 |
| 5-24 | a-5 | b-3 | c-8 |
| 6-1 | a-6 | b-1 | c-1 |
| 6-2 | a-6 | b-1 | c-2 |
| 6-3 | a-6 | b-1 | c-3 |
| 6-4 | a-6 | b-1 | c-4 |
| 6-5 | a-6 | b-1 | c-5 |
| 6-6 | a-6 | b-1 | c-6 |
| 6-7 | a-6 | b-1 | c-7 |
| 6-8 | a-6 | b-1 | c-8 |
| 6-9 | a-6 | b-2 | c-1 |
| 6-10 | a-6 | b-2 | c-2 |
| 6-11 | a-6 | b-2 | c-3 |
| 6-12 | a-6 | b-2 | c-4 |
| 6-13 | a-6 | b-2 | c-5 |
| 6-14 | a-6 | b-2 | c-6 |
| 6-15 | a-6 | b-2 | c-7 |
| 6-16 | a-6 | b-2 | c-8 |
| 6-17 | a-6 | b-3 | c-1 |
| 6-18 | a-6 | b-3 | c-2 |
| 6-19 | a-6 | b-3 | c-3 |
| 6-20 | a-6 | b-3 | c-4 |
| 6-21 | a-6 | b-3 | c-5 |
| 6-22 | a-6 | b-3 | c-6 |
| 6-23 | a-6 | b-3 | c-7 |
| 6-24 | a-6 | b-3 | c-8 |

TABLE 9

| No. | A' | B' | R¹' |
|---|---|---|---|
| 7-1 | a-7 | b-1 | c-1 |
| 7-2 | a-7 | b-1 | c-2 |
| 7-3 | a-7 | b-1 | c-3 |
| 7-4 | a-7 | b-1 | c-4 |
| 7-5 | a-7 | b-1 | c-5 |
| 7-6 | a-7 | b-1 | c-6 |
| 7-7 | a-7 | b-1 | c-7 |
| 7-8 | a-7 | b-1 | c-8 |
| 7-9 | a-7 | b-2 | c-1 |
| 7-10 | a-7 | b-2 | c-2 |
| 7-11 | a-7 | b-2 | c-3 |
| 7-12 | a-7 | b-2 | c-4 |
| 7-13 | a-7 | b-2 | c-5 |
| 7-14 | a-7 | b-2 | c-6 |
| 7-15 | a-7 | b-2 | c-7 |
| 7-16 | a-7 | b-2 | c-8 |
| 7-17 | a-7 | b-3 | c-1 |
| 7-18 | a-7 | b-3 | c-2 |
| 7-19 | a-7 | b-3 | c-3 |
| 7-20 | a-7 | b-3 | c-4 |
| 7-21 | a-7 | b-3 | c-5 |
| 7-22 | a-7 | b-3 | c-6 |
| 7-23 | a-7 | b-3 | c-7 |
| 7-24 | a-7 | b-3 | c-8 |
| 8-1 | a-8 | b-1 | c-1 |
| 8-2 | a-8 | b-1 | c-2 |
| 8-3 | a-8 | b-1 | c-3 |
| 8-4 | a-8 | b-1 | c-4 |
| 8-5 | a-8 | b-1 | c-5 |
| 8-6 | a-8 | b-1 | c-6 |
| 8-7 | a-8 | b-1 | c-7 |
| 8-8 | a-8 | b-1 | c-8 |
| 8-9 | a-8 | b-2 | c-1 |

TABLE 9-continued

| No. | A' | B' | R¹' |
|---|---|---|---|
| 8-10 | a-8 | b-2 | c-2 |
| 8-11 | a-8 | b-2 | c-3 |
| 8-12 | a-8 | b-2 | c-4 |
| 8-13 | a-8 | b-2 | c-5 |
| 8-14 | a-8 | b-2 | c-6 |
| 8-15 | a-8 | b-2 | c-7 |
| 8-16 | a-8 | b-2 | c-8 |
| 8-17 | a-8 | b-3 | c-1 |
| 8-18 | a-8 | b-3 | c-2 |
| 8-19 | a-8 | b-3 | c-3 |
| 8-20 | a-8 | b-3 | c-4 |
| 8-21 | a-8 | b-3 | c-5 |
| 8-22 | a-8 | b-3 | c-6 |
| 8-23 | a-8 | b-3 | c-7 |
| 8-24 | a-8 | b-3 | c-8 |
| 9-1 | a-9 | b-1 | c-1 |
| 9-2 | a-9 | b-1 | c-2 |
| 9-3 | a-9 | b-1 | c-3 |
| 9-4 | a-9 | b-1 | c-4 |
| 9-5 | a-9 | b-1 | c-5 |
| 9-6 | a-9 | b-1 | c-6 |
| 9-7 | a-9 | b-1 | c-7 |
| 9-8 | a-9 | b-1 | c-8 |
| 9-9 | a-9 | b-2 | c-1 |
| 9-10 | a-9 | b-2 | c-2 |
| 9-11 | a-9 | b-2 | c-3 |
| 9-12 | a-9 | b-2 | c-4 |
| 9-13 | a-9 | b-2 | c-5 |
| 9-14 | a-9 | b-2 | c-6 |
| 9-15 | a-9 | b-2 | c-7 |
| 9-16 | a-9 | b-2 | c-8 |
| 9-17 | a-9 | b-3 | c-1 |
| 9-18 | a-9 | b-3 | c-2 |
| 9-19 | a-9 | b-3 | c-3 |
| 9-20 | a-9 | b-3 | c-4 |
| 9-21 | a-9 | b-3 | c-5 |
| 9-22 | a-9 | b-3 | c-6 |
| 9-23 | a-9 | b-3 | c-7 |
| 9-24 | a-9 | b-3 | c-8 |

TABLE 10

| No. | A' | B' | R¹' |
|---|---|---|---|
| 10-1 | a-10 | b-1 | c-1 |
| 10-2 | a-10 | b-1 | c-2 |
| 10-3 | a-10 | b-1 | c-3 |
| 10-4 | a-10 | b-1 | c-4 |
| 10-5 | a-10 | b-1 | c-5 |
| 10-6 | a-10 | b-1 | c-6 |
| 10-7 | a-10 | b-1 | c-7 |
| 10-8 | a-10 | b-1 | c-8 |
| 10-9 | a-10 | b-2 | c-1 |
| 10-10 | a-10 | b-2 | c-2 |
| 10-11 | a-10 | b-2 | c-3 |
| 10-12 | a-10 | b-2 | c-4 |
| 10-13 | a-10 | b-2 | c-5 |
| 10-14 | a-10 | b-2 | c-6 |
| 10-15 | a-10 | b-2 | c-7 |
| 10-16 | a-10 | b-2 | c-8 |
| 10-17 | a-10 | b-3 | c-1 |
| 10-18 | a-10 | b-3 | c-2 |
| 10-19 | a-10 | b-3 | c-3 |
| 10-20 | a-10 | b-3 | c-4 |
| 10-21 | a-10 | b-3 | c-5 |
| 10-22 | a-10 | b-3 | c-6 |
| 10-23 | a-10 | b-3 | c-7 |
| 10-24 | a-10 | b-3 | c-8 |
| 11-1 | a-11 | b-1 | c-1 |
| 11-2 | a-11 | b-1 | c-2 |
| 11-3 | a-11 | b-1 | c-3 |
| 11-4 | a-11 | b-1 | c-4 |
| 11-5 | a-11 | b-1 | c-5 |
| 11-6 | a-11 | b-1 | c-6 |
| 11-7 | a-11 | b-1 | c-7 |

TABLE 10-continued

| No. | A' | B' | R¹' |
|---|---|---|---|
| 11-8 | a-11 | b-1 | c-8 |
| 11-9 | a-11 | b-2 | c-1 |
| 11-10 | a-11 | b-2 | c-2 |
| 11-11 | a-11 | b-2 | c-3 |
| 11-12 | a-11 | b-2 | c-4 |
| 11-13 | a-11 | b-2 | c-5 |
| 11-14 | a-11 | b-2 | c-6 |
| 11-15 | a-11 | b-2 | c-7 |
| 11-16 | a-11 | b-2 | c-8 |
| 11-17 | a-11 | b-3 | c-1 |
| 11-18 | a-11 | b-3 | c-2 |
| 11-19 | a-11 | b-3 | c-3 |
| 11-20 | a-11 | b-3 | c-4 |
| 11-21 | a-11 | b-3 | c-5 |
| 11-22 | a-11 | b-3 | c-6 |
| 11-23 | a-11 | b-3 | c-7 |
| 11-24 | a-11 | b-3 | c-8 |
| 12-1 | a-12 | b-1 | c-1 |
| 12-2 | a-12 | b-1 | c-2 |
| 12-3 | a-12 | b-1 | c-3 |
| 12-4 | a-12 | b-1 | c-4 |
| 12-5 | a-12 | b-1 | c-5 |
| 12-6 | a-12 | b-1 | c-6 |
| 12-7 | a-12 | b-1 | c-7 |
| 12-8 | a-12 | b-1 | c-8 |
| 12-9 | a-12 | b-2 | c-1 |
| 12-10 | a-12 | b-2 | c-2 |
| 12-11 | a-12 | b-2 | c-3 |
| 12-12 | a-12 | b-2 | c-4 |
| 12-13 | a-12 | b-2 | c-5 |
| 12-14 | a-12 | b-2 | c-6 |
| 12-15 | a-12 | b-2 | c-7 |
| 12-16 | a-12 | b-2 | c-8 |
| 12-17 | a-12 | b-3 | c-1 |
| 12-18 | a-12 | b-3 | c-2 |
| 12-19 | a-12 | b-3 | c-3 |
| 12-20 | a-12 | b-3 | c-4 |
| 12-21 | a-12 | b-3 | c-5 |
| 12-22 | a-12 | b-3 | c-6 |
| 12-23 | a-12 | b-3 | c-7 |
| 12-24 | a-12 | b-3 | c-8 |

TABLE 11

| No. | A' | B' | R¹' |
|---|---|---|---|
| 13-1 | a-13 | b-1 | c-1 |
| 13-2 | a-13 | b-1 | c-2 |
| 13-3 | a-13 | b-1 | c-3 |
| 13-4 | a-13 | b-1 | c-4 |
| 13-5 | a-13 | b-1 | c-5 |
| 13-6 | a-13 | b-1 | c-6 |
| 13-7 | a-13 | b-1 | c-7 |
| 13-8 | a-13 | b-1 | c-8 |
| 13-9 | a-13 | b-2 | c-1 |
| 13-10 | a-13 | b-2 | c-2 |
| 13-11 | a-13 | b-2 | c-3 |
| 13-12 | a-13 | b-2 | c-4 |
| 13-13 | a-13 | b-2 | c-5 |
| 13-14 | a-13 | b-2 | c-6 |
| 13-15 | a-13 | b-2 | c-7 |
| 13-16 | a-13 | b-2 | c-8 |
| 13-17 | a-13 | b-3 | c-1 |
| 13-18 | a-13 | b-3 | c-2 |
| 13-19 | a-13 | b-3 | c-3 |
| 13-20 | a-13 | b-3 | c-4 |
| 13-21 | a-13 | b-3 | c-5 |
| 13-22 | a-13 | b-3 | c-6 |
| 13-23 | a-13 | b-3 | c-7 |
| 13-24 | a-13 | b-3 | c-8 |
| 14-1 | a-14 | b-1 | c-1 |
| 14-2 | a-14 | b-1 | c-2 |
| 14-3 | a-14 | b-1 | c-3 |
| 14-4 | a-14 | b-1 | c-4 |
| 14-5 | a-14 | b-1 | c-5 |

TABLE 11-continued

| No. | A' | B' | R¹' |
|---|---|---|---|
| 14-6 | a-14 | b-1 | c-6 |
| 14-7 | a-14 | b-1 | c-7 |
| 14-8 | a-14 | b-1 | c-8 |
| 14-9 | a-14 | b-2 | c-1 |
| 14-10 | a-14 | b-2 | c-2 |
| 14-11 | a-14 | b-2 | c-3 |
| 14-12 | a-14 | b-2 | c-4 |
| 14-13 | a-14 | b-2 | c-5 |
| 14-14 | a-14 | b-2 | c-6 |
| 14-15 | a-14 | b-2 | c-7 |
| 14-16 | a-14 | b-2 | c-8 |
| 14-17 | a-14 | b-3 | c-1 |
| 14-18 | a-14 | b-3 | c-2 |
| 14-19 | a-14 | b-3 | c-3 |
| 14-20 | a-14 | b-3 | c-4 |
| 14-21 | a-14 | b-3 | c-5 |
| 14-22 | a-14 | b-3 | c-6 |
| 14-23 | a-14 | b-3 | c-7 |
| 14-24 | a-14 | b-3 | c-8 |
| 15-1 | a-15 | b-1 | c-1 |
| 15-2 | a-15 | b-1 | c-2 |
| 15-3 | a-15 | b-1 | c-3 |
| 15-4 | a-15 | b-1 | c-4 |
| 15-5 | a-15 | b-1 | c-5 |
| 15-6 | a-15 | b-1 | c-6 |
| 15-7 | a-15 | b-1 | c-7 |
| 15-8 | a-15 | b-1 | c-8 |
| 15-9 | a-15 | b-2 | c-1 |
| 15-10 | a-15 | b-2 | c-2 |
| 15-11 | a-15 | b-2 | c-3 |
| 15-12 | a-15 | b-2 | c-4 |
| 15-13 | a-15 | b-2 | c-5 |
| 15-14 | a-15 | b-2 | c-6 |
| 15-15 | a-15 | b-2 | c-7 |
| 15-16 | a-15 | b-2 | c-8 |
| 15-17 | a-15 | b-3 | c-1 |
| 15-18 | a-15 | b-3 | c-2 |
| 15-19 | a-15 | b-3 | c-3 |
| 15-20 | a-15 | b-3 | c-4 |
| 15-21 | a-15 | b-3 | c-5 |
| 15-22 | a-15 | b-3 | c-6 |
| 15-23 | a-15 | b-3 | c-7 |
| 15-24 | a-15 | b-3 | c-8 |

TABLE 12

| No. | A' | B' | R¹' |
|---|---|---|---|
| 16-1 | a-16 | b-1 | c-1 |
| 16-2 | a-16 | b-1 | c-2 |
| 16-3 | a-16 | b-1 | c-3 |
| 16-4 | a-16 | b-1 | c-4 |
| 16-5 | a-16 | b-1 | c-5 |
| 16-6 | a-16 | b-1 | c-6 |
| 16-7 | a-16 | b-1 | c-7 |
| 16-8 | a-16 | b-1 | c-8 |
| 16-9 | a-16 | b-2 | c-1 |
| 16-10 | a-16 | b-2 | c-2 |
| 16-11 | a-16 | b-2 | c-3 |
| 16-12 | a-16 | b-2 | c-4 |
| 16-13 | a-16 | b-2 | c-5 |
| 16-14 | a-16 | b-2 | c-6 |
| 16-15 | a-16 | b-2 | c-7 |
| 16-16 | a-16 | b-2 | c-8 |
| 16-17 | a-16 | b-3 | c-1 |
| 16-18 | a-16 | b-3 | c-2 |
| 16-19 | a-16 | b-3 | c-3 |
| 16-20 | a-16 | b-3 | c-4 |
| 16-21 | a-16 | b-3 | c-5 |
| 16-22 | a-16 | b-3 | c-6 |
| 16-23 | a-16 | b-3 | c-7 |
| 16-24 | a-16 | b-3 | c-8 |
| 17-1 | a-17 | b-1 | c-1 |
| 17-2 | a-17 | b-1 | c-2 |
| 17-3 | a-17 | b-1 | c-3 |

TABLE 12-continued

| No. | A' | B' | R¹' |
|---|---|---|---|
| 17-4 | a-17 | b-1 | c-4 |
| 17-5 | a-17 | b-1 | c-5 |
| 17-6 | a-17 | b-1 | c-6 |
| 17-7 | a-17 | b-1 | c-7 |
| 17-8 | a-17 | b-1 | c-8 |
| 17-9 | a-17 | b-2 | c-1 |
| 17-10 | a-17 | b-2 | c-2 |
| 17-11 | a-17 | b-2 | c-3 |
| 17-12 | a-17 | b-2 | c-4 |
| 17-13 | a-17 | b-2 | c-5 |
| 17-14 | a-17 | b-2 | c-6 |
| 17-15 | a-17 | b-2 | c-7 |
| 17-16 | a-17 | b-2 | c-8 |
| 17-17 | a-17 | b-3 | c-1 |
| 17-18 | a-17 | b-3 | c-2 |
| 17-19 | a-17 | b-3 | c-3 |
| 17-20 | a-17 | b-3 | c-4 |
| 17-21 | a-17 | b-3 | c-5 |
| 17-22 | a-17 | b-3 | c-6 |
| 17-23 | a-17 | b-3 | c-7 |
| 17-24 | a-17 | b-3 | c-8 |
| 18-1 | a-18 | b-1 | c-1 |
| 18-2 | a-18 | b-1 | c-2 |
| 18-3 | a-18 | b-1 | c-3 |
| 18-4 | a-18 | b-1 | c-4 |
| 18-5 | a-18 | b-1 | c-5 |
| 18-6 | a-18 | b-1 | c-6 |
| 18-7 | a-18 | b-1 | c-7 |
| 18-8 | a-18 | b-1 | c-8 |
| 18-9 | a-18 | b-2 | c-1 |
| 18-10 | a-18 | b-2 | c-2 |
| 18-11 | a-18 | b-2 | c-3 |
| 18-12 | a-18 | b-2 | c-4 |
| 18-13 | a-18 | b-2 | c-5 |
| 18-14 | a-18 | b-2 | c-6 |
| 18-15 | a-18 | b-2 | c-7 |
| 18-16 | a-18 | b-2 | c-8 |
| 18-17 | a-18 | b-3 | c-1 |
| 18-18 | a-18 | b-3 | c-2 |
| 18-19 | a-18 | b-3 | c-3 |
| 18-20 | a-18 | b-3 | c-4 |
| 18-21 | a-18 | b-3 | c-5 |
| 18-22 | a-18 | b-3 | c-6 |
| 18-23 | a-18 | b-3 | c-7 |
| 18-24 | a-18 | b-3 | c-8 |

TABLE 13

| No. | A' | B' | R¹' |
|---|---|---|---|
| 19-1 | a-19 | b-1 | c-1 |
| 19-2 | a-19 | b-1 | c-2 |
| 19-3 | a-19 | b-1 | c-3 |
| 19-4 | a-19 | b-1 | c-4 |
| 19-5 | a-19 | b-1 | c-5 |
| 19-6 | a-19 | b-1 | c-6 |
| 19-7 | a-19 | b-1 | c-7 |
| 19-8 | a-19 | b-1 | c-8 |
| 19-9 | a-19 | b-2 | c-1 |
| 19-10 | a-19 | b-2 | c-2 |
| 19-11 | a-19 | b-2 | c-3 |
| 19-12 | a-19 | b-2 | c-4 |
| 19-13 | a-19 | b-2 | c-5 |
| 19-14 | a-19 | b-2 | c-6 |
| 19-15 | a-19 | b-2 | c-7 |
| 19-16 | a-19 | b-2 | c-8 |
| 19-17 | a-19 | b-3 | c-1 |
| 19-18 | a-19 | b-3 | c-2 |
| 19-19 | a-19 | b-3 | c-3 |
| 19-20 | a-19 | b-3 | c-4 |
| 19-21 | a-19 | b-3 | c-5 |
| 19-22 | a-19 | b-3 | c-6 |
| 19-23 | a-19 | b-3 | c-7 |
| 19-24 | a-19 | b-3 | c-8 |
| 20-1 | a-20 | b-1 | c-1 |

TABLE 13-continued

| No. | A' | B' | R¹' |
|---|---|---|---|
| 20-2 | a-20 | b-1 | c-2 |
| 20-3 | a-20 | b-1 | c-3 |
| 20-4 | a-20 | b-1 | c-4 |
| 20-5 | a-20 | b-1 | c-5 |
| 20-6 | a-20 | b-1 | c-6 |
| 20-7 | a-20 | b-1 | c-7 |
| 20-8 | a-20 | b-1 | c-8 |
| 20-9 | a-20 | b-2 | c-1 |
| 20-10 | a-20 | b-2 | c-2 |
| 20-11 | a-20 | b-2 | c-3 |
| 20-12 | a-20 | b-2 | c-4 |
| 20-13 | a-20 | b-2 | c-5 |
| 20-14 | a-20 | b-2 | c-6 |
| 20-15 | a-20 | b-2 | c-7 |
| 20-16 | a-20 | b-2 | c-8 |
| 20-17 | a-20 | b-3 | c-1 |
| 20-18 | a-20 | b-3 | c-2 |
| 20-19 | a-20 | b-3 | c-3 |
| 20-20 | a-20 | b-3 | c-4 |
| 20-21 | a-20 | b-3 | c-5 |
| 20-22 | a-20 | b-3 | c-6 |
| 20-23 | a-20 | b-3 | c-7 |
| 20-24 | a-20 | b-3 | c-8 |
| 21-1 | a-21 | b-1 | c-1 |
| 21-2 | a-21 | b-1 | c-2 |
| 21-3 | a-21 | b-1 | c-3 |
| 21-4 | a-21 | b-1 | c-4 |
| 21-5 | a-21 | b-1 | c-5 |
| 21-6 | a-21 | b-1 | c-6 |
| 21-7 | a-21 | b-1 | c-7 |
| 21-8 | a-21 | b-1 | c-8 |
| 21-9 | a-21 | b-2 | c-1 |
| 21-10 | a-21 | b-2 | c-2 |
| 21-11 | a-21 | b-2 | c-3 |
| 21-12 | a-21 | b-2 | c-4 |
| 21-13 | a-21 | b-2 | c-5 |
| 21-14 | a-21 | b-2 | c-6 |
| 21-15 | a-21 | b-2 | c-7 |
| 21-16 | a-21 | b-2 | c-8 |
| 21-17 | a-21 | b-3 | c-1 |
| 21-18 | a-21 | b-3 | c-2 |
| 21-19 | a-21 | b-3 | c-3 |
| 21-20 | a-21 | b-3 | c-4 |
| 21-21 | a-21 | b-3 | c-5 |
| 21-22 | a-21 | b-3 | c-6 |
| 21-23 | a-21 | b-3 | c-7 |
| 21-24 | a-21 | b-3 | c-8 |

TABLE 14

| No. | A' | B' | R¹' |
|---|---|---|---|
| 22-1 | a-22 | b-1 | c-1 |
| 22-2 | a-22 | b-1 | c-2 |
| 22-3 | a-22 | b-1 | c-3 |
| 22-4 | a-22 | b-1 | c-4 |
| 22-5 | a-22 | b-1 | c-5 |
| 22-6 | a-22 | b-1 | c-6 |
| 22-7 | a-22 | b-1 | c-7 |
| 22-8 | a-22 | b-1 | c-8 |
| 22-9 | a-22 | b-2 | c-1 |
| 22-10 | a-22 | b-2 | c-2 |
| 22-11 | a-22 | b-2 | c-3 |
| 22-12 | a-22 | b-2 | c-4 |
| 22-13 | a-22 | b-2 | c-5 |
| 22-14 | a-22 | b-2 | c-6 |
| 22-15 | a-22 | b-2 | c-7 |
| 22-16 | a-22 | b-2 | c-8 |
| 22-17 | a-22 | b-3 | c-1 |
| 22-18 | a-22 | b-3 | c-2 |
| 22-19 | a-22 | b-3 | c-3 |
| 22-20 | a-22 | b-3 | c-4 |
| 22-21 | a-22 | b-3 | c-5 |
| 22-22 | a-22 | b-3 | c-6 |
| 22-23 | a-22 | b-3 | c-7 |

TABLE 14-continued

| No. | A' | B' | R¹' |
|---|---|---|---|
| 22-24 | a-22 | b-3 | c-8 |
| 23-1 | a-23 | b-1 | c-1 |
| 23-2 | a-23 | b-1 | c-2 |
| 23-3 | a-23 | b-1 | c-3 |
| 23-4 | a-23 | b-1 | c-4 |
| 23-5 | a-23 | b-1 | c-5 |
| 23-6 | a-23 | b-1 | c-6 |
| 23-7 | a-23 | b-1 | c-7 |
| 23-8 | a-23 | b-1 | c-8 |
| 23-9 | a-23 | b-2 | c-1 |
| 23-10 | a-23 | b-2 | c-2 |
| 23-11 | a-23 | b-2 | c-3 |
| 23-12 | a-23 | b-2 | c-4 |
| 23-13 | a-23 | b-2 | c-5 |
| 23-14 | a-23 | b-2 | c-6 |
| 23-15 | a-23 | b-2 | c-7 |
| 23-16 | a-23 | b-2 | c-8 |
| 23-17 | a-23 | b-3 | c-1 |
| 23-18 | a-23 | b-3 | c-2 |
| 23-19 | a-23 | b-3 | c-3 |
| 23-20 | a-23 | b-3 | c-4 |
| 23-21 | a-23 | b-3 | c-5 |
| 23-22 | a-23 | b-3 | c-6 |
| 23-23 | a-23 | b-3 | c-7 |
| 23-24 | a-23 | b-3 | c-8 |
| 24-1 | a-24 | b-1 | c-1 |
| 24-2 | a-24 | b-1 | c-2 |
| 24-3 | a-24 | b-1 | c-3 |
| 24-4 | a-24 | b-1 | c-4 |
| 24-5 | a-24 | b-1 | c-5 |
| 24-6 | a-24 | b-1 | c-6 |
| 24-7 | a-24 | b-1 | c-7 |
| 24-8 | a-24 | b-1 | c-8 |
| 24-9 | a-24 | b-2 | c-1 |
| 24-10 | a-24 | b-2 | c-2 |
| 24-11 | a-24 | b-2 | c-3 |
| 24-12 | a-24 | b-2 | c-4 |
| 24-13 | a-24 | b-2 | c-5 |
| 24-14 | a-24 | b-2 | c-6 |
| 24-15 | a-24 | b-2 | c-7 |
| 24-16 | a-24 | b-2 | c-8 |
| 24-17 | a-24 | b-3 | c-1 |
| 24-18 | a-24 | b-3 | c-2 |
| 24-19 | a-24 | b-3 | c-3 |
| 24-20 | a-24 | b-3 | c-4 |
| 24-21 | a-24 | b-3 | c-5 |
| 24-22 | a-24 | b-3 | c-6 |
| 24-23 | a-24 | b-3 | c-7 |
| 24-24 | a-24 | b-3 | c-8 |

TABLE 15

| No. | A' | B' | R¹' |
|---|---|---|---|
| 25-1 | a-25 | b-1 | c-1 |
| 25-2 | a-25 | b-1 | c-2 |
| 25-3 | a-25 | b-1 | c-3 |
| 25-4 | a-25 | b-1 | c-4 |
| 25-5 | a-25 | b-1 | c-5 |
| 25-6 | a-25 | b-1 | c-6 |
| 25-7 | a-25 | b-1 | c-7 |
| 25-8 | a-25 | b-1 | c-8 |
| 25-9 | a-25 | b-2 | c-1 |
| 25-10 | a-25 | b-2 | c-2 |
| 25-11 | a-25 | b-2 | c-3 |
| 25-12 | a-25 | b-2 | c-4 |
| 25-13 | a-25 | b-2 | c-5 |
| 25-14 | a-25 | b-2 | c-6 |
| 25-15 | a-25 | b-2 | c-7 |
| 25-16 | a-25 | b-2 | c-8 |
| 25-17 | a-25 | b-3 | c-1 |
| 25-18 | a-25 | b-3 | c-2 |
| 25-19 | a-25 | b-3 | c-3 |
| 25-20 | a-25 | b-3 | c-4 |
| 25-21 | a-25 | b-3 | c-5 |

TABLE 15-continued

| No. | A' | B' | R¹' |
|---|---|---|---|
| 25-22 | a-25 | b-3 | c-6 |
| 25-23 | a-25 | b-3 | c-7 |
| 25-24 | a-25 | b-3 | c-8 |
| 26-1 | a-26 | b-1 | c-1 |
| 26-2 | a-26 | b-1 | c-2 |
| 26-3 | a-26 | b-1 | c-3 |
| 26-4 | a-26 | b-1 | c-4 |
| 26-5 | a-26 | b-1 | c-5 |
| 26-6 | a-26 | b-1 | c-6 |
| 26-7 | a-26 | b-1 | c-7 |
| 26-8 | a-26 | b-1 | c-8 |
| 26-9 | a-26 | b-2 | c-1 |
| 26-10 | a-26 | b-2 | c-2 |
| 26-11 | a-26 | b-2 | c-3 |
| 26-12 | a-26 | b-2 | c-4 |
| 26-13 | a-26 | b-2 | c-5 |
| 26-14 | a-26 | b-2 | c-6 |
| 26-15 | a-26 | b-2 | c-7 |
| 26-16 | a-26 | b-2 | c-8 |
| 26-17 | a-26 | b-3 | c-1 |
| 26-18 | a-26 | b-3 | c-2 |
| 26-19 | a-26 | b-3 | c-3 |
| 26-20 | a-26 | b-3 | c-4 |
| 26-21 | a-26 | b-3 | c-5 |
| 26-22 | a-26 | b-3 | c-6 |
| 26-23 | a-26 | b-3 | c-7 |
| 26-24 | a-26 | b-3 | c-8 |
| 27-1 | a-27 | b-1 | c-1 |
| 27-2 | a-27 | b-1 | c-2 |
| 27-3 | a-27 | b-1 | c-3 |
| 27-4 | a-27 | b-1 | c-4 |
| 27-5 | a-27 | b-1 | c-5 |
| 27-6 | a-27 | b-1 | c-6 |
| 27-7 | a-27 | b-1 | c-7 |
| 27-8 | a-27 | b-1 | c-8 |
| 27-9 | a-27 | b-2 | c-1 |
| 27-10 | a-27 | b-2 | c-2 |
| 27-11 | a-27 | b-2 | c-3 |
| 27-12 | a-27 | b-2 | c-4 |
| 27-13 | a-27 | b-2 | c-5 |
| 27-14 | a-27 | b-2 | c-6 |
| 27-15 | a-27 | b-2 | c-7 |
| 27-16 | a-27 | b-2 | c-8 |
| 27-17 | a-27 | b-3 | c-1 |
| 27-18 | a-27 | b-3 | c-2 |
| 27-19 | a-27 | b-3 | c-3 |
| 27-20 | a-27 | b-3 | c-4 |
| 27-21 | a-27 | b-3 | c-5 |
| 27-22 | a-27 | b-3 | c-6 |
| 27-23 | a-27 | b-3 | c-7 |
| 27-24 | a-27 | b-3 | c-8 |

TABLE 16

| No. | A' | B' | R¹' |
|---|---|---|---|
| 28-1 | a-28 | b-1 | c-1 |
| 28-2 | a-28 | b-1 | c-2 |
| 28-3 | a-28 | b-1 | c-3 |
| 28-4 | a-28 | b-1 | c-4 |
| 28-5 | a-28 | b-1 | c-5 |
| 28-6 | a-28 | b-1 | c-6 |
| 28-7 | a-28 | b-1 | c-7 |
| 28-8 | a-28 | b-1 | c-8 |
| 28-9 | a-28 | b-2 | c-1 |
| 28-10 | a-28 | b-2 | c-2 |
| 28-11 | a-28 | b-2 | c-3 |
| 28-12 | a-28 | b-2 | c-4 |
| 28-13 | a-28 | b-2 | c-5 |
| 28-14 | a-28 | b-2 | c-6 |
| 28-15 | a-28 | b-2 | c-7 |
| 28-16 | a-28 | b-2 | c-8 |
| 28-17 | a-28 | b-3 | c-1 |
| 28-18 | a-28 | b-3 | c-2 |
| 28-19 | a-28 | b-3 | c-3 |

TABLE 16-continued

| No. | A' | B' | R¹' |
|---|---|---|---|
| 28-20 | a-28 | b-3 | c-4 |
| 28-21 | a-28 | b-3 | c-5 |
| 28-22 | a-28 | b-3 | c-6 |
| 28-23 | a-28 | b-3 | c-7 |
| 28-24 | a-28 | b-3 | c-8 |
| 29-1 | a-29 | b-1 | c-1 |
| 29-2 | a-29 | b-1 | c-2 |
| 29-3 | a-29 | b-1 | c-3 |
| 29-4 | a-29 | b-1 | c-4 |
| 29-5 | a-29 | b-1 | c-5 |
| 29-6 | a-29 | b-1 | c-6 |
| 29-7 | a-29 | b-1 | c-7 |
| 29-8 | a-29 | b-1 | c-8 |
| 29-9 | a-29 | b-2 | c-1 |
| 29-10 | a-29 | b-2 | c-2 |
| 29-11 | a-29 | b-2 | c-3 |
| 29-12 | a-29 | b-2 | c-4 |
| 29-13 | a-29 | b-2 | c-5 |
| 29-14 | a-29 | b-2 | c-6 |
| 29-15 | a-29 | b-2 | c-7 |
| 29-16 | a-29 | b-2 | c-8 |
| 29-17 | a-29 | b-3 | c-1 |
| 29-18 | a-29 | b-3 | c-2 |
| 29-19 | a-29 | b-3 | c-3 |
| 29-20 | a-29 | b-3 | c-4 |
| 29-21 | a-29 | b-3 | c-5 |
| 29-22 | a-29 | b-3 | c-6 |
| 29-23 | a-29 | b-3 | c-7 |
| 29-24 | a-29 | b-3 | c-8 |
| 30-1 | a-30 | b-1 | c-1 |
| 30-2 | a-30 | b-1 | c-2 |
| 30-3 | a-30 | b-1 | c-3 |
| 30-4 | a-30 | b-1 | c-4 |
| 30-5 | a-30 | b-1 | c-5 |
| 30-6 | a-30 | b-1 | c-6 |
| 30-7 | a-30 | b-1 | c-7 |
| 30-8 | a-30 | b-1 | c-8 |
| 30-9 | a-30 | b-2 | c-1 |
| 30-10 | a-30 | b-2 | c-2 |
| 30-11 | a-30 | b-2 | c-3 |
| 30-12 | a-30 | b-2 | c-4 |
| 30-13 | a-30 | b-2 | c-5 |
| 30-14 | a-30 | b-2 | c-6 |
| 30-15 | a-30 | b-2 | c-7 |
| 30-16 | a-30 | b-2 | c-8 |
| 30-17 | a-30 | b-3 | c-1 |
| 30-18 | a-30 | b-3 | c-2 |
| 30-19 | a-30 | b-3 | c-3 |
| 30-20 | a-30 | b-3 | c-4 |
| 30-21 | a-30 | b-3 | c-5 |
| 30-22 | a-30 | b-3 | c-6 |
| 30-23 | a-30 | b-3 | c-7 |
| 30-24 | a-30 | b-3 | c-8 |

TABLE 17

| No. | A' | B' | R¹' |
|---|---|---|---|
| 31-1 | a-31 | b-1 | c-1 |
| 31-2 | a-31 | b-1 | c-2 |
| 31-3 | a-31 | b-1 | c-3 |
| 31-4 | a-31 | b-1 | c-4 |
| 31-5 | a-31 | b-1 | c-5 |
| 31-6 | a-31 | b-1 | c-6 |
| 31-7 | a-31 | b-1 | c-7 |
| 31-8 | a-31 | b-1 | c-8 |
| 31-9 | a-31 | b-2 | c-1 |
| 31-10 | a-31 | b-2 | c-2 |
| 31-11 | a-31 | b-2 | c-3 |
| 31-12 | a-31 | b-2 | c-4 |
| 31-13 | a-31 | b-2 | c-5 |
| 31-14 | a-31 | b-2 | c-6 |
| 31-15 | a-31 | b-2 | c-7 |
| 31-16 | a-31 | b-2 | c-8 |
| 31-17 | a-31 | b-3 | c-1 |

TABLE 17-continued

| No. | A' | B' | R¹' |
|---|---|---|---|
| 31-18 | a-31 | b-3 | c-2 |
| 31-19 | a-31 | b-3 | c-3 |
| 31-20 | a-31 | b-3 | c-4 |
| 31-21 | a-31 | b-3 | c-5 |
| 31-22 | a-31 | b-3 | c-6 |
| 31-23 | a-31 | b-3 | c-7 |
| 31-24 | a-31 | b-3 | c-8 |
| 32-1 | a-32 | b-1 | c-1 |
| 32-2 | a-32 | b-1 | c-2 |
| 32-3 | a-32 | b-1 | c-3 |
| 32-4 | a-32 | b-1 | c-4 |
| 32-5 | a-32 | b-1 | c-5 |
| 32-6 | a-32 | b-1 | c-6 |
| 32-7 | a-32 | b-1 | c-7 |
| 32-8 | a-32 | b-1 | c-8 |
| 32-9 | a-32 | b-2 | c-1 |
| 32-10 | a-32 | b-2 | c-2 |
| 32-11 | a-32 | b-2 | c-3 |
| 32-12 | a-32 | b-2 | c-4 |
| 32-13 | a-32 | b-2 | c-5 |
| 32-14 | a-32 | b-2 | c-6 |
| 32-15 | a-32 | b-2 | c-7 |
| 32-16 | a-32 | b-2 | c-8 |
| 32-17 | a-32 | b-3 | c-1 |
| 32-18 | a-32 | b-3 | c-2 |
| 32-19 | a-32 | b-3 | c-3 |
| 32-20 | a-32 | b-3 | c-4 |
| 32-21 | a-32 | b-3 | c-5 |
| 32-22 | a-32 | b-3 | c-6 |
| 32-23 | a-32 | b-3 | c-7 |
| 32-24 | a-32 | b-3 | c-8 |
| 33-1 | a-33 | b-1 | c-1 |
| 33-2 | a-33 | b-1 | c-2 |
| 33-3 | a-33 | b-1 | c-3 |
| 33-4 | a-33 | b-1 | c-4 |
| 33-5 | a-33 | b-1 | c-5 |
| 33-6 | a-33 | b-1 | c-6 |
| 33-7 | a-33 | b-1 | c-7 |
| 33-8 | a-33 | b-1 | c-8 |
| 33-9 | a-33 | b-2 | c-1 |
| 33-10 | a-33 | b-2 | c-2 |
| 33-11 | a-33 | b-2 | c-3 |
| 33-12 | a-33 | b-2 | c-4 |
| 33-13 | a-33 | b-2 | c-5 |
| 33-14 | a-33 | b-2 | c-6 |
| 33-15 | a-33 | b-2 | c-7 |
| 33-16 | a-33 | b-2 | c-8 |
| 33-17 | a-33 | b-3 | c-1 |
| 33-18 | a-33 | b-3 | c-2 |
| 33-19 | a-33 | b-3 | c-3 |
| 33-20 | a-33 | b-3 | c-4 |
| 33-21 | a-33 | b-3 | c-5 |
| 33-22 | a-33 | b-3 | c-6 |
| 33-23 | a-33 | b-3 | c-7 |
| 33-24 | a-33 | b-3 | c-8 |

TABLE 18

| No. | A' | B' | R¹' |
|---|---|---|---|
| 34-1 | a-34 | b-1 | c-1 |
| 34-2 | a-34 | b-1 | c-2 |
| 34-3 | a-34 | b-1 | c-3 |
| 34-4 | a-34 | b-1 | c-4 |
| 34-5 | a-34 | b-1 | c-5 |
| 34-6 | a-34 | b-1 | c-6 |
| 34-7 | a-34 | b-1 | c-7 |
| 34-8 | a-34 | b-1 | c-8 |
| 34-9 | a-34 | b-2 | c-1 |
| 34-10 | a-34 | b-2 | c-2 |
| 34-11 | a-34 | b-2 | c-3 |
| 34-12 | a-34 | b-2 | c-4 |
| 34-13 | a-34 | b-2 | c-5 |
| 34-14 | a-34 | b-2 | c-6 |
| 34-15 | a-34 | b-2 | c-7 |
| 34-16 | a-34 | b-2 | c-8 |
| 34-17 | a-34 | b-3 | c-1 |
| 34-18 | a-34 | b-3 | c-2 |
| 34-19 | a-34 | b-3 | c-3 |
| 34-20 | a-34 | b-3 | c-4 |
| 34-21 | a-34 | b-3 | c-5 |
| 34-22 | a-34 | b-3 | c-6 |
| 34-23 | a-34 | b-3 | c-7 |
| 34-24 | a-34 | b-3 | c-8 |
| 35-1 | a-35 | b-1 | c-1 |
| 35-2 | a-35 | b-1 | c-2 |
| 35-3 | a-35 | b-1 | c-3 |
| 35-4 | a-35 | b-1 | c-4 |
| 35-5 | a-35 | b-1 | c-5 |
| 35-6 | a-35 | b-1 | c-6 |
| 35-7 | a-35 | b-1 | c-7 |
| 35-8 | a-35 | b-1 | c-8 |
| 35-9 | a-35 | b-2 | c-1 |
| 35-10 | a-35 | b-2 | c-2 |
| 35-11 | a-35 | b-2 | c-3 |
| 35-12 | a-35 | b-2 | c-4 |
| 35-13 | a-35 | b-2 | c-5 |
| 35-14 | a-35 | b-2 | c-6 |
| 35-15 | a-35 | b-2 | c-7 |
| 35-16 | a-35 | b-2 | c-8 |
| 35-17 | a-35 | b-3 | c-1 |
| 35-18 | a-35 | b-3 | c-2 |
| 35-19 | a-35 | b-3 | c-3 |
| 35-20 | a-35 | b-3 | c-4 |
| 35-21 | a-35 | b-3 | c-5 |
| 35-22 | a-35 | b-3 | c-6 |
| 35-23 | a-35 | b-3 | c-7 |
| 35-24 | a-35 | b-3 | c-8 |
| 36-1 | a-36 | b-1 | c-1 |
| 36-2 | a-36 | b-1 | c-2 |
| 36-3 | a-36 | b-1 | c-3 |
| 36-4 | a-36 | b-1 | c-4 |
| 36-5 | a-36 | b-1 | c-5 |
| 36-6 | a-36 | b-1 | c-6 |
| 36-7 | a-36 | b-1 | c-7 |
| 36-8 | a-36 | b-1 | c-8 |
| 36-9 | a-36 | b-2 | c-1 |
| 36-10 | a-36 | b-2 | c-2 |
| 36-11 | a-36 | b-2 | c-3 |
| 36-12 | a-36 | b-2 | c-4 |
| 36-13 | a-36 | b-2 | c-5 |
| 36-14 | a-36 | b-2 | c-6 |
| 36-15 | a-36 | b-2 | c-7 |
| 36-16 | a-36 | b-2 | c-8 |
| 36-17 | a-36 | b-3 | c-1 |
| 36-18 | a-36 | b-3 | c-2 |
| 36-19 | a-36 | b-3 | c-3 |
| 36-20 | a-36 | b-3 | c-4 |
| 36-21 | a-36 | b-3 | c-5 |
| 36-22 | a-36 | b-3 | c-6 |
| 36-23 | a-36 | b-3 | c-7 |
| 36-24 | a-36 | b-3 | c-8 |

TABLE 19

| No. | A' | B' | R¹' |
|---|---|---|---|
| 37-1 | a-37 | b-1 | c-1 |
| 37-2 | a-37 | b-1 | c-2 |
| 37-3 | a-37 | b-1 | c-3 |
| 37-4 | a-37 | b-1 | c-4 |
| 37-5 | a-37 | b-1 | c-5 |
| 37-6 | a-37 | b-1 | c-6 |
| 37-7 | a-37 | b-1 | c-7 |
| 37-8 | a-37 | b-1 | c-8 |
| 37-9 | a-37 | b-2 | c-1 |
| 37-10 | a-37 | b-2 | c-2 |
| 37-11 | a-37 | b-2 | c-3 |
| 37-12 | a-37 | b-2 | c-4 |
| 37-13 | a-37 | b-2 | c-5 |

TABLE 19-continued

| No. | A' | B' | R1' |
|---|---|---|---|
| 37-14 | a-37 | b-2 | c-6 |
| 37-15 | a-37 | b-2 | c-7 |
| 37-16 | a-37 | b-2 | c-8 |
| 37-17 | a-37 | b-3 | c-1 |
| 37-18 | a-37 | b-3 | c-2 |
| 37-19 | a-37 | b-3 | c-3 |
| 37-20 | a-37 | b-3 | c-4 |
| 37-21 | a-37 | b-3 | c-5 |
| 37-22 | a-37 | b-3 | c-6 |
| 37-23 | a-37 | b-3 | c-7 |
| 37-24 | a-37 | b-3 | c-8 |
| 38-1 | a-38 | b-1 | c-1 |
| 38-2 | a-38 | b-1 | c-2 |
| 38-3 | a-38 | b-1 | c-3 |
| 38-4 | a-38 | b-1 | c-4 |
| 38-5 | a-38 | b-1 | c-5 |
| 38-6 | a-38 | b-1 | c-6 |
| 38-7 | a-38 | b-1 | c-7 |
| 38-8 | a-38 | b-1 | c-8 |
| 38-9 | a-38 | b-2 | c-1 |
| 38-10 | a-38 | b-2 | c-2 |
| 38-11 | a-38 | b-2 | c-3 |
| 38-12 | a-38 | b-2 | c-4 |
| 38-13 | a-38 | b-2 | c-5 |
| 38-14 | a-38 | b-2 | c-6 |
| 38-15 | a-38 | b-2 | c-7 |
| 38-16 | a-38 | b-2 | c-8 |
| 38-17 | a-38 | b-3 | c-1 |
| 38-18 | a-38 | b-3 | c-2 |
| 38-19 | a-38 | b-3 | c-3 |
| 38-20 | a-38 | b-3 | c-4 |
| 38-21 | a-38 | b-3 | c-5 |
| 38-22 | a-38 | b-3 | c-6 |
| 38-23 | a-38 | b-3 | c-7 |
| 38-24 | a-38 | b-3 | c-8 |
| 39-1 | a-39 | b-1 | c-1 |
| 39-2 | a-39 | b-1 | c-2 |
| 39-3 | a-39 | b-1 | c-3 |
| 39-4 | a-39 | b-1 | c-4 |
| 39-5 | a-39 | b-1 | c-5 |
| 39-6 | a-39 | b-1 | c-6 |
| 39-7 | a-39 | b-1 | c-7 |
| 39-8 | a-39 | b-1 | c-8 |
| 39-9 | a-39 | b-2 | c-1 |
| 39-10 | a-39 | b-2 | c-2 |
| 39-11 | a-39 | b-2 | c-3 |
| 39-12 | a-39 | b-2 | c-4 |
| 39-13 | a-39 | b-2 | c-5 |
| 39-14 | a-39 | b-2 | c-6 |
| 39-15 | a-39 | b-2 | c-7 |
| 39-16 | a-39 | b-2 | c-8 |
| 39-17 | a-39 | b-3 | c-1 |
| 39-18 | a-39 | b-3 | c-2 |
| 39-19 | a-39 | b-3 | c-3 |
| 39-20 | a-39 | b-3 | c-4 |
| 39-21 | a-39 | b-3 | c-5 |
| 39-22 | a-39 | b-3 | c-6 |
| 39-23 | a-39 | b-3 | c-7 |
| 39-24 | a-39 | b-3 | c-8 |
| 43-1 | a-43 | b-1 | c-1 |
| 43-2 | a-43 | b-1 | c-2 |
| 43-3 | a-43 | b-1 | c-3 |
| 43-4 | a-43 | b-1 | c-4 |
| 43-5 | a-43 | b-1 | c-5 |
| 43-6 | a-43 | b-1 | c-6 |
| 43-7 | a-43 | b-1 | c-7 |
| 43-8 | a-43 | b-1 | c-8 |
| 43-9 | a-43 | b-2 | c-1 |
| 43-10 | a-43 | b-2 | c-2 |
| 43-11 | a-43 | b-2 | c-3 |
| 43-12 | a-43 | b-2 | c-4 |
| 43-13 | a-43 | b-2 | c-5 |
| 43-14 | a-43 | b-2 | c-6 |
| 43-15 | a-43 | b-2 | c-7 |
| 43-16 | a-43 | b-2 | c-8 |
| 43-17 | a-43 | b-3 | c-1 |
| 43-18 | a-43 | b-3 | c-2 |
| 43-19 | a-43 | b-3 | c-3 |
| 43-20 | a-43 | b-3 | c-4 |
| 43-21 | a-43 | b-3 | c-5 |
| 43-22 | a-43 | b-3 | c-6 |
| 43-23 | a-43 | b-3 | c-7 |
| 43-24 | a-43 | b-3 | c-8 |
| 44-1 | a-44 | b-1 | c-1 |
| 44-2 | a-44 | b-1 | c-2 |
| 44-3 | a-44 | b-1 | c-3 |
| 44-4 | a-44 | b-1 | c-4 |
| 44-5 | a-44 | b-1 | c-5 |
| 44-6 | a-44 | b-1 | c-6 |
| 44-7 | a-44 | b-1 | c-7 |
| 44-8 | a-44 | b-1 | c-8 |
| 44-9 | a-44 | b-2 | c-1 |
| 44-10 | a-44 | b-2 | c-2 |
| 44-11 | a-44 | b-2 | c-3 |
| 44-12 | a-44 | b-2 | c-4 |
| 44-13 | a-44 | b-2 | c-5 |
| 44-14 | a-44 | b-2 | c-6 |
| 44-15 | a-44 | b-2 | c-7 |
| 44-16 | a-44 | b-2 | c-8 |
| 44-17 | a-44 | b-3 | c-1 |
| 44-18 | a-44 | b-3 | c-2 |
| 44-19 | a-44 | b-3 | c-3 |
| 44-20 | a-44 | b-3 | c-4 |
| 44-21 | a-44 | b-3 | c-5 |
| 44-22 | a-44 | b-3 | c-6 |
| 44-23 | a-44 | b-3 | c-7 |
| 44-24 | a-44 | b-3 | c-8 |
| 45-1 | a-45 | b-1 | c-1 |
| 45-2 | a-45 | b-1 | c-2 |
| 45-3 | a-45 | b-1 | c-3 |
| 45-4 | a-45 | b-1 | c-4 |
| 45-5 | a-45 | b-1 | c-5 |
| 45-6 | a-45 | b-1 | c-6 |
| 45-7 | a-45 | b-1 | c-7 |
| 45-8 | a-45 | b-1 | c-8 |
| 45-9 | a-45 | b-2 | c-1 |
| 45-10 | a-45 | b-2 | c-2 |
| 45-11 | a-45 | b-2 | c-3 |
| 45-12 | a-45 | b-2 | c-4 |
| 45-13 | a-45 | b-2 | c-5 |
| 45-14 | a-45 | b-2 | c-6 |
| 45-15 | a-45 | b-2 | c-7 |
| 45-16 | a-45 | b-2 | c-8 |
| 45-17 | a-45 | b-3 | c-1 |
| 45-18 | a-45 | b-3 | c-2 |
| 45-19 | a-45 | b-3 | c-3 |
| 45-20 | a-45 | b-3 | c-4 |
| 45-21 | a-45 | b-3 | c-5 |
| 45-22 | a-45 | b-3 | c-6 |
| 45-23 | a-45 | b-3 | c-7 |
| 45-24 | a-45 | b-3 | c-8 |

TABLE 22

| No. | A' | B' | R1' |
|---|---|---|---|
| 46-1 | a-46 | b-1 | c-1 |
| 46-2 | a-46 | b-1 | c-2 |
| 46-3 | a-46 | b-1 | c-3 |
| 46-4 | a-46 | b-1 | c-4 |
| 46-5 | a-46 | b-1 | c-5 |
| 46-6 | a-46 | b-1 | c-6 |
| 46-7 | a-46 | b-1 | c-7 |
| 46-8 | a-46 | b-1 | c-8 |
| 46-9 | a-46 | b-2 | c-1 |
| 46-10 | a-46 | b-2 | c-2 |
| 46-11 | a-46 | b-2 | c-3 |
| 46-12 | a-46 | b-2 | c-4 |
| 46-13 | a-46 | b-2 | c-5 |
| 46-14 | a-46 | b-2 | c-6 |
| 46-15 | a-46 | b-2 | c-7 |
| 46-16 | a-46 | b-2 | c-8 |
| 46-17 | a-46 | b-3 | c-1 |

TABLE 22-continued

| No. | A' | B' | R¹' |
|---|---|---|---|
| 46-18 | a-46 | b-3 | c-2 |
| 46-19 | a-46 | b-3 | c-3 |
| 46-20 | a-46 | b-3 | c-4 |
| 46-21 | a-46 | b-3 | c-5 |
| 46-22 | a-46 | b-3 | c-6 |
| 46-23 | a-46 | b-3 | c-7 |
| 46-24 | a-46 | b-3 | c-8 |
| 47-1 | a-47 | b-1 | c-1 |
| 47-2 | a-47 | b-1 | c-2 |
| 47-3 | a-47 | b-1 | c-3 |
| 47-4 | a-47 | b-1 | c-4 |
| 47-5 | a-47 | b-1 | c-5 |
| 47-6 | a-47 | b-1 | c-6 |
| 47-7 | a-47 | b-1 | c-7 |
| 47-8 | a-47 | b-1 | c-8 |
| 47-9 | a-47 | b-2 | c-1 |
| 47-10 | a-47 | b-2 | c-2 |
| 47-11 | a-47 | b-2 | c-3 |
| 47-12 | a-47 | b-2 | c-4 |
| 47-13 | a-47 | b-2 | c-5 |
| 47-14 | a-47 | b-2 | c-6 |
| 47-15 | a-47 | b-2 | c-7 |
| 47-16 | a-47 | b-2 | c-8 |
| 47-17 | a-47 | b-3 | c-1 |
| 47-18 | a-47 | b-3 | c-2 |
| 47-19 | a-47 | b-3 | c-3 |
| 47-20 | a-47 | b-3 | c-4 |
| 47-21 | a-47 | b-3 | c-5 |
| 47-22 | a-47 | b-3 | c-6 |
| 47-23 | a-47 | b-3 | c-7 |
| 47-24 | a-47 | b-3 | c-8 |
| 48-1 | a-48 | b-1 | c-1 |
| 48-2 | a-48 | b-1 | c-2 |
| 48-3 | a-48 | b-1 | c-3 |
| 48-4 | a-48 | b-1 | c-4 |
| 48-5 | a-48 | b-1 | c-5 |
| 48-6 | a-48 | b-1 | c-6 |
| 48-7 | a-48 | b-1 | c-7 |
| 48-8 | a-48 | b-1 | c-8 |
| 48-9 | a-48 | b-2 | c-1 |
| 48-10 | a-48 | b-2 | c-2 |
| 48-11 | a-48 | b-2 | c-3 |
| 48-12 | a-48 | b-2 | c-4 |
| 48-13 | a-48 | b-2 | c-5 |
| 48-14 | a-48 | b-2 | c-6 |
| 48-15 | a-48 | b-2 | c-7 |
| 48-16 | a-48 | b-2 | c-8 |
| 48-17 | a-48 | b-3 | c-1 |
| 48-18 | a-48 | b-3 | c-2 |
| 48-19 | a-48 | b-3 | c-3 |
| 48-20 | a-48 | b-3 | c-4 |
| 48-21 | a-48 | b-3 | c-5 |
| 48-22 | a-48 | b-3 | c-6 |
| 48-23 | a-48 | b-3 | c-7 |
| 48-24 | a-48 | b-3 | c-8 |

TABLE 23

| No. | A' | B' | R¹' |
|---|---|---|---|
| 49-1 | a-49 | b-1 | c-1 |
| 49-2 | a-49 | b-1 | c-2 |
| 49-3 | a-49 | b-1 | c-3 |
| 49-4 | a-49 | b-1 | c-4 |
| 49-5 | a-49 | b-1 | c-5 |
| 49-6 | a-49 | b-1 | c-6 |
| 49-7 | a-49 | b-1 | c-7 |
| 49-8 | a-49 | b-1 | c-8 |
| 49-9 | a-49 | b-2 | c-1 |
| 49-10 | a-49 | b-2 | c-2 |
| 49-11 | a-49 | b-2 | c-3 |
| 49-12 | a-49 | b-2 | c-4 |
| 49-13 | a-49 | b-2 | c-5 |
| 49-14 | a-49 | b-2 | c-6 |
| 49-15 | a-49 | b-2 | c-7 |

TABLE 23-continued

| No. | A' | B' | R¹' |
|---|---|---|---|
| 49-16 | a-49 | b-2 | c-8 |
| 49-17 | a-49 | b-3 | c-1 |
| 49-18 | a-49 | b-3 | c-2 |
| 49-19 | a-49 | b-3 | c-3 |
| 49-20 | a-49 | b-3 | c-4 |
| 49-21 | a-49 | b-3 | c-5 |
| 49-22 | a-49 | b-3 | c-6 |
| 49-23 | a-49 | b-3 | c-7 |
| 49-24 | a-49 | b-3 | c-8 |
| 50-1 | a-50 | b-1 | c-1 |
| 50-2 | a-50 | b-1 | c-2 |
| 50-3 | a-50 | b-1 | c-3 |
| 50-4 | a-50 | b-1 | c-4 |
| 50-5 | a-50 | b-1 | c-5 |
| 50-6 | a-50 | b-1 | c-6 |
| 50-7 | a-50 | b-1 | c-7 |
| 50-8 | a-50 | b-1 | c-8 |
| 50-9 | a-50 | b-2 | c-1 |
| 50-10 | a-50 | b-2 | c-2 |
| 50-11 | a-50 | b-2 | c-3 |
| 50-12 | a-50 | b-2 | c-4 |
| 50-13 | a-50 | b-2 | c-5 |
| 50-14 | a-50 | b-2 | c-6 |
| 50-15 | a-50 | b-2 | c-7 |
| 50-16 | a-50 | b-2 | c-8 |
| 50-17 | a-50 | b-3 | c-1 |
| 50-18 | a-50 | b-3 | c-2 |
| 50-19 | a-50 | b-3 | c-3 |
| 50-20 | a-50 | b-3 | c-4 |
| 50-21 | a-50 | b-3 | c-5 |
| 50-22 | a-50 | b-3 | c-6 |
| 50-23 | a-50 | b-3 | c-7 |
| 50-24 | a-50 | b-3 | c-8 |
| 51-1 | a-51 | b-1 | c-1 |
| 51-2 | a-51 | b-1 | c-2 |
| 51-3 | a-51 | b-1 | c-3 |
| 51-4 | a-51 | b-1 | c-4 |
| 51-5 | a-51 | b-1 | c-5 |
| 51-6 | a-51 | b-1 | c-6 |
| 51-7 | a-51 | b-1 | c-7 |
| 51-8 | a-51 | b-1 | c-8 |
| 51-9 | a-51 | b-2 | c-1 |
| 51-10 | a-51 | b-2 | c-2 |
| 51-11 | a-51 | b-2 | c-3 |
| 51-12 | a-51 | b-2 | c-4 |
| 51-13 | a-51 | b-2 | c-5 |
| 51-14 | a-51 | b-2 | c-6 |
| 51-15 | a-51 | b-2 | c-7 |
| 51-16 | a-51 | b-2 | c-8 |
| 51-17 | a-51 | b-3 | c-1 |
| 51-18 | a-51 | b-3 | c-2 |
| 51-19 | a-51 | b-3 | c-3 |
| 51-20 | a-51 | b-3 | c-4 |
| 51-21 | a-51 | b-3 | c-5 |
| 51-22 | a-51 | b-3 | c-6 |
| 51-23 | a-51 | b-3 | c-7 |
| 51-24 | a-51 | b-3 | c-8 |

TABLE 24

| No. | A' | B' | R¹' |
|---|---|---|---|
| 52-1 | a-52 | b-1 | c-1 |
| 52-2 | a-52 | b-1 | c-2 |
| 52-3 | a-52 | b-1 | c-3 |
| 52-4 | a-52 | b-1 | c-4 |
| 52-5 | a-52 | b-1 | c-5 |
| 52-6 | a-52 | b-1 | c-6 |
| 52-7 | a-52 | b-1 | c-7 |
| 52-8 | a-52 | b-1 | c-8 |
| 52-9 | a-52 | b-2 | c-1 |
| 52-10 | a-52 | b-2 | c-2 |
| 52-11 | a-52 | b-2 | c-3 |
| 52-12 | a-52 | b-2 | c-4 |
| 52-13 | a-52 | b-2 | c-5 |

TABLE 24-continued

| No. | A' | B' | R¹' |
|---|---|---|---|
| 52-14 | a-52 | b-2 | c-6 |
| 52-15 | a-52 | b-2 | c-7 |
| 52-16 | a-52 | b-2 | c-8 |
| 52-17 | a-52 | b-3 | c-1 |
| 52-18 | a-52 | b-3 | c-2 |
| 52-19 | a-52 | b-3 | c-3 |
| 52-20 | a-52 | b-3 | c-4 |
| 52-21 | a-52 | b-3 | c-5 |
| 52-22 | a-52 | b-3 | c-6 |
| 52-23 | a-52 | b-3 | c-7 |
| 52-24 | a-52 | b-3 | c-8 |
| 53-1 | a-53 | b-1 | c-1 |
| 53-2 | a-53 | b-1 | c-2 |
| 53-3 | a-53 | b-1 | c-3 |
| 53-4 | a-53 | b-1 | c-4 |
| 53-5 | a-53 | b-1 | c-5 |
| 53-6 | a-53 | b-1 | c-6 |
| 53-7 | a-53 | b-1 | c-7 |
| 53-8 | a-53 | b-1 | c-8 |
| 53-9 | a-53 | b-2 | c-1 |
| 53-10 | a-53 | b-2 | c-2 |
| 53-11 | a-53 | b-2 | c-3 |
| 53-12 | a-53 | b-2 | c-4 |
| 53-13 | a-53 | b-2 | c-5 |
| 53-14 | a-53 | b-2 | c-6 |
| 53-15 | a-53 | b-2 | c-7 |
| 53-16 | a-53 | b-2 | c-8 |
| 53-17 | a-53 | b-3 | c-1 |
| 53-18 | a-53 | b-3 | c-2 |
| 53-19 | a-53 | b-3 | c-3 |
| 53-20 | a-53 | b-3 | c-4 |
| 53-21 | a-53 | b-3 | c-5 |
| 53-22 | a-53 | b-3 | c-6 |
| 53-23 | a-53 | b-3 | c-7 |
| 53-24 | a-53 | b-3 | c-8 |
| 54-1 | a-54 | b-1 | c-1 |
| 54-2 | a-54 | b-1 | c-2 |
| 54-3 | a-54 | b-1 | c-3 |
| 54-4 | a-54 | b-1 | c-4 |
| 54-5 | a-54 | b-1 | c-5 |
| 54-6 | a-54 | b-1 | c-6 |
| 54-7 | a-54 | b-1 | c-7 |
| 54-8 | a-54 | b-1 | c-8 |
| 54-9 | a-54 | b-2 | c-1 |
| 54-10 | a-54 | b-2 | c-2 |
| 54-11 | a-54 | b-2 | c-3 |
| 54-12 | a-54 | b-2 | c-4 |
| 54-13 | a-54 | b-2 | c-5 |
| 54-14 | a-54 | b-2 | c-6 |
| 54-15 | a-54 | b-2 | c-7 |
| 54-16 | a-54 | b-2 | c-8 |
| 54-17 | a-54 | b-3 | c-1 |
| 54-18 | a-54 | b-3 | c-2 |
| 54-19 | a-54 | b-3 | c-3 |
| 54-20 | a-54 | b-3 | c-4 |
| 54-21 | a-54 | b-3 | c-5 |
| 54-22 | a-54 | b-3 | c-6 |
| 54-23 | a-54 | b-3 | c-7 |
| 54-24 | a-54 | b-3 | c-8 |

TABLE 25

| No. | A' | B' | R¹' |
|---|---|---|---|
| 55-1 | a-55 | b-1 | c-1 |
| 55-2 | a-55 | b-1 | c-2 |
| 55-3 | a-55 | b-1 | c-3 |
| 55-4 | a-55 | b-1 | c-4 |
| 55-5 | a-55 | b-1 | c-5 |
| 55-6 | a-55 | b-1 | c-6 |
| 55-7 | a-55 | b-1 | c-7 |
| 55-8 | a-55 | b-1 | c-8 |
| 55-9 | a-55 | b-2 | c-1 |
| 55-10 | a-55 | b-2 | c-2 |
| 55-11 | a-55 | b-2 | c-3 |
| 55-12 | a-55 | b-2 | c-4 |
| 55-13 | a-55 | b-2 | c-5 |
| 55-14 | a-55 | b-2 | c-6 |
| 55-15 | a-55 | b-2 | c-7 |
| 55-16 | a-55 | b-2 | c-8 |
| 55-17 | a-55 | b-3 | c-1 |
| 55-18 | a-55 | b-3 | c-2 |
| 55-19 | a-55 | b-3 | c-3 |
| 55-20 | a-55 | b-3 | c-4 |
| 55-21 | a-55 | b-3 | c-5 |
| 55-22 | a-55 | b-3 | c-6 |
| 55-23 | a-55 | b-3 | c-7 |
| 55-24 | a-55 | b-3 | c-8 |
| 56-1 | a-56 | b-1 | c-1 |
| 56-2 | a-56 | b-1 | c-2 |
| 56-3 | a-56 | b-1 | c-3 |
| 56-4 | a-56 | b-1 | c-4 |
| 56-5 | a-56 | b-1 | c-5 |
| 56-6 | a-56 | b-1 | c-6 |
| 56-7 | a-56 | b-1 | c-7 |
| 56-8 | a-56 | b-1 | c-8 |
| 56-9 | a-56 | b-2 | c-1 |
| 56-10 | a-56 | b-2 | c-2 |
| 56-11 | a-56 | b-2 | c-3 |
| 56-12 | a-56 | b-2 | c-4 |
| 56-13 | a-56 | b-2 | c-5 |
| 56-14 | a-56 | b-2 | c-6 |
| 56-15 | a-56 | b-2 | c-7 |
| 56-16 | a-56 | b-2 | c-8 |
| 56-17 | a-56 | b-3 | c-1 |
| 56-18 | a-56 | b-3 | c-2 |
| 56-19 | a-56 | b-3 | c-3 |
| 56-20 | a-56 | b-3 | c-4 |
| 56-21 | a-56 | b-3 | c-5 |
| 56-22 | a-56 | b-3 | c-6 |
| 56-23 | a-56 | b-3 | c-7 |
| 56-24 | a-56 | b-3 | c-8 |
| 57-1 | a-57 | b-1 | c-1 |
| 57-2 | a-57 | b-1 | c-2 |
| 57-3 | a-57 | b-1 | c-3 |
| 57-4 | a-57 | b-1 | c-4 |
| 57-5 | a-57 | b-1 | c-5 |
| 57-6 | a-57 | b-1 | c-6 |
| 57-7 | a-57 | b-1 | c-7 |
| 57-8 | a-57 | b-1 | c-8 |
| 57-9 | a-57 | b-2 | c-1 |
| 57-10 | a-57 | b-2 | c-2 |
| 57-11 | a-57 | b-2 | c-3 |
| 57-12 | a-57 | b-2 | c-4 |
| 57-13 | a-57 | b-2 | c-5 |
| 57-14 | a-57 | b-2 | c-6 |
| 57-15 | a-57 | b-2 | c-7 |
| 57-16 | a-57 | b-2 | c-8 |
| 57-17 | a-57 | b-3 | c-1 |
| 57-18 | a-57 | b-3 | c-2 |
| 57-19 | a-57 | b-3 | c-3 |
| 57-20 | a-57 | b-3 | c-4 |
| 57-21 | a-57 | b-3 | c-5 |
| 57-22 | a-57 | b-3 | c-6 |
| 57-23 | a-57 | b-3 | c-7 |
| 57-24 | a-57 | b-3 | c-8 |

TABLE 26

| No. | A' | B' | R¹' |
|---|---|---|---|
| 58-1 | a-58 | b-1 | c-1 |
| 58-2 | a-58 | b-1 | c-2 |
| 58-3 | a-58 | b-1 | c-3 |
| 58-4 | a-58 | b-1 | c-4 |
| 58-5 | a-58 | b-1 | c-5 |
| 58-6 | a-58 | b-1 | c-6 |
| 58-7 | a-58 | b-1 | c-7 |
| 58-8 | a-58 | b-1 | c-8 |
| 58-9 | a-58 | b-2 | c-1 |

TABLE 26-continued

| No. | A' | B' | R¹' |
|---|---|---|---|
| 58-10 | a-58 | b-2 | c-2 |
| 58-11 | a-58 | b-2 | c-3 |
| 58-12 | a-58 | b-2 | c-4 |
| 58-13 | a-58 | b-2 | c-5 |
| 58-14 | a-58 | b-2 | c-6 |
| 58-15 | a-58 | b-2 | c-7 |
| 58-16 | a-58 | b-2 | c-8 |
| 58-17 | a-58 | b-3 | c-1 |
| 58-18 | a-58 | b-3 | c-2 |
| 58-19 | a-58 | b-3 | c-3 |
| 58-20 | a-58 | b-3 | c-4 |
| 58-21 | a-58 | b-3 | c-5 |
| 58-22 | a-58 | b-3 | c-6 |
| 58-23 | a-58 | b-3 | c-7 |
| 58-24 | a-58 | b-3 | c-8 |
| 59-1 | a-59 | b-1 | c-1 |
| 59-2 | a-59 | b-1 | c-2 |
| 59-3 | a-59 | b-1 | c-3 |
| 59-4 | a-59 | b-1 | c-4 |
| 59-5 | a-59 | b-1 | c-5 |
| 59-6 | a-59 | b-1 | c-6 |
| 59-7 | a-59 | b-1 | c-7 |
| 59-8 | a-59 | b-1 | c-8 |
| 59-9 | a-59 | b-2 | c-1 |
| 59-10 | a-59 | b-2 | c-2 |
| 59-11 | a-59 | b-2 | c-3 |
| 59-12 | a-59 | b-2 | c-4 |
| 59-13 | a-59 | b-2 | c-5 |
| 59-14 | a-59 | b-2 | c-6 |
| 59-15 | a-59 | b-2 | c-7 |
| 59-16 | a-59 | b-2 | c-8 |
| 59-17 | a-59 | b-3 | c-1 |
| 59-18 | a-59 | b-3 | c-2 |
| 59-19 | a-59 | b-3 | c-3 |
| 59-20 | a-59 | b-3 | c-4 |
| 59-21 | a-59 | b-3 | c-5 |
| 59-22 | a-59 | b-3 | c-6 |
| 59-23 | a-59 | b-3 | c-7 |
| 59-24 | a-59 | b-3 | c-8 |
| 60-1 | a-60 | b-1 | c-1 |
| 60-2 | a-60 | b-1 | c-2 |
| 60-3 | a-60 | b-1 | c-3 |
| 60-4 | a-60 | b-1 | c-4 |
| 60-5 | a-60 | b-1 | c-5 |
| 60-6 | a-60 | b-1 | c-6 |
| 60-7 | a-60 | b-1 | c-7 |
| 60-8 | a-60 | b-1 | c-8 |
| 60-9 | a-60 | b-2 | c-1 |
| 60-10 | a-60 | b-2 | c-2 |
| 60-11 | a-60 | b-2 | c-3 |
| 60-12 | a-60 | b-2 | c-4 |
| 60-13 | a-60 | b-2 | c-5 |
| 60-14 | a-60 | b-2 | c-6 |
| 60-15 | a-60 | b-2 | c-7 |
| 60-16 | a-60 | b-2 | c-8 |
| 60-17 | a-60 | b-3 | c-1 |
| 60-18 | a-60 | b-3 | c-2 |
| 60-19 | a-60 | b-3 | c-3 |
| 60-20 | a-60 | b-3 | c-4 |
| 60-21 | a-60 | b-3 | c-5 |
| 60-22 | a-60 | b-3 | c-6 |
| 60-23 | a-60 | b-3 | c-7 |
| 60-24 | a-60 | b-3 | c-8 |

TABLE 27

| No. | A' | B' | R¹' |
|---|---|---|---|
| 61-1 | a-61 | b-1 | c-1 |
| 61-2 | a-61 | b-1 | c-2 |
| 61-3 | a-61 | b-1 | c-3 |
| 61-4 | a-61 | b-1 | c-4 |
| 61-5 | a-61 | b-1 | c-5 |
| 61-6 | a-61 | b-1 | c-6 |
| 61-7 | a-61 | b-1 | c-7 |

TABLE 27-continued

| No. | A' | B' | R¹' |
|---|---|---|---|
| 61-8 | a-61 | b-1 | c-8 |
| 61-9 | a-61 | b-2 | c-1 |
| 61-10 | a-61 | b-2 | c-2 |
| 61-11 | a-61 | b-2 | c-3 |
| 61-12 | a-61 | b-2 | c-4 |
| 61-13 | a-61 | b-2 | c-5 |
| 61-14 | a-61 | b-2 | c-6 |
| 61-15 | a-61 | b-2 | c-7 |
| 61-16 | a-61 | b-2 | c-8 |
| 61-17 | a-61 | b-3 | c-1 |
| 61-18 | a-61 | b-3 | c-2 |
| 61-19 | a-61 | b-3 | c-3 |
| 61-20 | a-61 | b-3 | c-4 |
| 61-21 | a-61 | b-3 | c-5 |
| 61-22 | a-61 | b-3 | c-6 |
| 61-23 | a-61 | b-3 | c-7 |
| 61-24 | a-61 | b-3 | c-8 |

EXAMPLE D

The present invention provides a compound of the formula (I''):

(I'')

[Chemical Formula 284]

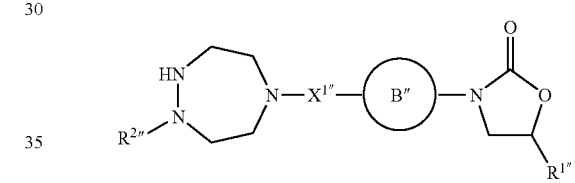

wherein $X^{1''}$ is a single bond;

$R^{2''}$ is as defined in Tables 28 to 31;

B'' is as defined in Table 32; and $R^{1''}$ is as defined in Table 33.

Examples of the compounds of the above formula (I'') are listed in Tables 34 to 77 in which No. means the Example No.

TABLE 28

| No. | $R^{2''}$— |
|---|---|
| d-1 |  |
| d-2 | 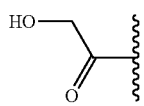 |
| d-3 | 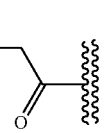 |

TABLE 28-continued

| No. | R²''— |
|---|---|
| d-4 | (CHO group) |
| d-5 | (HOCH₂-CH(OH)-C(=O)- group) |
| d-6 | (HOCH₂-CH(OH)-C(=O)- group, other stereochem) |
| d-7 | (N≡C- group) |
| d-8 | (HOCH₂-C(=S)- group) |
| d-9 | (HO-CH₂CH₂-C(=S)- group) |
| d-10 | (H-C(=S)- group) |
| d-11 | (HOCH₂-CH(OH)-C(=S)- group) |
| d-12 | (HOCH₂-CH(OH)-C(=S)- group, other stereochem) |
| d-13 | (phenyl) |
| d-14 | (4-nitrophenyl) |
| d-15 | (pyridin-2-yl) |
| d-16 | (5-nitropyridin-2-yl) |
| d-17 | (pyridin-3-ylmethyl) |
| d-18 | (pyridin-3-ylmethyl) |
| d-19 | (quinolin-2-ylmethyl) |
| d-20 | (quinolin-4-ylmethyl) |
| d-21 | (pyridin-3-yl-C(=O)-) |
| d-22 | (pyridin-4-yl-C(=O)-) |
| d-23 | (quinolin-3-yl-C(=O)-) |

TABLE 28-continued
| No. | R²— |
|---|---|
| d-24 | 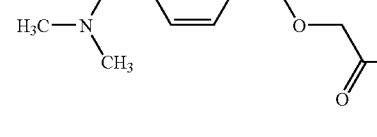 |
| d-25 | 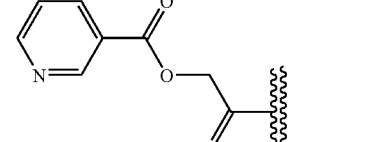 |
| d-26 | 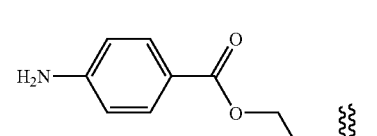 |
| d-27 | 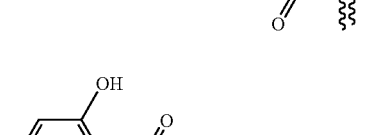 |
| d-28 | 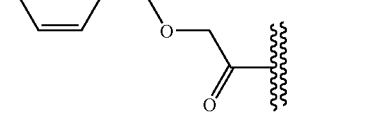 |
| d-29 |  |
| d-30 |  |
TABLE 29
| No. | R²— |
|---|---|
| d-31 |  |
TABLE 29-continued
| No. | R²— |
|---|---|
| d-32 | |
| d-33 | |
| d-34 | |
| d-35 | |
| d-36 | |
| d-37 | |
| d-38 | |
| d-39 | |
| d-40 | |

TABLE 29-continued
| No. | R²″— |
|---|---|
| d-41 | 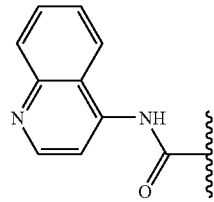 |
| d-42 | 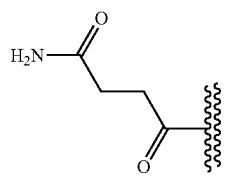 [SMILES: *C(=O)CCC(N)=O] |
| d-43 | 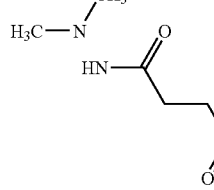 |
| d-44 | 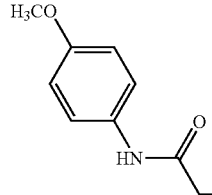 |
| d-45 | 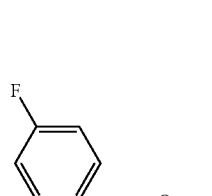 |
| d-46 | 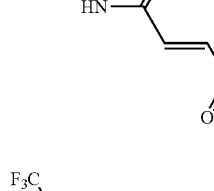 |
TABLE 29-continued
| No. | R²″— |
|---|---|
| d-47 | 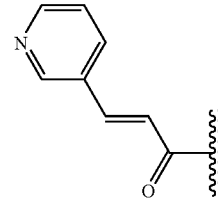 |
| d-48 | 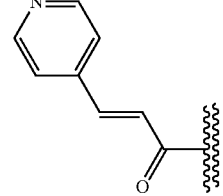 |
| d-49 | 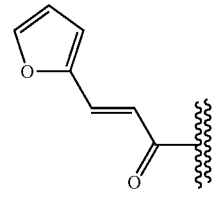 [SMILES: *C(=O)/C=C/c1ccco1] |
| d-50 | 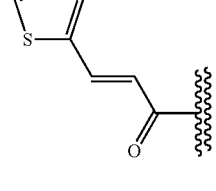 |
| d-51 | 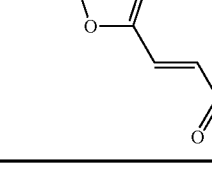 |
TABLE 30
| No. | R²″— |
|---|---|
| d-52 | 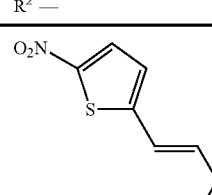 |
| d-53 | 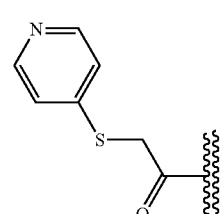 |

TABLE 30-continued
| No. | R²''— |
|---|---|
| d-54 | 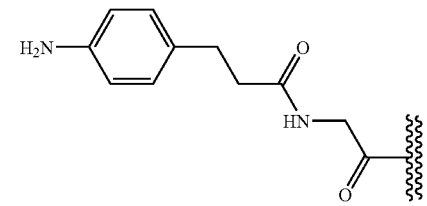 [SMILES: *C(=O)CNC(=O)CCc1ccc(N)cc1] |
| d-55 | 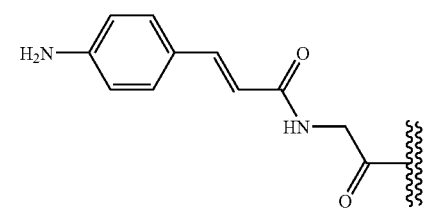 [SMILES: *C(=O)CNC(=O)/C=C/c1ccc(N)cc1] |
| d-56 | 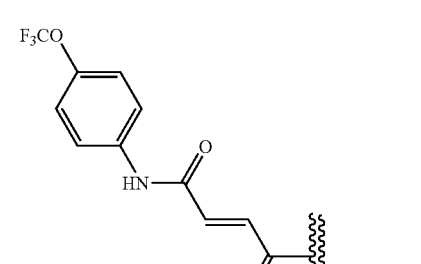 |
| d-57 | 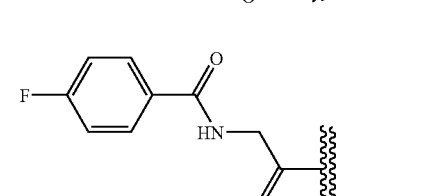 |
| d-58 | 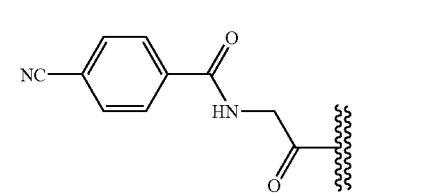 |
| d-59 | 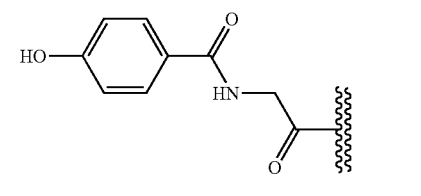 |
| d-60 | 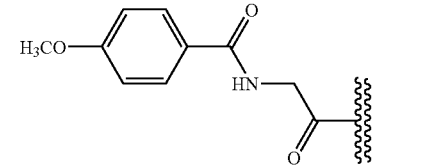 [SMILES: *C(=O)CNC(=O)c1ccc(OC)cc1] |
| d-61 | |
| d-62 | |
| d-63 | |
| d-64 | |
| d-65 | |
| d-66 | |
| d-67 | |

TABLE 30-continued
| No. | R²"— |
|---|---|
| d-68 | 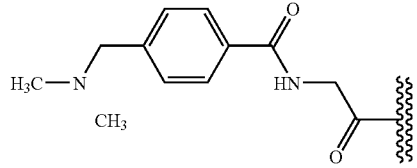 |
| d-69 | 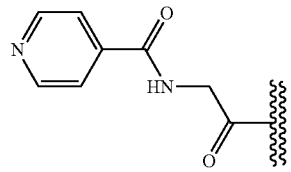 [SMILES: *C(=O)CNC(=O)c1ccncc1] |
| d-70 | 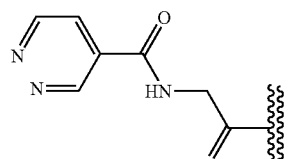 |
| d-71 | 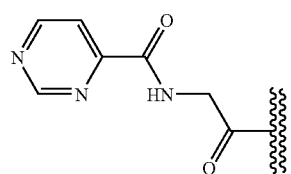 [SMILES: *C(=O)CNC(=O)c1ccncn1] |
| d-72 | 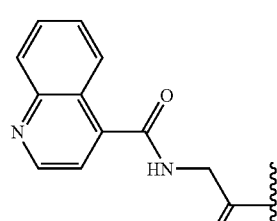 |
| d-73 | 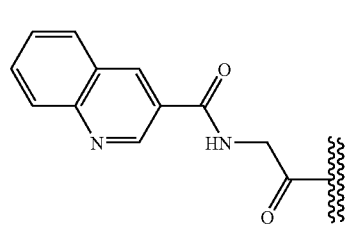 [SMILES: *C(=O)CNC(=O)c1cnc2ccccc2c1] |
| d-74 | 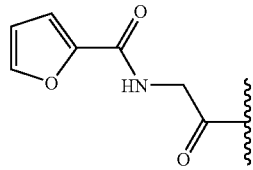 |
| d-75 | 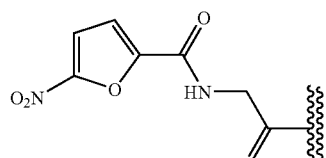 |
TABLE 31
| No. | R²"— |
|---|---|
| d-76 | 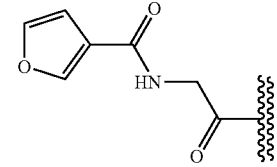 [SMILES: *C(=O)CNC(=O)c1ccoc1] |
| d-77 | 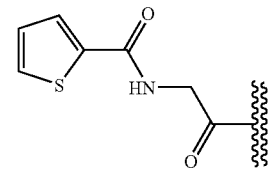 [SMILES: *C(=O)CNC(=O)c1cccs1] |
| d-78 | 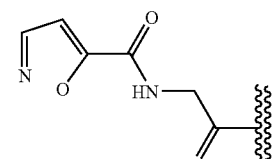 |
| d-79 | 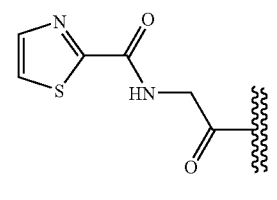 [SMILES: *C(=O)CNC(=O)c1nccs1] |
| d-80 | 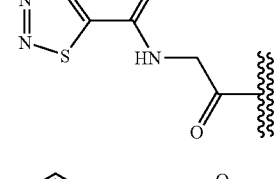 |
| d-81 | 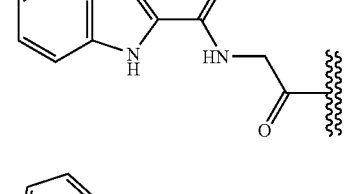 |
| d-82 | 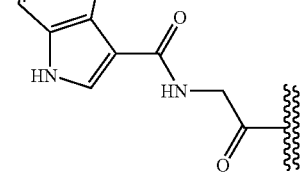 |
| d-83 | 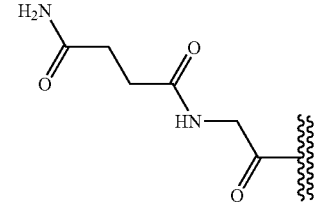 [SMILES: *C(=O)CNC(=O)CCC(N)=O] |

TABLE 31-continued

| No. | R²"— |
|---|---|
| d-84 | (H₂N-CO-CH=CH-CO-NH-CH₂-CO-) structure |
| d-85 | (H₂N-CO-CH₂CH₂CH₂-CO-NH-CH₂-CO-) structure |
| d-86 | (4-methoxybenzyl with α-NH₂, -CO-) structure |
| d-87 | (4-methoxyphenethyl-NH-CH₂-CO-) structure |

TABLE 32

| No. | B" 環 |
|---|---|
| e-1 | 1,4-phenylene |
| e-2 | 3-fluoro-1,4-phenylene |
| e-3 | 2,6-difluoro-1,4-phenylene |

TABLE 33

| No. | R¹" |
|---|---|
| f-1 | -CH₂-NH-C(=O)-CH₃ |
| f-2 | -CH₂-NH-C(=S)-CH₃ |
| f-3 | -CH₂-NH-C(=S)-CHF₂ |
| f-4 | -CH₂-NH-C(=S)-CH₂CH₃ |
| f-5 | -CH₂-NH-C(=S)-NH₂ |
| f-6 | -CH₂-NH-C(=S)-OCH₃ |
| f-7 | -CH₂-(1,2,3-triazol-1-yl) |
| f-8 | -CH₂-NH-(isoxazol-3-yl) |
| f-9 | -CH₂-O-(isoxazol-3-yl) |

TABLE 33-continued

| No. | R¹'' |
|---|---|
| f-10 | (structure: -CH2-NH-CN) |
| f-11 | (structure: -CH2-NH-pyrazol-3-yl (1H-pyrazole)) |
| f-12 | (structure: -CH2-NH-thiazol-2-yl) |
| f-13 | (structure: -CH2-NH-1,3,4-thiadiazol-2-yl) |
| f-14 | (structure: -CH2-NH-(3-methylisothiazol-5-yl)) |
| f-15 | (structure: -CH2-NH-(5-methyl-1,3,4-oxadiazol-2-yl)) |

TABLE 34

| No. | R²'' | B'' | R¹'' |
|---|---|---|---|
| 62-1 | d-1 | e-1 | f-1 |
| 62-2 | d-1 | e-1 | f-2 |
| 62-3 | d-1 | e-1 | f-3 |
| 62-4 | d-1 | e-1 | f-4 |
| 62-5 | d-1 | e-1 | f-5 |
| 62-6 | d-1 | e-1 | f-6 |
| 62-7 | d-1 | e-1 | f-7 |
| 62-8 | d-1 | e-1 | f-8 |
| 62-9 | d-1 | e-1 | f-9 |
| 62-10 | d-1 | e-1 | f-10 |
| 62-11 | d-1 | e-1 | f-11 |
| 62-12 | d-1 | e-1 | f-12 |
| 62-13 | d-1 | e-1 | f-13 |
| 62-14 | d-1 | e-1 | f-14 |
| 62-15 | d-1 | e-1 | f-15 |
| 62-16 | d-1 | e-2 | f-1 |
| 62-17 | d-1 | e-2 | f-2 |
| 62-18 | d-1 | e-2 | f-3 |
| 62-19 | d-1 | e-2 | f-4 |
| 62-20 | d-1 | e-2 | f-5 |
| 62-21 | d-1 | e-2 | f-6 |
| 62-22 | d-1 | e-2 | f-7 |
| 62-23 | d-1 | e-2 | f-8 |
| 62-24 | d-1 | e-2 | f-9 |
| 62-25 | d-1 | e-2 | f-10 |
| 62-26 | d-1 | e-2 | f-11 |
| 62-27 | d-1 | e-2 | f-12 |
| 62-28 | d-1 | e-2 | f-13 |
| 62-29 | d-1 | e-2 | f-14 |
| 62-30 | d-1 | e-2 | f-15 |
| 62-31 | d-1 | e-3 | f-1 |
| 62-32 | d-1 | e-3 | f-2 |
| 62-33 | d-1 | e-3 | f-3 |
| 62-34 | d-1 | e-3 | f-4 |
| 62-35 | d-1 | e-3 | f-5 |
| 62-36 | d-1 | e-3 | f-6 |
| 62-37 | d-1 | e-3 | f-7 |
| 62-38 | d-1 | e-3 | f-8 |
| 62-39 | d-1 | e-3 | f-9 |
| 62-40 | d-1 | e-3 | f-10 |
| 62-41 | d-1 | e-3 | f-11 |
| 62-42 | d-1 | e-3 | f-12 |
| 62-43 | d-1 | e-3 | f-13 |
| 62-44 | d-1 | e-3 | f-14 |
| 62-45 | d-1 | e-3 | f-15 |
| 63-1 | d-2 | e-1 | f-1 |
| 63-2 | d-2 | e-1 | f-2 |
| 63-3 | d-2 | e-1 | f-3 |
| 63-4 | d-2 | e-1 | f-4 |
| 63-5 | d-2 | e-1 | f-5 |
| 63-6 | d-2 | e-1 | f-6 |
| 63-7 | d-2 | e-1 | f-7 |
| 63-8 | d-2 | e-1 | f-8 |
| 63-9 | d-2 | e-1 | f-9 |
| 63-10 | d-2 | e-1 | f-10 |
| 63-11 | d-2 | e-1 | f-11 |
| 63-12 | d-2 | e-1 | f-12 |
| 63-13 | d-2 | e-1 | f-13 |
| 63-14 | d-2 | e-1 | f-14 |
| 63-15 | d-2 | e-1 | f-15 |
| 63-16 | d-2 | e-2 | f-1 |
| 63-17 | d-2 | e-2 | f-2 |
| 63-18 | d-2 | e-2 | f-3 |
| 63-19 | d-2 | e-2 | f-4 |
| 63-20 | d-2 | e-2 | f-5 |
| 63-21 | d-2 | e-2 | f-6 |
| 63-22 | d-2 | e-2 | f-7 |
| 63-23 | d-2 | e-2 | f-8 |
| 63-24 | d-2 | e-2 | f-9 |
| 63-25 | d-2 | e-2 | f-10 |
| 63-26 | d-2 | e-2 | f-11 |
| 63-27 | d-2 | e-2 | f-12 |
| 63-28 | d-2 | e-2 | f-13 |
| 63-29 | d-2 | e-2 | f-14 |
| 63-30 | d-2 | e-2 | f-15 |
| 63-31 | d-2 | e-3 | f-1 |
| 63-32 | d-2 | e-3 | f-2 |
| 63-33 | d-2 | e-3 | f-3 |
| 63-34 | d-2 | e-3 | f-4 |
| 63-35 | d-2 | e-3 | f-5 |
| 63-36 | d-2 | e-3 | f-6 |
| 63-37 | d-2 | e-3 | f-7 |
| 63-38 | d-2 | e-3 | f-8 |
| 63-39 | d-2 | e-3 | f-9 |
| 63-40 | d-2 | e-3 | f-10 |
| 63-41 | d-2 | e-3 | f-11 |
| 63-42 | d-2 | e-3 | f-12 |
| 63-43 | d-2 | e-3 | f-13 |
| 63-44 | d-2 | e-3 | f-14 |
| 63-45 | d-2 | e-3 | f-15 |

TABLE 35

| No. | R²'' | B'' | R¹'' |
|---|---|---|---|
| 64-1 | d-3 | e-1 | f-1 |
| 64-2 | d-3 | e-1 | f-2 |
| 64-3 | d-3 | e-1 | f-3 |
| 64-4 | d-3 | e-1 | f-4 |
| 64-5 | d-3 | e-1 | f-5 |
| 64-6 | d-3 | e-1 | f-6 |
| 64-7 | d-3 | e-1 | f-7 |
| 64-8 | d-3 | e-1 | f-8 |

TABLE 35-continued

| No. | R²" | B" | R¹" |
|---|---|---|---|
| 64-9 | d-3 | e-1 | f-9 |
| 64-10 | d-3 | e-1 | f-10 |
| 64-11 | d-3 | e-1 | f-11 |
| 64-12 | d-3 | e-1 | f-12 |
| 64-13 | d-3 | e-1 | f-13 |
| 64-14 | d-3 | e-1 | f-14 |
| 64-15 | d-3 | e-1 | f-15 |
| 64-16 | d-3 | e-2 | f-1 |
| 64-17 | d-3 | e-2 | f-2 |
| 64-18 | d-3 | e-2 | f-3 |
| 64-19 | d-3 | e-2 | f-4 |
| 64-20 | d-3 | e-2 | f-5 |
| 64-21 | d-3 | e-2 | f-6 |
| 64-22 | d-3 | e-2 | f-7 |
| 64-23 | d-3 | e-2 | f-8 |
| 64-24 | d-3 | e-2 | f-9 |
| 64-25 | d-3 | e-2 | f-10 |
| 64-26 | d-3 | e-2 | f-11 |
| 64-27 | d-3 | e-2 | f-12 |
| 64-28 | d-3 | e-2 | f-13 |
| 64-29 | d-3 | e-2 | f-14 |
| 64-30 | d-3 | e-2 | f-15 |
| 64-31 | d-3 | e-3 | f-1 |
| 64-32 | d-3 | e-3 | f-2 |
| 64-33 | d-3 | e-3 | f-3 |
| 64-34 | d-3 | e-3 | f-4 |
| 64-35 | d-3 | e-3 | f-5 |
| 64-36 | d-3 | e-3 | f-6 |
| 64-37 | d-3 | e-3 | f-7 |
| 64-38 | d-3 | e-3 | f-8 |
| 64-39 | d-3 | e-3 | f-9 |
| 64-40 | d-3 | e-3 | f-10 |
| 64-41 | d-3 | e-3 | f-11 |
| 64-42 | d-3 | e-3 | f-12 |
| 64-43 | d-3 | e-3 | f-13 |
| 64-44 | d-3 | e-3 | f-14 |
| 64-45 | d-3 | e-3 | f-15 |
| 65-1 | d-4 | e-1 | f-1 |
| 65-2 | d-4 | e-1 | f-2 |
| 65-3 | d-4 | e-1 | f-3 |
| 65-4 | d-4 | e-1 | f-4 |
| 65-5 | d-4 | e-1 | f-5 |
| 65-6 | d-4 | e-1 | f-6 |
| 65-7 | d-4 | e-1 | f-7 |
| 65-8 | d-4 | e-1 | f-8 |
| 65-9 | d-4 | e-1 | f-9 |
| 65-10 | d-4 | e-1 | f-10 |
| 65-11 | d-4 | e-1 | f-11 |
| 65-12 | d-4 | e-1 | f-12 |
| 65-13 | d-4 | e-1 | f-13 |
| 65-14 | d-4 | e-1 | f-14 |
| 65-15 | d-4 | e-1 | f-15 |
| 65-16 | d-4 | e-2 | f-1 |
| 65-17 | d-4 | e-2 | f-2 |
| 65-18 | d-4 | e-2 | f-3 |
| 65-19 | d-4 | e-2 | f-4 |
| 65-20 | d-4 | e-2 | f-5 |
| 65-21 | d-4 | e-2 | f-6 |
| 65-22 | d-4 | e-2 | f-7 |
| 65-23 | d-4 | e-2 | f-8 |
| 65-24 | d-4 | e-2 | f-9 |
| 65-25 | d-4 | e-2 | f-10 |
| 65-26 | d-4 | e-2 | f-11 |
| 65-27 | d-4 | e-2 | f-12 |
| 65-28 | d-4 | e-2 | f-13 |
| 65-29 | d-4 | e-2 | f-14 |
| 65-30 | d-4 | e-2 | f-15 |
| 65-31 | d-4 | e-3 | f-1 |
| 65-32 | d-4 | e-3 | f-2 |
| 65-33 | d-4 | e-3 | f-3 |
| 65-34 | d-4 | e-3 | f-4 |
| 65-35 | d-4 | e-3 | f-5 |
| 65-36 | d-4 | e-3 | f-6 |
| 65-37 | d-4 | e-3 | f-7 |
| 65-38 | d-4 | e-3 | f-8 |
| 65-39 | d-4 | e-3 | f-9 |
| 65-40 | d-4 | e-3 | f-10 |
| 65-41 | d-4 | e-3 | f-11 |
| 65-42 | d-4 | e-3 | f-12 |
| 65-43 | d-4 | e-3 | f-13 |
| 65-44 | d-4 | e-3 | f-14 |
| 65-45 | d-4 | e-3 | f-15 |

TABLE 36

| No. | R²" | B" | R¹" |
|---|---|---|---|
| 66-1 | d-5 | e-1 | f-1 |
| 66-2 | d-5 | e-1 | f-2 |
| 66-3 | d-5 | e-1 | f-3 |
| 66-4 | d-5 | e-1 | f-4 |
| 66-5 | d-5 | e-1 | f-5 |
| 66-6 | d-5 | e-1 | f-6 |
| 66-7 | d-5 | e-1 | f-7 |
| 66-8 | d-5 | e-1 | f-8 |
| 66-9 | d-5 | e-1 | f-9 |
| 66-10 | d-5 | e-1 | f-10 |
| 66-11 | d-5 | e-1 | f-11 |
| 66-12 | d-5 | e-1 | f-12 |
| 66-13 | d-5 | e-1 | f-13 |
| 66-14 | d-5 | e-1 | f-14 |
| 66-15 | d-5 | e-1 | f-15 |
| 66-16 | d-5 | e-2 | f-1 |
| 66-17 | d-5 | e-2 | f-2 |
| 66-18 | d-5 | e-2 | f-3 |
| 66-19 | d-5 | e-2 | f-4 |
| 66-20 | d-5 | e-2 | f-5 |
| 66-21 | d-5 | e-2 | f-6 |
| 66-22 | d-5 | e-2 | f-7 |
| 66-23 | d-5 | e-2 | f-8 |
| 66-24 | d-5 | e-2 | f-9 |
| 66-25 | d-5 | e-2 | f-10 |
| 66-26 | d-5 | e-2 | f-11 |
| 66-27 | d-5 | e-2 | f-12 |
| 66-28 | d-5 | e-2 | f-13 |
| 66-29 | d-5 | e-2 | f-14 |
| 66-30 | d-5 | e-2 | f-15 |
| 66-31 | d-5 | e-3 | f-1 |
| 66-32 | d-5 | e-3 | f-2 |
| 66-33 | d-5 | e-3 | f-3 |
| 66-34 | d-5 | e-3 | f-4 |
| 66-35 | d-5 | e-3 | f-5 |
| 66-36 | d-5 | e-3 | f-6 |
| 66-37 | d-5 | e-3 | f-7 |
| 66-38 | d-5 | e-3 | f-8 |
| 66-39 | d-5 | e-3 | f-9 |
| 66-40 | d-5 | e-3 | f-10 |
| 66-41 | d-5 | e-3 | f-11 |
| 66-42 | d-5 | e-3 | f-12 |
| 66-43 | d-5 | e-3 | f-13 |
| 66-44 | d-5 | e-3 | f-14 |
| 66-45 | d-5 | e-3 | f-15 |
| 67-1 | d-6 | e-1 | f-1 |
| 67-2 | d-6 | e-1 | f-2 |
| 67-3 | d-6 | e-1 | f-3 |
| 67-4 | d-6 | e-1 | f-4 |
| 67-5 | d-6 | e-1 | f-5 |
| 67-6 | d-6 | e-1 | f-6 |
| 67-7 | d-6 | e-1 | f-7 |
| 67-8 | d-6 | e-1 | f-8 |
| 67-9 | d-6 | e-1 | f-9 |
| 67-10 | d-6 | e-1 | f-10 |
| 67-11 | d-6 | e-1 | f-11 |
| 67-12 | d-6 | e-1 | f-12 |
| 67-13 | d-6 | e-1 | f-13 |
| 67-14 | d-6 | e-1 | f-14 |
| 67-15 | d-6 | e-1 | f-15 |
| 67-16 | d-6 | e-2 | f-1 |
| 67-17 | d-6 | e-2 | f-2 |
| 67-18 | d-6 | e-2 | f-3 |
| 67-19 | d-6 | e-2 | f-4 |
| 67-20 | d-6 | e-2 | f-5 |
| 67-21 | d-6 | e-2 | f-6 |

TABLE 36-continued

| No. | $R^{2\prime\prime}$ | $B\prime\prime$ | $R^{1\prime\prime}$ |
|---|---|---|---|
| 67-22 | d-6 | e-2 | f-7 |
| 67-23 | d-6 | e-2 | f-8 |
| 67-24 | d-6 | e-2 | f-9 |
| 67-25 | d-6 | e-2 | f-10 |
| 67-26 | d-6 | e-2 | f-11 |
| 67-27 | d-6 | e-2 | f-12 |
| 67-28 | d-6 | e-2 | f-13 |
| 67-29 | d-6 | e-2 | f-14 |
| 67-30 | d-6 | e-2 | f-15 |
| 67-31 | d-6 | e-3 | f-1 |
| 67-32 | d-6 | e-3 | f-2 |
| 67-33 | d-6 | e-3 | f-3 |
| 67-34 | d-6 | e-3 | f-4 |
| 67-35 | d-6 | e-3 | f-5 |
| 67-36 | d-6 | e-3 | f-6 |
| 67-37 | d-6 | e-3 | f-7 |
| 67-38 | d-6 | e-3 | f-8 |
| 67-39 | d-6 | e-3 | f-9 |
| 67-40 | d-6 | e-3 | f-10 |
| 67-41 | d-6 | e-3 | f-11 |
| 67-42 | d-6 | e-3 | f-12 |
| 67-43 | d-6 | e-3 | f-13 |
| 67-44 | d-6 | e-3 | f-14 |
| 67-45 | d-6 | e-3 | f-15 |

TABLE 37

| No. | $R^{2\prime\prime}$ | $B\prime\prime$ | $R^{1\prime\prime}$ |
|---|---|---|---|
| 68-1 | d-7 | e-1 | f-1 |
| 68-2 | d-7 | e-1 | f-2 |
| 68-3 | d-7 | e-1 | f-3 |
| 68-4 | d-7 | e-1 | f-4 |
| 68-5 | d-7 | e-1 | f-5 |
| 68-6 | d-7 | e-1 | f-6 |
| 68-7 | d-7 | e-1 | f-7 |
| 68-8 | d-7 | e-1 | f-8 |
| 68-9 | d-7 | e-1 | f-9 |
| 68-10 | d-7 | e-1 | f-10 |
| 68-11 | d-7 | e-1 | f-11 |
| 68-12 | d-7 | e-1 | f-12 |
| 68-13 | d-7 | e-1 | f-13 |
| 68-14 | d-7 | e-1 | f-14 |
| 68-15 | d-7 | e-1 | f-15 |
| 68-16 | d-7 | e-2 | f-1 |
| 68-17 | d-7 | e-2 | f-2 |
| 68-18 | d-7 | e-2 | f-3 |
| 68-19 | d-7 | e-2 | f-4 |
| 68-20 | d-7 | e-2 | f-5 |
| 68-21 | d-7 | e-2 | f-6 |
| 68-22 | d-7 | e-2 | f-7 |
| 68-23 | d-7 | e-2 | f-8 |
| 68-24 | d-7 | e-2 | f-9 |
| 68-25 | d-7 | e-2 | f-10 |
| 68-26 | d-7 | e-2 | f-11 |
| 68-27 | d-7 | e-2 | f-12 |
| 68-28 | d-7 | e-2 | f-13 |
| 68-29 | d-7 | e-2 | f-14 |
| 68-30 | d-7 | e-2 | f-15 |
| 68-31 | d-7 | e-3 | f-1 |
| 68-32 | d-7 | e-3 | f-2 |
| 68-33 | d-7 | e-3 | f-3 |
| 68-34 | d-7 | e-3 | f-4 |
| 68-35 | d-7 | e-3 | f-5 |
| 68-36 | d-7 | e-3 | f-6 |
| 68-37 | d-7 | e-3 | f-7 |
| 68-38 | d-7 | e-3 | f-8 |
| 68-39 | d-7 | e-3 | f-9 |
| 68-40 | d-7 | e-3 | f-10 |
| 68-41 | d-7 | e-3 | f-11 |
| 68-42 | d-7 | e-3 | f-12 |
| 68-43 | d-7 | e-3 | f-13 |
| 68-44 | d-7 | e-3 | f-14 |
| 68-45 | d-7 | e-3 | f-15 |
| 69-1 | d-8 | e-1 | f-1 |

TABLE 37-continued

| No. | $R^{2\prime\prime}$ | $B\prime\prime$ | $R^{1\prime\prime}$ |
|---|---|---|---|
| 69-2 | d-8 | e-1 | f-2 |
| 69-3 | d-8 | e-1 | f-3 |
| 69-4 | d-8 | e-1 | f-4 |
| 69-5 | d-8 | e-1 | f-5 |
| 69-6 | d-8 | e-1 | f-6 |
| 69-7 | d-8 | e-1 | f-7 |
| 69-8 | d-8 | e-1 | f-8 |
| 69-9 | d-8 | e-1 | f-9 |
| 69-10 | d-8 | e-1 | f-10 |
| 69-11 | d-8 | e-1 | f-11 |
| 69-12 | d-8 | e-1 | f-12 |
| 69-13 | d-8 | e-1 | f-13 |
| 69-14 | d-8 | e-1 | f-14 |
| 69-15 | d-8 | e-1 | f-15 |
| 69-16 | d-8 | e-2 | f-1 |
| 69-17 | d-8 | e-2 | f-2 |
| 69-18 | d-8 | e-2 | f-3 |
| 69-19 | d-8 | e-2 | f-4 |
| 69-20 | d-8 | e-2 | f-5 |
| 69-21 | d-8 | e-2 | f-6 |
| 69-22 | d-8 | e-2 | f-7 |
| 69-23 | d-8 | e-2 | f-8 |
| 69-24 | d-8 | e-2 | f-9 |
| 69-25 | d-8 | e-2 | f-10 |
| 69-26 | d-8 | e-2 | f-11 |
| 69-27 | d-8 | e-2 | f-12 |
| 69-28 | d-8 | e-2 | f-13 |
| 69-29 | d-8 | e-2 | f-14 |
| 69-30 | d-8 | e-2 | f-15 |
| 69-31 | d-8 | e-3 | f-1 |
| 69-32 | d-8 | e-3 | f-2 |
| 69-33 | d-8 | e-3 | f-3 |
| 69-34 | d-8 | e-3 | f-4 |
| 69-35 | d-8 | e-3 | f-5 |
| 69-36 | d-8 | e-3 | f-6 |
| 69-37 | d-8 | e-3 | f-7 |
| 69-38 | d-8 | e-3 | f-8 |
| 69-39 | d-8 | e-3 | f-9 |
| 69-40 | d-8 | e-3 | f-10 |
| 69-41 | d-8 | e-3 | f-11 |
| 69-42 | d-8 | e-3 | f-12 |
| 69-43 | d-8 | e-3 | f-13 |
| 69-44 | d-8 | e-3 | f-14 |
| 69-45 | d-8 | e-3 | f-15 |

TABLE 38

| No. | $R^{2\prime\prime}$ | $B\prime\prime$ | $R^{1\prime\prime}$ |
|---|---|---|---|
| 70-1 | d-9 | e-1 | f-1 |
| 70-2 | d-9 | e-1 | f-2 |
| 70-3 | d-9 | e-1 | f-3 |
| 70-4 | d-9 | e-1 | f-4 |
| 70-5 | d-9 | e-1 | f-5 |
| 70-6 | d-9 | e-1 | f-6 |
| 70-7 | d-9 | e-1 | f-7 |
| 70-8 | d-9 | e-1 | f-8 |
| 70-9 | d-9 | e-1 | f-9 |
| 70-10 | d-9 | e-1 | f-10 |
| 70-11 | d-9 | e-1 | f-11 |
| 70-12 | d-9 | e-1 | f-12 |
| 70-13 | d-9 | e-1 | f-13 |
| 70-14 | d-9 | e-1 | f-14 |
| 70-15 | d-9 | e-1 | f-15 |
| 70-16 | d-9 | e-2 | f-1 |
| 70-17 | d-9 | e-2 | f-2 |
| 70-18 | d-9 | e-2 | f-3 |
| 70-19 | d-9 | e-2 | f-4 |
| 70-20 | d-9 | e-2 | f-5 |
| 70-21 | d-9 | e-2 | f-6 |
| 70-22 | d-9 | e-2 | f-7 |
| 70-23 | d-9 | e-2 | f-8 |
| 70-24 | d-9 | e-2 | f-9 |
| 70-25 | d-9 | e-2 | f-10 |
| 70-26 | d-9 | e-2 | f-11 |

TABLE 38-continued

| No. | R²ʺ | Bʺ | R¹ʺ |
|---|---|---|---|
| 70-27 | d-9 | e-2 | f-12 |
| 70-28 | d-9 | e-2 | f-13 |
| 70-29 | d-9 | e-2 | f-14 |
| 70-30 | d-9 | e-2 | f-15 |
| 70-31 | d-9 | e-3 | f-1 |
| 70-32 | d-9 | e-3 | f-2 |
| 70-33 | d-9 | e-3 | f-3 |
| 70-34 | d-9 | e-3 | f-4 |
| 70-35 | d-9 | e-3 | f-5 |
| 70-36 | d-9 | e-3 | f-6 |
| 70-37 | d-9 | e-3 | f-7 |
| 70-38 | d-9 | e-3 | f-8 |
| 70-39 | d-9 | e-3 | f-9 |
| 70-40 | d-9 | e-3 | f-10 |
| 70-41 | d-9 | e-3 | f-11 |
| 70-42 | d-9 | e-3 | f-12 |
| 70-43 | d-9 | e-3 | f-13 |
| 70-44 | d-9 | e-3 | f-14 |
| 70-45 | d-9 | e-3 | f-15 |
| 71-1 | d-10 | e-1 | f-1 |
| 71-2 | d-10 | e-1 | f-2 |
| 71-3 | d-10 | e-1 | f-3 |
| 71-4 | d-10 | e-1 | f-4 |
| 71-5 | d-10 | e-1 | f-5 |
| 71-6 | d-10 | e-1 | f-6 |
| 71-7 | d-10 | e-1 | f-7 |
| 71-8 | d-10 | e-1 | f-8 |
| 71-9 | d-10 | e-1 | f-9 |
| 71-10 | d-10 | e-1 | f-10 |
| 71-11 | d-10 | e-1 | f-11 |
| 71-12 | d-10 | e-1 | f-12 |
| 71-13 | d-10 | e-1 | f-13 |
| 71-14 | d-10 | e-1 | f-14 |
| 71-15 | d-10 | e-1 | f-15 |
| 71-16 | d-10 | e-2 | f-1 |
| 71-17 | d-10 | e-2 | f-2 |
| 71-18 | d-10 | e-2 | f-3 |
| 71-19 | d-10 | e-2 | f-4 |
| 71-20 | d-10 | e-2 | f-5 |
| 71-21 | d-10 | e-2 | f-6 |
| 71-22 | d-10 | e-2 | f-7 |
| 71-23 | d-10 | e-2 | f-8 |
| 71-24 | d-10 | e-2 | f-9 |
| 71-25 | d-10 | e-2 | f-10 |
| 71-26 | d-10 | e-2 | f-11 |
| 71-27 | d-10 | e-2 | f-12 |
| 71-28 | d-10 | e-2 | f-13 |
| 71-29 | d-10 | e-2 | f-14 |
| 71-30 | d-10 | e-2 | f-15 |
| 71-31 | d-10 | e-3 | f-1 |
| 71-32 | d-10 | e-3 | f-2 |
| 71-33 | d-10 | e-3 | f-3 |
| 71-34 | d-10 | e-3 | f-4 |
| 71-35 | d-10 | e-3 | f-5 |
| 71-36 | d-10 | e-3 | f-6 |
| 71-37 | d-10 | e-3 | f-7 |
| 71-38 | d-10 | e-3 | f-8 |
| 71-39 | d-10 | e-3 | f-9 |
| 71-40 | d-10 | e-3 | f-10 |
| 71-41 | d-10 | e-3 | f-11 |
| 71-42 | d-10 | e-3 | f-12 |
| 71-43 | d-10 | e-3 | f-13 |
| 71-44 | d-10 | e-3 | f-14 |
| 71-45 | d-10 | e-3 | f-15 |

TABLE 39

| No. | R²ʺ | Bʺ | R¹ʺ |
|---|---|---|---|
| 72-1 | d-11 | e-1 | f-1 |
| 72-2 | d-11 | e-1 | f-2 |
| 72-3 | d-11 | e-1 | f-3 |
| 72-4 | d-11 | e-1 | f-4 |
| 72-5 | d-11 | e-1 | f-5 |
| 72-6 | d-11 | e-1 | f-6 |
| 72-7 | d-11 | e-1 | f-7 |
| 72-8 | d-11 | e-1 | f-8 |
| 72-9 | d-11 | e-1 | f-9 |
| 72-10 | d-11 | e-1 | f-10 |
| 72-11 | d-11 | e-1 | f-11 |
| 72-12 | d-11 | e-1 | f-12 |
| 72-13 | d-11 | e-1 | f-13 |
| 72-14 | d-11 | e-1 | f-14 |
| 72-15 | d-11 | e-1 | f-15 |
| 72-16 | d-11 | e-2 | f-1 |
| 72-17 | d-11 | e-2 | f-2 |
| 72-18 | d-11 | e-2 | f-3 |
| 72-19 | d-11 | e-2 | f-4 |
| 72-20 | d-11 | e-2 | f-5 |
| 72-21 | d-11 | e-2 | f-6 |
| 72-22 | d-11 | e-2 | f-7 |
| 72-23 | d-11 | e-2 | f-8 |
| 72-24 | d-11 | e-2 | f-9 |
| 72-25 | d-11 | e-2 | f-10 |
| 72-26 | d-11 | e-2 | f-11 |
| 72-27 | d-11 | e-2 | f-12 |
| 72-28 | d-11 | e-2 | f-13 |
| 72-29 | d-11 | e-2 | f-14 |
| 72-30 | d-11 | e-2 | f-15 |
| 72-31 | d-11 | e-3 | f-1 |
| 72-32 | d-11 | e-3 | f-2 |
| 72-33 | d-11 | e-3 | f-3 |
| 72-34 | d-11 | e-3 | f-4 |
| 72-35 | d-11 | e-3 | f-5 |
| 72-36 | d-11 | e-3 | f-6 |
| 72-37 | d-11 | e-3 | f-7 |
| 72-38 | d-11 | e-3 | f-8 |
| 72-39 | d-11 | e-3 | f-9 |
| 72-40 | d-11 | e-3 | f-10 |
| 72-41 | d-11 | e-3 | f-11 |
| 72-42 | d-11 | e-3 | f-12 |
| 72-43 | d-11 | e-3 | f-13 |
| 72-44 | d-11 | e-3 | f-14 |
| 72-45 | d-11 | e-3 | f-15 |
| 73-1 | d-12 | e-1 | f-1 |
| 73-2 | d-12 | e-1 | f-2 |
| 73-3 | d-12 | e-1 | f-3 |
| 73-4 | d-12 | e-1 | f-4 |
| 73-5 | d-12 | e-1 | f-5 |
| 73-6 | d-12 | e-1 | f-6 |
| 73-7 | d-12 | e-1 | f-7 |
| 73-8 | d-12 | e-1 | f-8 |
| 73-9 | d-12 | e-1 | f-9 |
| 73-10 | d-12 | e-1 | f-10 |
| 73-11 | d-12 | e-1 | f-11 |
| 73-12 | d-12 | e-1 | f-12 |
| 73-13 | d-12 | e-1 | f-13 |
| 73-14 | d-12 | e-1 | f-14 |
| 73-15 | d-12 | e-1 | f-15 |
| 73-16 | d-12 | e-2 | f-1 |
| 73-17 | d-12 | e-2 | f-2 |
| 73-18 | d-12 | e-2 | f-3 |
| 73-19 | d-12 | e-2 | f-4 |
| 73-20 | d-12 | e-2 | f-5 |
| 73-21 | d-12 | e-2 | f-6 |
| 73-22 | d-12 | e-2 | f-7 |
| 73-23 | d-12 | e-2 | f-8 |
| 73-24 | d-12 | e-2 | f-9 |
| 73-25 | d-12 | e-2 | f-10 |
| 73-26 | d-12 | e-2 | f-11 |
| 73-27 | d-12 | e-2 | f-12 |
| 73-28 | d-12 | e-2 | f-13 |
| 73-29 | d-12 | e-2 | f-14 |
| 73-30 | d-12 | e-2 | f-15 |
| 73-31 | d-12 | e-3 | f-1 |
| 73-32 | d-12 | e-3 | f-2 |
| 73-33 | d-12 | e-3 | f-3 |
| 73-34 | d-12 | e-3 | f-4 |
| 73-35 | d-12 | e-3 | f-5 |
| 73-36 | d-12 | e-3 | f-6 |
| 73-37 | d-12 | e-3 | f-7 |
| 73-38 | d-12 | e-3 | f-8 |
| 73-39 | d-12 | e-3 | f-9 |

TABLE 39-continued

| No. | R²'' | B'' | R¹''' |
|---|---|---|---|
| 73-40 | d-12 | e-3 | f-10 |
| 73-41 | d-12 | e-3 | f-11 |
| 73-42 | d-12 | e-3 | f-12 |
| 73-43 | d-12 | e-3 | f-13 |
| 73-44 | d-12 | e-3 | f-14 |
| 73-45 | d-12 | e-3 | f-15 |

TABLE 40

| No. | R²'' | B'' | R¹''' |
|---|---|---|---|
| 74-1 | d-13 | e-1 | f-1 |
| 74-2 | d-13 | e-1 | f-2 |
| 74-3 | d-13 | e-1 | f-3 |
| 74-4 | d-13 | e-1 | f-4 |
| 74-5 | d-13 | e-1 | f-5 |
| 74-6 | d-13 | e-1 | f-6 |
| 74-7 | d-13 | e-1 | f-7 |
| 74-8 | d-13 | e-1 | f-8 |
| 74-9 | d-13 | e-1 | f-9 |
| 74-10 | d-13 | e-1 | f-10 |
| 74-11 | d-13 | e-1 | f-11 |
| 74-12 | d-13 | e-1 | f-12 |
| 74-13 | d-13 | e-1 | f-13 |
| 74-14 | d-13 | e-1 | f-14 |
| 74-15 | d-13 | e-1 | f-15 |
| 74-16 | d-13 | e-2 | f-1 |
| 74-17 | d-13 | e-2 | f-2 |
| 74-18 | d-13 | e-2 | f-3 |
| 74-19 | d-13 | e-2 | f-4 |
| 74-20 | d-13 | e-2 | f-5 |
| 74-21 | d-13 | e-2 | f-6 |
| 74-22 | d-13 | e-2 | f-7 |
| 74-23 | d-13 | e-2 | f-8 |
| 74-24 | d-13 | e-2 | f-9 |
| 74-25 | d-13 | e-2 | f-10 |
| 74-26 | d-13 | e-2 | f-11 |
| 74-27 | d-13 | e-2 | f-12 |
| 74-28 | d-13 | e-2 | f-13 |
| 74-29 | d-13 | e-2 | f-14 |
| 74-30 | d-13 | e-2 | f-15 |
| 74-31 | d-13 | e-3 | f-1 |
| 74-32 | d-13 | e-3 | f-2 |
| 74-33 | d-13 | e-3 | f-3 |
| 74-34 | d-13 | e-3 | f-4 |
| 74-35 | d-13 | e-3 | f-5 |
| 74-36 | d-13 | e-3 | f-6 |
| 74-37 | d-13 | e-3 | f-7 |
| 74-38 | d-13 | e-3 | f-8 |
| 74-39 | d-13 | e-3 | f-9 |
| 74-40 | d-13 | e-3 | f-10 |
| 74-41 | d-13 | e-3 | f-11 |
| 74-42 | d-13 | e-3 | f-12 |
| 74-43 | d-13 | e-3 | f-13 |
| 74-44 | d-13 | e-3 | f-14 |
| 74-45 | d-13 | e-3 | f-15 |
| 75-1 | d-14 | e-1 | f-1 |
| 75-2 | d-14 | e-1 | f-2 |
| 75-3 | d-14 | e-1 | f-3 |
| 75-4 | d-14 | e-1 | f-4 |
| 75-5 | d-14 | e-1 | f-5 |
| 75-6 | d-14 | e-1 | f-6 |
| 75-7 | d-14 | e-1 | f-7 |
| 75-8 | d-14 | e-1 | f-8 |
| 75-9 | d-14 | e-1 | f-9 |
| 75-10 | d-14 | e-1 | f-10 |
| 75-11 | d-14 | e-1 | f-11 |
| 75-12 | d-14 | e-1 | f-12 |
| 75-13 | d-14 | e-1 | f-13 |
| 75-14 | d-14 | e-1 | f-14 |
| 75-15 | d-14 | e-1 | f-15 |
| 75-16 | d-14 | e-2 | f-1 |
| 75-17 | d-14 | e-2 | f-2 |
| 75-18 | d-14 | e-2 | f-3 |
| 75-19 | d-14 | e-2 | f-4 |

TABLE 40-continued

| No. | R²'' | B'' | R¹''' |
|---|---|---|---|
| 75-20 | d-14 | e-2 | f-5 |
| 75-21 | d-14 | e-2 | f-6 |
| 75-22 | d-14 | e-2 | f-7 |
| 75-23 | d-14 | e-2 | f-8 |
| 75-24 | d-14 | e-2 | f-9 |
| 75-25 | d-14 | e-2 | f-10 |
| 75-26 | d-14 | e-2 | f-11 |
| 75-27 | d-14 | e-2 | f-12 |
| 75-28 | d-14 | e-2 | f-13 |
| 75-29 | d-14 | e-2 | f-14 |
| 75-30 | d-14 | e-2 | f-15 |
| 75-31 | d-14 | e-3 | f-1 |
| 75-32 | d-14 | e-3 | f-2 |
| 75-33 | d-14 | e-3 | f-3 |
| 75-34 | d-14 | e-3 | f-4 |
| 75-35 | d-14 | e-3 | f-5 |
| 75-36 | d-14 | e-3 | f-6 |
| 75-37 | d-14 | e-3 | f-7 |
| 75-38 | d-14 | e-3 | f-8 |
| 75-39 | d-14 | e-3 | f-9 |
| 75-40 | d-14 | e-3 | f-10 |
| 75-41 | d-14 | e-3 | f-11 |
| 75-42 | d-14 | e-3 | f-12 |
| 75-43 | d-14 | e-3 | f-13 |
| 75-44 | d-14 | e-3 | f-14 |
| 75-45 | d-14 | e-3 | f-15 |

TABLE 41

| No. | R²'' | B'' | R¹''' |
|---|---|---|---|
| 76-1 | d-15 | e-1 | f-1 |
| 76-2 | d-15 | e-1 | f-2 |
| 76-3 | d-15 | e-1 | f-3 |
| 76-4 | d-15 | e-1 | f-4 |
| 76-5 | d-15 | e-1 | f-5 |
| 76-6 | d-15 | e-1 | f-6 |
| 76-7 | d-15 | e-1 | f-7 |
| 76-8 | d-15 | e-1 | f-8 |
| 76-9 | d-15 | e-1 | f-9 |
| 76-10 | d-15 | e-1 | f-10 |
| 76-11 | d-15 | e-1 | f-11 |
| 76-12 | d-15 | e-1 | f-12 |
| 76-13 | d-15 | e-1 | f-13 |
| 76-14 | d-15 | e-1 | f-14 |
| 76-15 | d-15 | e-1 | f-15 |
| 76-16 | d-15 | e-2 | f-1 |
| 76-17 | d-15 | e-2 | f-2 |
| 76-18 | d-15 | e-2 | f-3 |
| 76-19 | d-15 | e-2 | f-4 |
| 76-20 | d-15 | e-2 | f-5 |
| 76-21 | d-15 | e-2 | f-6 |
| 76-22 | d-15 | e-2 | f-7 |
| 76-23 | d-15 | e-2 | f-8 |
| 76-24 | d-15 | e-2 | f-9 |
| 76-25 | d-15 | e-2 | f-10 |
| 76-26 | d-15 | e-2 | f-11 |
| 76-27 | d-15 | e-2 | f-12 |
| 76-28 | d-15 | e-2 | f-13 |
| 76-29 | d-15 | e-2 | f-14 |
| 76-30 | d-15 | e-2 | f-15 |
| 76-31 | d-15 | e-3 | f-1 |
| 76-32 | d-15 | e-3 | f-2 |
| 76-33 | d-15 | e-3 | f-3 |
| 76-34 | d-15 | e-3 | f-4 |
| 76-35 | d-15 | e-3 | f-5 |
| 76-36 | d-15 | e-3 | f-6 |
| 76-37 | d-15 | e-3 | f-7 |
| 76-38 | d-15 | e-3 | f-8 |
| 76-39 | d-15 | e-3 | f-9 |
| 76-40 | d-15 | e-3 | f-10 |
| 76-41 | d-15 | e-3 | f-11 |
| 76-42 | d-15 | e-3 | f-12 |
| 76-43 | d-15 | e-3 | f-13 |
| 76-44 | d-15 | e-3 | f-14 |

TABLE 41-continued

| No. | R²" | B" | R¹" |
|---|---|---|---|
| 76-45 | d-15 | e-3 | f-15 |
| 77-1 | d-16 | e-1 | f-1 |
| 77-2 | d-16 | e-1 | f-2 |
| 77-3 | d-16 | e-1 | f-3 |
| 77-4 | d-16 | e-1 | f-4 |
| 77-5 | d-16 | e-1 | f-5 |
| 77-6 | d-16 | e-1 | f-6 |
| 77-7 | d-16 | e-1 | f-7 |
| 77-8 | d-16 | e-1 | f-8 |
| 77-9 | d-16 | e-1 | f-9 |
| 77-10 | d-16 | e-1 | f-10 |
| 77-11 | d-16 | e-1 | f-11 |
| 77-12 | d-16 | e-1 | f-12 |
| 77-13 | d-16 | e-1 | f-13 |
| 77-14 | d-16 | e-1 | f-14 |
| 77-15 | d-16 | e-1 | f-15 |
| 77-16 | d-16 | e-2 | f-1 |
| 77-17 | d-16 | e-2 | f-2 |
| 77-18 | d-16 | e-2 | f-3 |
| 77-19 | d-16 | e-2 | f-4 |
| 77-20 | d-16 | e-2 | f-5 |
| 77-21 | d-16 | e-2 | f-6 |
| 77-22 | d-16 | e-2 | f-7 |
| 77-23 | d-16 | e-2 | f-8 |
| 77-24 | d-16 | e-2 | f-9 |
| 77-25 | d-16 | e-2 | f-10 |
| 77-26 | d-16 | e-2 | f-11 |
| 77-27 | d-16 | e-2 | f-12 |
| 77-28 | d-16 | e-2 | f-13 |
| 77-29 | d-16 | e-2 | f-14 |
| 77-30 | d-16 | e-2 | f-15 |
| 77-31 | d-16 | e-3 | f-1 |
| 77-32 | d-16 | e-3 | f-2 |
| 77-33 | d-16 | e-3 | f-3 |
| 77-34 | d-16 | e-3 | f-4 |
| 77-35 | d-16 | e-3 | f-5 |
| 77-36 | d-16 | e-3 | f-6 |
| 77-37 | d-16 | e-3 | f-7 |
| 77-38 | d-16 | e-3 | f-8 |
| 77-39 | d-16 | e-3 | f-9 |
| 77-40 | d-16 | e-3 | f-10 |
| 77-41 | d-16 | e-3 | f-11 |
| 77-42 | d-16 | e-3 | f-12 |
| 77-43 | d-16 | e-3 | f-13 |
| 77-44 | d-16 | e-3 | f-14 |
| 77-45 | d-16 | e-3 | f-15 |

TABLE 42

| No. | R²" | B" | R¹" |
|---|---|---|---|
| 78-1 | d-17 | e-1 | f-1 |
| 78-2 | d-17 | e-1 | f-2 |
| 78-3 | d-17 | e-1 | f-3 |
| 78-4 | d-17 | e-1 | f-4 |
| 78-5 | d-17 | e-1 | f-5 |
| 78-6 | d-17 | e-1 | f-6 |
| 78-7 | d-17 | e-1 | f-7 |
| 78-8 | d-17 | e-1 | f-8 |
| 78-9 | d-17 | e-1 | f-9 |
| 78-10 | d-17 | e-1 | f-10 |
| 78-11 | d-17 | e-1 | f-11 |
| 78-12 | d-17 | e-1 | f-12 |
| 78-13 | d-17 | e-1 | f-13 |
| 78-14 | d-17 | e-1 | f-14 |
| 78-15 | d-17 | e-1 | f-15 |
| 78-16 | d-17 | e-2 | f-1 |
| 78-17 | d-17 | e-2 | f-2 |
| 78-18 | d-17 | e-2 | f-3 |
| 78-19 | d-17 | e-2 | f-4 |
| 78-20 | d-17 | e-2 | f-5 |
| 78-21 | d-17 | e-2 | f-6 |
| 78-22 | d-17 | e-2 | f-7 |
| 78-23 | d-17 | e-2 | f-8 |
| 78-24 | d-17 | e-2 | f-9 |

TABLE 42-continued

| No. | R²" | B" | R¹" |
|---|---|---|---|
| 78-25 | d-17 | e-2 | f-10 |
| 78-26 | d-17 | e-2 | f-11 |
| 78-27 | d-17 | e-2 | f-12 |
| 78-28 | d-17 | e-2 | f-13 |
| 78-29 | d-17 | e-2 | f-14 |
| 78-30 | d-17 | e-2 | f-15 |
| 78-31 | d-17 | e-3 | f-1 |
| 78-32 | d-17 | e-3 | f-2 |
| 78-33 | d-17 | e-3 | f-3 |
| 78-34 | d-17 | e-3 | f-4 |
| 78-35 | d-17 | e-3 | f-5 |
| 78-36 | d-17 | e-3 | f-6 |
| 78-37 | d-17 | e-3 | f-7 |
| 78-38 | d-17 | e-3 | f-8 |
| 78-39 | d-17 | e-3 | f-9 |
| 78-40 | d-17 | e-3 | f-10 |
| 78-41 | d-17 | e-3 | f-11 |
| 78-42 | d-17 | e-3 | f-12 |
| 78-43 | d-17 | e-3 | f-13 |
| 78-44 | d-17 | e-3 | f-14 |
| 78-45 | d-17 | e-3 | f-15 |
| 79-1 | d-18 | e-1 | f-1 |
| 79-2 | d-18 | e-1 | f-2 |
| 79-3 | d-18 | e-1 | f-3 |
| 79-4 | d-18 | e-1 | f-4 |
| 79-5 | d-18 | e-1 | f-5 |
| 79-6 | d-18 | e-1 | f-6 |
| 79-7 | d-18 | e-1 | f-7 |
| 79-8 | d-18 | e-1 | f-8 |
| 79-9 | d-18 | e-1 | f-9 |
| 79-10 | d-18 | e-1 | f-10 |
| 79-11 | d-18 | e-1 | f-11 |
| 79-12 | d-18 | e-1 | f-12 |
| 79-13 | d-18 | e-1 | f-13 |
| 79-14 | d-18 | e-1 | f-14 |
| 79-15 | d-18 | e-1 | f-15 |
| 79-16 | d-18 | e-2 | f-1 |
| 79-17 | d-18 | e-2 | f-2 |
| 79-18 | d-18 | e-2 | f-3 |
| 79-19 | d-18 | e-2 | f-4 |
| 79-20 | d-18 | e-2 | f-5 |
| 79-21 | d-18 | e-2 | f-6 |
| 79-22 | d-18 | e-2 | f-7 |
| 79-23 | d-18 | e-2 | f-8 |
| 79-24 | d-18 | e-2 | f-9 |
| 79-25 | d-18 | e-2 | f-10 |
| 79-26 | d-18 | e-2 | f-11 |
| 79-27 | d-18 | e-2 | f-12 |
| 79-28 | d-18 | e-2 | f-13 |
| 79-29 | d-18 | e-2 | f-14 |
| 79-30 | d-18 | e-2 | f-15 |
| 79-31 | d-18 | e-3 | f-1 |
| 79-32 | d-18 | e-3 | f-2 |
| 79-33 | d-18 | e-3 | f-3 |
| 79-34 | d-18 | e-3 | f-4 |
| 79-35 | d-18 | e-3 | f-5 |
| 79-36 | d-18 | e-3 | f-6 |
| 79-37 | d-18 | e-3 | f-7 |
| 79-38 | d-18 | e-3 | f-8 |
| 79-39 | d-18 | e-3 | f-9 |
| 79-40 | d-18 | e-3 | f-10 |
| 79-41 | d-18 | e-3 | f-11 |
| 79-42 | d-18 | e-3 | f-12 |
| 79-43 | d-18 | e-3 | f-13 |
| 79-44 | d-18 | e-3 | f-14 |
| 79-45 | d-18 | e-3 | f-15 |

TABLE 43

| No. | R²" | B" | R¹" |
|---|---|---|---|
| 80-1 | d-19 | e-1 | f-1 |
| 80-2 | d-19 | e-1 | f-2 |
| 80-3 | d-19 | e-1 | f-3 |
| 80-4 | d-19 | e-1 | f-4 |

TABLE 43-continued

| No. | R²" | B" | R¹" |
|---|---|---|---|
| 80-5 | d-19 | e-1 | f-5 |
| 80-6 | d-19 | e-1 | f-6 |
| 80-7 | d-19 | e-1 | f-7 |
| 80-8 | d-19 | e-1 | f-8 |
| 80-9 | d-19 | e-1 | f-9 |
| 80-10 | d-19 | e-1 | f-10 |
| 80-11 | d-19 | e-1 | f-11 |
| 80-12 | d-19 | e-1 | f-12 |
| 80-13 | d-19 | e-1 | f-13 |
| 80-14 | d-19 | e-1 | f-14 |
| 80-15 | d-19 | e-1 | f-15 |
| 80-16 | d-19 | e-2 | f-1 |
| 80-17 | d-19 | e-2 | f-2 |
| 80-18 | d-19 | e-2 | f-3 |
| 80-19 | d-19 | e-2 | f-4 |
| 80-20 | d-19 | e-2 | f-5 |
| 80-21 | d-19 | e-2 | f-6 |
| 80-22 | d-19 | e-2 | f-7 |
| 80-23 | d-19 | e-2 | f-8 |
| 80-24 | d-19 | e-2 | f-9 |
| 80-25 | d-19 | e-2 | f-10 |
| 80-26 | d-19 | e-2 | f-11 |
| 80-27 | d-19 | e-2 | f-12 |
| 80-28 | d-19 | e-2 | f-13 |
| 80-29 | d-19 | e-2 | f-14 |
| 80-30 | d-19 | e-2 | f-15 |
| 80-31 | d-19 | e-3 | f-1 |
| 80-32 | d-19 | e-3 | f-2 |
| 80-33 | d-19 | e-3 | f-3 |
| 80-34 | d-19 | e-3 | f-4 |
| 80-35 | d-19 | e-3 | f-5 |
| 80-36 | d-19 | e-3 | f-6 |
| 80-37 | d-19 | e-3 | f-7 |
| 80-38 | d-19 | e-3 | f-8 |
| 80-39 | d-19 | e-3 | f-9 |
| 80-40 | d-19 | e-3 | f-10 |
| 80-41 | d-19 | e-3 | f-11 |
| 80-42 | d-19 | e-3 | f-12 |
| 80-43 | d-19 | e-3 | f-13 |
| 80-44 | d-19 | e-3 | f-14 |
| 80-45 | d-19 | e-3 | f-15 |
| 81-1 | d-20 | e-1 | f-1 |
| 81-2 | d-20 | e-1 | f-2 |
| 81-3 | d-20 | e-1 | f-3 |
| 81-4 | d-20 | e-1 | f-4 |
| 81-5 | d-20 | e-1 | f-5 |
| 81-6 | d-20 | e-1 | f-6 |
| 81-7 | d-20 | e-1 | f-7 |
| 81-8 | d-20 | e-1 | f-8 |
| 81-9 | d-20 | e-1 | f-9 |
| 81-10 | d-20 | e-1 | f-10 |
| 81-11 | d-20 | e-1 | f-11 |
| 81-12 | d-20 | e-1 | f-12 |
| 81-13 | d-20 | e-1 | f-13 |
| 81-14 | d-20 | e-1 | f-14 |
| 81-15 | d-20 | e-1 | f-15 |
| 81-16 | d-20 | e-2 | f-1 |
| 81-17 | d-20 | e-2 | f-2 |
| 81-18 | d-20 | e-2 | f-3 |
| 81-19 | d-20 | e-2 | f-4 |
| 81-20 | d-20 | e-2 | f-5 |
| 81-21 | d-20 | e-2 | f-6 |
| 81-22 | d-20 | e-2 | f-7 |
| 81-23 | d-20 | e-2 | f-8 |
| 81-24 | d-20 | e-2 | f-9 |
| 81-25 | d-20 | e-2 | f-10 |
| 81-26 | d-20 | e-2 | f-11 |
| 81-27 | d-20 | e-2 | f-12 |
| 81-28 | d-20 | e-2 | f-13 |
| 81-29 | d-20 | e-2 | f-14 |
| 81-30 | d-20 | e-2 | f-15 |
| 81-31 | d-20 | e-3 | f-1 |
| 81-32 | d-20 | e-3 | f-2 |
| 81-33 | d-20 | e-3 | f-3 |
| 81-34 | d-20 | e-3 | f-4 |
| 81-35 | d-20 | e-3 | f-5 |
| 81-36 | d-20 | e-3 | f-6 |
| 81-37 | d-20 | e-3 | f-7 |
| 81-38 | d-20 | e-3 | f-8 |
| 81-39 | d-20 | e-3 | f-9 |
| 81-40 | d-20 | e-3 | f-10 |
| 81-41 | d-20 | e-3 | f-11 |
| 81-42 | d-20 | e-3 | f-12 |
| 81-43 | d-20 | e-3 | f-13 |
| 81-44 | d-20 | e-3 | f-14 |
| 81-45 | d-20 | e-3 | f-15 |

TABLE 44

| No. | R²" | B" | R¹" |
|---|---|---|---|
| 82-1 | d-21 | e-1 | f-1 |
| 82-2 | d-21 | e-1 | f-2 |
| 82-3 | d-21 | e-1 | f-3 |
| 82-4 | d-21 | e-1 | f-4 |
| 82-5 | d-21 | e-1 | f-5 |
| 82-6 | d-21 | e-1 | f-6 |
| 82-7 | d-21 | e-1 | f-7 |
| 82-8 | d-21 | e-1 | f-8 |
| 82-9 | d-21 | e-1 | f-9 |
| 82-10 | d-21 | e-1 | f-10 |
| 82-11 | d-21 | e-1 | f-11 |
| 82-12 | d-21 | e-1 | f-12 |
| 82-13 | d-21 | e-1 | f-13 |
| 82-14 | d-21 | e-1 | f-14 |
| 82-15 | d-21 | e-1 | f-15 |
| 82-16 | d-21 | e-2 | f-1 |
| 82-17 | d-21 | e-2 | f-2 |
| 82-18 | d-21 | e-2 | f-3 |
| 82-19 | d-21 | e-2 | f-4 |
| 82-20 | d-21 | e-2 | f-5 |
| 82-21 | d-21 | e-2 | f-6 |
| 82-22 | d-21 | e-2 | f-7 |
| 82-23 | d-21 | e-2 | f-8 |
| 82-24 | d-21 | e-2 | f-9 |
| 82-25 | d-21 | e-2 | f-10 |
| 82-26 | d-21 | e-2 | f-11 |
| 82-27 | d-21 | e-2 | f-12 |
| 82-28 | d-21 | e-2 | f-13 |
| 82-29 | d-21 | e-2 | f-14 |
| 82-30 | d-21 | e-2 | f-15 |
| 82-31 | d-21 | e-3 | f-1 |
| 82-32 | d-21 | e-3 | f-2 |
| 82-33 | d-21 | e-3 | f-3 |
| 82-34 | d-21 | e-3 | f-4 |
| 82-35 | d-21 | e-3 | f-5 |
| 82-36 | d-21 | e-3 | f-6 |
| 82-37 | d-21 | e-3 | f-7 |
| 82-38 | d-21 | e-3 | f-8 |
| 82-39 | d-21 | e-3 | f-9 |
| 82-40 | d-21 | e-3 | f-10 |
| 82-41 | d-21 | e-3 | f-11 |
| 82-42 | d-21 | e-3 | f-12 |
| 82-43 | d-21 | e-3 | f-13 |
| 82-44 | d-21 | e-3 | f-14 |
| 82-45 | d-21 | e-3 | f-15 |
| 83-1 | d-22 | e-1 | f-1 |
| 83-2 | d-22 | e-1 | f-2 |
| 83-3 | d-22 | e-1 | f-3 |
| 83-4 | d-22 | e-1 | f-4 |
| 83-5 | d-22 | e-1 | f-5 |
| 83-6 | d-22 | e-1 | f-6 |
| 83-7 | d-22 | e-1 | f-7 |
| 83-8 | d-22 | e-1 | f-8 |
| 83-9 | d-22 | e-1 | f-9 |
| 83-10 | d-22 | e-1 | f-10 |
| 83-11 | d-22 | e-1 | f-11 |
| 83-12 | d-22 | e-1 | f-12 |
| 83-13 | d-22 | e-1 | f-13 |
| 83-14 | d-22 | e-1 | f-14 |
| 83-15 | d-22 | e-1 | f-15 |
| 83-16 | d-22 | e-2 | f-1 |
| 83-17 | d-22 | e-2 | f-2 |

TABLE 44-continued

| No. | R²'' | B'' | R¹'' |
|---|---|---|---|
| 83-18 | d-22 | e-2 | f-3 |
| 83-19 | d-22 | e-2 | f-4 |
| 83-20 | d-22 | e-2 | f-5 |
| 83-21 | d-22 | e-2 | f-6 |
| 83-22 | d-22 | e-2 | f-7 |
| 83-23 | d-22 | e-2 | f-8 |
| 83-24 | d-22 | e-2 | f-9 |
| 83-25 | d-22 | e-2 | f-10 |
| 83-26 | d-22 | e-2 | f-11 |
| 83-27 | d-22 | e-2 | f-12 |
| 83-28 | d-22 | e-2 | f-13 |
| 83-29 | d-22 | e-2 | f-14 |
| 83-30 | d-22 | e-2 | f-15 |
| 83-31 | d-22 | e-3 | f-1 |
| 83-32 | d-22 | e-3 | f-2 |
| 83-33 | d-22 | e-3 | f-3 |
| 83-34 | d-22 | e-3 | f-4 |
| 83-35 | d-22 | e-3 | f-5 |
| 83-36 | d-22 | e-3 | f-6 |
| 83-37 | d-22 | e-3 | f-7 |
| 83-38 | d-22 | e-3 | f-8 |
| 83-39 | d-22 | e-3 | f-9 |
| 83-40 | d-22 | e-3 | f-10 |
| 83-41 | d-22 | e-3 | f-11 |
| 83-42 | d-22 | e-3 | f-12 |
| 83-43 | d-22 | e-3 | f-13 |
| 83-44 | d-22 | e-3 | f-14 |
| 83-45 | d-22 | e-3 | f-15 |

TABLE 45

| No. | R²'' | B'' | R¹'' |
|---|---|---|---|
| 84-1 | d-23 | e-1 | f-1 |
| 84-2 | d-23 | e-1 | f-2 |
| 84-3 | d-23 | e-1 | f-3 |
| 84-4 | d-23 | e-1 | f-4 |
| 84-5 | d-23 | e-1 | f-5 |
| 84-6 | d-23 | e-1 | f-6 |
| 84-7 | d-23 | e-1 | f-7 |
| 84-8 | d-23 | e-1 | f-8 |
| 84-9 | d-23 | e-1 | f-9 |
| 84-10 | d-23 | e-1 | f-10 |
| 84-11 | d-23 | e-1 | f-11 |
| 84-12 | d-23 | e-1 | f-12 |
| 84-13 | d-23 | e-1 | f-13 |
| 84-14 | d-23 | e-1 | f-14 |
| 84-15 | d-23 | e-1 | f-15 |
| 84-16 | d-23 | e-2 | f-1 |
| 84-17 | d-23 | e-2 | f-2 |
| 84-18 | d-23 | e-2 | f-3 |
| 84-19 | d-23 | e-2 | f-4 |
| 84-20 | d-23 | e-2 | f-5 |
| 84-21 | d-23 | e-2 | f-6 |
| 84-22 | d-23 | e-2 | f-7 |
| 84-23 | d-23 | e-2 | f-8 |
| 84-24 | d-23 | e-2 | f-9 |
| 84-25 | d-23 | e-2 | f-10 |
| 84-26 | d-23 | e-2 | f-11 |
| 84-27 | d-23 | e-2 | f-12 |
| 84-28 | d-23 | e-2 | f-13 |
| 84-29 | d-23 | e-2 | f-14 |
| 84-30 | d-23 | e-2 | f-15 |
| 84-31 | d-23 | e-3 | f-1 |
| 84-32 | d-23 | e-3 | f-2 |
| 84-33 | d-23 | e-3 | f-3 |
| 84-34 | d-23 | e-3 | f-4 |
| 84-35 | d-23 | e-3 | f-5 |
| 84-36 | d-23 | e-3 | f-6 |
| 84-37 | d-23 | e-3 | f-7 |
| 84-38 | d-23 | e-3 | f-8 |
| 84-39 | d-23 | e-3 | f-9 |
| 84-40 | d-23 | e-3 | f-10 |
| 84-41 | d-23 | e-3 | f-11 |
| 84-42 | d-23 | e-3 | f-12 |

TABLE 45-continued

| No. | R²'' | B'' | R¹'' |
|---|---|---|---|
| 84-43 | d-23 | e-3 | f-13 |
| 84-44 | d-23 | e-3 | f-14 |
| 84-45 | d-23 | e-3 | f-15 |
| 85-1 | d-24 | e-1 | f-1 |
| 85-2 | d-24 | e-1 | f-2 |
| 85-3 | d-24 | e-1 | f-3 |
| 85-4 | d-24 | e-1 | f-4 |
| 85-5 | d-24 | e-1 | f-5 |
| 85-6 | d-24 | e-1 | f-6 |
| 85-7 | d-24 | e-1 | f-7 |
| 85-8 | d-24 | e-1 | f-8 |
| 85-9 | d-24 | e-1 | f-9 |
| 85-10 | d-24 | e-1 | f-10 |
| 85-11 | d-24 | e-1 | f-11 |
| 85-12 | d-24 | e-1 | f-12 |
| 85-13 | d-24 | e-1 | f-13 |
| 85-14 | d-24 | e-1 | f-14 |
| 85-15 | d-24 | e-1 | f-15 |
| 85-16 | d-24 | e-2 | f-1 |
| 85-17 | d-24 | e-2 | f-2 |
| 85-18 | d-24 | e-2 | f-3 |
| 85-19 | d-24 | e-2 | f-4 |
| 85-20 | d-24 | e-2 | f-5 |
| 85-21 | d-24 | e-2 | f-6 |
| 85-22 | d-24 | e-2 | f-7 |
| 85-23 | d-24 | e-2 | f-8 |
| 85-24 | d-24 | e-2 | f-9 |
| 85-25 | d-24 | e-2 | f-10 |
| 85-26 | d-24 | e-2 | f-11 |
| 85-27 | d-24 | e-2 | f-12 |
| 85-28 | d-24 | e-2 | f-13 |
| 85-29 | d-24 | e-2 | f-14 |
| 85-30 | d-24 | e-2 | f-15 |
| 85-31 | d-24 | e-3 | f-1 |
| 85-32 | d-24 | e-3 | f-2 |
| 85-33 | d-24 | e-3 | f-3 |
| 85-34 | d-24 | e-3 | f-4 |
| 85-35 | d-24 | e-3 | f-5 |
| 85-36 | d-24 | e-3 | f-6 |
| 85-37 | d-24 | e-3 | f-7 |
| 85-38 | d-24 | e-3 | f-8 |
| 85-39 | d-24 | e-3 | f-9 |
| 85-40 | d-24 | e-3 | f-10 |
| 85-41 | d-24 | e-3 | f-11 |
| 85-42 | d-24 | e-3 | f-12 |
| 85-43 | d-24 | e-3 | f-13 |
| 85-44 | d-24 | e-3 | f-14 |
| 85-45 | d-24 | e-3 | f-15 |

TABLE 46

| No. | R²'' | B'' | R¹'' |
|---|---|---|---|
| 86-1 | d-25 | e-1 | f-1 |
| 86-2 | d-25 | e-1 | f-2 |
| 86-3 | d-25 | e-1 | f-3 |
| 86-4 | d-25 | e-1 | f-4 |
| 86-5 | d-25 | e-1 | f-5 |
| 86-6 | d-25 | e-1 | f-6 |
| 86-7 | d-25 | e-1 | f-7 |
| 86-8 | d-25 | e-1 | f-8 |
| 86-9 | d-25 | e-1 | f-9 |
| 86-10 | d-25 | e-1 | f-10 |
| 86-11 | d-25 | e-1 | f-11 |
| 86-12 | d-26 | e-1 | f-12 |
| 86-13 | d-25 | e-1 | f-13 |
| 86-14 | d-25 | e-1 | f-14 |
| 86-15 | d-25 | e-1 | f-15 |
| 86-16 | d-25 | e-2 | f-1 |
| 86-17 | d-25 | e-2 | f-2 |
| 86-18 | d-25 | e-2 | f-3 |
| 86-19 | d-25 | e-2 | f-4 |
| 86-20 | d-25 | e-2 | f-5 |
| 86-21 | d-25 | e-2 | f-6 |
| 86-22 | d-25 | e-2 | f-7 |

TABLE 46-continued

| No. | R²" | B" | R¹" |
|---|---|---|---|
| 86-23 | d-25 | e-2 | f-8 |
| 86-24 | d-25 | e-2 | f-9 |
| 86-25 | d-25 | e-2 | f-10 |
| 86-26 | d-25 | e-2 | f-11 |
| 86-27 | d-25 | e-2 | f-12 |
| 86-28 | d-25 | e-2 | f-13 |
| 86-29 | d-25 | e-2 | f-14 |
| 86-30 | d-25 | e-2 | f-15 |
| 86-31 | d-25 | e-3 | f-1 |
| 86-32 | d-25 | e-3 | f-2 |
| 86-33 | d-25 | e-3 | f-3 |
| 86-34 | d-25 | e-3 | f-4 |
| 86-35 | d-25 | e-3 | f-5 |
| 86-36 | d-25 | e-3 | f-6 |
| 86-37 | d-25 | e-3 | f-7 |
| 86-38 | d-25 | e-3 | f-8 |
| 86-39 | d-25 | e-3 | f-9 |
| 86-40 | d-25 | e-3 | f-10 |
| 86-41 | d-25 | e-3 | f-11 |
| 86-42 | d-25 | e-3 | f-12 |
| 86-43 | d-25 | e-3 | f-13 |
| 86-44 | d-25 | e-3 | f-14 |
| 86-45 | d-25 | e-3 | f-15 |
| 87-1 | d-26 | e-1 | f-1 |
| 87-2 | d-26 | e-1 | f-2 |
| 87-3 | d-26 | e-1 | f-3 |
| 87-4 | d-26 | e-1 | f-4 |
| 87-5 | d-26 | e-1 | f-5 |
| 87-6 | d-26 | e-1 | f-6 |
| 87-7 | d-26 | e-1 | f-7 |
| 87-8 | d-26 | e-1 | f-8 |
| 87-9 | d-26 | e-1 | f-9 |
| 87-10 | d-26 | e-1 | f-10 |
| 87-11 | d-26 | e-1 | f-11 |
| 87-12 | d-26 | e-1 | f-12 |
| 87-13 | d-26 | e-1 | f-13 |
| 87-14 | d-26 | e-1 | f-14 |
| 87-15 | d-26 | e-1 | f-15 |
| 87-16 | d-26 | e-2 | f-1 |
| 87-17 | d-26 | e-2 | f-2 |
| 87-18 | d-26 | e-2 | f-3 |
| 87-19 | d-26 | e-2 | f-4 |
| 87-20 | d-26 | e-2 | f-5 |
| 87-21 | d-26 | e-2 | f-6 |
| 87-22 | d-26 | e-2 | f-7 |
| 87-23 | d-26 | e-2 | f-8 |
| 87-24 | d-26 | e-2 | f-9 |
| 87-25 | d-26 | e-2 | f-10 |
| 87-26 | d-26 | e-2 | f-11 |
| 87-27 | d-26 | e-2 | f-12 |
| 87-28 | d-26 | e-2 | f-13 |
| 87-29 | d-26 | e-2 | f-14 |
| 87-30 | d-26 | e-2 | f-15 |
| 87-31 | d-26 | e-3 | f-1 |
| 87-32 | d-26 | e-3 | f-2 |
| 87-33 | d-26 | e-3 | f-3 |
| 87-34 | d-26 | e-3 | f-4 |
| 87-35 | d-26 | e-3 | f-5 |
| 87-36 | d-26 | e-3 | f-6 |
| 87-37 | d-26 | e-3 | f-7 |
| 87-38 | d-26 | e-3 | f-8 |
| 87-39 | d-26 | e-3 | f-9 |
| 87-40 | d-26 | e-3 | f-10 |
| 87-41 | d-26 | e-3 | f-11 |
| 87-42 | d-26 | e-3 | f-12 |
| 87-43 | d-26 | e-3 | f-13 |
| 87-44 | d-26 | e-3 | f-14 |
| 87-45 | d-26 | e-3 | f-15 |

TABLE 47

| No. | R²" | B" | R¹" |
|---|---|---|---|
| 88-1 | d-27 | e-1 | f-1 |
| 88-2 | d-27 | e-1 | f-2 |
| 88-3 | d-27 | e-1 | f-3 |
| 88-4 | d-27 | e-1 | f-4 |
| 88-5 | d-27 | e-1 | f-5 |
| 88-6 | d-27 | e-1 | f-6 |
| 88-7 | d-27 | e-1 | f-7 |
| 88-8 | d-27 | e-1 | f-8 |
| 88-9 | d-27 | e-1 | f-9 |
| 88-10 | d-27 | e-1 | f-10 |
| 88-11 | d-27 | e-1 | f-11 |
| 88-12 | d-27 | e-1 | f-12 |
| 88-13 | d-27 | e-1 | f-13 |
| 88-14 | d-27 | e-1 | f-14 |
| 88-15 | d-27 | e-1 | f-15 |
| 88-16 | d-27 | e-2 | f-1 |
| 88-17 | d-27 | e-2 | f-2 |
| 88-18 | d-27 | e-2 | f-3 |
| 88-19 | d-27 | e-2 | f-4 |
| 88-20 | d-27 | e-2 | f-5 |
| 88-21 | d-27 | e-2 | f-6 |
| 88-22 | d-27 | e-2 | f-7 |
| 88-23 | d-27 | e-2 | f-8 |
| 88-24 | d-27 | e-2 | f-9 |
| 88-25 | d-27 | e-2 | f-10 |
| 88-26 | d-27 | e-2 | f-11 |
| 88-27 | d-27 | e-2 | f-12 |
| 88-28 | d-27 | e-2 | f-13 |
| 88-29 | d-27 | e-2 | f-14 |
| 88-30 | d-27 | e-2 | f-15 |
| 88-31 | d-27 | e-3 | f-1 |
| 88-32 | d-27 | e-3 | f-2 |
| 88-33 | d-27 | e-3 | f-3 |
| 88-34 | d-27 | e-3 | f-4 |
| 88-35 | d-27 | e-3 | f-5 |
| 88-36 | d-27 | e-3 | f-6 |
| 88-37 | d-27 | e-3 | f-7 |
| 88-38 | d-27 | e-3 | f-8 |
| 88-39 | d-27 | e-3 | f-9 |
| 88-40 | d-27 | e-3 | f-10 |
| 88-41 | d-27 | e-3 | f-11 |
| 88-42 | d-27 | e-3 | f-12 |
| 88-43 | d-27 | e-3 | f-13 |
| 88-44 | d-27 | e-3 | f-14 |
| 88-45 | d-27 | e-3 | f-15 |
| 89-1 | d-28 | e-1 | f-1 |
| 89-2 | d-28 | e-1 | f-2 |
| 89-3 | d-28 | e-1 | f-3 |
| 89-4 | d-28 | e-1 | f-4 |
| 89-5 | d-28 | e-1 | f-5 |
| 89-6 | d-28 | e-1 | f-6 |
| 89-7 | d-28 | e-1 | f-7 |
| 89-8 | d-28 | e-1 | f-8 |
| 89-9 | d-28 | e-1 | f-9 |
| 89-10 | d-28 | e-1 | f-10 |
| 89-11 | d-28 | e-1 | f-11 |
| 89-12 | d-28 | e-1 | f-12 |
| 89-13 | d-28 | e-1 | f-13 |
| 89-14 | d-28 | e-1 | f-14 |
| 89-15 | d-28 | e-1 | f-15 |
| 89-16 | d-28 | e-2 | f-1 |
| 89-17 | d-28 | e-2 | f-2 |
| 89-18 | d-28 | e-2 | f-3 |
| 89-19 | d-28 | e-2 | f-4 |
| 89-20 | d-28 | e-2 | f-5 |
| 89-21 | d-28 | e-2 | f-6 |
| 89-22 | d-28 | e-2 | f-7 |
| 89-23 | d-28 | e-2 | f-8 |
| 89-24 | d-28 | e-2 | f-9 |
| 89-25 | d-28 | e-2 | f-10 |
| 89-26 | d-28 | e-2 | f-11 |
| 89-27 | d-28 | e-2 | f-12 |
| 89-28 | d-28 | e-2 | f-13 |
| 89-29 | d-28 | e-2 | f-14 |
| 89-30 | d-28 | e-2 | f-15 |
| 89-31 | d-28 | e-3 | f-1 |
| 89-32 | d-28 | e-3 | f-2 |
| 89-33 | d-28 | e-3 | f-3 |
| 89-34 | d-28 | e-3 | f-4 |
| 89-35 | d-28 | e-3 | f-5 |

TABLE 47-continued

| No. | R²" | B" | R¹" |
|---|---|---|---|
| 89-36 | d-28 | e-3 | f-6 |
| 89-37 | d-28 | e-3 | f-7 |
| 89-38 | d-28 | e-3 | f-8 |
| 89-39 | d-28 | e-3 | f-9 |
| 89-40 | d-28 | e-3 | f-10 |
| 89-41 | d-28 | e-3 | f-11 |
| 89-42 | d-28 | e-3 | f-12 |
| 89-43 | d-28 | e-3 | f-13 |
| 89-44 | d-28 | e-3 | f-14 |
| 89-45 | d-28 | e-3 | f-15 |

TABLE 48

| No. | R²" | B" | R¹" |
|---|---|---|---|
| 90-1 | d-29 | e-1 | f-1 |
| 90-2 | d-29 | e-1 | f-2 |
| 90-3 | d-29 | e-1 | f-3 |
| 90-4 | d-29 | e-1 | f-4 |
| 90-5 | d-29 | e-1 | f-5 |
| 90-6 | d-29 | e-1 | f-6 |
| 90-7 | d-29 | e-1 | f-7 |
| 90-8 | d-29 | e-1 | f-8 |
| 90-9 | d-29 | e-1 | f-9 |
| 90-10 | d-29 | e-1 | f-10 |
| 90-11 | d-29 | e-1 | f-11 |
| 90-12 | d-29 | e-1 | f-12 |
| 90-13 | d-29 | e-1 | f-13 |
| 90-14 | d-29 | e-1 | f-14 |
| 90-15 | d-29 | e-1 | f-15 |
| 90-16 | d-29 | e-2 | f-1 |
| 90-17 | d-29 | e-2 | f-2 |
| 90-18 | d-29 | e-2 | f-3 |
| 90-19 | d-29 | e-2 | f-4 |
| 90-20 | d-29 | e-2 | f-5 |
| 90-21 | d-29 | e-2 | f-6 |
| 90-22 | d-29 | e-2 | f-7 |
| 90-23 | d-29 | e-2 | f-8 |
| 90-24 | d-29 | e-2 | f-9 |
| 90-25 | d-29 | e-2 | f-10 |
| 90-26 | d-29 | e-2 | f-11 |
| 90-27 | d-29 | e-2 | f-12 |
| 90-28 | d-29 | e-2 | f-13 |
| 90-29 | d-29 | e-2 | f-14 |
| 90-30 | d-29 | e-2 | f-15 |
| 90-31 | d-29 | e-3 | f-1 |
| 90-32 | d-29 | e-3 | f-2 |
| 90-33 | d-29 | e-3 | f-3 |
| 90-34 | d-29 | e-3 | f-4 |
| 90-35 | d-29 | e-3 | f-5 |
| 90-36 | d-29 | e-3 | f-6 |
| 90-37 | d-29 | e-3 | f-7 |
| 90-38 | d-29 | e-3 | f-8 |
| 90-39 | d-29 | e-3 | f-9 |
| 90-40 | d-29 | e-3 | f-10 |
| 90-41 | d-29 | e-3 | f-11 |
| 90-42 | d-29 | e-3 | f-12 |
| 90-43 | d-29 | e-3 | f-13 |
| 90-44 | d-29 | e-3 | f-14 |
| 90-45 | d-29 | e-3 | f-15 |
| 91-1 | d-30 | e-1 | f-1 |
| 91-2 | d-30 | e-1 | f-2 |
| 91-3 | d-30 | e-1 | f-3 |
| 91-4 | d-30 | e-1 | f-4 |
| 91-5 | d-30 | e-1 | f-5 |
| 91-6 | d-30 | e-1 | f-6 |
| 91-7 | d-30 | e-1 | f-7 |
| 91-8 | d-30 | e-1 | f-8 |
| 91-9 | d-30 | e-1 | f-9 |
| 91-10 | d-30 | e-1 | f-10 |
| 91-11 | d-30 | e-1 | f-11 |
| 91-12 | d-30 | e-1 | f-12 |
| 91-13 | d-30 | e-1 | f-13 |
| 91-14 | d-30 | e-1 | f-14 |
| 91-15 | d-30 | e-1 | f-15 |

TABLE 48-continued

| No. | R²" | B" | R¹" |
|---|---|---|---|
| 91-16 | d-30 | e-2 | f-1 |
| 91-17 | d-30 | e-2 | f-2 |
| 91-18 | d-30 | e-2 | f-3 |
| 91-19 | d-30 | e-2 | f-4 |
| 91-20 | d-30 | e-2 | f-5 |
| 91-21 | d-30 | e-2 | f-6 |
| 91-22 | d-30 | e-2 | f-7 |
| 91-23 | d-30 | e-2 | f-8 |
| 91-24 | d-30 | e-2 | f-9 |
| 91-25 | d-30 | e-2 | f-10 |
| 91-26 | d-30 | e-2 | f-11 |
| 91-27 | d-30 | e-2 | f-12 |
| 91-28 | d-30 | e-2 | f-13 |
| 91-29 | d-30 | e-2 | f-14 |
| 91-30 | d-30 | e-2 | f-15 |
| 91-31 | d-30 | e-3 | f-1 |
| 91-32 | d-30 | e-3 | f-2 |
| 91-33 | d-30 | e-3 | f-3 |
| 91-34 | d-30 | e-3 | f-4 |
| 91-35 | d-30 | e-3 | f-5 |
| 91-36 | d-30 | e-3 | f-6 |
| 91-37 | d-30 | e-3 | f-7 |
| 91-38 | d-30 | e-3 | f-8 |
| 91-39 | d-30 | e-3 | f-9 |
| 91-40 | d-30 | e-3 | f-10 |
| 91-41 | d-30 | e-3 | f-11 |
| 91-42 | d-30 | e-3 | f-12 |
| 91-43 | d-30 | e-3 | f-13 |
| 91-44 | d-30 | e-3 | f-14 |
| 91-45 | d-30 | e-3 | f-15 |

TABLE 49

| No. | R²" | B" | R¹" |
|---|---|---|---|
| 92-1 | d-31 | e-1 | f-1 |
| 92-2 | d-31 | e-1 | f-2 |
| 92-3 | d-31 | e-1 | f-3 |
| 92-4 | d-31 | e-1 | f-4 |
| 92-5 | d-31 | e-1 | f-5 |
| 92-6 | d-31 | e-1 | f-6 |
| 92-7 | d-31 | e-1 | f-7 |
| 92-8 | d-31 | e-1 | f-8 |
| 92-9 | d-31 | e-1 | f-9 |
| 92-10 | d-31 | e-1 | f-10 |
| 92-11 | d-31 | e-1 | f-11 |
| 92-12 | 4-31 | e-1 | f-12 |
| 92-13 | d-31 | e-1 | f-13 |
| 92-14 | d-31 | e-1 | f-14 |
| 92-15 | d-31 | e-1 | f-15 |
| 92-16 | d-31 | e-2 | f-1 |
| 92-17 | d-31 | e-2 | f-2 |
| 92-18 | d-31 | e-2 | f-3 |
| 92-19 | d-31 | e-2 | f-4 |
| 92-20 | d-31 | e-2 | f-5 |
| 92-21 | d-31 | e-2 | f-6 |
| 92-22 | d-31 | e-2 | f-7 |
| 92-23 | d-31 | e-2 | f-8 |
| 92-24 | d-31 | e-2 | f-9 |
| 92-25 | d-31 | e-2 | f-10 |
| 92-26 | d-31 | e-2 | f-11 |
| 92-27 | d-31 | e-2 | f-12 |
| 92-28 | d-31 | e-2 | f-13 |
| 92-29 | d-31 | e-2 | f-14 |
| 92-30 | d-31 | e-2 | f-15 |
| 92-31 | d-31 | e-3 | f-1 |
| 92-32 | d-31 | e-3 | f-2 |
| 92-33 | d-31 | e-3 | f-3 |
| 92-34 | d-31 | e-3 | f-4 |
| 92-35 | d-31 | e-3 | f-5 |
| 92-36 | d-31 | e-3 | f-6 |
| 92-37 | d-31 | e-3 | f-7 |
| 92-38 | d-31 | e-3 | f-8 |
| 92-39 | d-31 | e-3 | f-9 |
| 92-40 | d-31 | e-3 | f-10 |

TABLE 49-continued

| No. | R²" | B" | R¹" |
|---|---|---|---|
| 92-41 | d-31 | e-3 | f-11 |
| 92-42 | d-31 | e-3 | f-12 |
| 92-43 | d-31 | e-3 | f-13 |
| 92-44 | d-31 | e-3 | f-14 |
| 92-45 | d-31 | e-3 | f-15 |
| 93-1 | d-32 | e-1 | f-1 |
| 93-2 | d-32 | e-1 | f-2 |
| 93-3 | d-32 | e-1 | f-3 |
| 93-4 | d-32 | e-1 | f-4 |
| 93-5 | d-32 | e-1 | f-5 |
| 93-6 | d-32 | e-1 | f-6 |
| 93-7 | d-32 | e-1 | f-7 |
| 93-8 | d-32 | e-1 | f-8 |
| 93-9 | d-32 | e-1 | f-9 |
| 93-10 | d-32 | e-1 | f-10 |
| 93-11 | d-32 | e-1 | f-11 |
| 93-12 | d-32 | e-1 | f-12 |
| 93-13 | d-32 | e-1 | f-13 |
| 93-14 | d-32 | e-1 | f-14 |
| 93-15 | d-32 | e-1 | f-15 |
| 93-16 | d-32 | e-2 | f-1 |
| 93-17 | d-32 | e-2 | f-2 |
| 93-18 | d-32 | e-2 | f-3 |
| 93-19 | d-32 | e-2 | f-4 |
| 93-20 | d-32 | e-2 | f-5 |
| 93-21 | d-32 | e-2 | f-6 |
| 93-22 | d-32 | e-2 | f-7 |
| 93-23 | d-32 | e-2 | f-8 |
| 93-24 | d-32 | e-2 | f-9 |
| 93-25 | d-32 | e-2 | f-10 |
| 93-26 | d-32 | e-2 | f-11 |
| 93-27 | d-32 | e-2 | f-12 |
| 93-28 | d-32 | e-2 | f-13 |
| 93-29 | d-32 | e-2 | f-14 |
| 93-30 | d-32 | e-2 | f-15 |
| 93-31 | d-32 | e-3 | f-1 |
| 93-32 | d-32 | e-3 | f-2 |
| 93-33 | d-32 | e-3 | f-3 |
| 93-34 | d-32 | e-3 | f-4 |
| 93-35 | d-32 | e-3 | f-5 |
| 93-36 | d-32 | e-3 | f-6 |
| 93-37 | d-32 | e-3 | f-7 |
| 93-38 | d-32 | e-3 | f-8 |
| 93-39 | d-32 | e-3 | f-9 |
| 93-40 | d-32 | e-3 | f-10 |
| 93-41 | d-32 | e-3 | f-11 |
| 93-42 | d-32 | e-3 | f-12 |
| 93-43 | d-32 | e-3 | f-13 |
| 93-44 | d-32 | e-3 | f-14 |
| 93-45 | d-32 | e-3 | f-15 |

TABLE 50

| No. | R²" | B" | R¹" |
|---|---|---|---|
| 94-1 | d-33 | e-1 | f-1 |
| 94-2 | d-33 | e-1 | f-2 |
| 94-3 | d-33 | e-1 | f-3 |
| 94-4 | d-33 | e-1 | f-4 |
| 94-5 | d-33 | e-1 | f-5 |
| 94-6 | d-33 | e-1 | f-6 |
| 94-7 | d-33 | e-1 | f-7 |
| 94-8 | d-33 | e-1 | f-8 |
| 94-9 | d-33 | e-1 | f-9 |
| 94-10 | d-33 | e-1 | f-10 |
| 94-11 | d-33 | e-1 | f-11 |
| 94-12 | d-33 | e-1 | f-12 |
| 94-13 | d-33 | e-1 | f-13 |
| 94-14 | d-33 | e-1 | f-14 |
| 94-15 | d-33 | e-1 | f-15 |
| 94-16 | d-33 | e-2 | f-1 |
| 94-17 | d-33 | e-2 | f-2 |
| 94-18 | d-33 | e-2 | f-3 |
| 94-19 | d-33 | e-2 | f-4 |
| 94-20 | d-33 | e-2 | f-5 |
| 94-21 | d-33 | e-2 | f-6 |
| 94-22 | d-33 | e-2 | f-7 |
| 94-23 | d-33 | e-2 | f-8 |
| 94-24 | d-33 | e-2 | f-9 |
| 94-25 | d-33 | e-2 | f-10 |
| 94-26 | d-33 | e-2 | f-11 |
| 94-27 | d-33 | e-2 | f-12 |
| 94-28 | d-33 | e-2 | f-13 |
| 94-29 | d-33 | e-2 | f-14 |
| 94-30 | d-33 | e-2 | f-15 |
| 94-31 | d-33 | e-3 | f-1 |
| 94-32 | d-33 | e-3 | f-2 |
| 94-33 | d-33 | e-3 | f-3 |
| 94-34 | d-33 | e-3 | f-4 |
| 94-35 | d-33 | e-3 | f-5 |
| 94-36 | d-33 | e-3 | f-6 |
| 94-37 | d-33 | e-3 | f-7 |
| 94-38 | d-33 | e-3 | f-8 |
| 94-39 | d-33 | e-3 | f-9 |
| 94-40 | d-33 | e-3 | f-10 |
| 94-41 | d-33 | e-3 | f-11 |
| 94-42 | d-33 | e-3 | f-12 |
| 94-43 | d-33 | e-3 | f-13 |
| 94-44 | d-33 | e-3 | f-14 |
| 94-45 | d-33 | e-3 | f-15 |
| 95-1 | d-34 | e-1 | f-1 |
| 95-2 | d-34 | e-1 | f-2 |
| 95-3 | d-34 | e-1 | f-3 |
| 95-4 | d-34 | e-1 | f-4 |
| 95-5 | d-34 | e-1 | f-5 |
| 95-6 | d-34 | e-1 | f-6 |
| 95-7 | d-34 | e-1 | f-7 |
| 95-8 | d-34 | e-1 | f-8 |
| 95-9 | d-34 | e-1 | f-9 |
| 95-10 | d-34 | e-1 | f-10 |
| 95-11 | d-34 | e-1 | f-11 |
| 95-12 | d-34 | e-1 | f-12 |
| 95-13 | d-34 | e-1 | f-13 |
| 95-14 | d-34 | e-1 | f-14 |
| 95-15 | d-34 | e-1 | f-15 |
| 95-16 | d-34 | e-2 | f-1 |
| 95-17 | d-34 | e-2 | f-2 |
| 95-18 | d-34 | e-2 | f-3 |
| 95-19 | d-34 | e-2 | f-4 |
| 95-20 | d-34 | e-2 | f-5 |
| 95-21 | d-34 | e-2 | f-6 |
| 95-22 | d-34 | e-2 | f-7 |
| 95-23 | d-34 | e-2 | f-8 |
| 95-24 | d-34 | e-2 | f-9 |
| 95-25 | d-34 | e-2 | f-10 |
| 95-26 | d-34 | e-2 | f-11 |
| 95-27 | d-34 | e-2 | f-12 |
| 95-28 | d-34 | e-2 | f-13 |
| 95-29 | d-34 | e-2 | f-14 |
| 95-30 | d-34 | e-2 | f-15 |
| 95-31 | d-34 | e-3 | f-1 |
| 95-32 | d-34 | e-3 | f-2 |
| 95-33 | d-34 | e-3 | f-3 |
| 95-34 | d-34 | e-3 | f-4 |
| 95-35 | d-34 | e-3 | f-5 |
| 95-36 | d-34 | e-3 | f-6 |
| 95-37 | d-34 | e-3 | f-7 |
| 95-38 | d-34 | e-3 | f-8 |
| 95-39 | d-34 | e-3 | f-9 |
| 95-40 | d-34 | e-3 | f-10 |
| 95-41 | d-34 | e-3 | f-11 |
| 95-42 | d-34 | e-3 | f-12 |
| 95-43 | d-34 | e-3 | f-13 |
| 95-44 | d-34 | e-3 | f-14 |
| 95-45 | d-34 | e-3 | f-15 |

TABLE 51

| No. | R²" | B" | R¹" |
|---|---|---|---|
| 96-1 | d-35 | e-1 | f-1 |
| 96-2 | d-35 | e-1 | f-2 |
| 96-3 | d-35 | e-1 | f-3 |
| 96-4 | d-35 | e-1 | f-4 |
| 96-5 | d-35 | e-1 | f-5 |
| 96-6 | d-35 | e-1 | f-6 |
| 96-7 | d-35 | e-1 | f-7 |
| 96-8 | d-35 | e-1 | f-8 |
| 96-9 | d-35 | e-1 | f-9 |
| 96-10 | d-35 | e-1 | f-10 |
| 96-11 | d-35 | e-1 | f-11 |
| 96-12 | d-35 | e-1 | f-12 |
| 96-13 | d-35 | e-1 | f-13 |
| 96-14 | d-35 | e-1 | f-14 |
| 96-15 | d-35 | e-1 | f-15 |
| 96-16 | d-35 | e-2 | f-1 |
| 96-17 | d-35 | e-2 | f-2 |
| 96-18 | d-35 | e-2 | f-3 |
| 96-19 | d-35 | e-2 | f-4 |
| 96-20 | d-35 | e-2 | f-5 |
| 96-21 | d-35 | e-2 | f-6 |
| 96-22 | d-35 | e-2 | f-7 |
| 96-23 | d-35 | e-2 | f-8 |
| 96-24 | d-35 | e-2 | f-9 |
| 96-25 | d-35 | e-2 | f-10 |
| 96-26 | d-35 | e-2 | f-11 |
| 96-27 | d-35 | e-2 | f-12 |
| 96-28 | d-35 | e-2 | f-13 |
| 96-29 | d-35 | e-2 | f-14 |
| 96-30 | d-35 | e-2 | f-15 |
| 96-31 | d-35 | e-3 | f-1 |
| 96-32 | d-35 | e-3 | f-2 |
| 96-33 | d-35 | e-3 | f-3 |
| 96-34 | d-35 | e-3 | f-4 |
| 96-35 | d-35 | e-3 | f-5 |
| 96-36 | d-35 | e-3 | f-6 |
| 96-37 | d-35 | e-3 | f-7 |
| 96-38 | d-35 | e-3 | f-8 |
| 96-39 | d-35 | e-3 | f-9 |
| 96-40 | d-35 | e-3 | f-10 |
| 96-41 | d-35 | e-3 | f-11 |
| 96-42 | d-35 | e-3 | f-12 |
| 96-43 | d-35 | e-3 | f-13 |
| 96-44 | d-35 | e-3 | f-14 |
| 96-45 | d-35 | e-3 | f-15 |
| 97-1 | d-36 | e-1 | f-1 |
| 97-2 | d-36 | e-1 | f-2 |
| 97-3 | d-36 | e-1 | f-3 |
| 97-4 | d-36 | e-1 | f-4 |
| 97-5 | d-36 | e-1 | f-5 |
| 97-6 | d-36 | e-1 | f-6 |
| 97-7 | d-36 | e-1 | f-7 |
| 97-8 | d-36 | e-1 | f-8 |
| 97-9 | d-36 | e-1 | f-9 |
| 97-10 | d-36 | e-1 | f-10 |
| 97-11 | d-36 | e-1 | f-11 |
| 97-12 | d-36 | e-1 | f-12 |
| 97-13 | d-36 | e-1 | f-13 |
| 97-14 | d-36 | e-1 | f-14 |
| 97-15 | d-36 | e-1 | f-15 |
| 97-16 | d-36 | e-2 | f-1 |
| 97-17 | d-36 | e-2 | f-2 |
| 97-18 | d-36 | e-2 | f-3 |
| 97-19 | d-36 | e-2 | f-4 |
| 97-20 | d-36 | e-2 | f-5 |
| 97-21 | d-36 | e-2 | f-6 |
| 97-22 | d-36 | e-2 | f-7 |
| 97-23 | d-36 | e-2 | f-8 |
| 97-24 | d-36 | e-2 | f-9 |
| 97-25 | d-36 | e-2 | f-10 |
| 97-26 | d-36 | e-2 | f-11 |
| 97-27 | d-36 | e-2 | f-12 |
| 97-28 | d-36 | e-2 | f-13 |
| 97-29 | d-36 | e-2 | f-14 |
| 97-30 | d-36 | e-2 | f-15 |
| 97-31 | d-36 | e-3 | f-1 |
| 97-32 | d-36 | e-3 | f-2 |
| 97-33 | d-36 | e-3 | f-3 |
| 97-34 | d-36 | e-3 | f-4 |
| 97-35 | d-36 | e-3 | f-5 |
| 97-36 | d-36 | e-3 | f-6 |
| 97-37 | d-36 | e-3 | f-7 |
| 97-38 | d-36 | e-3 | f-8 |
| 97-39 | d-36 | e-3 | f-9 |
| 97-40 | d-36 | e-3 | f-10 |
| 97-41 | d-36 | e-3 | f-11 |
| 97-42 | d-36 | e-3 | f-12 |
| 97-43 | d-36 | e-3 | f-13 |
| 97-44 | d-36 | e-3 | f-14 |
| 97-45 | d-36 | e-3 | f-15 |

TABLE 52

| No. | R²" | B" | R¹" |
|---|---|---|---|
| 98-1 | d-37 | e-1 | f-1 |
| 98-2 | d-37 | e-1 | f-2 |
| 98-3 | d-37 | e-1 | f-3 |
| 98-4 | d-37 | e-1 | f-4 |
| 98-5 | d-37 | e-1 | f-5 |
| 98-6 | d-37 | e-1 | f-6 |
| 98-7 | d-37 | e-1 | f-7 |
| 98-8 | d-37 | e-1 | f-8 |
| 98-9 | d-37 | e-1 | f-9 |
| 98-10 | d-37 | e-1 | f-10 |
| 98-11 | d-37 | e-1 | f-11 |
| 98-12 | d-37 | e-1 | f-12 |
| 98-13 | d-37 | e-1 | f-13 |
| 98-14 | d-37 | e-1 | f-14 |
| 98-15 | d-37 | e-1 | f-15 |
| 98-16 | d-37 | e-2 | f-1 |
| 98-17 | d-37 | e-2 | f-2 |
| 98-18 | d-37 | e-2 | f-3 |
| 98-19 | d-37 | e-2 | f-4 |
| 98-20 | d-37 | e-2 | f-5 |
| 98-21 | d-37 | e-2 | f-6 |
| 98-22 | d-37 | e-2 | f-7 |
| 98-23 | d-37 | e-2 | f-8 |
| 98-24 | d-37 | e-2 | f-9 |
| 98-25 | d-37 | e-2 | f-10 |
| 98-26 | d-37 | e-2 | f-11 |
| 98-27 | d-37 | e-2 | f-12 |
| 98-28 | d-37 | e-2 | f-13 |
| 98-29 | d-37 | e-2 | f-14 |
| 98-30 | d-37 | e-2 | f-15 |
| 98-31 | d-37 | e-3 | f-1 |
| 98-32 | d-37 | e-3 | f-2 |
| 98-33 | d-37 | e-3 | f-3 |
| 98-34 | d-37 | e-3 | f-4 |
| 98-35 | d-37 | e-3 | f-5 |
| 98-36 | d-37 | e-3 | f-6 |
| 98-37 | d-37 | e-3 | f-7 |
| 98-38 | d-37 | e-3 | f-8 |
| 98-39 | d-37 | e-3 | f-9 |
| 98-40 | d-37 | e-3 | f-10 |
| 98-41 | d-37 | e-3 | f-11 |
| 98-42 | d-37 | e-3 | f-12 |
| 98-43 | d-37 | e-3 | f-13 |
| 98-44 | d-37 | e-3 | f-14 |
| 98-45 | d-37 | e-3 | f-15 |
| 99-1 | d-38 | e-1 | f-1 |
| 99-2 | d-38 | e-1 | f-2 |
| 99-3 | d-38 | e-1 | f-3 |
| 99-4 | d-38 | e-1 | f-4 |
| 99-5 | d-38 | e-1 | f-5 |
| 99-6 | d-38 | e-1 | f-6 |
| 99-7 | d-38 | e-1 | f-7 |
| 99-8 | d-38 | e-1 | f-8 |
| 99-9 | d-38 | e-1 | f-9 |
| 99-10 | d-38 | e-1 | f-10 |
| 99-11 | d-38 | e-1 | f-11 |
| 99-12 | d-38 | e-1 | f-12 |
| 99-13 | d-38 | e-1 | f-13 |

TABLE 52-continued

| No. | R²" | B" | R¹" |
|---|---|---|---|
| 99-14 | d-38 | e-1 | f-14 |
| 99-15 | d-38 | e-1 | f-15 |
| 99-16 | d-38 | e-2 | f-1 |
| 99-17 | d-38 | e-2 | f-2 |
| 99-18 | d-38 | e-2 | f-3 |
| 99-19 | d-38 | e-2 | f-4 |
| 99-20 | d-38 | e-2 | f-5 |
| 99-21 | d-38 | e-2 | f-6 |
| 99-22 | d-38 | e-2 | f-7 |
| 99-23 | d-38 | e-2 | f-8 |
| 99-24 | d-38 | e-2 | f-9 |
| 99-25 | d-38 | e-2 | f-10 |
| 99-26 | d-38 | e-2 | f-11 |
| 99-27 | d-38 | e-2 | f-12 |
| 99-28 | d-38 | e-2 | f-13 |
| 99-29 | d-38 | e-2 | f-14 |
| 99-30 | d-38 | e-2 | f-15 |
| 99-31 | d-38 | e-3 | f-1 |
| 99-32 | d-38 | e-3 | f-2 |
| 99-33 | d-38 | e-3 | f-3 |
| 99-34 | d-38 | e-3 | f-4 |
| 99-35 | d-38 | e-3 | f-5 |
| 99-36 | d-38 | e-3 | f-6 |
| 99-37 | d-38 | e-3 | f-7 |
| 99-38 | d-38 | e-3 | f-8 |
| 99-39 | d-38 | e-3 | f-9 |
| 99-40 | d-38 | e-3 | f-10 |
| 99-41 | d-38 | e-3 | f-11 |
| 99-42 | d-38 | e-3 | f-12 |
| 99-43 | d-38 | e-3 | f-13 |
| 99-44 | d-38 | e-3 | f-14 |
| 99-45 | d-38 | e-3 | f-15 |

TABLE 53

| No. | R²" | B" | R¹" |
|---|---|---|---|
| 100-1 | d-39 | e-1 | f-1 |
| 100-2 | d-39 | e-1 | f-2 |
| 100-3 | d-39 | e-1 | f-3 |
| 100-4 | d-39 | e-1 | f-4 |
| 100-5 | d-39 | e-1 | f-5 |
| 100-6 | d-39 | e-1 | f-6 |
| 100-7 | d-39 | e-1 | f-7 |
| 100-8 | d-39 | e-1 | f-8 |
| 100-9 | d-39 | e-1 | f-9 |
| 100-10 | d-39 | e-1 | f-10 |
| 100-11 | d-39 | e-1 | f-11 |
| 100-12 | d-39 | e-1 | f-12 |
| 100-13 | d-39 | e-1 | f-13 |
| 100-14 | d-39 | e-1 | f-14 |
| 100-15 | d-39 | e-1 | f-15 |
| 100-16 | d-39 | e-2 | f-1 |
| 100-17 | d-39 | e-2 | f-2 |
| 100-18 | d-39 | e-2 | f-3 |
| 100-19 | d-39 | e-2 | f-4 |
| 100-20 | d-39 | e-2 | f-5 |
| 100-21 | d-39 | e-2 | f-6 |
| 100-22 | d-39 | e-2 | f-7 |
| 100-23 | d-39 | e-2 | f-8 |
| 100-24 | d-39 | e-2 | f-9 |
| 100-25 | d-39 | e-2 | f-10 |
| 100-26 | d-39 | e-2 | f-11 |
| 100-27 | d-39 | e-2 | f-12 |
| 100-28 | d-39 | e-2 | f-13 |
| 100-29 | d-39 | e-2 | f-14 |
| 100-30 | d-39 | e-2 | f-15 |
| 100-31 | d-39 | e-3 | f-1 |
| 100-32 | d-39 | e-3 | f-2 |
| 100-33 | d-39 | e-3 | f-3 |
| 100-34 | d-39 | e-3 | f-4 |
| 100-35 | d-39 | e-3 | f-5 |
| 100-36 | d-39 | e-3 | f-6 |
| 100-37 | d-39 | e-3 | f-7 |
| 100-38 | d-39 | e-3 | f-8 |

TABLE 53-continued

| No. | R²" | B" | R¹" |
|---|---|---|---|
| 100-39 | d-39 | e-3 | f-9 |
| 100-40 | d-39 | e-3 | f-10 |
| 100-41 | d-39 | e-3 | f-11 |
| 100-42 | d-39 | e-3 | f-12 |
| 100-43 | d-39 | e-3 | f-13 |
| 100-44 | d-39 | e-3 | f-14 |
| 100-45 | d-39 | e-3 | f-15 |
| 101-1 | d-40 | e-1 | f-1 |
| 101-2 | d-40 | e-1 | f-2 |
| 101-3 | d-40 | e-1 | f-3 |
| 101-4 | d-40 | e-1 | f-4 |
| 101-5 | d-40 | e-1 | f-5 |
| 101-6 | d-40 | e-1 | f-6 |
| 101-7 | d-40 | e-1 | f-7 |
| 101-8 | d-40 | e-1 | f-8 |
| 101-9 | d-40 | e-1 | f-9 |
| 101-10 | d-40 | e-1 | f-10 |
| 101-11 | d-40 | e-1 | f-11 |
| 101-12 | d-40 | e-1 | f-12 |
| 101-13 | d-40 | e-1 | f-13 |
| 101-14 | d-40 | e-1 | f-14 |
| 101-15 | d-40 | e-1 | f-15 |
| 101-16 | d-40 | e-2 | f-1 |
| 101-17 | d-40 | e-2 | f-2 |
| 101-18 | d-40 | e-2 | f-3 |
| 101-19 | d-40 | e-2 | f-4 |
| 101-20 | d-40 | e-2 | f-5 |
| 101-21 | d-40 | e-2 | f-6 |
| 101-22 | d-40 | e-2 | f-7 |
| 101-23 | d-40 | e-2 | f-8 |
| 101-24 | d-40 | e-2 | f-9 |
| 101-25 | d-40 | e-2 | f-10 |
| 101-26 | d-40 | e-2 | f-11 |
| 101-27 | d-40 | e-2 | f-12 |
| 101-28 | d-40 | e-2 | f-13 |
| 101-29 | d-40 | e-2 | f-14 |
| 101-30 | d-40 | e-2 | f-15 |
| 101-31 | d-40 | e-3 | f-1 |
| 101-32 | d-40 | e-3 | f-2 |
| 101-33 | d-40 | e-3 | f-3 |
| 101-34 | d-40 | e-3 | f-4 |
| 101-35 | d-40 | e-3 | f-5 |
| 101-36 | d-40 | e-3 | f-6 |
| 101-37 | d-40 | e-3 | f-7 |
| 101-38 | d-40 | e-3 | f-8 |
| 101-39 | d-40 | e-3 | f-9 |
| 101-40 | d-40 | e-3 | f-10 |
| 101-41 | d-40 | e-3 | f-11 |
| 101-42 | d-40 | e-3 | f-12 |
| 101-43 | d-40 | e-3 | f-13 |
| 101-44 | d-40 | e-3 | f-14 |
| 101-45 | d-40 | e-3 | f-15 |

TABLE 54

| No. | R²" | B" | R¹" |
|---|---|---|---|
| 102-1 | d-41 | e-1 | f-1 |
| 102-2 | d-41 | e-1 | f-2 |
| 102-3 | d-41 | e-1 | f-3 |
| 102-4 | d-41 | e-1 | f-4 |
| 102-5 | d-41 | e-1 | f-5 |
| 102-6 | d-41 | e-1 | f-6 |
| 102-7 | d-41 | e-1 | f-7 |
| 102-8 | d-41 | e-1 | f-8 |
| 102-9 | d-41 | e-1 | f-9 |
| 102-10 | d-41 | e-1 | f-10 |
| 102-11 | d-41 | e-1 | f-11 |
| 102-12 | d-41 | e-1 | f-12 |
| 102-13 | d-41 | e-1 | f-13 |
| 102-14 | d-41 | e-1 | f-14 |
| 102-15 | d-41 | e-1 | f-15 |
| 102-16 | d-41 | e-2 | f-1 |
| 102-17 | d-41 | e-2 | f-2 |
| 102-18 | d-41 | e-2 | f-3 |

TABLE 54-continued

| No. | R²" | B" | R¹" |
|---|---|---|---|
| 102-19 | d-41 | e-2 | f-4 |
| 102-20 | d-41 | e-2 | f-5 |
| 102-21 | d-41 | e-2 | f-6 |
| 102-22 | d-41 | e-2 | f-7 |
| 102-23 | d-41 | e-2 | f-8 |
| 102-24 | d-41 | e-2 | f-9 |
| 102-25 | d-41 | e-2 | f-10 |
| 102-26 | d-41 | e-2 | f-11 |
| 102-27 | d-41 | e-2 | f-12 |
| 102-28 | d-41 | e-2 | f-13 |
| 102-29 | d-41 | e-2 | f-14 |
| 102-30 | d-41 | e-2 | f-15 |
| 102-31 | d-41 | e-3 | f-1 |
| 102-32 | d-41 | e-3 | f-2 |
| 102-33 | d-41 | e-3 | f-3 |
| 102-34 | d-41 | e-3 | f-4 |
| 102-35 | d-41 | e-3 | f-5 |
| 102-36 | d-41 | e-3 | f-6 |
| 102-37 | d-41 | e-3 | f-7 |
| 102-38 | d-41 | e-3 | f-8 |
| 102-39 | d-41 | e-3 | f-9 |
| 102-40 | d-41 | e-3 | f-10 |
| 102-41 | d-41 | e-3 | f-11 |
| 102-42 | d-41 | e-3 | f-12 |
| 102-43 | d-41 | e-3 | f-13 |
| 102-44 | d-41 | e-3 | f-14 |
| 102-45 | d-41 | e-3 | f-15 |
| 103-1 | d-42 | e-1 | f-1 |
| 103-2 | d-42 | e-1 | f-2 |
| 103-3 | d-42 | e-1 | f-3 |
| 103-4 | d-42 | e-1 | f-4 |
| 103-5 | d-42 | e-1 | f-5 |
| 103-6 | d-42 | e-1 | f-6 |
| 103-7 | d-42 | e-1 | f-7 |
| 103-8 | d-42 | e-1 | f-8 |
| 103-9 | d-42 | e-1 | f-9 |
| 103-10 | d-42 | e-1 | f-10 |
| 103-11 | d-42 | e-1 | f-11 |
| 103-12 | d-42 | e-1 | f-12 |
| 103-13 | d-42 | e-1 | f-13 |
| 103-14 | d-42 | e-1 | f-14 |
| 103-15 | d-42 | e-1 | f-15 |
| 103-16 | d-42 | e-2 | f-1 |
| 103-17 | d-42 | e-2 | f-2 |
| 103-18 | d-42 | e-2 | f-3 |
| 103-19 | d-42 | e-2 | f-4 |
| 103-20 | d-42 | e-2 | f-5 |
| 103-21 | d-42 | e-2 | f-6 |
| 103-22 | d-42 | e-2 | f-7 |
| 103-23 | d-42 | e-2 | f-8 |
| 103-24 | d-42 | e-2 | f-9 |
| 103-25 | d-42 | e-2 | f-10 |
| 103-26 | d-42 | e-2 | f-11 |
| 103-27 | d-42 | e-2 | f-12 |
| 103-28 | d-42 | e-2 | f-13 |
| 103-29 | d-42 | e-2 | f-14 |
| 103-30 | d-42 | e-2 | f-15 |
| 103-31 | d-42 | e-3 | f-1 |
| 103-32 | d-42 | e-3 | f-2 |
| 103-33 | d-42 | e-3 | f-3 |
| 103-34 | d-42 | e-3 | f-4 |
| 103-35 | d-42 | e-3 | f-5 |
| 103-36 | d-42 | e-3 | f-6 |
| 103-37 | d-42 | e-3 | f-7 |
| 103-38 | d-42 | e-3 | f-8 |
| 103-39 | d-42 | e-3 | f-9 |
| 103-40 | d-42 | e-3 | f-10 |
| 103-41 | d-42 | e-3 | f-11 |
| 103-42 | d-42 | e-3 | f-12 |
| 103-43 | d-42 | e-3 | f-13 |
| 103-44 | d-42 | e-3 | f-14 |
| 103-45 | d-42 | e-3 | f-15 |

TABLE 55

| No. | R²" | B" | R¹" |
|---|---|---|---|
| 104-1 | d-43 | e-1 | f-1 |
| 104-2 | d-43 | e-1 | f-2 |
| 104-3 | d-43 | e-1 | f-3 |
| 104-4 | d-43 | e-1 | f-4 |
| 104-5 | d-43 | e-1 | f-5 |
| 104-6 | d-43 | e-1 | f-6 |
| 104-7 | d-43 | e-1 | f-7 |
| 104-8 | d-43 | e-1 | f-8 |
| 104-9 | d-43 | e-1 | f-9 |
| 104-10 | d-43 | e-1 | f-10 |
| 104-11 | d-43 | e-1 | f-11 |
| 104-12 | d-43 | e-1 | f-12 |
| 104-13 | d-43 | e-1 | f-13 |
| 104-14 | d-43 | e-1 | f-14 |
| 104-15 | d-43 | e-1 | f-15 |
| 104-16 | d-43 | e-2 | f-1 |
| 104-17 | d-43 | e-2 | f-2 |
| 104-18 | d-43 | e-2 | f-3 |
| 104-19 | d-43 | e-2 | f-4 |
| 104-20 | d-43 | e-2 | f-5 |
| 104-21 | d-43 | e-2 | f-6 |
| 104-22 | d-43 | e-2 | f-7 |
| 104-23 | d-43 | e-2 | f-8 |
| 104-24 | d-43 | e-2 | f-9 |
| 104-25 | d-43 | e-2 | f-10 |
| 104-26 | d-43 | e-2 | f-11 |
| 104-27 | d-43 | e-2 | f-12 |
| 104-28 | d-43 | e-2 | f-13 |
| 104-29 | d-43 | e-2 | f-14 |
| 104-30 | d-43 | e-2 | f-15 |
| 104-31 | d-43 | e-3 | f-1 |
| 104-32 | d-43 | e-3 | f-2 |
| 104-33 | d-43 | e-3 | f-3 |
| 104-34 | d-43 | e-3 | f-4 |
| 104-35 | d-43 | e-3 | f-5 |
| 104-36 | d-43 | e-3 | f-6 |
| 104-37 | d-43 | e-3 | f-7 |
| 104-38 | d-43 | e-3 | f-8 |
| 104-39 | d-43 | e-3 | f-9 |
| 104-40 | d-43 | e-3 | f-10 |
| 104-41 | d-43 | e-3 | f-11 |
| 104-42 | d-43 | e-3 | f-12 |
| 104-43 | d-43 | e-3 | f-13 |
| 104-44 | d-43 | e-3 | f-14 |
| 104-45 | d-43 | e-3 | f-15 |
| 105-1 | d-44 | e-1 | f-1 |
| 105-2 | d-44 | e-1 | f-2 |
| 105-3 | d-44 | e-1 | f-3 |
| 105-4 | d-44 | e-1 | f-4 |
| 105-5 | d-44 | e-1 | f-5 |
| 105-6 | d-44 | e-1 | f-6 |
| 105-7 | d-44 | e-1 | f-7 |
| 105-8 | d-44 | e-1 | f-8 |
| 105-9 | d-44 | e-1 | f-9 |
| 105-10 | d-44 | e-1 | f-10 |
| 105-11 | d-44 | e-1 | f-11 |
| 105-12 | d-44 | e-1 | f-12 |
| 105-13 | d-44 | e-1 | f-13 |
| 105-14 | d-44 | e-1 | f-14 |
| 105-15 | d-44 | e-1 | f-15 |
| 105-16 | d-44 | e-2 | f-1 |
| 105-17 | d-44 | e-2 | f-2 |
| 105-18 | d-44 | e-2 | f-3 |
| 105-19 | d-44 | e-2 | f-4 |
| 105-20 | d-44 | e-2 | f-5 |
| 105-21 | d-44 | e-2 | f-6 |
| 105-22 | d-44 | e-2 | f-7 |
| 105-23 | d-44 | e-2 | f-8 |
| 105-24 | d-44 | e-2 | f-9 |
| 105-25 | d-44 | e-2 | f-10 |
| 105-26 | d-44 | e-2 | f-11 |
| 105-27 | d-44 | e-2 | f-12 |
| 105-28 | d-44 | e-2 | f-13 |
| 105-29 | d-44 | e-2 | f-14 |
| 105-30 | d-44 | e-2 | f-15 |
| 105-31 | d-44 | e-3 | f-1 |
| 105-32 | d-44 | e-3 | f-2 |
| 105-33 | d-44 | e-3 | f-3 |

TABLE 55-continued

| No. | R²" | B" | R¹" |
|---|---|---|---|
| 105-34 | d-44 | e-3 | f-4 |
| 105-35 | d-44 | e-3 | f-5 |
| 105-36 | d-44 | e-3 | f-6 |
| 105-37 | d-44 | e-3 | f-7 |
| 105-38 | d-44 | e-3 | f-8 |
| 105-39 | d-44 | e-3 | f-9 |
| 105-40 | d-44 | e-3 | f-10 |
| 105-41 | d-44 | e-3 | f-11 |
| 105-42 | d-44 | e-3 | f-12 |
| 105-43 | d-44 | e-3 | f-13 |
| 105-44 | d-44 | e-3 | f-14 |
| 105-45 | d-44 | e-3 | f-15 |

TABLE 56

| No. | R²" | B" | R¹" |
|---|---|---|---|
| 106-1 | d-45 | e-1 | f-1 |
| 106-2 | d-45 | e-1 | f-2 |
| 106-3 | d-45 | e-1 | f-3 |
| 106-4 | d-45 | e-1 | f-4 |
| 106-5 | d-45 | e-1 | f-5 |
| 106-6 | d-45 | e-1 | f-6 |
| 106-7 | d-45 | e-1 | f-7 |
| 106-8 | d-45 | e-1 | f-8 |
| 106-9 | d-45 | e-1 | f-9 |
| 106-10 | d-45 | e-1 | f-10 |
| 106-11 | d-45 | e-1 | f-11 |
| 106-12 | d-45 | e-1 | f-12 |
| 106-13 | d-45 | e-1 | f-13 |
| 106-14 | d-45 | e-1 | f-14 |
| 106-15 | d-45 | e-1 | f-15 |
| 106-16 | d-45 | e-2 | f-1 |
| 106-17 | d-45 | e-2 | f-2 |
| 106-18 | d-45 | e-2 | f-3 |
| 106-19 | d-45 | e-2 | f-4 |
| 106-20 | d-45 | e-2 | f-5 |
| 106-21 | d-45 | e-2 | f-6 |
| 106-22 | d-45 | e-2 | f-7 |
| 106-23 | d-45 | e-2 | f-8 |
| 106-24 | d-45 | e-2 | f-9 |
| 106-25 | d-45 | e-2 | f-10 |
| 106-26 | d-45 | e-2 | f-11 |
| 106-27 | d-45 | e-2 | f-12 |
| 106-28 | d-45 | e-2 | f-13 |
| 106-29 | d-45 | e-2 | f-14 |
| 106-30 | d-45 | e-2 | f-15 |
| 106-31 | d-45 | e-3 | f-1 |
| 106-32 | d-45 | e-3 | f-2 |
| 106-33 | d-45 | e-3 | f-3 |
| 106-34 | d-45 | e-3 | f-4 |
| 106-35 | d-45 | e-3 | f-5 |
| 106-36 | d-45 | e-3 | f-6 |
| 106-37 | d-45 | e-3 | f-7 |
| 106-38 | d-45 | e-3 | f-8 |
| 106-39 | d-45 | e-3 | f-9 |
| 106-40 | d-45 | e-3 | f-10 |
| 106-41 | d-45 | e-3 | f-11 |
| 106-42 | d-45 | e-3 | f-12 |
| 106-43 | d-45 | e-3 | f-13 |
| 106-44 | d-45 | e-3 | f-14 |
| 106-45 | d-45 | e-3 | f-15 |
| 107-1 | d-46 | e-1 | f-1 |
| 107-2 | d-46 | e-1 | f-2 |
| 107-3 | d-46 | e-1 | f-3 |
| 107-4 | d-46 | e-1 | f-4 |
| 107-5 | d-46 | e-1 | f-5 |
| 107-6 | d-46 | e-1 | f-6 |
| 107-7 | d-46 | e-1 | f-7 |
| 107-8 | d-46 | e-1 | f-8 |
| 107-9 | d-46 | e-1 | f-9 |
| 107-10 | d-46 | e-1 | f-10 |
| 107-11 | d-46 | e-1 | f-11 |
| 107-12 | d-46 | e-1 | f-12 |
| 107-13 | d-46 | e-1 | f-13 |

TABLE 56-continued

| No. | R²" | B" | R¹" |
|---|---|---|---|
| 107-14 | d-46 | e-1 | f-14 |
| 107-15 | d-46 | e-1 | f-15 |
| 107-16 | d-46 | e-2 | f-1 |
| 107-17 | d-46 | e-2 | f-2 |
| 107-18 | d-46 | e-2 | f-3 |
| 107-19 | d-46 | e-2 | f-4 |
| 107-20 | d-46 | e-2 | f-5 |
| 107-21 | d-46 | e-2 | f-6 |
| 107-22 | d-46 | e-2 | f-7 |
| 107-23 | d-46 | e-2 | f-8 |
| 107-24 | d-46 | e-2 | f-9 |
| 107-25 | d-46 | e-2 | f-10 |
| 107-26 | d-46 | e-2 | f-11 |
| 107-27 | d-46 | e-2 | f-12 |
| 107-28 | d-46 | e-2 | f-13 |
| 107-29 | d-46 | e-2 | f-14 |
| 107-30 | d-46 | e-2 | f-15 |
| 107-31 | d-46 | e-3 | f-1 |
| 107-32 | d-46 | e-3 | f-2 |
| 107-33 | d-46 | e-3 | f-3 |
| 107-34 | d-46 | e-3 | f-4 |
| 107-35 | d-46 | e-3 | f-5 |
| 107-36 | d-46 | e-3 | f-6 |
| 107-37 | d-46 | e-3 | f-7 |
| 107-38 | d-46 | e-3 | f-8 |
| 107-39 | d-46 | e-3 | f-9 |
| 107-40 | d-46 | e-3 | f-10 |
| 107-41 | d-46 | e-3 | f-11 |
| 107-42 | d-46 | e-3 | f-12 |
| 107-43 | d-46 | e-3 | f-13 |
| 107-44 | d-46 | e-3 | f-14 |
| 107-45 | d-46 | e-3 | f-15 |

TABLE 57

| No. | R²" | B" | R¹" |
|---|---|---|---|
| 108-1 | d-47 | e-1 | f-1 |
| 108-2 | d-47 | e-1 | f-2 |
| 108-3 | d-47 | e-1 | f-3 |
| 108-4 | d-47 | e-1 | f-4 |
| 108-5 | d-47 | e-1 | f-5 |
| 108-6 | d-47 | e-1 | f-6 |
| 108-7 | d-47 | e-1 | f-7 |
| 108-8 | d-47 | e-1 | f-8 |
| 108-9 | d-47 | e-1 | f-9 |
| 108-10 | d-47 | e-1 | f-10 |
| 108-11 | d-47 | e-1 | f-11 |
| 108-12 | d-47 | e-1 | f-12 |
| 108-13 | d-47 | e-1 | f-13 |
| 108-14 | d-47 | e-1 | f-14 |
| 108-15 | d-47 | e-1 | f-15 |
| 108-16 | d-47 | e-2 | f-1 |
| 108-17 | d-47 | e-2 | f-2 |
| 108-18 | d-47 | e-2 | f-3 |
| 108-19 | d-47 | e-2 | f-4 |
| 108-20 | d-47 | e-2 | f-5 |
| 108-21 | d-47 | e-2 | f-6 |
| 108-22 | d-47 | e-2 | f-7 |
| 108-23 | d-47 | e-2 | f-8 |
| 108-24 | d-47 | e-2 | f-9 |
| 108-25 | d-47 | e-2 | f-10 |
| 108-26 | d-47 | e-2 | f-11 |
| 108-27 | d-47 | e-2 | f-12 |
| 108-28 | d-47 | e-2 | f-13 |
| 108-29 | d-47 | e-2 | f-14 |
| 108-30 | d-47 | e-2 | f-15 |
| 108-31 | d-47 | e-3 | f-1 |
| 108-32 | d-47 | e-3 | f-2 |
| 108-33 | d-47 | e-3 | f-3 |
| 108-34 | d-47 | e-3 | f-4 |
| 108-35 | d-47 | e-3 | f-5 |
| 108-36 | d-47 | e-3 | f-6 |
| 108-37 | d-47 | e-3 | f-7 |
| 108-38 | d-47 | e-3 | f-8 |

TABLE 57-continued

| No. | R²" | B" | R¹" |
|---|---|---|---|
| 108-39 | d-47 | e-3 | f-9 |
| 108-40 | d-47 | e-3 | f-10 |
| 108-41 | d-47 | e-3 | f-11 |
| 108-42 | d-47 | e-3 | f-12 |
| 108-43 | d-47 | e-3 | f-13 |
| 108-44 | d-47 | e-3 | f-14 |
| 108-45 | d-47 | e-3 | f-15 |
| 109-1 | d-48 | e-1 | f-1 |
| 109-2 | d-48 | e-1 | f-2 |
| 109-3 | d-48 | e-1 | f-3 |
| 109-4 | d-48 | e-1 | f-4 |
| 109-5 | d-48 | e-1 | f-5 |
| 109-6 | d-48 | e-1 | f-6 |
| 109-7 | d-48 | e-1 | f-7 |
| 109-8 | d-48 | e-1 | f-8 |
| 109-9 | d-48 | e-1 | f-9 |
| 109-10 | d-48 | e-1 | f-10 |
| 109-11 | d-48 | e-1 | f-11 |
| 109-12 | d-48 | e-1 | f-12 |
| 109-13 | d-48 | e-1 | f-13 |
| 109-14 | d-48 | e-1 | f-14 |
| 109-15 | d-48 | e-1 | f-15 |
| 109-16 | d-48 | e-2 | f-1 |
| 109-17 | d-48 | e-2 | f-2 |
| 109-18 | d-48 | e-2 | f-3 |
| 109-19 | d-48 | e-2 | f-4 |
| 109-20 | d-48 | e-2 | f-5 |
| 109-21 | d-48 | e-2 | f-6 |
| 109-22 | d-48 | e-2 | f-7 |
| 109-23 | d-48 | e-2 | f-8 |
| 109-24 | d-48 | e-2 | f-9 |
| 109-25 | d-48 | e-2 | f-10 |
| 109-26 | d-48 | e-2 | f-11 |
| 109-27 | d-48 | e-2 | f-12 |
| 109-28 | d-48 | e-2 | f-13 |
| 109-29 | d-48 | e-2 | f-14 |
| 109-30 | d-48 | e-2 | f-15 |
| 109-31 | d-48 | e-3 | f-1 |
| 109-32 | d-48 | e-3 | f-2 |
| 109-33 | d-48 | e-3 | f-3 |
| 109-34 | d-48 | e-3 | f-4 |
| 109-35 | d-48 | e-3 | f-5 |
| 109-36 | d-48 | e-3 | f-6 |
| 109-37 | d-48 | e-3 | f-7 |
| 109-38 | d-48 | e-3 | f-8 |
| 109-39 | d-48 | e-3 | f-9 |
| 109-40 | d-48 | e-3 | f-10 |
| 109-41 | d-48 | e-3 | f-11 |
| 109-42 | d-48 | e-3 | f-12 |
| 109-43 | d-48 | e-3 | f-13 |
| 109-44 | d-48 | e-3 | f-14 |
| 109-45 | d-48 | e-3 | f-15 |

TABLE 58

| No. | R²" | B" | R¹" |
|---|---|---|---|
| 110-1 | d-49 | e-1 | f-1 |
| 110-2 | d-49 | e-1 | f-2 |
| 110-3 | d-49 | e-1 | f-3 |
| 110-4 | d-49 | e-1 | f-4 |
| 110-5 | d-49 | e-1 | f-5 |
| 110-6 | d-49 | e-1 | f-6 |
| 110-7 | d-49 | e-1 | f-7 |
| 110-8 | d-49 | e-1 | f-8 |
| 110-9 | d-49 | e-1 | f-9 |
| 110-10 | d-49 | e-1 | f-10 |
| 110-11 | d-49 | e-1 | f-11 |
| 110-12 | d-49 | e-1 | f-12 |
| 110-13 | d-49 | e-1 | f-13 |
| 110-14 | d-49 | e-1 | f-14 |
| 110-15 | d-49 | e-1 | f-15 |
| 110-16 | d-49 | e-2 | f-1 |
| 110-17 | d-49 | e-2 | f-2 |
| 110-18 | d-49 | e-2 | f-3 |

TABLE 58-continued

| No. | R²" | B" | R¹" |
|---|---|---|---|
| 110-19 | d-49 | e-2 | f-4 |
| 110-20 | d-49 | e-2 | f-5 |
| 110-21 | d-49 | e-2 | f-6 |
| 110-22 | d-49 | e-2 | f-7 |
| 110-23 | d-49 | e-2 | f-8 |
| 110-24 | d-49 | e-2 | f-9 |
| 110-25 | d-49 | e-2 | f-10 |
| 110-26 | d-49 | e-2 | f-11 |
| 110-27 | d-49 | e-2 | f-12 |
| 110-28 | d-49 | e-2 | f-13 |
| 110-29 | d-49 | e-2 | f-14 |
| 110-30 | d-49 | e-2 | f-15 |
| 110-31 | d-49 | e-3 | f-1 |
| 110-32 | d-49 | e-3 | f-2 |
| 110-33 | d-49 | e-3 | f-3 |
| 110-34 | d-49 | e-3 | f-4 |
| 110-35 | d-49 | e-3 | f-5 |
| 110-36 | d-49 | e-3 | f-6 |
| 110-37 | d-49 | e-3 | f-7 |
| 110-38 | d-49 | e-3 | f-8 |
| 110-39 | d-49 | e-3 | f-9 |
| 110-40 | d-49 | e-3 | f-10 |
| 110-41 | d-49 | e-3 | f-11 |
| 110-42 | d-49 | e-3 | f-12 |
| 110-43 | d-49 | e-3 | f-13 |
| 110-44 | d-49 | e-3 | f-14 |
| 110-45 | d-49 | e-3 | f-15 |
| 111-1 | d-50 | e-1 | f-1 |
| 111-2 | d-50 | e-1 | f-2 |
| 111-3 | d-50 | e-1 | f-3 |
| 111-4 | d-50 | e-1 | f-4 |
| 111-5 | d-50 | e-1 | f-5 |
| 111-6 | d-50 | e-1 | f-6 |
| 111-7 | d-50 | e-1 | f-7 |
| 111-8 | d-50 | e-1 | f-8 |
| 111-9 | d-50 | e-1 | f-9 |
| 111-10 | d-50 | e-1 | f-10 |
| 111-11 | d-50 | e-1 | f-11 |
| 111-12 | d-50 | e-1 | f-12 |
| 111-13 | d-50 | e-1 | f-13 |
| 111-14 | d-50 | e-1 | f-14 |
| 111-15 | d-50 | e-1 | f-15 |
| 111-16 | d-50 | e-2 | f-1 |
| 111-17 | d-50 | e-2 | f-2 |
| 111-18 | d-50 | e-2 | f-3 |
| 111-19 | d-50 | e-2 | f-4 |
| 111-20 | d-50 | e-2 | f-5 |
| 111-21 | d-50 | e-2 | f-6 |
| 111-22 | d-50 | e-2 | f-7 |
| 111-23 | d-50 | e-2 | f-8 |
| 111-24 | d-50 | e-2 | f-9 |
| 111-25 | d-50 | e-2 | f-10 |
| 111-26 | d-50 | e-2 | f-11 |
| 111-27 | d-50 | e-2 | f-12 |
| 111-28 | d-50 | e-2 | f-13 |
| 111-29 | d-50 | e-2 | f-14 |
| 111-30 | d-50 | e-2 | f-15 |
| 111-31 | d-50 | e-3 | f-1 |
| 111-32 | d-50 | e-3 | f-2 |
| 111-33 | d-50 | e-3 | f-3 |
| 111-34 | d-50 | e-3 | f-4 |
| 111-35 | d-50 | e-3 | f-5 |
| 111-36 | d-50 | e-3 | f-6 |
| 111-37 | d-50 | e-3 | f-7 |
| 111-38 | d-50 | e-3 | f-8 |
| 111-39 | d-50 | e-3 | f-9 |
| 111-40 | d-50 | e-3 | f-10 |
| 111-41 | d-50 | e-3 | f-11 |
| 111-42 | d-50 | e-3 | f-12 |
| 111-43 | d-50 | e-3 | f-13 |
| 111-44 | d-50 | e-3 | f-14 |
| 111-45 | d-50 | e-3 | f-15 |

TABLE 59

| No. | R²″ | B″ | R¹″ |
|---|---|---|---|
| 112-1 | d-51 | e-1 | f-1 |
| 112-2 | d-51 | e-1 | f-2 |
| 112-3 | d-51 | e-1 | f-3 |
| 112-4 | d-51 | e-1 | f-4 |
| 112-5 | d-51 | e-1 | f-5 |
| 112-6 | d-51 | e-1 | f-6 |
| 112-7 | d-51 | e-1 | f-7 |
| 112-8 | d-51 | e-1 | f-8 |
| 112-9 | d-51 | e-1 | f-9 |
| 112-10 | d-51 | e-1 | f-10 |
| 112-11 | d-51 | e-1 | f-11 |
| 112-12 | d-51 | e-1 | f-12 |
| 112-13 | d-51 | e-1 | f-13 |
| 112-14 | d-51 | e-1 | f-14 |
| 112-15 | d-51 | e-1 | f-15 |
| 112-16 | d-51 | e-2 | f-1 |
| 112-17 | d-51 | e-2 | f-2 |
| 112-18 | d-51 | e-2 | f-3 |
| 112-19 | d-51 | e-2 | f-4 |
| 112-20 | d-51 | e-2 | f-5 |
| 112-21 | d-51 | e-2 | f-6 |
| 112-22 | d-51 | e-2 | f-7 |
| 112-23 | d-51 | e-2 | f-8 |
| 112-24 | d-51 | e-2 | f-9 |
| 112-25 | d-51 | e-2 | f-10 |
| 112-26 | d-51 | e-2 | f-11 |
| 112-27 | d-51 | e-2 | f-12 |
| 112-28 | d-51 | e-2 | f-13 |
| 112-29 | d-51 | e-2 | f-14 |
| 112-30 | d-51 | e-2 | f-15 |
| 112-31 | d-51 | e-3 | f-1 |
| 112-32 | d-51 | e-3 | f-2 |
| 112-33 | d-51 | e-3 | f-3 |
| 112-34 | d-51 | e-3 | f-4 |
| 112-35 | d-51 | e-3 | f-5 |
| 112-36 | d-51 | e-3 | f-6 |
| 112-37 | d-51 | e-3 | f-7 |
| 112-38 | d-51 | e-3 | f-8 |
| 112-39 | d-51 | e-3 | f-9 |
| 112-40 | d-51 | e-3 | f-10 |
| 112-41 | d-51 | e-3 | f-11 |
| 112-42 | d-51 | e-3 | f-12 |
| 112-43 | d-51 | e-3 | f-13 |
| 112-44 | d-51 | e-3 | f-14 |
| 112-45 | d-51 | e-3 | f-15 |
| 113-1 | d-52 | e-1 | f-1 |
| 113-2 | d-52 | e-1 | f-2 |
| 113-3 | d-52 | e-1 | f-3 |
| 113-4 | d-52 | e-1 | f-4 |
| 113-5 | d-52 | e-1 | f-5 |
| 113-6 | d-52 | e-1 | f-6 |
| 113-7 | d-52 | e-1 | f-7 |
| 113-8 | d-52 | e-1 | f-8 |
| 113-9 | d-52 | e-1 | f-9 |
| 113-10 | d-52 | e-1 | f-10 |
| 113-11 | d-52 | e-1 | f-11 |
| 113-12 | d-52 | e-1 | f-12 |
| 113-13 | d-52 | e-1 | f-13 |
| 113-14 | d-52 | e-1 | f-14 |
| 113-15 | d-52 | e-1 | f-15 |
| 113-16 | d-52 | e-2 | f-1 |
| 113-17 | d-52 | e-2 | f-2 |
| 113-18 | d-52 | e-2 | f-3 |
| 113-19 | d-52 | e-2 | f-4 |
| 113-20 | d-52 | e-2 | f-5 |
| 113-21 | d-52 | e-2 | f-6 |
| 113-22 | d-52 | e-2 | f-7 |
| 113-23 | d-52 | e-2 | f-8 |
| 113-24 | d-52 | e-2 | f-9 |
| 113-25 | d-52 | e-2 | f-10 |
| 113-26 | d-52 | e-2 | f-11 |
| 113-27 | d-52 | e-2 | f-12 |
| 113-28 | d-52 | e-2 | f-13 |
| 113-29 | d-52 | e-2 | f-14 |
| 113-30 | d-52 | e-2 | f-15 |
| 113-31 | d-52 | e-3 | f-1 |
| 113-32 | d-52 | e-3 | f-2 |
| 113-33 | d-52 | e-3 | f-3 |
| 113-34 | d-52 | e-3 | f-4 |
| 113-35 | d-52 | e-3 | f-5 |
| 113-36 | d-52 | e-3 | f-6 |
| 113-37 | d-52 | e-3 | f-7 |
| 113-38 | d-52 | e-3 | f-8 |
| 113-39 | d-52 | e-3 | f-9 |
| 113-40 | d-52 | e-3 | f-10 |
| 113-41 | d-52 | e-3 | f-11 |
| 113-42 | d-52 | e-3 | f-12 |
| 113-43 | d-52 | e-3 | f-13 |
| 113-44 | d-52 | e-3 | f-14 |
| 113-45 | d-52 | e-3 | f-15 |

TABLE 60

| No. | R²″ | B″ | R¹″ |
|---|---|---|---|
| 114-1 | d-53 | e-1 | f-1 |
| 114-2 | d-53 | e-1 | f-2 |
| 114-3 | d-53 | e-1 | f-3 |
| 114-4 | d-53 | e-1 | f-4 |
| 114-5 | d-53 | e-1 | f-5 |
| 114-6 | d-53 | e-1 | f-6 |
| 114-7 | d-53 | e-1 | f-7 |
| 114-8 | d-53 | e-1 | f-8 |
| 114-9 | d-53 | e-1 | f-9 |
| 114-10 | d-53 | e-1 | f-10 |
| 114-11 | d-53 | e-1 | f-11 |
| 114-12 | d-53 | e-1 | f-12 |
| 114-13 | d-53 | e-1 | f-13 |
| 114-14 | d-53 | e-1 | f-14 |
| 114-15 | d-53 | e-1 | f-15 |
| 114-16 | d-53 | e-2 | f-1 |
| 114-17 | d-53 | e-2 | f-2 |
| 114-18 | d-53 | e-2 | f-3 |
| 114-19 | d-53 | e-2 | f-4 |
| 114-20 | d-53 | e-2 | f-5 |
| 114-21 | d-53 | e-2 | f-6 |
| 114-22 | d-53 | e-2 | f-7 |
| 114-23 | d-53 | e-2 | f-8 |
| 114-24 | d-53 | e-2 | f-9 |
| 114-25 | d-53 | e-2 | f-10 |
| 114-26 | d-53 | e-2 | f-11 |
| 114-27 | d-53 | e-2 | f-12 |
| 114-28 | d-53 | e-2 | f-13 |
| 114-29 | d-53 | e-2 | f-14 |
| 114-30 | d-53 | e-2 | f-15 |
| 114-31 | d-53 | e-3 | f-1 |
| 114-32 | d-53 | e-3 | f-2 |
| 114-33 | d-53 | e-3 | f-3 |
| 114-34 | d-53 | e-3 | f-4 |
| 114-35 | d-53 | e-3 | f-5 |
| 114-36 | d-53 | e-3 | f-6 |
| 114-37 | d-53 | e-3 | f-7 |
| 114-38 | d-53 | e-3 | f-8 |
| 114-39 | d-53 | e-3 | f-9 |
| 114-40 | d-53 | e-3 | f-10 |
| 114-41 | d-53 | e-3 | f-11 |
| 114-42 | d-53 | e-3 | f-12 |
| 114-43 | d-53 | e-3 | f-13 |
| 114-44 | d-53 | e-3 | f-14 |
| 114-45 | d-53 | e-3 | f-15 |
| 115-1 | d-54 | e-1 | f-1 |
| 115-2 | d-54 | e-1 | f-2 |
| 115-3 | d-54 | e-1 | f-3 |
| 115-4 | d-54 | e-1 | f-4 |
| 115-5 | d-54 | e-1 | f-5 |
| 115-6 | d-54 | e-1 | f-6 |
| 115-7 | d-54 | e-1 | f-7 |
| 115-8 | d-54 | e-1 | f-8 |
| 115-9 | d-54 | e-1 | f-9 |
| 115-10 | d-54 | e-1 | f-10 |
| 115-11 | d-54 | e-1 | f-11 |
| 115-12 | d-54 | e-1 | f-12 |
| 115-13 | d-54 | e-1 | f-13 |

TABLE 60-continued

| No. | R²" | B" | R¹" |
|---|---|---|---|
| 115-14 | d-54 | e-1 | f-14 |
| 115-15 | d-54 | e-1 | f-15 |
| 115-16 | d-54 | e-2 | f-1 |
| 115-17 | d-54 | e-2 | f-2 |
| 115-18 | d-54 | e-2 | f-3 |
| 115-19 | d-54 | e-2 | f-4 |
| 115-20 | d-54 | e-2 | f-5 |
| 115-21 | d-54 | e-2 | f-6 |
| 115-22 | d-54 | e-2 | f-7 |
| 115-23 | d-54 | e-2 | f-8 |
| 115-24 | d-54 | e-2 | f-9 |
| 115-25 | d-54 | e-2 | f-10 |
| 115-26 | d-54 | e-2 | f-11 |
| 115-27 | d-54 | e-2 | f-12 |
| 115-28 | d-54 | e-2 | f-13 |
| 115-29 | d-54 | e-2 | f-14 |
| 115-30 | d-54 | e-2 | f-15 |
| 115-31 | d-54 | e-3 | f-1 |
| 115-32 | d-54 | e-3 | f-2 |
| 115-33 | d-54 | e-3 | f-3 |
| 115-34 | d-54 | e-3 | f-4 |
| 115-35 | d-54 | e-3 | f-5 |
| 115-36 | d-54 | e-3 | f-6 |
| 115-37 | d-54 | e-3 | f-7 |
| 115-38 | d-54 | e-3 | f-8 |
| 115-39 | d-54 | e-3 | f-9 |
| 115-40 | d-54 | e-3 | f-10 |
| 115-41 | d-54 | e-3 | f-11 |
| 115-42 | d-54 | e-3 | f-12 |
| 115-43 | d-54 | e-3 | f-13 |
| 115-44 | d-54 | e-3 | f-14 |
| 115-45 | d-54 | e-3 | f-15 |

TABLE 61

| No. | R²" | B" | R¹" |
|---|---|---|---|
| 116-1 | d-55 | e-1 | f-1 |
| 116-2 | d-55 | e-1 | f-2 |
| 116-3 | d-55 | e-1 | f-3 |
| 116-4 | d-55 | e-1 | f-4 |
| 116-5 | d-55 | e-1 | f-5 |
| 116-6 | d-55 | e-1 | f-6 |
| 116-7 | d-55 | e-1 | f-7 |
| 116-8 | d-55 | e-1 | f-8 |
| 116-9 | d-55 | e-1 | f-9 |
| 116-10 | d-55 | e-1 | f-10 |
| 116-11 | d-55 | e-1 | f-11 |
| 116-12 | d-55 | e-1 | f-12 |
| 116-13 | d-55 | e-1 | f-13 |
| 116-14 | d-55 | e-1 | f-14 |
| 116-15 | d-55 | e-1 | f-15 |
| 116-16 | d-55 | e-2 | f-1 |
| 116-17 | d-55 | e-2 | f-2 |
| 116-18 | d-55 | e-2 | f-3 |
| 116-19 | d-55 | e-2 | f-4 |
| 116-20 | d-55 | e-2 | f-5 |
| 116-21 | d-55 | e-2 | f-6 |
| 116-22 | d-55 | e-2 | f-7 |
| 116-23 | d-55 | e-2 | f-8 |
| 116-24 | d-55 | e-2 | f-9 |
| 116-25 | d-55 | e-2 | f-10 |
| 116-26 | d-55 | e-2 | f-11 |
| 116-27 | d-55 | e-2 | f-12 |
| 116-28 | d-55 | e-2 | f-13 |
| 116-29 | d-55 | e-2 | f-14 |
| 116-30 | d-55 | e-2 | f-15 |
| 116-31 | d-55 | e-3 | f-1 |
| 116-32 | d-55 | e-3 | f-2 |
| 116-33 | d-55 | e-3 | f-3 |
| 116-34 | d-55 | e-3 | f-4 |
| 116-35 | d-55 | e-3 | f-5 |
| 116-36 | d-55 | e-3 | f-6 |
| 116-37 | d-55 | e-3 | f-7 |
| 116-38 | d-55 | e-3 | f-8 |

TABLE 61-continued

| No. | R²" | B" | R¹" |
|---|---|---|---|
| 116-39 | d-55 | e-3 | f-9 |
| 116-40 | d-55 | e-3 | f-10 |
| 116-41 | d-55 | e-3 | f-11 |
| 116-42 | d-55 | e-3 | f-12 |
| 116-43 | d-55 | e-3 | f-13 |
| 116-44 | d-55 | e-3 | f-14 |
| 116-45 | d-55 | e-3 | f-15 |
| 117-1 | d-56 | e-1 | f-1 |
| 117-2 | d-56 | e-1 | f-2 |
| 117-3 | d-56 | e-1 | f-3 |
| 117-4 | d-56 | e-1 | f-4 |
| 117-5 | d-56 | e-1 | f-5 |
| 117-6 | d-56 | e-1 | f-6 |
| 117-7 | d-56 | e-1 | f-7 |
| 117-8 | d-56 | e-1 | f-8 |
| 117-9 | d-56 | e-1 | f-9 |
| 117-10 | d-56 | e-1 | f-10 |
| 117-11 | d-56 | e-1 | f-11 |
| 117-12 | d-56 | e-1 | f-12 |
| 117-13 | d-56 | e-1 | f-13 |
| 117-14 | d-56 | e-1 | f-14 |
| 117-15 | d-56 | e-1 | f-15 |
| 117-16 | d-56 | e-2 | f-1 |
| 117-17 | d-56 | e-2 | f-2 |
| 117-18 | d-56 | e-2 | f-3 |
| 117-19 | d-56 | e-2 | f-4 |
| 117-20 | d-56 | e-2 | f-5 |
| 117-21 | d-56 | e-2 | f-6 |
| 117-22 | d-56 | e-2 | f-7 |
| 117-23 | d-56 | e-2 | f-8 |
| 117-24 | d-56 | e-2 | f-9 |
| 117-25 | d-56 | e-2 | f-10 |
| 117-26 | d-56 | e-2 | f-11 |
| 117-27 | d-56 | e-2 | f-12 |
| 117-28 | d-56 | e-2 | f-13 |
| 117-29 | d-56 | e-2 | f-14 |
| 117-30 | d-56 | e-2 | f-15 |
| 117-31 | d-56 | e-3 | f-1 |
| 117-32 | d-56 | e-3 | f-2 |
| 117-33 | d-56 | e-3 | f-3 |
| 117-34 | d-56 | e-3 | f-4 |
| 117-35 | d-56 | e-3 | f-5 |
| 117-36 | d-56 | e-3 | f-6 |
| 117-37 | d-56 | e-3 | f-7 |
| 117-38 | d-56 | e-3 | f-8 |
| 117-39 | d-56 | e-3 | f-9 |
| 117-40 | d-56 | e-3 | f-10 |
| 117-41 | d-56 | e-3 | f-11 |
| 117-42 | d-56 | e-3 | f-12 |
| 117-43 | d-56 | e-3 | f-13 |
| 117-44 | d-56 | e-3 | f-14 |
| 117-45 | d-56 | e-3 | f-15 |

TABLE 62

| No. | R²" | B" | R¹" |
|---|---|---|---|
| 118-1 | d-57 | e-1 | f-1 |
| 118-2 | d-57 | e-1 | f-2 |
| 118-3 | d-57 | e-1 | f-3 |
| 118-4 | d-57 | e-1 | f-4 |
| 118-5 | d-57 | e-1 | f-5 |
| 118-6 | d-57 | e-1 | f-6 |
| 118-7 | d-57 | e-1 | f-7 |
| 118-8 | d-57 | e-1 | f-8 |
| 118-9 | d-57 | e-1 | f-9 |
| 118-10 | d-57 | e-1 | f-10 |
| 118-11 | d-57 | e-1 | f-11 |
| 118-12 | d-57 | e-1 | f-12 |
| 118-13 | d-57 | e-1 | f-13 |
| 118-14 | d-57 | e-1 | f-14 |
| 118-15 | d-57 | e-1 | f-15 |
| 118-16 | d-57 | e-2 | f-1 |
| 118-17 | d-57 | e-2 | f-2 |
| 118-18 | d-57 | e-2 | f-3 |

TABLE 62-continued

| No. | R²″ | B″ | R¹″ |
|---|---|---|---|
| 118-19 | d-57 | e-2 | f-4 |
| 118-20 | d-57 | e-2 | f-5 |
| 118-21 | d-57 | e-2 | f-6 |
| 118-22 | d-57 | e-2 | f-7 |
| 118-23 | d-57 | e-2 | f-8 |
| 118-24 | d-57 | e-2 | f-9 |
| 118-25 | d-57 | e-2 | f-10 |
| 118-26 | d-57 | e-2 | f-11 |
| 118-27 | d-57 | e-2 | f-12 |
| 118-28 | d-57 | e-2 | f-13 |
| 118-29 | d-57 | e-2 | f-14 |
| 118-30 | d-57 | e-2 | f-15 |
| 118-31 | d-57 | e-3 | f-1 |
| 118-32 | d-57 | e-3 | f-2 |
| 118-33 | d-57 | e-3 | f-3 |
| 118-34 | d-57 | e-3 | f-4 |
| 118-35 | d-57 | e-3 | f-5 |
| 118-36 | d-57 | e-3 | f-6 |
| 118-37 | d-57 | e-3 | f-7 |
| 118-38 | d-57 | e-3 | f-8 |
| 118-39 | d-57 | e-3 | f-9 |
| 118-40 | d-57 | e-3 | f-10 |
| 118-41 | d-57 | e-3 | f-11 |
| 118-42 | d-57 | e-3 | f-12 |
| 118-43 | d-57 | e-3 | f-13 |
| 118-44 | d-57 | e-3 | f-14 |
| 118-45 | d-57 | e-3 | f-15 |
| 119-1 | d-58 | e-1 | f-1 |
| 119-2 | d-58 | e-1 | f-2 |
| 119-3 | d-58 | e-1 | f-3 |
| 119-4 | d-58 | e-1 | f-4 |
| 119-5 | d-58 | e-1 | f-5 |
| 119-6 | d-58 | e-1 | f-6 |
| 119-7 | d-58 | e-1 | f-7 |
| 119-8 | d-58 | e-1 | f-8 |
| 119-9 | d-58 | e-1 | f-9 |
| 119-10 | d-58 | e-1 | f-10 |
| 119-11 | d-58 | e-1 | f-11 |
| 119-12 | d-58 | e-1 | f-12 |
| 119-13 | d-58 | e-1 | f-13 |
| 119-14 | d-58 | e-1 | f-14 |
| 119-15 | d-58 | e-1 | f-15 |
| 119-16 | d-58 | e-2 | f-1 |
| 119-17 | d-58 | e-2 | f-2 |
| 119-18 | d-58 | e-2 | f-3 |
| 119-19 | d-58 | e-2 | f-4 |
| 119-20 | d-58 | e-2 | f-5 |
| 119-21 | d-58 | e-2 | f-6 |
| 119-22 | d-58 | e-2 | f-7 |
| 119-23 | d-58 | e-2 | f-8 |
| 119-24 | d-58 | e-2 | f-9 |
| 119-25 | d-58 | e-2 | f-10 |
| 119-26 | d-58 | e-2 | f-11 |
| 119-27 | d-58 | e-2 | f-12 |
| 119-28 | d-58 | e-2 | f-13 |
| 119-29 | d-58 | e-2 | f-14 |
| 119-30 | d-58 | e-2 | f-15 |
| 119-31 | d-58 | e-3 | f-1 |
| 119-32 | d-58 | e-3 | f-2 |
| 119-33 | d-58 | e-3 | f-3 |
| 119-34 | d-58 | e-3 | f-4 |
| 119-35 | d-58 | e-3 | f-5 |
| 119-36 | d-58 | e-3 | f-6 |
| 119-37 | d-58 | e-3 | f-7 |
| 119-38 | d-58 | e-3 | f-8 |
| 119-39 | d-58 | e-3 | f-9 |
| 119-40 | d-58 | e-3 | f-10 |
| 119-41 | d-58 | e-3 | f-11 |
| 119-42 | d-58 | e-3 | f-12 |
| 119-43 | d-58 | e-3 | f-13 |
| 119-44 | d-58 | e-3 | f-14 |
| 119-45 | d-58 | e-3 | f-15 |

TABLE 63

| No. | R²″ | B″ | R¹″ |
|---|---|---|---|
| 120-1 | d-59 | e-1 | f-1 |
| 120-2 | d-59 | e-1 | f-2 |
| 120-3 | d-59 | e-1 | f-3 |
| 120-4 | d-59 | e-1 | f-4 |
| 120-5 | d-59 | e-1 | f-5 |
| 120-6 | d-59 | e-1 | f-6 |
| 120-7 | d-59 | e-1 | f-7 |
| 120-8 | d-59 | e-1 | f-8 |
| 120-9 | d-59 | e-1 | f-9 |
| 120-10 | d-59 | e-1 | f-10 |
| 120-11 | d-59 | e-1 | f-11 |
| 120-12 | d-59 | e-1 | f-12 |
| 120-13 | d-59 | e-1 | f-13 |
| 120-14 | d-59 | e-1 | f-14 |
| 120-15 | d-59 | e-1 | f-15 |
| 120-16 | d-59 | e-2 | f-1 |
| 120-17 | d-59 | e-2 | f-2 |
| 120-18 | d-59 | e-2 | f-3 |
| 120-19 | d-59 | e-2 | f-4 |
| 120-20 | d-59 | e-2 | f-5 |
| 120-21 | d-59 | e-2 | f-6 |
| 120-22 | d-59 | e-2 | f-7 |
| 120-23 | d-59 | e-2 | f-8 |
| 120-24 | d-59 | e-2 | f-9 |
| 120-25 | d-59 | e-2 | f-10 |
| 120-26 | d-59 | e-2 | f-11 |
| 120-27 | d-59 | e-2 | f-12 |
| 120-28 | d-59 | e-2 | f-13 |
| 120-29 | d-59 | e-2 | f-14 |
| 120-30 | d-59 | e-2 | f-15 |
| 120-31 | d-59 | e-3 | f-1 |
| 120-32 | d-59 | e-3 | f-2 |
| 120-33 | d-59 | e-3 | f-3 |
| 120-34 | d-59 | e-3 | f-4 |
| 120-35 | d-59 | e-3 | f-5 |
| 120-36 | d-59 | e-3 | f-6 |
| 120-37 | d-59 | e-3 | f-7 |
| 120-38 | d-59 | e-3 | f-8 |
| 120-39 | d-59 | e-3 | f-9 |
| 120-40 | d-59 | e-3 | f-10 |
| 120-41 | d-59 | e-3 | f-11 |
| 120-42 | d-59 | e-3 | f-12 |
| 120-43 | d-59 | e-3 | f-13 |
| 120-44 | d-59 | e-3 | f-14 |
| 120-45 | d-59 | e-3 | f-15 |
| 121-1 | d-60 | e-1 | f-1 |
| 121-2 | d-60 | e-1 | f-2 |
| 121-3 | d-60 | e-1 | f-3 |
| 121-4 | d-60 | e-1 | f-4 |
| 121-5 | d-60 | e-1 | f-5 |
| 121-6 | d-60 | e-1 | f-6 |
| 121-7 | d-60 | e-1 | f-7 |
| 121-8 | d-60 | e-1 | f-8 |
| 121-9 | d-60 | e-1 | f-9 |
| 121-10 | d-60 | e-1 | f-10 |
| 121-11 | d-60 | e-1 | f-11 |
| 121-12 | d-60 | e-1 | f-12 |
| 121-13 | d-60 | e-1 | f-13 |
| 121-14 | d-60 | e-1 | f-14 |
| 121-15 | d-60 | e-1 | f-15 |
| 121-16 | d-60 | e-2 | f-1 |
| 121-17 | d-60 | e-2 | f-2 |
| 121-18 | d-60 | e-2 | f-3 |
| 121-19 | d-60 | e-2 | f-4 |
| 121-20 | d-60 | e-2 | f-5 |
| 121-21 | d-60 | e-2 | f-6 |
| 121-22 | d-60 | e-2 | f-7 |
| 121-23 | d-60 | e-2 | f-8 |
| 121-24 | d-60 | e-2 | f-9 |
| 121-25 | d-60 | e-2 | f-10 |
| 121-26 | d-60 | e-2 | f-11 |
| 121-27 | d-60 | e-2 | f-12 |
| 121-28 | d-60 | e-2 | f-13 |
| 121-29 | d-60 | e-2 | f-14 |
| 121-30 | d-60 | e-2 | f-15 |
| 121-31 | d-60 | e-3 | f-1 |
| 121-32 | d-60 | e-3 | f-2 |
| 121-33 | d-60 | e-3 | f-3 |

TABLE 63-continued

| No. | R²" | B" | R¹" |
| --- | --- | --- | --- |
| 121-34 | d-60 | e-3 | f-4 |
| 121-35 | d-60 | e-3 | f-5 |
| 121-36 | d-60 | e-3 | f-6 |
| 121-37 | d-60 | e-3 | f-7 |
| 121-38 | d-60 | e-3 | f-8 |
| 121-39 | d-60 | e-3 | f-9 |
| 121-40 | d-60 | e-3 | f-10 |
| 121-41 | d-60 | e-3 | f-11 |
| 121-42 | d-60 | e-3 | f-12 |
| 121-43 | d-60 | e-3 | f-13 |
| 121-44 | d-60 | e-3 | f-14 |
| 121-45 | d-60 | e-3 | f-15 |

TABLE 64

| No. | R²" | B" | R¹" |
| --- | --- | --- | --- |
| 122-1 | d-61 | e-1 | f-1 |
| 122-2 | d-61 | e-1 | f-2 |
| 122-3 | d-61 | e-1 | f-3 |
| 122-4 | d-61 | e-1 | f-4 |
| 122-5 | d-61 | e-1 | f-5 |
| 122-6 | d-61 | e-1 | f-6 |
| 122-7 | d-61 | e-1 | f-7 |
| 122-8 | d-61 | e-1 | f-8 |
| 122-9 | d-61 | e-1 | f-9 |
| 122-10 | d-61 | e-1 | f-10 |
| 122-11 | d-61 | e-1 | f-11 |
| 122-12 | d-61 | e-1 | f-12 |
| 122-13 | d-61 | e-1 | f-13 |
| 122-14 | d-61 | e-1 | f-14 |
| 122-15 | d-61 | e-1 | f-15 |
| 122-16 | d-61 | e-2 | f-1 |
| 122-17 | d-61 | e-2 | f-2 |
| 122-18 | d-61 | e-2 | f-3 |
| 122-19 | d-61 | e-2 | f-4 |
| 122-20 | d-61 | e-2 | f-5 |
| 122-21 | d-61 | e-2 | f-6 |
| 122-22 | d-61 | e-2 | f-7 |
| 122-23 | d-61 | e-2 | f-8 |
| 122-24 | d-61 | e-2 | f-9 |
| 122-25 | d-61 | e-2 | f-10 |
| 122-26 | d-61 | e-2 | f-11 |
| 122-27 | d-61 | e-2 | f-12 |
| 122-28 | d-61 | e-2 | f-13 |
| 122-29 | d-61 | e-2 | f-14 |
| 122-30 | d-61 | e-2 | f-15 |
| 122-31 | d-61 | e-3 | f-1 |
| 122-32 | d-61 | e-3 | f-2 |
| 122-33 | d-61 | e-3 | f-3 |
| 122-34 | d-61 | e-3 | f-4 |
| 122-35 | d-61 | e-3 | f-5 |
| 122-36 | d-61 | e-3 | f-6 |
| 122-37 | d-61 | e-3 | f-7 |
| 122-38 | d-61 | e-3 | f-8 |
| 122-39 | d-61 | e-3 | f-9 |
| 122-40 | d-61 | e-3 | f-10 |
| 122-41 | d-61 | e-3 | f-11 |
| 122-42 | d-61 | e-3 | f-12 |
| 122-43 | d-61 | e-3 | f-13 |
| 122-44 | d-61 | e-3 | f-14 |
| 122-45 | d-61 | e-3 | f-15 |
| 123-1 | d-62 | e-1 | f-1 |
| 123-2 | d-62 | e-1 | f-2 |
| 123-3 | d-62 | e-1 | f-3 |
| 123-4 | d-62 | e-1 | f-4 |
| 123-5 | d-62 | e-1 | f-5 |
| 123-6 | d-62 | e-1 | f-6 |
| 123-7 | d-62 | e-1 | f-7 |
| 123-8 | d-62 | e-1 | f-8 |
| 123-9 | d-62 | e-1 | f-9 |
| 123-10 | d-62 | e-1 | f-10 |
| 123-11 | d-62 | e-1 | f-11 |
| 123-12 | d-62 | e-1 | f-12 |
| 123-13 | d-62 | e-1 | f-13 |

TABLE 64-continued

| No. | R²" | B" | R¹" |
| --- | --- | --- | --- |
| 123-14 | d-62 | e-1 | f-14 |
| 123-15 | d-62 | e-1 | f-15 |
| 123-16 | d-62 | e-2 | f-1 |
| 123-17 | d-62 | e-2 | f-2 |
| 123-18 | d-62 | e-2 | f-3 |
| 123-19 | d-62 | e-2 | f-4 |
| 123-20 | d-62 | e-2 | f-5 |
| 123-21 | d-62 | e-2 | f-6 |
| 123-22 | d-62 | e-2 | f-7 |
| 123-23 | d-62 | e-2 | f-8 |
| 123-24 | d-62 | e-2 | f-9 |
| 123-25 | d-62 | e-2 | f-10 |
| 123-26 | d-62 | e-2 | f-11 |
| 123-27 | d-62 | e-2 | f-12 |
| 123-28 | d-62 | e-2 | f-13 |
| 123-29 | d-62 | e-2 | f-14 |
| 123-30 | d-62 | e-2 | f-15 |
| 123-31 | d-62 | e-3 | f-1 |
| 123-32 | d-62 | e-3 | f-2 |
| 123-33 | d-62 | e-3 | f-3 |
| 123-34 | d-62 | e-3 | f-4 |
| 123-35 | d-62 | e-3 | f-5 |
| 123-36 | d-62 | e-3 | f-6 |
| 123-37 | d-62 | e-3 | f-7 |
| 123-38 | d-62 | e-3 | f-8 |
| 123-39 | d-62 | e-3 | f-9 |
| 123-40 | d-62 | e-3 | f-10 |
| 123-41 | d-62 | e-3 | f-11 |
| 123-42 | d-62 | e-3 | f-12 |
| 123-43 | d-62 | e-3 | f-13 |
| 123-44 | d-62 | e-3 | f-14 |
| 123-45 | d-62 | e-3 | f-15 |

TABLE 65

| No. | R²" | B" | R¹" |
| --- | --- | --- | --- |
| 124-1 | d-63 | e-1 | f-1 |
| 124-2 | d-63 | e-1 | f-2 |
| 124-3 | d-63 | e-1 | f-3 |
| 124-4 | d-63 | e-1 | f-4 |
| 124-5 | d-63 | e-1 | f-5 |
| 124-6 | d-63 | e-1 | f-6 |
| 124-7 | d-63 | e-1 | f-7 |
| 124-8 | d-63 | e-1 | f-8 |
| 124-9 | d-63 | e-1 | f-9 |
| 124-10 | d-63 | e-1 | f-10 |
| 124-11 | d-63 | e-1 | f-11 |
| 124-12 | d-63 | e-1 | f-12 |
| 124-13 | d-63 | e-1 | f-13 |
| 124-14 | d-63 | e-1 | f-14 |
| 124-15 | d-63 | e-1 | f-15 |
| 124-16 | d-63 | e-2 | f-1 |
| 124-17 | d-63 | e-2 | f-2 |
| 124-18 | d-63 | e-2 | f-3 |
| 124-19 | d-63 | e-2 | f-4 |
| 124-20 | d-63 | e-2 | f-5 |
| 124-21 | d-63 | e-2 | f-6 |
| 124-22 | d-63 | e-2 | f-7 |
| 124-23 | d-63 | e-2 | f-8 |
| 124-24 | d-63 | e-2 | f-9 |
| 124-25 | d-63 | e-2 | f-10 |
| 124-26 | d-63 | e-2 | f-11 |
| 124-27 | d-63 | e-2 | f-12 |
| 124-28 | d-63 | e-2 | f-13 |
| 124-29 | d-63 | e-2 | f-14 |
| 124-30 | d-63 | e-2 | f-15 |
| 124-31 | d-63 | e-3 | f-1 |
| 124-32 | d-63 | e-3 | f-2 |
| 124-33 | d-63 | e-3 | f-3 |
| 124-34 | d-63 | e-3 | f-4 |
| 124-35 | d-63 | e-3 | f-5 |
| 124-36 | d-63 | e-3 | f-6 |
| 124-37 | d-63 | e-3 | f-7 |
| 124-38 | d-63 | e-3 | f-8 |

TABLE 65-continued

| No. | R²" | B" | R¹" |
|---|---|---|---|
| 124-39 | d-63 | e-3 | f-9 |
| 124-40 | d-63 | e-3 | f-10 |
| 124-41 | d-63 | e-3 | f-11 |
| 124-42 | d-63 | e-3 | f-12 |
| 124-43 | d-63 | e-3 | f-13 |
| 124-44 | d-63 | e-3 | f-14 |
| 124-45 | d-63 | e-3 | f-15 |
| 125-1 | d-64 | e-1 | f-1 |
| 125-2 | d-64 | e-1 | f-2 |
| 125-3 | d-64 | e-1 | f-3 |
| 125-4 | d-64 | e-1 | f-4 |
| 125-5 | d-64 | e-1 | f-5 |
| 125-6 | d-64 | e-1 | f-6 |
| 125-7 | d-64 | e-1 | f-7 |
| 125-8 | d-64 | e-1 | f-8 |
| 125-9 | d-64 | e-1 | f-9 |
| 125-10 | d-64 | e-1 | f-10 |
| 125-11 | d-64 | e-1 | f-11 |
| 125-12 | d-64 | e-1 | f-12 |
| 125-13 | d-64 | e-1 | f-13 |
| 125-14 | d-64 | e-1 | f-14 |
| 125-15 | d-64 | e-1 | f-15 |
| 125-16 | d-64 | e-2 | f-1 |
| 125-17 | d-64 | e-2 | f-2 |
| 125-18 | d-64 | e-2 | f-3 |
| 125-19 | d-64 | e-2 | f-4 |
| 125-20 | d-64 | e-2 | f-5 |
| 125-21 | d-64 | e-2 | f-6 |
| 125-22 | d-64 | e-2 | f-7 |
| 125-23 | d-64 | e-2 | f-8 |
| 125-24 | d-64 | e-2 | f-9 |
| 125-25 | d-64 | e-2 | f-10 |
| 125-26 | d-64 | e-2 | f-11 |
| 125-27 | d-64 | e-2 | f-12 |
| 125-28 | d-64 | e-2 | f-13 |
| 125-29 | d-64 | e-2 | f-14 |
| 125-30 | d-64 | e-2 | f-15 |
| 125-31 | d-64 | e-3 | f-1 |
| 125-32 | d-64 | e-3 | f-2 |
| 125-33 | d-64 | e-3 | f-3 |
| 125-34 | d-64 | e-3 | f-4 |
| 125-35 | d-64 | e-3 | f-5 |
| 125-36 | d-64 | e-3 | f-6 |
| 125-37 | d-64 | e-3 | f-7 |
| 125-38 | d-64 | e-3 | f-8 |
| 125-39 | d-64 | e-3 | f-9 |
| 125-40 | d-64 | e-3 | f-10 |
| 125-41 | d-64 | e-3 | f-11 |
| 125-42 | d-64 | e-3 | f-12 |
| 125-43 | d-64 | e-3 | f-13 |
| 125-44 | d-64 | e-3 | f-14 |
| 125-45 | d-64 | e-3 | f-15 |

TABLE 66

| No. | R²" | B" | R¹" |
|---|---|---|---|
| 126-1 | d-65 | e-1 | f-1 |
| 126-2 | d-65 | e-1 | f-2 |
| 126-3 | d-65 | e-1 | f-3 |
| 126-4 | d-65 | e-1 | f-4 |
| 126-5 | d-65 | e-1 | f-5 |
| 126-6 | d-65 | e-1 | f-6 |
| 126-7 | d-65 | e-1 | f-7 |
| 126-8 | d-65 | e-1 | f-8 |
| 126-9 | d-65 | e-1 | f-9 |
| 126-10 | d-65 | e-1 | f-10 |
| 126-11 | d-65 | e-1 | f-11 |
| 126-12 | d-65 | e-1 | f-12 |
| 126-13 | d-65 | e-1 | f-13 |
| 126-14 | d-65 | e-1 | f-14 |
| 126-15 | d-65 | e-1 | f-15 |
| 126-16 | d-65 | e-2 | f-1 |
| 126-17 | d-65 | e-2 | f-2 |
| 126-18 | d-65 | e-2 | f-3 |

TABLE 66-continued

| No. | R²" | B" | R¹" |
|---|---|---|---|
| 126-19 | d-65 | e-2 | f-4 |
| 126-20 | d-65 | e-2 | f-5 |
| 126-21 | d-65 | e-2 | f-6 |
| 126-22 | d-65 | e-2 | f-7 |
| 126-23 | d-65 | e-2 | f-8 |
| 126-24 | d-65 | e-2 | f-9 |
| 126-25 | d-65 | e-2 | f-10 |
| 126-26 | d-65 | e-2 | f-11 |
| 126-27 | d-65 | e-2 | f-12 |
| 126-28 | d-65 | e-2 | f-13 |
| 126-29 | d-65 | e-2 | f-14 |
| 126-30 | d-65 | e-2 | f-15 |
| 126-31 | d-65 | e-3 | f-1 |
| 126-32 | d-65 | e-3 | f-2 |
| 126-33 | d-65 | e-3 | f-3 |
| 126-34 | d-65 | e-3 | f-4 |
| 126-35 | d-65 | e-3 | f-5 |
| 126-36 | d-65 | e-3 | f-6 |
| 126-37 | d-65 | e-3 | f-7 |
| 126-38 | d-65 | e-3 | f-8 |
| 126-39 | d-65 | e-3 | f-9 |
| 126-40 | d-65 | e-3 | f-10 |
| 126-41 | d-65 | e-3 | f-11 |
| 126-42 | d-65 | e-3 | f-12 |
| 126-43 | d-65 | e-3 | f-13 |
| 126-44 | d-65 | e-3 | f-14 |
| 126-45 | d-65 | e-3 | f-15 |
| 127-1 | d-66 | e-1 | f-1 |
| 127-2 | d-66 | e-1 | f-2 |
| 127-3 | d-66 | e-1 | f-3 |
| 127-4 | d-66 | e-1 | f-4 |
| 127-5 | d-66 | e-1 | f-5 |
| 127-6 | d-66 | e-1 | f-6 |
| 127-7 | d-66 | e-1 | f-7 |
| 127-8 | d-66 | e-1 | f-8 |
| 127-9 | d-66 | e-1 | f-9 |
| 127-10 | d-66 | e-1 | f-10 |
| 127-11 | d-66 | e-1 | f-11 |
| 127-12 | d-66 | e-1 | f-12 |
| 127-13 | d-66 | e-1 | f-13 |
| 127-14 | d-66 | e-1 | f-14 |
| 127-15 | d-66 | e-1 | f-15 |
| 127-16 | d-66 | e-2 | f-1 |
| 127-17 | d-66 | e-2 | f-2 |
| 127-18 | d-66 | e-2 | f-3 |
| 127-19 | d-66 | e-2 | f-4 |
| 127-20 | d-66 | e-2 | f-5 |
| 127-21 | d-66 | e-2 | f-6 |
| 127-22 | d-66 | e-2 | f-7 |
| 127-23 | d-66 | e-2 | f-8 |
| 127-24 | d-66 | e-2 | f-9 |
| 127-25 | d-66 | e-2 | f-10 |
| 127-26 | d-66 | e-2 | f-11 |
| 127-27 | d-66 | e-2 | f-12 |
| 127-28 | d-66 | e-2 | f-13 |
| 127-29 | d-66 | e-2 | f-14 |
| 127-30 | d-66 | e-2 | f-15 |
| 127-31 | d-66 | e-3 | f-1 |
| 127-32 | d-66 | e-3 | f-2 |
| 127-33 | d-66 | e-3 | f-3 |
| 127-34 | d-66 | e-3 | f-4 |
| 127-35 | d-66 | e-3 | f-5 |
| 127-36 | d-66 | e-3 | f-6 |
| 127-37 | d-66 | e-3 | f-7 |
| 127-38 | d-66 | e-3 | f-8 |
| 127-39 | d-66 | e-3 | f-9 |
| 127-40 | d-66 | e-3 | f-10 |
| 127-41 | d-66 | e-3 | f-11 |
| 127-42 | d-66 | e-3 | f-12 |
| 127-43 | d-66 | e-3 | f-13 |
| 127-44 | d-66 | e-3 | f-14 |
| 127-45 | d-66 | e-3 | f-15 |

TABLE 67

| No. | R²″ | B″ | R¹″ |
|---|---|---|---|
| 128-1 | d-67 | e-1 | f-1 |
| 128-2 | d-67 | e-1 | f-2 |
| 128-3 | d-67 | e-1 | f-3 |
| 128-4 | d-67 | e-1 | f-4 |
| 128-5 | d-67 | e-1 | f-5 |
| 128-6 | d-67 | e-1 | f-6 |
| 128-7 | d-67 | e-1 | f-7 |
| 128-8 | d-67 | e-1 | f-8 |
| 128-9 | d-67 | e-1 | f-9 |
| 128-10 | d-67 | e-1 | f-10 |
| 128-11 | d-67 | e-1 | f-11 |
| 128-12 | d-67 | e-1 | f-12 |
| 128-13 | d-67 | e-1 | f-13 |
| 128-14 | d-67 | e-1 | f-14 |
| 128-15 | d-67 | e-1 | f-15 |
| 128-16 | d-67 | e-2 | f-1 |
| 128-17 | d-67 | e-2 | f-2 |
| 128-18 | d-67 | e-2 | f-3 |
| 128-19 | d-67 | e-2 | f-4 |
| 128-20 | d-67 | e-2 | f-5 |
| 128-21 | d-67 | e-2 | f-6 |
| 128-22 | d-67 | e-2 | f-7 |
| 128-23 | d-67 | e-2 | f-8 |
| 128-24 | d-67 | e-2 | f-9 |
| 128-25 | d-67 | e-2 | f-10 |
| 128-26 | d-67 | e-2 | f-11 |
| 128-27 | d-67 | e-2 | f-12 |
| 128-28 | d-67 | e-2 | f-13 |
| 128-29 | d-67 | e-2 | f-14 |
| 128-30 | d-67 | e-2 | f-15 |
| 128-31 | d-67 | e-3 | f-1 |
| 128-32 | d-67 | e-3 | f-2 |
| 128-33 | d-67 | e-3 | f-3 |
| 128-34 | d-67 | e-3 | f-4 |
| 128-35 | d-67 | e-3 | f-5 |
| 128-36 | d-67 | e-3 | f-6 |
| 128-37 | d-67 | e-3 | f-7 |
| 128-38 | d-67 | e-3 | f-8 |
| 128-39 | d-67 | e-3 | f-9 |
| 128-40 | d-67 | e-3 | f-10 |
| 128-41 | d-67 | e-3 | f-11 |
| 128-42 | d-67 | e-3 | f-12 |
| 128-43 | d-67 | e-3 | f-13 |
| 128-44 | d-67 | e-3 | f-14 |
| 128-45 | d-67 | e-3 | f-15 |
| 129-1 | d-68 | e-1 | f-1 |
| 129-2 | d-68 | e-1 | f-2 |
| 129-3 | d-68 | e-1 | f-3 |
| 129-4 | d-68 | e-1 | f-4 |
| 129-5 | d-68 | e-1 | f-5 |
| 129-6 | d-68 | e-1 | f-6 |
| 129-7 | d-68 | e-1 | f-7 |
| 129-8 | d-68 | e-1 | f-8 |
| 129-9 | d-68 | e-1 | f-9 |
| 129-10 | d-68 | e-1 | f-10 |
| 129-11 | d-68 | e-1 | f-11 |
| 129-12 | d-68 | e-1 | f-12 |
| 129-13 | d-68 | e-1 | f-13 |
| 129-14 | d-68 | e-1 | f-14 |
| 129-15 | d-68 | e-1 | f-15 |
| 129-16 | d-68 | e-2 | f-1 |
| 129-17 | d-68 | e-2 | f-2 |
| 129-18 | d-68 | e-2 | f-3 |
| 129-19 | d-68 | e-2 | f-4 |
| 129-20 | d-68 | e-2 | f-5 |
| 129-21 | d-68 | e-2 | f-6 |
| 129-22 | d-68 | e-2 | f-7 |
| 129-23 | d-68 | e-2 | f-8 |
| 129-24 | d-68 | e-2 | f-9 |
| 129-25 | d-68 | e-2 | f-10 |
| 129-26 | d-68 | e-2 | f-11 |
| 129-27 | d-68 | e-2 | f-12 |
| 129-28 | d-68 | e-2 | f-13 |
| 129-29 | d-68 | e-2 | f-14 |
| 129-30 | d-68 | e-2 | f-15 |
| 129-31 | d-68 | e-3 | f-1 |
| 129-32 | d-68 | e-3 | f-2 |
| 129-33 | d-68 | e-3 | f-3 |
| 129-34 | d-68 | e-3 | f-4 |
| 129-35 | d-68 | e-3 | f-5 |
| 129-36 | d-68 | e-3 | f-6 |
| 129-37 | d-68 | e-3 | f-7 |
| 129-38 | d-68 | e-3 | f-8 |
| 129-39 | d-68 | e-3 | f-9 |
| 129-40 | d-68 | e-3 | f-10 |
| 129-41 | d-68 | e-3 | f-11 |
| 129-42 | d-68 | e-3 | f-12 |
| 129-43 | d-68 | e-3 | f-13 |
| 129-44 | d-68 | e-3 | f-14 |
| 129-45 | d-68 | e-3 | f-15 |

TABLE 68

| No. | R²″ | B″ | R¹″ |
|---|---|---|---|
| 130-1 | d-69 | e-1 | f-1 |
| 130-2 | d-69 | e-1 | f-2 |
| 130-3 | d-69 | e-1 | f-3 |
| 130-4 | d-69 | e-1 | f-4 |
| 130-5 | d-69 | e-1 | f-5 |
| 130-6 | d-69 | e-1 | f-6 |
| 130-7 | d-69 | e-1 | f-7 |
| 130-8 | d-69 | e-1 | f-8 |
| 130-9 | d-69 | e-1 | f-9 |
| 130-10 | d-69 | e-1 | f-10 |
| 130-11 | d-69 | e-1 | f-11 |
| 130-12 | d-69 | e-1 | f-12 |
| 130-13 | d-69 | e-1 | f-13 |
| 130-14 | d-69 | e-1 | f-14 |
| 130-15 | d-69 | e-1 | f-15 |
| 130-16 | d-69 | e-2 | f-1 |
| 130-17 | d-69 | e-2 | f-2 |
| 130-18 | d-69 | e-2 | f-3 |
| 130-19 | d-69 | e-2 | f-4 |
| 130-20 | d-69 | e-2 | f-5 |
| 130-21 | d-69 | e-2 | f-6 |
| 130-22 | d-69 | e-2 | f-7 |
| 130-23 | d-69 | e-2 | f-8 |
| 130-24 | d-69 | e-2 | f-9 |
| 130-25 | d-69 | e-2 | f-10 |
| 130-26 | d-69 | e-2 | f-11 |
| 130-27 | d-69 | e-2 | f-12 |
| 130-28 | d-69 | e-2 | f-13 |
| 130-29 | d-69 | e-2 | f-14 |
| 130-30 | d-69 | e-2 | f-15 |
| 130-31 | d-69 | e-3 | f-1 |
| 130-32 | d-69 | e-3 | f-2 |
| 130-33 | d-69 | e-3 | f-3 |
| 130-34 | d-69 | e-3 | f-4 |
| 130-35 | d-69 | e-3 | f-5 |
| 130-36 | d-69 | e-3 | f-6 |
| 130-37 | d-69 | e-3 | f-7 |
| 130-38 | d-69 | e-3 | f-8 |
| 130-39 | d-69 | e-3 | f-9 |
| 130-40 | d-69 | e-3 | f-10 |
| 130-41 | d-69 | e-3 | f-11 |
| 130-42 | d-69 | e-3 | f-12 |
| 130-43 | d-69 | e-3 | f-13 |
| 130-44 | d-69 | e-3 | f-14 |
| 130-45 | d-69 | e-3 | f-15 |
| 131-1 | d-70 | e-1 | f-1 |
| 131-2 | d-70 | e-1 | f-2 |
| 131-3 | d-70 | e-1 | f-3 |
| 131-4 | d-70 | e-1 | f-4 |
| 131-5 | d-70 | e-1 | f-5 |
| 131-6 | d-70 | e-1 | f-6 |
| 131-7 | d-70 | e-1 | f-7 |
| 131-8 | d-70 | e-1 | f-8 |
| 131-9 | d-70 | e-1 | f-9 |
| 131-10 | d-70 | e-1 | f-10 |
| 131-11 | d-70 | e-1 | f-11 |
| 131-12 | d-70 | e-1 | f-12 |
| 131-13 | d-70 | e-1 | f-13 |

TABLE 68-continued

| No. | R²" | B" | R¹" |
|---|---|---|---|
| 131-14 | d-70 | e-1 | f-14 |
| 131-15 | d-70 | e-1 | f-15 |
| 131-16 | d-70 | e-2 | f-1 |
| 131-17 | d-70 | e-2 | f-2 |
| 131-18 | d-70 | e-2 | f-3 |
| 131-19 | d-70 | e-2 | f-4 |
| 131-20 | d-70 | e-2 | f-5 |
| 131-21 | d-70 | e-2 | f-6 |
| 131-22 | d-70 | e-2 | f-7 |
| 131-23 | d-70 | e-2 | f-8 |
| 131-24 | d-70 | e-2 | f-9 |
| 131-25 | d-70 | e-2 | f-10 |
| 131-26 | d-70 | e-2 | f-11 |
| 131-27 | d-70 | e-2 | f-12 |
| 131-28 | d-70 | e-2 | f-13 |
| 131-29 | d-70 | e-2 | f-14 |
| 131-30 | d-70 | e-2 | f-15 |
| 131-31 | d-70 | e-3 | f-1 |
| 131-32 | d-70 | e-3 | f-2 |
| 131-33 | d-70 | e-3 | f-3 |
| 131-34 | d-70 | e-3 | f-4 |
| 131-35 | d-70 | e-3 | f-5 |
| 131-36 | d-70 | e-3 | f-6 |
| 131-37 | d-70 | e-3 | f-7 |
| 131-38 | d-70 | e-3 | f-8 |
| 131-39 | d-70 | e-3 | f-9 |
| 131-40 | d-70 | e-3 | f-10 |
| 131-41 | d-70 | e-3 | f-11 |
| 131-42 | d-70 | e-3 | f-12 |
| 131-43 | d-70 | e-3 | f-13 |
| 131-44 | d-70 | e-3 | f-14 |
| 131-45 | d-70 | e-3 | f-15 |

TABLE 69

| No. | R²" | B" | R¹" |
|---|---|---|---|
| 132-1 | d-71 | e-1 | f-1 |
| 132-2 | d-71 | e-1 | f-2 |
| 132-3 | d-71 | e-1 | f-3 |
| 132-4 | d-71 | e-1 | f-4 |
| 132-5 | d-71 | e-1 | f-5 |
| 132-6 | d-71 | e-1 | f-6 |
| 132-7 | d-71 | e-1 | f-7 |
| 132-8 | d-71 | e-1 | f-8 |
| 132-9 | d-71 | e-1 | f-9 |
| 132-10 | d-71 | e-1 | f-10 |
| 132-11 | d-71 | e-1 | f-11 |
| 132-12 | d-71 | e-1 | f-12 |
| 132-13 | d-71 | e-1 | f-13 |
| 132-14 | d-71 | e-1 | f-14 |
| 132-15 | d-71 | e-1 | f-15 |
| 132-16 | d-71 | e-2 | f-1 |
| 132-17 | d-71 | e-2 | f-2 |
| 132-18 | d-71 | e-2 | f-3 |
| 132-19 | d-71 | e-2 | f-4 |
| 132-20 | d-71 | e-2 | f-5 |
| 132-21 | d-71 | e-2 | f-6 |
| 132-22 | d-71 | e-2 | f-7 |
| 132-23 | d-71 | e-2 | f-8 |
| 132-24 | d-71 | e-2 | f-9 |
| 132-25 | d-71 | e-2 | f-10 |
| 132-26 | d-71 | e-2 | f-11 |
| 132-27 | d-71 | e-2 | f-12 |
| 132-28 | d-71 | e-2 | f-13 |
| 132-29 | d-71 | e-2 | f-14 |
| 132-30 | d-71 | e-2 | f-15 |
| 132-31 | d-71 | e-3 | f-1 |
| 132-32 | d-71 | e-3 | f-2 |
| 132-33 | d-71 | e-3 | f-3 |
| 132-34 | d-71 | e-3 | f-4 |
| 132-35 | d-71 | e-3 | f-5 |
| 132-36 | d-71 | e-3 | f-6 |
| 132-37 | d-71 | e-3 | f-7 |
| 132-38 | d-71 | e-3 | f-8 |

TABLE 69-continued

| No. | R²" | B" | R¹" |
|---|---|---|---|
| 132-39 | d-71 | e-3 | f-9 |
| 132-40 | d-71 | e-3 | f-10 |
| 132-41 | d-71 | e-3 | f-11 |
| 132-42 | d-71 | e-3 | f-12 |
| 132-43 | d-71 | e-3 | f-13 |
| 132-44 | d-71 | e-3 | f-14 |
| 132-45 | d-71 | e-3 | f-15 |
| 133-1 | d-72 | e-1 | f-1 |
| 133-2 | d-72 | e-1 | f-2 |
| 133-3 | d-72 | e-1 | f-3 |
| 133-4 | d-72 | e-1 | f-4 |
| 133-5 | d-72 | e-1 | f-5 |
| 133-6 | d-72 | e-1 | f-6 |
| 133-7 | d-72 | e-1 | f-7 |
| 133-8 | d-72 | e-1 | f-8 |
| 133-9 | d-72 | e-1 | f-9 |
| 133-10 | d-72 | e-1 | f-10 |
| 133-11 | d-72 | e-1 | f-11 |
| 133-12 | d-72 | e-1 | f-12 |
| 133-13 | d-72 | e-1 | f-13 |
| 133-14 | d-72 | e-1 | f-14 |
| 133-15 | d-72 | e-1 | f-15 |
| 133-16 | d-72 | e-2 | f-1 |
| 133-17 | d-72 | e-2 | f-2 |
| 133-18 | d-72 | e-2 | f-3 |
| 133-19 | d-72 | e-2 | f-4 |
| 133-20 | d-72 | e-2 | f-5 |
| 133-21 | d-72 | e-2 | f-6 |
| 133-22 | d-72 | e-2 | f-7 |
| 133-23 | d-72 | e-2 | f-8 |
| 133-24 | d-72 | e-2 | f-9 |
| 133-25 | d-72 | e-2 | f-10 |
| 133-26 | d-72 | e-2 | f-11 |
| 133-27 | d-72 | e-2 | f-12 |
| 133-28 | d-72 | e-2 | f-13 |
| 133-29 | d-72 | e-2 | f-14 |
| 133-30 | d-72 | e-2 | f-15 |
| 133-31 | d-72 | e-3 | f-1 |
| 133-32 | d-72 | e-3 | f-2 |
| 133-33 | d-72 | e-3 | f-3 |
| 133-34 | d-72 | e-3 | f-4 |
| 133-35 | d-72 | e-3 | f-5 |
| 133-36 | d-72 | e-3 | f-6 |
| 133-37 | d-72 | e-3 | f-7 |
| 133-38 | d-72 | e-3 | f-8 |
| 133-39 | d-72 | e-3 | f-9 |
| 133-40 | d-72 | e-3 | f-10 |
| 133-41 | d-72 | e-3 | f-11 |
| 133-42 | d-72 | e-3 | f-12 |
| 133-43 | d-72 | e-3 | f-13 |
| 133-44 | d-72 | e-3 | f-14 |
| 133-45 | d-72 | e-3 | f-15 |

TABLE 70

| No. | R²" | B" | R¹" |
|---|---|---|---|
| 134-1 | d-73 | e-1 | f-1 |
| 134-2 | d-73 | e-1 | f-2 |
| 134-3 | d-73 | e-1 | f-3 |
| 134-4 | d-73 | e-1 | f-4 |
| 134-5 | d-73 | e-1 | f-5 |
| 134-6 | d-73 | e-1 | f-6 |
| 134-7 | d-73 | e-1 | f-7 |
| 134-8 | d-73 | e-1 | f-8 |
| 134-9 | d-73 | e-1 | f-9 |
| 134-10 | d-73 | e-1 | f-10 |
| 134-11 | d-73 | e-1 | f-11 |
| 134-12 | d-73 | e-1 | f-12 |
| 134-13 | d-73 | e-1 | f-13 |
| 134-14 | d-73 | e-1 | f-14 |
| 134-15 | d-73 | e-1 | f-15 |
| 134-16 | d-73 | e-2 | f-1 |
| 134-17 | d-73 | e-2 | f-2 |
| 134-18 | d-73 | e-2 | f-3 |

TABLE 70-continued

| No. | R²" | B" | R¹" |
|---|---|---|---|
| 134-19 | d-73 | e-2 | f-4 |
| 134-20 | d-73 | e-2 | f-5 |
| 134-21 | d-73 | e-2 | f-6 |
| 134-22 | d-73 | e-2 | f-7 |
| 134-23 | d-73 | e-2 | f-8 |
| 134-24 | d-73 | e-2 | f-9 |
| 134-25 | d-73 | e-2 | f-10 |
| 134-26 | d-73 | e-2 | f-11 |
| 134-27 | d-73 | e-2 | f-12 |
| 134-28 | d-73 | e-2 | f-13 |
| 134-29 | d-73 | e-2 | f-14 |
| 134-30 | d-73 | e-2 | f-15 |
| 134-31 | d-73 | e-3 | f-1 |
| 134-32 | d-73 | e-3 | f-2 |
| 134-33 | d-73 | e-3 | f-3 |
| 134-34 | d-73 | e-3 | f-4 |
| 134-35 | d-73 | e-3 | f-5 |
| 134-36 | d-73 | e-3 | f-6 |
| 134-37 | d-73 | e-3 | f-7 |
| 134-38 | d-73 | e-3 | f-8 |
| 134-39 | d-73 | e-3 | f-9 |
| 134-40 | d-73 | e-3 | f-10 |
| 134-41 | d-73 | e-3 | f-11 |
| 134-42 | d-73 | e-3 | f-12 |
| 134-43 | d-73 | e-3 | f-13 |
| 134-44 | d-73 | e-3 | f-14 |
| 134-45 | d-73 | e-3 | f-15 |
| 135-1 | d-74 | e-1 | f-1 |
| 135-2 | d-74 | e-1 | f-2 |
| 135-3 | d-74 | e-1 | f-3 |
| 135-4 | d-74 | e-1 | f-4 |
| 135-5 | d-74 | e-1 | f-5 |
| 135-6 | d-74 | e-1 | f-6 |
| 135-7 | d-74 | e-1 | f-7 |
| 135-8 | d-74 | e-1 | f-8 |
| 135-9 | d-74 | e-1 | f-9 |
| 135-10 | d-74 | e-1 | f-10 |
| 135-11 | d-74 | e-1 | f-11 |
| 135-12 | d-74 | e-1 | f-12 |
| 135-13 | d-74 | e-1 | f-13 |
| 135-14 | d-74 | e-1 | f-14 |
| 135-15 | d-74 | e-1 | f-15 |
| 135-16 | d-74 | e-2 | f-1 |
| 135-17 | d-74 | e-2 | f-2 |
| 135-18 | d-74 | e-2 | f-3 |
| 135-19 | d-74 | e-2 | f-4 |
| 135-20 | d-74 | e-2 | f-5 |
| 135-21 | d-74 | e-2 | f-6 |
| 135-22 | d-74 | e-2 | f-7 |
| 135-23 | d-74 | e-2 | f-8 |
| 135-24 | d-74 | e-2 | f-9 |
| 135-25 | d-74 | e-2 | f-10 |
| 135-26 | d-74 | e-2 | f-11 |
| 135-27 | d-74 | e-2 | f-12 |
| 135-28 | d-74 | e-2 | f-13 |
| 135-29 | d-74 | e-2 | f-14 |
| 135-30 | d-74 | e-2 | f-15 |
| 135-31 | d-74 | e-3 | f-1 |
| 135-32 | d-74 | e-3 | f-2 |
| 135-33 | d-74 | e-3 | f-3 |
| 135-34 | d-74 | e-3 | f-4 |
| 135-35 | d-74 | e-3 | f-5 |
| 135-36 | d-74 | e-3 | f-6 |
| 135-37 | d-74 | e-3 | f-7 |
| 135-38 | d-74 | e-3 | f-8 |
| 135-39 | d-74 | e-3 | f-9 |
| 135-40 | d-74 | e-3 | f-10 |
| 135-41 | d-74 | e-3 | f-11 |
| 135-42 | d-74 | e-3 | f-12 |
| 135-43 | d-74 | e-3 | f-13 |
| 135-44 | d-74 | e-3 | f-14 |
| 135-45 | d-74 | e-3 | f-15 |

TABLE 71

| No. | R²" | B" | R¹" |
|---|---|---|---|
| 136-1 | d-75 | e-1 | f-1 |
| 136-2 | d-75 | e-1 | f-2 |
| 136-3 | d-75 | e-1 | f-3 |
| 136-4 | d-75 | e-1 | f-4 |
| 136-5 | d-75 | e-1 | f-5 |
| 136-6 | d-75 | e-1 | f-6 |
| 136-7 | d-75 | e-1 | f-7 |
| 136-8 | d-75 | e-1 | f-8 |
| 136-9 | d-75 | e-1 | f-9 |
| 136-10 | d-75 | e-1 | f-10 |
| 136-11 | d-75 | e-1 | f-11 |
| 136-12 | d-75 | e-1 | f-12 |
| 136-13 | d-75 | e-1 | f-13 |
| 136-14 | d-75 | e-1 | f-14 |
| 136-15 | d-75 | e-1 | f-15 |
| 136-16 | d-75 | e-2 | f-1 |
| 136-17 | d-75 | e-2 | f-2 |
| 136-18 | d-75 | e-2 | f-3 |
| 136-19 | d-75 | e-2 | f-4 |
| 136-20 | d-75 | e-2 | f-5 |
| 136-21 | d-75 | e-2 | f-6 |
| 136-22 | d-75 | e-2 | f-7 |
| 136-23 | d-75 | e-2 | f-8 |
| 136-24 | d-75 | e-2 | f-9 |
| 136-25 | d-75 | e-2 | f-10 |
| 136-26 | d-75 | e-2 | f-11 |
| 136-27 | d-75 | e-2 | f-12 |
| 136-28 | d-75 | e-2 | f-13 |
| 136-29 | d-75 | e-2 | f-14 |
| 136-30 | d-75 | e-2 | f-15 |
| 136-31 | d-75 | e-3 | f-1 |
| 136-32 | d-75 | e-3 | f-2 |
| 136-33 | d-75 | e-3 | f-3 |
| 136-34 | d-75 | e-3 | f-4 |
| 136-35 | d-75 | e-3 | f-5 |
| 136-36 | d-75 | e-3 | f-6 |
| 136-37 | d-75 | e-3 | f-7 |
| 136-38 | d-75 | e-3 | f-8 |
| 136-39 | d-75 | e-3 | f-9 |
| 136-40 | d-75 | e-3 | f-10 |
| 136-41 | d-75 | e-3 | f-11 |
| 136-42 | d-75 | e-3 | f-12 |
| 136-43 | d-75 | e-3 | f-13 |
| 136-44 | d-75 | e-3 | f-14 |
| 136-45 | d-75 | e-3 | f-15 |
| 137-1 | d-76 | e-1 | f-1 |
| 137-2 | d-76 | e-1 | f-2 |
| 137-3 | d-76 | e-1 | f-3 |
| 137-4 | d-76 | e-1 | f-4 |
| 137-5 | d-76 | e-1 | f-5 |
| 137-6 | d-76 | e-1 | f-6 |
| 137-7 | d-76 | e-1 | f-7 |
| 137-8 | d-76 | e-1 | f-8 |
| 137-9 | d-76 | e-1 | f-9 |
| 137-10 | d-76 | e-1 | f-10 |
| 137-11 | d-76 | e-1 | f-11 |
| 137-12 | d-76 | e-1 | f-12 |
| 137-13 | d-76 | e-1 | f-13 |
| 137-14 | d-76 | e-1 | f-14 |
| 137-15 | d-76 | e-1 | f-15 |
| 137-16 | d-76 | e-2 | f-1 |
| 137-17 | d-76 | e-2 | f-2 |
| 137-18 | d-76 | e-2 | f-3 |
| 137-19 | d-76 | e-2 | f-4 |
| 137-20 | d-76 | e-2 | f-5 |
| 137-21 | d-76 | e-2 | f-6 |
| 137-22 | d-76 | e-2 | f-7 |
| 137-23 | d-76 | e-2 | f-8 |
| 137-24 | d-76 | e-2 | f-9 |
| 137-25 | d-76 | e-2 | f-10 |
| 137-26 | d-76 | e-2 | f-11 |
| 137-27 | d-76 | e-2 | f-12 |
| 137-28 | d-76 | e-2 | f-13 |
| 137-29 | d-76 | e-2 | f-14 |
| 137-30 | d-76 | e-2 | f-15 |
| 137-31 | d-76 | e-3 | f-1 |
| 137-32 | d-76 | e-3 | f-2 |
| 137-33 | d-76 | e-3 | f-3 |

TABLE 71-continued

| No. | R²" | B" | R¹" |
|---|---|---|---|
| 137-34 | d-76 | e-3 | f-4 |
| 137-35 | d-76 | e-3 | f-5 |
| 137-36 | d-76 | e-3 | f-6 |
| 137-37 | d-76 | e-3 | f-7 |
| 137-38 | d-76 | e-3 | f-8 |
| 137-39 | d-76 | e-3 | f-9 |
| 137-40 | d-76 | e-3 | f-10 |
| 137-41 | d-76 | e-3 | f-11 |
| 137-42 | d-76 | e-3 | f-12 |
| 137-43 | d-76 | e-3 | f-13 |
| 137-44 | d-76 | e-3 | f-14 |
| 137-45 | d-76 | e-3 | f-15 |

TABLE 72

| No. | R²" | B" | R¹" |
|---|---|---|---|
| 138-1 | d-77 | e-1 | f-1 |
| 138-2 | d-77 | e-1 | f-2 |
| 138-3 | d-77 | e-1 | f-3 |
| 138-4 | d-77 | e-1 | f-4 |
| 138-5 | d-77 | e-1 | f-5 |
| 138-6 | d-77 | e-1 | f-6 |
| 138-7 | d-77 | e-1 | f-7 |
| 138-8 | d-77 | e-1 | f-8 |
| 138-9 | d-77 | e-1 | f-9 |
| 138-10 | d-77 | e-1 | f-10 |
| 138-11 | d-77 | e-1 | f-11 |
| 138-12 | d-77 | e-1 | f-12 |
| 138-13 | d-77 | e-1 | f-13 |
| 138-14 | d-77 | e-1 | f-14 |
| 138-15 | d-77 | e-1 | f-15 |
| 138-16 | d-77 | e-2 | f-1 |
| 138-17 | d-77 | e-2 | f-2 |
| 138-18 | d-77 | e-2 | f-3 |
| 138-19 | d-77 | e-2 | f-4 |
| 138-20 | d-77 | e-2 | f-5 |
| 138-21 | d-77 | e-2 | f-6 |
| 138-22 | d-77 | e-2 | f-7 |
| 138-23 | d-77 | e-2 | f-8 |
| 138-24 | d-77 | e-2 | f-9 |
| 138-25 | d-77 | e-2 | f-10 |
| 138-26 | d-77 | e-2 | f-11 |
| 138-27 | d-77 | e-2 | f-12 |
| 138-28 | d-77 | e-2 | f-13 |
| 138-29 | d-77 | e-2 | f-14 |
| 138-30 | d-77 | e-2 | f-15 |
| 138-31 | d-77 | e-3 | f-1 |
| 138-32 | d-77 | e-3 | f-2 |
| 138-33 | d-77 | e-3 | f-3 |
| 138-34 | d-77 | e-3 | f-4 |
| 138-35 | d-77 | e-3 | f-5 |
| 138-36 | d-77 | e-3 | f-6 |
| 138-37 | d-77 | e-3 | f-7 |
| 138-38 | d-77 | e-3 | f-8 |
| 138-39 | d-77 | e-3 | f-9 |
| 138-40 | d-77 | e-3 | f-10 |
| 138-41 | d-77 | e-3 | f-11 |
| 138-42 | d-77 | e-3 | f-12 |
| 138-43 | d-77 | e-3 | f-13 |
| 138-44 | d-77 | e-3 | f-14 |
| 138-45 | d-77 | e-3 | f-15 |
| 139-1 | d-78 | e-1 | f-1 |
| 139-2 | d-78 | e-1 | f-2 |
| 139-3 | d-78 | e-1 | f-3 |
| 139-4 | d-78 | e-1 | f-4 |
| 139-5 | d-78 | e-1 | f-5 |
| 139-6 | d-78 | e-1 | f-6 |
| 139-7 | d-78 | e-1 | f-7 |
| 139-8 | d-78 | e-1 | f-8 |
| 139-9 | d-78 | e-1 | f-9 |
| 139-10 | d-78 | e-1 | f-10 |
| 139-11 | d-78 | e-1 | f-11 |
| 139-12 | d-78 | e-1 | f-12 |
| 139-13 | d-78 | e-1 | f-13 |

TABLE 72-continued

| No. | R²" | B" | R¹" |
|---|---|---|---|
| 139-14 | d-78 | e-1 | f-14 |
| 139-15 | d-78 | e-1 | f-15 |
| 139-16 | d-78 | e-2 | f-1 |
| 139-17 | d-78 | e-2 | f-2 |
| 139-18 | d-78 | e-2 | f-3 |
| 139-19 | d-78 | e-2 | f-4 |
| 139-20 | d-78 | e-2 | f-5 |
| 139-21 | d-78 | e-2 | f-6 |
| 139-22 | d-78 | e-2 | f-7 |
| 139-23 | d-78 | e-2 | f-8 |
| 139-24 | d-78 | e-2 | f-9 |
| 139-25 | d-78 | e-2 | f-10 |
| 139-26 | d-78 | e-2 | f-11 |
| 139-27 | d-78 | e-2 | f-12 |
| 139-28 | d-78 | e-2 | f-13 |
| 139-29 | d-78 | e-2 | f-14 |
| 139-30 | d-78 | e-2 | f-15 |
| 139-31 | d-78 | e-3 | f-1 |
| 139-32 | d-78 | e-3 | f-2 |
| 139-33 | d-78 | e-3 | f-3 |
| 139-34 | d-78 | e-3 | f-4 |
| 139-35 | d-78 | e-3 | f-5 |
| 139-36 | d-78 | e-3 | f-6 |
| 139-37 | d-78 | e-3 | f-7 |
| 139-38 | d-78 | e-3 | f-8 |
| 139-39 | d-78 | e-3 | f-9 |
| 139-40 | d-78 | e-3 | f-10 |
| 139-41 | d-78 | e-3 | f-11 |
| 139-42 | d-78 | e-3 | f-12 |
| 139-43 | d-78 | e-3 | f-13 |
| 139-44 | d-78 | e-3 | f-14 |
| 139-45 | d-78 | e-3 | f-15 |

TABLE 73

| No. | R²" | B" | R¹" |
|---|---|---|---|
| 140-1 | d-79 | e-1 | f-1 |
| 140-2 | d-79 | e-1 | f-2 |
| 140-3 | d-79 | e-1 | f-3 |
| 140-4 | d-79 | e-1 | f-4 |
| 140-5 | d-79 | e-1 | f-5 |
| 140-6 | d-79 | e-1 | f-6 |
| 140-7 | d-79 | e-1 | f-7 |
| 140-8 | d-79 | e-1 | f-8 |
| 140-9 | d-79 | e-1 | f-9 |
| 140-10 | d-79 | e-1 | f-10 |
| 140-11 | d-79 | e-1 | f-11 |
| 140-12 | d-79 | e-1 | f-12 |
| 140-13 | d-79 | e-1 | f-13 |
| 140-14 | d-79 | e-1 | f-14 |
| 140-15 | d-79 | e-1 | f-15 |
| 140-16 | d-79 | e-2 | f-1 |
| 140-17 | d-79 | e-2 | f-2 |
| 140-18 | d-79 | e-2 | f-3 |
| 140-19 | d-79 | e-2 | f-4 |
| 140-20 | d-79 | e-2 | f-5 |
| 140-21 | d-79 | e-2 | f-6 |
| 140-22 | d-79 | e-2 | f-7 |
| 140-23 | d-79 | e-2 | f-8 |
| 140-24 | d-79 | e-2 | f-9 |
| 140-25 | d-79 | e-2 | f-10 |
| 140-26 | d-79 | e-2 | f-11 |
| 140-27 | d-79 | e-2 | f-12 |
| 140-28 | d-79 | e-2 | f-13 |
| 140-29 | d-79 | e-2 | f-14 |
| 140-30 | d-79 | e-2 | f-15 |
| 140-31 | d-79 | e-3 | f-1 |
| 140-32 | d-79 | e-3 | f-2 |
| 140-33 | d-79 | e-3 | f-3 |
| 140-34 | d-79 | e-3 | f-4 |
| 140-35 | d-79 | e-3 | f-5 |
| 140-36 | d-79 | e-3 | f-6 |
| 140-37 | d-79 | e-3 | f-7 |
| 140-38 | d-79 | e-3 | f-8 |

TABLE 73-continued

| No. | R²" | B" | R¹" |
|---|---|---|---|
| 140-39 | d-79 | e-3 | f-9 |
| 140-40 | d-79 | e-3 | f-10 |
| 140-41 | d-79 | e-3 | f-11 |
| 140-42 | d-79 | e-3 | f-12 |
| 140-43 | d-79 | e-3 | f-13 |
| 140-44 | d-79 | e-3 | f-14 |
| 140-45 | d-79 | e-3 | f-15 |
| 141-1 | d-80 | e-1 | f-1 |
| 141-2 | d-80 | e-1 | f-2 |
| 141-3 | d-80 | e-1 | f-3 |
| 141-4 | d-80 | e-1 | f-4 |
| 141-5 | d-80 | e-1 | f-5 |
| 141-6 | d-80 | e-1 | f-6 |
| 141-7 | d-80 | e-1 | f-7 |
| 141-8 | d-80 | e-1 | f-8 |
| 141-9 | d-80 | e-1 | f-9 |
| 141-10 | d-80 | e-1 | f-10 |
| 141-11 | d-80 | e-1 | f-11 |
| 141-12 | d-80 | e-1 | f-12 |
| 141-13 | d-80 | e-1 | f-13 |
| 141-14 | d-80 | e-1 | f-14 |
| 141-15 | d-80 | e-1 | f-15 |
| 141-16 | d-80 | e-2 | f-1 |
| 141-17 | d-80 | e-2 | f-2 |
| 141-18 | d-80 | e-2 | f-3 |
| 141-19 | d-80 | e-2 | f-4 |
| 141-20 | d-80 | e-2 | f-5 |
| 141-21 | d-80 | e-2 | f-6 |
| 141-22 | d-80 | e-2 | f-7 |
| 141-23 | d-80 | e-2 | f-8 |
| 141-24 | d-80 | e-2 | f-9 |
| 141-25 | d-80 | e-2 | f-10 |
| 141-26 | d-80 | e-2 | f-11 |
| 141-27 | d-80 | e-2 | f-12 |
| 141-28 | d-80 | e-2 | f-13 |
| 141-29 | d-80 | e-2 | f-14 |
| 141-30 | d-80 | e-2 | f-15 |
| 141-31 | d-80 | e-3 | f-1 |
| 141-32 | d-80 | e-3 | f-2 |
| 141-33 | d-80 | e-3 | f-3 |
| 141-34 | d-80 | e-3 | f-4 |
| 141-35 | d-80 | e-3 | f-5 |
| 141-36 | d-80 | e-3 | f-6 |
| 141-37 | d-80 | e-3 | f-7 |
| 141-38 | d-80 | e-3 | f-8 |
| 141-39 | d-80 | e-3 | f-9 |
| 141-40 | d-80 | e-3 | f-10 |
| 141-41 | d-80 | e-3 | f-11 |
| 141-42 | d-80 | e-3 | f-12 |
| 141-43 | d-80 | e-3 | f-13 |
| 141-44 | d-80 | e-3 | f-14 |
| 141-45 | d-80 | e-3 | f-15 |

TABLE 74

| No. | R²" | B" | R¹" |
|---|---|---|---|
| 142-1 | d-81 | e-1 | f-1 |
| 142-2 | d-81 | e-1 | f-2 |
| 142-3 | d-81 | e-1 | f-3 |
| 142-4 | d-81 | e-1 | f-4 |
| 142-5 | d-81 | e-1 | f-5 |
| 142-6 | d-81 | e-1 | f-6 |
| 142-7 | d-81 | e-1 | f-7 |
| 142-8 | d-81 | e-1 | f-8 |
| 142-9 | d-81 | e-1 | f-9 |
| 142-10 | d-81 | e-1 | f-10 |
| 142-11 | d-81 | e-1 | f-11 |
| 142-12 | d-81 | e-1 | f-12 |
| 142-13 | d-81 | e-1 | f-13 |
| 142-14 | d-81 | e-1 | f-14 |
| 142-15 | d-81 | e-1 | f-15 |
| 142-16 | d-81 | e-2 | f-1 |
| 142-17 | d-81 | e-2 | f-2 |
| 142-18 | d-81 | e-2 | f-3 |
| 142-19 | d-81 | e-2 | f-4 |
| 142-20 | d-81 | e-2 | f-5 |
| 142-21 | d-81 | e-2 | f-6 |
| 142-22 | d-81 | e-2 | f-7 |
| 142-23 | d-81 | e-2 | f-8 |
| 142-24 | d-81 | e-2 | f-9 |
| 142-25 | d-81 | e-2 | f-10 |
| 142-26 | d-81 | e-2 | f-11 |
| 142-27 | d-81 | e-2 | f-12 |
| 142-28 | d-81 | e-2 | f-13 |
| 142-29 | d-81 | e-2 | f-14 |
| 142-30 | d-81 | e-2 | f-15 |
| 142-31 | d-81 | e-3 | f-1 |
| 142-32 | d-81 | e-3 | f-2 |
| 142-33 | d-81 | e-3 | f-3 |
| 142-34 | d-81 | e-3 | f-4 |
| 142-35 | d-81 | e-3 | f-5 |
| 142-36 | d-81 | e-3 | f-6 |
| 142-37 | d-81 | e-3 | f-7 |
| 142-38 | d-81 | e-3 | f-8 |
| 142-39 | d-81 | e-3 | f-9 |
| 142-40 | d-81 | e-3 | f-10 |
| 142-41 | d-81 | e-3 | f-11 |
| 142-42 | d-81 | e-3 | f-12 |
| 142-43 | d-81 | e-3 | f-13 |
| 142-44 | d-81 | e-3 | f-14 |
| 142-45 | d-81 | e-3 | f-15 |
| 143-1 | d-82 | e-1 | f-1 |
| 143-2 | d-82 | e-1 | f-2 |
| 143-3 | d-82 | e-1 | f-3 |
| 143-4 | d-82 | e-1 | f-4 |
| 143-5 | d-82 | e-1 | f-5 |
| 143-6 | d-82 | e-1 | f-6 |
| 143-7 | d-82 | e-1 | f-7 |
| 143-8 | d-82 | e-1 | f-8 |
| 143-9 | d-82 | e-1 | f-9 |
| 143-10 | d-82 | e-1 | f-10 |
| 143-11 | d-82 | e-1 | f-11 |
| 143-12 | d-82 | e-1 | f-12 |
| 143-13 | d-82 | e-1 | f-13 |
| 143-14 | d-82 | e-1 | f-14 |
| 143-15 | d-82 | e-1 | f-15 |
| 143-16 | d-82 | e-2 | f-1 |
| 143-17 | d-82 | e-2 | f-2 |
| 143-18 | d-82 | e-2 | f-3 |
| 143-19 | d-82 | e-2 | f-4 |
| 143-20 | d-82 | e-2 | f-5 |
| 143-21 | d-82 | e-2 | f-6 |
| 143-22 | d-82 | e-2 | f-7 |
| 143-23 | d-82 | e-2 | f-8 |
| 143-24 | d-82 | e-2 | f-9 |
| 143-25 | d-82 | e-2 | f-10 |
| 143-26 | d-82 | e-2 | f-11 |
| 143-27 | d-82 | e-2 | f-12 |
| 143-28 | d-82 | e-2 | f-13 |
| 143-29 | d-82 | e-2 | f-14 |
| 143-30 | d-82 | e-2 | f-15 |
| 143-31 | d-82 | e-3 | f-1 |
| 143-32 | d-82 | e-3 | f-2 |
| 143-33 | d-82 | e-3 | f-3 |
| 143-34 | d-82 | e-3 | f-4 |
| 143-35 | d-82 | e-3 | f-5 |
| 143-36 | d-82 | e-3 | f-6 |
| 143-37 | d-82 | e-3 | f-7 |
| 143-38 | d-82 | e-3 | f-8 |
| 143-39 | d-82 | e-3 | f-9 |
| 143-40 | d-82 | e-3 | f-10 |
| 143-41 | d-82 | e-3 | f-11 |
| 143-42 | d-82 | e-3 | f-12 |
| 143-43 | d-82 | e-3 | f-13 |
| 143-44 | d-82 | e-3 | f-14 |
| 143-45 | d-82 | e-3 | f-15 |

TABLE 75

| No. | R²'' | B'' | R¹'' |
|---|---|---|---|
| 144-1 | d-83 | e-1 | f-1 |
| 144-2 | d-83 | e-1 | f-2 |
| 144-3 | d-83 | e-1 | f-3 |
| 144-4 | d-83 | e-1 | f-4 |
| 144-5 | d-83 | e-1 | f-5 |
| 144-6 | d-83 | e-1 | f-6 |
| 144-7 | d-83 | e-1 | f-7 |
| 144-8 | d-83 | e-1 | f-8 |
| 144-9 | d-83 | e-1 | f-9 |
| 144-10 | d-83 | e-1 | f-10 |
| 144-11 | d-83 | e-1 | f-11 |
| 144-12 | d-83 | e-1 | f-12 |
| 144-13 | d-83 | e-1 | f-13 |
| 144-14 | d-83 | e-1 | f-14 |
| 144-15 | d-83 | e-1 | f-15 |
| 144-16 | d-83 | e-2 | f-1 |
| 144-17 | d-83 | e-2 | f-2 |
| 144-18 | d-83 | e-2 | f-3 |
| 144-19 | d-83 | e-2 | f-4 |
| 144-20 | d-83 | e-2 | f-5 |
| 144-21 | d-83 | e-2 | f-6 |
| 144-22 | d-83 | e-2 | f-7 |
| 144-23 | d-83 | e-2 | f-8 |
| 144-24 | d-83 | e-2 | f-9 |
| 144-25 | d-83 | e-2 | f-10 |
| 144-26 | d-83 | e-2 | f-11 |
| 144-27 | d-83 | e-2 | f-12 |
| 144-28 | d-83 | e-2 | f-13 |
| 144-29 | d-83 | e-2 | f-14 |
| 144-30 | d-83 | e-2 | f-15 |
| 144-31 | d-83 | e-3 | f-1 |
| 144-32 | d-83 | e-3 | f-2 |
| 144-33 | d-83 | e-3 | f-3 |
| 144-34 | d-83 | e-3 | f-4 |
| 144-35 | d-83 | e-3 | f-5 |
| 144-36 | d-83 | e-3 | f-6 |
| 144-37 | d-83 | e-3 | f-7 |
| 144-38 | d-83 | e-3 | f-8 |
| 144-39 | d-83 | e-3 | f-9 |
| 144-40 | d-83 | e-3 | f-10 |
| 144-41 | d-83 | e-3 | f-11 |
| 144-42 | d-83 | e-3 | f-12 |
| 144-43 | d-83 | e-3 | f-13 |
| 144-44 | d-83 | e-3 | f-14 |
| 144-45 | d-83 | e-3 | f-15 |
| 145-1 | d-84 | e-1 | f-1 |
| 145-2 | d-84 | e-1 | f-2 |
| 145-3 | d-84 | e-1 | f-3 |
| 145-4 | d-84 | e-1 | f-4 |
| 145-5 | d-84 | e-1 | f-5 |
| 145-6 | d-84 | e-1 | f-6 |
| 145-7 | d-84 | e-1 | f-7 |
| 145-8 | d-84 | e-1 | f-8 |
| 145-9 | d-84 | e-1 | f-9 |
| 145-10 | d-84 | e-1 | f-10 |
| 145-11 | d-84 | e-1 | f-11 |
| 145-12 | d-84 | e-1 | f-12 |
| 145-13 | d-84 | e-1 | f-13 |
| 145-14 | d-84 | e-1 | f-14 |
| 145-15 | d-84 | e-1 | f-15 |
| 145-16 | d-84 | e-2 | f-1 |
| 145-17 | d-84 | e-2 | f-2 |
| 145-18 | d-84 | e-2 | f-3 |
| 145-19 | d-84 | e-2 | f-4 |
| 145-20 | d-84 | e-2 | f-5 |
| 145-21 | d-84 | e-2 | f-6 |
| 145-22 | d-84 | e-2 | f-7 |
| 145-23 | d-84 | e-2 | f-8 |
| 145-24 | d-84 | e-2 | f-9 |
| 145-25 | d-84 | e-2 | f-10 |
| 145-26 | d-84 | e-2 | f-11 |
| 145-27 | d-84 | e-2 | f-12 |
| 145-28 | d-84 | e-2 | f-13 |
| 145-29 | d-84 | e-2 | f-14 |
| 145-30 | d-84 | e-2 | f-15 |
| 145-31 | d-84 | e-3 | f-1 |
| 145-32 | d-84 | e-3 | f-2 |
| 145-33 | d-84 | e-3 | f-3 |
| 145-34 | d-84 | e-3 | f-4 |
| 145-35 | d-84 | e-3 | f-5 |
| 145-36 | d-84 | e-3 | f-6 |
| 145-37 | d-84 | e-3 | f-7 |
| 145-38 | d-84 | e-3 | f-8 |
| 145-39 | d-84 | e-3 | f-9 |
| 145-40 | d-84 | e-3 | f-10 |
| 145-41 | d-84 | e-3 | f-11 |
| 145-42 | d-84 | e-3 | f-12 |
| 145-43 | d-84 | e-3 | f-13 |
| 145-44 | d-84 | e-3 | f-14 |
| 145-45 | d-84 | e-3 | f-15 |

TABLE 76

| No. | R²'' | B'' | R¹'' |
|---|---|---|---|
| 146-1 | d-85 | e-1 | f-1 |
| 146-2 | d-85 | e-1 | f-2 |
| 146-3 | d-85 | e-1 | f-3 |
| 146-4 | d-85 | e-1 | f-4 |
| 146-5 | d-85 | e-1 | f-5 |
| 146-6 | d-85 | e-1 | f-6 |
| 146-7 | d-85 | e-1 | f-7 |
| 146-8 | d-85 | e-1 | f-8 |
| 146-9 | d-85 | e-1 | f-9 |
| 146-10 | d-85 | e-1 | f-10 |
| 146-11 | d-85 | e-1 | f-11 |
| 146-12 | d-85 | e-1 | f-12 |
| 146-13 | d-85 | e-1 | f-13 |
| 146-14 | d-85 | e-1 | f-14 |
| 146-15 | d-85 | e-1 | f-15 |
| 146-16 | d-85 | e-2 | f-1 |
| 146-17 | d-85 | e-2 | f-2 |
| 146-18 | d-85 | e-2 | f-3 |
| 146-19 | d-85 | e-2 | f-4 |
| 146-20 | d-85 | e-2 | f-5 |
| 146-21 | d-85 | e-2 | f-6 |
| 146-22 | d-85 | e-2 | f-7 |
| 146-23 | d-85 | e-2 | f-8 |
| 146-24 | d-85 | e-2 | f-9 |
| 146-25 | d-85 | e-2 | f-10 |
| 146-26 | d-85 | e-2 | f-11 |
| 146-27 | d-85 | e-2 | f-12 |
| 146-28 | d-85 | e-2 | f-13 |
| 146-29 | d-85 | e-2 | f-14 |
| 146-30 | d-85 | e-2 | f-15 |
| 146-31 | d-85 | e-3 | f-1 |
| 146-32 | d-85 | e-3 | f-2 |
| 146-33 | d-85 | e-3 | f-3 |
| 146-34 | d-85 | e-3 | f-4 |
| 146-35 | d-85 | e-3 | f-5 |
| 146-36 | d-85 | e-3 | f-6 |
| 146-37 | d-85 | e-3 | f-7 |
| 146-38 | d-85 | e-3 | f-8 |
| 146-39 | d-85 | e-3 | f-9 |
| 146-40 | d-85 | e-3 | f-10 |
| 146-41 | d-85 | e-3 | f-11 |
| 146-42 | d-85 | e-3 | f-12 |
| 146-43 | d-85 | e-3 | f-13 |
| 146-44 | d-85 | e-3 | f-14 |
| 146-45 | d-85 | e-3 | f-15 |
| 147-1 | d-86 | e-1 | f-1 |
| 147-2 | d-86 | e-1 | f-2 |
| 147-3 | d-86 | e-1 | f-3 |
| 147-4 | d-86 | e-1 | f-4 |
| 147-5 | d-86 | e-1 | f-5 |
| 147-6 | d-86 | e-1 | f-6 |
| 147-7 | d-86 | e-1 | f-7 |
| 147-8 | d-86 | e-1 | f-8 |
| 147-9 | d-86 | e-1 | f-9 |
| 147-10 | d-86 | e-1 | f-10 |
| 147-11 | d-86 | e-1 | f-11 |
| 147-12 | d-86 | e-1 | f-12 |
| 147-13 | d-86 | e-1 | f-13 |

TABLE 76-continued

| No. | R²'' | B'' | R¹''' |
|---|---|---|---|
| 147-14 | d-86 | e-1 | f-14 |
| 147-15 | d-86 | e-1 | f-15 |
| 147-16 | d-86 | e-2 | f-1 |
| 147-17 | d-86 | e-2 | f-2 |
| 147-18 | d-86 | e-2 | f-3 |
| 147-19 | d-86 | e-2 | f-4 |
| 147-20 | d-86 | e-2 | f-5 |
| 147-21 | d-86 | e-2 | f-6 |
| 147-22 | d-86 | e-2 | f-7 |
| 147-23 | d-86 | e-2 | f-8 |
| 147-24 | d-86 | e-2 | f-9 |
| 147-25 | d-86 | e-2 | f-10 |
| 147-26 | d-86 | e-2 | f-11 |
| 147-27 | d-86 | e-2 | f-12 |
| 147-28 | d-86 | e-2 | f-13 |
| 147-29 | d-86 | e-2 | f-14 |
| 147-30 | d-86 | e-2 | f-15 |
| 147-31 | d-86 | e-3 | f-1 |
| 147-32 | d-86 | e-3 | f-2 |
| 147-33 | d-86 | e-3 | f-3 |
| 147-34 | d-86 | e-3 | f-4 |
| 147-35 | d-86 | e-3 | f-5 |
| 147-36 | d-86 | e-3 | f-6 |
| 147-37 | d-86 | e-3 | f-7 |
| 147-38 | d-86 | e-3 | f-8 |
| 147-39 | d-86 | e-3 | f-9 |
| 147-40 | d-86 | e-3 | f-10 |
| 147-41 | d-86 | e-3 | f-11 |
| 147-42 | d-86 | e-3 | f-12 |
| 147-43 | d-86 | e-3 | f-13 |
| 147-44 | d-86 | e-3 | f-14 |
| 147-45 | d-86 | e-3 | f-15 |

TABLE 77

| No. | R²'' | B'' | R¹''' |
|---|---|---|---|
| 148-1 | d-87 | e-1 | f-1 |
| 148-2 | d-87 | e-1 | f-2 |
| 148-3 | d-87 | e-1 | f-3 |
| 148-4 | d-87 | e-1 | f-4 |
| 148-5 | d-87 | e-1 | f-5 |
| 148-6 | d-87 | e-1 | f-6 |
| 148-7 | d-87 | e-1 | f-7 |
| 148-8 | d-87 | e-1 | f-8 |
| 148-9 | d-87 | e-1 | f-9 |
| 148-10 | d-87 | e-1 | f-10 |
| 148-11 | d-87 | e-1 | f-11 |
| 148-12 | d-87 | e-1 | f-12 |
| 148-13 | d-87 | e-1 | f-13 |
| 148-14 | d-87 | e-1 | f-14 |
| 148-15 | d-87 | e-1 | f-15 |
| 148-16 | d-87 | e-2 | f-1 |
| 148-17 | d-87 | e-2 | f-2 |
| 148-18 | d-87 | e-2 | f-3 |
| 148-19 | d-87 | e-2 | f-4 |
| 148-20 | d-87 | e-2 | f-5 |
| 148-21 | d-87 | e-2 | f-6 |
| 148-22 | d-87 | e-2 | f-7 |
| 148-23 | d-87 | e-2 | f-8 |
| 148-24 | d-87 | e-2 | f-9 |
| 148-25 | d-87 | e-2 | f-10 |
| 148-26 | d-87 | e-2 | f-11 |
| 148-27 | d-87 | e-2 | f-12 |
| 148-28 | d-87 | e-2 | f-13 |
| 148-29 | d-87 | e-2 | f-14 |
| 148-30 | d-87 | e-2 | f-15 |
| 148-31 | d-87 | e-3 | f-1 |
| 148-32 | d-87 | e-3 | f-2 |
| 148-33 | d-87 | e-3 | f-3 |
| 148-34 | d-87 | e-3 | f-4 |
| 148-35 | d-87 | e-3 | f-5 |
| 148-36 | d-87 | e-3 | f-6 |
| 148-37 | d-87 | e-3 | f-7 |
| 148-38 | d-87 | e-3 | f-8 |

TABLE 77-continued

| No. | R²'' | B'' | R¹''' |
|---|---|---|---|
| 148-39 | d-87 | e-3 | f-9 |
| 148-40 | d-87 | e-3 | f-10 |
| 148-41 | d-87 | e-3 | f-11 |
| 148-42 | d-87 | e-3 | f-12 |
| 148-43 | d-87 | e-3 | f-13 |
| 148-44 | d-87 | e-3 | f-14 |
| 148-45 | d-87 | e-3 | f-15 |

The present invention further provides synthetic intermediates as follows.

EXAMPLE E

[Chemical Formula 285]

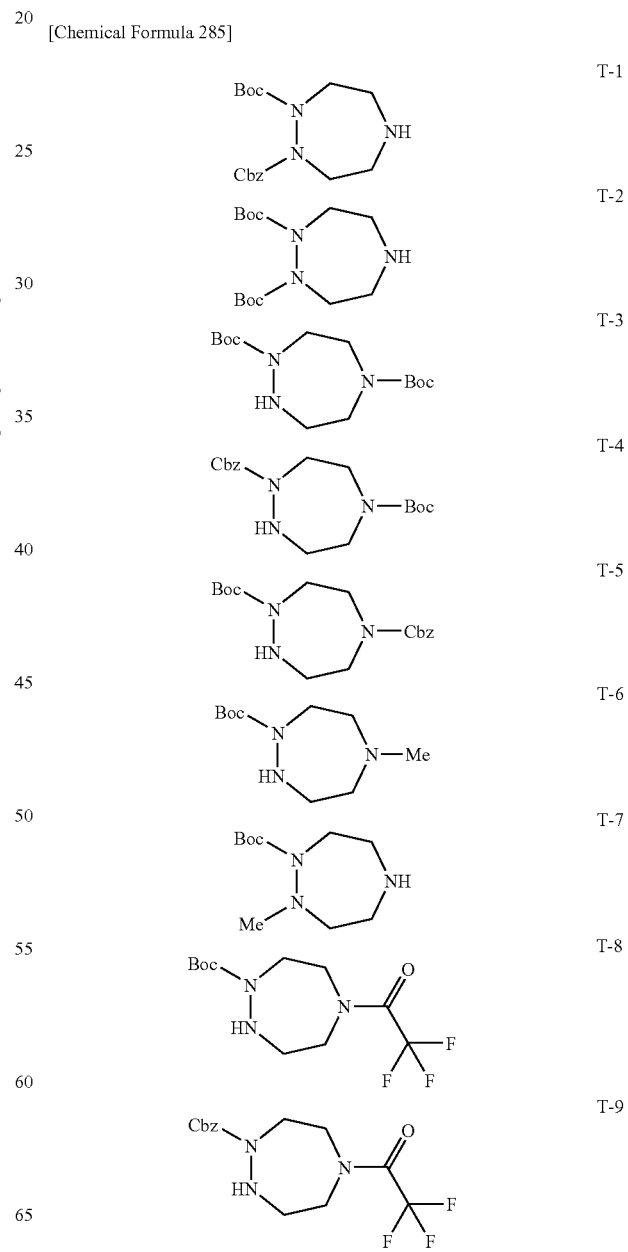

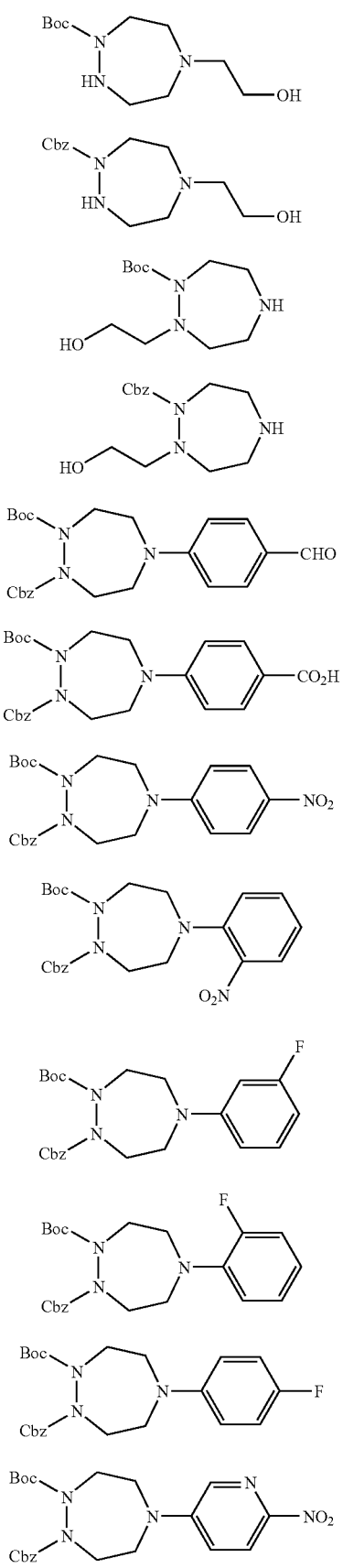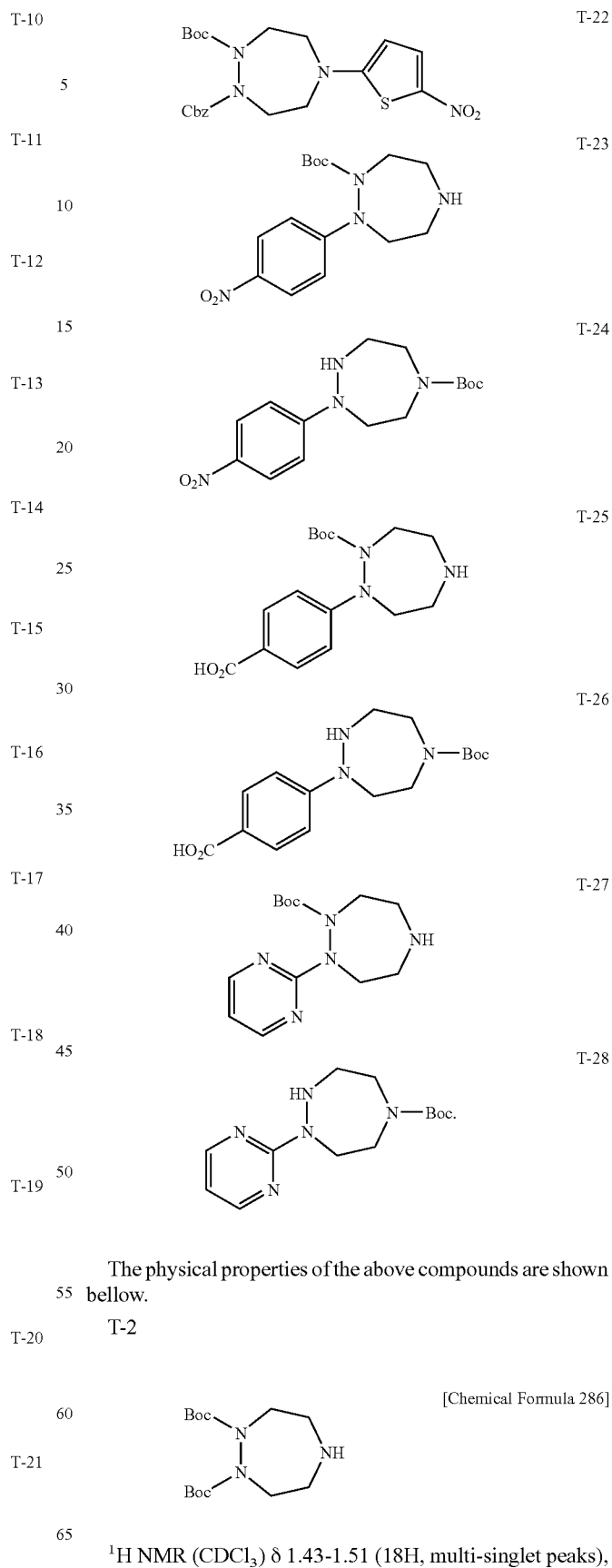
The physical properties of the above compounds are shown bellow.
T-2
[Chemical Formula 286]
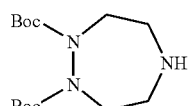
$^1$H NMR (CDCl$_3$) δ 1.43-1.51 (18H, multi-singlet peaks), 2.96-3.54 (6H, m), and 3.98-4.26 (2H, m).

T-3

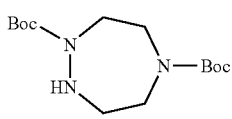

[Chemical Formula 287]

¹H NMR (CDCl₃) δ 1.40-1.52 (18H, multi-singlet peaks), 2.88-2.96 (2H, m), and 3.37-3.64 (6H, m).

EXAMPLE E-2

T-29

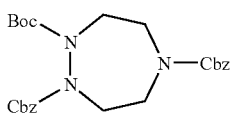

[Chemical Formula 288]

¹H NMR (CDCl₃) δ 1.30-1.50 (9H, multi-singlet peaks), 3.06-4.28 (8H, m), 5.04-5.30 (4H, m), and 7.25-7.38 (10H, m).

T-30

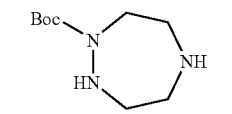

[Chemical Formula 289]

¹H NMR (CDCl₃) δ 1.49 (9H, s), 2.33 (2H, br s), 2.93-3.03 (4H, m), 3.09 (2H, t, J=6.1 Hz), and 3.58 (2H, t, J=6.1 Hz).

T-31

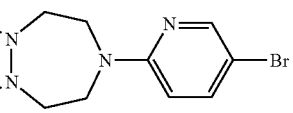

[Chemical Formula 290]

¹H-NMR (CDCl₃) δ 1.42 (18H, s), 3.30-3.08 (2H, m), 3.75-3.59 (2H, m), 3.89-3.75 (2H, m), 4.26-4.06 (2H, m), 6.43 (1H, dd, J=9.2, 1.5 Hz), 7.50 (1H, dd, J=9.2, 2.9 Hz), and 8.16-8.12 (1H, m).

T-32

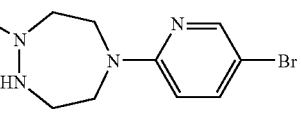

[Chemical Formula 291]

¹H-NMR (CDCl₃) δ 1.30 (9H, s), 3.04 (2H, t, J=5.5 Hz), 3.68-3.85 (6H, m), 4.83 (1H, br s), 6.42 (1H, d, J=9.1 Hz), 7.48 (1H, dd, J=2.5, 9.1 Hz), and 8.14 (1H, d, J=2.5 Hz).

T-33

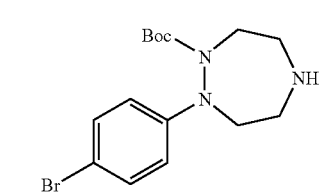

[Chemical Formula 292]

¹H NMR (CDCl₃) δ 1.33-1.51 (9H, multi-singlet peaks), 2.29 (1H, br s), 2.70-4.27 (8H, m), 6.53 (1H, d, J=9.1 Hz), 7.55 (1H, dd, J=2.5, 9.1 Hz), and 8.20 (1H, d, J=2.5 Hz).

T-34

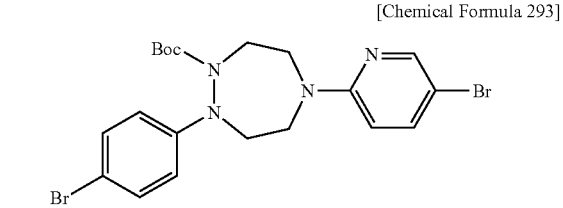 [SMILES: CC(C)(C)OC(=O)N1CCN(c2ccc(Br)cn2)CCN1c1ccc(Br)cc1]

[Chemical Formula 293]

¹H NMR (CDCl₃) δ 1.31 & 1.43 (9H, s, t-Bu), 3.08-4.59 (8H, m), 6.46 & 6.52 (1H, d, J=9.1 Hz), 7.49 & 7.53 (1H, dd, J=2.5, 9.1 Hz), and 8.12 & 8.16 (1H, d, J=2.5 Hz).

T-35

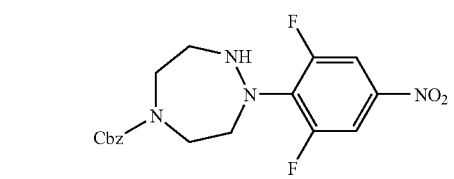

[Chemical Formula 294]

¹H NMR (CDCl₃) δ 3.04-3.19 (2H, m), 3.44-3.53 (2H, m), 3.64-3.77 (4H, m), 5.18 (2H, s, CH₂Ph), 7.32-7.39 (5H, m), and 7.77 (2H, d, J=9.3 Hz).

T-36

[Chemical Formula 295]

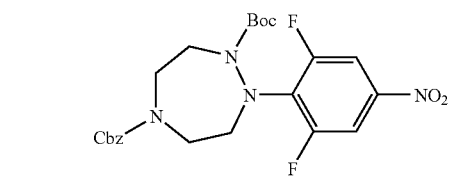

¹H NMR (CDCl₃) δ 1.29-1.48 (9H, multi-singlet peaks, t-Bu), 3.32-4.28 (8H, m), 5.09-5.22 (2H, multi-singlet peaks, CH₂Ph), 7.25-7.38 (5H, m), and 7.70-7.83 (2H, m).

T-37
[Chemical Formula 296]
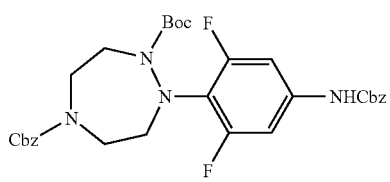
$^1$H NMR (CDCl$_3$) δ 1.24-1.42 (9H, multi-singlet peaks, t-Bu), 3.27-4.18 (8H, m), 5.11-5.20 (4H, multi-singlet peaks, CH$_2$Ph), 6.69 (1H, s, NHCbz), 6.95 (2H, d, J=11.0 Hz), and 7.26-7.40 (10H, m).
EXAMPLE F
[Chemical Formula 297]
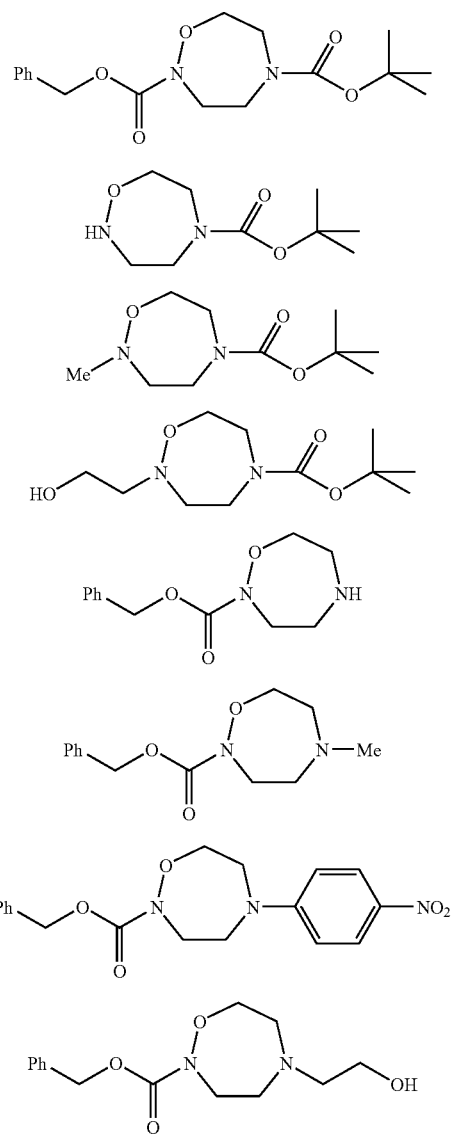
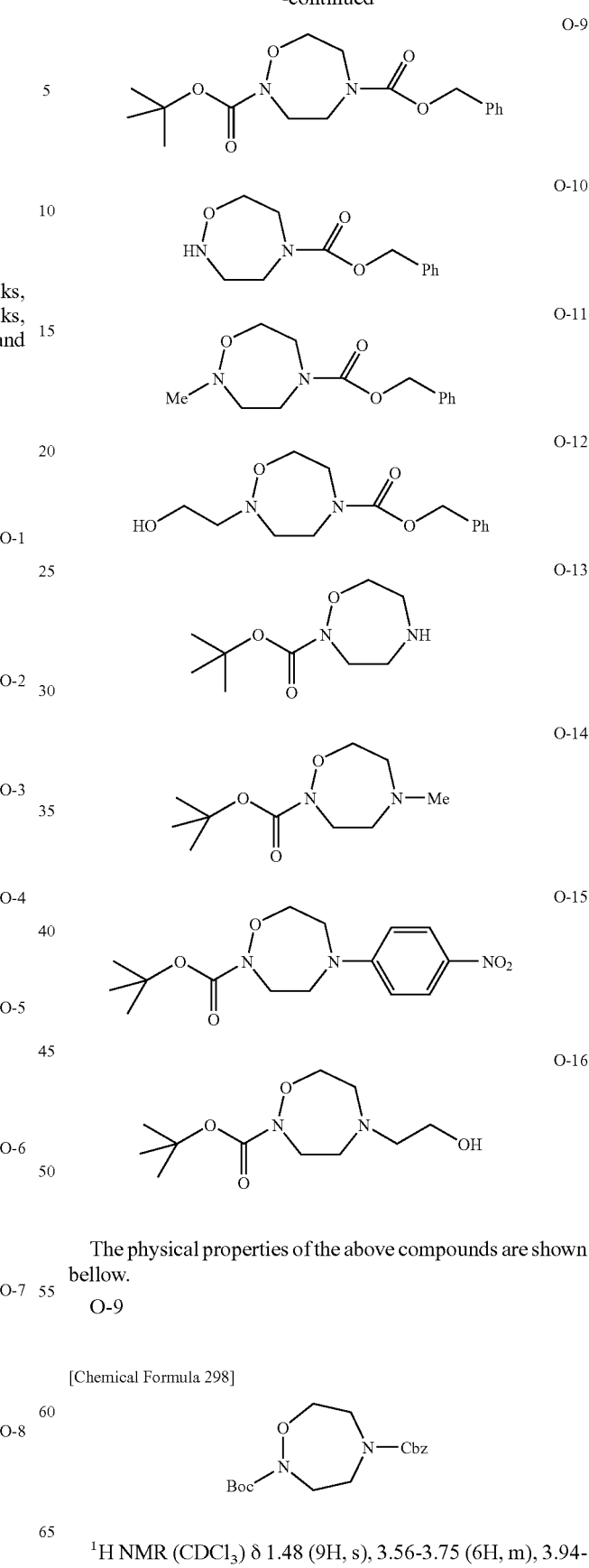
The physical properties of the above compounds are shown bellow.
O-9
[Chemical Formula 298]
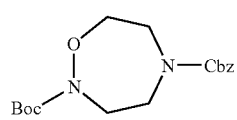
$^1$H NMR (CDCl$_3$) δ 1.48 (9H, s), 3.56-3.75 (6H, m), 3.94-4.05 (2H, m), 5.14 (2H, s), and 7.32 (5H, s).

O-13

[Chemical Formula 299]

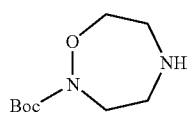

$^1$H NMR (CDCl$_3$) δ 1.51 (9H, s), 3.41-3.53 (4H, m), 3.99 (2H, t, J=6 Hz), and 4.32 (2H, t, J=5 Hz).

EXAMPLE G1

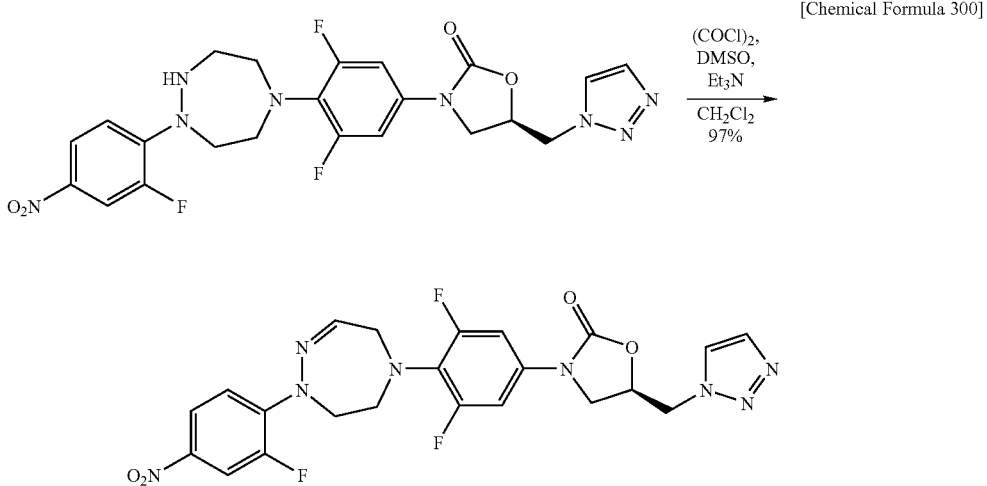

[Chemical Formula 300]

(COCl)$_2$ (0.10 cm$^3$, 1.146 mmol) was charged in a 35 cm$^3$ eggplant-shape flask, and CH$_2$Cl$_2$ (10 cm$^3$) was added to dissolve and cooled to −78° C. under Ar atmosphere. DMSO (0.10 cm$^3$, 1.409 mmol) was dropped slowly at this temperature and stirred for 10 min. The starting compound (155.4 mg, 0.300 mmol) in CH$_2$Cl$_2$ (3 cm$^3$) was dropped slowly at the same temperature and stirred for 30 min. Et$_3$N (0.32 cm$^3$, 2.277 mmol) was dropped at the same temperature, and warmed to room temperature and stirred for 20 min. H$_2$O (20 cm$^3$) was as added, the mixture was extracted three times with 5% MeOH/CHCl$_3$. After dryness over anhydrous Na$_2$SO$_4$, the solvent was removed, and the residue was purified by silica gel column chromatography (BW-200, 8 g, eluent; 1%→1.5%→2%→3% MeOH/CHCl$_3$) to afford G1 (149.8 mg, 0.290 mmol, 97%).

$^1$H NMR (CDCl$_3$) δ 3.56-3.62 (2H, m), 3.80-3.86 (2H, m), 3.90 (1H, dd, J=6.0, 9.1 Hz), 4.06 (2H, d, J=3.8 Hz), 4.10 (1H, t, J=9.1 Hz), 4.79 (2H, d, J=4.1 Hz), 5.02-5.12 (1H, m), 6.98 (2H, d, J=10.5 Hz), 7.07 (1H, t, J=3.8 Hz), 7.75 (1H, br s), 7.77 (1H, br s), 7.87 (1H, t, J=9.1 Hz), and 7.92-8.02 (2H, m).

EXAMPLE G2

[Chemical Formula 301]

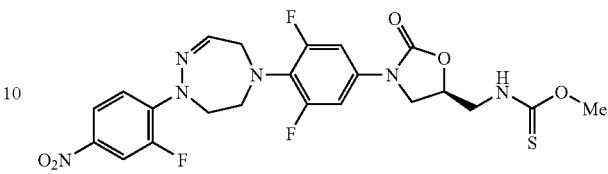

$^1$H NMR (CDCl$_3$) δ 3.07-3.14 (2H, m), 3.36-3.50 (4H, m), 3.74-3.85 (3H, m), 3.94-4.15 (3H, m), 4.01 (3H, s), 4.87-4.97 (1H, m), 6.70 (1H, br t, J=6 Hz), 7.11 (2H, d, J=10.5 Hz), 7.60 (1H, t, J=9.1 Hz), 7.89 (1H, dd, J=2.5, 13.8 Hz), and 7.96 (1H, dd, J=2.5, 9.1 Hz).

EXAMPLE G3

[Chemical Formula 302]

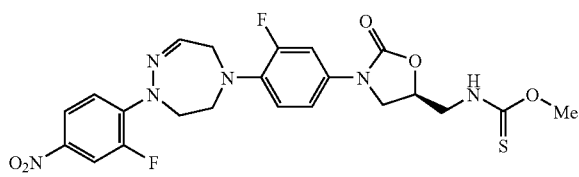

$^1$H NMR (CDCl$_3$) δ 3.15-3.23 (2H, m), 3.44-3.58 (4H, m), 3.78-3.87 (2H, m), 3.92-4.15 (4H, m), 4.00 (3H, s), 4.85-4.97 (1H, m), 6.77 (1H, br t, J=6 Hz), 6.94 (1H, t, J=9.1 Hz), 7.06 (1H, br d, J=9 Hz), 7.40 (1H, dd, J=2.5, 14.6 Hz), 7.55 (1H, t, J=9.1 Hz), 7.88 (1H, dd, J=2.5, 13.8 Hz), and 7.95 (1H, dd, J=2.5, 9.1 Hz).

EXAMPLE H1

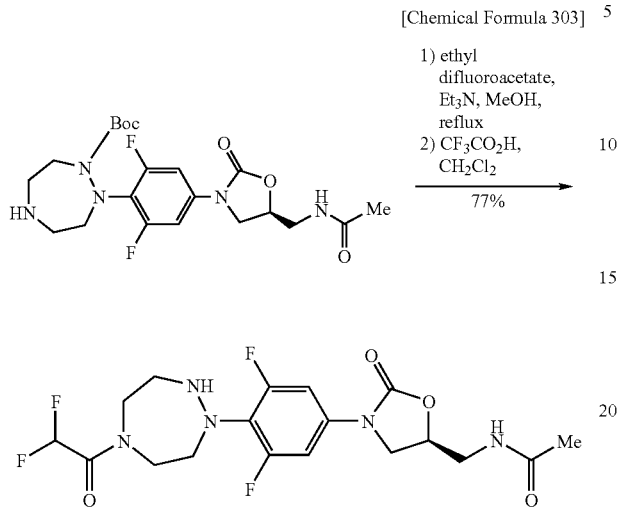

In a 35 cm³ eggplant-shape flask, the amino compound (145.2 mg, 0.309 mmol) was dissolved in MeOH (3 cm³), and ethyl difluoroacetate (195.4 mg, 1.575 mmol) and Et₃N (0.22 cm³, 1.565 mmol) were added and stirred for 30 min. DMAP (12.8 mg, 0.105 mmol) was added and heated under reflux for 17 hours. 10% citric acid aq. (20 cm³) was added and extracted four times with CHCl₃ and dried over anhydrous Na₂SO₄. The solvent was removed, and the residue was dissolved in CH₂Cl₂ (4 cm³). CF₃CO₂H (0.5 cm³) was added and stirred for 3 hours. After neutralization with 10% Na₂CO₃ aq. (10 cm³), extraction with 10% MeOH/CHCl₃ (×8), and dryness over anhydrous Na₂SO₄. The solvent was removed, and the residue was purified by silica gel column chromatography (BW-200, 6 g, eluent; 3%→5%→8% MeOH/CHCl₃) to afford F1 (106.5 mg, 0.238 mmol, 77%).

¹H NMR (CDCl₃) δ 2.02 (3H, s), 3.11-3.20 (2H, m), 3.33-3.44 (2H, m), 3.62-3.91 (7H, m), 3.99 (1H, t, J=9.1 Hz), 4.73-4.83 (1H, m), 6.17 (0.5H, t, J=53.8 Hz), 6.18 (0.5H, t, J=53.8 Hz), 6.50 (0.5H, br t, J=6 Hz), 6.51 (0.5H, br t, J=6 Hz), 7.10 (1H, d, J=10.4 Hz), and 7.11 (1H, d, J=10.4 Hz).

EXAMPLE H2

[Chemical Formula 304]

¹H NMR (CDCl₃) δ 3.10-3.19 (2H, m), 3.32-3.41 (2H, m), 3.76-3.93 (5H, m), 4.11 (1H, t, J=9.1 Hz), 4.79 (2H, AB), 5.02-5.12 (1H, m), 6.15 (0.5H, t, J=53.8 Hz), 6.16 (0.5H, t, J=53.8 Hz), 7.00 (2H, d, J=10.4 Hz), 7.74 (1H, br s), and 7.77 (1H, br s).

EXAMPLE H3

[Chemical Formula 305]

¹H NMR (CDCl₃) δ 3.10-3.18 (2H, m), 3.31-3.40 (2H, m), 3.56-3.65 (4H, m), 3.86-3.93 (1H, m), 4.12 (1H, t, J=9.1 Hz), 4.79 (2H, AB), 5.03-5.13 (1H, m), 7.01 (2H, d, J=10.4 Hz), 7.73 (1H, br s), 7.78 (1H, br s), 8.12 (0.5H, s), and 8.17 (0.5H, s).

EXAMPLE H4

[Chemical Formula 306]

¹H NMR (CDCl₃) δ 3.02-3.14 (2H, m), 3.25-3.34 (2H, m), 3.57-3.80 (4H, m), 3.74 (3H, s), 3.88 (1H, dd, J=6.1, 9.3 Hz), 4.11 (1H, t, J=9.3 Hz), 4.79 (2H, AB), 5.02-5.12 (1H, m), 6.99 (2H, d, J=10.4 Hz), 7.74 (1H, br s), and 7.78 (1H, br s).

EXAMPLE H5

[Chemical Formula 307]

¹H NMR (CDCl₃) δ 3.06-3.72 (6H, m), 3.83-3.93 (1H, m), 4.06-4.16 (1H, m), 4.25-4.48 (2H, m), 4.75-4.81 (2H, m), 5.01-5.12 (1H, m), 5.25 (0.6H, br t, J=6 Hz), 5.55 (0.4H, br t, J=6 Hz), 6.93-7.06 (2H, m), 7.21-7.28 (1H, m), 7.64-7.78 (3H, m), and 8.45-8.54 (2H, m).

EXAMPLE H6

[Chemical Formula 308]

¹H NMR (CDCl₃) δ 3.16 (2H, br t, J=5 Hz), 3.38 (2H, br t, J=5 Hz), 3.76-3.91 (5H, m), 4.10 (1H, t, J=9.1 Hz), 4.78 (2H, AB), 5.01-5.11 (1H, m), 6.99 (2H, d, J=10.5 Hz), 7.04 (1H, d, J=1.7 Hz), 7.74 (1H, br s), 7.77 (1H, br s), 8.22 (1H, d, J=1.7 Hz), and 8.68 (1H, s).

EXAMPLE I1

[Chemical Formula 309]

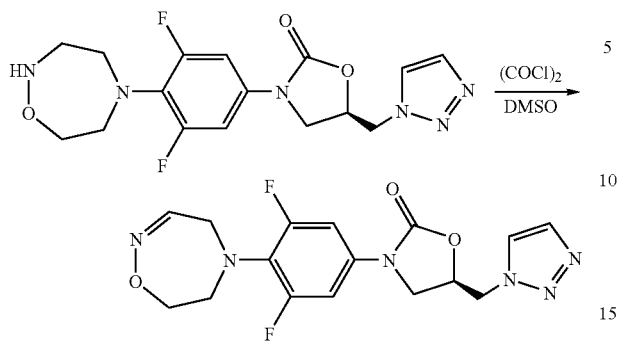

Oxalyl chloride (0.30 cm³) was added to DMSO (0.4 cm³) in chloroform (10 cm³) and stirred at −78° C. After 15 minutes, the amino compound (288 mg) in chloroform (10 cm³) was added and stirred at −78° C. for 15 minutes. Additionally, triethylamine (0.50 cm³) was added and stirred over 7 hours until the temperature is warmed to room temperature. Aqueous NaHCO₃ solution was added, and extracted with chloroform-methanol (9:1), washed with water and dried. The solvent was removed, and the residue was purified by preparative thin-layer chromatography (methanol-chloroform (3:47)) to afford Compound (G1) (188 mg, 66%).

¹H NMR (CDCl₃) δ 3.42-3.50 (2H, m), 3.87-3.96 (3H, m), 4.11-4.21 (3H, m), 4.80 (1H, dd, 5, 15 Hz), 4.84 (1H, dd, 4, 15 Hz), 5.07-5.16 (1H, m), 6.96-7.07 (2H, m), 7.66 (1H, t, J=5 Hz), 7.72 (1H, d, J=1 Hz), and 7.82 (1H, d, J=1 Hz).

EXAMPLE J1

[Chemical Formula 310]

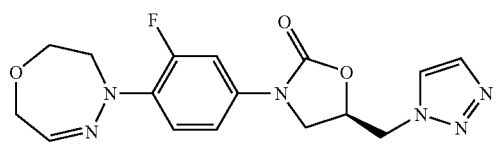

¹H-NMR (CDCl₃) δ: 7.77 (2H, dd, J=12.28, 0.99 Hz), 7.67 (1H, t, J=9.07 Hz), 7.38 (1H, dd, J=13.50, 2.52 Hz), 6.99-6.94 (2H, m), 5.10-5.02 (1H, m), 4.82-4.76 (2H, m), 4.29 (2H, d, J=3.97 Hz), 4.15 (1H, t, J=9.07 Hz), 3.94-3.84 (3H, m), 3.48 (2H, td, J=4.35, 1.22 Hz).

EXAMPLE J2

[Chemical Formula 311]

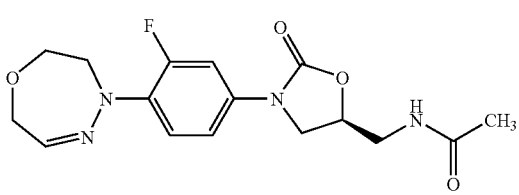

¹H-NMR (CDCl₃) δ: 7.67 (1H, t, J=9.07 Hz), 7.49 (1H, dd, J=13.65, 2.52 Hz), 7.09-7.00 (1H, m), 6.95 (1H, q, J=3.97 Hz), 6.55-6.44 (1H, br m), 4.83-4.71 (1H, m), 4.28 (2H, d, J=3.66 Hz), 4.07-3.98 (1H, m), 3.93-3.84 (2H, m), 3.80-3.74 (1H, m), 3.67-3.59 (2H, m), 3.52-3.46 (2H, m), 1.83 (3H, s).

EXAMPLE J3

[Chemical Formula 312]

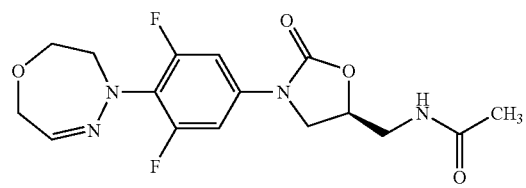

¹H-NMR (DMSO-d₆) δ: 8.24 (1H, t, J=5.57 Hz), 7.38-7.25 (2H, m), 6.80 (1H, t, J=3.74 Hz), 4.79-4.68 (1H, m), 4.21 (2H, d, J=3.66 Hz), 4.16-4.06 (1H, m), 3.76-3.64 (3H, m), 3.57-3.48 (2H, m), 3.41 (2H, t, J=5.49 Hz), 1.83 (3H, s).

EXAMPLE J4

[Chemical Formula 313]

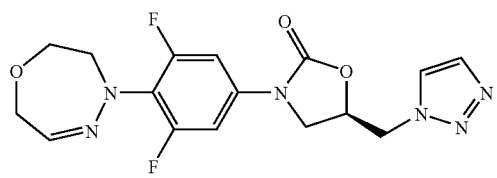

¹H-NMR (DMSO-d₆) δ: 8.16 (1H, d, J=0.99 Hz), 7.76 (1H, d, J=0.99 Hz), 7.29 (2H, d, J=11.29 Hz), 6.80 (1H, t, J=3.74 Hz), 5.21-5.09 (1H, m), 4.83 (2H, d, J=5.03 Hz), 4.26-4.18 (3H, m), 3.89 (1H, dd, J=9.53, 5.57 Hz), 3.73-3.66 (2H, m), 3.54-3.49 (2H, m).

EXAMPLE J5

[Chemical Formula 314]

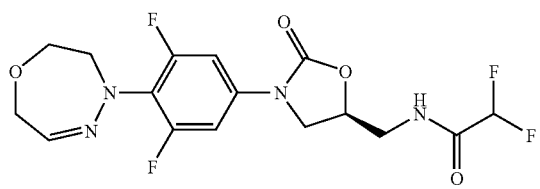

¹H-NMR (DMSO-dd δ: 9.17 (1H, t, J=5.64 Hz), 7.33 (2H, d, J=10.98 Hz), 6.80 (1H, t, J=3.66 Hz), 6.25 (1H, t, J=53.46 Hz), 4.88-4.76 (1H, m), 4.21 (2H, d, J=3.66 Hz), 4.14 (1H, t, J=9.15 Hz), 3.77 (1H, dd, J=9.38, 6.18 Hz), 3.73-3.67 (2H, m), 3.57-3.49 (4H, m).

TEXT EXAMPLE 1

The compounds of the invention were tested for antimicrobial activity.
(Test Method)
Minimal inhibitory concentration (MIC: μg/ml) against different strains of bacteria was determined according to the standard method recommended by CLSI (clinical and laboratory standards institute). Samples were prepared by dissolving a test compound solution into DMSO (1280 μg/mL), followed by two fold dilution with DMSO. The sample was added to a bacteria suspension at the concentration of 5%, and MIC was determined. Mueller Hinton Broth was adjusted for cation concentration and used as a culture media. The inoculation concentration was about 5×10$^5$ CFU/mL.

(Result)

The compound of the invention showed strong antimicrobial activity, which was comparable to or more (e.g., four times or more) than linezolid and vancomycin, against various strains of bacteria, including MRSA (methicillin-resistant *Staphylococcus aureus*), PRSP (penicillin resistant *Streptococcus pneumoniae*), VRE (vancomycin resistance enterococcus), VISA (vancomycin-intermediate *Staphylococcus aureus*). For example, the MIC values of the compounds of the working examples (e.g., Examples A91 and B38) were equal to or less. than 1 μg/mL, against these strains of bacteria.

INDUSTRIAL APPLICABILITY

The compound of the invention is useful as a pharmaceutical active ingredient or as an intermediate in the synthesis thereof. Particularly, the compound of the invention is useful as antimicrobial agent based on its antimicrobial activity.

What is claimed is:

1. A compound or a pharmaceutically acceptable salt thereof, wherein the compound is selected from the group consisting of the following compounds:

T-1
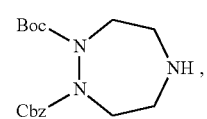

T-2
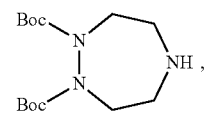

T-3
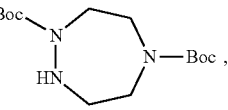

T-4
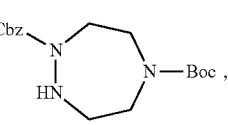

T-5
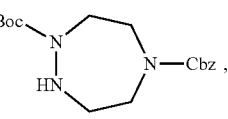

T-6
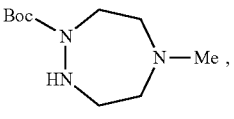

T-7
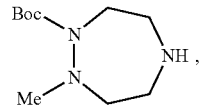

T-8
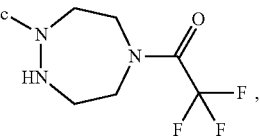

T-9
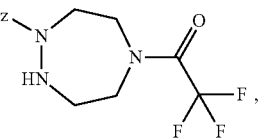

T-10
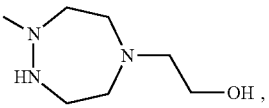

T-11
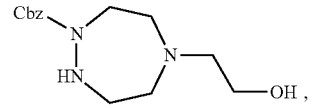

T-12
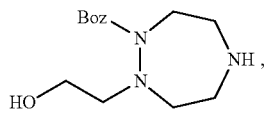

T-13
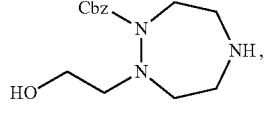

T-23
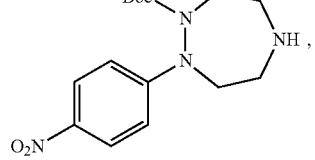

T-24
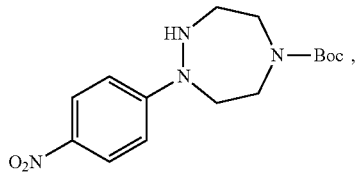

T-25
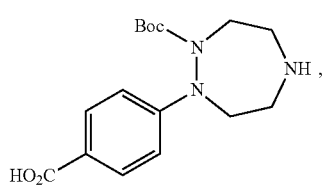

-continued

T-26 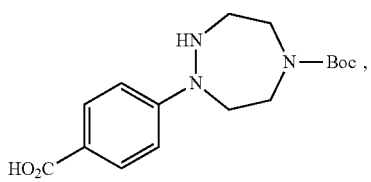

T-27 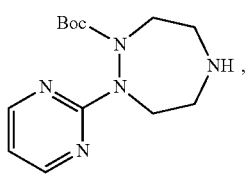

T-28 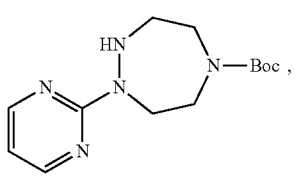

T-29 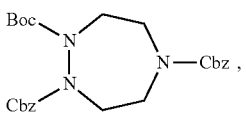

T-30 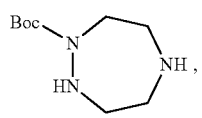

T-31 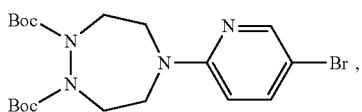

T-32 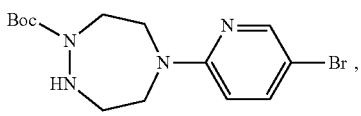

T-33 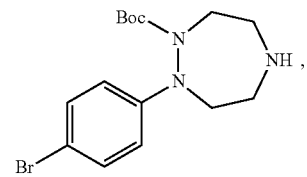

T-34 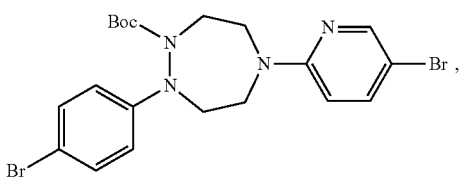

T-35 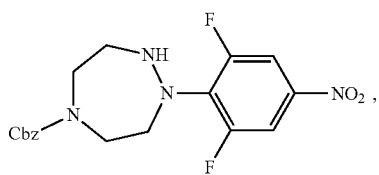

-continued

T-36 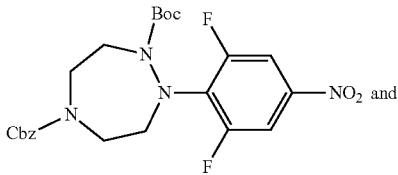

T-37 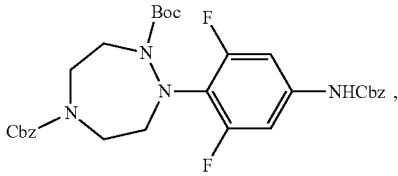

wherein Boc is tert-butoxycarbonyl and Cbz is benzyloxycarbonyl.

2. A compound of the formula (I - 12):

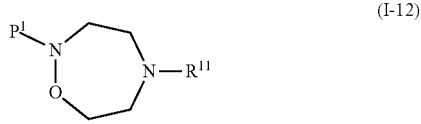

(I-12)

or a pharmaceutically acceptable salt thereof,
wherein
P$^1$ is hydrogen, a substituent selected from Substituent Group S1 or an amino protecting group;
R$^{11}$ is hydrogen, a substituent selected from Substituent Group S1 or an amino protecting group, with the proviso that R$^{11}$ is not —CO(CH$_2$)$_3$—CO$_2$H, —Ph and —CH$_2$Ph wherein Ph is phenyl;
wherein Substituent Group S1 is selected from the group consisting of optionally substituted lower alkyl, optionally substituted lower alkenyl, optionally substituted cycloalkyl, optionally substituted formyl, optionally substituted (lower alkyl)carbonyl, optionally substituted cycloalkylcarbonyl, optionally substituted (lower alkyl)oxycarbonyl, optionally substituted (lower alkyl)oxythiocarbonyl, optionally substituted arylcarbonyl, optionally substituted aryloxycarbonyl, optionally substituted heterocyclecarbonyl, optionally substituted heterocycleoxycarbonyl, optionally substituted carbamoyl, optionally substituted carbamoylcarbonyl, optionally substituted thiocarbamoyl, optionally substituted (lower alkyl)thiocarbonyl, optionally substituted cycloalkylthiocarbonyl, optionally substituted arylthiocarbonyl, optionally substituted heterocyclic thiocarbonyl, optionally substituted (lower alkyl)sulfonyl, optionally substituted phenylsulfonyl, optionally substituted aromatic heterocyclic sulfonyl, optionally substituted aminosulfonyl, optionally substituted aryl, optionally substituted heterocyclic group, cyano, optionally substituted thioformyl, and optionally substituted (lower alkenyl)carbonyl.

3. The compound according to claim 2, or a pharmaceutically acceptable salt thereof, wherein P$^1$ and R$^{11}$ are independently hydrogen, an amino protecting group, or lower alkyl optionally substituted with hydroxy.

4. The compound according to claim 2, or a pharmaceutically acceptable salt thereof, wherein P$^1$ is hydrogen; and R$^{11}$ is an amino protecting group or lower alkyl optionally substituted with hydroxy.

5. The compound according to claim 2, or a pharmaceutically acceptable salt thereof, wherein $P^1$ is hydrogen; and $R^{11}$ is tert-butoxycarbonyl, benzyloxycarbonyl or lower alkyl optionally substituted with hydroxy.

6. The compound according to claim 2, or a pharmaceutically acceptable salt thereof, wherein $R^{11}$ is hydrogen; and $P^1$ is an amino protecting group or lower alkyl optionally substituted with hydroxy.

7. The compound according to claim 2, or a pharmaceutically acceptable salt thereof, wherein $R^{11}$ is hydrogen; and $P^1$ is lower alkyl optionally substituted with hydroxy, or tert-butoxycarbonyl or benzyloxycarbonyl.

8. The compound according to claim 2, or a pharmaceutically acceptable salt thereof, wherein the compound is selected from the group consisting of the following compounds:

O-1
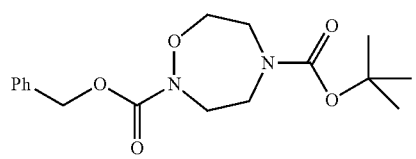

O-2
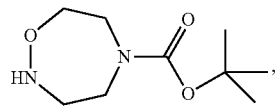

O-3
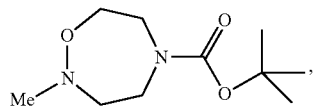

O-4
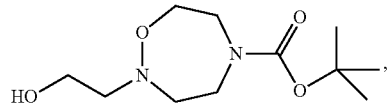

O-5
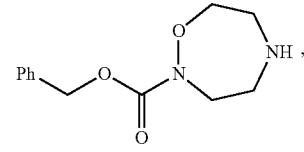

O-6
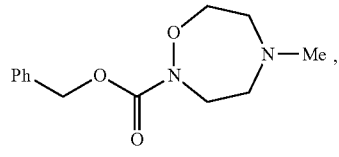

O-8
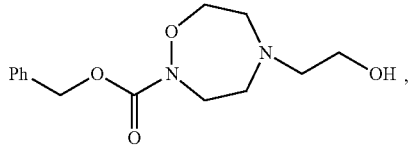

O-9
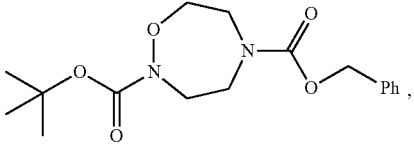

O-10
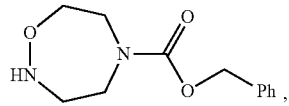

O-11
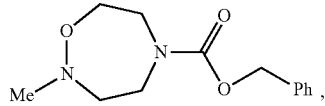

O-12
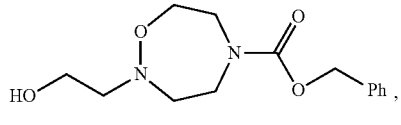

O-13
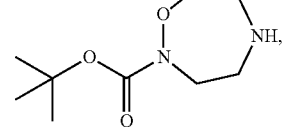

O-14
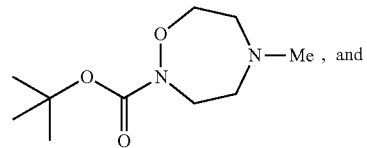

O-16
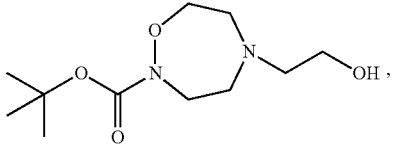

wherein Ph is phenyl and Me is methyl.

* * * * *